United States Patent
Cohnen et al.

(10) Patent No.: US 12,203,110 B2
(45) Date of Patent: Jan. 21, 2025

(54) RNA-PROGRAMMABLE ENDONUCLEASE SYSTEMS AND USES THEREOF

(71) Applicants: CRISPR THERAPEUTICS AG, Zug (CH); BAYER HEALTHCARE LLC, Whippany, NJ (US)

(72) Inventors: Andre Cohnen, Titz-Hasselsweiler (DE); Moritz Schmidt, Cologne (DE); Wayne Coco, Pulheim (DE); Michael Biag Gamalinda, Leverkusen (DE); Ashish Gupta, Leverkusen (DE); Christian Pitzler, Leverkusen (DE); Florian Richter, Leverkusen (DE); Jan Tebbe, Leverkusen (DE); Christopher Cheng, Cambridge, MA (US); Ryo Takeuchi, Cambridge, MA (US); Caroline W. Reiss, Cambridge, MA (US)

(73) Assignees: CRISPR THERAPEUTICS AG, Zug (CH); BAYER HEALTHCARE LLC, Whippany, NJ (US)

( * ) Notice: Subject to any disclaimer, the term of this patent is extended or adjusted under 35 U.S.C. 154(b) by 1087 days.

(21) Appl. No.: 16/982,433

(22) PCT Filed: Mar. 19, 2019

(86) PCT No.: PCT/US2019/023044
§ 371 (c)(1),
(2) Date: Sep. 18, 2020

(87) PCT Pub. No.: WO2019/183150
PCT Pub. Date: Sep. 26, 2019

(65) Prior Publication Data
US 2021/0054353 A1    Feb. 25, 2021

Related U.S. Application Data

(60) Provisional application No. 62/745,239, filed on Oct. 12, 2018, provisional application No. 62/745,238, filed on Oct. 12, 2018, provisional application No. 62/745,246, filed on Oct. 12, 2018, provisional application No. 62/745,240, filed on Oct. 12, 2018.

(30) Foreign Application Priority Data

| Mar. 19, 2018 | (EP) | 18162681 |
| Mar. 19, 2018 | (EP) | 18162683 |
| May 16, 2018 | (EP) | 18172625 |
| May 29, 2018 | (EP) | 18174707 |
| Jul. 4, 2018 | (EP) | 18181680 |

(51) Int. Cl.
C12N 9/22 (2006.01)
C12N 15/11 (2006.01)
C12N 15/113 (2010.01)
C12N 15/90 (2006.01)

(52) U.S. Cl.
CPC .............. *C12N 9/22* (2013.01); *C12N 15/11* (2013.01); *C12N 15/113* (2013.01); *C12N 15/907* (2013.01); *C12N 2310/20* (2017.05); *C12N 2800/80* (2013.01)

(58) Field of Classification Search
CPC ........ C12N 9/22; C12N 15/11; C12N 15/113; C12N 15/907; C12N 2310/20; C12N 2800/80
See application file for complete search history.

(56) References Cited

U.S. PATENT DOCUMENTS

| 3,687,808 A | 8/1972 | Merigan et al. |
| 4,469,863 A | 9/1984 | Ts et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,023,243 A | 6/1991 | Tullis |
| 5,034,506 A | 7/1991 | Summerton et al. |

(Continued)

FOREIGN PATENT DOCUMENTS

| JP | 2015-523856 A | 8/2015 |
| WO | WO1993/003769 | 3/1993 |

(Continued)

OTHER PUBLICATIONS

Witkowski et al., Biochemistry 38:11643-11650, 1999.*

(Continued)

*Primary Examiner* — Delia M Ramirez

(74) *Attorney, Agent, or Firm* — Casimir Jones, S.C.; J. Mitchell Jones

(57) ABSTRACT

Aspects of this invention, inter alia, relate to novel systems for targeting, editing or manipulating DNA in a cell, using novel synthetic RNA-guided nucleases (sRGNs). The sRGNs are derived from wildtype or parental small type II CRISPR Cas9 endonucleases.

10 Claims, 9 Drawing Sheets

Specification includes a Sequence Listing.

(56) References Cited

U.S. PATENT DOCUMENTS

| | | |
|---|---|---|
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,222,982 A | 6/1993 | Ommaya |
| 5,235,033 A | 8/1993 | Summerton et al. |
| 5,245,022 A | 9/1993 | Weis et al. |
| 5,254,469 A | 10/1993 | Warren et al. |
| 5,258,506 A | 11/1993 | Urdea et al. |
| 5,262,536 A | 11/1993 | Hobbs |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,385,582 A | 1/1995 | Ommaya |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,451,513 A | 9/1995 | Maliga et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,545,817 A | 8/1996 | Mcbride et al. |
| 5,545,818 A | 8/1996 | Mcbride et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,576,198 A | 11/1996 | Mcbride et al. |
| 5,578,717 A | 11/1996 | Urdea et al. |
| 5,578,718 A | 11/1996 | Cook et al. |
| 5,580,731 A | 12/1996 | Chang et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,786,211 A | 7/1998 | Johnson |
| 5,830,653 A | 11/1998 | Froehler et al. |
| 5,843,780 A | 12/1998 | Thomson |
| 5,871,982 A | 2/1999 | Wilson et al. |
| 6,005,096 A | 12/1999 | Matteucci et al. |
| 6,200,806 B1 | 3/2001 | Thomson |
| 6,258,595 B1 | 7/2001 | Gao et al. |
| 6,287,860 B1 | 9/2001 | Monia et al. |
| 7,029,913 B2 | 4/2006 | Thomson |
| 7,078,387 B1 | 7/2006 | Leiden et al. |
| 7,153,684 B1 | 12/2006 | Hogan |
| 7,169,874 B2 | 1/2007 | Salamone et al. |
| 8,158,601 B2 | 4/2012 | Chen et al. |
| 2003/0022831 A1 | 1/2003 | Rothbard et al. |
| 2003/0032593 A1 | 2/2003 | Wender et al. |
| 2003/0083256 A1 | 5/2003 | Rothbard et al. |
| 2003/0158403 A1 | 8/2003 | Manoharan et al. |
| 2003/0220334 A1 | 11/2003 | Wender et al. |
| 2004/0142025 A1 | 7/2004 | MacLachlan et al. |
| 2007/0042031 A1 | 2/2007 | MacLachlan et al. |
| 2007/0254842 A1 | 11/2007 | Bankiewicz |
| 2008/0081064 A1 | 4/2008 | Jelle et al. |
| 2009/0047263 A1 | 2/2009 | Yamanaka et al. |
| 2009/0068742 A1 | 3/2009 | Yamanaka et al. |
| 2009/0191159 A1 | 7/2009 | Sakurada et al. |
| 2009/0196903 A1 | 8/2009 | Kliman |
| 2009/0227032 A1 | 9/2009 | Yamanaka et al. |
| 2009/0246875 A1 | 10/2009 | Yamanaka et al. |
| 2009/0304646 A1 | 12/2009 | Sakurada et al. |
| 2018/0127786 A1 | 5/2018 | Bouchon et al. |

FOREIGN PATENT DOCUMENTS

| | | |
|---|---|---|
| WO | WO1993/007883 | 4/1993 |
| WO | WO1993/009239 | 5/1993 |
| WO | WO1993/019191 | 9/1993 |
| WO | WO1994/012649 | 6/1994 |
| WO | WO1994/028938 | 12/1994 |
| WO | WO1995/000655 | 1/1995 |
| WO | WO1995/011984 | 5/1995 |
| WO | WO1995/013365 | 5/1995 |

(56) References Cited

FOREIGN PATENT DOCUMENTS

| | | |
|---|---|---|
| WO | WO1995/013392 | 5/1995 |
| WO | WO1995/016783 | 6/1995 |
| WO | WO1996/017947 | 6/1996 |
| WO | WO1997/006243 | 2/1997 |
| WO | WO1997/008298 | 3/1997 |
| WO | WO1997/009441 | 3/1997 |
| WO | WO1997/021825 | 6/1997 |
| WO | WO1998/039352 | 9/1998 |
| WO | WO1999/011764 | 3/1999 |
| WO | WO1999/014226 | 3/1999 |
| WO | WO1999/020741 | 4/1999 |
| WO | WO2001/018048 | 3/2001 |
| WO | WO2001/051616 | 7/2001 |
| WO | WO2001/083692 | 11/2001 |
| WO | WO2003/020920 | 3/2003 |
| WO | WO2013/176722 | 11/2013 |
| WO | WO-2013/176772 A1 | 11/2013 |
| WO | WO2014/008334 | 1/2014 |
| WO | 2015/077318 A1 | 5/2015 |
| WO | WO2015/089419 | 6/2015 |
| WO | WO2015/095340 | 6/2015 |
| WO | 2015/103153 A1 | 7/2015 |
| WO | WO2015/130584 | 9/2015 |
| WO | WO-2015/153780 A1 | 10/2015 |
| WO | 2016/205613 A1 | 12/2016 |
| WO | WO-2017/048969 A1 | 3/2017 |
| WO | WO2017/070622 | 4/2017 |
| WO | WO2017/070632 | 4/2017 |
| WO | WO2017/099823 | 6/2017 |
| WO | WO2017/144630 | 8/2017 |
| WO | WO2017/173054 | 10/2017 |
| WO | WO2018/002719 | 1/2018 |
| WO | WO-2018/002812 A1 | 1/2018 |
| WO | 2018/039145 A1 | 3/2018 |
| WO | WO2018/058064 | 3/2018 |
| WO | WO2018/081480 | 5/2018 |
| WO | WO2018/107026 | 6/2018 |
| WO | 2019/183150 A1 | 9/2019 |
| WO | WO-2020112908 A2 | 6/2020 |

OTHER PUBLICATIONS

Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Krishnan et al., "CRISPR deletion of the C9ORF72 promoter in ALS/FTD patient motor neurons abolishes production of dipeptide repeat proteins and rescues neurodegeneration", Acta Neuropathologica, 140:81-84, Apr. 7, 2020.
Aguilera et al., "Systemic in vivo distribution of activatable cell penetrating peptides is superior to that of cell penetrating peptides," Integrative Biology 2009, 1(5-6), 371-381.
Akyürek et al., "SM22 α Promoter Targets Gene Expression to Vascular Smooth Muscle Cells In Vitro and In Vivo," Molecular Medicine 2000, 6, 983-991.
Ali et al., "Adeno-associated virus gene transfer to mouse retina," Human Gene Therapy 1998, 9(1), 81-86.
Ali et al., "Gene transfer into the mouse retina mediated by an adeno-associated viral vector," Human Molecular Genetics 1996, 5(5), 591-594.
Altschul et al., "Basic local alignment search tool," Journal of Molecular Biology 1990, 215(3), 403-410.
Anders & Jinek, "In vitro enzymology of Cas9," Methods in Enzymology 2014, 546, 1-20.
Angart et al., "Design of siRNA therapeutics from the molecular scale," Pharmaceuticals 2013, 6(4), 440-468.
Angel & Yanik, "Innate immune suppression enables frequent transfection with RNA encoding reprogramming proteins," PloS One 2010, 5(7), in 7 pages.

Baetge et al., "Transgenic mice express the human phenylethanolamine N-methyltransferase gene in adrenal medulla and retina," Proceedings of the National Academy of Sciences 1988, 85(10), 3648-3652.
Barbour et al., "Characterization of the bipartite degron that regulates ubiquitin-independent degradation of thymidylate synthase," Bioscience Reports 2013, 33(1), in 19 pages.
Behlke, "Chemical modification of siRNAs for in vivo use," Oligonucleotides 2008, 18(4), 305-320.
Bennett et al., "Real-time, noninvasive in vivo assessment of adeno-associated virus-mediated retinal transduction," Investigative Ophthalmology & Visual Science 1997, 38(13), 2857-2863.
Beumer et al., "Efficient gene targeting in Drosophila by direct embryo injection with zinc-finger nucleases," Proceedings of the National Academy of Sciences 2008, 105(50), 19821-19826.
Bevan, "Binary Agrobacterium vectors for plant transformation," Nucleic Acids Research 1984, 12(22), 8711-8721.
Bitter et al., "[33] Expression and secretion vectors for yeast," Methods in Enzymology 1987, 153, 516-544.
Borrás et al., "Adenoviral reporter gene transfer to the human trabecular meshwork does not alter aqueous humor outflow. Relevance for potential gene therapy of glaucoma," Gene Therapy 1999, 6(4), 515-524.
Boundy et al., "Regulation of tyrosine hydroxylase promoter activity by chronic morphine in TH9. 0-LacZ transgenic mice," Journal of Neuroscience 1998, 18(23), 9989-9995.
Boynton & Gillham, "[37] Chloroplast transformation in Chlamydomonas," Methods in Enzymology 1993, 217, 510-536.
Braasch et al., "Novel antisense and peptide nucleic acid strategies for controlling gene expression," Biochemistry 2002, 41(14), 4503-4510.
Bramsen & Kjems, "Development of therapeutic-grade small interfering RNAs by chemical engineering," Frontiers in Genetics 2012, 3, in 22 pages.
Brinkman et al., "Easy quantitative assessment of genome editing by sequence trace decomposition," Nucleic Acids Research 2014, 42(22), in 8 pages.
Burnett et al., "Current progress of siRNA/shRNA therapeutics in clinical trials," Biotechnology Journal 2011, 6(9), 1130-1146.
Carter, "Adeno-associated virus vectors," Current Opinion in Biotechnology 1992, 3(5), 533-539.
Casanova et al., "A CamKIIα iCre BAC allows brain-specific gene inactivation," Genesis 2001, 31(1), 37-42.
Ceccaldi et al., "Homologous-recombination-deficient tumours are dependent on Polθ-mediated repair," Nature 2015, 518 (7538), 258-262.
Cekaite et al., "Gene expression analysis in blood cells in response to unmodified and 2'-modified siRNAs reveals TLR-dependent and independent effects," Journal of Molecular Biology 2007, 365(1), 90-108.
Chakrabarti, "Promoting adipose specificity: the adiponectin promoter," Endocrinology 2010, 151(6), 2408-2410.
Chang & Wilson, "Modification of DNA ends can decrease end joining relative to homologous recombination in mammalian cells," Proceedings of the National Academy of Sciences 1987, 84(14), 4959-4963.
Chen et al., "A lymphoproliferative abnormality associated with inappropriate expression of the Thy-1 antigen in transgenic mice," Cell 1987, 51(1), 7-19.
Chen et al., "Analysis of a 762-bp proximal leptin promoter to drive and control regulation of transgene expression of growth hormone receptor in mice," Biochemical and Biophysical Research Communications 1999, 262(1), 187-192.
Chernolovskaya & Zenkova, "Chemical modification of siRNA," Current Opinion in Molecular Therapeutics 2010, 12(2), 158-167.
Cho & Greenberg, "Familiar ends with alternative endings," Nature 2015, 518(7538), 174-175.
Cho et al., "Generation of transgenic mice," Current Protocols in Cell Biology 2009, 42(1), 19-11.
Christou et al., "Production of transgenic rice (Oryza sativa L.) plants from agronomically important indica and japonica varieties via electric discharge particle acceleration of exogenous DNA into immature zygotic embryos," Bio/technology 1991, 9(10), 957-962.

(56) References Cited

OTHER PUBLICATIONS

Chu et al., "Recent progress with FKBP-derived destabilizing domains," Bioorganic & Medicinal Chemistry Letters 2008, 18(22), 5941-5944.
Citartan et al., "Assays for aptamer-based platforms," Biosensors and Bioelectronics 2012, 34(1), in 11 pages.
Clark et al., "A stable cell line carrying adenovirus-inducible rep and cap genes allows for infectivity titration of adeno-associated virus vectors," Gene Therapy 1996, 3(12), 1124-1132.
Comb et al., "Proteins bound at adjacent DNA elements act synergistically to regulate human proenkephalin cAMP inducible transcription," The EMBO Journal 1988, 7(12), 3793-3805.
Cox et al., "Therapeutic genome editing: prospects and challenges," Nature Medicine 2015, 21(2), 121-131.
Crooke et al., "Pharmacokinetic properties of several novel oligonucleotide analogs in mice," Journal of Pharmacology and Experimental Therapeutics 1996, 277(2), 923-937.
Daniell et al., "Containment of herbicide resistance through genetic engineering of the chloroplast genome," Nature Biotechnology 1998, 16(4), 345-348.
De Mesmaeker et al., "Antisense oligonucleotides," Accounts of Chemical Research 1995, 28(9), 366-374.
Deleavey et al., "Chemical modification of siRNA," Current Protocols in Nucleic Acid Chemistry 2009, 39(1), in 22 pages.
Derossi et al., "Cell internalization of the third helix of the Antennapedia homeodomain is receptor-independent," Journal of Biological Chemistry 1996, 271(30), 18188-18193.
Devereux et al., "A comprehensive set of sequence analysis programs for the VAX," Nucleic Acids Research 1984, 12(1), 387-395.
Dohmen et al., "Heat-inducible degron: a method for constructing temperature-sensitive mutants," Science 1994, 263(5151), 1273-1276.
Englisch & Gauss, "Chemically modified oligonucleotides as probes and inhibitors," Angewandte Chemie International Edition in English 1991, 30(6), 613-629.
European Nucleotide Archive, "Sequence: X51956.1 Human ENO2 gene for neuron specific (gamma) enolase," nih.gov 2023, in 2 page2.
Feng et al., "High-level expression and mutagenesis of recombinant human phosphatidylcholine transfer protein using a synthetic gene: evidence for a C-terminal membrane binding domain," Biochemistry 2000, 39(50), 15399-15409.
First Office Action dated Oct. 8, 2023 in Chinese Patent Application No. 201980090537.2.
Flannery et al., "Efficient photoreceptor-targeted gene expression in vivo by recombinant adeno-associated virus," Proceedings of the National Academy of Sciences 1997, 94(13), 6916-6921.
Finn et al., "A Single Administration of CRISPR/Cas9 Lipid Nanoparticles Achieves Robust and Persistent In Vivo Genome Editing," Cell Reports 2018, 22(9), 2227-2235.
Flotte et al., "Stable in vivo expression of the cystic fibrosis transmembrane conductance regulator with an adeno-associated virus vector," Proceedings of the National Academy of Sciences 1993, 90(22), 10613-10617.
Franz et al., "Analysis of tissue-specific gene delivery by recombinant adenoviruses containing cardiac-specific promoters," Cardiovascular Research 1997, 35(3), 560-566.
Fucini et al., "Adenosine modification may be preferred for reducing siRNA immune stimulation," Nucleic Acid Therapeutics 2012, 22(3), 205-210.
Futaki et al., "Structural variety of membrane permeable peptides," Current Protein and Peptide Science 2003, 4(2), 87-96.
Gaglione & Messere, "Recent progress in chemically modified siRNAs," Mini Reviews in Medicinal Chemistry 2010, 10(7), 578-595.
Gama Sosa et al., "Animal transgenesis: an overview," Brain Structure and Function 2010, 214, 91-109.
Gaudelli et al., "Programmable base editing of A• T to G• C in genomic DNA without DNA cleavage," Nature 2017, 551(7681), 464-471.

Gebeyehu et al., "Novel biotinylated nucleotide-analogs for labeling and colorimetric detection of DNA," Nucleic Acids Research 1987, 15(11), 4513-4534.
Gibbs et al., "Degenerate oligonucleotide gene shuffling (DOGS): a method for enhancing the frequency of recombination with family shuffling," Gene 2001, 271(1), 13-20.
Glaser et al., "GFP to BFP conversion: a versatile assay for the quantification of CRISPR/Cas9-mediated genome editing," Molecular Therapy-Nucleic Acids 2016, 5, in 4 pages.
Gordon-Kamm et al., "Transformation of maize cells and regeneration of fertile transgenic plants," The Plant Cell 1990, 2(7), 603-618.
Greussing et al., "Monitoring of ubiquitin-proteasome activity in living cells using a Degron (dgn)-destabilized green fluorescent protein (GFP)-based reporter protein," JoVE (Journal of Visualized Experiments) 2012, 69, in 8 pages.
Hajj & Whitehead, "Tools for translation: non-viral materials for therapeutic mRNA delivery," Nature Reviews Materials 2017, 2(10), in 17 pages.
Heasman, "Morpholino oligos: making sense of antisense?," Developmental Biology 2002, 243(2), 209-214.
Hermonat & Muzyczka, "Use of adeno-associated virus as a mammalian DNA cloning vector: transduction of neomycin resistance into mammalian tissue culture cells," Proceedings of the National Academy of Sciences 1984, 81(20), 6466-6470.
Herrera-Estrella et al., "Expression of chimaeric genes transferred into plant cells using a Ti-plasmid-derived vector," Nature 1983, 303(5914), 209-213.
Hu et al., "Physiological roles of asialoglycoprotein receptors (ASGPRs) variants and recent advances in hepatic-targeted delivery of therapeutic molecules via ASGPRs," Protein and Peptide Letters 2014, 21(10), 1025-1030.
Hunter et al., "Targeting gene expression to specific cardiovascular cell types in transgenic mice," Hypertension 1993, 22(4), 608-617.
Husaini et al., "Approaches for gene targeting and targeted gene expression in plants," GM Crops 2011, 2(3), 150-162.
International Search Report and Written Opinion dated Jul. 20, 2020 in International Application No. PCT/US2019/063456.
Ishida et al., "High efficiency transformation of maize (*Zea mays* L.) mediated by Agrobacterium tumefaciens," Nature Biotechnology 1996, 14(6), 745-750.
Joern, "DNA shuffling," Directed Evolution Library Creation: Methods and Protocols 2003, 231, 85-89.
Jomary et al., "Rescue of photoreceptor function by AAV-mediated gene transfer in a mouse model of inherited retinal degeneration," Gene Therapy 1997, 4(7), 683-690.
Judge & MacLachlan, "Overcoming the innate immune response to small interfering RNA," Human Gene Therapy 2008, 19(2), 111-124.
Judge et al., "Design of noninflammatory synthetic siRNA mediating potent gene silencing in vivo," Molecular Therapy 2006, 13(3), 494-505.
Kabanov et al., "A new class of antivirals: antisense oligonucleotides combined with a hydrophobic substituent effectively inhibit influenza virus reproduction and synthesis of virus-specific proteins in MDCK cells," FEBS letters 1990, 259(2), 327-330.
Kanasty et al., "Action and reaction: the biological response to siRNA and its delivery vehicles," Molecular Therapy 2012, 20(3), 513-524.
Kaneda et al., "Tissue-specific and high-level expression of the human tyrosine hydroxylase gene in transgenic mice," Neuron 1991, 6(4), 583-594.
Kanemaki, "Frontiers of protein expression control with conditional degrons," Pflügers Archiv-European Journal of Physiology 2013, 465, 419-425.
Karikó et al., "Suppression of RNA recognition by Toll-like receptors: the impact of nucleoside modification and the evolutionary origin of RNA," Immunity 2005, 23(2), 165-175.
Kawai et al., "Transformation of *Saccharomyces cerevisiae* and other fungi: methods and possible underlying mechanism," Bioengineered Bugs 2010, 1(6), 395-403.
Kazutaka Katoh, "MAFFT version 7," mafft.cbrc.jp 2023, in 2 pages.

(56) References Cited

OTHER PUBLICATIONS

Kent et al., "Mechanism of microhomology-mediated end-joining promoted by human DNA polymerase θ," Nature Structural & Molecular Biology 2015, 22(3), 230-237.
Kim et al. "A serum response factor-dependent transcriptional regulatory program identifies distinct smooth muscle cell sublineages." Molecular and Cellular Biology 1997, 17(4), 2266-2278.
Kim et al., "In vivo genome editing with a small Cas9 orthologue derived from Campylobacter jejuni," Nature Communications 2017, 8, in 12 pages.
Kim et al., "Increasing the genome-targeting scope and precision of base editing with engineered Cas9-cytidine deaminase fusions," Nature Biotechnology 2017, 35(4), 371-376.
Kita et al., "Identification of the promoter region required for human adiponectin gene transcription: association with CCAAT/enhancer binding protein-β and tumor necrosis factor-α," Biochemical and Biophysical Research Communications 2005, 331(2), 484-490.
Klee et al., "Vectors for transformation of higher plants," Bio/technology 1985, 3(7), 637-642.
Klein et al., "High-velocity microprojectiles for delivering nucleic acids into living cells," Nature 1987, 327(6117), 70-73.
Knight et al., "Regulation of the human GLUT4 gene promoter: interaction between a transcriptional activator and myocyte enhancer factor 2A," Proceedings of the National Academy of Sciences 2003, 100(25), 14725-14730.
Knoblauch et al., "A galinstan expansion femtosyringe for microinjection of eukaryotic organelles and prokaryotes," Nature Biotechnology 1999, 17(9), 906-909.
Kole et al., "RNA therapeutics: beyond RNA interference and antisense oligonucleotides," Nature Reviews Drug Discovery 2012, 11(2), 125-140.
Komor et al., "Improved base excision repair inhibition and bacteriophage Mu Gam protein yields C: G-to-T: A base editors with higher efficiency and product purity," Science Advances 2017, 3(8), in 10 pages.
Komor et al., "Programmable editing of a target base in genomic DNA without double-stranded DNA cleavage," Nature 2016, 533(7603), 420-424.
Kormann et al., "Expression of therapeutic proteins after delivery of chemically modified mRNA in mice," Nature biotechnology 2011, 29(2), 154-157.
Koshimizu et al., "Functional requirement of gp130-mediated signaling for growth and survival of mouse primordial germ cells in vitro and derivation of embryonic germ (EG) cells," Development 1996, 122(4), 1235-1242.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron 1998, 54(14), 3607-3630.
Kuriki et al., "Structural and functional analysis of a new upstream promoter of the human FAT/CD36 gene," Biological and Pharmaceutical Bulletin 2002, 25(11), 1476-1478.
Lacerra et al., "Restoration of hemoglobin A synthesis in erythroid cells from peripheral blood of thalassemic patients," Proceedings of the National Academy of Sciences 2000, 97(17), 9591-9596.
Langer, "New methods of drug delivery," Science 1990, 249(4976), 1527-1533.
Laughlin et al., "Cloning of infectious adeno-associated virus genomes in bacterial plasmids," Gene 1983, 23(1), 65-73.
Lebkowski et al. "Adeno-associated virus: a vector system for efficient introduction and integration of DNA into a variety of mammalian cell types," Molecular and Cellular Biology 1988, 8(10), 3988-3996.
Letsinger et al., "Cholesteryl-conjugated oligonucleotides: synthesis, properties, and activity as inhibitors of replication of human immunodeficiency virus in cell culture," Proceedings of the National Academy of Sciences 1989, 86(17), 6553-6556.

Li & Davidson, "Phenotype correction in retinal pigment epithelium in murine mucopolysaccharidosis VII by adenovirus-mediated gene transfer," Proceedings of the National Academy of Sciences 1995, 92(17), 7700-7704.
Li et al., "Expression of the SM22alpha promoter in transgenic mice provides evidence for distinct transcriptional regulatory programs in vascular and visceral smooth muscle cells," The Journal of Cell Biology 1996, 132(5), 849-859.
Li et al., "In vivo transfer of a reporter gene to the retina mediated by an adenoviral vector," Investigative Ophthalmology & Visual Science 1994, 35(5), 2543-2549.
Liberman & Wedekind, "Riboswitch structure in the ligand-free state," Wiley Interdisciplinary Reviews: RNA 2012, 3(3), 369-384.
Linn et al., "Conservation of an AE3 Cl-/HCO3—exchanger cardiac-specific exon and promoter region and AE3 mRNA expression patterns in murine and human hearts," Circulation Research 1995, 76(4), 584-591.
Liu et al., "CMV enhancer/human PDGF-β promoter for neuron-specific transgene expression," Gene Therapy 2004, 11(1), 52-60.
Llewellyn et al., "Orderly recruitment of motor units under optical control in vivo," Nature Medicine 2010, 16(10), 1161-1165.
Loakes & Brown, "5-Nitroindole as an universal base analogue," Nucleic Acids Research 1994, 22(20), 4039-4043.
Ma et al., "Pol III promoters to express small RNAs: delineation of transcription initiation," Molecular Therapy-Nucleic Acids 2014, 3, in 11 pages.
Mäe et al., "Chemically modified cell-penetrating peptides for the delivery of nucleic acids," Expert Opinion on Drug Delivery 2009, 6(11), 1195-1205.
Makrides, "Gene transfer and expression in mammalian cells," Gulf Professional Publishing, 2003, in 680 pages.
Manoharan et al., "Chemical modifications to improve uptake and bioavailability of antisense oligonucleotides," Annals of the New York Academy of Sciences 1992, 660(1), 306-309.
Manoharan et al., "Cholic acid-oligonucleotide conjugates for antisense applications," Bioorganic & Medicinal Chemistry Letters 1994, 4(8), 1053-1060.
Manoharan et al., "Introduction of a lipophilic thioether tether in the minor groove of nucleic acids for antisense applications," Bioorganic & Medicinal Chemistry Letters 1993, 3(12), 2765-2770.
Manoharan et al., "Lipidic nucleic acids," Tetrahedron Letters 1995, 36(21), 3651-3654.
Manoharan et al., "Oligonucleotide conjugates: alteration of the pharmacokinetic properties of antisense agents," Nucleosides, Nucleotides & Nucleic Acids 1995, 14(3-5), 969-973.
Martin, "Ein neuer Zugang zu 2'-O-Alkylribonucleosiden und Eigenschaflen deren Oligonucleotide," Helv. Chim. Acta 1995, 78(2), 486-504.
Mason et al., "Regulation of leptin promoter function by Sp1, C/EBP, and a novel factor," Endocrinology 1998, 139(3), 1013-1022.
Mateos-Gomez et al., "Mammalian polymerase θ promotes alternative NHEJ and suppresses recombination," Nature 2015, 518(7538), 254-257.
Matsui et al., "Derivation of pluripotential embryonic stem cells from murine primordial germ cells in culture," Cell 1992, 70(5), 841-847.
Mayford et al., "The 3'-untranslated region of CaMKIIα is a cis-acting signal for the localization and translation of mRNA in dendrites," Proceedings of the National Academy of Sciences 1996, 93(23), 13250-13255.
McBride et al., "Controlled expression of plastid transgenes in plants based on a nuclear DNA-encoded and plastid-targeted T7 RNA polymerase," Proceedings of the National Academy of Sciences 1994, 91(15), 7301-7305.
McLaughlin et al., "Adeno-associated virus general transduction vectors: analysis of proviral structures," Journal of Virology 1988, 62(6), 1963-1973.
Mendelson et al., "Expression and rescue of a nonselected marker from an integrated AAV vector," Virology 1988, 166(1), 154-165.
Miller et al., "An improved zinc-finger nuclease architecture for highly specific genome editing," Nature Biotechnology 2007, 25(7), 778-785.

(56) References Cited

OTHER PUBLICATIONS

Mishra et al., "Improved leishmanicidal effect of phosphorotioate antisense oligonucleotides by LDL-mediated delivery," Biochimica et Biophysica Acta (BBA)-Gene Structure and Expression 1995, 1264(2), 229-237.
Miyagishi & Taira, "U6 promoter-driven siRNAs with four uridine 3' overhangs efficiently suppress targeted gene expression in mammalian cells," Nature Biotechnology 2002, 20(5), 497-500.
Miyoshi et al., "Stable and efficient gene transfer into the retina using an HIV-based lentiviral vector," Proceedings of the National Academy of Sciences 1997, 94(19), 10319-10323.
Moessler et al., "The SM 22 promoter directs tissue-specific expression in arterial but not in venous or visceral smooth muscle cells in transgenic mice," Development 1996, 122(8), 2415-2425.
Morrison et al., "Regulatory mechanisms in stem cell biology," Cell 1997, 88(3), 287-298.
Mullis, "The polymerase chain reaction," Springer Science & Business Media 1994, 41(5), in 458 pages.
Muzyczka, "Use of adeno-associated virus as a general transduction vector for mammalian cells," Viral Expression Vectors 1992, 97-129.
Nakamura et al., "RNA plasticity and selectivity applicable to therapeutics and novel biosensor development," Genes to Cells 2012, 17(5), 344-364.
Nasevicius & Ekker, "Effective targeted gene 'knockdown' in zebrafish," Nature Genetics 2000, 26(2), 216-220.
National Library of Medicine, "5-HT1C serotonin receptor {promoter region} [mice, Genomic, 1859 nt] GenBank: S62283.1," nih.gov 2023, in 1 page.
National Library of Medicine, "Adeno-associated virus—1, complete genome NCBI Reference Sequence: NC_002077.1," nih.gov 2023, in 3 pages.
National Library of Medicine, "Adeno-associated virus—2, complete genome NCBI Reference Sequence: NC_001401.2," nih.gov 2023, in 5 pages.
National Library of Medicine, "Adeno-associated virus—3, complete genome NCBI Reference Sequence: NC_001729.1," nih.gov 2023, in 3 pages.
National Library of Medicine, "Adeno-associated virus—4, complete genome NCBI Reference Sequence: NC_001829.1," nih.gov 2023, in 3 pages.
National Library of Medicine, "Adeno-associated virus—7, complete genome NCBI Reference Sequence: NC_006260.1," nih.gov 2023, in 3 pages.
National Library of Medicine, "Adeno-associated virus—8, complete genome NCBI Reference Sequence: NC_006261.1," nih.gov 2023, in 3 pages.
National Library of Medicine, "Adeno-associated virus 10 nonstructural protein and capsid protein genes, complete cds GenBank: AY631965.1," nih.gov 2023, in 2 pages.
National Library of Medicine, "Adeno-associated virus 11 nonstructural protein and capsid protein genes, complete cds GenBank: AY631966.1," nih.gov 2023, in 2 pages.
National Library of Medicine, "Adeno-associated virus 12 Rep78 and VP1 genes, complete cds GenBank: DQ813647.1," nih.gov 2023, in 2 pages.
National Library of Medicine, "Adeno-associated virus 13 nonstructural protein and capsid protein genes, complete cds GenBank: EU285562.1," nih.gov 2023, in 2 pages.
National Library of Medicine, "Adeno-associated virus 3B, complete genome GenBank: AF028705.1," nih.gov 2023, in 2 pages.
National Library of Medicine, "Adeno-associated virus 5, complete genome NCBI Reference Sequence: NC_006152.1," nih.gov 2023, in 3 pages.
National Library of Medicine, "Adeno-associated virus 6, complete genome GenBank: AF028704.1," nih.gov 2023, in 2 pages.
National Library of Medicine, "CRISPR-associated protein Cas9, partial [Staphylococcus coagulans] NCBI Reference Sequence: WP_103356723.1," nih.gov 2023, in 1 page.
National Library of Medicine, "HNH endonuclease domain-containing protein, partial [Staphylococcus simulans] NCBI Reference Sequence: WP_107604002.1," nih.gov 2023, in 1 page.
National Library of Medicine, "HNH endonuclease domain-containing protein [Staphylococcus schleiferi] NCBI Reference Sequence: WP_016424981.1," nih.gov 2023, in 1 page.
National Library of Medicine, "HNH endonuclease domain-containing protein [Chryseomicrobium excrementi] NCBI Reference Sequence: WP_100353964.1," nih.gov 2023, in 1 page.
National Library of Medicine, "HNH endonuclease domain-containing protein [Bacillus sp. SA1-12] NCBI Reference Sequence: WP_046517046.1," nih.gov 2023, in 1 page.
National Library of Medicine, "Human neurofilament light chain (NEFL) gene, promoter region GenBank: L04147.1," nih.gov 2023, in 2 pages.
National Library of Medicine, "Human synapsin I gene, 5' end GenBank: M55301.1," nih.gov 2023, in 2 pages.
National Library of Medicine, "hypothetical protein [Alkalibacillus haloalkaliphilus] NCBI Reference Sequence: WP_050980543.1," nih.gov 2023, in 1 page.
National Library of Medicine, "hypothetical protein [Anoxybacillus sp. KU2-6(11)] NCBI Reference Sequence: WP_052025682.1," nih.gov 2023, in 1 page.
National Library of Medicine, "hypothetical protein [Heyndrickxia sporothermodurans] NCBI Reference Sequence: WP_066230975.1," nih.gov 2023, in 1 page.
National Library of Medicine, "hypothetical protein [Listeria fleischmannii] NCBI Reference Sequence: WP_077914265.1," nih.gov 2023, in 1 page.
National Library of Medicine, "hypothetical protein [Listeria fleischmannii] NCBI Reference Sequence: WP_077914264.1," nih.gov 2023, in 1 page.
National Library of Medicine, "hypothetical protein [Mammaliicoccus sciuri] NCBI Reference Sequence: WP_103361956.1," nih.gov 2023, in 1 page.
National Library of Medicine, "hypothetical protein [Salinicoccus sediminis] NCBI Reference Sequence: WP_046580811.1," nih.gov 2023, in 1 page.
National Library of Medicine, "hypothetical protein [Staphylococcus simulans] NCBI Reference Sequence: WP_107593719.1," nih.gov 2023, in 1 page.
National Library of Medicine, "hypothetical protein [Staphylococcus agnetis] NCBI Reference Sequence: WP_107371387.1," nih.gov 2023, in 1 page.
National Library of Medicine, "hypothetical protein [Staphylococcus sp. HMSC065D05] NCBI Reference Sequence: WP_070592992.1," nih.gov 2023, in 1 page.
National Library of Medicine, "hypothetical protein [Staphylococcus warneri] NCBI Reference Sequence: WP_107536245.1," nih.gov 2023, in 1 page.
National Library of Medicine, "hypothetical protein [Staphylococcus agnetis] NCBI Reference Sequence: WP_107368971.1," nih.gov 2023, in 1 page.
National Library of Medicine, "Multispecies: ABC transporter permease [Mammaliicoccus] NCBI Reference Sequence: WP_017000597.1," nih.gov 2023, in 1 page.
National Library of Medicine, "Multispecies: hypothetical protein [Staphylococcus] NCBI Reference Sequence: WP_060803559.1," nih.gov 2023, in 1 page.
National Library of Medicine, "Multispecies: type II CRISPR RNA-guided endonuclease Cas9 [Staphylococcus] NCBI Reference Sequence: WP_082709447.1," nih.gov 2023, in 2 pages.
National Library of Medicine, "Multispecies: type II CRISPR RNA-guided endonuclease Cas9 [Staphylococcus] NCBI Reference Sequence: WP_083326835.1," nih.gov 2023, in 2 pages.
National Library of Medicine, "Multispecies: type II CRISPR RNA-guided endonuclease Cas9 [Staphylococcus] NCBI Reference Sequence: WP_104681501.1," nih.gov 2023, in 2 pages.
National Library of Medicine, "Multispecies: type II CRISPR RNA-guided endonuclease Cas9 [Staphylococcus] NCBI Reference Sequence: WP_016424980.1," nih.gov 2023, in 2 pages.

(56) References Cited

OTHER PUBLICATIONS

National Library of Medicine, "Multispecies: type II CRISPR RNA-guided endonuclease Cas9 [*Staphylococcus*] NCBI Reference Sequence: WP_060803934.1," nih.gov 2023, in 2 pages.
National Library of Medicine, "Multispecies: type II CRISPR RNA-guided endonuclease Cas9 [*Staphylococcus*] NCBI Reference Sequence: WP_107376447.1," nih.gov 2023, in 2 pages.
National Library of Medicine, "Multispecies: type II CRISPR RNA-guided endonuclease Cas9 [unclassified *Staphylococcus*] NCBI Reference Sequence: WP_070848771.1," nih.gov 2023, in 2 pages.
National Library of Medicine, "Multispecies: type II CRISPR RNA-guided endonuclease Cas9 [Listeria] NCBI Reference Sequence: WP_088825434.1," nih.gov 2023, in 2 pages.
National Library of Medicine, "Multispecies: type II CRISPR RNA-guided endonuclease Cas9 [*Staphylococcus*] NCBI Reference Sequence: WP_075777761.1," nih.gov 2023, in 2 pages.
National Library of Medicine, "Multispecies: type II CRISPR RNA-guided endonuclease Cas9 [Listeria] NCBI Reference Sequence: WP_088816271.1," nih.gov 2023, in 2 pages.
National Library of Medicine, "Multispecies: type II CRISPR RNA-guided endonuclease Cas9 [Bacillus cereus group] NCBI Reference Sequence: WP_048723014.1," nih.gov 2023, in 2 pages.
National Library of Medicine, "Multispecies: type II CRISPR RNA-guided endonuclease Cas9 [Geobacillus] NCBI Reference Sequence: WP_064213580.1," nih. gov 2023, in 2 pages.
National Library of Medicine, "Multispecies: type II CRISPR RNA-guided endonuclease Cas9 [Geobacillus] NCBI Reference Sequence: WP_033018780.1," nih.gov 2023, in 2 pages.
National Library of Medicine, "Multispecies: type II CRISPR RNA-guided endonuclease Cas9 [Bacillus cereus group] NCBI Reference Sequence: WP_088027793.1," nih.gov 2023, in 2 pages.
National Library of Medicine, "Multispecies: type II CRISPR RNA-guided endonuclease Cas9 [Bacillus cereus group] NCBI Reference Sequence: WP_048539452.1," nih.gov 2023, in 2 pages.
National Library of Medicine, "RNA-guided endonuclease IscB [Alicyclobacillus acidocaldarius] NCBI Reference Sequence: WP_008341324.1," nih.gov 2023, in 1 page.
National Library of Medicine, "Sequence 5 from Patent EP1310571 GenBank: AX753250.1," nih.gov 2023, in 2 pages.
National Library of Medicine, "type II CRISPR RNA-guided endonuclease Cas9 [*Staphylococcus pasteuri*] NCBI Reference Sequence: WP_023374365.1," nih.gov 2023, in 2 pages.
National Library of Medicine, "type II CRISPR RNA-guided endonuclease Cas9 [*Staphylococcus pasteuri*] NCBI Reference Sequence: WP_048803085.1," nih.gov 2023, in 2 pages.
National Library of Medicine, "type II CRISPR RNA-guided endonuclease Cas9 [*Staphylococcus haemolyticus*] NCBI Reference Sequence: WP_053019794.1," nih.gov 2023, in 2 pages.
National Library of Medicine, "type II CRISPR RNA-guided endonuclease Cas9 [*Staphylococcus hominis*] NCBI Reference Sequence: WP_071859985.1," nih.gov 2023, in 2 pages.
National Library of Medicine, "type II CRISPR RNA-guided endonuclease Cas9 [*Staphylococcus hominis*] NCBI Reference Sequence: WP_049437627.1," nih.gov 2023, in 2 pages.
National Library of Medicine, "type II CRISPR RNA-guided endonuclease Cas9 [*Staphylococcus equorum*] NCBI Reference Sequence: WP_081329738.1," nih.gov 2023, in 2 pages.
National Library of Medicine, "type II CRISPR RNA-guided endonuclease Cas9 [*Staphylococcus equorum*] NCBI Reference Sequence: WP_081330634.1," nih.gov 2023, in 2 pages.
National Library of Medicine, "type II CRISPR RNA-guided endonuclease Cas9 [*Staphylococcus epidermidis*] NCBI Reference Sequence: WP_088922804.1," nih.gov 2023, in 2 pages.
National Library of Medicine, "type II CRISPR RNA-guided endonuclease Cas9 [*Staphylococcus kloosii*] NCBI Reference Sequence: WP_061854099.1," nih.gov 2023, in 2 pages.
National Library of Medicine, "type II CRISPR RNA-guided endonuclease Cas9 [Mammaliicoccus sciuri] NCBI Reference Sequence: WP_096792116.1," nih.gov 2023, in 2 pages.
National Library of Medicine, "type II CRISPR RNA-guided endonuclease Cas9 [*Staphylococcus simulans*] NCBI Reference Sequence: WP_107588422.1," nih.gov 2023, in 2 pages.
National Library of Medicine, "type II CRISPR RNA-guided endonuclease Cas9 [*Staphylococcus simulans*] NCBI Reference Sequence: WP_107543406.1," nih.gov 2023, in 2 pages.
National Library of Medicine, "type II CRISPR RNA-guided endonuclease Cas9 [*Staphylococcus simulans*] NCBI Reference Sequence: WP_105966910.1," nih.gov 2023, in 2 pages.
National Library of Medicine, "type II CRISPR RNA-guided endonuclease Cas9 [*Staphylococcus simulans*] NCBI Reference Sequence: WP_107597066.1," nih.gov 2023, in 2 pages.
National Library of Medicine, "type II CRISPR RNA-guided endonuclease Cas9 [*Staphylococcus simulans*] NCBI Reference Sequence: WP_096754380.1," nih.gov 2023, in 2 pages.
National Library of Medicine, "type II CRISPR RNA-guided endonuclease Cas9 [*Staphylococcus simulans*] NCBI Reference Sequence: WP_082732265.1," nih.gov 2023, in 2 pages.
National Library of Medicine, "type II CRISPR RNA-guided endonuclease Cas9 [*Staphylococcus* sp. HMSC061G12] NCBI Reference Sequence: WP_083326931.1," nih.gov 2023, in 2 pages.
National Library of Medicine, "type II CRISPR RNA-guided endonuclease Cas9 [*Staphylococcus simulans*] NCBI Reference Sequence: WP_105980293.1," nih.gov 2023, in 2 pages.
National Library of Medicine, "type II CRISPR RNA-guided endonuclease Cas9, partial [Staphylococcus simulans] NCBI Reference Sequence: WP_107580550.1," nih.gov 2023, in 2 pages.
National Library of Medicine, "type II CRISPR RNA-guided endonuclease Cas9 [*Staphylococcus* sp. HMSC065D05] NCBI Reference Sequence: WP_083310250.1," nih.gov 2023, in 2 pages.
National Library of Medicine, "type II CRISPR RNA-guided endonuclease Cas9 [*Staphylococcus simulans*] NCBI Reference Sequence: WP_105977729.1," nih.gov 2023, in 2 pages.
National Library of Medicine, "type II CRISPR RNA-guided endonuclease Cas9 [*Staphylococcus simulans*] NCBI Reference Sequence: WP_105978400.1," nih.gov 2023, in 2 pages.
National Library of Medicine, "type II CRISPR RNA-guided endonuclease Cas9, partial [*Staphylococcus simulans*] NCBI Reference Sequence: WP_107530431.1," nih.gov 2023, in 2 pages.
National Library of Medicine, "type II CRISPR RNA-guided endonuclease Cas9 [*Staphylococcus simulans*] NCBI Reference Sequence: WP_107578657.1," nih.gov 2023, in 2 pages.
National Library of Medicine, "type II CRISPR RNA-guided endonuclease Cas9 [*Staphylococcus simulans*] NCBI Reference Sequence: WP_107539784.1," nih.gov 2023, in 2 pages.
National Library of Medicine, "type II CRISPR RNA-guided endonuclease Cas9 [*Staphylococcus simulans*] NCBI Reference Sequence: WP_107597643.1," nih.gov 2023, in 2 pages.
National Library of Medicine, "type II CRISPR RNA-guided endonuclease Cas9 [*Staphylococcus simulans*] NCBI Reference Sequence: WP_105994700.1," nih.gov 2023, in 2 pages.
National Library of Medicine, "type II CRISPR RNA-guided endonuclease Cas9 [*Staphylococcus simulans*] NCBI Reference Sequence: WP_107533955.1," nih.gov 2023, in 2 pages.
National Library of Medicine, "type II CRISPR RNA-guided endonuclease Cas9 [*Staphylococcus simulans*] NCBI Reference Sequence: WP_107596301.1," nih.gov 2023, in 2 pages.
National Library of Medicine, "type II CRISPR RNA-guided endonuclease Cas9, partial [*Staphylococcus simulans*] NCBI Reference Sequence: WP_107568091.1," nih.gov 2023, in 2 pages.
National Library of Medicine, "type II CRISPR RNA-guided endonuclease Cas9, partial [*Staphylococcus simulans*] NCBI Reference Sequence: WP_107544007.1," nih.gov 2023, in 2 pages.
National Library of Medicine, "type II CRISPR RNA-guided endonuclease Cas9 [*Staphylococcus simulans*] NCBI Reference Sequence: WP_107593728.1," nih.gov 2023, in 2 pages.
National Library of Medicine, "type II CRISPR RNA-guided endonuclease Cas9 [*Staphylococcus coagulans*] NCBI Reference Sequence: WP_050345681.1," nih.gov 2023, in 2 pages.
National Library of Medicine, "type II CRISPR RNA-guided endonuclease Cas9 [*Staphylococcus haemolyticus*] NCBI Reference Sequence: WP_107641154.1," nih.gov 2023, in 2 pages.

(56) References Cited

OTHER PUBLICATIONS

National Library of Medicine, "type II CRISPR RNA-guided endonuclease Cas9 [*Staphylococcus agnetis*] NCBI Reference Sequence: WP_107378676.1," nih.gov 2023, in 2 pages.
National Library of Medicine, "type II CRISPR RNA-guided endonuclease Cas9 [*Staphylococcus pseudintermedius*] NCBI Reference Sequence: WP_104039168.1," nih.gov 2023, in 2 pages.
National Library of Medicine, "type II Crispr RNA-guided endonuclease Cas9, partial [*Staphylococcus chromogenes*] NCBI Reference Sequence: WP_107366415.1," nih.gov 2023, in 2 pages.
National Library of Medicine, "type II CRISPR RNA-guided endonuclease Cas9 [*Staphylococcus agnetis*] NCBI Reference Sequence: WP_107371508.1," nih. gov 2023, in 2 pages.
National Library of Medicine, "type II CRISPR RNA-guided endonuclease Cas9, partial [*Staphylococcus simulans*] NCBI Reference Sequence: WP_107547877.1," nih.gov 2023, in 2 pages.
National Library of Medicine, "type II CRISPR RNA-guided endonuclease Cas9, partial [*Staphylococcus haemolyticus*] NCBI Reference Sequence: WP_107642811.1," nih.gov 2023, in 2 pages.
National Library of Medicine, "type II CRISPR RNA-guided endonuclease Cas9 [*Staphylococcus warneri*] NCBI Reference Sequence: WP_107560076.1," nih. gov 2023, in 2 pages.
National Library of Medicine, "type II CRISPR RNA-guided endonuclease Cas9 [*Staphylococcus pseudintermedius*] NCBI Reference Sequence: WP_101457463.1," nih.gov 2023, in 2 pages.
National Library of Medicine, "type II CRISPR RNA-guided endonuclease Cas9 [*Staphylococcus pseudintermedius*] NCBI Reference Sequence: WP_063278948.1," nih.gov 2023, in 2 pages.
National Library of Medicine, "type II CRISPR RNA-guided endonuclease Cas9 [*Staphylococcus cornubiensis*] NCBI Reference Sequence: WP_086428210.1," nih.gov 2023, in 2 pages.
National Library of Medicine, "type II CRISPR RNA-guided endonuclease Cas9, partial [*Staphylococcus simulans*] NCBI Reference Sequence: WP_107544006.1," nih.gov 2023, in 2 pages.
National Library of Medicine, "type II Crispr RNA-guided endonuclease Cas9 [*Staphylococcus simulans*] NCBI Reference Sequence: WP_105966809.1," nih.gov 2023, in 2 pages.
National Library of Medicine, "type II CRISPR RNA-guided endonuclease Cas9 [*Staphylococcus simulans*] NCBI Reference Sequence: WP_105978348.1," nih.gov 2023, in 2 pages.
National Library of Medicine, "type II CRISPR RNA-guided endonuclease Cas9 [*Staphylococcus simulans*] NCBI Reference Sequence: WP_107567989.1," nih.gov 2023, in 2 pages.
National Library of Medicine, "type II CRISPR RNA-guided endonuclease Cas9, partial [*Staphylococcus simulans*] NCBI Reference Sequence: WP_107580472.1," nih.gov 2023, in 2 pages.
National Library of Medicine, "type II CRISPR RNA-guided endonuclease Cas9 [Paraliobacillus ryukyuensis] NCBI Reference Sequence: WP_079708828.1," nih.gov 2023, in 2 pages.
National Library of Medicine, "type II CRISPR RNA-guided endonuclease Cas9 [Salinicoccus sediminis] NCBI Reference Sequence: WP_082099322.1," nih.gov 2023, in 1 page.
National Library of Medicine, "type II CRISPR RNA-guided endonuclease Cas9 [Bacillus niameyensis] NCBI Reference Sequence: WP_084781893.1," nih.gov 2023, in 2 pages.
National Library of Medicine, "type II CRISPR RNA-guided endonuclease Cas9 [Listeria fleischmannii] NCBI Reference Sequence: WP_007547525.1," nih.gov 2023, in 2 pages.
National Library of Medicine, "type II CRISPR RNA-guided endonuclease Cas9 [Alicyclobacillus tengchongensis] NCBI Reference Sequence: WP_058095017.1," nih.gov 2023, in 2 pages.
National Library of Medicine, "type II CRISPR RNA-guided endonuclease Cas9 [Bacillus cereus] NCBI Reference Sequence: WP_001271092.1," nih.gov 2023, in 2 pages.
National Library of Medicine, "type II CRISPR RNA-guided endonuclease Cas9 [Bacillus thuringiensis] NCBI Reference Sequence: WP_088031364.1," nih.gov 2023, in 2 pages.
National Library of Medicine, "type II CRISPR RNA-guided endonuclease Cas9 [Bacillus smithii] NCBI Reference Sequence: WP_003354196.1," nih.gov 2023, in 2 pages.
National Library of Medicine, "type II CRISPR RNA-guided endonuclease Cas9 [Mammaliicoccus sciuri] NCBI Reference Sequence: WP_103361957.1," nih.gov 2023, in 2 pages.
National Library of Medicine, "type II CRISPR RNA-guided endonuclease Cas9 [*Staphylococcus devriesei*] NCBI Reference Sequence: WP_103167028.1," nih.gov 2023, in 2 pages.
National Library of Medicine, "type II CRISPR RNA-guided endonuclease Cas9 [*Staphylococcus warneri*] NCBI Reference Sequence: WP_107546539.1," nih.gov 2023, in 2 pages.
National Library of Medicine, "type II CRISPR RNA-guided endonuclease Cas9 [*Staphylococcus haemolyticus*] NCBI Reference Sequence: WP_053017934.1," nih.gov 2023, in 2 pages.
National Library of Medicine, "type II CRISPR RNA-guided endonuclease Cas9 [*Staphylococcus auricularis*] NCBI Reference Sequence: WP_107392933.1," nih.gov 2023, in 2 pages.
National Library of Medicine, "type II CRISPR RNA-guided endonuclease Cas9 [*Staphylococcus agnetis*] NCBI Reference Sequence: WP_060552032.1," nih.gov 2023, in 2 pages.
National Library of Medicine, "type II CRISPR RNA-guided endonuclease Cas9 [*Staphylococcus pseudintermedius*] NCBI Reference Sequence: WP_104052030.1," nih.gov 2023, in 2 pages.
National Library of Medicine, "type II CRISPR RNA-guided endonuclease Cas9, partial [*Staphylococcus agnetis*] NCBI Reference Sequence: WP_107393309.1," nih.gov 2023, in 2 pages.
National Library of Medicine, "type II CRISPR RNA-guided endonuclease Cas9, partial [*Staphylococcus simulans*] NCBI Reference Sequence: WP_107538271.1," nih.gov 2023, in 2 pages.
National Library of Medicine, "type II CRISPR RNA-guided endonuclease Cas9, partial [*Staphylococcus haemolyticus*] NCBI Reference Sequence: WP_107634675.1," nih.gov 2023, in 2 pages.
National Library of Medicine, "type II CRISPR RNA-guided endonuclease Cas9, partial [*Staphylococcus petrasii*] NCBI Reference Sequence: WP_103298901.1," nih.gov 2023, in 2 pages.
National Library of Medicine, "type II CRISPR RNA-guided endonuclease Cas9, partial [*Staphylococcus agnetis*] NCBI Reference Sequence: WP_107368542.1," nih.gov 2023, in 2 pages.
National Library of Medicine, "type II Crispr RNA-guided endonuclease Cas9 [*Staphylococcus massiliensis*] NCBI Reference Sequence: WP_009382362.1," nih.gov 2023, in 2 pages.
National Library of Medicine, "type II CRISPR RNA-guided endonuclease Cas9, partial [*Staphylococcus haemolyticus*] NCBI Reference Sequence: WP_107637979.1," nih.gov 2023, in 1 page.
National Library of Medicine, "type II CRISPR RNA-guided endonuclease Cas9 [*Staphylococcus pseudintermedius*] NCBI Reference Sequence: WP_105503156.1," nih.gov 2023, in 2 pages.
National Library of Medicine, "type II CRISPR RNA-guided endonuclease Cas9 [*Staphylococcus intermedius*] NCBI Reference Sequence: WP_096601671.1," nih.gov 2023, in 2 pages.
National Library of Medicine, "type II CRISPR RNA-guided endonuclease Cas9 [*Staphylococcus delphini*] NCBI Reference Sequence: WP_096665615.1," nih.gov 2023, in 2 pages.
National Library of Medicine, "type II CRISPR RNA-guided endonuclease Cas9, partial [*Staphylococcus simulans*] NCBI Reference Sequence: WP_107538330.1," nih.gov 2023, in 2 pages.
National Library of Medicine, "type II CRISPR RNA-guided endonuclease Cas9 [*Staphylococcus* sp. HMSC12H08] NCBI Reference Sequence: WP_070469119.1," nih.gov 2023, in 2 pages.
National Library of Medicine, "type II CRISPR RNA-guided endonuclease Cas9, partial [*Staphylococcus simulans*] NCBI Reference Sequence: WP_107549437.1," nih.gov 2023, in 2 pages.
National Library of Medicine, "type II CRISPR RNA-guided endonuclease Cas9 [*Staphylococcus delphini*] NCBI Reference Sequence: WP_096598476.1," nih.gov 2023, in 2 pages.
National Library of Medicine, "type II CRISPR RNA-guided endonuclease Cas9 [*Staphylococcus delphini*] NCBI Reference Sequence: WP_096544347.1," nih.gov 2023, in 2 pages.
National Library of Medicine, "type II CRISPR RNA-guided endonuclease Cas9, partial [*Staphylococcus simulans*] NCBI Reference Sequence: WP_107530433.1," nih.gov 2023, in 2 pages.
National Library of Medicine, "type II CRISPR RNA-guided endonuclease Cas9 [*Staphylococcus simulans*] NCBI Reference Sequence: WP_107571609.1," nih.gov 2023, in 2 pages.

(56) References Cited

OTHER PUBLICATIONS

National Library of Medicine, "type II CRISPR RNA-guided endonuclease Cas9 [Macrococcus caseolyticus] NCBI Reference Sequence: WP_101040307.1," nih.gov 2023, in 2 pages.
National Library of Medicine, "type II CRISPR RNA-guided endonuclease Cas9, partial [Alkalibacillus haloalkaliphilus] NCBI Reference Sequence: WP_017185731.1," nih.gov 2023, in 2 pages.
National Library of Medicine, "type II CRISPR RNA-guided endonuclease Cas9 [*Lentibacillus* sp. Marseille-P4043] NCBI Reference Sequence: WP_106494556.1," nih.gov 2023, in 2 pages.
National Library of Medicine, "type II CRISPR RNA-guided endonuclease Cas9 [Heyndrickxia sporothermodurans] NCBI Reference Sequence: WP_084347835.1," nih.gov 2023, in 2 pages.
National Library of Medicine, "type II CRISPR RNA-guided endonuclease Cas9 [Alicyclobacillus hesperidum] NCBI Reference Sequence: WP_006446566.1," nih.gov 2023, in 2 pages.
National Library of Medicine, "type II CRISPR RNA-guided endonuclease Cas9 [Bacillus thuringiensis] NCBI Reference Sequence: WP_087971021.1," nih.gov 2023, in 2 pages.
National Library of Medicine, "type II CRISPR RNA-guided endonuclease Cas9 [Bacillus mycoides] NCBI Reference Sequence: WP_088038716.1," nih.gov 2023, in 2 pages.
National Library of Medicine, "type II CRISPR RNA-guided endonuclease Cas9 [*Anoxybacillus* sp. P3H1B] NCBI Reference Sequence: WP_066148467.1," nih.gov 2023, in 2 pages.
National Library of Medicine, "type II CRISPR RNA-guided endonuclease Cas9 [*Staphylococcus aureus*] NCBI Reference Sequence: WP_001573634.1," nih.gov 2023, in 2 pages.
National Library of Medicine, "type II CRISPR RNA-guided endonuclease Cas9 [*Staphylococcus warneri*] NCBI Reference Sequence: WP_107532850.1," nih.gov 2023, in 2 pages.
National Library of Medicine, "type II CRISPR RNA-guided endonuclease Cas9 [*Staphylococcus warneri*] NCBI Reference Sequence: WP_058710220.1," nih.gov 2023, in 2 pages.
National Library of Medicine, "type II CRISPR RNA-guided endonuclease Cas9 [*Staphylococcus warneri*] NCBI Reference Sequence: WP_049415449.1," nih.gov 2023, in 2 pages.
National Library of Medicine, "type II CRISPR RNA-guided endonuclease Cas9 [*Staphylococcus chromogenes*] NCBI Reference Sequence: WP_107389582.1," nih.gov 2023, in 2 pages.
National Library of Medicine, "type II CRISPR RNA-guided endonuclease Cas9 [*Staphylococcus lutrae*] NCBI Reference Sequence: WP_085237539.1," nih.gov 2023, in 2 pages.
National Library of Medicine, "type II CRISPR RNA-guided endonuclease Cas9 [*Staphylococcus hyicus*] NCBI Reference Sequence: WP_107633689.1," nih.gov 2023, in 2 pages.
National Library of Medicine, "type II CRISPR RNA-guided endonuclease Cas9, partial [*Staphylococcus hyicus*] NCBI Reference Sequence: WP_107642914.1," nih.gov 2023, in 2 pages.
National Library of Medicine, "type II CRISPR RNA-guided endonuclease Cas9, partial [*Staphylococcus warneri*] NCBI Reference Sequence: WP_107532082.1," nih.gov 2023, in 2 pages.
National Library of Medicine, "type II CRISPR RNA-guided endonuclease Cas9, partial [*Staphylococcus haemolyticus*] NCBI Reference Sequence: WP_107611983.1," nih.gov 2023, in 2 pages.
National Library of Medicine, "type II CRISPR RNA-guided endonuclease Cas9 [*Staphylococcus massiliensis*] NCBI Reference Sequence: WP_081502240.1," nih.gov 2023, in 2 pages.
National Library of Medicine, "type II CRISPR RNA-guided endonuclease Cas9 [*Staphylococcus aureus*] NCBI Reference Sequence: WP_001573633.1," nih.gov 2023, in 2 pages.
National Library of Medicine, "type II CRISPR RNA-guided endonuclease Cas9, partial [*Staphylococcus haemolyticus*] NCBI Reference Sequence: WP_107612621.1," nih.gov 2023, in 1 page.
National Library of Medicine, "type II CRISPR RNA-guided endonuclease Cas9 [*Staphylococcus pseudintermedius*] NCBI Reference Sequence: WP_096548249.1," nih.gov 2023, in 2 pages.
National Library of Medicine, "type II CRISPR RNA-guided endonuclease Cas9 [*Staphylococcus pseudintermedius*] NCBI Reference Sequence: WP_103863320.1," nih.gov 2023, in 2 pages.
National Library of Medicine, "type II CRISPR RNA-guided endonuclease Cas9 [*Staphylococcus simulans*] NCBI Reference Sequence: WP_105976295.1," nih.gov 2023, in 2 pages.
National Library of Medicine, "type II CRISPR RNA-guided endonuclease Cas9 [*Staphylococcus delphini*] NCBI Reference Sequence: WP_096589032.1," nih.gov 2023, in 2 pages.
National Library of Medicine, "type II CRISPR RNA-guided endonuclease Cas9 [*Staphylococcus simulans*] NCBI Reference Sequence: WP_107579080.1," nih.gov 2023, in 2 pages.
National Library of Medicine, "type II CRISPR RNA-guided endonuclease Cas9 [*Staphylococcus simulans*] NCBI Reference Sequence: WP_107587102.1," nih.gov 2023, in 2 pages.
National Library of Medicine, "type II CRISPR RNA-guided endonuclease Cas9 [*Staphylococcus simulans*] NCBI Reference Sequence: WP_023015764.1," nih.gov 2023, in 2 pages.
National Library of Medicine, "type II CRISPR RNA-guided endonuclease Cas9, partial [*Staphylococcus simulans*] NCBI Reference Sequence: WP_107580731.1," nih.gov 2023, in 2 pages.
National Library of Medicine, "type II CRISPR RNA-guided endonuclease Cas9, partial [*Staphylococcus simulans*] NCBI Reference Sequence: WP_107559911.1," nih.gov 2023, in 2 pages.
National Library of Medicine, "type II CRISPR RNA-guided endonuclease Cas9 [*Virgibacillus senegalensis*] NCBI Reference Sequence: WP_053216997.1," nih.gov 2023, in 2 pages.
National Library of Medicine, "type II CRISPR RNA-guided endonuclease Cas9 [*Bacillus* sp. V3-13] NCBI Reference Sequence: WP_101662761.1," nih.gov 2023, in 2 pages.
National Library of Medicine, "type II CRISPR RNA-guided endonuclease Cas9 [*Nosocomiicoccus* sp. HMSC059G07] NCBI Reference Sequence: WP_070710475.1," nih.gov 2023, in 2 pages.
National Library of Medicine, "type II CRISPR RNA-guided endonuclease Cas9 [Alicyclobacillus hesperidum] NCBI Reference Sequence: WP_074693676.1," nih.gov 2023, in 2 pages.
National Library of Medicine, "type II CRISPR RNA-guided endonuclease Cas9 [Bacillus cereus] NCBI Reference Sequence: WP_061668060.1," nih.gov 2023, in 2 pages.
National Library of Medicine, "type II CRISPR RNA-guided endonuclease Cas9 [Listeria fleischmannii] NCBI Reference Sequence: WP_007476473.1," nih.gov 2023, in 1 page.
National Library of Medicine, "type II CRISPR RNA-guided endonuclease Cas9 [Acidibacillus ferrooxidans] NCBI Reference Sequence: WP_082806588.1," nih.gov 2023, in 2 pages.
National Library of Medicine, "type II CRISPR RNA-guided endonuclease Cas9, partial [*Staphylococcus simulans*] NCBI Reference Sequence: WP_107576310.1," nih.gov 2023, in 2 pages.
National Library of Medicine, "type II CRISPR RNA-guided endonuclease Cas9 [*Staphylococcus lugdunensis*] NCBI Reference Sequence: WP_002460848.1," nih.gov 2023, in 2 pages.
National Library of Medicine, "type II CRISPR RNA-guided endonuclease Cas9 [*Staphylococcus schleiferi*] NCBI Reference Sequence: WP_060829977.1," nih.gov 2023, in 2 pages.
National Library of Medicine, "type II CRISPR RNA-guided endonuclease Cas9 [*Staphylococcus agnetis*] NCBI Reference Sequence: WP_107390356.1," nih. gov 2023, in 2 pages.
National Library of Medicine, "type II CRISPR RNA-guided endonuclease Cas9 [*Staphylococcus hyicus*] NCBI Reference Sequence: WP_039643679.1," nih.gov 2023, in 2 pages.
National Library of Medicine, "type II CRISPR RNA-guided endonuclease Cas9 [*Staphylococcus rostri*] NCBI Reference Sequence: WP_103357343.1," nih.gov 2023, in 2 pages.
National Library of Medicine, "type II CRISPR RNA-guided endonuclease Cas9, partial [*Staphylococcus agnetis*] NCBI Reference Sequence: WP_107397003.1," nih.gov 2023, in 2 pages.
National Library of Medicine, "type II CRISPR RNA-guided endonuclease Cas9, partial [*Staphylococcus warneri*] NCBI Reference Sequence: WP_107536061.1," nih.gov 2023, in 2 pages.
National Library of Medicine, "type II CRISPR RNA-guided endonuclease Cas9, partial [*Staphylococcus simulans*] NCBI Reference Sequence: WP_107604007.1," nih.gov 2023, in 2 pages.
National Library of Medicine, "type II CRISPR RNA-guided endonuclease Cas9 [*Staphylococcus haemolyticus*] NCBI Reference Sequence: WP_107623815.1," nih.gov 2023, in 2 pages.

(56) References Cited

OTHER PUBLICATIONS

National Library of Medicine, "type II CRISPR RNA-guided endonuclease Cas9, partial [*Staphylococcus haemolyticus*] NCBI Reference Sequence: WP_107642817.1," nih.gov 2023, in 1 page.
National Library of Medicine, "type II CRISPR RNA-guided endonuclease Cas9 [*Staphylococcus felis*] NCBI Reference Sequence: WP_103209613.1," nih.gov 2023, in 2 pages.
National Library of Medicine, "type II CRISPR RNA-guided endonuclease Cas9 [*Staphylococcus pseudintermedius*] NCBI Reference Sequence: WP_096536567.1," nih.gov 2023, in 2 pages.
National Library of Medicine, "type II CRISPR RNA-guided endonuclease Cas9 [*Staphylococcus intermedius*] NCBI Reference Sequence: WP_096559644.1," nih.gov 2023, in 2 pages.
National Library of Medicine, "type II CRISPR RNA-guided endonuclease Cas9 [*Staphylococcus simulans*] NCBI Reference Sequence: WP_107576302.1," nih.gov 2023, in 2 pages.
National Library of Medicine, "type II CRISPR RNA-guided endonuclease Cas9 [*Staphylococcus delphini*] NCBI Reference Sequence: WP_096605716.1," nih.gov 2023, in 2 pages.
National Library of Medicine, "type II CRISPR RNA-guided endonuclease Cas9 [*Staphylococcus simulans*] NCBI Reference Sequence: WP_105996442.1," nih.gov 2023, in 2 pages.
National Library of Medicine, "type II CRISPR RNA-guided endonuclease Cas9 [*Staphylococcus simulans*] NCBI Reference Sequence: WP_107547813.1," nih.gov 2023, in 2 pages.
National Library of Medicine, "type II CRISPR RNA-guided endonuclease Cas9, partial [Staphylococcus simulans] NCBI Reference Sequence: WP_107533825.1," nih.gov 2023, in 2 pages.
National Library of Medicine, "type II CRISPR RNA-guided endonuclease Cas9, partial [*Staphylococcus lutrae*] NCBI Reference Sequence: WP_103322053.1," nih.gov 2023, in 2 pages.
National Library of Medicine, "type II CRISPR RNA-guided endonuclease Cas9, partial [*Staphylococcus simulans*] NCBI Reference Sequence: WP_107571610.1," nih.gov 2023, in 1 page.
National Library of Medicine, "type II CRISPR RNA-guided endonuclease Cas9 [Massilibacterium senegalense] NCBI Reference Sequence: WP_062197343.1," nih.gov 2023, in 2 pages.
National Library of Medicine, "type II CRISPR RNA-guided endonuclease Cas9 [Salsuginibacillus halophilus] NCBI Reference Sequence: WP_106588293.1," nih.gov 2023, in 2 pages.
National Library of Medicine, "type II CRISPR RNA-guided endonuclease Cas9 [Bacillus massilionigeriensis] NCBI Reference Sequence: WP_084780162.1," nih.gov 2023, in 2 pages.
National Library of Medicine, "type II CRISPR RNA-guided endonuclease Cas9 [Listeria fleischmannii] NCBI Reference Sequence: WP_077907981.1," nih.gov 2023, in 2 pages.
National Library of Medicine, "type II CRISPR RNA-guided endonuclease Cas9 [Bacillus cereus] NCBI Reference Sequence: WP_016119566.1," nih.gov 2023, in 2 pages.
National Library of Medicine, "type II CRISPR RNA-guided endonuclease Cas9 [Brevibacillus laterosporus] NCBI Reference Sequence: WP_003343632.1," nih.gov 2023, in 2 pages.
National Library of Medicine, "type II CRISPR RNA-guided endonuclease Cas9 [Bacillus cytotoxicus] NCBI Reference Sequence: WP_087094968.1," nih.gov 2023, in 2 pages.
National Library of Medicine, "type II CRISPR RNA-guided endonuclease Cas9, partial [*Staphylococcus simulans*] NCBI Reference Sequence: WP_107571611.1," nih.gov 2023, in 2 pages.
National Library of Medicine, "type II CRISPR RNA-guided endonuclease Cas9 [*Staphylococcus devriesei*] NCBI Reference Sequence: WP_107506206.1," nih.gov 2023, in 2 pages.
National Library of Medicine, "type II CRISPR RNA-guided endonuclease Cas9 [*Staphylococcus coagulans*] NCBI Reference Sequence: WP_050331073.1," nih.gov 2023, in 2 pages.
National Library of Medicine, "type II CRISPR RNA-guided endonuclease Cas9 [*Staphylococcus* sp. HMSC34C02] NCBI Reference Sequence: WP_070855141.1," nih.gov 2023, in 2 pages.
National Library of Medicine, "type II CRISPR RNA-guided endonuclease Cas9 [*Staphylococcus chromogenes*] NCBI Reference Sequence: WP_107378401.1," nih.gov 2023, in 2 pages.
National Library of Medicine, "type II CRISPR RNA-guided endonuclease Cas9 [*Staphylococcus pseudintermedius*] NCBI Reference Sequence: WP_101457364.1," nih.gov 2023, in 2 pages.
National Library of Medicine, "type II CRISPR RNA-guided endonuclease Cas9 [*Staphylococcus microti*] NCBI Reference Sequence: WP_044361501.1," nih.gov 2023, in 2 pages.
National Library of Medicine, "type II CRISPR RNA-guided endonuclease Cas9, partial [*Staphylococcus agnetis*] NCBI Reference Sequence: WP_107386954.1," nih.gov 2023, in 2 pages.
National Library of Medicine, "type II CRISPR RNA-guided endonuclease Cas9, partial [*Staphylococcus simulans*] NCBI Reference Sequence: WP_107605852.1," nih.gov 2023, in 2 pages.
National Library of Medicine, "type II CRISPR RNA-guided endonuclease Cas9, partial [*Staphylococcus coagulans*] NCBI Reference Sequence: WP_103356745.1," nih. gov 2023, in 2 pages.
National Library of Medicine, "type II CRISPR RNA-guided endonuclease Cas9, partial [*Staphylococcus devriesei*] NCBI Reference Sequence: WP_107522281.1," nih.gov 2023, in 2 pages.
National Library of Medicine, "type II CRISPR RNA-guided endonuclease Cas9 [*Staphylococcus chromogenes*] NCBI Reference Sequence: WP_107377516.1," nih.gov 2023, in 2 pages.
National Library of Medicine, "type II CRISPR RNA-guided endonuclease Cas9, partial [*Staphylococcus petrasii*] NCBI Reference Sequence: WP_103298687.1," nih.gov 2023, in 2 pages.
National Library of Medicine, "type II CRISPR RNA-guided endonuclease Cas9 [*Staphylococcus pseudintermedius*] NCBI Reference Sequence: WP_063284667.1," nih.gov 2023, in 2 pages.
National Library of Medicine, "type Ii Crispr RNA-guided endonuclease Cas9 [Staphylococcus pseudintermedius] NCBI Reference Sequence: WP_014613259.1," nih.gov 2023, in 2 pages.
National Library of Medicine, "type II CRISPR RNA-guided endonuclease Cas9 [*Staphylococcus intermedius*] NCBI Reference Sequence: WP_019167918.1," nih.gov 2023, in 2 pages.
National Library of Medicine, "type II CRISPR RNA-guided endonuclease Cas9 [*Staphylococcus simulans*] NCBI Reference Sequence: WP_105977863.1," nih.gov 2023, in 2 pages.
National Library of Medicine, "type II CRISPR RNA-guided endonuclease Cas9 [*Staphylococcus piscifermentans*] NCBI Reference Sequence: WP_095105824.1," nih.gov 2023, in 2 pages.
National Library of Medicine, "type II CRISPR RNA-guided endonuclease Cas9 [*Staphylococcus simulans*] NCBI Reference Sequence: WP_107552556.1," nih.gov 2023, in 2 pages.
National Library of Medicine, "type II CRISPR RNA-guided endonuclease Cas9 [*Staphylococcus simulans*] NCBI Reference Sequence: WP_107591747.1," nih.gov 2023, in 2 pages.
National Library of Medicine, "type II CRISPR RNA-guided endonuclease Cas9, partial [*Staphylococcus simulans*] NCBI Reference Sequence: WP_107588308.1," nih.gov 2023, in 2 pages.
National Library of Medicine, "type II CRISPR RNA-guided endonuclease Cas9, partial [*Staphylococcus simulans*] NCBI Reference Sequence: WP_107559912.1," nih.gov 2023, in 2 pages.
National Library of Medicine, "type II CRISPR RNA-guided endonuclease Cas9, partial [*Staphylococcus simulans*] NCBI Reference Sequence: WP_107530436.1," nih.gov 2023, in 1 page.
National Library of Medicine, "type II CRISPR RNA-guided endonuclease Cas9 [Halalkalibacillus halophilus] NCBI Reference Sequence: WP_035512507.1," nih.gov 2023, in 2 pages.
National Library of Medicine, "type II CRISPR RNA-guided endonuclease Cas9 [Alkalicoccus saliphilus] NCBI Reference Sequence: WP_107585021.1," nih.gov 2023, in 2 pages.
National Library of Medicine, "type II CRISPR RNA-guided endonuclease Cas9 [Ureibacillus thermosphaericus] NCBI Reference Sequence: WP_016837331.1," nih.gov 2023, in 2 pages.
National Library of Medicine, "type II CRISPR RNA-guided endonuclease Cas9 [Listeria fleischmannii] NCBI Reference Sequence: WP_059140148.1," nih.gov 2023, in 2 pages.
National Library of Medicine, "type II CRISPR RNA-guided endonuclease Cas9 [Gracilibacillus boraciitolerans] NCBI Reference Sequence: WP_035723552.1," nih.gov 2023, in 1 page.
National Library of Medicine, "type II CRISPR RNA-guided endonuclease Cas9 [Bacillus toyonensis] NCBI Reference Sequence: WP_001271093.1," nih.gov 2023, in 2 pages.

(56) References Cited

OTHER PUBLICATIONS

National Library of Medicine, "type II CRISPR RNA-guided endonuclease Cas9 [Bacillus toyonensis] NCBI Reference Sequence: WP_016106885.1," nih.gov 2023, in 2 pages.
National Library of Medicine, "type II CRISPR RNA-guided endonuclease Cas9 [Virgibacillus dakarensis] NCBI Reference Sequence: WP_088049424.1," nih.gov 2023, in 2 pages.
National Library of Medicine, "type II CRISPR RNA-guided endonuclease Cas9 [Geobacillus subterraneus] NCBI Reference Sequence: WP_033844707.1," nih.gov 2023, in 2 pages.
National Library of Medicine, "type II CRISPR RNA-guided endonuclease Cas9 [*Bacillus* sp. FJAT-20673] NCBI Reference Sequence: WP_063577905.1," nih.gov 2023, in 2 pages.
National Library of Medicine, "type II CRISPR RNA-guided endonuclease Cas9 [Effusibacillus pohliae] NCBI Reference Sequence: WP_018130201.1," nih.gov 2023, in 2 pages.
National Library of Medicine, "type II CRISPR RNA-guided endonuclease Cas9 [Bacillus cereus] NCBI Reference Sequence: WP_001105082.1," nih.gov 2023, in 2 pages.
National Library of Medicine, "type II CRISPR RNA-guided endonuclease Cas9 [Listeria monocytogenes] NCBI Reference Sequence: WP_070034634.1," nih.gov 2023, in 2 pages.
National Library of Medicine, "type II CRISPR RNA-guided endonuclease Cas9 [Listeria seeligeri] NCBI Reference Sequence: WP_046323366.1," nih.gov 2023, in 2 pages.
National Library of Medicine, "type II CRISPR RNA-guided endonuclease Cas9, partial [Listeria seeligeri] NCBI Reference Sequence: WP_003749665.1," nih.gov 2023, in 2 pages.
National Library of Medicine, "type II CRISPR RNA-guided endonuclease Cas9 [Listeria monocytogenes] NCBI Reference Sequence: WP_085392451.1," nih.gov 2023, in 2 pages.
National Library of Medicine, "type II CRISPR RNA-guided endonuclease Cas9 [Macrococcus caseolyticus] NCBI Reference Sequence: WP_101143453.1," nih.gov 2023, in 2 pages.
National Library of Medicine, "type II CRISPR RNA-guided endonuclease Cas9 [Listeria monocytogenes] NCBI Reference Sequence: WP_085400884.1," nih.gov 2023, in 2 pages.
National Library of Medicine, "type II CRISPR RNA-guided endonuclease Cas9 [Listeria innocua] NCBI Reference Sequence: WP_010991369.1," nih.gov 2023, in 2 pages.
National Library of Medicine, "type II CRISPR RNA-guided endonuclease Cas9 [Listeria monocytogenes] NCBI Reference Sequence: WP_003733029.1," nih.gov 2023, in 2 pages.
National Library of Medicine, "type II CRISPR RNA-guided endonuclease Cas9 [Listeria monocytogenes] NCBI Reference Sequence: WP_070274575.1," nih.gov 2023, in 2 pages.
National Library of Medicine, "type II CRISPR RNA-guided endonuclease Cas9 [Listeria monocytogenes] NCBI Reference Sequence: WP_031665337.1," nih.gov 2023, in 2 pages.
National Library of Medicine, "type II CRISPR RNA-guided endonuclease Cas9 [Listeria monocytogenes] NCBI Reference Sequence: WP_070307355.1," nih.gov 2023, in 2 pages.
National Library of Medicine, "type II CRISPR RNA-guided endonuclease Cas9 [Listeria monocytogenes] NCBI Reference Sequence: WP_069009724.1," nih.gov 2023, in 2 pages.
National Library of Medicine, "type II CRISPR RNA-guided endonuclease Cas9 [Listeria monocytogenes] NCBI Reference Sequence: WP_060587936.1," nih.gov 2023, in 2 pages.
National Library of Medicine, "type II CRISPR RNA-guided endonuclease Cas9 [Listeria monocytogenes] NCBI Reference Sequence: WP_058876445.1," nih.gov 2023, in 2 pages.
National Library of Medicine, "type II CRISPR RNA-guided endonuclease Cas9, partial [Listeria monocytogenes] NCBI Reference Sequence: WP_080151624.1," nih.gov 2023, in 2 pages.
National Library of Medicine, "type II CRISPR RNA-guided endonuclease Cas9, partial [Listeria monocytogenes] NCBI Reference Sequence: WP_072240445.1," nih.gov 2023, in 1 page.
National Library of Medicine, "type II CRISPR RNA-guided endonuclease Cas9, partial [Listeria monocytogenes] NCBI Reference Sequence: WP_080151712.1," nih.gov 2023, in 1 page.
National Library of Medicine, "type II CRISPR RNA-guided endonuclease Cas9 [*Geobacillus* sp. Sah69] NCBI Reference Sequence: WP_055358891.1," nih.gov 2023, in 2 pages.
National Library of Medicine, "type II CRISPR RNA-guided endonuclease Cas9 [*Geobacillus* sp. 46C-IIa] NCBI Reference Sequence: WP_081209836.1," nih.gov 2023, in 2 pages.
National Library of Medicine, "type II CRISPR RNA-guided endonuclease Cas9 [*Geobacillus* sp. MAS1] NCBI Reference Sequence: WP_023633350.1," nih.gov 2023, in 2 pages.
National Library of Medicine, "type II CRISPR RNA-guided endonuclease Cas9 [*Geobacillus* sp. 47C-IIb] NCBI Reference Sequence: WP_081157433.1," nih.gov 2023, in 2 pages.
National Library of Medicine, "type II CRISPR RNA-guided endonuclease Cas9 [Geobacillus thermodenitrificans] NCBI Reference Sequence: WP_087959824.1," nih.gov 2023, in 2 pages.
National Library of Medicine, "type II CRISPR RNA-guided endonuclease Cas9 [*Geobacillus genomo*sp. 3] NCBI Reference Sequence: WP_041267823.1," nih.gov 2023, in 2 pages.
National Library of Medicine, "type II CRISPR RNA-guided endonuclease Cas9 [Salsuginibacillus kocurii] NCBI Reference Sequence: WP_018922791.1," nih.gov 2023, in 2 pages.
National Library of Medicine, "type II CRISPR RNA-guided endonuclease Cas9 [Geobacillus jurassicus] NCBI Reference Sequence: WP_066227285.1," nih.gov 2023, in 2 pages.
National Library of Medicine, "type II CRISPR RNA-guided endonuclease Cas9 [Geobacillus kaustophilus] NCBI Reference Sequence: WP_044736072.1," nih.gov 2023, in 2 pages.
National Library of Medicine, "type II CRISPR RNA-guided endonuclease Cas9 [Geobacillus stearothermophilus] NCBI Reference Sequence: WP_033016936.1," nih.gov 2023, in 2 pages.
National Library of Medicine, "type II CRISPR RNA-guided endonuclease Cas9 [*Geobacillus* sp. WSUCF-018B] NCBI Reference Sequence: WP_100664518.1," nih.gov 2023, in 2 pages.
National Library of Medicine, "type II CRISPR RNA-guided endonuclease Cas9 [Geobacillus stearothermophilus] NCBI Reference Sequence: WP_053532223.1," nih.gov 2023, in 2 pages.
National Library of Medicine, "type II CRISPR RNA-guided endonuclease Cas9 [Oceanobacillus manasiensis] NCBI Reference Sequence: WP_042224718.1," nih.gov 2023, in 2 pages.
National Library of Medicine, "type II CRISPR RNA-guided endonuclease Cas9 [Alkalihalobacillus okhensis] NCBI Reference Sequence: WP_084138993.1," nih.gov 2023, in 2 pages.
National Library of Medicine, "type II CRISPR RNA-guided endonuclease Cas9 [Sporolactobacillus vineae] NCBI Reference Sequence: WP_010632729.1," nih.gov 2023, in 2 pages.
National Library of Medicine, "type II CRISPR RNA-guided endonuclease Cas9 [Bacillus thuringiensis] NCBI Reference Sequence: WP_065212529.1," nih.gov 2023, in 2 pages.
National Library of Medicine, "type II CRISPR RNA-guided endonuclease Cas9 [Bacillus paranthracis] NCBI Reference Sequence: WP_001105083.1," nih.gov 2023, in 2 pages.
National Library of Medicine, "type II CRISPR RNA-guided endonuclease Cas9 [Bacillus thuringiensis] NCBI Reference Sequence: WP_086397116.1," nih.gov 2023, in 2 pages.
National Library of Medicine, "type II CRISPR RNA-guided endonuclease Cas9 [Bacillus thuringiensis] NCBI Reference Sequence: WP_086390158.1," nih.gov 2023, in 2 pages.
National Library of Medicine, "type II CRISPR RNA-guided endonuclease Cas9 [Listeria monocytogenes] NCBI Reference Sequence: WP_070006567.1," nih.gov 2023, in 2 pages.
National Library of Medicine, "type II CRISPR RNA-guided endonuclease Cas9 [Listeria monocytogenes] NCBI Reference Sequence: WP_003739838.1," nih.gov 2023, in 2 pages.
National Library of Medicine, "type II CRISPR RNA-guided endonuclease Cas9 [Listeria seeligeri] NCBI Reference Sequence: WP_075702521.1," nih.gov 2023, in 2 pages.
National Library of Medicine, "type II CRISPR RNA-guided endonuclease Cas9 [Brochothrix thermosphacta] NCBI Reference Sequence: WP_029090905.1," nih.gov 2023, in 2 pages.
National Library of Medicine, "type II CRISPR RNA-guided endonuclease Cas9 [Listeria ivanovii] NCBI Reference Sequence: WP_038409211.1," nih.gov 2023, in 2 pages.

(56) References Cited

OTHER PUBLICATIONS

National Library of Medicine, "type II CRISPR RNA-guided endonuclease Cas9 [Brochothrix thermosphacta] NCBI Reference Sequence: WP_069125601.1," nih.gov 2023, in 2 pages.
National Library of Medicine, "type II CRISPR RNA-guided endonuclease Cas9 [Listeria monocytogenes] NCBI Reference Sequence: WP_069887401.1," nih.gov 2023, in 2 pages.
National Library of Medicine, "type II CRISPR RNA-guided endonuclease Cas9 [Brochothrix thermosphacta] NCBI Reference Sequence: WP_069134523.1," nih.gov 2023, in 2 pages.
National Library of Medicine, "type II CRISPR RNA-guided endonuclease Cas9 [Listeria monocytogenes] NCBI Reference Sequence: WP_061665472.1," nih.gov 2023, in 2 pages.
National Library of Medicine, "type II CRISPR RNA-guided endonuclease Cas9 [Listeria monocytogenes] NCBI Reference Sequence: WP_070294293.1," nih.gov 2023, in 2 pages.
National Library of Medicine, "type II CRISPR RNA-guided endonuclease Cas9 [Listeria monocytogenes] NCBI Reference Sequence: WP_070784981.1," nih.gov 2023, in 2 pages.
National Library of Medicine, "type II CRISPR RNA-guided endonuclease Cas9 [Listeria monocytogenes] NCBI Reference Sequence: WP_031669209.1," nih.gov 2023, in 2 pages.
National Library of Medicine, "type II CRISPR RNA-guided endonuclease Cas9 [Brochothrix thermosphacta] NCBI Reference Sequence: WP_106787163.1," nih.gov 2023, in 2 pages.
National Library of Medicine, "type II CRISPR RNA-guided endonuclease Cas9 [Listeria monocytogenes] NCBI Reference Sequence: WP_077287021.1," nih.gov 2023, in 2 pages.
National Library of Medicine, "type II CRISPR RNA-guided endonuclease Cas9 [Listeria monocytogenes] NCBI Reference Sequence: WP_023548323.1," nih.gov 2023, in 2 pages.
National Library of Medicine, "type II CRISPR RNA-guided endonuclease Cas9 [Listeria monocytogenes] NCBI Reference Sequence: WP_061108493.1," nih.gov 2023, in 2 pages.
National Library of Medicine, "type II CRISPR RNA-guided endonuclease Cas9 [Macrococcus caseolyticus] NCBI Reference Sequence: WP_101152964.1," nih.gov 2023, in 2 pages.
National Library of Medicine, "type II CRISPR RNA-guided endonuclease Cas9 [Macrococcus caseolyticus] NCBI Reference Sequence: WP_101143843.1," nih.gov 2023, in 2 pages.
National Library of Medicine, "type II CRISPR RNA-guided endonuclease Cas9 [Macrococcus caseolyticus] NCBI Reference Sequence: WP_101140817.1," nih.gov 2023, in 2 pages.
National Library of Medicine, "type II CRISPR RNA-guided endonuclease Cas9 [Caryophanon latum] NCBI Reference Sequence: WP_066465432.1," nih.gov 2023, in 2 pages.
National Library of Medicine, "type II CRISPR RNA-guided endonuclease Cas9 [Listeria monocytogenes] NCBI Reference Sequence: WP_033920898.1," nih.gov 2023, in 2 pages.
National Library of Medicine, "type II CRISPR RNA-guided endonuclease Cas9 [Listeria monocytogenes] NCBI Reference Sequence: WP_069001072.1," nih.gov 2023, in 2 pages.
National Library of Medicine, "type II CRISPR RNA-guided endonuclease Cas9 [Macrococcus caseolyticus] NCBI Reference Sequence: WP_101057368.1," nih.gov 2023, in 2 pages.
National Library of Medicine, "type II CRISPR RNA-guided endonuclease Cas9 [*Listeria* sp. ILCC792] NCBI Reference Sequence: WP_088838826.1," nih.gov 2023, in 2 pages.
National Library of Medicine, "type II CRISPR RNA-guided endonuclease Cas9, partial [Listeria monocytogenes] NCBI Reference Sequence: WP_072240946.1," nih.gov 2023, in 2 pages.
National Library of Medicine, "type II CRISPR RNA-guided endonuclease Cas9 [Listeria innocua] NCBI Reference Sequence: WP_033838504.1," nih.gov 2023, in 2 pages.
National Library of Medicine, "type II CRISPR RNA-guided endonuclease Cas9, partial [Listeria monocytogenes] NCBI Reference Sequence: WP_072218760.1," nih.gov 2023, in 2 pages.
National Library of Medicine, "type II CRISPR RNA-guided endonuclease Cas9 [Listeria innocua] NCBI Reference Sequence: WP_072238933.1," nih.gov 2023, in 2 pages.
National Library of Medicine, "type II CRISPR RNA-guided endonuclease Cas9 [Listeria monocytogenes] NCBI Reference Sequence: WP_070227966.1," nih.gov 2023, in 2 pages.
National Library of Medicine, "type II CRISPR RNA-guided endonuclease Cas9 [Listeria monocytogenes] NCBI Reference Sequence: WP_061663015.1," nih.gov 2023, in 2 pages.
National Library of Medicine, "type II CRISPR RNA-guided endonuclease Cas9 [Macrococcus caseolyticus] NCBI Reference Sequence: WP_101142252.1," nih.gov 2023, in 2 pages.
National Library of Medicine, "type II CRISPR RNA-guided endonuclease Cas9 [Listeria monocytogenes] NCBI Reference Sequence: WP_070031693.1," nih.gov 2023, in 2 pages.
National Library of Medicine, "type II CRISPR RNA-guided endonuclease Cas9 [Listeria monocytogenes] NCBI Reference Sequence: WP_070785826.1," nih.gov 2023, in 2 pages.
National Library of Medicine, "type II CRISPR RNA-guided endonuclease Cas9 [Listeria monocytogenes] NCBI Reference Sequence: WP_003730785.1," nih.gov 2023, in 2 pages.
National Library of Medicine, "type II CRISPR RNA-guided endonuclease Cas9 [Listeria monocytogenes] NCBI Reference Sequence: WP_003727705.1," nih.gov 2023, in 2 pages.
National Library of Medicine, "type II CRISPR RNA-guided endonuclease Cas9 [Listeria monocytogenes] NCBI Reference Sequence: WP_069890501.1," nih.gov 2023, in 2 pages.
National Library of Medicine, "type II CRISPR RNA-guided endonuclease Cas9 [Listeria monocytogenes] NCBI Reference Sequence: WP_070233243.1," nih.gov 2023, in 2 pages.
National Library of Medicine, "type II CRISPR RNA-guided endonuclease Cas9 [Listeria monocytogenes] NCBI Reference Sequence: WP_070039312.1," nih.gov 2023, in 2 pages.
National Library of Medicine, "type II CRISPR RNA-guided endonuclease Cas9 [Listeria monocytogenes] NCBI Reference Sequence: WP_070222802.1," nih.gov 2023, in 2 pages.
National Library of Medicine, "type II CRISPR RNA-guided endonuclease Cas9 [Listeria monocytogenes] NCBI Reference Sequence: WP_070264592.1," nih.gov 2023, in 2 pages.
National Library of Medicine, "type II CRISPR RNA-guided endonuclease Cas9 [Listeria monocytogenes] NCBI Reference Sequence: WP_103682188.1," nih.gov 2023, in 2 pages.
National Library of Medicine, "type II CRISPR RNA-guided endonuclease Cas9 [Listeria monocytogenes] NCBI Reference Sequence: WP_070299153.1," nih.gov 2023, in 2 pages.
National Library of Medicine, "type II CRISPR RNA-guided endonuclease Cas9 [Listeria monocytogenes] NCBI Reference Sequence: WP_061395959.1," nih.gov 2023, in 2 pages.
National Library of Medicine, "type II CRISPR RNA-guided endonuclease Cas9 [Listeria monocytogenes] NCBI Reference Sequence: WP_070764199.1," nih.gov 2023, in 2 pages.
National Library of Medicine, "type II CRISPR RNA-guided endonuclease Cas9 [Listeria monocytogenes] NCBI Reference Sequence: WP_061128889.1," nih.gov 2023, in 2 pages.
National Library of Medicine, "type II CRISPR RNA-guided endonuclease Cas9 [Listeria monocytogenes] NCBI Reference Sequence: WP_070283519.1," nih.gov 2023, in 2 pages.
National Library of Medicine, "type II CRISPR RNA-guided endonuclease Cas9 [Listeria monocytogenes] NCBI Reference Sequence: WP_070228842.1," nih.gov 2023, in 2 pages.
National Library of Medicine, "type II CRISPR RNA-guided endonuclease Cas9 [Listeria monocytogenes] NCBI Reference Sequence: WP_014601172.1," nih.gov 2023, in 2 pages.
National Library of Medicine, "type II CRISPR RNA-guided endonuclease Cas9 [Listeria monocytogenes] NCBI Reference Sequence: WP_103757671.1," nih.gov 2023, in 2 pages.
National Library of Medicine, "type II CRISPR RNA-guided endonuclease Cas9 [Listeria monocytogenes] NCBI Reference Sequence: WP_070293394.1," nih.gov 2023, in 2 pages.
National Library of Medicine, "type II CRISPR RNA-guided endonuclease Cas9 [Listeria monocytogenes] NCBI Reference Sequence: WP_070238603.1," nih.gov 2023, in 2 pages.
National Library of Medicine, "type II CRISPR RNA-guided endonuclease Cas9 [Listeria monocytogenes] NCBI Reference Sequence: WP_070215465.1," nih.gov 2023, in 2 pages.

(56) References Cited

OTHER PUBLICATIONS

National Library of Medicine, "type II CRISPR RNA-guided endonuclease Cas9 [Listeria monocytogenes] NCBI Reference Sequence: WP_003723650.1," nih.gov 2023, in 2 pages.
National Library of Medicine, "type II CRISPR RNA-guided endonuclease Cas9 [Listeria monocytogenes] NCBI Reference Sequence: WP_070214481.1," nih.gov 2023, in 2 pages.
National Library of Medicine, "type II CRISPR RNA-guided endonuclease Cas9 [Listeria monocytogenes] NCBI Reference Sequence: WP_060567941.1," nih.gov 2023, in 2 pages.
National Library of Medicine, "type II CRISPR RNA-guided endonuclease Cas9 [Kurthia huakuii] NCBI Reference Sequence: WP_029499861.1," nih.gov 2023, in 2 pages.
National Library of Medicine, "type II CRISPR RNA-guided endonuclease Cas9 [Gemella cuniculi] NCBI Reference Sequence: WP_027129613.1," nih.gov 2023, in 2 pages.
National Library of Medicine, "type II CRISPR RNA-guided endonuclease Cas9 [Gemella haemolysans] NCBI Reference Sequence: WP_003145379.1," nih.gov 2023, in 2 pages.
National Library of Medicine, "type II CRISPR RNA-guided endonuclease Cas9 [Gemella bergeri] NCBI Reference Sequence: WP_021752441.1," nih.gov 2023, in 2 pages.
National Library of Medicine, "type II CRISPR RNA-guided endonuclease Cas9 [Brochothrix thermosphacta] NCBI Reference Sequence: WP_069132012.1," nih.gov 2023, in 2 pages.
National Library of Medicine, "type II CRISPR RNA-guided endonuclease Cas9 [Brochothrix campestris] NCBI Reference Sequence: WP_084038511.1," nih.gov 2023, in 2 pages.
National Library of Medicine, "type II CRISPR RNA-guided endonuclease Cas9 [Gemella morbillorum] NCBI Reference Sequence: WP_004632196.1," nih.gov 2023, in 2 pages.
National Library of Medicine, "type II CRISPR RNA-guided endonuclease Cas9 [Gemella massiliensis] NCBI Reference Sequence: WP_072520207.1," nih.gov 2023, in 2 pages.
National Library of Medicine, "type II CRISPR RNA-guided endonuclease Cas9 [*Gemella* sp. oral taxon 928] NCBI Reference Sequence: WP_082729137.1," nih. gov 2023, in 2 pages.
National Library of Medicine, "type II CRISPR RNA-guided endonuclease Cas9, partial [Listeria monocytogenes] NCBI Reference Sequence: WP_080149038.1," nih.gov 2023, in 1 page.
National Library of Medicine, "type II CRISPR RNA-guided endonuclease Cas9, partial [Listeria monocytogenes] NCBI Reference Sequence: WP_072233091.1," nih.gov 2023, in 1 page.
National Library of Medicine, "type II CRISPR RNA-guided endonuclease Cas9, partial [Listeria monocytogenes] NCBI Reference Sequence: WP_072218465.1," nih.gov 2023, in 1 page.
National Library of Medicine, "type II CRISPR RNA-guided endonuclease Cas9, partial [Listeria monocytogenes] NCBI Reference Sequence: WP_072239624.1," nih.gov 2023, in 1 page.
National Library of Medicine, "type II CRISPR RNA-guided endonuclease Cas9, partial [Listeria monocytogenes] NCBI Reference Sequence: WP_080151670.1," nih.gov 2023, in 1 page.
Nehls et al., "Two genetically separable steps in the differentiation of thymic epithelium," Science 1996, 272(5263), 886-889.
Nichols et al., "A universal nucleoside for use at ambiguous sites in DNA primers," Nature 1994, 369(6480), 492-493.
Nicoud et al., "Development of photoreceptor-specific promoters and their utility to investigate EIAV lentiviral vector mediated gene transfer to photoreceptors," The Journal of Gene Medicine 2007, 9(12), 1015-1023.
Nielsen et al., "Sequence-selective recognition of DNA by strand displacement with a thymine-substituted polyamide," Science 1991, 254(5037), 1497-1500.
Nishimasu et al., "Crystal structure of *Staphylococcus aureus* Cas9," Cell 2015, 162(5), 1113-1126.
Noguchi et al., "PDX-1 protein containing its own antennapedia-like protein transduction domain can transduce pancreatic duct and islet cells," Diabetes 2003, 52(7), 1732-1737.
Notice of Reasons for Rejection dated Aug. 25, 2023 in Japanese Patent Application No. 2020-550714.

Notice of Reasons for Rejection dated Feb. 28, 2023 in Japanese Patent Application No. 2020-550714.
Notice of Reasons for Rejection dated Oct. 5, 2023 in Japanese Patent Application No. 2021-530251.
O'Neill et al., "Chloroplast transformation in plants: polyethylene glycol (PEG) treatment of protoplasts is an alternative to biolistic delivery systems," The Plant Journal 1993, 3(5), 729-738.
Oakes et al., "Protein engineering of Cas9 for enhanced function," Methods in Enzymology 2014, 546, 491-511.
Oberdick et al., "A promoter that drives transgene expression in cerebellar Purkinje and retinal bipolar neurons," Science 1990, 248(4952), 223-226.
Oberhauser & Wagner, "Effective incorporation of 2'-O-methyl-oligoribonuclectides into liposomes and enhanced cell association through modification with thiocholesterol," Nucleic Acids Research 1992, 20(3), 533-538.
Oh et al., "Expression of transgenes in midbrain dopamine neurons using the tyrosine hydroxylase promoter," Gene Therapy 2009, 16(3), 437-440.
Olson et al., "Preparation of liposomes of defined size distribution by extrusion through polycarbonate membranes," Biochimica et Biophysica Acta (BBA)-Biomembranes 1979, 557(1), 9-23.
Outchkourov et al., "Optimization of the expression of equistatin in Pichia pastoris," Protein Expression and Purification 2002, 24(1), 18-24.
Pajvani et al., "Fat apoptosis through targeted activation of caspase 8: a new mouse model of inducible and reversible lipoatrophy," Nature Medicine 2005, 11(7), 797-803.
Panyam & Labhasetwar, "Biodegradable nanoparticles for drug and gene delivery to cells and tissue," Advanced Drug Delivery Reviews 2012, 64(Suplement), 61-71.
Parmacek et al., "A novel myogenic regulatory circuit controls slow/cardiac troponin C gene transcription in skeletal muscle," Molecular and Cellular Biology 1994, 14(3), 1870-1885.
Paul et al., "Increased viral titer through concentration of viral harvests from retroviral packaging lines," Human Gene Therapy 1993, 4(5), 609-615.
Peer & Lieberman, "Special delivery: targeted therapy with small RNAs," Gene Therapy 2011, 18(12), 1127-1133.
Perrin et al., "An experimental rabies vaccine produced with a new BHK-21 suspension cell culture process: use of serum-free medium and perfusion-reactor system," Vaccine 1995, 13(13), 1244-1250.
Platt et al., "Obesity-linked regulation of the adipsin gene promoter in transgenic mice," Proceedings of the National Academy of Sciences 1989, 86(19), 7490-7494.
Podesta & Kostarelos, "Engineering cationic liposome: sirna complexes for in vitro and in vivo delivery," Methods in Enzymology 2009, 464, 343-354.
Radovick et al. "Migratory arrest of gonadotropin-releasing hormone neurons in transgenic mice," Proceedings of the National Academy of Sciences 1991, 88(8), 3402-3406.
Ran et al., "In vivo genome editing using *Staphylococcus aureus* Cas9," Nature 2015, 520, 186-191.
Restriction Requirement dated Oct. 27, 2023 in U.S. Appl. No. 16/982,433.
Riaz, "Liposomes preparation methods," Pakistan Journal of Pharmaceutical Sciences 1996, 9(1), 65-77.
Robbins et al., "In vivo definition of a cardiac specific promoter and its potential utility in remodeling the heart," Annals of the New York Academy of Sciences 1995, 752(1), 492-505.
Rolling et al., "Evaluation of adeno-associated virus-mediated gene transfer into the rat retina by clinical fluorescence photography," Human Gene Therapy 1999, 10(4), 641-648.
Ross et al., "A fat-specific enhancer is the primary determinant of gene expression for adipocyte P2 in vivo," Proceedings of the National Academy of Sciences 1990, 87(24), 9590-9594.
Saison-Behmoaras et al., "Short modified antisense oligonucleotides directed against Ha-ras point mutation induce selective cleavage of the mRNA and inhibit T24 cells proliferation," The EMBO Journal 1991, 10(5), 1111-1118.
Sakamoto et al., "A vitrectomy improves the transfection efficiency of adenoviral vector-mediated gene transfer to Müller cells," Gene Therapy 1998, 5(8), 1088-1097.

(56) References Cited

OTHER PUBLICATIONS

Samulski et al., "Cloning of adeno-associated virus into pBR322: rescue of intact virus from the recombinant plasmid in human cells," Proceedings of the National Academy of Sciences 1982, 79(6), 2077-2081.

Samulski et al., "Helper-free stocks of recombinant adeno-associated viruses: normal integration does not require viral gene expression," Journal of Virology 1989, 63(9), 3822-3828.

Santos et al., "Mipomersen, an antisense oligonucleotide to apolipoprotein B-100, reduces lipoprotein (a) in various populations with hypercholesterolemia: results of 4 phase III trials," Arteriosclerosis, Thrombosis, and Vascular Biology 2015, 35(3), 689-699.

Sartorelli et al., "Myocardial activation of the human cardiac alpha-actin promoter by helix-loop-helix proteins," Proceedings of the National Academy of Sciences 1992, 89(9), 4047-4051.

Sasaoka et al., "Analysis of the human tyrosine hydroxylase promoter-chloramphenicol acetyltransferase chimeric gene expression in transgenic mice," Molecular Brain Research 1992, 16(3-4), 274-286.

Sato et al., "Dual promoter structure of mouse and human fatty acid translocase/CD36 genes and unique transcriptional activation by peroxisome proliferator-activated receptor α and γ ligands," Journal of Biological Chemistry 2002, 277(18), 15703-15711.

Schoeber et al., "Conditional fast expression and function of multimeric TRPV5 channels using Shield-1," American Journal of Physiology-Renal Physiology 2009, 296(1), F204-F211.

Search Report and Search Opinion dated Jun. 28, 2023 in European Patent Application No. 19712889.5.

Senapathy & Carter, "Molecular cloning of adeno-associated virus variant genomes and generation of infectious virus by recombination in mammalian cells," Journal of Biological Chemistry 1984, 259(7), 4661-4666.

Seo et al., "Functional characterization of the human resistin promoter with adipocyte determination- and differentiation-dependent factor 1/sterol regulatory element binding protein 1c and CCAAT enhancer binding protein-α," Molecular Endocrinology 2003, 17(8), 1522-1533.

Shamblott et al., "Derivation of pluripotent stem cells from cultured human primordial germ cells," Proceedings of the National Academy of Sciences 1998, 95(23), 13726-13731.

Shamblott et al., "Human embryonic germ cell derivatives express a broad range of developmentally distinct markers and proliferate extensively in vitro," Proceedings of the National Academy of Sciences 2001, 98(1), 113-118.

Shea et al., "Synthesis, hybridization properties and antiviral activity of lipid-oligodeoxynucleotide conjugates," Nucleic Acids Research 1990, 18(13), 3777-3783.

Singh et al., "LNA (locked nucleic acids): synthesis and high-affinity nucleic acid recognition," Chemical Communications 1998, 4, 455-456.

Smith & Waterman, "Comparison of biosequences," Advances in Applied Mathematics 1981, 2(4), 482-489.

Soutschek et al., "Therapeutic silencing of an endogenous gene by systemic administration of modified siRNAs," Nature 2004, 432(7014), 173-178.

Staub et al., "High-yield production of a human therapeutic protein in tobacco chloroplasts," Nature Biotechnology 2000, 18(3), 333-338.

Svab & Maliga, "High-frequency plastid transformation in tobacco by selection for a chimeric aadA gene," Proceedings of the National Academy of Sciences 1993, 90(3), 913-917.

Svinarchuk et al., "Inhibition of HIV proliferation in MT-4 cells by antisense oligonucleotide conjugated to lipophilic groups," Biochimie 1993, 75(1-2), 49-54.

Szoka et al., "Preparation of unilamellar liposomes of intermediate size (0.1-0.2 μm) by a combination of reverse phase evaporation and extrusion through polycarbonate membranes," Biochimica et Biophysica Acta (BBA)-Biomembranes 1980, 601, 559-571.

Tabor et al., "Identification of conserved cis-elements and transcription factors required for sterol-regulated transcription of stearoyl-CoA desaturase 1 and 2," Journal of Biological Chemistry 1999, 274(29), 20603-20610.

Takahashi et al., "Induction of pluripotent stem cells from adult human fibroblasts by defined factors," Cell 2007, 131(5), 861-872.

Takahashi et al., "Induction of pluripotent stem cells from fibroblast cultures," Nature Protocols 2007, 2(12), 3081-3089.

Takahashi et al., "Rescue from photoreceptor degeneration in the rd mouse by human immunodeficiency virus vector-mediated gene transfer," Journal of Virology 1999, 73(9), 7812-7816.

Tanaka et al., "Conformational variations in an infectious protein determine prion strain differences," Nature 2004, 428(6980), 323-328.

Thomson et al., "Blastocysts embryonic stem cell lines derived from human," Science 1998, 282(5391), 1145-1147.

Thomson et al., "Isolation of a primate embryonic stem cell line," Proceedings of the National Academy of Sciences 1995, 92(17), 7844-7848.

Thomson et al., "Pluripotent cell lines derived from common marmoset (*Callithrix jacchus*) blastocysts," Biology of Reproduction 1996, 55(2), 254-259.

Tozzo et al., "Amelioration of insulin resistance in streptozotocin diabetic mice by transgenic overexpression of GLUT4 driven by an adipose-specific promoter," Endocrinology 1997, 138(4), 1604-1611.

Tratschin et al., "A human parvovirus, adeno-associated virus, as a eucaryotic vector: transient expression and encapsidation of the procaryotic gene for chloramphenicol acetyltransferase," Molecular and Cellular Biology 1984, 4(10), 2072-2081.

Tratschin et al., "Adeno-associated virus vector for high-frequency integration, expression, and rescue of genes in mammalian cells," Molecular and Cellular Biology 1985, 5(11), 3251-3260.

Tréhin et al., "Cellular uptake but low permeation of human calcitonin-derived cell penetrating peptides and Tat (47-57) through well-differentiated epithelial models," Pharmaceutical Research 2004, 21, 1248-1256.

Uemura et al., "Short Polymers of Arginine Rapidly Translocate Into Vascular Cells Effects on Nitric Oxide Synthesis," Circulation Journal 2002, 66(12), 1155-1160.

Vasil et al., "Rapid production of transgenic wheat plants by direct bombardment of cultured immature embryos," Bio/technology 1993, 11(12), 1553-1558.

Vavalle & Cohen, "The REG1 anticoagulation system: a novel actively controlled factor IX inhibitor using RNA aptamer technology for treatment of acute coronary syndrome," Future Cardiology 2012, 8(3), 371-382.

Vemuri & Rhodes, "Preparation and characterization of liposomes as therapeutic delivery systems: a review," Pharmaceutica Acta Helvetiae 1995, 70(2), 95-111.

Viney et al., "Antisense oligonucleotides targeting apolipoprotein (a) in people with raised lipoprotein (a): two randomised, double-blind, placebo-controlled, dose-ranging trials," The Lancet 2016, 388(10057), 2239-2253.

Volkov et al., "Selective protection of nuclease-sensitive sites in siRNA prolongs silencing effect," Oligonucleotides 2009, 19(2), 191-202.

Wahlestedt et al., "Potent and nontoxic antisense oligonucleotides containing locked nucleic acids," Proceedings of the National Academy of Sciences 2000, 97(10), 5633-5638.

Wan & Lemaux, "Generation of large numbers of independently transformed fertile barley plants," Plant Physiology 1994, 104(1), 37-48.

Wang et al., "Cyclohexene Nucleic Acids (CeNA): Serum Stable Oligonucleotides that Activate RNase H and Increase Duplex Stability with Complementary RNA," J. Am. Chem. Soc. 2000, 122(36), 8595-8602.

Warren et al., "Highly efficient reprogramming to pluripotency and directed differentiation of human cells with synthetic modified mRNA," Cell Stem Cell 2010, 7(5), 618-630.

Watkimns & Santalucia, "Nearest-neighbor thermodynamics of deoxyinosine pairs in DNA duplexes," Nucleic Acids Research 2005, 33(19), 6258-6267.

(56) References Cited

OTHER PUBLICATIONS

Watwe & BELLARE, "Manufacture of liposomes: a review," Current Science 1995, 68 715-724.
Weeks et al., "Rapid production of multiple independent lines of fertile transgenic wheat (*Triticum aestivum*)," Plant Physiology 1993, 102(4), 1077-1084.
Wender et al., "The design, synthesis, and evaluation of molecules that enable or enhance cellular uptake: peptoid molecular transporters," Proceedings of the National Academy of Sciences 2000, 97(24), 13003-13008.
Whitehead et al., "Silencing or stimulation? siRNA delivery and the immune system," Annual Review of Chemical and Biomolecular Engineering 2011, 2, 77-96.
Winkler, "Oligonucleotide conjugates for therapeutic applications," Therapeutic Delivery 2013, 4(7), 791-809.
Xia et al., "An enhanced U6 promoter for synthesis of short hairpin RNA," Nucleic Acids Research 2003, 31(17), in 5 pages.
Yang & Bedford, "Titivated for destruction: the methyl degron," Molecular Cell 2012, 48(4), 487-488.
Yokoyama et al., "Photoreceptor-specific activity of the human interphotoreceptor retinoid-binding protein (IRBP) promoter in transgenic mice," Experimental Eye Research 1992, 55(2), 225-233.
Young et al., "A short, highly active photoreceptor-specific enhancer/promoter region upstream of the human rhodopsin kinase gene," Investigative Ophthalmology & Visual Science 2003, 44(9), 4076-4085.
Yu et al., "Induced pluripotent stem cell lines derived from human somatic cells," Science 2007, 318(5858), 1917-1920.
Zender et al., "VP22-mediated intercellular transport of p53 in hepatoma cells in vitro and in vivo," Cancer Gene Therapy 2002, 9(6), 489-496.
Zhang & Madden, "PowerBLAST: a new network BLAST application for interactive or automated sequence analysis and annotation," Genome Research 1997, 7(6), 649-656.
Bolukbasi, M-F et al., "Creating and evaluating accurate CRISPR-Cas9 scalpels for genomic surgery," Nature Methods, vol. 13(1):41-50 (2016).
Database Accession No. A0A133QCR3, "CRISPR-associated endonuclease Cas9," Database UniProt, retrieved from EBI, Jun. 8, 2016.
Harayama S: "Artificial evolution by DNA shuffling," Trends in Biotechnology, vol. 16(2): 76-82 (1998).
International Preliminary Report on Patentabiliy, PCT/US2019/023044, dated Sep. 22, 2020, 9 pages.
International Search Report and Written Opinion, PCT/US2019/023044, dated Jul. 5, 2019, 13 pages.

* cited by examiner

SEQUENCE LISTING

<160> NUMBER OF SEQ ID NOS: 538

<210> SEQ ID NO 1
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of Gib11

<400> SEQUENCE: 1

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Gln Gly Ser Pro
    210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
            260                 265                 270

Gln Arg Asp Asn Ser Glu Lys Leu Glu Tyr His Glu Lys Tyr His Ile
        275                 280                 285

Ile Glu Asn Val Phe Lys Gln Lys Lys Lys Pro Thr Leu Lys Gln Ile
    290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu

-continued

```
                340             345             350
Leu Asn Gln Ile Ala Glu Ile Leu Thr Ile Tyr Gln Asp Lys Asp Ser
            355             360             365
Ile Val Ala Glu Leu Gly Gln Leu Glu Tyr Leu Met Ser Glu Ala Asp
        370             375             380
Lys Gln Ser Ile Ser Glu Leu Thr Gly Tyr Thr Gly Thr His Ser Leu
385             390             395             400
Ser Leu Lys Cys Met Asn Met Ile Ile Asp Glu Leu Trp His Ser Ser
                405             410             415
Met Asn Gln Met Glu Val Phe Thr Tyr Leu Asn Met Arg Pro Lys Lys
            420             425             430
Tyr Glu Leu Lys Gly Tyr Gln Arg Ile Pro Thr Asp Met Ile Asp Asp
        435             440             445
Ala Ile Leu Ser Pro Val Val Lys Arg Thr Phe Ile Gln Ser Ile Asn
        450             455             460
Val Ile Asn Lys Val Ile Glu Lys Tyr Gly Ile Pro Glu Asp Ile Ile
465             470             475             480
Ile Glu Leu Ala Arg Glu Asn Ser Asp Asp Arg Lys Lys Phe Ile
                485             490             495
Asn Asn Leu Gln Lys Lys Asn Glu Ala Thr Arg Lys Arg Ile Asn Glu
            500             505             510
Ile Ile Gly Gln Thr Gly Asn Gln Asn Ala Lys Arg Ile Val Glu Lys
        515             520             525
Ile Arg Leu His Asp Gln Gln Glu Gly Lys Cys Leu Tyr Ser Leu Glu
        530             535             540
Ser Ile Pro Leu Glu Asp Leu Leu Asn Asn Pro Asn His Tyr Glu Val
545             550             555             560
Asp His Ile Ile Pro Arg Ser Val Ser Phe Asp Asn Ser Tyr His Asn
                565             570             575
Lys Val Leu Val Lys Gln Ser Glu Asn Ser Lys Lys Ser Asn Leu Thr
            580             585             590
Pro Tyr Gln Tyr Phe Asn Ser Gly Lys Ser Lys Leu Ser Tyr Asn Gln
        595             600             605
Phe Lys Gln His Ile Leu Asn Leu Ser Lys Ser Gln Asp Arg Ile Ser
        610             615             620
Lys Lys Lys Lys Glu Tyr Leu Leu Glu Glu Arg Asp Ile Asn Lys Phe
625             630             635             640
Glu Val Gln Lys Glu Phe Ile Asn Arg Asn Leu Val Asp Thr Arg Tyr
                645             650             655
Ala Thr Arg Glu Leu Thr Asn Tyr Leu Lys Ala Tyr Phe Ser Ala Asn
            660             665             670
Asn Met Asn Val Lys Val Lys Thr Ile Asn Gly Ser Phe Thr Asp Tyr
        675             680             685
Leu Arg Lys Val Trp Lys Phe Lys Lys Glu Arg Asn His Gly Tyr Lys
        690             695             700
His His Ala Glu Asp Ala Leu Ile Ile Ala Asn Ala Asp Phe Leu Phe
705             710             715             720
Lys Glu Asn Lys Lys Leu Lys Ala Val Asn Ser Val Leu Glu Lys Pro
                725             730             735
Glu Ile Glu Thr Lys Gln Leu Asp Ile Gln Val Asp Ser Glu Asp Asn
            740             745             750
Tyr Ser Glu Met Phe Ile Ile Pro Lys Gln Val Gln Asp Ile Lys Asp
        755             760             765
```

```
Phe Arg Asn Phe Lys Tyr Ser His Arg Val Asp Lys Pro Asn Arg
            770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
                805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
        835                 840                 845

Tyr Ala Asn Glu Lys Asn Pro Leu Ala Lys Tyr His Glu Glu Thr Gly
    850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
                885                 890                 895

His Gln Phe Lys Ser Ser Thr Lys Lys Leu Val Lys Leu Ser Ile Lys
            900                 905                 910

Pro Tyr Arg Phe Asp Val Tyr Leu Thr Asp Lys Gly Tyr Lys Phe Ile
        915                 920                 925

Thr Ile Ser Tyr Leu Asp Val Leu Lys Lys Asp Asn Tyr Tyr Tyr Ile
    930                 935                 940

Pro Glu Gln Lys Tyr Asp Lys Leu Lys Leu Gly Lys Ala Ile Asp Lys
945                 950                 955                 960

Asn Ala Lys Phe Ile Ala Ser Phe Tyr Lys Asn Asp Leu Ile Lys Leu
                965                 970                 975

Asp Gly Glu Ile Tyr Lys Ile Ile Gly Val Asn Ser Asp Thr Arg Asn
            980                 985                 990

Met Ile Glu Leu Asp Leu Pro Asp Ile Arg Tyr Lys Glu Tyr Cys Glu
        995                 1000                1005

Leu Asn Asn Ile Lys Gly Glu Pro Arg Ile Lys Lys Thr Ile Gly
        1010                1015                1020

Lys Lys Val Asn Ser Ile Glu Lys Leu Thr Thr Asp Val Leu Gly
        1025                1030                1035

Asn Val Phe Thr Asn Thr Gln Tyr Thr Lys Pro Gln Leu Leu Phe
        1040                1045                1050

Lys Arg Gly Asn
        1055

<210> SEQ ID NO 2
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of Gib11Spa-1

<400> SEQUENCE: 2

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45
```

```
Ser Lys Arg Gly Ser Arg Arg Leu Lys Arg Arg Ile His Arg Leu
    50                  55                  60

Glu Arg Val Lys Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                    85                  90                  95

Ser Glu Ile Leu Ser Lys Asp Glu Leu Ala Ile Ala Leu Leu His Leu
                100                 105                 110

Ala Lys Arg Arg Gly Ile His Asn Val Asp Val Ala Ala Asp Lys Glu
            115                 120                 125

Glu Thr Ala Ser Asp Ser Leu Ser Thr Lys Asp Gln Ile Asn Lys Asn
130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
                180                 185                 190

Tyr Tyr Pro Glu Ile Asp Glu Thr Phe Lys Glu Lys Tyr Ile Ser Leu
                195                 200                 205

Val Glu Thr Arg Arg Glu Tyr Phe Glu Gly Pro Gly Gln Gly Ser Pro
210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
                260                 265                 270

Gln Arg Asp Asn Ser Glu Lys Leu Glu Tyr His Glu Lys Tyr His Ile
                275                 280                 285

Ile Glu Asn Val Phe Lys Gln Lys Lys Pro Thr Leu Lys Gln Ile
290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu
                340                 345                 350

Leu Asn Gln Ile Ala Glu Ile Leu Thr Ile Tyr Gln Asp Lys Asp Ser
                355                 360                 365

Ile Val Ala Glu Leu Gly Gln Leu Glu Tyr Leu Met Ser Glu Ala Asp
370                 375                 380

Lys Gln Ser Ile Ser Glu Leu Thr Gly Tyr Thr Gly Thr His Ser Leu
385                 390                 395                 400

Ser Leu Lys Cys Met Asn Met Ile Ile Asp Glu Leu Trp His Ser Ser
                405                 410                 415

Met Asn Gln Met Glu Val Phe Thr Tyr Leu Asn Met Arg Pro Lys Lys
                420                 425                 430

Tyr Glu Leu Lys Gly Tyr Gln Arg Ile Pro Thr Asp Met Ile Asp Asp
                435                 440                 445

Ala Ile Leu Ser Pro Val Val Lys Arg Thr Phe Ile Gln Ser Ile Asn
450                 455                 460
```

-continued

```
Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
        515                 520                 525

Ile Arg Leu His Asp Gln Gln Glu Gly Lys Cys Leu Tyr Ser Leu Glu
    530                 535                 540

Ser Ile Pro Leu Glu Asp Leu Leu Asn Asn Pro Asn His Tyr Glu Val
545                 550                 555                 560

Asp His Ile Ile Pro Arg Ser Val Ser Phe Asp Asn Ser Tyr His Asn
                565                 570                 575

Lys Val Leu Val Lys Gln Ser Glu Asn Ser Lys Lys Ser Asn Leu Thr
            580                 585                 590

Pro Tyr Gln Tyr Phe Asn Ser Gly Lys Ser Lys Leu Ser Tyr Asn Gln
        595                 600                 605

Phe Lys Gln His Ile Leu Asn Leu Ser Lys Ser Gln Asp Arg Ile Ser
    610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Ser Ala Asn
            660                 665                 670

Asn Met Asn Val Lys Val Lys Thr Ile Asn Gly Ser Phe Thr Asp Tyr
        675                 680                 685

Leu Arg Lys Val Trp Lys Phe Lys Lys Glu Arg Asn His Gly Tyr Lys
    690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Tyr Ser His Arg Val Asp Lys Lys Pro Asn Arg
    770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
                805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
        835                 840                 845

Tyr Ala Asn Glu Lys Asn Pro Leu Ala Lys Tyr His Glu Glu Thr Gly
    850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
```

```
                        885                 890                 895
His Gln Phe Lys Ser Ser Thr Lys Lys Leu Val Lys Leu Ser Ile Lys
            900                 905                 910

Asn Tyr Arg Phe Asp Val Tyr Leu Thr Glu Lys Gly Tyr Lys Phe Val
            915                 920                 925

Thr Ile Ala Tyr Leu Asn Val Phe Lys Lys Asp Asn Tyr Tyr Tyr Ile
            930                 935                 940

Pro Lys Asp Lys Tyr Gln Glu Leu Lys Glu Lys Lys Ile Lys Asp
945                 950                 955                 960

Thr Asp Gln Phe Ile Ala Ser Phe Tyr Lys Asn Asp Leu Ile Lys Leu
            965                 970                 975

Asn Gly Asp Leu Tyr Lys Ile Ile Gly Val Asn Ser Asp Asp Arg Asn
            980                 985                 990

Ile Ile Glu Leu Asp Tyr Tyr Asp Ile Lys Tyr Lys Asp Tyr Cys Glu
            995                 1000                1005

Ile Asn Asn Ile Lys Gly Glu Pro Arg Ile Lys Lys Thr Ile Gly
            1010                1015                1020

Lys Lys Thr Glu Ser Ile Glu Lys Phe Thr Thr Asp Val Leu Gly
            1025                1030                1035

Asn Leu Tyr Leu His Ser Thr Glu Lys Ala Pro Gln Leu Ile Phe
            1040                1045                1050

Lys Arg Gly Leu
            1055

<210> SEQ ID NO 3
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of Gib11Spa-2

<400> SEQUENCE: 3

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
            35                  40                  45

Ser Lys Arg Gly Ser Arg Arg Leu Lys Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
            85                  90                  95

Ser Glu Ile Leu Ser Lys Asp Glu Leu Ala Ile Ala Leu Leu His Leu
            100                 105                 110

Ala Lys Arg Arg Gly Ile His Asn Val Asp Val Ala Asp Lys Glu
            115                 120                 125

Glu Thr Ala Ser Asp Ser Leu Ser Thr Lys Asp Gln Ile Asn Lys Asn
            130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
```

```
            165                 170                 175
Lys Asp Ile Val Arg Glu Ala Lys Lys Ile Asp Thr Gln Met Gln
            180                 185                 190
Tyr Tyr Pro Glu Ile Asp Glu Thr Phe Lys Glu Lys Tyr Ile Ser Leu
            195                 200                 205
Val Glu Thr Arg Arg Glu Tyr Phe Glu Gly Pro Gln Gly Ser Pro
            210                 215                 220
Phe Gly Trp Asn Gly Asp Leu Lys Lys Trp Tyr Glu Met Leu Met Gly
225                 230                 235                 240
His Cys Thr Tyr Phe Pro Gln Glu Leu Arg Ser Val Lys Tyr Ala Tyr
                    245                 250                 255
Ser Ala Asp Leu Phe Asn Ala Leu Asn Asp Leu Asn Leu Ile Ile
            260                 265                 270
Gln Arg Asp Asn Ser Glu Lys Leu Glu Tyr His Glu Lys Tyr His Ile
            275                 280                 285
Ile Glu Asn Val Phe Lys Gln Lys Lys Pro Thr Leu Lys Gln Ile
290                 295                 300
Ala Lys Glu Ile Gly Val Asn Pro Glu Asp Ile Lys Gly Tyr Arg Ile
305                 310                 315                 320
Thr Lys Ser Gly Thr Pro Glu Phe Thr Ser Phe Lys Leu Phe His Asp
                    325                 330                 335
Leu Lys Lys Val Val Lys Asp His Ala Ile Leu Asp Asp Ile Asp Leu
            340                 345                 350
Leu Asn Gln Ile Ala Glu Ile Leu Thr Ile Tyr Gln Asp Lys Asp Ser
            355                 360                 365
Ile Val Ala Glu Leu Gly Gln Leu Glu Tyr Leu Met Ser Glu Ala Asp
370                 375                 380
Lys Gln Ser Ile Ser Glu Leu Thr Gly Tyr Thr Gly Thr His Ser Leu
385                 390                 395                 400
Ser Leu Lys Cys Met Asn Met Ile Ile Asp Glu Leu Trp His Ser Ser
                    405                 410                 415
Met Asn Gln Met Glu Val Phe Thr Tyr Leu Asn Met Arg Pro Lys Lys
            420                 425                 430
Tyr Glu Leu Lys Gly Tyr Gln Arg Ile Pro Thr Asp Met Ile Asp Asp
            435                 440                 445
Ala Ile Leu Ser Pro Val Val Lys Arg Thr Phe Ile Gln Ser Ile Asn
            450                 455                 460
Val Ile Asn Lys Val Ile Glu Lys Tyr Gly Ile Pro Glu Asp Ile Ile
465                 470                 475                 480
Ile Glu Leu Ala Arg Glu Asn Asn Ser Asp Asp Arg Lys Lys Phe Ile
                    485                 490                 495
Asn Asn Leu Gln Lys Lys Asn Glu Ala Thr Arg Lys Arg Ile Asn Glu
            500                 505                 510
Ile Ile Gly Gln Thr Gly Asn Gln Asn Ala Lys Arg Ile Val Glu Lys
            515                 520                 525
Ile Arg Leu His Asp Gln Gln Glu Gly Lys Cys Leu Tyr Ser Leu Glu
            530                 535                 540
Ser Ile Pro Leu Glu Asp Leu Leu Asn Asn Pro Asn His Tyr Glu Val
545                 550                 555                 560
Asp His Ile Ile Pro Arg Ser Val Ser Phe Asp Asn Ser Tyr His Asn
                    565                 570                 575
Lys Val Leu Val Lys Gln Ser Glu Asn Ser Lys Lys Ser Asn Leu Thr
            580                 585                 590
```

```
Pro Tyr Gln Tyr Phe Asn Ser Gly Lys Ser Lys Leu Ser Tyr Asn Gln
        595                 600                 605

Phe Lys Gln His Ile Leu Asn Leu Ser Lys Ser Gln Asp Arg Ile Ser
    610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Ser Ala Asn
            660                 665                 670

Asn Met Asn Val Lys Val Lys Thr Ile Asn Gly Ser Phe Thr Asp Tyr
        675                 680                 685

Leu Arg Lys Val Trp Lys Phe Lys Lys Glu Arg Asn His Gly Tyr Lys
    690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Phe Ser His Arg Val Asp Lys Lys Pro Asn Arg
    770                 775                 780

Gln Leu Ile Asn Asp Thr Leu Tyr Ser Thr Arg Met Lys Asp Glu His
785                 790                 795                 800

Asp Tyr Ile Val Gln Thr Ile Thr Asp Ile Tyr Gly Lys Asp Asn Thr
                805                 810                 815

Asn Leu Lys Lys Gln Phe Asn Lys Asn Pro Glu Lys Phe Leu Met Tyr
            820                 825                 830

Gln Asn Asp Pro Lys Thr Phe Glu Lys Leu Ser Ile Ile Met Lys Gln
        835                 840                 845

Tyr Ser Asp Glu Lys Asn Pro Leu Ala Lys Tyr Tyr Glu Glu Thr Gly
    850                 855                 860

Glu Tyr Leu Thr Lys Tyr Ser Lys Lys Asn Asn Gly Pro Ile Val Lys
865                 870                 875                 880

Lys Ile Lys Leu Leu Gly Asn Lys Val Gly Asn His Leu Asp Val Thr
                885                 890                 895

Asn Lys Tyr Glu Asn Ser Thr Lys Lys Leu Val Lys Leu Ser Ile Lys
            900                 905                 910

Asn Tyr Arg Phe Asp Val Tyr Leu Thr Glu Lys Gly Tyr Lys Phe Val
        915                 920                 925

Thr Ile Ala Tyr Leu Asn Val Phe Lys Lys Asp Asn Tyr Tyr Ile
    930                 935                 940

Pro Lys Asp Lys Tyr Gln Glu Leu Lys Glu Lys Lys Ile Lys Asp
945                 950                 955                 960

Thr Asp Gln Phe Ile Ala Ser Phe Tyr Lys Asn Asp Leu Ile Lys Leu
                965                 970                 975

Asn Gly Asp Leu Tyr Lys Ile Ile Gly Val Asn Ser Asp Asp Arg Asn
            980                 985                 990

Ile Ile Glu Leu Asp Tyr Tyr Asp  Ile Lys Tyr Lys Asp  Tyr Cys Glu
        995                 1000                1005
```

```
Ile Asn Asn Ile Lys Gly Glu Pro Arg Ile Lys Lys Thr Ile Gly
1010                1015                1020

Lys Lys Thr Glu Ser Ile Glu Lys Phe Thr Thr Asp Val Leu Gly
    1025                1030                1035

Asn Leu Tyr Leu His Ser Thr Glu Lys Ala Pro Gln Leu Ile Phe
        1040                1045                1050

Lys Arg Gly Leu
    1055

<210> SEQ ID NO 4
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of Gib11Spa-3

<400> SEQUENCE: 4

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Gln Gly Ser Pro
    210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
            260                 265                 270

Gln Arg Asp Asn Ser Glu Lys Leu Glu Tyr His Glu Lys Tyr His Ile
        275                 280                 285
```

```
Ile Glu Asn Val Phe Lys Gln Lys Lys Pro Thr Leu Lys Gln Ile
290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu
                340                 345                 350

Leu Asn Gln Ile Ala Glu Ile Leu Thr Ile Tyr Gln Asp Lys Asp Ser
                355                 360                 365

Ile Val Ala Glu Leu Gly Gln Leu Glu Tyr Leu Met Ser Glu Ala Asp
370                 375                 380

Lys Gln Ser Ile Ser Glu Leu Thr Gly Tyr Thr Gly Thr His Ser Leu
385                 390                 395                 400

Ser Leu Lys Cys Met Asn Met Ile Ile Asp Glu Leu Trp His Ser Ser
                405                 410                 415

Met Asn Gln Met Glu Val Phe Thr Tyr Leu Asn Met Arg Pro Lys Lys
                420                 425                 430

Tyr Glu Leu Lys Gly Tyr Gln Arg Ile Pro Thr Asp Met Ile Asp Asp
                435                 440                 445

Ala Ile Leu Ser Pro Val Val Lys Arg Thr Phe Ile Gln Ser Ile Asn
450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
                500                 505                 510

Ile Ile Gly Gln Thr Gly Asn Gln Asn Ala Lys Arg Ile Val Glu Lys
                515                 520                 525

Ile Arg Leu His Asp Gln Gln Glu Gly Lys Cys Leu Tyr Ser Leu Glu
530                 535                 540

Ser Ile Pro Leu Glu Asp Leu Leu Asn Asn Pro Asn His Tyr Glu Val
545                 550                 555                 560

Asp His Ile Ile Pro Arg Ser Val Ser Phe Asp Asn Ser Tyr His Asn
                565                 570                 575

Lys Val Leu Val Lys Gln Ser Glu Asn Ser Lys Lys Ser Asn Leu Thr
                580                 585                 590

Pro Tyr Gln Tyr Phe Asn Ser Gly Lys Ser Lys Leu Ser Tyr Asn Gln
                595                 600                 605

Phe Lys Gln His Ile Leu Asn Leu Ser Lys Ser Gln Asp Arg Ile Ser
610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Ser Tyr Leu Lys Ala Tyr Phe Ser Ala Asn
                660                 665                 670

Asn Met Asp Val Lys Val Lys Thr Ile Asn Gly Ser Phe Thr Asn His
                675                 680                 685

Leu Arg Lys Val Trp Arg Phe Asp Lys Tyr Arg Asn His Gly Tyr Lys
690                 695                 700

His His Ala Glu Asp Ala Leu Ile Ile Ala Asn Ala Asp Phe Leu Phe
```

```
                705                 710                 715                 720
Lys Glu Asn Lys Lys Leu Gln Asn Thr Asn Lys Ile Leu Gly Lys Pro
                    725                 730                 735

Thr Ile Glu Asn Asn Thr Lys Lys Val Thr Glu Lys Glu Glu Asp
                740                 745                 750

Tyr Asn Asn Val Phe Glu Thr Pro Lys Leu Val Glu Asp Ile Lys Gln
                755                 760                 765

Tyr Arg Asp Tyr Lys Phe Ser His Arg Val Lys Lys Pro Asn Arg
    770                 775                 780

Gln Leu Ile Asn Asp Thr Leu Tyr Ser Thr Arg Met Lys Asp Glu His
785                 790                 795                 800

Asp Tyr Ile Val Gln Thr Ile Thr Asp Ile Tyr Gly Lys Asp Asn Thr
                    805                 810                 815

Asn Leu Lys Lys Gln Phe Asn Lys Asn Pro Glu Lys Phe Leu Met Tyr
                820                 825                 830

Gln Asn Asp Pro Lys Thr Phe Glu Lys Leu Ser Ile Ile Met Lys Gln
                835                 840                 845

Tyr Ser Asp Glu Lys Asn Pro Leu Ala Lys Tyr Tyr Glu Glu Thr Gly
850                 855                 860

Glu Tyr Leu Thr Lys Tyr Ser Lys Asn Asn Gly Pro Ile Val Lys
865                 870                 875                 880

Lys Ile Lys Leu Leu Gly Asn Lys Val Gly Asn His Leu Asp Val Thr
                    885                 890                 895

Asn Lys Tyr Glu Asn Ser Thr Lys Lys Leu Val Lys Leu Ser Ile Lys
                900                 905                 910

Asn Tyr Arg Phe Asp Val Tyr Leu Thr Glu Lys Gly Tyr Lys Phe Val
            915                 920                 925

Thr Ile Ala Tyr Leu Asn Val Phe Lys Lys Asp Asn Tyr Tyr Ile
        930                 935                 940

Pro Lys Asp Lys Tyr Gln Glu Leu Lys Glu Lys Lys Ile Lys Asp
945                 950                 955                 960

Thr Asp Gln Phe Ile Ala Ser Phe Tyr Lys Asn Asp Leu Ile Lys Leu
                965                 970                 975

Asn Gly Asp Leu Tyr Lys Ile Ile Gly Val Asn Ser Asp Asp Arg Asn
                980                 985                 990

Ile Ile Glu Leu Asp Tyr Tyr Asp Ile Lys Tyr Lys Asp Tyr Cys Glu
            995                 1000                1005

Ile Asn Asn Ile Lys Gly Glu Pro Arg Ile Lys Lys Thr Ile Gly
    1010                1015                1020

Lys Lys Thr Glu Ser Ile Glu Lys Phe Thr Thr Asp Val Leu Gly
    1025                1030                1035

Asn Leu Tyr Leu His Ser Thr Glu Lys Ala Pro Gln Leu Ile Phe
    1040                1045                1050

Lys Arg Gly Leu
    1055

<210> SEQ ID NO 5
<211> LENGTH: 1054
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of P2H12
```

-continued

```
<400> SEQUENCE: 5

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Ile His Arg Leu
    50                  55                  60

Glu Arg Val Lys Lys Leu Leu Glu Asp Tyr Asn Leu Leu Asp Gln Ser
65                  70                  75                  80

Gln Ile Pro Gln Ser Thr Asn Pro Tyr Ala Ile Arg Val Lys Gly Leu
                85                  90                  95

Ser Glu Ala Leu Ser Lys Asp Glu Leu Val Ile Ala Leu Leu His Ile
            100                 105                 110

Ala Lys Arg Arg Gly Ile His Asn Ile Asn Val Ser Ser Glu Asp Glu
        115                 120                 125

Asp Ala Ser Asn Glu Leu Ser Thr Lys Glu Gln Ile Asn Arg Asn Asn
    130                 135                 140

Lys Leu Leu Lys Asp Lys Tyr Val Cys Glu Val Gln Leu Gln Arg Leu
145                 150                 155                 160

Lys Glu Gly Gln Ile Arg Gly Glu Lys Asn Arg Phe Lys Thr Thr Asp
                165                 170                 175

Ile Leu Lys Glu Ile Asp Gln Leu Leu Lys Val Gln Lys Asp Tyr His
            180                 185                 190

Asn Leu Asp Ile Asp Phe Ile Asn Gln Tyr Lys Glu Ile Val Glu Thr
        195                 200                 205

Arg Arg Glu Tyr Phe Glu Gly Pro Gly Lys Gly Ser Pro Tyr Gly Trp
    210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
        275                 280                 285

Val Phe Lys Gln Lys Lys Lys Pro Thr Leu Lys Gln Ile Ala Asn Glu
    290                 295                 300

Ile Asn Val Asn Pro Glu Asp Ile Lys Gly Tyr Arg Ile Thr Lys Ser
305                 310                 315                 320

Gly Lys Pro Glu Phe Thr Ser Phe Lys Leu Phe His Asp Leu Lys Lys
                325                 330                 335

Val Val Lys Asp His Ala Ile Leu Asp Asp Ile Asp Leu Leu Asn Gln
            340                 345                 350

Ile Ala Glu Ile Leu Thr Ile Tyr Gln Asp Lys Asp Ser Ile Val Ala
        355                 360                 365

Glu Leu Gly Gln Leu Glu Tyr Leu Met Ser Glu Ala Asp Lys Gln Ser
    370                 375                 380

Ile Ser Glu Leu Thr Gly Tyr Thr Gly Thr His Ser Leu Ser Leu Lys
385                 390                 395                 400

Cys Met Asn Met Ile Ile Asp Glu Leu Trp His Ser Ser Met Asn Gln
                405                 410                 415
```

Met Glu Val Phe Thr Tyr Leu Asn Met Arg Pro Lys Lys Tyr Glu Leu
                420                 425                 430

Lys Gly Tyr Gln Arg Ile Pro Thr Asp Met Ile Asp Ala Ile Leu
            435                 440                 445

Ser Pro Val Val Lys Arg Thr Phe Ile Gln Ser Ile Asn Val Ile Asn
450                 455                 460

Lys Val Ile Glu Lys Tyr Gly Ile Pro Glu Asp Ile Ile Glu Leu
465                 470                 475                 480

Ala Arg Glu Asn Asn Ser Asp Asp Arg Lys Lys Phe Ile Asn Asn Leu
                485                 490                 495

Gln Lys Lys Asn Glu Ala Thr Arg Lys Arg Ile Asn Glu Ile Ile Gly
                500                 505                 510

Gln Thr Gly Asn Gln Asn Ala Lys Arg Ile Val Glu Lys Ile Arg Leu
            515                 520                 525

His Asp Gln Gln Glu Gly Lys Cys Leu Tyr Ser Leu Glu Ser Ile Pro
        530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
                565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
        595                 600                 605

His Ile Leu Asn Leu Ser Lys Ser Gln Asp Arg Ile Ser Lys Lys Lys
        610                 615                 620

Lys Glu Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
            675                 680                 685

Val Trp Lys Phe Lys Lys Glu Arg Asn His Gly Tyr Lys His His Ala
        690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
        755                 760                 765

Phe Lys Tyr Ser His Arg Val Asp Lys Lys Pro Asn Arg Gln Leu Ile
        770                 775                 780

Asn Asp Thr Leu Tyr Ser Thr Arg Lys Lys Asp Asn Ser Thr Tyr Ile
785                 790                 795                 800

Val Gln Thr Ile Lys Asp Ile Tyr Ala Lys Asp Asn Thr Thr Leu Lys
                805                 810                 815

Lys Gln Phe Asp Lys Ser Pro Glu Lys Phe Leu Met Tyr Gln His Asp
            820                 825                 830

```
Pro Arg Thr Phe Glu Lys Leu Glu Val Ile Met Lys Gln Tyr Ala Asn
            835                 840                 845

Glu Lys Asn Pro Leu Ala Lys Tyr His Glu Thr Gly Glu Tyr Leu
    850                 855                 860

Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
                885                 890                 895

Lys Ser Ser Thr Lys Lys Leu Val Lys Leu Ser Ile Lys Pro Tyr Arg
            900                 905                 910

Phe Asp Val Tyr Leu Thr Asp Lys Gly Tyr Lys Phe Ile Thr Ile Ser
            915                 920                 925

Tyr Leu Asp Val Leu Lys Lys Asp Asn Tyr Tyr Ile Pro Glu Gln
    930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                965                 970                 975

Ile Tyr Lys Ile Ile Gly Val Asn Ser Asp Thr Arg Asn Met Ile Glu
                980                 985                 990

Leu Asp Leu Pro Asp Ile Arg Tyr  Lys Glu Tyr Cys Glu  Leu Asn Asn
            995                 1000                1005

Ile Lys  Gly Glu Pro Arg Ile  Lys Lys Thr Ile Gly  Lys Lys Val
        1010                1015                1020

Asn Ser  Ile Glu Lys Leu Thr  Thr Asp Val Leu Gly  Asn Val Phe
        1025                1030                1035

Thr Asn  Thr Gln Tyr Thr Lys  Pro Gln Leu Leu Phe  Lys Arg Gly
        1040                1045                1050

Asn
```

```
<210> SEQ ID NO 6
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of E2

<400> SEQUENCE: 6
```

```
Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
                20                  25                  30

Val Arg Leu Phe Pro Glu Ala Asn Val Glu Asn Asn Glu Gly Arg Arg
            35                  40                  45

Ser Lys Arg Gly Ser Arg Arg Leu Lys Arg Arg Ile His Arg Leu
    50                  55                  60

Asp Arg Val Lys His Leu Leu Ala Glu Tyr Asp Leu Leu Asp Leu Thr
65                  70                  75                  80

Asn Ile Pro Lys Ser Thr Asn Pro Tyr Gln Thr Arg Val Lys Gly Leu
                85                  90                  95

Asn Glu Lys Leu Ser Lys Asp Glu Leu Val Ile Ala Leu Leu His Ile
                100                 105                 110

Ala Lys Arg Arg Gly Ile His Asn Val Asp Val Ala Ala Asp Lys Glu
```

-continued

```
            115                 120                 125
Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Lys Gly Ser Pro
    210                 215                 220

Phe Gly Trp Glu Gly Asn Ile Lys Lys Trp Phe Glu Gln Met Met Gly
225                 230                 235                 240

His Cys Thr Tyr Phe Pro Glu Glu Leu Arg Ser Val Lys Tyr Ser Tyr
                245                 250                 255

Ser Ala Glu Leu Phe Asn Ala Leu Asn Asp Leu Asn Asn Leu Val Ile
            260                 265                 270

Thr Arg Asp Glu Asp Ala Lys Leu Asn Tyr Gly Glu Lys Phe Gln Ile
        275                 280                 285

Ile Glu Asn Val Phe Lys Gln Lys Lys Thr Pro Asn Leu Lys Gln Ile
    290                 295                 300

Ala Ile Glu Ile Gly Val His Glu Thr Glu Ile Lys Gly Tyr Arg Val
305                 310                 315                 320

Asn Lys Ser Gly Thr Pro Glu Phe Thr Glu Phe Lys Leu Tyr His Asp
                325                 330                 335

Leu Lys Ser Ile Val Phe Asp Lys Ser Ile Leu Glu Asn Glu Ala Ile
            340                 345                 350

Leu Asp Gln Ile Ala Glu Ile Leu Thr Ile Tyr Gln Asp Glu Gln Ser
        355                 360                 365

Ile Lys Glu Glu Leu Asn Lys Leu Pro Glu Ile Leu Asn Glu Gln Asp
    370                 375                 380

Lys Ala Glu Ile Ala Lys Leu Ile Gly Tyr Asn Gly Thr His Arg Leu
385                 390                 395                 400

Ser Leu Lys Cys Ile His Leu Ile Asn Glu Glu Leu Trp Gln Thr Ser
                405                 410                 415

Arg Asn Gln Met Glu Ile Phe Asn Tyr Leu Asn Ile Lys Pro Asn Lys
            420                 425                 430

Val Asp Leu Ser Glu Gln Asn Lys Ile Pro Lys Asp Met Val Asn Asp
        435                 440                 445

Phe Ile Leu Ser Pro Val Val Lys Arg Thr Phe Ile Gln Ser Ile Asn
    450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
        515                 520                 525

Ile Arg Leu His Asp Gln Gln Glu Gly Lys Cys Leu Tyr Ser Leu Lys
    530                 535                 540
```

```
Asp Ile Pro Leu Glu Asp Leu Leu Arg Asn Pro Asn Tyr Asp Ile
545                 550                 555                 560

Asp His Ile Ile Pro Arg Ser Val Ser Phe Asp Ser Met His Asn
            565                 570                 575

Lys Val Leu Val Arg Arg Glu Gln Asn Ala Lys Lys Asn Asn Gln Thr
                580                 585                 590

Pro Tyr Gln Tyr Leu Thr Ser Gly Tyr Ala Asp Ile Lys Tyr Ser Val
        595                 600                 605

Phe Lys Gln His Val Leu Asn Leu Ala Glu Asn Lys Asp Arg Met Thr
610                 615                 620

Lys Lys Lys Arg Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Ser Ala Asn
            660                 665                 670

Asn Met Asn Val Lys Val Lys Thr Ile Asn Gly Ser Phe Thr Asp Tyr
        675                 680                 685

Leu Arg Lys Val Trp Lys Phe Lys Lys Glu Arg Asn His Gly Tyr Lys
690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Tyr Ser His Arg Val Asp Lys Lys Pro Asn Arg
770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
                805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
        835                 840                 845

Tyr Ala Asn Glu Lys Asn Pro Leu Ala Lys Tyr His Glu Glu Thr Gly
850                 855                 860

Glu Tyr Leu Thr Lys Tyr Ser Lys Asn Asn Gly Pro Ile Val Lys
865                 870                 875                 880

Ser Leu Lys Tyr Ile Gly Asn Lys Leu Gly Ser His Leu Asp Val Thr
                885                 890                 895

His Gln Phe Lys Ser Ser Thr Lys Lys Leu Val Lys Leu Ser Ile Lys
            900                 905                 910

Pro Tyr Arg Phe Asp Val Tyr Leu Thr Asp Lys Gly Tyr Lys Phe Ile
        915                 920                 925

Thr Ile Ser Tyr Leu Asp Val Leu Lys Lys Asp Asn Tyr Tyr Tyr Ile
930                 935                 940

Pro Glu Gln Lys Tyr Asp Lys Leu Lys Leu Gly Lys Ala Ile Asp Lys
945                 950                 955                 960
```

```
Asn Ala Lys Phe Ile Ala Ser Phe Tyr Lys Asn Asp Leu Ile Lys Leu
                965                 970                 975

Asp Gly Glu Ile Tyr Lys Ile Ile Gly Val Asn Ser Asp Thr Arg Asn
            980                 985                 990

Met Ile Glu Leu Asp Leu Pro Asp Ile Arg Tyr Lys Glu Tyr Cys Glu
            995                 1000                1005

Leu Asn Asn Ile Lys Gly Glu Pro Arg Ile Lys Lys Thr Ile Gly
    1010                1015                1020

Lys Lys Val Asn Ser Ile Glu Lys Leu Thr Thr Asp Val Leu Gly
    1025                1030                1035

Asn Val Phe Thr Asn Thr Gln Tyr Thr Lys Pro Gln Leu Leu Phe
    1040                1045                1050

Lys Arg Gly Asn
    1055

<210> SEQ ID NO 7
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of E2-K741D-L743K

<400> SEQUENCE: 7

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

Asp Arg Val Lys His Leu Leu Ala Glu Tyr Asp Leu Leu Asp Leu Thr
65                  70                  75                  80

Asn Ile Pro Lys Ser Thr Asn Pro Tyr Gln Thr Arg Val Lys Gly Leu
                85                  90                  95

Asn Glu Lys Leu Ser Lys Asp Glu Leu Val Ile Ala Leu Leu His Ile
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Lys Tyr Ile Ser Leu
        195                 200                 205

Val Glu Thr Arg Arg Glu Tyr Phe Glu Gly Pro Gly Lys Gly Ser Pro
    210                 215                 220

Phe Gly Trp Glu Gly Asn Ile Lys Trp Phe Glu Gln Met Met Gly
225                 230                 235                 240
```

His Cys Thr Tyr Phe Pro Glu Glu Leu Arg Ser Val Lys Tyr Ser Tyr
                245                 250                 255

Ser Ala Glu Leu Phe Asn Ala Leu Asn Asp Leu Asn Asn Leu Val Ile
        260                 265                 270

Thr Arg Asp Glu Asp Ala Lys Leu Asn Tyr Gly Glu Lys Phe Gln Ile
        275                 280                 285

Ile Glu Asn Val Phe Lys Gln Lys Lys Thr Pro Asn Leu Lys Gln Ile
    290                 295                 300

Ala Ile Glu Ile Gly Val His Glu Thr Glu Ile Lys Gly Tyr Arg Val
305                 310                 315                 320

Asn Lys Ser Gly Thr Pro Glu Phe Thr Glu Phe Lys Leu Tyr His Asp
                325                 330                 335

Leu Lys Ser Ile Val Phe Asp Lys Ser Ile Leu Glu Asn Glu Ala Ile
                340                 345                 350

Leu Asp Gln Ile Ala Glu Ile Leu Thr Ile Tyr Gln Asp Glu Gln Ser
            355                 360                 365

Ile Lys Glu Glu Leu Asn Lys Leu Pro Glu Ile Leu Asn Glu Gln Asp
    370                 375                 380

Lys Ala Glu Ile Ala Lys Leu Ile Gly Tyr Asn Gly Thr His Arg Leu
385                 390                 395                 400

Ser Leu Lys Cys Ile His Leu Ile Asn Glu Glu Leu Trp Gln Thr Ser
                405                 410                 415

Arg Asn Gln Met Glu Ile Phe Asn Tyr Leu Asn Ile Lys Pro Asn Lys
                420                 425                 430

Val Asp Leu Ser Glu Gln Asn Lys Ile Pro Lys Asp Met Val Asn Asp
            435                 440                 445

Phe Ile Leu Ser Pro Val Val Lys Arg Thr Phe Ile Gln Ser Ile Asn
    450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
    515                 520                 525

Ile Arg Leu His Asp Gln Gln Glu Gly Lys Cys Leu Tyr Ser Leu Lys
    530                 535                 540

Asp Ile Pro Leu Glu Asp Leu Leu Arg Asn Pro Asn Asn Tyr Asp Ile
545                 550                 555                 560

Asp His Ile Ile Pro Arg Ser Val Ser Phe Asp Asp Ser Met His Asn
                565                 570                 575

Lys Val Leu Val Arg Arg Glu Gln Asn Ala Lys Lys Asn Asn Gln Thr
            580                 585                 590

Pro Tyr Gln Tyr Leu Thr Ser Gly Tyr Ala Asp Ile Lys Tyr Ser Val
        595                 600                 605

Phe Lys Gln His Val Leu Asn Leu Ala Glu Asn Lys Asp Arg Met Thr
    610                 615                 620

Lys Lys Lys Arg Glu Tyr Leu Leu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Ser Ala Asn

```
                        660                 665                 670
Asn Met Asn Val Lys Val Lys Thr Ile Asn Gly Ser Phe Thr Asp Tyr
            675                 680                 685

Leu Arg Lys Val Trp Lys Phe Lys Lys Glu Arg Asn His Gly Tyr Lys
        690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Asp Gln Lys Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Tyr Ser His Arg Val Asp Lys Lys Pro Asn Arg
    770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
                805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
        835                 840                 845

Tyr Ala Asn Glu Lys Asn Pro Leu Ala Lys Tyr His Glu Glu Thr Gly
    850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
                885                 890                 895

His Gln Phe Lys Ser Ser Thr Lys Lys Leu Val Lys Leu Ser Ile Lys
            900                 905                 910

Pro Tyr Arg Phe Asp Val Tyr Leu Thr Asp Lys Gly Tyr Lys Phe Ile
        915                 920                 925

Thr Ile Ser Tyr Leu Asp Val Leu Lys Lys Asp Asn Tyr Tyr Tyr Ile
    930                 935                 940

Pro Glu Gln Lys Tyr Asp Lys Leu Lys Leu Gly Lys Ala Ile Asp Lys
945                 950                 955                 960

Asn Ala Lys Phe Ile Ala Ser Phe Tyr Lys Asn Asp Leu Ile Lys Leu
                965                 970                 975

Asp Gly Glu Ile Tyr Lys Ile Ile Gly Val Asn Ser Asp Thr Arg Asn
            980                 985                 990

Met Ile Glu Leu Asp Leu Pro Asp Ile Arg Tyr Lys Glu Tyr Cys Glu
        995                 1000                1005

Leu Asn Asn Ile Lys Gly Glu Pro Arg Ile Lys Lys Thr Ile Gly
        1010                1015                1020

Lys Lys Val Asn Ser Ile Glu Lys Leu Thr Thr Asp Val Leu Gly
        1025                1030                1035

Asn Val Phe Thr Asn Thr Gln Tyr Thr Lys Pro Gln Leu Leu Phe
        1040                1045                1050

Lys Arg Gly Asn
        1055

<210> SEQ ID NO 8
```

```
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of E2-S670T-N675D

<400

```
Ile Lys Glu Glu Leu Asn Lys Leu Pro Glu Ile Leu Asn Glu Gln Asp
    370                 375                 380

Lys Ala Glu Ile Ala Lys Leu Ile Gly Tyr Asn Gly Thr His Arg Leu
385                 390                 395                 400

Ser Leu Lys Cys Ile His Leu Ile Asn Glu Glu Leu Trp Gln Thr Ser
                405                 410                 415

Arg Asn Gln Met Glu Ile Phe Asn Tyr Leu Asn Ile Lys Pro Asn Lys
            420                 425                 430

Val Asp Leu Ser Glu Gln Asn Lys Ile Pro Lys Asp Met Val Asn Asp
        435                 440                 445

Phe Ile Leu Ser Pro Val Val Lys Arg Thr Phe Ile Gln Ser Ile Asn
    450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
        515                 520                 525

Ile Arg Leu His Asp Gln Gln Glu Gly Lys Cys Leu Tyr Ser Leu Lys
    530                 535                 540

Asp Ile Pro Leu Glu Asp Leu Leu Arg Asn Pro Asn Asn Tyr Asp Ile
545                 550                 555                 560

Asp His Ile Ile Pro Arg Ser Val Ser Phe Asp Ser Met His Asn
                565                 570                 575

Lys Val Leu Val Arg Arg Glu Gln Asn Ala Lys Lys Asn Asn Gln Thr
            580                 585                 590

Pro Tyr Gln Tyr Leu Thr Ser Gly Tyr Ala Asp Ile Lys Tyr Ser Val
        595                 600                 605

Phe Lys Gln His Val Leu Asn Leu Ala Glu Asn Lys Asp Arg Met Thr
    610                 615                 620

Lys Lys Lys Arg Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Thr Ala Asn
            660                 665                 670

Asn Met Asp Val Lys Val Lys Thr Ile Asn Gly Ser Phe Thr Asp Tyr
        675                 680                 685

Leu Arg Lys Val Trp Lys Phe Lys Lys Glu Arg Asn His Gly Tyr Lys
    690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Tyr Ser His Arg Val Asp Lys Lys Pro Asn Arg
    770                 775                 780
```

```
Gln Leu Ile Asn Asp Thr Leu Tyr Ser Thr Arg Lys Asp Asn Ser
785                 790                 795                 800

Thr Tyr Ile Val Gln Thr Ile Lys Asp Ile Tyr Ala Lys Asp Asn Thr
                805                 810                 815

Thr Leu Lys Lys Gln Phe Asp Lys Ser Pro Glu Lys Phe Leu Met Tyr
                820                 825                 830

Gln His Asp Pro Arg Thr Phe Glu Lys Leu Glu Val Ile Met Lys Gln
                835                 840                 845

Tyr Ala Asn Glu Lys Asn Pro Leu Ala Lys Tyr His Glu Glu Thr Gly
            850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
                885                 890                 895

His Gln Phe Lys Ser Ser Thr Lys Lys Leu Val Lys Leu Ser Ile Lys
                900                 905                 910

Pro Tyr Arg Phe Asp Val Tyr Leu Thr Asp Lys Gly Tyr Lys Phe Ile
                915                 920                 925

Thr Ile Ser Tyr Leu Asp Val Leu Lys Lys Asp Asn Tyr Tyr Tyr Ile
            930                 935                 940

Pro Glu Gln Lys Tyr Asp Lys Leu Lys Leu Gly Lys Ala Ile Asp Lys
945                 950                 955                 960

Asn Ala Lys Phe Ile Ala Ser Phe Tyr Lys Asn Asp Leu Ile Lys Leu
                965                 970                 975

Asp Gly Glu Ile Tyr Lys Ile Ile Gly Val Asn Ser Asp Thr Arg Asn
                980                 985                 990

Met Ile Glu Leu Asp Leu Pro Asp Ile Arg Tyr Lys Glu Tyr Cys Glu
                995                 1000                1005

Leu Asn Asn Ile Lys Gly Glu Pro Arg Ile Lys Lys Thr Ile Gly
    1010                1015                1020

Lys Lys Val Asn Ser Ile Glu Lys Leu Thr Thr Asp Val Leu Gly
    1025                1030                1035

Asn Val Phe Thr Asn Thr Gln Tyr Thr Lys Pro Gln Leu Leu Phe
    1040                1045                1050

Lys Arg Gly Asn
    1055

<210> SEQ ID NO 9
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of E2-K741N-L743N

<400> SEQUENCE: 9

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
                20                  25                  30

Val Arg Leu Phe Pro Glu Ala Asn Val Glu Asn Asn Glu Gly Arg Arg
            35                  40                  45

Ser Lys Arg Gly Ser Arg Arg Leu Lys Arg Arg Arg Ile His Arg Leu
        50                  55                  60
```

-continued

Asp Arg Val Lys His Leu Ala Glu Tyr Asp Leu Leu Asp Leu Thr
65                  70                  75                  80

Asn Ile Pro Lys Ser Thr Asn Pro Tyr Gln Thr Arg Val Lys Gly Leu
            85                  90                  95

Asn Glu Lys Leu Ser Lys Asp Glu Leu Val Ile Ala Leu Leu His Ile
            100                 105                 110

Ala Lys Arg Arg Gly Ile His Asn Val Asp Val Ala Asp Lys Glu
        115                 120                 125

Glu Thr Ala Ser Asp Ser Leu Ser Thr Lys Asp Gln Ile Asn Lys Asn
        130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
                180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Lys Gly Ser Pro
210                 215                 220

Phe Gly Trp Glu Gly Asn Ile Lys Lys Trp Phe Glu Gln Met Met Gly
225                 230                 235                 240

His Cys Thr Tyr Phe Pro Glu Glu Leu Arg Ser Val Lys Tyr Ser Tyr
                245                 250                 255

Ser Ala Glu Leu Phe Asn Ala Leu Asn Asp Leu Asn Asn Leu Val Ile
                260                 265                 270

Thr Arg Asp Glu Asp Ala Lys Leu Asn Tyr Gly Glu Lys Phe Gln Ile
                275                 280                 285

Ile Glu Asn Val Phe Lys Gln Lys Thr Pro Asn Leu Lys Gln Ile
        290                 295                 300

Ala Ile Glu Ile Gly Val His Glu Thr Glu Ile Lys Gly Tyr Arg Val
305                 310                 315                 320

Asn Lys Ser Gly Thr Pro Glu Phe Thr Glu Phe Lys Leu Tyr His Asp
                325                 330                 335

Leu Lys Ser Ile Val Phe Asp Lys Ser Ile Leu Glu Asn Glu Ala Ile
            340                 345                 350

Leu Asp Gln Ile Ala Glu Ile Leu Thr Ile Tyr Gln Asp Glu Gln Ser
        355                 360                 365

Ile Lys Glu Glu Leu Asn Lys Leu Pro Glu Ile Leu Asn Glu Gln Asp
        370                 375                 380

Lys Ala Glu Ile Ala Lys Leu Ile Gly Tyr Asn Gly Thr His Arg Leu
385                 390                 395                 400

Ser Leu Lys Cys Ile His Leu Ile Asn Glu Glu Leu Trp Gln Thr Ser
                405                 410                 415

Arg Asn Gln Met Glu Ile Phe Asn Tyr Leu Asn Ile Lys Pro Asn Lys
                420                 425                 430

Val Asp Leu Ser Glu Gln Asn Lys Ile Pro Lys Asp Met Val Asn Asp
            435                 440                 445

Phe Ile Leu Ser Pro Val Val Lys Arg Thr Phe Ile Gln Ser Ile Asn
            450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile

```
                485                 490                 495
Asn Asn Leu Gln Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
            515                 520                 525

Ile Arg Leu His Asp Gln Gln Glu Gly Lys Cys Leu Tyr Ser Leu Lys
            530                 535                 540

Asp Ile Pro Leu Glu Asp Leu Leu Arg Asn Pro Asn Asn Tyr Asp Ile
545                 550                 555                 560

Asp His Ile Ile Pro Arg Ser Val Ser Phe Asp Asp Ser Met His Asn
            565                 570                 575

Lys Val Leu Val Arg Arg Glu Gln Asn Ala Lys Lys Asn Asn Gln Thr
            580                 585                 590

Pro Tyr Gln Tyr Leu Thr Ser Gly Tyr Ala Asp Ile Lys Tyr Ser Val
            595                 600                 605

Phe Lys Gln His Val Leu Asn Leu Ala Glu Asn Lys Asp Arg Met Thr
            610                 615                 620

Lys Lys Lys Arg Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                    645                 650                 655

Ala Thr Arg Glu Leu Thr Asn Tyr Leu Lys Ala Tyr Phe Ser Ala Asn
                    660                 665                 670

Asn Met Asn Val Lys Val Lys Thr Ile Asn Gly Ser Phe Thr Asp Tyr
            675                 680                 685

Leu Arg Lys Val Trp Lys Phe Lys Lys Glu Arg Asn His Gly Tyr Lys
            690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                    725                 730                 735

Glu Ile Glu Thr Asn Gln Asn Asp Ile Gln Val Asp Ser Glu Asp Asn
                    740                 745                 750

Tyr Ser Glu Met Phe Ile Ile Pro Lys Gln Val Gln Asp Ile Lys Asp
            755                 760                 765

Phe Arg Asn Phe Lys Tyr Ser His Arg Val Asp Lys Lys Pro Asn Arg
770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
            805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
            835                 840                 845

Tyr Ala Asn Glu Lys Asn Pro Leu Ala Lys Tyr His Glu Glu Thr Gly
            850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
            885                 890                 895

His Gln Phe Lys Ser Ser Thr Lys Lys Leu Val Lys Leu Ser Ile Lys
            900                 905                 910
```

```
Pro Tyr Arg Phe Asp Val Tyr Leu Thr Asp Lys Gly Tyr Lys Phe Ile
        915                 920                 925

Thr Ile Ser Tyr Leu Asp Val Leu Lys Lys Asp Asn Tyr Tyr Tyr Ile
        930                 935                 940

Pro Glu Gln Lys Tyr Asp Lys Leu Lys Leu Gly Lys Ala Ile Asp Lys
945                 950                 955                 960

Asn Ala Lys Phe Ile Ala Ser Phe Tyr Lys Asn Asp Leu Ile Lys Leu
        965                 970                 975

Asp Gly Glu Ile Tyr Lys Ile Gly Val Asn Ser Asp Thr Arg Asn
        980                 985                 990

Met Ile Glu Leu Asp Leu Pro Asp  Ile Arg Tyr Lys Glu  Tyr Cys Glu
        995                1000                 1005

Leu Asn  Asn Ile Lys Gly Glu  Pro Arg Ile Lys Lys  Thr Ile Gly
     1010                1015                 1020

Lys Lys  Val Asn Ser Ile Glu  Lys Leu Thr Thr Asp  Val Leu Gly
    1025                1030                 1035

Asn Val  Phe Thr Asn Thr Gln  Tyr Thr Lys Pro Gln  Leu Leu Phe
     1040                1045                 1050

Lys Arg  Gly Asn
     1055

<210> SEQ ID NO 10
<211> LENGTH: 1053
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of F8

<400> SEQUENCE: 10

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Ile His Arg Leu
    50                  55                  60

Glu Arg Val Lys Ser Leu Leu Ser Glu Tyr Lys Ile Ile Ser Gly Leu
65                  70                  75                  80

Ala Pro Thr Asn Asn Gln Pro Tyr Asn Ile Arg Val Lys Gly Leu Thr
            85                  90                  95

Glu Gln Leu Thr Lys Asp Glu Leu Ala Val Ala Leu Leu His Ile Ala
            100                 105                 110

Lys Arg Arg Gly Ile His Lys Ile Asp Val Ile Asp Ser Asn Asp Asp
        115                 120                 125

Val Gly Asn Glu Leu Ser Thr Lys Glu Gln Leu Asn Lys Asn Ser Lys
    130                 135                 140

Leu Leu Lys Asp Lys Phe Val Cys Gln Ile Gln Leu Glu Arg Met Asn
145                 150                 155                 160

Glu Gly Gln Val Arg Gly Glu Lys Asn Arg Phe Lys Thr Ala Asp Ile
            165                 170                 175

Ile Lys Glu Ile Ile Gln Leu Leu Asn Val Gln Lys Asn Phe His Gln
            180                 185                 190
```

```
Leu Asp Glu Asn Phe Ile Asn Lys Tyr Ile Glu Leu Val Glu Met Arg
        195                 200                 205

Arg Glu Tyr Phe Glu Gly Pro Gly Gln Gly Ser Pro Phe Gly Trp Asn
    210                 215                 220

Gly Asp Leu Lys Lys Trp Tyr Glu Met Leu Met Gly His Cys Thr Tyr
225                 230                 235                 240

Phe Pro Gln Glu Leu Arg Ser Val Lys Tyr Ala Tyr Ser Ala Asp Leu
                245                 250                 255

Phe Asn Ala Leu Asn Asp Leu Asn Asn Leu Ile Ile Gln Arg Asp Asn
            260                 265                 270

Ser Glu Lys Leu Glu Tyr His Glu Lys Tyr His Ile Ile Glu Asn Val
        275                 280                 285

Phe Lys Gln Lys Lys Pro Thr Leu Lys Gln Ile Ala Lys Glu Ile
    290                 295                 300

Gly Val Asn Pro Glu Asp Ile Lys Gly Tyr Arg Ile Thr Lys Ser Gly
305                 310                 315                 320

Thr Pro Glu Phe Thr Glu Phe Lys Leu Tyr His Asp Leu Lys Ser Val
                325                 330                 335

Leu Phe Asp Gln Ser Ile Leu Glu Asn Glu Asp Val Leu Asp Gln Ile
            340                 345                 350

Ala Glu Ile Leu Thr Ile Tyr Gln Asp Lys Asp Ser Ile Lys Ser Lys
        355                 360                 365

Leu Thr Glu Leu Asp Ile Leu Leu Asn Glu Glu Asp Lys Glu Asn Ile
    370                 375                 380

Ala Gln Leu Thr Gly Tyr Asn Gly Thr His Arg Leu Ser Leu Lys Cys
385                 390                 395                 400

Ile Arg Leu Val Leu Glu Glu Gln Trp Tyr Ser Ser Arg Asn Gln Met
                405                 410                 415

Glu Ile Phe Thr His Leu Asn Ile Lys Pro Lys Lys Ile Asn Leu Thr
            420                 425                 430

Ala Ala Asn Lys Ile Pro Lys Ala Met Ile Asp Glu Phe Ile Leu Ser
        435                 440                 445

Pro Val Val Lys Arg Thr Phe Ile Gln Ser Ile Asn Val Ile Asn Lys
    450                 455                 460

Val Ile Glu Lys Tyr Gly Ile Pro Glu Asp Ile Ile Glu Leu Ala
465                 470                 475                 480

Arg Glu Asn Asn Ser Asp Asp Arg Lys Lys Phe Ile Asn Asn Leu Gln
                485                 490                 495

Lys Lys Asn Glu Ala Thr Arg Lys Arg Ile Asn Glu Ile Ile Gly Gln
            500                 505                 510

Thr Gly Asn Gln Asn Ala Lys Arg Ile Val Glu Lys Ile Arg Leu His
        515                 520                 525

Asp Gln Gln Glu Gly Lys Cys Leu Tyr Ser Leu Glu Ser Ile Ala Leu
    530                 535                 540

Met Asp Leu Leu Asn Asn Pro Gln Asn Tyr Glu Val Asp His Ile Ile
545                 550                 555                 560

Pro Arg Ser Val Ala Phe Asp Asn Ser Ile His Asn Lys Val Leu Val
                565                 570                 575

Lys Gln Ile Glu Asn Ser Lys Lys Gly Asn Arg Thr Pro Tyr Gln Tyr
            580                 585                 590

Leu Asn Ser Ser Asp Ala Lys Leu Ser Tyr Asn Gln Phe Lys Gln His
        595                 600                 605
```

```
Ile Leu Asn Leu Ser Lys Ser Lys Asp Arg Ile Ser Lys Lys Lys
610             615                 620

Asp Tyr Leu Leu Glu Glu Arg Asp Ile Asn Lys Phe Glu Val Gln Lys
625             630                 635                 640

Glu Phe Ile Asn Arg Asn Leu Val Asp Thr Arg Tyr Ala Thr Arg Glu
                645                 650                 655

Leu Thr Ser Tyr Leu Lys Ala Tyr Phe Ser Ala Asn Asn Met Asp Val
        660                 665                 670

Lys Val Lys Thr Ile Asn Gly Ser Phe Thr Asn His Leu Arg Lys Val
    675                 680                 685

Trp Arg Phe Asp Lys Tyr Arg Asn His Gly Tyr Lys His His Ala Glu
690             695                 700

Asp Ala Leu Ile Ile Ala Asn Ala Asp Phe Leu Phe Lys Glu Asn Lys
705             710                 715                 720

Lys Leu Lys Ala Val Asn Ser Val Leu Glu Lys Pro Glu Ile Glu Thr
                725                 730                 735

Lys Gln Leu Asp Ile Gln Val Asp Ser Glu Asp Asn Tyr Ser Glu Met
        740                 745                 750

Phe Ile Ile Pro Lys Gln Val Gln Asp Ile Lys Asp Phe Arg Asn Phe
    755                 760                 765

Lys Tyr Ser His Arg Val Asp Lys Lys Pro Asn Arg Gln Leu Ile Asn
770             775                 780

Asp Thr Leu Tyr Ser Thr Arg Lys Lys Asp Asn Ser Thr Tyr Ile Val
785             790                 795                 800

Gln Thr Ile Lys Asp Ile Tyr Ala Lys Asp Asn Thr Thr Leu Lys Lys
                805                 810                 815

Gln Phe Asp Lys Ser Pro Glu Lys Phe Leu Met Tyr Gln His Asp Pro
        820                 825                 830

Arg Thr Phe Glu Lys Leu Glu Val Ile Met Lys Gln Tyr Ala Asn Glu
    835                 840                 845

Lys Asn Pro Leu Ala Lys Tyr His Glu Glu Thr Gly Glu Tyr Leu Thr
850             855                 860

Lys Tyr Ser Lys Lys Asn Asn Gly Pro Ile Val Lys Ser Leu Lys Tyr
865             870                 875                 880

Ile Gly Asn Lys Leu Gly Ser His Leu Asp Val Thr His Gln Phe Lys
                885                 890                 895

Ser Ser Thr Lys Lys Leu Val Lys Leu Ser Ile Lys Pro Tyr Arg Phe
        900                 905                 910

Asp Val Tyr Leu Thr Asp Lys Gly Tyr Lys Phe Ile Thr Ile Ser Tyr
    915                 920                 925

Leu Asp Val Leu Lys Lys Asp Asn Tyr Tyr Ile Pro Glu Gln Lys
930             935                 940

Tyr Asp Lys Leu Lys Leu Gly Lys Ala Ile Asp Lys Asn Ala Lys Phe
945             950                 955                 960

Ile Ala Ser Phe Tyr Lys Asn Asp Leu Ile Lys Leu Asp Gly Glu Ile
                965                 970                 975

Tyr Lys Ile Ile Gly Val Asn Ser Asp Thr Arg Asn Met Ile Glu Leu
        980                 985                 990

Asp Leu Pro Asp Ile Arg Tyr Lys Glu Tyr Cys Glu Leu Asn Asn Ile
    995                 1000                1005

Lys Gly Glu Pro Arg Ile Lys Lys Thr Ile Gly Lys Lys Val Asn
    1010                1015                1020

Ser Ile Glu Lys Leu Thr Thr Asp Val Leu Gly Asn Val Phe Thr
```

```
            1025                1030               1035
Asn Thr  Gln Tyr Thr Lys Pro  Gln Leu Leu Phe Lys  Arg Gly Asn
         1040                 1045               1050

<210> SEQ ID NO 11
<211> LENGTH: 1053
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of F8-K737D-L739K

<400> SEQUENCE: 11

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Ile His Arg Leu
50                  55                  60

Glu Arg Val Lys Ser Leu Leu Ser Glu Tyr Lys Ile Ile Ser Gly Leu
65                  70                  75                  80

Ala Pro Thr Asn Asn Gln Pro Tyr Asn Ile Arg Val Lys Gly Leu Thr
                85                  90                  95

Glu Gln Leu Thr Lys Asp Glu Leu Ala Val Ala Leu Leu His Ile Ala
            100                 105                 110

Lys Arg Arg Gly Ile His Lys Ile Asp Val Ile Asp Ser Asn Asp Asp
        115                 120                 125

Val Gly Asn Glu Leu Ser Thr Lys Glu Gln Leu Asn Lys Asn Ser Lys
130                 135                 140

Leu Leu Lys Asp Lys Phe Val Cys Gln Ile Gln Leu Glu Arg Met Asn
145                 150                 155                 160

Glu Gly Gln Val Arg Gly Glu Lys Asn Arg Phe Lys Thr Ala Asp Ile
                165                 170                 175

Ile Lys Glu Ile Ile Gln Leu Leu Asn Val Gln Lys Asn Phe His Gln
            180                 185                 190

Leu Asp Glu Asn Phe Ile Asn Lys Tyr Ile Glu Leu Val Glu Met Arg
        195                 200                 205

Arg Glu Tyr Phe Glu Gly Pro Gly Gln Gly Ser Pro Phe Gly Trp Asn
210                 215                 220

Gly Asp Leu Lys Lys Trp Tyr Glu Met Leu Met Gly His Cys Thr Tyr
225                 230                 235                 240

Phe Pro Gln Glu Leu Arg Ser Val Lys Tyr Ala Tyr Ser Ala Asp Leu
                245                 250                 255

Phe Asn Ala Leu Asn Asp Leu Asn Asn Leu Ile Ile Gln Arg Asp Asn
            260                 265                 270

Ser Glu Lys Leu Glu Tyr His Glu Lys Tyr His Ile Ile Glu Asn Val
        275                 280                 285

Phe Lys Gln Lys Lys Lys Pro Thr Leu Lys Gln Ile Ala Lys Glu Ile
290                 295                 300

Gly Val Asn Pro Glu Asp Ile Lys Gly Tyr Arg Ile Thr Lys Ser Gly
305                 310                 315                 320

Thr Pro Glu Phe Thr Glu Phe Lys Leu Tyr His Asp Leu Lys Ser Val
```

```
                       325                 330                 335
Leu Phe Asp Gln Ser Ile Leu Glu Asn Glu Asp Val Leu Asp Gln Ile
                  340                 345                 350

Ala Glu Ile Leu Thr Ile Tyr Gln Asp Lys Asp Ser Ile Lys Ser Lys
                  355                 360                 365

Leu Thr Glu Leu Asp Ile Leu Leu Asn Glu Glu Asp Lys Glu Asn Ile
              370                 375                 380

Ala Gln Leu Thr Gly Tyr Asn Gly Thr His Arg Leu Ser Leu Lys Cys
385                 390                 395                 400

Ile Arg Leu Val Leu Glu Glu Gln Trp Tyr Ser Ser Arg Asn Gln Met
                  405                 410                 415

Glu Ile Phe Thr His Leu Asn Ile Lys Pro Lys Ile Asn Leu Thr
                  420                 425                 430

Ala Ala Asn Lys Ile Pro Lys Ala Met Ile Asp Glu Phe Ile Leu Ser
                  435                 440                 445

Pro Val Val Lys Arg Thr Phe Ile Gln Ser Ile Asn Val Ile Asn Lys
              450                 455                 460

Val Ile Glu Lys Tyr Gly Ile Pro Glu Asp Ile Ile Glu Leu Ala
465                 470                 475                 480

Arg Glu Asn Asn Ser Asp Asp Arg Lys Lys Phe Ile Asn Asn Leu Gln
                      485                 490                 495

Lys Lys Asn Glu Ala Thr Arg Lys Arg Ile Asn Glu Ile Ile Gly Gln
                  500                 505                 510

Thr Gly Asn Gln Asn Ala Lys Arg Ile Val Glu Lys Ile Arg Leu His
              515                 520                 525

Asp Gln Gln Glu Gly Lys Cys Leu Tyr Ser Leu Glu Ser Ile Ala Leu
          530                 535                 540

Met Asp Leu Leu Asn Asn Pro Gln Asn Tyr Glu Val Asp His Ile Ile
545                 550                 555                 560

Pro Arg Ser Val Ala Phe Asp Asn Ser Ile His Asn Lys Val Leu Val
                  565                 570                 575

Lys Gln Ile Glu Asn Ser Lys Lys Gly Asn Arg Thr Pro Tyr Gln Tyr
              580                 585                 590

Leu Asn Ser Ser Asp Ala Lys Leu Ser Tyr Asn Gln Phe Lys Gln His
              595                 600                 605

Ile Leu Asn Leu Ser Lys Ser Lys Asp Arg Ile Ser Lys Lys Lys Lys
          610                 615                 620

Asp Tyr Leu Leu Glu Glu Arg Asp Ile Asn Lys Phe Glu Val Gln Lys
625                 630                 635                 640

Glu Phe Ile Asn Arg Asn Leu Val Asp Thr Arg Tyr Ala Thr Arg Glu
                  645                 650                 655

Leu Thr Ser Tyr Leu Lys Ala Tyr Phe Ser Ala Asn Asn Met Asp Val
              660                 665                 670

Lys Val Lys Thr Ile Asn Gly Ser Phe Thr Asn His Leu Arg Lys Val
              675                 680                 685

Trp Arg Phe Asp Lys Tyr Arg Asn His Gly Tyr Lys His His Ala Glu
          690                 695                 700

Asp Ala Leu Ile Ile Ala Asn Ala Asp Phe Leu Phe Lys Glu Asn Lys
705                 710                 715                 720

Lys Leu Lys Ala Val Asn Ser Val Leu Glu Lys Pro Glu Ile Glu Thr
                  725                 730                 735

Asp Gln Lys Asp Ile Gln Val Asp Ser Glu Asp Asn Tyr Ser Glu Met
              740                 745                 750
```

```
Phe Ile Ile Pro Lys Gln Val Gln Asp Ile Lys Asp Phe Arg Asn Phe
            755                 760                 765

Lys Tyr Ser His Arg Val Asp Lys Lys Pro Asn Arg Gln Leu Ile Asn
    770                 775                 780

Asp Thr Leu Tyr Ser Thr Arg Lys Lys Asp Asn Ser Thr Tyr Ile Val
785                 790                 795                 800

Gln Thr Ile Lys Asp Ile Tyr Ala Lys Asp Asn Thr Thr Leu Lys Lys
                805                 810                 815

Gln Phe Asp Lys Ser Pro Glu Lys Phe Leu Met Tyr Gln His Asp Pro
                820                 825                 830

Arg Thr Phe Glu Lys Leu Glu Val Ile Met Lys Gln Tyr Ala Asn Glu
                835                 840                 845

Lys Asn Pro Leu Ala Lys Tyr His Glu Glu Thr Gly Glu Tyr Leu Thr
850                 855                 860

Lys Tyr Ser Lys Lys Asn Asn Gly Pro Ile Val Lys Ser Leu Lys Tyr
865                 870                 875                 880

Ile Gly Asn Lys Leu Gly Ser His Leu Asp Val Thr His Gln Phe Lys
                885                 890                 895

Ser Ser Thr Lys Lys Leu Val Lys Leu Ser Ile Lys Pro Tyr Arg Phe
                900                 905                 910

Asp Val Tyr Leu Thr Asp Lys Gly Tyr Lys Phe Ile Thr Ile Ser Tyr
            915                 920                 925

Leu Asp Val Leu Lys Lys Asp Asn Tyr Tyr Tyr Ile Pro Glu Gln Lys
            930                 935                 940

Tyr Asp Lys Leu Lys Leu Gly Lys Ala Ile Asp Lys Asn Ala Lys Phe
945                 950                 955                 960

Ile Ala Ser Phe Tyr Lys Asn Asp Leu Ile Lys Leu Asp Gly Glu Ile
                965                 970                 975

Tyr Lys Ile Ile Gly Val Asn Ser Asp Thr Arg Asn Met Ile Glu Leu
            980                 985                 990

Asp Leu Pro Asp Ile Arg Tyr Lys Glu Tyr Cys Glu Leu Asn Asn Ile
            995                 1000                1005

Lys Gly Glu Pro Arg Ile Lys Lys Thr Ile Gly Lys Lys Val Asn
    1010                1015                1020

Ser Ile Glu Lys Leu Thr Thr Asp Val Leu Gly Asn Val Phe Thr
    1025                1030                1035

Asn Thr Gln Tyr Thr Lys Pro Gln Leu Leu Phe Lys Arg Gly Asn
    1040                1045                1050

<210> SEQ ID NO 12
<211> LENGTH: 1053
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Polypeptide sequence of F8-K737N-L739N

<400> SEQUENCE: 12

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
                20                  25                  30

Val Arg Leu Phe Pro Glu Ala Asn Val Glu Asn Asn Glu Gly Arg Arg
            35                  40                  45
```

-continued

```
Ser Lys Arg Gly Ser Arg Leu Lys Arg Arg Ile His Arg Leu
    50                  55                  60
Glu Arg Val Lys Ser Leu Leu Ser Glu Tyr Lys Ile Ile Ser Gly Leu
65                  70                  75                  80
Ala Pro Thr Asn Asn Gln Pro Tyr Asn Ile Arg Val Lys Gly Leu Thr
                85                  90                  95
Glu Gln Leu Thr Lys Asp Glu Leu Ala Val Ala Leu Leu His Ile Ala
                100                 105                 110
Lys Arg Arg Gly Ile His Lys Ile Asp Val Ile Asp Ser Asn Asp Asp
                115                 120                 125
Val Gly Asn Glu Leu Ser Thr Lys Glu Gln Leu Asn Lys Asn Ser Lys
130                 135                 140
Leu Leu Lys Asp Lys Phe Val Cys Gln Ile Gln Leu Glu Arg Met Asn
145                 150                 155                 160
Glu Gly Gln Val Arg Gly Glu Lys Asn Arg Phe Lys Thr Ala Asp Ile
                165                 170                 175
Ile Lys Glu Ile Ile Gln Leu Leu Asn Val Gln Lys Asn Phe His Gln
                180                 185                 190
Leu Asp Glu Asn Phe Ile Asn Lys Tyr Ile Glu Leu Val Glu Met Arg
                195                 200                 205
Arg Glu Tyr Phe Glu Gly Pro Gly Gln Gly Ser Pro Phe Gly Trp Asn
                210                 215                 220
Gly Asp Leu Lys Lys Trp Tyr Glu Met Leu Met Gly His Cys Thr Tyr
225                 230                 235                 240
Phe Pro Gln Glu Leu Arg Ser Val Lys Tyr Ala Tyr Ser Ala Asp Leu
                245                 250                 255
Phe Asn Ala Leu Asn Asp Leu Asn Asn Leu Ile Ile Gln Arg Asp Asn
                260                 265                 270
Ser Glu Lys Leu Glu Tyr His Glu Lys Tyr His Ile Ile Glu Asn Val
                275                 280                 285
Phe Lys Gln Lys Lys Lys Pro Thr Leu Lys Gln Ile Ala Lys Glu Ile
                290                 295                 300
Gly Val Asn Pro Glu Asp Ile Lys Gly Tyr Arg Ile Thr Lys Ser Gly
305                 310                 315                 320
Thr Pro Glu Phe Thr Glu Phe Lys Leu Tyr His Asp Leu Lys Ser Val
                325                 330                 335
Leu Phe Asp Gln Ser Ile Leu Glu Asn Glu Asp Val Leu Asp Gln Ile
                340                 345                 350
Ala Glu Ile Leu Thr Ile Tyr Gln Asp Lys Asp Ser Ile Lys Ser Lys
                355                 360                 365
Leu Thr Glu Leu Asp Ile Leu Leu Asn Glu Glu Asp Lys Glu Asn Ile
                370                 375                 380
Ala Gln Leu Thr Gly Tyr Asn Gly Thr His Arg Leu Ser Leu Lys Cys
385                 390                 395                 400
Ile Arg Leu Val Leu Glu Glu Gln Trp Tyr Ser Ser Arg Asn Gln Met
                405                 410                 415
Glu Ile Phe Thr His Leu Asn Ile Lys Pro Lys Lys Ile Asn Leu Thr
                420                 425                 430
Ala Ala Asn Lys Ile Pro Lys Ala Met Ile Asp Glu Phe Ile Leu Ser
                435                 440                 445
Pro Val Val Lys Arg Thr Phe Ile Gln Ser Ile Asn Val Ile Asn Lys
450                 455                 460
```

```
Val Ile Glu Lys Tyr Gly Ile Pro Glu Asp Ile Ile Glu Leu Ala
465                 470                 475                 480

Arg Glu Asn Asn Ser Asp Asp Arg Lys Lys Phe Ile Asn Asn Leu Gln
            485                 490                 495

Lys Lys Asn Glu Ala Thr Arg Lys Arg Ile Asn Glu Ile Ile Gly Gln
            500                 505                 510

Thr Gly Asn Gln Asn Ala Lys Arg Ile Val Glu Lys Ile Arg Leu His
            515                 520                 525

Asp Gln Gln Glu Gly Lys Cys Leu Tyr Ser Leu Glu Ser Ile Ala Leu
            530                 535                 540

Met Asp Leu Leu Asn Asn Pro Gln Asn Tyr Glu Val Asp His Ile Ile
545                 550                 555                 560

Pro Arg Ser Val Ala Phe Asp Asn Ser Ile His Asn Lys Val Leu Val
                565                 570                 575

Lys Gln Ile Glu Asn Ser Lys Lys Gly Asn Arg Thr Pro Tyr Gln Tyr
                580                 585                 590

Leu Asn Ser Ser Asp Ala Lys Leu Ser Tyr Asn Gln Phe Lys Gln His
                595                 600                 605

Ile Leu Asn Leu Ser Lys Ser Lys Asp Arg Ile Ser Lys Lys Lys
610                 615                 620

Asp Tyr Leu Leu Glu Glu Arg Asp Ile Asn Lys Phe Glu Val Gln Lys
625                 630                 635                 640

Glu Phe Ile Asn Arg Asn Leu Val Asp Thr Arg Tyr Ala Thr Arg Glu
                645                 650                 655

Leu Thr Ser Tyr Leu Lys Ala Tyr Phe Ser Ala Asn Asn Met Asp Val
                660                 665                 670

Lys Val Lys Thr Ile Asn Gly Ser Phe Thr Asn His Leu Arg Lys Val
                675                 680                 685

Trp Arg Phe Asp Lys Tyr Arg Asn His Gly Tyr Lys His His Ala Glu
                690                 695                 700

Asp Ala Leu Ile Ile Ala Asn Ala Asp Phe Leu Phe Lys Glu Asn Lys
705                 710                 715                 720

Lys Leu Lys Ala Val Asn Ser Val Leu Glu Lys Pro Glu Ile Glu Thr
                725                 730                 735

Asn Gln Asn Asp Ile Gln Val Asp Ser Glu Asp Asn Tyr Ser Glu Met
                740                 745                 750

Phe Ile Ile Pro Lys Gln Val Gln Asp Ile Lys Asp Phe Arg Asn Phe
                755                 760                 765

Lys Tyr Ser His Arg Val Asp Lys Lys Pro Asn Arg Gln Leu Ile Asn
                770                 775                 780

Asp Thr Leu Tyr Ser Thr Arg Lys Lys Asp Asn Ser Thr Tyr Ile Val
785                 790                 795                 800

Gln Thr Ile Lys Asp Ile Tyr Ala Lys Asp Asn Thr Thr Leu Lys Lys
                805                 810                 815

Gln Phe Asp Lys Ser Pro Glu Lys Phe Leu Met Tyr Gln His Asp Pro
                820                 825                 830

Arg Thr Phe Glu Lys Leu Glu Val Ile Met Lys Gln Tyr Ala Asn Glu
                835                 840                 845

Lys Asn Pro Leu Ala Lys Tyr His Glu Glu Thr Gly Glu Tyr Leu Thr
                850                 855                 860

Lys Tyr Ser Lys Lys Asn Asn Gly Pro Ile Val Lys Ser Leu Lys Tyr
865                 870                 875                 880

Ile Gly Asn Lys Leu Gly Ser His Leu Asp Val Thr His Gln Phe Lys
```

```
          885                 890                 895
Ser Ser Thr Lys Lys Leu Val Lys Leu Ser Ile Lys Pro Tyr Arg Phe
            900                 905                 910

Asp Val Tyr Leu Thr Asp Lys Gly Tyr Lys Phe Ile Thr Ile Ser Tyr
            915                 920                 925

Leu Asp Val Leu Lys Lys Asp Asn Tyr Tyr Ile Pro Glu Gln Lys
        930                 935                 940

Tyr Asp Lys Leu Lys Leu Gly Lys Ala Ile Asp Lys Asn Ala Lys Phe
945                 950                 955                 960

Ile Ala Ser Phe Tyr Lys Asn Asp Leu Ile Lys Leu Asp Gly Glu Ile
                965                 970                 975

Tyr Lys Ile Ile Gly Val Asn Ser Asp Thr Arg Asn Met Ile Glu Leu
            980                 985                 990

Asp Leu Pro Asp Ile Arg Tyr Lys  Glu Tyr Cys Glu Leu  Asn Asn Ile
            995                 1000                1005

Lys Gly  Glu Pro Arg Ile Lys  Lys Thr Ile Gly Lys  Lys Val Asn
    1010                1015                1020

Ser Ile  Glu Lys Leu Thr Thr  Asp Val Leu Gly Asn  Val Phe Thr
    1025                1030                1035

Asn Thr  Gln Tyr Thr Lys Pro  Gln Leu Leu Phe Lys  Arg Gly Asn
    1040                1045                1050
```

<210> SEQ ID NO 13
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding Gib11

<400> SEQUENCE: 13

```
atgaaccaga aatttatcct gggtctggat attggtatta ccagcgttgg ttatggcctg      60
attgattacg aaaccaaaaa cattattgat gccggtgttc gtctgttttc cggaagcaaat    120 gttgaaaata tgaaggtcg tcgtagcaaa cgtggtagcc gtcgtctgaa acgtcgtcgt      180
attcatcgtc tggaacgtgt taaactgctg ctgaccgaat atgatctgat taacaaagag    240
cagattccga ccagcaataa cccgtatcag attcgtgtta aggtctgag cgaaatcctg      300 agcaaagatg aactggcaat tgcactgctg catctggcaa aacgccgtgg cattcataat    360
gttgatgttg cagcagataa agaagaaacc gcaagcgata gcctgagcac aaagatcag      420 attaacaaaa acgccaaatt tctggaaagc cgctatgttt gtgaactgca gaaagaacgt    480
ctggaaaatg aaggtcatgt tcgtggtgtt gaaaatcgct ttctgacgaa agatattgtg    540
cgtgaggcca aaaaatcat cgatacccag atgcagtatt acccggaaat tgatgaaacc    600
ttcaaagaga aatatatcag cctggttgaa accgtcgcg aatatttga aggtcctggt      660 cagggtagcc cgtttggttg aatggtgat ctgaaaaaat ggtacgaaat gctgatgggt      720
cactgtacct attttccgca agaactgcgt agcgttaaat atgcctatag cgcagacctg    780
tttaatgcac tgaatgatct gaacaacctg attattcagc gcgataatag cgagaaactg    840
gaataccatg agaagtatca catcatcgag aacgtgttca agcagaaaaa aaagccgacg    900
ctgaaacaaa tcgcaaaaga gattggcgtt aacccggaag atattaaagg ttatcgtatt      960
accaaaagcg gcacaccgga gtttacatcc tttaaactgt tccacgatct gaaaaagtg    1020
```

| | |
|---|---|
| gtgaaagatc atgccatcct ggatgatatt gatctgctga atcagattgc agaaatcctg | 1080 |
| accatctatc aggataaaga tagcattgtt gcagaactgg gtcagctgga atatctgatg | 1140 |
| agcgaagccg ataaacagag cattagcgaa ctgaccggtt ataccggtac acatagcctg | 1200 |
| tcactgaaat gcatgaacat gattatcgat gaactgtggc atagcagcat gaaccagatg | 1260 |
| gaagttttta cctatctgaa tatgcgtccg aaaaagtatg agctgaaagg ttatcagcgt | 1320 |
| attccgaccg atatgattga tgatgcaatt ctgagtccgg ttgtgaaacg cacctttatt | 1380 |
| cagagcatca acgtgatcaa caaagtgatc gagaaatatg catcccccga agatatcatt | 1440 |
| atcgaactgg cacgtgaaaa taactccgat gatcgcaaaa agttcatcaa caacctgcag | 1500 |
| aaaaagaatg aagcaacccg caaacgcatt aacgaaatta ttggtcagac cggtaatcag | 1560 |
| aatgccaaac gtattgtgga aaaaatccgt ctgcatgatc agcaagaggg caaatgtctg | 1620 |
| tatagcctgg aaagcattcc tctggaagat ctgctgaaca tccgaatca ttatgaagtg | 1680 |
| gatcacatta ttccgcgtag cgtgagcttt gataattcct atcataataa agtgctggtg | 1740 |
| aaacagagcg aaaactccaa aaaatccaac ctgacaccgt atcagtattt caatagcggc | 1800 |
| aaatccaaac tgagctacaa ccagtttaaa cagcatattc tgaacctgag caaaagccag | 1860 |
| gatcgcatca gcaagaagaa gaaggagtac ctgctggaag aacgcgacat caacaaattt | 1920 |
| gaagtgcaga aagaatttat caaccgcaac ctggttgata cccgttatgc aacccgtgaa | 1980 |
| ctgaccaatt atctgaaagc atatttcagc gccaacaaca tgaacgtgaa agtgaaaacg | 2040 |
| attaacggca gctttaccga ttatctgcgt aaagtgtgga aattcaaaaa agaacgcaac | 2100 |
| cacggctata aacatcatgc cgaagatgcc ctgattattg caaatgcaga tttcctgttt | 2160 |
| aaagaaaaca aaaaactgaa agccgtcaac agcgtgctgg aaaaaccgga aattgagaca | 2220 |
| aaacagctgg acattcaggt tgatagcgaa gataattaca gcgaaatgtt tatcatcccg | 2280 |
| aaacaggtgc aggatatcaa agattttcgc aacttcaaat atagccaccg cgttgacaaa | 2340 |
| aaacctaatc gtcagctgat taacgatacc ctgtatagca cccgcaaaaa agataacagc | 2400 |
| acctatattg tgcagaccat taaagacatc tacgccaaag ataataccac cctgaaaaaa | 2460 |
| cagttcgaca aaagcccaga aaaatttctg atgtatcagc atgatccgcg taccttcgaa | 2520 |
| aaactggaag ttattatgaa acagtatgcc aacgagaaaa atccgctggc caaatatcac | 2580 |
| gaagaaaccg gtaatatct gaccaaatat tccaagaaga caacggtcc gatcgttaaa | 2640 |
| tccctgaaat atatcggtaa taaactgggc agccatctgg atgttaccca tcagtttaaa | 2700 |
| agctccacaa agaagctggt taaactgtcc atcaaaccgt atcgctttga tgtgtatctg | 2760 |
| accgacaaag gctataaatt cattaccatc agctatctgg acgtgctgaa aaaagacaac | 2820 |
| tattattata tcccggaaca gaaatatgat aaactgaaac tgggtaaagc catcgataaa | 2880 |
| aacgccaaat ttatcgccag cttctacaaa aacgacctga ttaaactgga tggcgagatc | 2940 |
| tataaaatca tcggtgttaa tagcgacacc cgcaatatga ttgagctgga tctgccggat | 3000 |
| attcgctata agaatattg cgaactgaac aacattaaag gcgaaccgcg tatcaaaaag | 3060 |
| accatcggca aaaagtgaa tagcatcgag aaactgacca ccgatgttct gggtaatgtg | 3120 |
| tttaccaata cccagtatac caaacctcag ctgctgttca aacgcggtaa t | 3171 |

<210> SEQ ID NO 14
<211> LENGTH: 3171
<212> TYPE: DNA
<213> ORGANISM: Artificial sequence
<220> FEATURE:
<223> OTHER INFORMATION: Synthetic polynucleotide

```
<220> FEATURE:
<221> NAME/KEY: misc_feature
<223> OTHER INFORMATION: DNA sequence encoding Gib11Spa-1

<400> SEQUENCE: 14
atgaaccaga aatttatcct gggtctggat attggtatta ccagcgttgg ttatggcctg      60
attgattacg aaaccaaaaa cattattgat gccggtgttc gtctgtttcc ggaagcaaat     120
gttgaaaata tgaaggtcg tcgtagcaaa cgtggtagcc gtcgtctgaa acgtcgtcgt      180
attcatcgtc tggaacgtgt taaactgctg ctgaccgaat atgatctgat taacaaagag     240
cagattccga ccagcaataa cccgtatcag attcgtgtta aggtctgag cgaaatcctg      300
agcaaagatg aactggcaat tgcactgctg catctggcaa aacgccgtgg cattcataat     360
gttgatgttg cagcagataa agaagaaacc gcaagcgata gcctgagcac aaagatcag     420
attaacaaaa acgccaaatt tctggaaagc cgctatgttt gtgaactgca gaaagaacgt     480
ctggaaaatg aaggtcatgt tcgtggtgtt gaaaatcgct ttctgacgaa agatattgtg     540
cgtgaggcca aaaaaatcat cgatacccag atgcagtatt acccggaaat tgatgaaacc     600
ttcaaagaga aatatatcag cctggttgaa acccgtcgcg aatattttga aggtcctggt     660
cagggtagcc cgtttggttg gaatggtgat ctgaaaaaat ggtacgaaat gctgatgggt     720
cactgtacct attttccgca agaactgcgt agcgttaaat atgcctatag cgcagacctg     780
tttaatgcac tgaatgatct gaacaacctg attattcagc gcgataatag cgagaaactg     840
gaataccatg agaagtatca catcatcgag aacgtgttca gcagaaaaaa aaagccgacg     900
ctgaaacaaa tcgcaaaaga gattggcgtt aacccggaag atattaaagg ttatcgtatt     960
accaaaagcg gcacaccgga gtttacatcc tttaaactgt tccacgatct gaaaaaagtg    1020
gtgaaagatc atgccatcct ggatgatatt gatctgctga tcagattgc agaaatcctg     1080
accatctatc aggataaaga tagcattgtt gcagaactgg gtcagctgga atatctgatg    1140
agcgaagccg ataaacagag cattagcgaa ctgaccggtt ataccggtac acatagcctg    1200
tcactgaaat gcatgaacat gattatcgat gaactgtggc atagcagcat gaaccagatg    1260
gaagttttta cctatctgaa tatgcgtccg aaaaagtatg agctgaaagg ttatcagcgt    1320
attccgaccg atatgattga tgatgcaatt ctgagtccgg ttgtgaaacg cacctttatt    1380
cagagcatca acgtgatcaa caaagtgatc gagaaatatg gcatccccga agatatcatt    1440
atcgaactgg cacgtgaaaa taactccgat gatcgcaaaa agttcatcaa caacctgcag    1500
aaaaagaatg aagcaacccg caaacgcatt aacgaaatta ttggtcagac cggtaatcag    1560
aatgccaaac gtattgtgga aaaaatccgt ctgcatgatc agcaagaggg caaatgtctg    1620
tatagcctgg aaagcattcc tctggaagat ctgctgaaca atccgaatca ttatgaagtg    1680
gatcacatta ttccgcgtag cgtgagcttt gataattcct atcataataa agtgctggtg    1740
aaacagagcg aaaactccaa aaaatccaac ctgacaccgt atcagtattt caatagcggc    1800
aaatccaaac tgagctacaa ccagtttaaa cagcatattc tgaacctgag caaagccag     1860
gatcgcatca gcaagaagaa gaaggagtac ctgctggaag aacgcgatat taacaaattt    1920
gaagtgcaga aagaatttat caaccgcaac ctggttgata cccgttatgc aacccgtgaa    1980
ctgaccaatt atctgaaagc atatttcagc gccaacaaca tgaacgtgaa agtgaaaacg    2040
attaacggca gctttaccga ttatctgcgt aaagtgtgga aattcaaaaa agaacgcaac    2100
cacggctata acatcatgc cgaagatgcc ctgattattg caaatgcaga tttcctgttt    2160
aaagaaaaca aaaaactgaa agccgtcaac agcgtgctgg aaaaaccgga aattgagaca    2220
```

-continued

| | |
|---|---|
| aaacagctgg acattcaggt tgatagcgaa gataattaca gcgaaatgtt tatcatcccg | 2280 |
| aaacaggtgc aggatatcaa agattttcgc aacttcaaat atagccaccg cgttgacaaa | 2340 |
| aaacctaatc gtcagctgat taacgatacc ctgtatagca cccgcaaaaa agataacagc | 2400 |
| acctatattg tgcagaccat taaagacatc tacgccaaag ataataccac cctgaaaaaa | 2460 |
| cagttcgaca aaagcccaga aaaatttctg atgtatcagc atgatccgcg taccttcgaa | 2520 |
| aaactggaag ttattatgaa acagtatgcc aacgagaaaa tccgctggc caaatatcac | 2580 |
| gaagaaaccg gtgaatatct gaccaaatat ccaagaaga caacggtcc gatcgttaaa | 2640 |
| tccctgaaat atatcggtaa taaactgggc agccatctgg atgttaccca tcagtttaaa | 2700 |
| agctccacaa agaagctggt taagctgtcc attaaaaact atcgcttcga tgtgtatctg | 2760 |
| accgagaaag ttataagtt tgtgaccatt gcctacctga atgtgttcaa aaaagacaac | 2820 |
| tattactata ttccgaaaga caaataccaa gaacttaaag agaagaagaa aatcaaggac | 2880 |
| accgatcagt ttatcgccag cttctataaa acgatctga tcaagctgaa cggcgacctg | 2940 |
| tataaaatca ttggtgtgaa tagtgatgac cgcaacatca ttgagctgga ttattacgac | 3000 |
| atcaaataca aggattactg cgagatcaac aacattaaag gtgaaccgcg tatcaaaaag | 3060 |
| accattggca aaaaacgga agcatcgaa aagtttacca ccgatgttct gggtaatctg | 3120 |
| tatctgcata gtaccgaaaa agcaccgcag ctgattttca aacgcggtct g | 3171 |

<210> SEQ ID NO 15
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized Gib11Spa-1 polynucleotide

<400> SEQUENCE: 15

| | |
|---|---|
| atgaaccaga agttcattct cggtctggac attggcatta ctagcgtggg atacggcttg | 60 |
| attgactacg agactaagaa catcatcgat gccggcgtcc gcctgttccc ggaagccaac | 120 |
| gtggagaaca atgagggccg gaggtcgaag agaggctccc gccgcctgaa gcggcggcga | 180 |
| atccaccggc tggagagagt gaagctgctg ctcaccgaat cgacctgat caacaaagaa | 240 |
| cagatcccga cctccaacaa cccgtaccag atcagagtga agggtctgtc agaaatcctg | 300 |
| tccaaggacg aactggcaat cgccctgctg cacctggcca gcggcgcgg aatccacaac | 360 |
| gtggatgtgg ctgccgacaa ggaagaaacc gcttccgact ccctgagcac taaggaccag | 420 |
| atcaacaaga acgccaagtt cttggagtcc cgctacgtgt gcgagctgca gaaggaacgg | 480 |
| ctggaaaacg aaggtcacgt gcgcggagtg gaaaaccggt tcctgacaaa ggacattgtg | 540 |
| cgcgaagcga agaagatcat tgatacccaa atgcagtact accctgaaat cgacgagact | 600 |
| ttcaaggaaa agtacatttc cctggtggaa acccggcggg aatacttcga aggccccgga | 660 |
| cagggatcgc cgttcggatg aacggggac ctcaagaagt ggtacgagat gctgatgggg | 720 |
| cactgtacct actttccgca agaactgcgc tccgtgaagt acgcgtactc cgcggatctc | 780 |
| ttcaacgcgt tgaatgacct gaacaacctg atcattcaga gagacaattc cgaaaagctc | 840 |
| gagtaccacg agaagtatca catcatcgag aatgtgttca gcagaagaa gaaaccgacc | 900 |
| ctcaagcaaa tcgccaagga gattggcgtc aacccagagg acatcaaggg atatcggatt | 960 |
| accaagagcg gcactcccga gtttaccct tccaagctgt ttcatgatct gaagaaagtc | 1020 |

```
gtgaaggacc atgccattct cgacgacatt gatctcctga atcagatcgc agagatcctg    1080
actatctacc aagacaagga ctcgattgtg gcagagctgg gtcagctcga atacctgatg    1140
tccgaggccg acaagcagtc catctccgaa ctgacagggt acacggggac tcatagcctg    1200
tcgctgaagt gcatgaacat gatcattgat gaactgtggc acagctccat gaaccaaatg    1260
gaagtgttta cctacctcaa catgcgccct aagaagtacg aactgaaagg ctaccagcgc    1320
atccccaccg acatgatcga cgacgcgatc ttgtccctg tggtcaagag gaccttcatt    1380
caatccatca acgtgatcaa caaggtcatc gaaaagtacg gaataccaga agatatcatc    1440
attgagctcg ctcgggagaa caactcggat gaccggaaga agttcatcaa caatcttcag    1500
aagaagaacg aagcgactcg gaaacggatc aacgagatca tcggacagac cggaaaccag    1560
aacgccaaac ggattgtcga aaagattaga ctgcacgacc agcaggaagg gaagtgcctg    1620
tactcactcg agtcaatacc gctcgaggac ctgttgaaca accctaacca ctatgaagtg    1680
gaccacatca tccctcggtc cgtgagcttc gacaactcgt accacaacaa agtgctcgtg    1740
aagcagtccg aaaactccaa gaaatccaac ctgaccccgt accaatactt caattcggga    1800
aagtcgaagc tgtcgtacaa ccagttcaaa caacacatac tcaaccttag caaaagccag    1860
gatcgcattt ccaagaagaa gaaggaatac ctcctcgagg aaagggacat caacaagttc    1920
gaagtgcaga aagagttcat caatcgcaac ttggtggata ccagatatgc cacccgggaa    1980
ctcaccaact atctcaaggc ctactttcc gccaacaaca tgaacgtgaa ggtcaagacc    2040
atcaacgggt ccttcactga ctacctgaga aaggtctgga agttcaagaa ggaacgcaac    2100
cacggataca agcaccacgc tgaggacgct ctgatcatcg ccaatgccga cttcctgttc    2160
aaggaaaaca gaagctgaa agctgtcaac tcagtgctgg aaaagcctga atcgagact    2220 aagcagctgg atatccaagt ggactctgag gacaactaca gcgagatgtt catcatccct    2280
aaacaagtgc aggatatcaa ggactttcgc aacttcaagt actcacaccg ggtggacaag    2340
aaaccgaata gacagctgat caacgacacg ttgtattcca cccggaagaa ggataactca    2400
acctacattg tgcagactat caaggatatc tacgccaaag ataacactac tctgaagaaa    2460
caattcgaca agtccccaga gaagttcctg atgtaccagc acgacccccg aacctttgag    2520
aagcttgaag tgatcatgaa gcagtacgcc aacgagaaga acccgctggc caagtaccat    2580
gaagaaaccg gagaatacct gaccaagtac agcaagaaga caacggtcc cattgtcaag    2640 agcctgaagt acatcggcaa caagctggga tcccacctcg acgtgacaca tcagttcaag    2700
tcgtcgacta agaagcttgt gaagctgtca atcaagaact atagattcga cgtgtacttg    2760
accgaaaagg gatacaagtt cgtgaccata gcctatctga acgtgttcaa gaaagataac    2820
tactactaca tccccaagga caagtaccag gagctcaaag aaaagaagaa gatcaaagac    2880
accgaccagt tcattgcctc cttctacaag aacgacctga tcaaactgaa cggcgacctc    2940
tacaagatca ttggagtgaa cagcgatgac aggaacatca ttgagctgga ctactacgac    3000
atcaagtaca aggactactg cgagatcaac aacatcaagg gcgaaccccg gatcaagaaa    3060
actattggaa agaaaaccga gtccattgag aagttcacca ctgacgtgct gggaaacctt    3120
tacctccact ccaccgagaa ggcaccacaa ctgatcttca agcgcggcct g             3171

<210> SEQ ID NO 16
<211> LENGTH: 3171
<212> TYPE: DNA
<213> ORGANISM: Artificial sequence
<220> FEATURE:
```

<223> OTHER INFORMATION: Synthetic polynucleotide
<220> FEATURE:
<221> NAME/KEY: misc_feature
<223> OTHER INFORMATION: DNA sequence encoding Gib11Spa-2

<400> SEQUENCE: 16

| | | | | | |
|---|---|---|---|---|---|
| atgaaccaga | aatttatcct | gggtctggat | attggtatta | ccagcgttgg | ttatggcctg | 60 |
| attgattacg | aaaccaaaaa | cattattgat | gccggtgttc | gtctgtttcc | ggaagcaaat | 120 |
| gttgaaaata | atgaaggtcg | tcgtagcaaa | cgtggtagcc | gtcgtctgaa | acgtcgtcgt | 180 |
| attcatcgtc | tggaacgtgt | taaactgctg | ctgaccgaat | atgatctgat | taacaaagag | 240 |
| cagattccga | ccagcaataa | cccgtatcag | attcgtgtta | aggtctgag | cgaaatcctg | 300 |
| agcaaagatg | aactggcaat | tgcactgctg | catctggcaa | aacgccgtgg | cattcataat | 360 |
| gttgatgttg | cagcagataa | agaagaaacc | gcaagcgata | gcctgagcac | caaagatcag | 420 |
| attaacaaaa | acgccaaatt | tctggaaagc | cgctatgttt | gtgaactgca | gaaagaacgt | 480 |
| ctggaaaatg | aaggtcatgt | tcgtggtgtt | gaaaatcgct | ttctgacgaa | agatattgtg | 540 |
| cgtgaggcca | aaaaaatcat | cgatacccag | atgcagtatt | acccggaaat | tgatgaaacc | 600 |
| ttcaaagaga | aatatatcag | cctggttgaa | acccgtcgcg | aatattttga | aggtcctggt | 660 |
| cagggtagcc | cgtttggttg | aatggtgat | ctgaaaaaat | ggtacgaaat | gctgatgggt | 720 |
| cactgtacct | attttccgca | agaactgcgt | agcgttaaat | atgcctatag | cgcagacctg | 780 |
| tttaatgcac | tgaatgatct | gaacaacctg | attattcagc | gcgataatag | cgagaaactg | 840 |
| gaataccatg | agaagtatca | catcatcgag | aacgtgttca | agcagaaaaa | aaagccgacg | 900 |
| ctgaaacaaa | tcgcaaaaga | gattggcgtt | aacccggaag | atattaaagg | ttatcgtatt | 960 |
| accaaaagcg | gcacaccgga | gtttacatcc | tttaaactgt | tccacgatct | gaaaaaagtg | 1020 |
| gtgaaagatc | atgccatcct | ggatgatatt | gatctgctga | atcagattgc | agaaatcctg | 1080 |
| accatctatc | aggataaaga | tagcattgtt | gcagaactgg | gtcagctgga | atatctgatg | 1140 |
| agcgaagccg | ataaacagag | cattagcgaa | ctgaccggtt | ataccggtac | acatagcctg | 1200 |
| tcactgaaat | gcatgaacat | gattatcgat | gaactgtggc | atagcagcat | gaaccagatg | 1260 |
| gaagttttta | cctatctgaa | tatgcgtccg | aaaaagtatg | agctgaaagg | ttatcagcgt | 1320 |
| attccgaccg | atatgattga | tgatgcaatt | ctgagtccgg | ttgtgaaacg | cacctttatt | 1380 |
| cagagcatca | acgtgatcaa | caaagtgatc | gagaaatatg | gcatcccga | agatatcatt | 1440 |
| atcgaactgg | cacgtgaaaa | taactccgat | gatcgcaaaa | agttcatcaa | caacctgcag | 1500 |
| aaaaagaatg | aagcaacccg | caaacgcatt | aacgaaatta | ttggtcagac | cggtaatcag | 1560 |
| aatgccaaac | gtattgtgga | aaaaatccgt | ctgcatgatc | agcaagaggg | caaatgtctg | 1620 |
| tatagcctgg | aaagcattcc | tctggaagat | ctgctgaaca | tccgaatca | ttatgaagtg | 1680 |
| gatcacatta | ttccgcgtag | cgtgagcttt | gataattcct | atcataataa | agtgctggtg | 1740 |
| aaacagagcg | aaaactccaa | aaaatccaac | ctgacaccgt | atcagtattt | caatagcggc | 1800 |
| aaatccaaac | tgagctacaa | ccagtttaaa | cagcatattc | tgaacctgag | caaaagccag | 1860 |
| gatcgcatca | gcaagaagaa | gaaggagtac | ctgctggaag | aacgcgatat | taacaaattt | 1920 |
| gaagtgcaga | agaatttat | caaccgcaac | ctggttgata | cccgttatgc | aacccgtgaa | 1980 |
| ctgaccaatt | atctgaaagc | atatttcagc | gccaacaaca | tgaacgtgaa | agtgaaaacg | 2040 |
| attaacggca | gctttaccga | ttatctgcgt | aaagtgtgga | aattcaaaaa | agaacgcaac | 2100 |
| cacggctata | acatcatgc | cgaagatgcc | ctgattattg | caaatgcaga | tttcctgttt | 2160 |

```
aaagaaaaca aaaaactgaa agccgtcaac agcgtgctgg aaaaaccgga aattgagaca    2220
aaacagctgg acattcaggt tgatagcgaa gataattaca gcgaaatgtt tatcatcccg    2280
aaacaggtgc aggatatcaa agattttcgc aacttcaaat tcagccaccg cgttgataaa    2340
aaaccgaatc gtcagctgat taacgatacc ctgtatagca cccgtatgaa agatgagcat    2400
gattatattg tgcagaccat cacggatatc tatggcaaag ataataccaa cctgaaaaaa    2460
cagttcaaca aaacccggaa aaatttctg atgtatcaga cgatccgaa aacctttgag     2520 aaactgagca tcatcatgaa acagtacagc gacgaaaaaa acccgctggc caaatattac    2580
gaagaaaccg tgaatatct gaccaaatat agcaagaaaa acaacggtcc gatcgtgaaa    2640
aagatcaaac tgctgggtaa taaagtgggc aatcatctgg atgtgaccaa caaatatgaa    2700
aactccacga gaagctggt taagctgtcc attaaaaact atcgcttcga tgtgtatctg     2760
accgagaaag gttataagtt tgtgaccatt gcctacctga atgtgttcaa aaaagacaac    2820
tattactata ttccgaaaga caaataccaa gaacttaaag agaagaagaa aatcaaggac    2880
accgatcagt ttatcgccag cttctataaa aacgatctga tcaagctgaa cggcgacctg    2940
tataaaatca ttggtgtgaa tagtgatgac cgcaacatca ttgagctgga ttattacgac    3000
atcaaataca aggattactg cgagatcaac aacattaaag gtgaaccgcg tatcaaaaag    3060
accattggca aaaaacgga agcatcgaa aagtttacca ccgatgttct gggtaatctg      3120
tatctgcata gtaccgaaaa agcaccgcag ctgattttca aacgcggtct g             3171
```

<210> SEQ ID NO 17  
<211> LENGTH: 3171  
<212> TYPE: DNA  
<213> ORGANISM: Artificial sequence  
<220> FEATURE:  
<223> OTHER INFORMATION: Synthetic polynucleotide  
<220> FEATURE:  
<221> NAME/KEY: misc_feature  
<223> OTHER INFORMATION: DNA sequence encoding Gib11Spa-3

<400> SEQUENCE: 17

```
atgaaccaga aatttatcct gggtctggat attggtatta ccagcgttgg ttatggcctg     60
attgattacg aaaccaaaaa cattattgat gccggtgttc gtctgtttcc ggaagcaaat    120
gttgaaaata tgaaggtcg tcgtagcaaa cgtggtagcc gtcgtctgaa acgtcgtcgt     180
attcatcgtc tggaacgtgt taaactgctg ctgaccgaat atgatctgat taacaaagag    240
cagattccga ccagcaataa cccgtatcag attcgtgtta aggtctgag cgaaatcctg    300 agcaaagatg aactggcaat tgcactgctg catctggcaa acgccgtgg cattcataat     360 gttgatgttg cagcagataa agaagaaacc gcaagcgata gcctgagcac caaagatcag    420
attaacaaaa acgccaaatt tctggaaagc cgctatgttt gtgaactgca gaaagaacgt    480
ctggaaaatg aaggtcatgt tcgtggtgtt gaaaatcgct ttctgacgaa agatattgtg    540
cgtgaggcca aaaaatcat cgatacccag atgcagtatt acccggaaat tgatgaaacc    600
ttcaaagaga atatatcag cctggttgaa acccgtcgcg aatattttga aggtcctggt     660
cagggtagcc cgtttggttg aatggtgat ctgaaaaaat ggtacgaaat gctgatgggt    720
cactgtacct attttccgca agaactgcgt agcgttaaat atgcctatag cgcagacctg    780
tttaatgcac tgaatgatct gaacaacctg attattcagc gcgataatag cgagaaactg    840
gaataccatg agaagtatca catcatcgag aacgtgttca agcagaaaaa aaagccgacg    900
ctgaaacaaa tcgcaaaaga gattggcgtt aacccggaag atattaaagg ttatcgtatt    960
```

```
accaaaagcg gcacaccgga gtttacatcc tttaaactgt tccacgatct gaaaaaagtg    1020
gtgaaagatc atgccatcct ggatgatatt gatctgctga atcagattgc agaaatcctg    1080
accatctatc aggataaaga tagcattgtt gcagaactgg gtcagctgga atatctgatg    1140
agcgaagccg ataaacagag cattagcgaa ctgaccggtt ataccggtac acatagcctg    1200
tcactgaaat gcatgaacat gattatcgat gaactgtggc atagcagcat gaaccagatg    1260
gaagttttta cctatctgaa tatgcgtccg aaaaagtatg agctgaaagg ttatcagcgt    1320
attccgaccg atatgattga tgatgcaatt ctgagtccgg ttgtgaaacg cacctttatt    1380
cagagcatca acgtgatcaa caaagtgatc gagaaatatg gcatccccga agatatcatt    1440
atcgaactgg cacgtgaaaa taactccgat gatcgcaaaa agttcatcaa caacctgcag    1500
aaaaagaatg aagcaacccg caaacgcatt aacgaaatta ttggtcagac cggtaatcag    1560
aatgccaaac gtattgtgga aaaaatccgt ctgcatgatc agcaagaggg caaatgtctg    1620
tatagcctgg aaagcattcc tctggaagat ctgctgaaca atccgaatca ttatgaagtg    1680
gatcacatta ttccgcgtag cgtgagcttt gataattcct atcataataa agtgctggtg    1740
aaacagagcg aaaactccaa aaaatccaac ctgacaccgt atcagtattt caatagcggc    1800
aaatccaaac tgagctacaa ccagtttaaa cagcatattc tgaacctgag caaaagccag    1860
gatcgcatca gcaagaagaa gaaggagtac ctgctggaag aacgcgatat caacaaattt    1920
gaagtccaga aagagtttat caaccgcaat ctggttgata cccgttatgc aacccgtgaa    1980
ctgaccagct atctgaaagc atatttcagc gccaataaca tggacgtgaa agtgaaaaca    2040
attaacggca gctttaccaa ccatctgcgt aaagtttggc gctttgataa atatcgcaac    2100
cacggctata acatcatgc cgaagatgca ctgattattg ccaatgcaga tttcctgttc    2160
aaagaaaaca aaaaactgca gaacaccaac aagatcctgg aaaaaccgac cattgaaaac    2220
aacaccaaaa aagtgaccgt cgagaagaa gaggattaca caacgttttt tgaaaccccg    2280
aaactggtcg aggatattaa acagtatcgc gactataaat tcagccaccg cgttgataaa    2340
aaaccgaatc gtcagctgat taacgatacc ctgtatagca cccgtatgaa agatgagcat    2400
gattatattg tgcagaccat cacggatatc tatggcaaag ataataccaa cctgaaaaaa    2460
cagttcaaca aaaacccgga aaaatttctg atgtatcaga cgatccgaa aacctttgag    2520 aaactgagca tcatcatgaa acagtacagc gacgaaaaaa acccgctggc caaatattac    2580
gaagaaaccg gtgaatatct gaccaaatat agcaagaaaa caacggtcc gatcgtgaaa    2640 aagatcaaac tgctgggtaa taagtgggc aatcatctgg atgtgaccaa caaatatgaa    2700
aactccacga agaagctggt taagctgtcc attaaaaact atcgcttcga tgtgtatctg    2760
accgagaaag gttataagtt tgtgaccatt gcctacctga atgtgttcaa aaaagacaac    2820
tattactata ttccgaaaga caaataccaa gaacttaaag agaagaagaa atcaaggac    2880 accgatcagt ttatcgccag cttctataaa aacgatctga tcaagctgaa cggcgacctg    2940
tataaaatca ttggtgtgaa tagtgatgac cgcaacatca ttgagctgga ttattacgac    3000
atcaaataca aggattactg cgagatcaac aacattaaag gtgaaccgcg tatcaaaaag    3060
accattggca aaaaaacgga aagcatcgaa aagtttacca ccgatgttct gggtaatctg    3120
tatctgcata gtaccgaaaa agcaccgcag ctgatttttca aacgcggtct g              3171
```

<210> SEQ ID NO 18
<211> LENGTH: 3171
<212> TYPE: DNA
<213> ORGANISM: Artificial sequence

```
<220> FEATURE:
<223> OTHER INFORMATION: Synthetic polynucleotide
<220> FEATURE:
<221> NAME/KEY: misc_feature
<223> OTHER INFORMATION: Codon-optimized Gib11Spa-3 polynucleotide

<400> SEQUENCE: 18
atgaaccaga agttcattct cggtctggac attggcatta ctagcgtggg atacggcttg      60
attgactacg agactaagaa catcatcgat gccggcgtcc gcctgttccc ggaagccaac     120
gtggagaaca atgagggccg gaggtcgaag agaggctccc gccgcctgaa gcggcggcga     180
atccaccggc tggagagagt gaagctgctg ctcaccgaat acgacctgat caacaaagaa     240
cagatcccga cctccaacaa cccgtaccag atcagagtga agggtctgtc agaaatcctg     300
tccaaggacg aactggcaat cgccctgctg cacctggcca gcggcgcgg aatccacaac     360
gtggatgtgg ctgccgacaa ggaagaaacc gcttccgact ccctgagcac taaggaccag     420
atcaacaaga cgccaagtt cttggagtcc cgctacgtgt gcgagctgca gaaggaacgg     480
ctggaaaacg aaggtcacgt gcgcggagtg gaaaaccggt cctgacaaa ggacattgtg     540
cgcgaagcga agaagatcat tgatacccaa atgcagtact accctgaaat cgacgagact     600
ttcaaggaaa agtacatttc cctggtggaa acccggcggg aatacttcga aggcccgga     660
cagggatcgc cgttcggatg aacggggac ctcaagaagt ggtacgagat gctgatgggg     720
cactgtacct actttccgca agaactgcgc tccgtgaagt acgcgtactc cgcggatctc     780
ttcaacgcgt tgaatgacct gaacaacctg atcattcaga gagacaattc cgaaaagctc     840
gagtaccacg agaagtatca catcatcgag aatgtgttca gcagaagaa gaaaccgacc     900
ctcaagcaaa tcgccaagga gattggcgtc aacccagagg acatcaaggg atatcggatt     960
accaagagcg gcactcccga gtttacctct ttcaagctgt ttcatgatct gaagaaagtc    1020
gtgaaggacc atgccattct cgacgacatt gatctcctga atcagatcgc agagatcctg    1080
actatctacc aagacaagga ctcgattgtg gcagagctgg gtcagctcga atacctgatg    1140
tccgaggccg acaagcagtc catctccgaa ctgacagggt acacggggac tcatagcctg    1200
tcgctgaagt gcatgaacat gatcattgat gaactgtggc acagctccat gaaccaaatg    1260
gaagtgttta cctacctcaa catgcgccct aagaagtacg aactgaaagg ctaccagcgc    1320
atccccaccg acatgatcga cgacgcgatc ttgtcccctg tggtcaagag gaccttcatt    1380
caatccatca acgtgatcaa caaggtcatc gaaaagtacg gtattccaga agatatcatc    1440
attgagctcg ctcgggagaa caactcggat gaccggaaga agttcatcaa caatcttcag    1500
aagaagaacg aagcgactcg gaaacggatc aacgagatca tcggacagac cggaaaccag    1560
aacgccaaac ggattgtcga aaagattaga ctgcacgacc agcaggaagg gaagtgcctg    1620
tactcactcg agtcaatacc gctcgaggac ctgttgaaca accctaacca ctatgaagtg    1680
gaccacatca tccctcggtc cgtgagcttc gacaactcgt accacaacaa agtgctcgtg    1740
aagcagtccg aaaactccaa gaatccaac ctgaccccgt accaatactt caattcggga    1800
aagtcgaagc tgtcgtacaa ccagttcaaa caacacatac tcaaccttag caaaagccag    1860
gatcgcattt ccaagaagaa gaaggaatac ctcctcgagg aaagggacat caacaagttc    1920
gaagtgcaga aagagttcat caatcgcaac ttggtggata ccagatatgc cacccgggaa    1980
ctcaccagct atctcaaggc ctactttttcc gccaacaaca tggacgtgaa ggtcaagacc    2040
atcaacgggg ccttcactaa ccatctgaga aaggtctggc ggtttgacaa gtaccgcaac    2100
cacggataca agcaccacgc tgaagacgct ctgatcatcg ccaatgccga cttcctgttc    2160
```

```
aaggaaaaca agaagctgca gaacacgaac aagattctgg aaaagcctac cattgagaac    2220
aacactaaga aggtcaccgt ggagaaggaa gaggactaca caacgtgtt cgaaactcct     2280 aaactggtgg aggatatcaa gcaataccgc gactacaagt tctcacaccg ggtggacaag    2340
aaaccgaata gacagctgat caacgacacg ttgtattcca cccggatgaa ggatgagcat    2400
gactacattg tgcagactat caccgatatc tacggaaaag ataacactaa cctgaagaaa    2460
caattcaaca agaacccaga gaagttcctg atgtaccaga cgaccccaa gacctttgag     2520 aagctttcca tcatcatgaa gcagtactcc gacgagaaga cccgctggc caagtactac     2580 gaagaaaccg gagaatacct gaccaagtac agcaagaaga caacggtcc cattgtcaag     2640 aagatcaagc tgctcggcaa caaggtcgga aaccacctcg acgtgacaaa caagtacgag    2700
aactcgacta gaagcttgt gaagctgtca atcaagaact atagattcga cgtgtacttg     2760
accgaaaagg gatacaagtt cgtgaccata gcctatctga acgtgttcaa gaaagataac    2820
tactactaca tcccaagga caagtaccag gagctcaaag aaaagaagaa gatcaaagac     2880
accgaccagt tcattgcctc cttctacaag aacgacctga tcaaactgaa cggcgaccct   2940
tacaagatca ttggagtgaa cagcgatgac aggaacatca ttgagctgga ctactacgac   3000
atcaagtaca aggactactg cgagatcaac aacatcaagg gcgaaccccg gatcaagaaa    3060
actattggaa agaaaaccga gtccattgag aagttcacca ctgacgtgct gggaaacctt    3120
tacctccact ccaccgagaa ggcaccacaa ctgatcttca gcgcgggcct g            3171

<210> SEQ ID NO 19
<211> LENGTH: 3166
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding P2H12

<400> SEQUENCE: 19
atgaaccaga aatttatcct gggtctggat attggtatta ccagcgttgg ttatggcctg      60
attgattacg aaaccaaaaa cattattgat gccggtgttc gtctgtttcc ggaagcaaat     120
gttgaaaata tgaaggtcg tcgtagcaaa cgtggtagcc gtcgtctgaa cgtcgtcgt      180 attcatcgtc tggaacgtgt taaaaaactg ctggaagatt ataacctgct ggatcagagc     240
cagattccgc agagcaccaa tccgtatgca attcgtgtta aggtctgag cgaagcactg      300 agcaaagatg aactggttat tgcactgctg catattgcaa acgccgtgg cattcataat     360 atcaatgtta gcagcgaaga tgaggatgca agcaatgaac tgagcaccaa gaacaaatt     420 aaccgcaata taagctgct gaaggacaaa tatgtttgcg aagttcagct gcagcgtctg      480
aaagaaggtc agattcgcgg agaaaaaaat cgctttaaaa ccaccgatat cctgaaagaa     540
attgatcagc tgcttaaagt gcagaaggat tatcataacc tggacatcga tttcatcaac    600
cagtacaaag aaatcgttga aaccgtcgc gaatattttg aaggtccggg taaaggtagc      660
ccgtatggtt gggaaggtga tccgaaagca tggtatgaaa ccctgatggg tcattgtacc     720
tattttccgg atgaactgcg tagcgttaaa tatgcctata gcgcagacct gtttaatgca    780
ctgaatgatc tgaataacct ggtgattcag cgtgatggtc tgagcaaact ggaatatcat    840
gagaaatatc acatcatcga aacgtgttc aaacagaaga gaaaccgac cctgaaacaa      900 atcgccaacg aaattaatgt gaacccggaa gatattaaag gctaccgtat taccaaaagc     960
```

```
ggcaaaccgg aatttacatc ctttaaactg ttccacgatc tgaaaaaagt ggtgaaagat    1020
catgccatcc tggatgatat tgatctgctg aatcagattg cagaaatcct gaccatctat    1080
caggataaag atagcattgt tgcagaactg ggtcagctgg aatatctgat gagcgaagcc    1140
gataaacaga gcattagcga actgaccggt tataccggta cacatagcct gtcactgaaa    1200
tgcatgaaca tgattatcga tgaactgtgg catagcagca tgaaccagat ggaagttttt    1260
acctatctga atatgcgtcc gaaaaagtat gagctgaaag ttatcagcg tattccgacc     1320 gatatgattg atgatgcaat tctgagtccg gttgtgaaac gcacctttat tcagagcatc    1380
aacgtgatca caaagtgat cgagaaatat ggcatccccg aagatatcat tatcgaactg     1440
gcacgtgaaa ataactccga tgatcgcaaa aagttcatca acaacctgca gaaaaagaat    1500
gaagcaaccc gcaaacgcat taacgaaatt attggtcaga ccggtaatca gaatgccaaa    1560
cgtattgtgg aaaaaatccg tctgcatgat cagcaagagg gtaaatgtct gtatagcctg    1620
gaaagcattc ctctggaaga tctgctgaac aatccgaatc attatgaagt ggatcacatt    1680
attccgcgta gcgtgagctt tgataattcc tatcataata agtgctggt gaaacagagc     1740 gaaaactcca aaaatccaa cctgacaccg tatcagtatt tcaatagcgg caaatccaaa     1800
ctgagctaca accagtttaa acagcatatt ctgaacctga gcaaaagcca ggatcgcatc    1860
agcaagaaga gaaggagta cctgctggaa gaacgcgata ttaacaaatt tgaagtgcag     1920
aaagaattta tcaaccgcaa cctggttgat acccgttatg caacccgtga actgaccaat    1980
tatctgaaag catatttcag cgccaacaac atgaacgtga agtgaaaac gattaacggc     2040 agctttaccg attatctgcg taaagtgtgg aaattcaaaa agaacgcaa ccacggctat     2100 aaacatcatg ccgaagatgc cctgattatt gcaaatgcag atttcctgtt taagaaaaac    2160
aaaaaactga agccgtcaa cagcgtgctg gaaaaaccgg aaattgagac aaaacagctg     2220
gacattcagg ttgatagcga agataattac agcgaaatgt ttatcatccc gaaacaggtg    2280
caggatatca aagatttcg caacttcaaa tatagccacc gcgttgacaa aaaacctaat     2340
cgtcagctga ttaacgatac cctgtatagc acccgcaaaa aagataacag cacctatatt    2400
gtgcagacca ttaaagacat ctacgccaaa gataatacca ccctgaaaaa acagttcgac    2460
aaaagcccag aaaatttct gatgtatcag catgatccgc gtaccttcga aaaactggaa     2520
gttattatga acagtatgc caacgagaaa atccgctgg ccaaatatca cgaagaaacc      2580
ggtgaatatc tgaccaaata ttccaagaag aacaacggtc cgatcgttaa atccctgaaa    2640
tatatcggta taaactggg cagccatctg gatgttaccc atcagtttaa aagctccaca    2700
aagaagctgg ttaaactgtc catcaaaccg tatcgctttg atgtgtatct gaccgacaaa    2760
ggctataaat tcattaccat cagctatctg gacgtgctga aaaagacaa ctattattat    2820 atcccggaac agaaatatga taaactgaaa ctgggtaaag ccatcgataa aaacgccaaa    2880
tttatcgcca gcttctacaa aaacgacctg attaaactgg atggcgagat ctataaaatc    2940
atcggtgtta atagcgacac ccgcaatatg attgagctgg atctgccgga tattcgctat    3000
aaagaatatt gcgaactgaa caacattaaa ggcgaaccgc gtatcaaaaa gaccatcggc    3060
aaaaaagtga atagcatcga gaactgacc accgatgttc tgggtaatgt gtttaccaat    3120
acccagtata ccaaacctca gctgctgttc aaacgcggta atggtg                  3166
```

<210> SEQ ID NO 20
<211> LENGTH: 3162
<212> TYPE: DNA

<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized P2H12 polynucleotide

<400> SEQUENCE: 20

```
atgaaccaaa agttcattct ggggctcgat atcggcatca cctccgtggg atatggtctg      60
atcgactacg agactaagaa catcatcgac gctggagtgc gactgttccc ggaagcgaac     120
gtggagaaca acgaaggccg cagatccaag cgcgggtcca aaggctcaa gaggcggagg      180
atccatagac tcgagagagt gaagaagctc cttgaagatt acaatctgtt ggaccagtca     240
cagattcccc aaagcaccaa cccgtacgcc atcagagtga agggcctgtc agaagcactg     300
tcgaaagatg aactggtcat tgccctgctg catattgcca acggcgcgg aatccataac      360
atcaacgtgt cgagcgaaga tgaggacgcg tccaacgaac tgtcaaccaa ggaacagatc     420
aaccggaaca caaaactgct gaaggacaaa tacgtctgcg aggtgcagct caacggctg      480
aaagagggac agatcagggg agagaaaaac cggttcaaga ccaccgacat ccttaaggag     540
atcgaccaac tcctgaaagt gcagaaggac tatcacaacc tcgacattga ttttatcaac     600
cagtacaagg agattgtgga actcggagg gagtacttcg agggacctgg aaagggatcc      660
ccttatggct gggaagggga ccccaaggct tggtacgaaa ccctgatggg ccattgcact     720
tactttccgg atgaactccg gtccgtgaag tacgcttact ctgccgacct gttcaatgca     780
ctcaacgacc ttaacaactt ggtgatccaa cgcgatggtc tttccaagtt ggagtaccac     840
gaaaagtacc acatcatcga gaacgtgttc aagcagaaaa agaagccaac tctgaagcag     900
attgccaacg aaattaacgt gaaccccgag gatatcaagg ataccggat taccaagtcc       960
ggcaaaccag agttcacctc attcaagctg tttcacgatc tgaagaaggt cgtgaaggac    1020
cacgccatcc tggatgacat tgatcttctg aaccagattg ctgagatcct gaccatctac    1080
caggacaagg actcgattgt ggccgaactg ggacagctcg agtacctgat gtccgaagcc    1140
gataagcagt ccatcagcga actcaccggt acaccggta cccactcctt gtcccttaag     1200
tgcatgaaca tgatcattga cgaactgtgg cactccagca tgaaccagat ggaggtgttc    1260
acctacttga acatgcgccc gaagaagtac gagctgaagg ctaccagcg cataccacg      1320
gacatgatcg acgacgccat cctctcaccg gtggtcaagc gcaccttcat tcaatctatc    1380
aacgtgatca acaaggtcat cgagaagtac ggcattcctg aggatatcat catcgagctg    1440
gctcgggaga caactcaga cgataggaag aagttcatta caaccctcca gaaaagaac     1500
gaggccactc gcaagcggat taatgagatc atcggtcaga ccgggaacca gaacgccaag    1560
cggatcgtgg aaaagattcg gctccacgac caacaggagg gaaagtgtct gtactcgctg    1620
gagtccattc ccctggagga cctcctgaac aacccaaacc actacgaggt cgatcacata    1680
atccccgca gcgtgtcatt cgacaactcc taccataaca aggtcctcgt gaagcagtcg     1740
gagaatagca agaagtcgaa cctgactccg taccagtact tcaactccgg caaatccaag    1800
ctgtcctaca atcagttcaa acagcacatt ctcaacctgt ccaagagcca ggacaggatt    1860
tcgaagaaga gaaggaata ccttctcgag aacgggata tcaataagtt cgaggtgcag     1920
aaggagttta tcaatagaaa cctggtggac actcgctatg ccacccgcga actgaccaac    1980
tacctgaagc gtacttctc cgccaacaac atgaacgtga aggtcaaaac tattaacggc    2040
agcttcaccg actatctgcg caaggtctgg aagttcaaga aggaacgcaa ccacggttac    2100
```

```
aagcaccacg cggaagatgc gctgattatc gccaacgctg acttcctgtt caaggaaaac    2160
aagaagctca aggccgtgaa ctcagtgctc gagaagcctg aaatcgagac taagcagctg    2220
gacatccagg tcgattcgga agataactac tccgaaatgt tcatcatccc taagcaagtg    2280
caggacatca aggacttcag gaatttcaag tacagccatc gcgtggacaa gaagccaaac    2340
agacagctga tcaacgatac actgtattcc acccggaaga aggacaactc cacctacatc    2400
gtccaaacca ttaaggacat ctacgcaaag gacaacacca cgcttaagaa gcagttcgac    2460
aagagccccg aaaagttcct catgtaccag cacgacccca gaaccttcga aagcttgaa    2520 gtgatcatga agcagtacgc caacgaaaag aacccactgg ctaagtacca cgaggaaacc    2580
ggcgaatacc tgaccaagta ctccaaaaag aacaacggac cgatcgtcaa gtccctgaag    2640
tacattggga caagctcgg ctcgcacctc gatgtgaccc accagttcaa gtcctcgacc    2700
aaaaagctcg tgaagctgtc catcaagccg taccggttcg acgtgtacct gactgacaag    2760
ggatataagt tcatcaccat ttcctacctc gacgtgttga agaaggataa ctactactac    2820
attccggaac agaagtacga caagctcaag ctcggaaagg ccatcgacaa aaatgcgaag    2880
ttcatcgcga gcttctacaa gaatgacttg atcaagctgg atggcgaaat ctacaagatc    2940
atcggggtca actccgatac ccgcaacatg attgagctgg atctgcccga cattcggtac    3000
aaggaatact gcgagctgaa caacatcaag ggagaaccgc ggatcaagaa aaccatcgga    3060
aagaaagtga acagcatcga gaaactgact actgacgtcc tgggaaacgt gttcaccaac    3120
acacaataca ccaaaccccca gctgctgttt aagcgcggga ac                      3162

<210> SEQ ID NO 21
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding E2

<400> SEQUENCE: 21
atgaaccaga aatttatcct gggtctggat attggtatta ccagcgttgg ttatggcctg      60
attgattacg aaaccaaaaa cattattgat gccggtgttc gtctgtttcc ggaagcaaat     120
gttgaaaata tgaaggtcg tcgtagcaaa cgtggtagcc gtcgtctgaa cgtcgtcgt     180 attcatcgtc tggatcgtgt taaacatctg ctggcagaat atgatctgct ggatctgacc     240
aatattccga aaagcaccaa tccgtatcag cccgtgttaa aggtctgaa tgaaaagctg     300 agcaaagatg aactggttat tgcactgctg catattgcaa acgccgtgg cattcataac     360 gttgatgttg cagcagataa agaagaaacc gcaagcgata gcctgagcac caagatcag     420 attaacaaaa cgccaaatt tctggaaagc cgctatgttt gtgaactgca gaaagaacgt     480
ctggaaaatg aaggtcatgt tcgtggtgtt gaaaatcgct ttctgacgaa agatattgtg     540
cgtgaggcca aaaaatcat cgatacccag atgcagtatt acccggaaat tgatgaaacc     600
ttcaaagaga atatatcag cctggttgaa acccgtcgcg aatattttga aggtccgggt     660
aaaggtagcc cgtttggttg ggaaggtaat atcaagaaat ggtttgagca gatgatgggc     720
cactgtacct atttttccaga gaactgcgt agcgtcaaat atagctattc agccgaactg     780
tttaacgccc tgaatgatct gaataatctg gtgattaccc gtgatgaaga tgccaaactg     840
aattatggtg agaaattcca gatcatcgaa aacgtgttca acagaagaa acaccgaac     900
```

```
ctgaaacaaa tcgccattga aattggtgtg catgaaaccg aaatcaaagg ttatcgtgtg      960
aacaaaagcg gtacaccgga atttaccgaa tttaaactgt atcatgacct gaaaagcatc     1020
gtgttcgata aaagcattct ggaaaatgaa gccatcctgg atcagattgc agaaattctg     1080
accatctatc aggatgagca gagcattaaa gaggaactga ataaactgcc ggaaatactg     1140
aacgaacagg ataaagcaga atcgccaaa ctgattggtt ataatggcac ccatcgtctg      1200
agcctgaaat gtattcacct gattaatgaa gaactgtggc agaccagccg taatcagatg     1260
gaaattttca actacctgaa catcaaaccg aacaaagtgg atctgagtga gcagaacaaa     1320
atcccgaaag atatggtgaa cgactttatt ctgagtccgg ttgtgaaacg cacctttatt     1380
cagagcatca acgtgatcaa caaagtgatc gagaaatatg gcatcccga agatatcatt      1440
atcgaactgg cacgtgaaaa taactccgat gatcgcaaaa agttcatcaa caacctgcag     1500
aaaaagaatg aagcaacccg caaacgcatt aacgaaatta ttggtcagac cggtaatcag     1560
aatgccaaac gtattgtgga aaaaatccgt ctgcatgatc agcaagaggg taaatgtctg     1620
tatagcctga agatatccc gctggaagat ctgctgcgca tccgaacaa ttatgatatc       1680
gaccatatta ttccgcgaag cgtgagcttt gatgatagca tgcataacaa agttctggtt     1740
cgtcgcgaac agaatgccaa aagaataat cagaccccgt atcagtatct gaccagtggt      1800
tatgcagata tcaaatacag cgtgtttaag cagcatgttc tgaatctggc cgaaaataaa     1860
gatcgcatga ccaaaaaaaa gcgcgagtat ctgctggaag aacgcgacat taacaaattt     1920
gaagtgcaga aagaatttat caaccgcaac ctggttgata cccgttatgc aacccgtgaa     1980
ctgaccaatt atctgaaagc atatttcagc gccaacaaca tgaacgtgaa agtgaaaacg     2040
attaacggca gctttaccga ttatctgcgt aaagtgtgga aattcaaaaa agaacgcaac     2100
cacggctata acatcatgc cgaagatgcc ctgattattg caaatgcaga tttcctgttt      2160
aaagaaaaca aaaaactgaa agccgtcaac agcgtgctgg aaaaaccgga aattgagaca     2220
aaacagctgg acattcaggt tgatagcgaa gataattaca gcgaaatgtt tatcatcccg     2280
aaacaggtgc aggatatcaa agattttcgc aacttcaaat atagccaccg cgttgacaaa     2340
aaacctaatc gtcagctgat taacgatacc ctgtatagca cccgcaaaaa agataacagc     2400
acctatattg tgcagaccat taaagacatc tacgccaaag ataataccac cctgaaaaaa     2460
cagttcgaca aaagcccaga aaaatttctg atgtatcagc atgatccgcg taccttcgaa     2520
aaactggaag ttattatgaa acagtatgcc aacgagaaaa atccgctggc caaatatcac     2580
gaagaaaccg gtaatatct gaccaaatat tccaagaaga caacggtcc gatcgttaaa       2640
tccctgaaat atatcggtaa taaactgggc agccatctgg atgttaccca tcagtttaaa     2700
agctccacaa agaagctggt taaactgtcc atcaaaccgt atcgctttga tgtgtatctg     2760
accgacaaag gctataaatt cattaccatc agctatctgg acgtgctgaa aaaagacaac     2820
tattattata tcccggaaca gaaatatgat aaactgaaac tgggtaaagc catcgataaa     2880
aacgccaaat ttatcgccag cttctacaaa aacgacctga ttaaactgga tggcgagatc     2940
tataaaatca tcggtgttaa tagcgacacc cgcaatatga ttgagctgga tctgccggat     3000
attcgctata agaatattg cgaactgaac aacattaaag gcgaaccgcg tatcaaaaag      3060
accatcggca aaaagtgaa tagcatcgag aaactgacca ccgatgttct gggtaatgtg      3120
tttaccaata cccagtatac caaacctcag ctgctgttca aacgcggtaa t              3171
```

<210> SEQ ID NO 22
<211> LENGTH: 3171

<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized E2 polynucleotide

<400> SEQUENCE: 22
atgaaccaaa agttcattct ggggctcgat atcggcatca cctccgtggg atatggtctg 60
atcgactacg agactaagaa catcatcgac gctggagtgc gactgttccc ggaagcgaac 120
gtggagaaca acgaaggccg cagatccaag cgcgggtcca gaaggctcaa gaggcggagg 180
atccatagac tcgacagagt gaagcacctc cttgccgaat acgatctgtt ggaccttacc 240
aacattccca agagcaccaa cccgtaccaa accagagtga agggcctgaa cgaaaagctg 300
tcgaaagatg aactggtcat tgccctgctg catattgcca aacggcgcgg aatccataac 360
gtggacgtgg ccgctgacaa ggaagagact gcgtccgact cgctgtcaac caaggaccag 420
atcaacaaga acgccaaatt cctggaaagc cgctacgtct gcgagcttca aaaagaacgg 480
ctggagaacg agggacacgt caggggagtg gagaaccggt tcctgaccaa ggacatcgtg 540
cgggaagcca agaagatcat cgacacccaa atgcagtatt atccggaaat tgatgaaact 600
tttaaggaga agtacatttc cctggtggaa actcggaggg agtacttcga gggacctgga 660
aagggatccc ctttcggctg ggaagggaac attaagaagt ggtttgaaca gatgatgggc 720
cattgcactt actttccgga agaactccgg tccgtgaagt actcatactc tgccgagctg 780
ttcaatgcac tcaacgacct taacaacttg gtgatcaccc gcgatgaaga tgccaagttg 840
aactacggag aaaagttcca gatcatcgag aacgtgttca agcagaaaaa gaccccaaat 900
ctgaagcaga ttgccatcga aattggcgtg cacgagactg agatcaaggg ataccgggtc 960
aacaagtccg gcacgccaga gttcaccgag ttcaagctgt accacgatct gaagtcgatc 1020
gtgtttgaca agtccatcct ggaaaacgaa gccattctgg accagattgc tgagatcctg 1080
accatctacc aggacgagca atcgattaag gaagaactga acaagctccc cgagattctg 1140
aacgaacagg ataaggccga gatcgcgaag ctcattggtt acaatggtac ccaccgcttg 1200
tcccttaagt gcatccatct gatcaatgag gaactgtggc agaccagccg gaaccagatg 1260
gagatcttca attacttgaa catcaagccg aacaaggtgg acctgtccga acagaacaag 1320
atacccaagg acatggtcaa cgactttatc ctctcaccgg tggtcaagcg caccttcatt 1380
caatctatca acgtgatcaa caaggtcatc gagaagtacg gcattcctga ggatatcatc 1440
atcgagctgg ctcgggagaa caactcagac gataggaaga agttcattaa caacctccag 1500
aaaaagaacg aggccactcg caagcggatt aatgagatca tcggtcagac cgggaaccag 1560
aacgccaagc ggatcgtgga aaagattcgg ctccacgacc aacaggaggg aaagtgtctg 1620
tactcgctga aggacattcc cctggaggac ctcctgagga acccaaacaa ctacgacatc 1680
gatcacataa tcccccgcag cgtgtcattc gacgattcca tgcataacaa ggtcctcgtg 1740
cggagagagc agaatgccaa gaagaacaac cagactccgt accagtacct gacgtccggc 1800
tacgcagaca tcaagtactc agtgttcaaa cagcacgtgc tcaacctggc cgagaacaag 1860
gacaggatga ccaagaagaa gcgcgaatac cttctcgagg aacgggatat caataagttc 1920
gaggtgcaga aggagtttat caatagaaac ctggtggaca ctcgctatgc cacccgcgaa 1980
ctgaccaact acctgaaggc gtacttctcc gccaacaaca tgaacgtgaa ggtcaaaact 2040
attaacggca gcttcaccga ctatctgcgc aaggtctgga agttcaagaa ggaacgcaac 2100

```
cacggttaca agcaccacgc ggaagatgcg ctgattatcg ccaacgctga cttcctgttc    2160
aaggaaaaca agaagctcaa ggccgtgaac tcagtgctcg agaagcctga aatcgagact    2220
aagcagctgg acatccaggt cgattcggaa gataactact ccgaaatgtt catcatccct    2280
aagcaagtgc aggacatcaa ggacttcagg aatttcaagt acagccatcg cgtggacaag    2340
aagccaaaca gacagctgat caacgataca ctgtattcca cccggaagaa ggacaactcc    2400
acctacatcg tccaaaccat taaggacatc tacgcaaagg acaacaccac gcttaagaag    2460
cagttcgaca gagccccga aaagttcctc atgtaccagc acgacccag aaccttcgag    2520 aagcttgaag tgatcatgaa gcagtacgcc aacgaaaaga ccccactggc taagtaccac    2580
gaggaaaccg gcgaatacct gaccaagtac tccaaaaaga caacggacc gatcgtcaag    2640 tccctgaagt acattgggaa caagctcggc tcgcacctcg atgtgaccca ccagttcaag    2700
tcctcgacca aaaagctcgt gaagctgtcc atcaagccgt accggttcga cgtgtacctg    2760
actgacaagg gatataagtt catcaccatt tcctacctcg acgtgttgaa gaaggataac    2820
tactactaca ttccggaaca gaagtacgac aagctcaagc tcggaaaggc catcgacaaa    2880
aatgcgaagt tcatcgcgag cttctacaag aatgacttga tcaagctgga tggcgaaatc    2940
tacaagatca tcggggtcaa ctccgatacc cgcaacatga ttgagctgga tctgcccgac    3000
attcggtaca aggaatactg cgagctgaac aacatcaagg gagaaccgcg gatcaagaaa    3060
accatcggaa agaaagtgaa cagcatcgag aaactgacta ctgacgtcct gggaaacgtg    3120
ttcaccaaca cacaatacac caaaccccag ctgctgttta agcgcgggaa c             3171
```

<210> SEQ ID NO 23
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding for E2-K741D-L743K

<400> SEQUENCE: 23

```
atgaaccaga aatttatcct gggtctggat attggtatta ccagcgttgg ttatggcctg    60
attgattacg aaaccaaaaa cattattgat gccggtgttc gtctgtttcc ggaagcaaat    120
gttgaaaata atgaaggtcg tcgtagcaaa cgtggtagcc gtcgtctgaa acgtcgtcgt    180
attcatcgtc tggatcgtgt taaacatctg ctggcagaat atgatctgct ggatctgacc    240
aatattccga aaagcaccaa tccgtatcag acccgtgtta aaggtctgaa tgaaaagctg    300
agcaaagatg aactggttat tgcactgctg catattgcaa acgccgtgg cattcataac    360 gttgatgttg cagcagataa agaagaaacc gcaagcgata gcctgagcac caaagatcag    420
attaacaaaa acgccaaatt tctggaaagc cgctatgttt gtgaactgca gaaagaacgt    480
ctggaaaatg aaggtcatgt tcgtggtgtt gaaaatcgct ttctgacgaa agatattgtg    540
cgtgaggcca aaaaatcat cgatacccag atgcagtatt acccggaaat tgatgaaacc    600
ttcaaagaga aatatatcag cctggttgaa acccgtcgcg aatattttga aggtccgggt    660
aaaggtagcc cgtttggttg ggaaggtaat atcaagaaat ggtttgagca gatgatgggc    720
cactgtacct attttccaga gaactgcgct agcgtcaaat atagctattc agccgaactg    780
tttaacgccc tgaatgatct gaataatctg gtgattaccc gtgatgaaga tgccaaactg    840
aattatggtg agaaattcca gatcatcgaa aacgtgttca acagaagaa acaccgaac    900
```

```
ctgaaacaaa tcgccattga aattggtgtg catgaaaccg aaatcaaagg ttatcgtgtg      960
aacaaaagcg gtacaccgga atttaccgaa tttaaactgt atcatgacct gaaaagcatc     1020
gtgttcgata aaagcattct ggaaaatgaa gccatcctgg atcagattgc agaaattctg     1080
accatctatc aggatgagca gagcattaaa gaggaactga taaaactgcc ggaaatactg     1140
aacgaacagg ataaagcaga atcgccaaaa ctgattggtt ataatggcac ccatcgtctg     1200
agcctgaaat gtattcacct gattaatgaa gaactgtggc agaccagccg taatcagatg     1260
gaaattttca actacctgaa catcaaaccg aacaaagtgg atctgagtga gcagaacaaa     1320
atcccgaaag atatggtgaa cgactttatt ctgagtccgg ttgtgaaacg cacctttatt     1380
cagagcatca acgtgatcaa caaagtgatc gagaaatatg gcatccccga agatatcatt     1440
atcgaactgg cacgtgaaaa taactccgat gatcgcaaaa agttcatcaa caacctgcag     1500
aaaaagaatg aagcaacccg caaacgcatt aacgaaatta ttggtcagac cggtaatcag     1560
aatgccaaac gtattgtgga aaaaatccgt ctgcatgatc agcaagaggg taaatgtctg     1620
tatagcctga agatatcccc gctggaagat ctgctgcgca tccgaacaa ttatgatatc      1680 gaccatatta ttccgcgaag cgtgagcttt gatgatagca tgcataacaa agttctggtt     1740
cgtcgcgaac agaatgccaa aaagaataat cagaccccgt atcagtatct gaccagtggt     1800
tatgcagata tcaaatacag cgtgtttaag cagcatgttc tgaatctggc cgaaaataaa     1860
gatcgcatga ccaaaaaaaa gcgcgagtat ctgctggaag aacgcgacat taacaaattt     1920
gaagtgcaga aagaatttat caaccgcaac ctggttgata cccgttatgc aacccgtgaa     1980
ctgaccaatt atctgaaagc atatttcagc gccaacaaca tgaacgtgaa agtgaaaacg     2040
attaacggca gctttaccga ttatctgcgt aaagtgtgga aattcaaaaa agaacgcaac     2100
cacggctata aacatcatgc cgaagatgcc ctgattattg caaatgcaga tttcctgttt     2160
aaagaaaaca aaaaactgaa agccgtcaac agcgtgctgg aaaaaccgga aattgagaca     2220
gatcagaaag acattcaggt tgatagcgaa gataattaca gcgaaatgtt tatcatcccg     2280
aaacaggtgc aggatatcaa agattttcgc aacttcaaat atagccaccg cgttgacaaa     2340
aaacctaatc gtcagctgat taacgatacc ctgtatagca cccgcaaaaa agataacagc     2400
acctatattg tgcagaccat taaagacatc tacgccaaag ataataccac cctgaaaaaa     2460
cagttcgaca aaagcccaga aaaatttctg atgtatcagc atgatccgcg taccttcgaa     2520
aaactggaag ttattatgaa acagtatgcc aacgagaaaa atccgctggc caaatatcac     2580
gaagaaaccg gtgaatatct gaccaaatat tccaagaaga caacggtcc gatcgttaaa      2640 tccctgaaat atatcggtaa taaactgggc agccatctgg atgttaccca tcagtttaaa     2700
agctccacaa gaagctggt taaactgtcc atcaaaccgt atcgctttga tgtgtatctg      2760
accgacaaag gctataaatt cattaccatc agctatctgg acgtgctgaa aaaagacaac     2820
tattattata tcccggaaca gaaatatgat aaactgaaac tgggtaaagc catcgataaa     2880
aacgccaaat ttatcgccag cttctacaaa aacgacctga ttaaactgga tggcgagatc     2940
tataaaatca tcggtgttaa tagcgacacc cgcaatatga ttgagctgga tctgccggat     3000
attcgctata agaatattg cgaactgaac aacattaaag cgaaccgcg tatcaaaaag       3060 accatcggca aaaagtgaa tagcatcgag aaactgacca ccgatgttct gggtaatgtg      3120
tttaccaata cccagtatac caaacctcag ctgctgttca aacgcggtaa t              3171
```

<210> SEQ ID NO 24

<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding for E2-S670T-N675D

<400> SEQUENCE: 24
atgaaccaga aatttatcct gggtctggat attggtatta ccagcgttgg ttatggcctg 60
attgattacg aaaccaaaaa cattattgat gccggtgttc gtctgtttcc ggaagcaaat 120
gttgaaaata atgaaggtcg tcgtagcaaa cgtggtagcc gtcgtctgaa acgtcgtcgt 180
attcatcgtc tggatcgtgt taaacatctg ctggcagaat atgatctgct ggatctgacc 240
aatattccga aaagcaccaa tccgtatcag acccgtgtta aaggtctgaa tgaaaagctg 300
agcaaagatg aactggttat tgcactgctg catattgcaa aacgccgtgg cattcataac 360
gttgatgttg cagcagataa agaagaaacc gcaagcgata gcctgagcac caaagatcag 420
attaacaaaa acgccaaatt tctggaaagc cgctatgttt gtgaactgca gaaagaacgt 480
ctggaaaatg aaggtcatgt tcgtggtgtt gaaaatcgct ttctgacgaa agatattgtg 540
cgtgaggcca aaaaaatcat cgatacccag atgcagtatt acccggaaat tgatgaaacc 600
ttcaaagaga aatatatcag cctggttgaa acccgtcgcg aatattttga aggtccgggt 660
aaaggtagcc cgtttggttg ggaaggtaat atcaagaaat ggtttgagca gatgatgggc 720
cactgtacct attttccaga agaactgcgt agcgtcaaat atagctattc agccgaactg 780
tttaacgccc tgaatgatct gaataatctg gtgattaccc gtgatgaaga tgccaaactg 840
aattatggtg agaaattcca gatcatcgaa aacgtgttca aacagaagaa aacaccgaac 900
ctgaaacaaa tcgccattga aattggtgtg catgaaaccg aaatcaaagg ttatcgtgtg 960
aacaaaagcg gtacaccgga atttaccgaa tttaaactgt atcatgacct gaaaagcatc 1020
gtgttcgata aaagcattct ggaaaatgaa gccatcctgg atcagattgc agaaattctg 1080
accatctatc aggatgagca gagcattaaa gaggaactga ataaactgcc ggaaatactg 1140
aacgaacagg ataaagcaga aatcgccaaa ctgattggtt ataatggcac ccatcgtctg 1200
agcctgaaat gtattcacct gattaatgaa gaactgtggc agaccagccg taatcagatg 1260
gaaattttca actacctgaa catcaaaccg aacaaagtgg atctgagtga gcagaacaaa 1320
atcccgaaag atatggtgaa cgactttatt ctgagtccgg ttgtgaaacg cacctttatt 1380
cagagcatca acgtgatcaa caaagtgatc gagaaatatg gcatccccga agatatcatt 1440
atcgaactgg cacgtgaaaa taactccgat gatcgcaaaa agttcatcaa caacctgcag 1500
aaaaagaatg aagcaacccg caaacgcatt aacgaaatta ttggtcagac cggtaatcag 1560
aatgccaaac gtattgtgga aaaaatccgt ctgcatgatc agcaagaggg taaatgtctg 1620
tatagcctga aagatatccc gctggaagat ctgctgcgca atccgaacaa ttatgatatc 1680
gaccatatta ttccgcgaag cgtgagcttt gatgatagca tgcataacaa agttctggtt 1740
cgtcgcgaac agaatgccaa aaagaataat cagaccccgt atcagtatct gaccagtggt 1800
tatgcagata tcaaatacag cgtgtttaag cagcatgttc tgaatctggc cgaaaataaa 1860
gatcgcatga ccaaaaaaaa gcgcgagtat ctgctggaag aacgcgacat taacaaattt 1920
gaagtgcaga aagaatttat caaccgcaac ctggttgata cccgttatgc aacccgtgaa 1980
ctgaccaatt atctgaaagc atatttcacc gccaacaaca tggatgtgaa agtgaaaacg 2040

-continued

| | |
|---|---|
| attaacggca gctttaccga ttatctgcgt aaagtgtgga aattcaaaaa agaacgcaac | 2100 |
| cacggctata aacatcatgc cgaagatgcc ctgattattg caaatgcaga tttcctgttt | 2160 |
| aaagaaaaca aaaaactgaa agccgtcaac agcgtgctgg aaaaaccgga aattgagaca | 2220 |
| aaacagctgg acattcaggt tgatagcgaa gataattaca gcgaaatgtt tatcatcccg | 2280 |
| aaacaggtgc aggatatcaa agattttcgc aacttcaaat atagccaccg cgttgacaaa | 2340 |
| aaacctaatc gtcagctgat taacgatacc ctgtatagca cccgcaaaaa agataacagc | 2400 |
| acctatattg tgcagaccat taaagacatc tacgccaaag ataataccac cctgaaaaaa | 2460 |
| cagttcgaca aaagcccaga aaatttctg atgtatcagc atgatccgcg taccttcgaa | 2520 |
| aaactggaag ttattatgaa acagtatgcc aacgagaaaa atccgctggc caaatatcac | 2580 |
| gaagaaaccg tgaatatctc gaccaaatat tccaagaaga caacggtcc gatcgttaaa | 2640 |
| tccctgaaat atatcggtaa taaactgggc agccatctgg atgttaccca tcagtttaaa | 2700 |
| agctccacaa agaagctggt taaactgtcc atcaaaccgt atcgctttga tgtgtatctg | 2760 |
| accgacaaag gctataaatt cattaccatc agctatctgg acgtgctgaa aaaagacaac | 2820 |
| tattattata tcccggaaca gaaatatgat aaactgaaac tgggtaaagc catcgataaa | 2880 |
| aacgccaaat ttatcgccag cttctacaaa acgacctga ttaaactgga tggcgagatc | 2940 |
| tataaaatca tcggtgttaa tagcgacacc cgcaatatga ttgagctgga tctgccggat | 3000 |
| attcgctata aagaatattg cgaactgaac aacattaaag cgaaccgcg tatcaaaaag | 3060 |
| accatcggca aaaagtgaa tagcatcgag aaactgacca ccgatgttct gggtaatgtg | 3120 |
| tttaccaata cccagtatac caaacctcag ctgctgttca aacgcggtaa t | 3171 |

<210> SEQ ID NO 25
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding for E2-K741N-L743N

<400> SEQUENCE: 25

| | |
|---|---|
| atgaaccaga aatttatcct gggtctggat attggtatta ccagcgttgg ttatggcctg | 60 |
| attgattacg aaaccaaaaa cattattgat gccggtgttc gtctgttcc ggaagcaaat | 120 |
| gttgaaaata tgaaggtcg tcgtagcaaa cgtggtagcc gtcgtctgaa acgtcgtcgt | 180 |
| attcatcgtc tggatcgtgt taaacatctg ctggcagaat atgatctgct ggatctgacc | 240 |
| aatattccga aaagcaccaa tccgtatcag acccgtgtta aaggtctgaa tgaaaagctg | 300 |
| agcaaagatg aactggttat tgcactgctg catattgcaa aacgccgtgg cattcataac | 360 |
| gttgatgttg cagcagataa agaagaaacc gcaagcgata gcctgagcac caaagatcag | 420 |
| attaacaaaa acgccaaatt tctggaaagc cgctatgttt gtgaactgca gaagaacgt | 480 |
| ctggaaaatg aaggtcatgt tcgtggtgtt gaaaatcgct ttctgacgaa agatattgtg | 540 |
| cgtgaggcca aaaaaatcat cgataccag atgcagtatt acccggaaat tgatgaaacc | 600 |
| ttcaaagaga atatatcag cctggttgaa acccgtcgcg aatattttga aggtccgggt | 660 |
| aaaggtagcc cgtttggttt ggaaggtaat atcaagaaat ggtttgagca gatgatgggc | 720 |
| cactgtacct atttccaga gaactgcgt agcgtcaaat atagctattc agccgaactg | 780 |
| tttaacgccc tgaatgatct gaataatctg gtgattaccc gtgatgaaga tgccaaactg | 840 |

```
aattatggtg agaaattcca gatcatcgaa aacgtgttca acagaagaa acaccgaac      900
ctgaaacaaa tcgccattga aattggtgtg catgaaaccg aaatcaaagg ttatcgtgtg    960
aacaaaagcg gtacaccgga atttaccgaa tttaaactgt atcatgacct gaaaagcatc    1020
gtgttcgata aaagcattct ggaaaatgaa gccatcctgg atcagattgc agaaattctg    1080
accatctatc aggatgagca gagcattaaa gaggaactga ataaactgcc ggaaatactg    1140
aacgaacagg ataaagcaga aatcgccaaa ctgattggtt ataatggcac catcgtctg     1200
agcctgaaat gtattcacct gattaatgaa gaactgtggc agaccagccg taatcagatg    1260
gaaattttca actacctgaa catcaaaccg aacaaagtgg atctgagtga gcagaacaaa    1320
atcccgaaag atatggtgaa cgactttatt ctgagtccgg ttgtgaaacg caccttatt    1380
cagagcatca acgtgatcaa caaagtgatc gagaaatatg gcatccccga agatatcatt    1440
atcgaactgg cacgtgaaaa taactccgat gatcgcaaaa agttcatcaa caacctgcag    1500
aaaaagaatg aagcaacccg caaacgcatt aacgaaatta ttggtcagac cggtaatcag    1560
aatgccaaac gtattgtgga aaaaatccgt ctgcatgatc agcaagaggg taaatgtctg    1620
tatagcctga agatatccc gctggaagat ctgctgcgca atccgaacaa ttatgatatc     1680
gaccatatta ttccgcgaag cgtgagcttt gatgatagca tgcataacaa agttctggtt    1740
cgtcgcgaac agaatgccaa aaagaataat cagaccccgt atcagtatct gaccagtggt    1800
tatgcagata tcaaatacag cgtgtttaag cagcatgttc tgaatctggc cgaaaataaa    1860
gatcgcatga ccaaaaaaaa gcgcgagtat ctgctggaag aacgcgacat taacaaattt    1920
gaagtgcaga agaatttat caaccgcaac ctggttgata cccgttatgc aacccgtgaa     1980
ctgaccaatt atctgaaagc atatttcagc gccaacaaca tgaacgtgaa agtgaaaacg    2040
attaacggca gctttaccga ttatctgcgt aaagtgtgga aattcaaaaa agaacgcaac    2100
cacggctata acatcatgc cgaagatgcc ctgattattg caaatgcaga tttcctgttt     2160
aaagaaaaca aaaaactgaa agccgtcaac agcgtgctgg aaaaaccgga aattgagaca    2220
aatcagaatg acattcaggt tgatagcgaa gataattaca gcgaaatgtt tatcatcccg    2280
aaacaggtgc aggatatcaa agattttcgc aacttcaaat atagccaccg cgttgacaaa    2340
aaacctaatc gtcagctgat taacgatacc ctgtatagca cccgcaaaaa agataacagc    2400
acctatattg tgcagaccat taaagacatc tacgccaaag ataataccac cctgaaaaaa    2460
cagttcgaca aaagcccaga aaaatttctg atgtatcagc atgatccgcg taccttcgaa    2520
aaactggaag ttattatgaa acagtatgcc aacgagaaaa atccgctggc caaatatcac    2580
gaagaaaccg gtgaatatct gaccaaatat tccaagaaga caacggtcc gatcgttaaa     2640
tccctgaaat atatcggtaa taaactgggc agccatctgg atgttaccca tcagtttaaa    2700
agctccacaa agaagctggt taaactgtcc atcaaaccgt atcgctttga tgtgtatctg    2760
accgacaaag gctataaatt cattaccatc agctatctgg acgtgctgaa aaaagacaac    2820
tattattata tcccggaaca gaaatatgat aaactgaaac tgggtaaagc catcgataaa    2880
aacgccaaat ttatcgccag cttctacaaa aacgacctga ttaaactgga tggcgagatc    2940
tataaaatca tcggtgttaa tagcgacacc cgcaatatga ttgagctgga tctgccggat    3000
attcgctata agaatattg cgaactgaac aacattaaag gcgaaccgcg tatcaaaaag    3060
accatcggca aaaagtgaa tagcatcgag aaactgacca ccgatgttct gggtaatgtg    3120
tttaccaata cccagtatac caaacctcag ctgctgttca aacgcggtaa t            3171
```

```
<210> SEQ ID NO 26
<211> LENGTH: 3159
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding F8

<400> SEQUENCE: 26
atgaaccaga aatttatcct gggtctggat attggtatta ccagcgttgg ttatggcctg      60
attgattacg aaaccaaaaa cattattgat gccggtgttc gtctgtttcc ggaagcaaat     120
gttgaaaata tgaaggtcg tcgtagcaaa cgtggtagcc gtcgtctgaa acgtcgtcgt     180
attcatcgtc tggaacgtgt taaaagcctg ctgagcgaat ataagattat tagcggtctg     240
gcaccgacca ataatcagcc gtataacatt cgtgttaaag gtctgaccga acagctgacc     300
aaagatgaac tggcagttgc actgctgcat attgccaaac gccgtggcat tcataaaatc     360
gatgtgattg atagcaatga cgatgtgggt aatgaactga gcaccaaaga acagctgaac     420
aaaaatagca aactgctgaa agacaaattc gtgtgtcaga ttcagctgga acgtatgaat     480
gaaggccagg ttcgtggtga aaagaatcgc tttaaaaccg cagacatcat caaagaaatt     540
atccagctgc tgaacgtgca gaaaaacttc atcagctgg atgaaaactt catcaacaaa     600
tacatcgagc tggttgaaat gcgtcgcgaa tattttgaag gtcctggtca gggtagcccg     660
tttggttgga tggtgatct gaaaaaatgg tacgaaatgc tgatgggtca ctgtacctat     720
tttccgcaag aactgcgtag cgttaaatat gcctatagcg cagacctgtt taatgcactg     780
aatgatctga caacctgat tattcagcgc gataatagcg agaaactgga ataccatgag     840
aagtatcaca tcatcgagaa cgtgttcaag cagaaaaaaa gccgacgct gaaacaaatc     900 gcaaaagaga ttggcgttaa cccggaagat attaaggtt atcgtattac caaaagcggt     960
acaccggaat tcaccgaatt taaactgtat cacgatctga aaagcgtgct gtttgatcag    1020
agcattctgg aaaatgaaga tgtgctggac agattgcag aaattctgac catttatcag    1080
gacaaagaca gcatcaaaag caaactgacc gaactggata ttctgctgaa tgaagaagat    1140
aaagagaaca ttgcacagct gaccggttat aacggcacac atcgcctgag cctgaaatgt    1200
attcgtctgg tactggaaga cagtggtat agcagccgta atcagatgga aatctttacc    1260
catctgaaca ttaaaccgaa gaaaatcaat ctgaccgcag ccaacaaaat tccgaaagcc    1320
atgattgatg agtttattct gagtccggtt gtgaaacgca cctttattca gagcatcaac    1380
gtgatcaaca aagtgatcga aaatatggc atccccgaag atatcattat cgaactggca    1440
cgtgaaaata ctccgatga tcgcaaaaag ttcatcaaca acctgcagaa aaagaatgaa    1500
gcaacccgca acgcattaa cgaaattatt ggtcagaccg gtaatcagaa tgccaaacgt    1560
attgtggaaa aaatccgtct gcatgatcag caagagggga atgtctgta tagcctggaa    1620 agcattgccc tgatggatct gctgaataac ccgcagaatt atgaagtgga tcatattatt    1680
ccgcgtagcg tggcatttga taattccatt cataacaaag tgctggtgaa gcagatcgag    1740
aatagcaaaa aagtaatcg tacgccgtat cagtatctga atagcagtga tgcaaaactg    1800
agctacaacc agtttaaaca gcatattctg aatctgagca aagcaaaga tcgcatcagc    1860 aaaaaaaaga aggactacct gctggaagaa cgcgatatca caaatttga agtccagaaa    1920 gagtttatca accgcaatct ggttgatacc cgttatgcaa cccgtgaact gaccagctat    1980
ctgaaagcat atttcagcgc caataacatg gacgtgaaag tgaaaacaat taacggcagc    2040
```

```
tttaccaacc atctgcgtaa agtttggcgc tttgataaat atcgcaacca cggctataaa    2100
catcatgcag aagatgccct gattattgca aatgcagatt tcctgtttaa agaaaacaaa    2160
aaactgaaag ccgtcaacag cgtgctggaa aaaccggaaa ttgagacaaa acagctggac    2220
attcaggttg atagcgaaga taattacagc gaaatgttta tcatcccgaa acaggtgcag    2280
gatatcaaag attttcgcaa cttcaaatat agccaccgcg ttgacaaaaa acctaatcgt    2340
cagctgatta cgatacccct gtatagcacc cgcaaaaaag ataacagcac ctatattgtg    2400
cagaccatta aagacatcta cgccaaagat aataccaccc tgaaaaaaca gttcgacaaa    2460
agcccagaaa aatttctgat gtatcagcat gatccgcgta ccttcgaaaa actggaagtt    2520
attatgaaac agtatgccaa cgagaaaaat ccgctggcca aatatcacga agaaaccggt    2580
gaatatctga ccaaatattc caagaagaac aacggtccga tcgttaaatc cctgaaatat    2640
atcggtaata aactgggcag ccatctggat gttacccatc agtttaaaag ctccacaaag    2700
aagctggtta aactgtccat caaaccgtat cgctttgatg tgtatctgac cgacaaaggc    2760
tataaattca ttaccatcag ctatctggac gtgctgaaaa agacaactta ttattatatc    2820
ccggaacaga aatatgataa actgaaactg ggtaaagcca tcgataaaaa cgccaaattt    2880
atcgccagct tctacaaaaa cgacctgatt aaactggatg cgagatcta taaaatcatc    2940 ggtgttaata gcgacacccg caatatgatt gagctggatc tgccggatat tcgctataaa    3000
gaatattgcg aactgaacaa cattaaaggc gaaccgcgta tcaaaagac catcggcaaa    3060 aaagtgaata gcatcgagaa actgaccacc gatgttctgg gtaatgtgtt taccaatacc    3120
cagtatacca aacctcagct gctgttcaaa cgcggtaat                          3159

<210> SEQ ID NO 27
<211> LENGTH: 3159
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized F8 polynucleotide

<400> SEQUENCE: 27
atgaaccaaa agttcattct ggggctcgat atcggcatca cctccgtggg atatggtctg      60
atcgactacg agactaagaa catcatcgac gctggagtgc gactgttccc ggaagcgaac     120
gtggagaaca acgaaggccg cagatccaag cgcgggtcca aaggctcaa gaggcggagg      180 atccatagac tcgagagagt gaagtcgctc ctttcggaat acaagattat cagcggtctt     240
gcccccacca caaccaaacc gtacaacatc agagtgaagg gcctgaccga acagctgacc     300
aaagatgaac tggccgtcgc cctgctgcat attgccaaac ggcgcggaat ccataagatc     360
gacgtgattg acagcaacga tgacgtggga acgagctgt caaccaagga acagcttaac     420
aagaacagca aattgctgaa ggacaagttt gtctgccaaa ttcaactgga acggatgaac     480
gagggacaag tcaggggaga gaaaaaccgg ttcaagaccg ccgacatcat caaggagatc     540
atccaactgc tgaacgtgca aagaacttc accaactgg atgaaaactt cattaacaag     600
tacattgaac tggtggaaat gcggagggag tacttcgagg acctggaca gggatcccct     660 ttcggctgga tgggaccct taagaagtgg tacgaaatgt tgatgggcca ttgcacttac     720
tttccgcaag aactccggtc cgtgaagtac gcatactctg ccgacctgtt caatgcactc     780
aacgacctta caacttgat catccagcgc gataactcgg aaaagttgga ataccacgaa      840
```

-continued

```
aagtatcaca tcatcgagaa cgtgttcaag cagaaaaaga agccaactct gaagcagatt    900
gccaaggaaa ttggcgtgaa tccggaggat atcaagggat accggatcac taagtccggc    960
acgccagagt tcaccgagtt caagctgtac cacgatctga agtcggtgct ctttgaccag   1020
tccatcctgg aaaacgaaga tgtgctggac cagattgctg agatcctgac catctaccag   1080
gacaaggact cgattaagtc caagctcacc gagctggaca ttctgctgaa cgaagaagat   1140
aaggagaaca tcgcgcagct caccggttac aatggtaccc accgcttgtc ccttaagtgc   1200
atccgcctgg tgctggagga acagtggtac tcgagccgga accagatgga gatcttcact   1260
cacttgaaca tcaagccgaa aaagattaac ctgactgccg ccaacaagat acccaaggcc   1320
atgatcgacg agtttatcct ctcaccggtg gtcaagcgca ccttcattca atctatcaac   1380
gtgatcaaca aggtcatcga gaagtacggc attcctgagg atatcatcat cgagctggct   1440
cgggagaaca actcagacga taggaagaag ttcattaaca acctccagaa aaagaacgag   1500
gccactcgca agcggattaa tgagatcatc ggtcagaccg ggaaccagaa cgccaagcgg   1560
atcgtggaaa agattcggct ccacgaccaa caggagggaa agtgtctgta ctcgctggag   1620
tcgattgcac tgatggacct cctgaacaac ccacagaact acgaagtcga tcacataatc   1680
ccccgcagcg tggcattcga caactccatc cataacaagg tcctcgtgaa gcagatcgag   1740
aatagcaaga aggggaaccg gactccgtac cagtacctga actcctccga cgccaagctg   1800
tcatacaatc agttcaaaca gcacattctc aacctgtcca gtcaaagga caggatctcc    1860
aagaagaaga aggactacct tctcgaggaa cgggatatca ataagttcga ggtgcagaag   1920
gagtttatca atagaaacct ggtggacact cgctatgcca cccgcgaact gaccagctac   1980
ctgaaggcgt acttctccgc caacaacatg gacgtgaagg tcaaaactat taacggcagc   2040
ttcaccaacc atctgcgcaa ggtctggagg ttcgacaagt accgcaacca cggttacaag   2100
caccacgcgg aagatgcgct gattatcgcc aacgctgact tcctgttcaa ggaaaacaag   2160
aagctcaagg ccgtgaactc agtgctcgag aagcctgaaa tcgagactaa gcagctggac   2220
atccaggtcg attcggaaga taactactcc gaaatgttca tcatccctaa gcaagtgcag   2280
gacatcaagg acttcaggaa tttcaagtac agccatcgcg tggacaagaa gccaaacaga   2340
cagctgatca cgatacact gtattccacc cggaagaagg acaactccac ctacatcgtc    2400
caaaccatta aggacatcta cgcaaaggac aacaccacgc ttaagaagca gttcgacaag   2460
agccccgaaa agttcctcat gtaccagcac gaccccagaa ccttcgagaa gcttgaagtg   2520
atcatgaagc agtacgccaa cgaaaagaac ccactggcta agtaccacga ggaaaccggc   2580
gaatacctga ccaagtactc caaaaagaac aacggaccga tcgtcaagtc cctgaagtac   2640
attgggaaca agctcggctc gcacctcgat gtgacccacc agttcaagtc ctcgaccaaa   2700
aagctcgtga agctgtccat caagccgtac cggttcgacg tgtacctgac tgacaaggga   2760
tataagttca tcaccatttc ctacctcgac gtgttgaaga aggataacta ctactacatt   2820
ccggaacaga agtacgacaa gctcaagctc ggaaaggcca tcgacaaaaa tgcgaagttc   2880
atcgcgagct tctacaagaa tgacttgatc aagctggatg gcgaaatcta caagatcatc   2940
ggggtcaact ccgatacccg caacatgatt gagctggatc tgcccgacat tcggtacaag   3000
gaatactgcg agctgaacaa catcaaggga gaaccgcgga tcaagaaaac catcggaaag   3060
aaagtgaaca gcatcgagaa actgactact gacgtcctgg gaaacgtgtt caccaacaca   3120
caatacacca acccccagct gctgtttaag cgcgggaac                         3159
```

<210> SEQ ID NO 28
<211> LENGTH: 3159
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding F8-K737D-L739K

<400> SEQUENCE: 28

```
atgaaccaga aatttatcct gggtctggat attggtatta ccagcgttgg ttatggcctg     60
attgattacg aaaccaaaaa cattattgat gccggtgttc gtctgtttcc ggaagcaaat    120
gttgaaaata tgaaggtcg tcgtagcaaa cgtggtagcc gtcgtctgaa acgtcgtcgt     180
attcatcgtc tggaacgtgt taaaagcctg ctgagcgaat ataagattat tagcggtctg    240
gcaccgacca ataatcagcc gtataacatt cgtgttaaag gtctgaccga acagctgacc    300
aaagatgaac tggcagttgc actgctgcat attgccaaac gccgtggcat tcataaaatc    360
gatgtgattg atagcaatga cgatgtgggt aatgaactga gcaccaaaga acagctgaac    420
aaaaatagca aactgctgaa agacaaattc gtgtgtcaga ttcagctgga acgtatgaat    480
gaaggccagg ttcgtggtga aaagaatcgc tttaaaaccg cagacatcat caaagaaatt    540
atccagctgc tgaacgtgca gaaaaacttc catcagctgg atgaaaactt catcaacaaa    600
tacatcgagc tggttgaaat gcgtcgcgaa tattttgaag gtcctggtca gggtagcccg    660
tttggttgga tggtgatct gaaaaaatgg tacgaaatgc tgatgggtca ctgtacctat    720
tttccgcaag aactgcgtag cgttaaatat gcctatagcg cagacctgtt taatgcactg    780
aatgatctga caacctgat tattcagcgc gataatagcg agaaactgga ataccatgag    840
aagtatcaca tcatcgagaa cgtgttcaag cagaaaaaaa gccgacgct gaaacaaatc    900
gcaaaagaga ttggcgttaa cccggaagat attaaaggtt atcgtattac caaaagcggt    960
acaccggaat tcaccgaatt taaactgtat cacgatctga aaagcgtgct gtttgatcag   1020
agcattctgg aaaatgaaga tgtgctggac cagattgcag aaattctgac catttatcag   1080
gacaaagaca gcatcaaaag caaactgacc gaactggata ttctgctgaa tgaagaagat   1140
aaagagaaca ttgcacagct gaccggttat aacggcacac atcgcctgag cctgaaatgt   1200
attcgtctgg tactggaaga acagtggtat agcagccgta tcagatgga atctttacc    1260
catctgaaca ttaaaccgaa gaaaatcaat ctgaccgcag ccaacaaaat tccgaaagcc   1320
atgattgatg agtttattct gagtccggtt gtgaaacgca cctttattca gagcatcaac   1380
gtgatcaaca agtgatcga gaaatatggc atccccgaag atatcattat cgaactggca   1440
cgtgaaaata ctccgatga tcgcaaaaag ttcatcaaca acctgcagaa aaagaatgaa   1500
gcaacccgca acgcattaa cgaaattatt ggtcagaccg gtaatcagaa tgccaaacgt   1560
attgtggaaa aaatccgtct gcatgatcag caagagggga atgtctgta gcctggaa    1620
agcattgccc tgatggatct gctgaataac ccgcagaatt atgaagtgga tcatattatt   1680
ccgcgtagcg tggcatttga taattccatt cataacaaag tgctggtgaa gcagatcgag   1740
aatagcaaaa aaggtaatcg tacgccgtat cagtatctga atagcagtga tgcaaaactg   1800
agctacaacc agtttaaaca gcatattctg aatctgagca aaagcaaaga tcgcatcagc   1860
aaaaaaaaga aggactacct gctggaagaa cgcgatatca caaatttga agtccagaaa   1920
gagtttatca accgcaatct ggttgatacc cgttatgcaa cccgtgaact gaccagctat   1980
```

| | |
|---|---|
| ctgaaagcat atttcagcgc caataacatg acgtgaaag tgaaaacaat taacggcagc | 2040 |
| tttaccaacc atctgcgtaa agtttggcgc tttgataaat atcgcaacca cggctataaa | 2100 |
| catcatgcag aagatgccct gattattgca aatgcagatt tcctgtttaa agaaaacaaa | 2160 |
| aaactgaaag ccgtcaacag cgtgctggaa aaaccggaaa ttgagacaga tcagaaagac | 2220 |
| attcaggttg atagcgaaga taattacagc gaaatgttta tcatcccgaa acaggtgcag | 2280 |
| gatatcaaag attttcgcaa cttcaaatat agccaccgcg ttgacaaaaa acctaatcgt | 2340 |
| cagctgatta acgataccct gtatagcacc cgcaaaaaag ataacagcac ctatattgtg | 2400 |
| cagaccatta agacatcta cgccaaagat aataccaccc tgaaaaaaca gttcgacaaa | 2460 |
| agcccagaaa aatttctgat gtatcagcat gatccgcgta ccttcgaaaa actggaagtt | 2520 |
| attatgaaac agtatgccaa cgagaaaaat ccgctggcca atatcacga agaaaccggt | 2580 |
| gaatatctga ccaaatattc caagaagaac aacggtccga tcgttaaatc cctgaaatat | 2640 |
| atcggtaata aactgggcag ccatctggat gttacccatc agtttaaaag ctccacaaag | 2700 |
| aagctggtta aactgtccat caaaccgtat cgctttgatg tgtatctgac cgacaaaggc | 2760 |
| tataaattca ttaccatcag ctatctggac gtgctgaaaa aagacaacta ttattatatc | 2820 |
| ccggaacaga aatatgataa actgaaactg gtaaagccaa tcgataaaaa cgccaaattt | 2880 |
| atcgccagct tctacaaaaa cgacctgatt aaactggatg gcgagatcta taaatcatc | 2940 |
| ggtgttaata gcgacacccg caatatgatt gagctggatc tgccggatat tcgctataaa | 3000 |
| gaatattgcg aactgaacaa cattaaaggc gaaccgcgta tcaaaaagac catcggcaaa | 3060 |
| aaagtgaata gcatcgagaa actgaccacc gatgttctgg gtaatgtgtt taccaatacc | 3120 |
| cagtatacca aacctcagct gctgttcaaa cgcggtaat | 3159 |

<210> SEQ ID NO 29
<211> LENGTH: 3159
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence encoding F8-K737N-L739N

<400> SEQUENCE: 29

| | |
|---|---|
| atgaaccaga aatttatcct gggtctggat attggtatta ccagcgttgg ttatggcctg | 60 |
| attgattacg aaaccaaaaa cattattgat gccggtgttc gtctgtttcc ggaagcaaat | 120 |
| gttgaaaata tgaaggtcg tcgtagcaaa cgtggtagcc gtcgtctgaa acgtcgtcgt | 180 |
| attcatcgtc tggaacgtgt taaaagcctg ctgagcgaat ataagattat agcggtctg | 240 |
| gcaccgacca taatcagcc gtataacatt cgtgttaaag gtctgaccga acagctgacc | 300 |
| aaagatgaac tggcagttgc actgctgcat attgccaaac cgtggcat tcataaaatc | 360 |
| gatgtgattg atagcaatga cgatgtgggt aatgaactga gcaccaaaga acagctgaac | 420 |
| aaaaatagca aactgctgaa agacaaattc gtgtgtcaga ttcagctgga acgtatgaat | 480 |
| gaaggccagg ttcgtggtga aaagaatcgc tttaaaaccg cagacatcat caaagaaatt | 540 |
| atccagctgc tgaacgtgca gaaaaacttc catcagctgg atgaaaactt catcaacaaa | 600 |
| tacatcgagc tggttgaaat gcgtcgcgaa tattttgaag gtcctggtca gggtagcccg | 660 |
| tttggttgga tggtgatct gaaaaaatgg tacgaaatgc tgatgggtca ctgtacctat | 720 |
| tttccgcaag aactgcgtag cgttaaatat gcctatagcg cagacctgtt taatgcactg | 780 |

```
aatgatctga caacctgat tattcagcgc gataatagcg agaaactgga ataccatgag    840
aagtatcaca tcatcgagaa cgtgttcaag cagaaaaaaa agccgacgct gaaacaaatc    900
gcaaaagaga ttggcgttaa cccggaagat attaaaggtt atcgtattac caaaagcggt    960
acaccggaat tcaccgaatt taaactgtat cacgatctga aaagcgtgct gtttgatcag   1020
agcattctgg aaaatgaaga tgtgctggac cagattgcag aaattctgac catttatcag   1080
gacaaagaca gcatcaaaag caaactgacc gaactggata ttctgctgaa tgaagaagat   1140
aaagagaaca ttgcacagct gaccggttat aacggcacac atcgcctgag cctgaaatgt   1200
attcgtctgg tactgaaaga acagtggtat agcagccgta atcagatgga aatctttacc   1260
catctgaaca ttaaaccgaa gaaaatcaat ctgaccgcag ccaacaaaat tccgaaagcc   1320
atgattgatg agtttattct gagtccggtt gtgaaacgca cctttattca gagcatcaac   1380
gtgatcaaca aagtgatcga gaaatatggc atccccgaag atatcattat cgaactggca   1440
cgtgaaaata ctccgatga tcgcaaaaag ttcatcaaca acctgcagaa aaagaatgaa   1500
gcaacccgca aacgcattaa cgaaattatt ggtcagaccg gtaatcagaa tgccaaacgt   1560
attgtggaaa aaatccgtct gcatgatcag caagagggga aatgtctgta tagcctggaa   1620
agcattgccc tgatggatct gctgaataac ccgcagaatt atgaagtgga tcatattatt   1680
ccgcgtagcg tggcatttga taattccatt cataacaaag tgctggtgaa gcagatcgag   1740
aatagcaaaa aaggtaatcg tacgccgtat cagtatctga atagcagtga tgcaaaactg   1800
agctacaacc agtttaaaca gcatattctg aatctgagca aaagcaaaga tcgcatcagc   1860
aaaaaaaaga aggactacct gctggaagaa cgcgatatca acaaatttga agtccagaaa   1920
gagtttatca accgcaatct ggttgatacc cgttatgcaa cccgtgaact gaccagctat   1980
ctgaaagcat atttcagcgc caataacatg acgtgaaag tgaaaacaat taacggcagc   2040
tttaccaacc atctgcgtaa agtttggcgc tttgataaat atcgcaacca cggctataaa   2100
catcatgcag aagatgccct gattattgca aatgcagatt tcctgtttaa agaaaacaaa   2160
aaactgaaag ccgtcaacag cgtgctggaa aaaccggaaa ttgagacaaa tcagaatgac   2220
attcaggttg atagcgaaga taattacagc gaaatgttta tcatcccgaa acaggtgcag   2280
gatatcaaag atttcgcaa cttcaaatat agccaccgcg ttgacaaaaa acctaatcgt   2340
cagctgatta cgataccct gtatagcacc cgcaaaaaag ataacagcac ctatattgtg   2400
cagaccatta aagacatcta cgccaaagat aataccaccc tgaaaaaaca gttcgacaaa   2460
agcccagaaa aatttctgat gtatcagcat gatccgcgta ccttcgaaaa actggaagtt   2520
attatgaaac agtatgccaa cgagaaaaat ccgctggcca aatatcacga agaaaccggt   2580
gaatatctga ccaaatattc caagaagaac aacggtccga tcgttaaatc cctgaaatat   2640
atcggtaata aactgggcag ccatctggat gttacccatc agtttaaaag ctccacaaag   2700
aagctggtta aactgtccat caaaccgtat cgctttgatg tgtatctgac cgacaaaggc   2760
tataaattca ttaccatcag ctatctggac gtgctgaaaa aagacaacta ttattatatc   2820
ccggaacaga atatgataa actgaaactg ggtaaagcca tcgataaaaa cgccaaattt   2880
atcgccagct tctacaaaaa cgacctgatt aaactggatg gcgagatcta aaaatcatc   2940
ggtgttaata gcgacacccg caatatgatt gagctggatc tgccggatat cgctataaa   3000
gaatattgcg aactgaacaa cattaaaggc gaaccgcgta tcaaaagac catcggcaaa   3060
aaagtgaata gcatcgagaa actgaccacc gatgttctgg gtaatgtgtt taccaatacc   3120
cagtatacca aacctcagct gctgttcaaa cgcggtaat                          3159
```

<210> SEQ ID NO 30
<211> LENGTH: 1054
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis Cas9

<400> SEQUENCE: 30

```
Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
                20                  25                  30

Val Arg Leu Phe Pro Glu Ala Asn Val Glu Asn Glu Gly Arg Arg
            35                  40                  45

Ser Lys Arg Gly Ser Arg Arg Leu Lys Arg Arg Arg Ile His Arg Leu
50                  55                  60

Glu Arg Val Lys Lys Leu Leu Glu Asp Tyr Asn Leu Leu Asp Gln Ser
65                  70                  75                  80

Gln Ile Pro Gln Ser Thr Asn Pro Tyr Ala Ile Arg Val Lys Gly Leu
                85                  90                  95

Ser Glu Ala Leu Ser Lys Asp Glu Leu Val Ile Ala Leu Leu His Ile
            100                 105                 110

Ala Lys Arg Arg Gly Ile His Lys Ile Asp Val Ile Asp Ser Asn Asp
        115                 120                 125

Asp Val Gly Asn Glu Leu Ser Thr Lys Glu Gln Leu Asn Lys Asn Ser
130                 135                 140

Lys Leu Leu Lys Asp Lys Phe Val Cys Gln Ile Gln Leu Glu Arg Met
145                 150                 155                 160

Asn Glu Gly Gln Val Arg Gly Glu Lys Asn Arg Phe Lys Thr Ala Asp
                165                 170                 175

Ile Ile Lys Glu Ile Ile Gln Leu Leu Asn Val Gln Lys Asn Phe His
            180                 185                 190

Gln Leu Asp Glu Asn Phe Ile Asn Lys Tyr Ile Glu Leu Val Glu Met
        195                 200                 205

Arg Arg Glu Tyr Phe Glu Gly Pro Gly Lys Gly Ser Pro Tyr Gly Trp
210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
        275                 280                 285

Val Phe Lys Gln Lys Lys Lys Pro Thr Leu Lys Gln Ile Ala Asn Glu
290                 295                 300

Ile Asn Val Asn Pro Glu Asp Ile Lys Gly Tyr Arg Ile Thr Lys Ser
305                 310                 315                 320

Gly Lys Pro Gln Phe Thr Glu Phe Lys Leu Tyr His Asp Leu Lys Ser
                325                 330                 335

Val Leu Phe Asp Gln Ser Ile Leu Glu Asn Glu Asp Val Leu Asp Gln
            340                 345                 350
```

-continued

```
Ile Ala Glu Ile Leu Thr Ile Tyr Gln Asp Lys Asp Ser Ile Lys Ser
            355                 360                 365

Lys Leu Thr Glu Leu Asp Ile Leu Leu Asn Glu Glu Asp Lys Glu Asn
    370                 375                 380

Ile Ala Gln Leu Thr Gly Tyr Thr Gly Thr His Arg Leu Ser Leu Lys
385                 390                 395                 400

Cys Ile Arg Leu Val Leu Glu Glu Gln Trp Tyr Ser Ser Arg Asn Gln
                405                 410                 415

Met Glu Ile Phe Thr His Leu Asn Ile Lys Pro Lys Lys Ile Asn Leu
            420                 425                 430

Thr Ala Ala Asn Lys Ile Pro Lys Ala Met Ile Asp Glu Phe Ile Leu
            435                 440                 445

Ser Pro Val Val Lys Arg Thr Phe Gly Gln Ala Ile Asn Leu Ile Asn
    450                 455                 460

Lys Ile Ile Glu Lys Tyr Gly Val Pro Glu Asp Ile Ile Glu Leu
465                 470                 475                 480

Ala Arg Glu Asn Asn Ser Lys Asp Lys Gln Lys Phe Ile Asn Glu Met
                485                 490                 495

Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
            515                 520                 525

His Asp Glu Gln Glu Gly Lys Cys Leu Tyr Ser Leu Glu Ser Ile Pro
    530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
                565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
        595                 600                 605

His Ile Leu Asn Leu Ser Lys Ser Gln Asp Arg Ile Ser Lys Lys Lys
    610                 615                 620

Lys Glu Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
            675                 680                 685

Val Trp Lys Phe Lys Lys Glu Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
    755                 760                 765
```

Phe Lys Tyr Ser His Arg Val Asp Lys Lys Pro Asn Arg Gln Leu Ile
770             775             780

Asn Asp Thr Leu Tyr Ser Thr Arg Lys Lys Asp Asn Ser Thr Tyr Ile
785             790             795             800

Val Gln Thr Ile Lys Asp Ile Tyr Ala Lys Asp Asn Thr Thr Leu Lys
        805             810             815

Lys Gln Phe Asp Lys Ser Pro Glu Lys Phe Leu Met Tyr Gln His Asp
        820             825             830

Pro Arg Thr Phe Glu Lys Leu Glu Val Ile Met Lys Gln Tyr Ala Asn
        835             840             845

Glu Lys Asn Pro Leu Ala Lys Tyr His Glu Glu Thr Gly Glu Tyr Leu
850             855             860

Thr Lys Tyr Ser Lys Lys Asn Asn Gly Pro Ile Val Lys Ser Leu Lys
865             870             875             880

Tyr Ile Gly Asn Lys Leu Gly Ser His Leu Asp Val Thr His Gln Phe
                885             890             895

Lys Ser Ser Thr Lys Lys Leu Val Lys Leu Ser Ile Lys Pro Tyr Arg
        900             905             910

Phe Asp Val Tyr Leu Thr Asp Lys Gly Tyr Lys Phe Ile Thr Ile Ser
        915             920             925

Tyr Leu Asp Val Leu Lys Lys Asp Asn Tyr Tyr Ile Pro Glu Gln
930             935             940

Lys Tyr Asp Lys Leu Lys Leu Gly Lys Ala Ile Asp Lys Asn Ala Lys
945             950             955             960

Phe Ile Ala Ser Phe Tyr Lys Asn Asp Leu Ile Lys Leu Asp Gly Glu
                965             970             975

Ile Tyr Lys Ile Ile Gly Val Asn Ser Asp Thr Arg Asn Met Ile Glu
                980             985             990

Leu Asp Leu Pro Asp Ile Arg Tyr Lys Glu Tyr Cys Glu Leu Asn Asn
                995             1000             1005

Ile Lys Gly Glu Pro Arg Ile Lys Lys Thr Ile Gly Lys Lys Val
        1010             1015             1020

Asn Ser Ile Glu Lys Leu Thr Thr Asp Val Leu Gly Asn Val Phe
        1025             1030             1035

Thr Asn Thr Gln Tyr Thr Lys Pro Gln Leu Leu Phe Lys Arg Gly
        1040             1045             1050

Asn

<210> SEQ ID NO 31
<211> LENGTH: 1054
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri Cas9

<400> SEQUENCE: 31

Met Lys Glu Lys Tyr Ile Leu Gly Leu Asp Leu Gly Ile Thr Ser Val
1               5               10              15

Gly Tyr Gly Ile Ile Asn Phe Glu Thr Lys Lys Ile Ile Asp Ala Gly
                20              25              30

Val Arg Leu Phe Pro Glu Ala Asn Val Asp Asn Asn Glu Gly Arg Arg
        35              40              45

Ser Lys Arg Gly Ser Arg Arg Leu Lys Arg Arg Arg Ile His Arg Leu

```
                50                  55                  60
Glu Arg Val Lys Leu Leu Leu Thr Glu Tyr Asp Leu Ile Asn Lys Glu
 65                  70                  75                  80

Gln Ile Pro Thr Ser Asn Asn Pro Tyr Gln Ile Arg Val Lys Gly Leu
                    85                  90                  95

Ser Glu Ile Leu Ser Lys Asp Glu Leu Ala Ile Ala Leu Leu His Leu
                100                 105                 110

Ala Lys Arg Arg Gly Ile His Asn Ile Asn Val Ser Ser Glu Asp Glu
            115                 120                 125

Asp Ala Ser Asn Glu Leu Ser Thr Lys Glu Gln Ile Asn Arg Asn Asn
130                 135                 140

Lys Leu Leu Lys Asp Lys Tyr Val Cys Glu Val Gln Leu Gln Arg Leu
145                 150                 155                 160

Lys Glu Gly Gln Ile Arg Gly Glu Lys Asn Arg Phe Lys Thr Thr Asp
                165                 170                 175

Ile Leu Lys Glu Ile Asp Gln Leu Leu Lys Val Gln Lys Asp Tyr His
                180                 185                 190

Asn Leu Asp Ile Asp Phe Ile Asn Gln Tyr Lys Glu Ile Val Glu Thr
            195                 200                 205

Arg Arg Glu Tyr Phe Glu Gly Pro Gly Gln Gly Ser Pro Phe Gly Trp
210                 215                 220

Asn Gly Asp Leu Lys Lys Trp Tyr Glu Met Leu Met Gly His Cys Thr
225                 230                 235                 240

Tyr Phe Pro Gln Glu Leu Arg Ser Val Lys Tyr Ala Tyr Ser Ala Asp
                245                 250                 255

Leu Phe Asn Ala Leu Asn Asp Leu Asn Asn Leu Ile Ile Gln Arg Asp
                260                 265                 270

Asn Ser Glu Lys Leu Glu Tyr His Glu Lys Tyr His Ile Ile Glu Asn
            275                 280                 285

Val Phe Lys Gln Lys Lys Lys Pro Thr Leu Lys Gln Ile Ala Lys Glu
            290                 295                 300

Ile Gly Val Asn Pro Glu Asp Ile Lys Gly Tyr Arg Ile Thr Lys Ser
305                 310                 315                 320

Gly Thr Pro Gln Phe Thr Glu Phe Lys Leu Tyr His Asp Leu Lys Ser
                325                 330                 335

Ile Val Phe Asp Lys Ser Ile Leu Glu Asn Glu Ala Ile Leu Asp Gln
                340                 345                 350

Ile Ala Glu Ile Leu Thr Ile Tyr Gln Asp Glu Gln Ser Ile Lys Glu
            355                 360                 365

Glu Leu Asn Lys Leu Pro Glu Ile Leu Asn Glu Gln Asp Lys Ala Glu
            370                 375                 380

Ile Ala Lys Leu Ile Gly Tyr Asn Gly Thr His Arg Leu Ser Leu Lys
385                 390                 395                 400

Cys Ile His Leu Ile Asn Glu Glu Leu Trp Gln Thr Ser Arg Asn Gln
                405                 410                 415

Met Glu Ile Phe Asn Tyr Leu Asn Ile Lys Pro Asn Lys Val Asp Leu
                420                 425                 430

Ser Glu Gln Asn Lys Ile Pro Lys Asp Met Val Asn Asp Phe Ile Leu
            435                 440                 445

Ser Pro Val Val Lys Arg Thr Phe Ile Gln Ser Ile Asn Val Ile Asn
450                 455                 460

Lys Val Ile Glu Lys Tyr Gly Ile Pro Glu Asp Ile Ile Ile Glu Leu
465                 470                 475                 480
```

Ala Arg Glu Asn Asn Ser Asp Arg Lys Lys Phe Ile Asn Asn Leu
            485             490             495

Gln Lys Lys Asn Glu Ala Thr Arg Lys Arg Ile Asn Glu Ile Ile Gly
            500             505             510

Gln Thr Gly Asn Gln Asn Ala Lys Arg Ile Val Glu Lys Ile Arg Leu
            515             520             525

His Asp Gln Gln Glu Gly Lys Cys Leu Tyr Ser Leu Glu Ser Ile Ala
            530             535             540

Leu Met Asp Leu Leu Asn Asn Pro Gln Asn Tyr Glu Val Asp His Ile
545             550             555             560

Ile Pro Arg Ser Val Ala Phe Asp Asn Ser Ile His Asn Lys Val Leu
            565             570             575

Val Lys Gln Ile Glu Asn Ser Lys Lys Gly Asn Arg Thr Pro Tyr Gln
            580             585             590

Tyr Leu Asn Ser Ser Asp Ala Lys Leu Ser Tyr Asn Gln Phe Lys Gln
            595             600             605

His Ile Leu Asn Leu Ser Lys Ser Lys Asp Arg Ile Ser Lys Lys Lys
            610             615             620

Lys Asp Tyr Leu Leu Glu Glu Arg Asp Ile Asn Lys Phe Glu Val Gln
625             630             635             640

Lys Glu Phe Ile Asn Arg Asn Leu Val Asp Thr Arg Tyr Ala Thr Arg
            645             650             655

Glu Leu Thr Ser Tyr Leu Lys Ala Tyr Phe Ser Ala Asn Asn Met Asp
            660             665             670

Val Lys Val Lys Thr Ile Asn Gly Ser Phe Thr Asn His Leu Arg Lys
            675             680             685

Val Trp Arg Phe Asp Lys Tyr Arg Asn His Gly Tyr Lys His His Ala
            690             695             700

Glu Asp Ala Leu Ile Ile Ala Asn Ala Asp Phe Leu Phe Lys Glu Asn
705             710             715             720

Lys Lys Leu Gln Asn Thr Asn Lys Ile Leu Glu Lys Pro Thr Ile Glu
            725             730             735

Asn Asn Thr Lys Lys Val Thr Val Glu Lys Glu Glu Asp Tyr Asn Asn
            740             745             750

Val Phe Glu Thr Pro Lys Leu Val Glu Asp Ile Lys Gln Tyr Arg Asp
            755             760             765

Tyr Lys Phe Ser His Arg Val Asp Lys Lys Pro Asn Arg Gln Leu Ile
            770             775             780

Asn Asp Thr Leu Tyr Ser Thr Arg Met Lys Asp Glu His Asp Tyr Ile
785             790             795             800

Val Gln Thr Ile Thr Asp Ile Tyr Gly Lys Asp Asn Thr Asn Leu Lys
            805             810             815

Lys Gln Phe Asn Lys Asn Pro Glu Lys Phe Leu Met Tyr Gln Asn Asp
            820             825             830

Pro Lys Thr Phe Glu Lys Leu Ser Ile Ile Met Lys Gln Tyr Ser Asp
            835             840             845

Glu Lys Asn Pro Leu Ala Lys Tyr Tyr Glu Glu Thr Gly Glu Tyr Leu
850             855             860

Thr Lys Tyr Ser Lys Lys Asn Asn Gly Pro Ile Val Lys Lys Ile Lys
865             870             875             880

Leu Leu Gly Asn Lys Val Gly Asn His Leu Asp Val Thr Asn Lys Tyr
            885             890             895

Glu Asn Ser Thr Lys Lys Leu Val Lys Leu Ser Ile Lys Asn Tyr Arg
            900             905             910

Phe Asp Val Tyr Leu Thr Glu Lys Gly Tyr Lys Phe Val Thr Ile Ala
        915             920             925

Tyr Leu Asn Val Phe Lys Lys Asp Asn Tyr Tyr Ile Pro Lys Asp
        930             935             940

Lys Tyr Gln Glu Leu Lys Glu Lys Lys Ile Lys Asp Thr Asp Gln
945             950             955             960

Phe Ile Ala Ser Phe Tyr Lys Asn Asp Leu Ile Lys Leu Asn Gly Asp
                965             970             975

Leu Tyr Lys Ile Ile Gly Val Asn Ser Asp Asp Arg Asn Ile Ile Glu
            980             985             990

Leu Asp Tyr Tyr Asp Ile Lys Tyr Lys Asp Tyr Cys Glu Ile Asn Asn
            995             1000            1005

Ile Lys Gly Glu Pro Arg Ile Lys Lys Thr Ile Gly Lys Lys Thr
            1010            1015            1020

Glu Ser Ile Glu Lys Phe Thr Thr Asp Val Leu Gly Asn Leu Tyr
            1025            1030            1035

Leu His Ser Thr Glu Lys Ala Pro Gln Leu Ile Phe Lys Arg Gly
            1040            1045            1050

Leu

<210> SEQ ID NO 32
<211> LENGTH: 1051
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus Cas9

<400> SEQUENCE: 32

Met Asn Asn Tyr Ile Leu Gly Leu Asp Ile Gly Ile Thr Ser Val Gly
1               5                   10                  15

Tyr Gly Ile Val Asp Ser Asp Thr Arg Glu Ile Lys Asp Ala Gly Val
            20                  25                  30

Arg Leu Phe Pro Glu Ala Asn Val Asp Asn Asn Glu Gly Arg Arg Ser
        35                  40                  45

Lys Arg Gly Ala Arg Arg Leu Lys Arg Arg Ile His Arg Leu Asp
50                  55                  60

Arg Val Lys His Leu Leu Ala Glu Tyr Asp Leu Leu Asp Leu Thr Asn
65                  70                  75                  80

Ile Pro Lys Ser Thr Asn Pro Tyr Gln Thr Arg Val Lys Gly Leu Asn
                85                  90                  95

Glu Lys Leu Ser Lys Asp Glu Leu Val Ile Ala Leu Leu His Ile Ala
            100                 105                 110

Lys Arg Arg Gly Ile His Asn Val Asn Val Met Met Asp Asp Asn Asp
        115                 120                 125

Ser Gly Asn Glu Leu Ser Thr Lys Asp Gln Leu Lys Lys Asn Ala Lys
    130                 135                 140

Ala Leu Ser Asp Lys Tyr Val Cys Glu Leu Gln Leu Glu Arg Phe Glu
145                 150                 155                 160

Gln Asp Tyr Lys Val Arg Gly Glu Lys Asn Arg Phe Lys Thr Glu Asp
                165                 170                 175

Phe Val Arg Glu Ala Arg Lys Leu Leu Glu Thr Gln Ser Lys Phe Phe

-continued

```
                180                 185                 190
Glu Ile Asp Gln Thr Phe Ile Met Arg Tyr Ile Glu Leu Ile Glu Thr
            195                 200                 205
Arg Arg Glu Tyr Phe Glu Gly Pro Gly Lys Gly Ser Pro Phe Gly Trp
        210                 215                 220
Glu Gly Asn Ile Lys Lys Trp Phe Glu Gln Met Met Gly His Cys Thr
225                 230                 235                 240
Tyr Phe Pro Glu Glu Leu Arg Ser Val Lys Tyr Ser Tyr Ser Ala Glu
                245                 250                 255
Leu Phe Asn Ala Leu Asn Asp Leu Asn Asn Leu Val Ile Thr Arg Asp
            260                 265                 270
Glu Asp Ala Lys Leu Asn Tyr Gly Glu Lys Phe Gln Ile Ile Glu Asn
        275                 280                 285
Val Phe Lys Gln Lys Lys Thr Pro Asn Leu Lys Gln Ile Ala Ile Glu
    290                 295                 300
Ile Gly Val His Glu Thr Glu Ile Lys Gly Tyr Arg Val Asn Lys Ser
305                 310                 315                 320
Gly Lys Pro Glu Phe Thr Gln Phe Lys Leu Tyr His Asp Leu Lys Asn
                325                 330                 335
Ile Phe Lys Asp Pro Lys Tyr Leu Asn Asp Ile Gln Leu Met Asp Asn
            340                 345                 350
Ile Ala Glu Ile Ile Thr Ile Tyr Gln Asp Ala Glu Ser Ile Ile Lys
        355                 360                 365
Glu Leu Asn Gln Leu Pro Glu Leu Leu Ser Glu Arg Glu Lys Glu Lys
    370                 375                 380
Ile Ser Ala Leu Ser Gly Tyr Ser Gly Thr His Arg Leu Ser Leu Lys
385                 390                 395                 400
Cys Ile Asn Leu Leu Leu Asp Asp Leu Trp Glu Ser Ser Leu Asn Gln
                405                 410                 415
Met Glu Leu Phe Thr Lys Leu Asn Leu Lys Pro Lys Lys Ile Asp Leu
            420                 425                 430
Ser Gln Gln His Lys Ile Pro Ser Lys Leu Val Asp Asp Phe Ile Leu
        435                 440                 445
Ser Pro Val Val Lys Arg Ala Phe Ile Gln Ser Ile Gln Val Val Asn
    450                 455                 460
Ala Ile Ile Asp Lys Tyr Gly Leu Pro Glu Asp Ile Ile Ile Glu Leu
465                 470                 475                 480
Ala Arg Glu Asn Asn Ser Asp Asp Arg Arg Lys Phe Leu Asn Gln Leu
                485                 490                 495
Gln Lys Gln Asn Glu Glu Thr Arg Lys Gln Val Glu Lys Val Leu Arg
            500                 505                 510
Glu Tyr Gly Asn Asp Asn Ala Lys Arg Ile Val Gln Lys Ile Lys Leu
        515                 520                 525
His Asn Met Gln Glu Gly Lys Cys Leu Tyr Ser Leu Lys Asp Ile Pro
    530                 535                 540
Leu Glu Asp Leu Leu Arg Asn Pro His His Tyr Glu Val Asp His Ile
545                 550                 555                 560
Ile Pro Arg Ser Val Ala Phe Asp Asn Ser Met His Asn Lys Val Leu
                565                 570                 575
Val Arg Ala Asp Glu Asn Ser Lys Lys Gly Asn Arg Thr Pro Tyr Gln
            580                 585                 590
Tyr Leu Asn Ser Ser Glu Ser Ser Leu Ser Tyr Asn Glu Phe Lys Gln
        595                 600                 605
```

```
His Ile Leu Asn Leu Ser Lys Thr Lys Asp Arg Ile Thr Lys Lys
            610                 615                 620

Arg Glu Tyr Leu Leu Glu Glu Arg Asp Ile Asn Lys Phe Asp Val Gln
625                 630                 635                 640

Lys Glu Phe Ile Asn Arg Asn Leu Val Asp Thr Arg Tyr Ala Thr Arg
                645                 650                 655

Glu Leu Thr Ser Leu Leu Lys Ala Tyr Phe Ser Ala Asn Asn Leu Asp
                660                 665                 670

Val Lys Val Lys Thr Ile Asn Gly Ser Phe Thr Asn Tyr Leu Arg Lys
            675                 680                 685

Val Trp Lys Phe Asp Lys Asp Arg Asn Lys Gly Tyr Lys His His Ala
    690                 695                 700

Glu Asp Ala Leu Ile Ile Ala Asn Ala Asp Phe Leu Phe Lys His Asn
705                 710                 715                 720

Lys Lys Leu Arg Asn Ile Asn Lys Val Leu Asp Ala Pro Ser Lys Glu
                725                 730                 735

Val Asp Lys Lys Arg Val Thr Val Gln Ser Glu Asp Glu Tyr Asn Gln
            740                 745                 750

Ile Phe Glu Asp Thr Gln Lys Ala Gln Ala Ile Lys Lys Phe Glu Ile
    755                 760                 765

Arg Lys Phe Ser His Arg Val Asp Lys Lys Pro Asn Arg Gln Leu Ile
770                 775                 780

Asn Asp Thr Leu Tyr Ser Thr Arg Asn Ile Asp Gly Ile Glu Tyr Val
785                 790                 795                 800

Val Glu Ser Ile Lys Asp Ile Tyr Ser Val Asn Asn Asp Lys Val Lys
                805                 810                 815

Thr Lys Phe Lys Lys Asp Pro His Arg Leu Leu Met Tyr Arg Asn Asp
            820                 825                 830

Pro Gln Thr Phe Glu Lys Phe Glu Lys Val Phe Lys Gln Tyr Glu Ser
                835                 840                 845

Glu Lys Asn Pro Phe Ala Lys Tyr Tyr Glu Glu Thr Gly Glu Lys Ile
    850                 855                 860

Arg Lys Phe Ser Lys Thr Gly Gln Gly Pro Tyr Ile Asn Lys Ile Lys
865                 870                 875                 880

Tyr Leu Arg Glu Arg Leu Gly Arg His Cys Asp Val Thr Asn Lys Tyr
                885                 890                 895

Ile Asn Ser Arg Asn Lys Ile Val Gln Leu Lys Ile Tyr Ser Tyr Arg
            900                 905                 910

Phe Asp Ile Tyr Gln Tyr Gly Asn Asn Tyr Lys Met Ile Thr Ile Ser
    915                 920                 925

Tyr Ile Asp Leu Glu Gln Lys Ser Asn Tyr Tyr Ile Ser Arg Glu
930                 935                 940

Lys Tyr Glu Gln Lys Lys Lys Asp Lys Gln Ile Asp Asp Ser Tyr Lys
945                 950                 955                 960

Phe Ile Gly Ser Phe Tyr Lys Asn Asp Ile Ile Asn Tyr Asn Gly Glu
                965                 970                 975

Met Tyr Arg Val Ile Gly Val Asn Asp Ser Glu Lys Asn Lys Ile Gln
            980                 985                 990

Leu Asp Met Ile Asp Ile Ser Ile Lys Asp Tyr Met Glu Leu Asn Asn
                995                1000                1005

Ile Lys Lys Thr Gly Val Ile Tyr Lys Thr Ile Gly Lys Ser Thr
   1010                1015                1020
```

```
Thr His Ile Glu Lys Tyr Thr Thr Asp Ile Leu Gly Asn Leu Tyr
    1025                1030                1035

Lys Ala Ala Pro Pro Lys Lys Pro Gln Leu Ile Phe Lys
    1040                1045                1050

<210> SEQ ID NO 33
<211> LENGTH: 1052
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti Cas9

<400> SEQUENCE: 33

Met Glu Lys Asp Tyr Ile Leu Gly Leu Asp Ile Gly Ile Gly Ser Val
1               5                   10                  15

Gly Tyr Gly Leu Ile Asp Tyr Asp Thr Lys Ser Ile Ile Asp Ala Gly
                20                  25                  30

Val Arg Leu Phe Pro Glu Ala Asn Ala Asp Asn Asn Leu Gly Arg Arg
            35                  40                  45

Ala Lys Arg Gly Ala Arg Arg Leu Lys Arg Arg Ile His Arg Leu
    50                  55                  60

Glu Arg Val Lys Ser Leu Leu Ser Glu Tyr Lys Ile Ile Ser Gly Leu
65                  70                  75                  80

Ala Pro Thr Asn Asn Gln Pro Tyr Asn Ile Arg Val Lys Gly Leu Thr
                85                  90                  95

Glu Gln Leu Thr Lys Asp Glu Leu Ala Val Ala Leu Leu His Ile Ala
            100                 105                 110

Lys Arg Arg Gly Ile His Asn Val Asp Val Ala Ala Asp Lys Glu Glu
        115                 120                 125

Thr Ala Ser Asp Ser Leu Ser Thr Lys Asp Gln Ile Asn Lys Asn Ala
    130                 135                 140

Lys Phe Leu Glu Ser Arg Tyr Val Cys Glu Leu Gln Lys Glu Arg Leu
145                 150                 155                 160

Glu Asn Glu Gly His Val Arg Gly Val Glu Asn Arg Phe Leu Thr Lys
                165                 170                 175

Asp Ile Val Arg Glu Ala Lys Lys Ile Ile Asp Thr Gln Met Gln Tyr
            180                 185                 190

Tyr Pro Glu Ile Asp Glu Thr Phe Lys Glu Lys Tyr Ile Ser Leu Val
        195                 200                 205

Glu Thr Arg Arg Glu Tyr Tyr Glu Gly Pro Gly Lys Gly Ser Pro Tyr
    210                 215                 220

Gly Trp Asp Ala Asp Val Lys Lys Trp Tyr Gln Leu Met Met Gly His
225                 230                 235                 240

Cys Thr Tyr Phe Pro Val Glu Phe Arg Ser Val Lys Tyr Ala Tyr Thr
                245                 250                 255

Ala Asp Leu Tyr Asn Ala Leu Asn Asp Leu Asn Asn Leu Thr Ile Ala
            260                 265                 270

Arg Asp Asp Asn Pro Lys Leu Glu Tyr His Glu Lys Tyr His Ile Ile
        275                 280                 285

Glu Asn Val Phe Lys Gln Lys Arg Asn Pro Thr Leu Lys Gln Ile Ala
    290                 295                 300

Lys Glu Ile Gly Val Asn Asp Ile Asn Ile Ser Gly Tyr Arg Val Thr
305                 310                 315                 320
```

```
Lys Ser Gly Lys Pro Gln Phe Thr Ser Phe Lys Leu Phe His Asp Leu
            325                 330                 335

Lys Lys Val Val Lys Asp His Ala Ile Leu Asp Asp Ile Asp Leu Leu
            340                 345                 350

Asn Gln Ile Ala Glu Ile Leu Thr Ile Tyr Gln Asp Lys Asp Ser Ile
            355                 360                 365

Val Ala Glu Leu Gly Gln Leu Glu Tyr Leu Met Ser Glu Ala Asp Lys
            370                 375                 380

Gln Ser Ile Ser Glu Leu Thr Gly Tyr Thr Gly Thr His Ser Leu Ser
385                 390                 395                 400

Leu Lys Cys Met Asn Met Ile Ile Asp Glu Leu Trp His Ser Ser Met
            405                 410                 415

Asn Gln Met Glu Val Phe Thr Tyr Leu Asn Met Arg Pro Lys Lys Tyr
            420                 425                 430

Glu Leu Lys Gly Tyr Gln Arg Ile Pro Thr Asp Met Ile Asp Asp Ala
            435                 440                 445

Ile Leu Ser Pro Val Val Lys Arg Ser Phe Lys Gln Ala Ile Gly Val
            450                 455                 460

Val Asn Ala Ile Ile Lys Lys Tyr Gly Leu Pro Lys Asp Ile Ile Ile
465                 470                 475                 480

Glu Leu Ala Arg Glu Ser Asn Ser Ala Glu Lys Ser Arg Tyr Leu Arg
            485                 490                 495

Ala Ile Gln Lys Lys Asn Glu Lys Thr Arg Glu Arg Ile Glu Ala Ile
            500                 505                 510

Ile Lys Glu Tyr Gly Asn Glu Asn Ala Lys Gly Leu Val Gln Lys Ile
            515                 520                 525

Lys Leu His Asp Ala Gln Glu Gly Lys Cys Leu Tyr Ser Leu Lys Asp
            530                 535                 540

Ile Pro Leu Glu Asp Leu Leu Arg Asn Pro Asn Asn Tyr Asp Ile Asp
545                 550                 555                 560

His Ile Ile Pro Arg Ser Val Ser Phe Asp Asp Ser Met His Asn Lys
            565                 570                 575

Val Leu Val Arg Arg Glu Gln Asn Ala Lys Lys Asn Asn Gln Thr Pro
            580                 585                 590

Tyr Gln Tyr Leu Thr Ser Gly Tyr Ala Asp Ile Lys Tyr Ser Val Phe
            595                 600                 605

Lys Gln His Val Leu Asn Leu Ala Glu Asn Lys Asp Arg Met Thr Lys
            610                 615                 620

Lys Lys Arg Glu Tyr Leu Leu Glu Glu Arg Asn Ile Asn Lys Tyr Asp
625                 630                 635                 640

Val Gln Lys Glu Phe Ile Asn Arg Asn Leu Val Asp Thr Arg Tyr Thr
            645                 650                 655

Thr Arg Glu Leu Thr Thr Leu Leu Lys Thr Tyr Phe Thr Ile Asn Asn
            660                 665                 670

Leu Asp Val Lys Val Lys Thr Ile Asn Gly Ser Phe Thr Asp Phe Leu
            675                 680                 685

Arg Lys Arg Trp Gly Phe Lys Lys Asn Arg Asp Glu Gly Tyr Lys His
            690                 695                 700

His Ala Glu Asp Ala Leu Ile Ile Ala Asn Ala Asp Tyr Leu Phe Lys
705                 710                 715                 720

Glu His Lys Leu Leu Lys Glu Ile Lys Asp Val Ser Asp Leu Ala Gly
            725                 730                 735

Asp Glu Arg Asn Ser Asn Val Lys Asp Glu Asp Gln Tyr Glu Glu Val
```

```
                    740                 745                 750
Phe Gly Gly Tyr Phe Lys Ile Glu Asp Ile Lys Lys Tyr Lys Ile Lys
                755                 760                 765

Lys Phe Ser His Arg Val Asp Lys Pro Asn Arg Gln Leu Ile Asn
        770                 775                 780

Asp Thr Ile Tyr Ser Thr Arg Val Lys Asp Lys Arg Tyr Leu Ile
785                 790                 795                 800

Asn Thr Leu Lys Asn Leu Tyr Asp Lys Ser Asn Gly Asp Leu Lys Glu
                805                 810                 815

Arg Met Gln Lys Asp Pro Glu Ser Leu Leu Met Tyr His His Asp Pro
                820                 825                 830

Gln Thr Phe Glu Lys Leu Lys Ile Val Met Ser Gln Tyr Glu Asn Glu
            835                 840                 845

Lys Asn Pro Leu Ala Lys Tyr Phe Glu Glu Thr Gly Gln Tyr Leu Thr
        850                 855                 860

Lys Tyr Ala Lys His Asp Asn Gly Pro Ala Ile His Lys Ile Lys Tyr
865                 870                 875                 880

Tyr Gly Asn Lys Leu Val Glu His Leu Asp Ile Thr Lys Asn Tyr His
                885                 890                 895

Asn Pro Gln Asn Lys Val Val Gln Leu Ser Gln Lys Ser Phe Arg Phe
            900                 905                 910

Asp Val Tyr Gln Thr Asp Lys Gly Tyr Lys Phe Ile Ser Ile Ala Tyr
            915                 920                 925

Leu Thr Leu Lys Asn Glu Lys Asn Tyr Tyr Ala Ile Ser Gln Glu Lys
        930                 935                 940

Tyr Asp Gln Leu Lys Ser Glu Lys Lys Ile Ser Asn Asn Ala Val Phe
945                 950                 955                 960

Ile Gly Ser Phe Tyr Thr Ser Asp Ile Ile Glu Ile Asn Asn Glu Lys
                965                 970                 975

Phe Arg Val Ile Gly Val Asn Ser Asp Lys Asn Asn Leu Ile Glu Val
            980                 985                 990

Asp Arg Ile Asp Ile Arg Gln Lys  Glu Phe Ile Glu Leu  Glu Glu Glu
        995                 1000                1005

Lys Lys  Asn Asn Arg Ile Lys  Val Thr Ile Gly Arg  Lys Thr Thr
    1010                1015                1020

Asn Ile  Glu Lys Phe His Thr  Asp Ile Leu Gly Asn  Met Tyr Lys
    1025                1030                1035

Ser Lys  Arg Pro Lys Ala Pro  Gln Leu Val Phe Lys  Lys Gly
    1040                1045                1050

<210> SEQ ID NO 34
<211> LENGTH: 67
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 1 from 8
      mini-domain library

<400> SEQUENCE: 34

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30
```

-continued

Val Arg Leu Phe Pro Glu Ala Asn Val Glu Asn Asn Glu Gly Arg Arg
         35                  40                  45

Ser Lys Arg Gly Ser Arg Leu Lys Arg Arg Ile His Arg Leu
 50                  55                  60

Glu Arg Val
 65

<210> SEQ ID NO 35
<211> LENGTH: 67
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 1 from 8
      mini-domain library

<400> SEQUENCE: 35

Met Lys Glu Lys Tyr Ile Leu Gly Leu Asp Leu Gly Ile Thr Ser Val
 1               5                  10                  15

Gly Tyr Gly Ile Ile Asn Phe Glu Thr Lys Lys Ile Ile Asp Ala Gly
                 20                  25                  30

Val Arg Leu Phe Pro Glu Ala Asn Val Asp Asn Asn Glu Gly Arg Arg
         35                  40                  45

Ser Lys Arg Gly Ser Arg Leu Lys Arg Arg Ile His Arg Leu
 50                  55                  60

Glu Arg Val
 65

<210> SEQ ID NO 36
<211> LENGTH: 66
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 1 from 8
      mini-domain library

<400> SEQUENCE: 36

Met Asn Asn Tyr Ile Leu Gly Leu Asp Ile Gly Ile Thr Ser Val Gly
 1               5                  10                  15

Tyr Gly Ile Val Asp Ser Asp Thr Arg Glu Ile Lys Asp Ala Gly Val
                 20                  25                  30

Arg Leu Phe Pro Glu Ala Asn Val Asp Asn Asn Glu Gly Arg Arg Ser
         35                  40                  45

Lys Arg Gly Ala Arg Arg Leu Lys Arg Arg Ile His Arg Leu Asp
 50                  55                  60

Arg Val
 65

<210> SEQ ID NO 37
<211> LENGTH: 67
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 1 from 8
      mini-domain library -continued

```
<400> SEQUENCE: 37

Met Glu Lys Asp Tyr Ile Leu Gly Leu Asp Ile Gly Ile Gly Ser Val
1               5                   10                  15

Gly Tyr Gly Leu Ile Asp Tyr Asp Thr Lys Ser Ile Ile Asp Ala Gly
            20                  25                  30

Val Arg Leu Phe Pro Glu Ala Asn Ala Asp Asn Asn Leu Gly Arg Arg
        35                  40                  45

Ala Lys Arg Gly Ala Arg Arg Leu Lys Arg Arg Ile His Arg Leu
    50                  55                  60

Glu Arg Val
65

<210> SEQ ID NO 38
<211> LENGTH: 52
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 2 from 8
      mini-domain library

<400> SEQUENCE: 38

Lys Lys Leu Leu Glu Asp Tyr Asn Leu Leu Asp Gln Ser Gln Ile Pro
1               5                   10                  15

Gln Ser Thr Asn Pro Tyr Ala Ile Arg Val Lys Gly Leu Ser Glu Ala
            20                  25                  30

Leu Ser Lys Asp Glu Leu Val Ile Ala Leu Leu His Ile Ala Lys Arg
        35                  40                  45

Arg Gly Ile His
    50

<210> SEQ ID NO 39
<211> LENGTH: 52
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 2 from 8
      mini-domain library

<400> SEQUENCE: 39

Lys Leu Leu Leu Thr Glu Tyr Asp Leu Ile Asn Lys Glu Gln Ile Pro
1               5                   10                  15

Thr Ser Asn Asn Pro Tyr Gln Ile Arg Val Lys Gly Leu Ser Glu Ile
            20                  25                  30

Leu Ser Lys Asp Glu Leu Ala Ile Ala Leu Leu His Leu Ala Lys Arg
        35                  40                  45

Arg Gly Ile His
    50

<210> SEQ ID NO 40
<211> LENGTH: 52
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 2 from 8
```

-continued mini-domain library

<400> SEQUENCE: 40

Lys His Leu Leu Ala Glu Tyr Asp Leu Leu Asp Leu Thr Asn Ile Pro
1               5                   10                  15

Lys Ser Thr Asn Pro Tyr Gln Thr Arg Val Lys Gly Leu Asn Glu Lys
            20                  25                  30

Leu Ser Lys Asp Glu Leu Val Ile Ala Leu Leu His Ile Ala Lys Arg
        35                  40                  45

Arg Gly Ile His
    50

<210> SEQ ID NO 41
<211> LENGTH: 51
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 2 from 8
      mini-domain library

<400> SEQUENCE: 41

Lys Ser Leu Leu Ser Glu Tyr Lys Ile Ile Ser Gly Leu Ala Pro Thr
1               5                   10                  15

Asn Asn Gln Pro Tyr Asn Ile Arg Val Lys Gly Leu Thr Glu Gln Leu
            20                  25                  30

Thr Lys Asp Glu Leu Ala Val Ala Leu Leu His Ile Ala Lys Arg Arg
        35                  40                  45

Gly Ile His
    50

<210> SEQ ID NO 42
<211> LENGTH: 92
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 3 from 8
      mini-domain library

<400> SEQUENCE: 42

Lys Ile Asp Val Ile Asp Ser Asn Asp Val Gly Asn Glu Leu Ser
1               5                   10                  15

Thr Lys Glu Gln Leu Asn Lys Asn Ser Lys Leu Leu Lys Asp Lys Phe
            20                  25                  30

Val Cys Gln Ile Gln Leu Glu Arg Met Asn Glu Gly Val Arg Gly
        35                  40                  45

Glu Lys Asn Arg Phe Lys Thr Ala Asp Ile Ile Lys Glu Ile Ile Gln
    50                  55                  60

Leu Leu Asn Val Gln Lys Asn Phe His Gln Leu Asp Glu Asn Phe Ile
65                  70                  75                  80

Asn Lys Tyr Ile Glu Leu Val Glu Met Arg Arg Glu
                85                  90

<210> SEQ ID NO 43
<211> LENGTH: 92
<212> TYPE: PRT
<213> ORGANISM: Artificial sequence

```
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 3 from 8
      mini-domain library

<400> SEQUENCE: 43

Asn Ile Asn Val Ser Ser Glu Asp Glu Asp Ala Ser Asn Glu Leu Ser
1               5                   10                  15

Thr Lys Glu Gln Ile Asn Arg Asn Lys Leu Leu Lys Asp Lys Tyr
            20                  25                  30

Val Cys Glu Val Gln Leu Gln Arg Leu Lys Glu Gly Gln Ile Arg Gly
        35                  40                  45

Glu Lys Asn Arg Phe Lys Thr Thr Asp Ile Leu Lys Glu Ile Asp Gln
    50                  55                  60

Leu Leu Lys Val Gln Lys Asp Tyr His Asn Leu Asp Ile Asp Phe Ile
65                  70                  75                  80

Asn Gln Tyr Lys Glu Ile Val Glu Thr Arg Arg Glu
                85                  90

<210> SEQ ID NO 44
<211> LENGTH: 93
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 3 from 8
      mini-domain library

<400> SEQUENCE: 44

Asn Val Asn Val Met Met Asp Asp Asn Asp Ser Gly Asn Glu Leu Ser
1               5                   10                  15

Thr Lys Asp Gln Leu Lys Lys Asn Ala Lys Ala Leu Ser Asp Lys Tyr
            20                  25                  30

Val Cys Glu Leu Gln Leu Glu Arg Phe Glu Gln Asp Tyr Lys Val Arg
        35                  40                  45

Gly Glu Lys Asn Arg Phe Lys Thr Glu Asp Phe Val Arg Glu Ala Arg
    50                  55                  60

Lys Leu Leu Glu Thr Gln Ser Lys Phe Phe Glu Ile Asp Gln Thr Phe
65                  70                  75                  80

Ile Met Arg Tyr Ile Glu Leu Ile Glu Thr Arg Arg Glu
                85                  90

<210> SEQ ID NO 45
<211> LENGTH: 95
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 3 from 8
      mini-domain library

<400> SEQUENCE: 45

Asn Val Asp Val Ala Ala Asp Lys Glu Glu Thr Ala Ser Asp Ser Leu
1               5                   10                  15

Ser Thr Lys Asp Gln Ile Asn Lys Asn Ala Lys Phe Leu Glu Ser Arg
            20                  25                  30
```

Tyr Val Cys Glu Leu Gln Lys Glu Arg Leu Glu Asn Glu Gly His Val
            35                  40                  45

Arg Gly Val Glu Asn Arg Phe Leu Thr Lys Asp Ile Val Arg Glu Ala
 50                  55                  60

Lys Lys Ile Ile Asp Thr Gln Met Gln Tyr Tyr Pro Glu Ile Asp Glu
 65                  70                  75                  80

Thr Phe Lys Glu Lys Tyr Ile Ser Leu Val Glu Thr Arg Arg Glu
                 85                  90                  95

<210> SEQ ID NO 46
<211> LENGTH: 111
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 4 from 8
      mini-domain library

<400> SEQUENCE: 46

Tyr Phe Glu Gly Pro Gly Lys Gly Ser Pro Tyr Gly Trp Glu Gly Asp
 1               5                  10                  15

Pro Lys Ala Trp Tyr Glu Thr Leu Met Gly His Cys Thr Tyr Phe Pro
                20                  25                  30

Asp Glu Leu Arg Ser Val Lys Tyr Ala Tyr Ser Ala Asp Leu Phe Asn
            35                  40                  45

Ala Leu Asn Asp Leu Asn Asn Leu Val Ile Gln Arg Asp Gly Leu Ser
 50                  55                  60

Lys Leu Glu Tyr His Glu Lys Tyr His Ile Ile Glu Asn Val Phe Lys
 65                  70                  75                  80

Gln Lys Lys Lys Pro Thr Leu Lys Gln Ile Ala Asn Glu Ile Asn Val
                 85                  90                  95

Asn Pro Glu Asp Ile Lys Gly Tyr Arg Ile Thr Lys Ser Gly Lys
                100                 105                 110

<210> SEQ ID NO 47
<211> LENGTH: 111
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 4 from 8
      mini-domain library

<400> SEQUENCE: 47

Tyr Phe Glu Gly Pro Gly Gln Gly Ser Pro Phe Gly Trp Asn Gly Asp
 1               5                  10                  15

Leu Lys Lys Trp Tyr Glu Met Leu Met Gly His Cys Thr Tyr Phe Pro
                20                  25                  30

Gln Glu Leu Arg Ser Val Lys Tyr Ala Tyr Ser Ala Asp Leu Phe Asn
            35                  40                  45

Ala Leu Asn Asp Leu Asn Asn Leu Ile Ile Gln Arg Asp Asn Ser Glu
 50                  55                  60

Lys Leu Glu Tyr His Glu Lys Tyr His Ile Ile Glu Asn Val Phe Lys
 65                  70                  75                  80

Gln Lys Lys Lys Pro Thr Leu Lys Gln Ile Ala Lys Glu Ile Gly Val
                 85                  90                  95

Asn Pro Glu Asp Ile Lys Gly Tyr Arg Ile Thr Lys Ser Gly Thr
                100                 105                 110

<210> SEQ ID NO 48
<211> LENGTH: 111
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 4 from 8
      mini-domain library

<400> SEQUENCE: 48

Tyr Phe Glu Gly Pro Gly Lys Gly Ser Pro Phe Gly Trp Glu Gly Asn
1               5                   10                  15

Ile Lys Lys Trp Phe Glu Gln Met Met Gly His Cys Thr Tyr Phe Pro
                20                  25                  30

Glu Glu Leu Arg Ser Val Lys Tyr Ser Tyr Ser Ala Glu Leu Phe Asn
            35                  40                  45

Ala Leu Asn Asp Leu Asn Asn Leu Val Ile Thr Arg Asp Glu Asp Ala
        50                  55                  60

Lys Leu Asn Tyr Gly Glu Lys Phe Gln Ile Ile Glu Asn Val Phe Lys
65                  70                  75                  80

Gln Lys Lys Thr Pro Asn Leu Lys Gln Ile Ala Ile Glu Ile Gly Val
                85                  90                  95

His Glu Thr Glu Ile Lys Gly Tyr Arg Val Asn Lys Ser Gly Lys
                100                 105                 110

<210> SEQ ID NO 49
<211> LENGTH: 111
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 4 from 8
      mini-domain library

<400> SEQUENCE: 49

Tyr Tyr Glu Gly Pro Gly Lys Gly Ser Pro Tyr Gly Trp Asp Ala Asp
1               5                   10                  15

Val Lys Lys Trp Tyr Gln Leu Met Met Gly His Cys Thr Tyr Phe Pro
                20                  25                  30

Val Glu Phe Arg Ser Val Lys Tyr Ala Tyr Thr Ala Asp Leu Tyr Asn
            35                  40                  45

Ala Leu Asn Asp Leu Asn Asn Leu Thr Ile Ala Arg Asp Asp Asn Pro
        50                  55                  60

Lys Leu Glu Tyr His Glu Lys Tyr His Ile Ile Glu Asn Val Phe Lys
65                  70                  75                  80

Gln Lys Arg Asn Pro Thr Leu Lys Gln Ile Ala Lys Glu Ile Gly Val
                85                  90                  95

Asn Asp Ile Asn Ile Ser Gly Tyr Arg Val Thr Lys Ser Gly Lys
                100                 105                 110

<210> SEQ ID NO 50
<211> LENGTH: 131
<212> TYPE: PRT
<213> ORGANISM: Artificial sequence
<220> FEATURE:

<223> OTHER INFORMATION: Synthetic polypeptide
<220> FEATURE:
<221> NAME/KEY: misc_feature
<223> OTHER INFORMATION: Staphylococcus lugdunensis mini-domain 5 from 8
      mini-domain library

<400> SEQUENCE: 50

Pro Gln Phe Thr Glu Phe Lys Leu Tyr His Asp Leu Lys Ser Val Leu
1               5                   10                  15

Phe Asp Gln Ser Ile Leu Glu Asn Glu Asp Val Leu Asp Gln Ile Ala
            20                  25                  30

Glu Ile Leu Thr Ile Tyr Gln Asp Lys Asp Ser Ile Lys Ser Lys Leu
        35                  40                  45

Thr Glu Leu Asp Ile Leu Leu Asn Glu Glu Asp Lys Glu Asn Ile Ala
    50                  55                  60

Gln Leu Thr Gly Tyr Thr Gly Thr His Arg Leu Ser Leu Lys Cys Ile
65                  70                  75                  80

Arg Leu Val Leu Glu Glu Gln Trp Tyr Ser Ser Arg Asn Gln Met Glu
                85                  90                  95

Ile Phe Thr His Leu Asn Ile Lys Pro Lys Lys Ile Asn Leu Thr Ala
            100                 105                 110

Ala Asn Lys Ile Pro Lys Ala Met Ile Asp Glu Phe Ile Leu Ser Pro
        115                 120                 125

Val Val Lys
    130

<210> SEQ ID NO 51
<211> LENGTH: 131
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 5 from 8
      mini-domain library

<400> SEQUENCE: 51

Pro Gln Phe Thr Glu Phe Lys Leu Tyr His Asp Leu Lys Ser Ile Val
1               5                   10                  15

Phe Asp Lys Ser Ile Leu Glu Asn Glu Ala Ile Leu Asp Gln Ile Ala
            20                  25                  30

Glu Ile Leu Thr Ile Tyr Gln Asp Glu Gln Ser Ile Lys Glu Glu Leu
        35                  40                  45

Asn Lys Leu Pro Glu Ile Leu Asn Glu Gln Asp Lys Ala Glu Ile Ala
    50                  55                  60

Lys Leu Ile Gly Tyr Asn Gly Thr His Arg Leu Ser Leu Lys Cys Ile
65                  70                  75                  80

His Leu Ile Asn Glu Glu Leu Trp Gln Thr Ser Arg Asn Gln Met Glu
                85                  90                  95

Ile Phe Asn Tyr Leu Asn Ile Lys Pro Asn Lys Val Asp Leu Ser Glu
            100                 105                 110

Gln Asn Lys Ile Pro Lys Asp Met Val Asn Asp Phe Ile Leu Ser Pro
        115                 120                 125

Val Val Lys
    130

<210> SEQ ID NO 52
<211> LENGTH: 131

```
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 5 from 8
      mini-domain library

<400> SEQUENCE: 52
```

| | | | | | | | | | | | | | | | |
|---|---|---|---|---|---|---|---|---|---|---|---|---|---|---|---|
|Pro|Glu|Phe|Thr|Gln|Phe|Lys|Leu|Tyr|His|Asp|Leu|Lys|Asn|Ile|Phe|
|1| | | |5| | | | |10| | | | |15| |
|Lys|Asp|Pro|Lys|Tyr|Leu|Asn|Asp|Ile|Gln|Leu|Met|Asp|Asn|Ile|Ala|
| | | |20| | | | |25| | | | |30| | |
|Glu|Ile|Ile|Thr|Ile|Tyr|Gln|Asp|Ala|Glu|Ser|Ile|Ile|Lys|Glu|Leu|
| | | | |35| | | | |40| | | | |45| |
|Asn|Gln|Leu|Pro|Glu|Leu|Leu|Ser|Glu|Arg|Glu|Lys|Glu|Lys|Ile|Ser|
| |50| | | | |55| | | | |60| | | | |
|Ala|Leu|Ser|Gly|Tyr|Ser|Gly|Thr|His|Arg|Leu|Ser|Leu|Lys|Cys|Ile|
|65| | | | |70| | | | |75| | | | |80|
|Asn|Leu|Leu|Asp|Asp|Leu|Trp|Glu|Ser|Ser|Leu|Asn|Gln|Met|Glu|
| | | | |85| | | | |90| | | | |95| |
|Leu|Phe|Thr|Lys|Leu|Asn|Leu|Lys|Pro|Lys|Lys|Ile|Asp|Leu|Ser|Gln|
| | | |100| | | | |105| | | | |110| | |
|Gln|His|Lys|Ile|Pro|Ser|Lys|Leu|Val|Asp|Asp|Phe|Ile|Leu|Ser|Pro|
| | |115| | | | |120| | | | |125| | | |
|Val|Val|Lys| | | | | | | | | | | | | |
| | |130| | | | | | | | | | | | | |

```
<210> SEQ ID NO 53
<211> LENGTH: 131
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 5 from 8
      mini-domain library

<400> SEQUENCE: 53
```

| | | | | | | | | | | | | | | | |
|---|---|---|---|---|---|---|---|---|---|---|---|---|---|---|---|
|Pro|Gln|Phe|Thr|Ser|Phe|Lys|Leu|Phe|His|Asp|Leu|Lys|Lys|Val|Val|
|1| | | |5| | | | |10| | | | |15| |
|Lys|Asp|His|Ala|Ile|Leu|Asp|Asp|Ile|Asp|Leu|Leu|Asn|Gln|Ile|Ala|
| | | |20| | | | |25| | | | |30| | |
|Glu|Ile|Leu|Thr|Ile|Tyr|Gln|Asp|Lys|Asp|Ser|Ile|Val|Ala|Glu|Leu|
| | | | |35| | | | |40| | | | |45| |
|Gly|Gln|Leu|Glu|Tyr|Leu|Met|Ser|Glu|Ala|Asp|Lys|Gln|Ser|Ile|Ser|
| |50| | | | |55| | | | |60| | | | |
|Glu|Leu|Thr|Gly|Tyr|Thr|Gly|Thr|His|Ser|Leu|Ser|Leu|Lys|Cys|Met|
|65| | | | |70| | | | |75| | | | |80|
|Asn|Met|Ile|Ile|Asp|Glu|Leu|Trp|His|Ser|Ser|Met|Asn|Gln|Met|Glu|
| | | | |85| | | | |90| | | | |95| |
|Val|Phe|Thr|Tyr|Leu|Asn|Met|Arg|Pro|Lys|Lys|Tyr|Glu|Leu|Lys|Gly|
| | | |100| | | | |105| | | | |110| | |
|Tyr|Gln|Arg|Ile|Pro|Thr|Asp|Met|Ile|Asp|Asp|Ala|Ile|Leu|Ser|Pro|
| | |115| | | | |120| | | | |125| | | |
|Val|Val|Lys| | | | | | | | | | | | | |
| | |130| | | | | | | | | | | | | |

<210> SEQ ID NO 54
<211> LENGTH: 89
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 6 from 8
      mini-domain library

<400> SEQUENCE: 54

Arg Thr Phe Gly Gln Ala Ile Asn Leu Ile Asn Lys Ile Ile Glu Lys
1               5                   10                  15

Tyr Gly Val Pro Glu Asp Ile Ile Glu Leu Ala Arg Glu Asn Asn
            20                  25                  30

Ser Lys Asp Lys Gln Lys Phe Ile Asn Glu Met Gln Lys Lys Asn Glu
            35                  40                  45

Asn Thr Arg Lys Arg Ile Asn Glu Ile Gly Lys Tyr Gly Asn Gln
        50                  55                  60

Asn Ala Lys Arg Leu Val Glu Lys Ile Arg Leu His Asp Gln Glu
65                  70                  75                  80

Gly Lys Cys Leu Tyr Ser Leu Glu Ser
                85

<210> SEQ ID NO 55
<211> LENGTH: 89
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 6 from 8
      mini-domain library

<400> SEQUENCE: 55

Arg Thr Phe Ile Gln Ser Ile Asn Val Ile Asn Lys Val Ile Glu Lys
1               5                   10                  15

Tyr Gly Ile Pro Glu Asp Ile Ile Ile Glu Leu Ala Arg Glu Asn Asn
            20                  25                  30

Ser Asp Asp Arg Lys Lys Phe Ile Asn Asn Leu Gln Lys Lys Asn Glu
            35                  40                  45

Ala Thr Arg Lys Arg Ile Asn Glu Ile Gly Gln Thr Gly Asn Gln
        50                  55                  60

Asn Ala Lys Arg Ile Val Glu Lys Ile Arg Leu His Asp Gln Gln Glu
65                  70                  75                  80

Gly Lys Cys Leu Tyr Ser Leu Glu Ser
                85

<210> SEQ ID NO 56
<211> LENGTH: 89
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 6 from 8
      mini-domain library

<400> SEQUENCE: 56

Arg Ala Phe Ile Gln Ser Ile Gln Val Val Asn Ala Ile Ile Asp Lys

-continued 1 5 10 15

Tyr Gly Leu Pro Glu Asp Ile Ile Ile Glu Leu Ala Arg Glu Asn Asn
20 25 30

Ser Asp Asp Arg Arg Lys Phe Leu Asn Gln Leu Gln Lys Gln Asn Glu
35 40 45

Glu Thr Arg Lys Gln Val Glu Lys Val Leu Arg Glu Tyr Gly Asn Asp
50 55 60

Asn Ala Lys Arg Ile Val Gln Lys Ile Lys Leu His Asn Met Gln Glu
65 70 75 80

Gly Lys Cys Leu Tyr Ser Leu Lys Asp
85

<210> SEQ ID NO 57
<211> LENGTH: 89
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 6 from 8 mini-domain library

<400> SEQUENCE: 57

Arg Ser Phe Lys Gln Ala Ile Gly Val Val Asn Ala Ile Ile Lys Lys
1 5 10 15

Tyr Gly Leu Pro Lys Asp Ile Ile Ile Glu Leu Ala Arg Glu Ser Asn
20 25 30

Ser Ala Glu Lys Ser Arg Tyr Leu Arg Ala Ile Gln Lys Lys Asn Glu
35 40 45

Lys Thr Arg Glu Arg Ile Glu Ala Ile Ile Lys Glu Tyr Gly Asn Glu
50 55 60

Asn Ala Lys Gly Leu Val Gln Lys Ile Lys Leu His Asp Ala Gln Glu
65 70 75 80

Gly Lys Cys Leu Tyr Ser Leu Lys Asp
85

<210> SEQ ID NO 58
<211> LENGTH: 116
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 7 from 8 mini-domain library

<400> SEQUENCE: 58

Ile Pro Leu Glu Asp Leu Leu Asn Asn Pro Asn His Tyr Glu Val Asp
1 5 10 15

His Ile Ile Pro Arg Ser Val Ser Phe Asp Asn Ser Tyr His Asn Lys
20 25 30

Val Leu Val Lys Gln Ser Glu Asn Ser Lys Lys Ser Asn Leu Thr Pro
35 40 45

Tyr Gln Tyr Phe Asn Ser Gly Lys Ser Lys Leu Ser Tyr Asn Gln Phe
50 55 60

Lys Gln His Ile Leu Asn Leu Ser Lys Ser Gln Asp Arg Ile Ser Lys
65 70 75 80

Lys Lys Lys Glu Tyr Leu Leu Glu Glu Arg Asp Ile Asn Lys Phe Glu

```
                85                  90                  95

Val Gln Lys Glu Phe Ile Asn Arg Asn Leu Val Asp Thr Arg Tyr Ala
            100                 105                 110

Thr Arg Glu Leu
        115
```

<210> SEQ ID NO 59
<211> LENGTH: 116
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 7 from 8
      mini-domain library

<400> SEQUENCE: 59

```
Ile Ala Leu Met Asp Leu Leu Asn Asn Pro Gln Asn Tyr Glu Val Asp
1               5                   10                  15

His Ile Ile Pro Arg Ser Val Ala Phe Asp Asn Ser Ile His Asn Lys
            20                  25                  30

Val Leu Val Lys Gln Ile Glu Asn Ser Lys Lys Gly Asn Arg Thr Pro
        35                  40                  45

Tyr Gln Tyr Leu Asn Ser Ser Asp Ala Lys Leu Ser Tyr Asn Gln Phe
    50                  55                  60

Lys Gln His Ile Leu Asn Leu Ser Lys Ser Lys Asp Arg Ile Ser Lys
65                  70                  75                  80

Lys Lys Lys Asp Tyr Leu Leu Glu Glu Arg Asp Ile Asn Lys Phe Glu
                85                  90                  95

Val Gln Lys Glu Phe Ile Asn Arg Asn Leu Val Asp Thr Arg Tyr Ala
            100                 105                 110

Thr Arg Glu Leu
        115
```

<210> SEQ ID NO 60
<211> LENGTH: 116
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 7 from 8
      mini-domain library

<400> SEQUENCE: 60

```
Ile Pro Leu Glu Asp Leu Leu Arg Asn Pro His His Tyr Glu Val Asp
1               5                   10                  15

His Ile Ile Pro Arg Ser Val Ala Phe Asp Asn Ser Met His Asn Lys
            20                  25                  30

Val Leu Val Arg Ala Asp Glu Asn Ser Lys Lys Gly Asn Arg Thr Pro
        35                  40                  45

Tyr Gln Tyr Leu Asn Ser Ser Glu Ser Ser Leu Ser Tyr Asn Glu Phe
    50                  55                  60

Lys Gln His Ile Leu Asn Leu Ser Lys Thr Lys Asp Arg Ile Thr Lys
65                  70                  75                  80

Lys Lys Arg Glu Tyr Leu Leu Glu Glu Arg Asp Ile Asn Lys Phe Asp
                85                  90                  95

Val Gln Lys Glu Phe Ile Asn Arg Asn Leu Val Asp Thr Arg Tyr Ala
```

```
                    100                 105                 110

Thr Arg Glu Leu
        115

<210> SEQ ID NO 61
<211> LENGTH: 116
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 7 from 8
      mini-domain library

<400> SEQUENCE: 61

Ile Pro Leu Glu Asp Leu Leu Arg Asn Pro Asn Asn Tyr Asp Ile Asp
1               5                   10                  15

His Ile Ile Pro Arg Ser Val Ser Phe Asp Asp Ser Met His Asn Lys

```
                        115                 120                 125
Thr Leu Tyr Ser Thr Arg Lys Lys Asp Asn Ser Thr Tyr Ile Val Gln
        130                 135                 140

Thr Ile Lys Asp Ile Tyr Ala Lys Asp Asn Thr Thr Leu Lys Lys Gln
145                 150                 155                 160

Phe Asp Lys Ser Pro Glu Lys Phe Leu Met Tyr Gln His Asp Pro Arg
                165                 170                 175

Thr Phe Glu Lys Leu Glu Val Ile Met Lys Gln Tyr Ala Asn Glu Lys
            180                 185                 190

Asn Pro Leu Ala Lys Tyr His Glu Glu Thr Gly Glu Tyr Leu Thr Lys
        195                 200                 205

Tyr Ser Lys Lys Asn Asn Gly Pro Ile Val Lys Ser Leu Lys Tyr Ile
    210                 215                 220

Gly Asn Lys Leu Gly Ser His Leu Asp Val Thr His Gln Phe Lys Ser
225                 230                 235                 240

Ser Thr Lys Lys Leu Val Lys Leu Ser Ile Lys Pro Tyr Arg Phe Asp
                245                 250                 255

Val Tyr Leu Thr Asp Lys Gly Tyr Lys Phe Ile Thr Ile Ser Tyr Leu
            260                 265                 270

Asp Val Leu Lys Lys Asp Asn Tyr Tyr Ile Pro Glu Gln Lys Tyr
        275                 280                 285

Asp Lys Leu Lys Leu Gly Lys Ala Ile Asp Lys Asn Ala Lys Phe Ile
    290                 295                 300

Ala Ser Phe Tyr Lys Asn Asp Leu Ile Lys Leu Asp Gly Glu Ile Tyr
305                 310                 315                 320

Lys Ile Ile Gly Val Asn Ser Asp Thr Arg Asn Met Ile Glu Leu Asp
                325                 330                 335

Leu Pro Asp Ile Arg Tyr Lys Glu Tyr Cys Glu Leu Asn Asn Ile Lys
            340                 345                 350

Gly Glu Pro Arg Ile Lys Lys Thr Ile Gly Lys Val Asn Ser Ile
        355                 360                 365

Glu Lys Leu Thr Thr Asp Val Leu Gly Asn Val Phe Thr Asn Thr Gln
    370                 375                 380

Tyr Thr Lys Pro Gln Leu Leu Phe Lys Arg Gly Asn
385                 390                 395
```

<210> SEQ ID NO 63
<211> LENGTH: 396
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 8 from 8
      mini-domain library

<400> SEQUENCE: 63

```
Thr Ser Tyr Leu Lys Ala Tyr Phe Ser Ala Asn Asn Met Asp Val Lys
1               5                   10                  15

Val Lys Thr Ile Asn Gly Ser Phe Thr Asn His Leu Arg Lys Val Trp
            20                  25                  30

Arg Phe Asp Lys Tyr Arg Asn His Gly Tyr Lys His His Ala Glu Asp
        35                  40                  45

Ala Leu Ile Ile Ala Asn Ala Asp Phe Leu Phe Lys Glu Asn Lys Lys
    50                  55                  60
```

```
Leu Gln Asn Thr Asn Lys Ile Leu Glu Lys Pro Thr Ile Glu Asn Asn
 65                  70                  75                  80

Thr Lys Lys Val Thr Val Glu Lys Glu Asp Tyr Asn Asn Val Phe
                 85                  90                  95

Glu Thr Pro Lys Leu Val Glu Asp Ile Lys Gln Tyr Arg Asp Tyr Lys
                100                 105                 110

Phe Ser His Arg Val Asp Lys Lys Pro Asn Arg Gln Leu Ile Asn Asp
            115                 120                 125

Thr Leu Tyr Ser Thr Arg Met Lys Asp Glu His Asp Tyr Ile Val Gln
        130                 135                 140

Thr Ile Thr Asp Ile Tyr Gly Lys Asp Asn Thr Asn Leu Lys Lys Gln
145                 150                 155                 160

Phe Asn Lys Asn Pro Glu Lys Phe Leu Met Tyr Gln Asn Asp Pro Lys
                165                 170                 175

Thr Phe Glu Lys Leu Ser Ile Ile Met Lys Gln Tyr Ser Asp Glu Lys
                180                 185                 190

Asn Pro Leu Ala Lys Tyr Glu Glu Thr Gly Glu Tyr Leu Thr Lys
            195                 200                 205

Tyr Ser Lys Lys Asn Asn Gly Pro Ile Val Lys Lys Ile Lys Leu Leu
210                 215                 220

Gly Asn Lys Val Gly Asn His Leu Asp Val Thr Asn Lys Tyr Glu Asn
225                 230                 235                 240

Ser Thr Lys Lys Leu Val Lys Leu Ser Ile Lys Asn Tyr Arg Phe Asp
                245                 250                 255

Val Tyr Leu Thr Glu Lys Gly Tyr Lys Phe Val Thr Ile Ala Tyr Leu
                260                 265                 270

Asn Val Phe Lys Lys Asp Asn Tyr Tyr Ile Pro Lys Asp Lys Tyr
            275                 280                 285

Gln Glu Leu Lys Glu Lys Lys Ile Lys Asp Thr Asp Gln Phe Ile
            290                 295                 300

Ala Ser Phe Tyr Lys Asn Asp Leu Ile Lys Leu Asn Gly Asp Leu Tyr
305                 310                 315                 320

Lys Ile Ile Gly Val Asn Ser Asp Asp Arg Asn Ile Ile Glu Leu Asp
                325                 330                 335

Tyr Tyr Asp Ile Lys Tyr Lys Asp Tyr Cys Glu Ile Asn Asn Ile Lys
            340                 345                 350

Gly Glu Pro Arg Ile Lys Lys Thr Ile Gly Lys Lys Thr Glu Ser Ile
                355                 360                 365

Glu Lys Phe Thr Thr Asp Val Leu Gly Asn Leu Tyr Leu His Ser Thr
            370                 375                 380

Glu Lys Ala Pro Gln Leu Ile Phe Lys Arg Gly Leu
385                 390                 395

<210> SEQ ID NO 64
<211> LENGTH: 393
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 8 from 8
      mini-domain library

<400> SEQUENCE: 64

Thr Ser Leu Leu Lys Ala Tyr Phe Ser Ala Asn Asn Leu Asp Val Lys
1               5                   10                  15
```

Val Lys Thr Ile Asn Gly Ser Phe Thr Asn Tyr Leu Arg Lys Val Trp
            20                  25                  30

Lys Phe Asp Lys Asp Arg Asn Lys Gly Tyr Lys His His Ala Glu Asp
        35                  40                  45

Ala Leu Ile Ile Ala Asn Ala Asp Phe Leu Phe Lys His Asn Lys Lys
50                  55                  60

Leu Arg Asn Ile Asn Lys Val Leu Asp Ala Pro Ser Lys Glu Val Asp
65                  70                  75                  80

Lys Lys Arg Val Thr Val Gln Ser Glu Asp Glu Tyr Asn Gln Ile Phe
                85                  90                  95

Glu Asp Thr Gln Lys Ala Gln Ala Ile Lys Lys Phe Glu Ile Arg Lys
            100                 105                 110

Phe Ser His Arg Val Asp Lys Lys Pro Asn Arg Gln Leu Ile Asn Asp
        115                 120                 125

Thr Leu Tyr Ser Thr Arg Asn Ile Asp Gly Ile Glu Tyr Val Val Glu
130                 135                 140

Ser Ile Lys Asp Ile Tyr Ser Val Asn Asn Asp Lys Val Lys Thr Lys
145                 150                 155                 160

Phe Lys Lys Asp Pro His Arg Leu Leu Met Tyr Arg Asn Asp Pro Gln
                165                 170                 175

Thr Phe Glu Lys Phe Glu Lys Val Phe Lys Gln Tyr Glu Ser Glu Lys
            180                 185                 190

Asn Pro Phe Ala Lys Tyr Tyr Glu Glu Thr Gly Glu Lys Ile Arg Lys
        195                 200                 205

Phe Ser Lys Thr Gly Gln Gly Pro Tyr Ile Asn Lys Ile Lys Tyr Leu
210                 215                 220

Arg Glu Arg Leu Gly Arg His Cys Asp Val Thr Asn Lys Tyr Ile Asn
225                 230                 235                 240

Ser Arg Asn Lys Ile Val Gln Leu Lys Ile Tyr Ser Tyr Arg Phe Asp
                245                 250                 255

Ile Tyr Gln Tyr Gly Asn Asn Tyr Lys Met Ile Thr Ile Ser Tyr Ile
            260                 265                 270

Asp Leu Glu Gln Lys Ser Asn Tyr Tyr Ile Ser Arg Glu Lys Tyr
        275                 280                 285

Glu Gln Lys Lys Lys Asp Lys Gln Ile Asp Asp Ser Tyr Lys Phe Ile
290                 295                 300

Gly Ser Phe Tyr Lys Asn Asp Ile Ile Asn Tyr Asn Gly Glu Met Tyr
305                 310                 315                 320

Arg Val Ile Gly Val Asn Asp Ser Glu Lys Asn Lys Ile Gln Leu Asp
                325                 330                 335

Met Ile Asp Ile Ser Ile Lys Asp Tyr Met Glu Leu Asn Asn Ile Lys
            340                 345                 350

Lys Thr Gly Val Ile Tyr Lys Thr Ile Gly Lys Ser Thr Thr His Ile
        355                 360                 365

Glu Lys Tyr Thr Thr Asp Ile Leu Gly Asn Leu Tyr Lys Ala Ala Pro
370                 375                 380

Pro Lys Lys Pro Gln Leu Ile Phe Lys
385                 390

<210> SEQ ID NO 65
<211> LENGTH: 392
<212> TYPE: PRT
<213> ORGANISM: Artificial sequence
<220> FEATURE:

<223> OTHER INFORMATION: Synthetic polypeptide
<220> FEATURE:
<221> NAME/KEY: misc_feature
<223> OTHER INFORMATION: Staphylococcus microti mini-domain 8 from 8
      mini-domain library

<400> SEQUENCE: 65

Thr Thr Leu Leu Lys Thr Tyr Phe Thr Ile Asn Asn Leu Asp Val Lys
1               5                   10                  15

Val Lys Thr Ile Asn Gly Ser Phe Thr Asp Phe Leu Arg Lys Arg Trp
            20                  25                  30

Gly Phe Lys Lys Asn Arg Asp Glu Gly Tyr Lys His His Ala Glu Asp
            35                  40                  45

Ala Leu Ile Ile Ala Asn Ala Asp Tyr Leu Phe Lys Glu His Lys Leu
        50                  55                  60

Leu Lys Glu Ile Lys Asp Val Ser Asp Leu Ala Gly Asp Glu Arg Asn
65                  70                  75                  80

Ser Asn Val Lys Asp Glu Asp Gln Tyr Glu Glu Val Phe Gly Gly Tyr
85 90 95

Phe Lys Ile Glu Asp Ile Lys Lys Tyr Lys Ile Lys Lys Phe Ser His
100 105 110

Arg Val Asp Lys Lys Pro Asn Arg Gln Leu Ile Asn Asp Thr Ile Tyr
115 120 125

Ser Thr Arg Val Lys Asp Asp Lys Arg Tyr Leu Ile Asn Thr Leu Lys
130 135 140

Asn Leu Tyr Asp Lys Ser Asn Gly Asp Leu Lys Glu Arg Met Gln Lys
145 150 155 160

Asp Pro Glu Ser Leu Leu Met Tyr His His Asp Pro Gln Thr Phe Glu
165 170 175

Lys Leu Lys Ile Val Met Ser Gln Tyr Glu Asn Glu Lys Asn Pro Leu
180 185 190

Ala Lys Tyr Phe Glu Glu Thr Gly Gln Tyr Leu Thr Lys Tyr Ala Lys
195 200 205

His Asp Asn Gly Pro Ala Ile His Lys Ile Lys Tyr Tyr Gly Asn Lys
210 215 220

Leu Val Glu His Leu Asp Ile Thr Lys Asn Tyr His Asn Pro Gln Asn
225 230 235 240

Lys Val Val Gln Leu Ser Gln Lys Ser Phe Arg Phe Asp Val Tyr Gln
245 250 255

Thr Asp Lys Gly Tyr Lys Phe Ile Ser Ile Ala Tyr Leu Thr Leu Lys
260 265 270

Asn Glu Lys Asn Tyr Tyr Ala Ile Ser Gln Glu Lys Tyr Asp Gln Leu
275 280 285

Lys Ser Glu Lys Lys Ile Ser Asn Asn Ala Val Phe Ile Gly Ser Phe
290 295 300

Tyr Thr Ser Asp Ile Ile Glu Ile Asn Asn Glu Lys Phe Arg Val Ile
305 310 315 320

Gly Val Asn Ser Asp Lys Asn Asn Leu Ile Glu Val Asp Arg Ile Asp
325 330 335

Ile Arg Gln Lys Glu Phe Ile Glu Leu Glu Glu Glu Lys Lys Asn Asn
340 345 350

Arg Ile Lys Val Thr Ile Gly Arg Lys Thr Thr Asn Ile Glu Lys Phe
355 360 365

His Thr Asp Ile Leu Gly Asn Met Tyr Lys Ser Lys Arg Pro Lys Ala
370 375 380

```
Pro Gln Leu Val Phe Lys Lys Gly
385                 390

<210> SEQ ID NO 66
<211> LENGTH: 41
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 1 from
      12 mini-domain library

<400> SEQUENCE: 66

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val
        35                  40

<210> SEQ ID NO 67
<211> LENGTH: 41
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 1 from 12
      mini-domain library

<400> SEQUENCE: 67

Met Lys Glu Lys Tyr Ile Leu Gly Leu Asp Leu Gly Ile Thr Ser Val
1               5                   10                  15

Gly Tyr Gly Ile Ile Asn Phe Glu Thr Lys Lys Ile Ile Asp Ala Gly
            20                  25                  30

Val Arg Leu Phe Pro Glu Ala Asn Val
        35                  40

<210> SEQ ID NO 68
<211> LENGTH: 40
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 1 from 12
      mini-domain library

<400> SEQUENCE: 68

Met Asn Asn Tyr Ile Leu Gly Leu Asp Ile Gly Ile Thr Ser Val Gly
1               5                   10                  15

Tyr Gly Ile Val Asp Ser Asp Thr Arg Glu Ile Lys Asp Ala Gly Val
            20                  25                  30

Arg Leu Phe Pro Glu Ala Asn Val
        35                  40

<210> SEQ ID NO 69
<211> LENGTH: 41
<212> TYPE: PRT
<213> ORGANISM: Artificial sequence
<220> FEATURE:
```

```
<223> OTHER INFORMATION: Synthetic polypeptide
<220> FEATURE:
<221> NAME/KEY: misc_feature
<223> OTHER INFORMATION: Staphylococcus microti mini-domain 1 from 12
      mini-domain library

<400> SEQUENCE: 69

Met Glu Lys Asp Tyr Ile Leu Gly Leu Asp Ile Gly Ile Gly Ser Val
1               5                   10                  15

Gly Tyr Gly Leu Ile Asp Tyr Asp Thr Lys Ser Ile Ile Asp Ala Gly
            20                  25                  30

Val Arg Leu Phe Pro Glu Ala Asn Ala
            35                  40

<210> SEQ ID NO 70
<211> LENGTH: 23
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 2 from
      12 mini-domain library

<400> SEQUENCE: 70

Glu Asn Asn Glu Gly Arg Arg Ser Lys Arg Gly Ser Arg Arg Leu Lys
1               5                   10                  15

Arg Arg Arg Ile His Arg Leu
            20

<210> SEQ ID NO 71
<211> LENGTH: 23
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 2from 12
      mini-domain library

<400> SEQUENCE: 71

Asp Asn Asn Glu Gly Arg Arg Ser Lys Arg Gly Ser Arg Arg Leu Lys
1               5                   10                  15

Arg Arg Arg Ile His Arg Leu
            20

<210> SEQ ID NO 72
<211> LENGTH: 23
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 2 from 12
      mini-domain library

<400> SEQUENCE: 72

Asp Asn Asn Glu Gly Arg Arg Ser Lys Arg Gly Ala Arg Arg Leu Lys
1               5                   10                  15

Arg Arg Arg Ile His Arg Leu
            20

<210> SEQ ID NO 73
```

```
<211> LENGTH: 23
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 2 from 12
      mini-domain library

<400> SEQUENCE: 73

Asp Asn Asn Leu Gly Arg Arg Ala Lys Arg Gly Ala Arg Arg Leu Lys
1               5                   10                  15

Arg Arg Arg Ile His Arg Leu
            20

<210> SEQ ID NO 74
<211> LENGTH: 55
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 3 from
      12 mini-domain library

<400> SEQUENCE: 74

Glu Arg Val Lys Lys Leu Leu Glu Asp Tyr Asn Leu Leu Asp Gln Ser
1               5                   10                  15

Gln Ile Pro Gln Ser Thr Asn Pro Tyr Ala Ile Arg Val Lys Gly Leu
            20                  25                  30

Ser Glu Ala Leu Ser Lys Asp Glu Leu Val Ile Ala Leu Leu His Ile
        35                  40                  45

Ala Lys Arg Arg Gly Ile His
    50                  55

<210> SEQ ID NO 75
<211> LENGTH: 55
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 3 from 12
      mini-domain library

<400> SEQUENCE: 75

Glu Arg Val Lys Leu Leu Leu Thr Glu Tyr Asp Leu Ile Asn Lys Glu
1               5                   10                  15

Gln Ile Pro Thr Ser Asn Asn Pro Tyr Gln Ile Arg Val Lys Gly Leu
            20                  25                  30

Ser Glu Ile Leu Ser Lys Asp Glu Leu Ala Ile Ala Leu Leu His Leu
        35                  40                  45

Ala Lys Arg Arg Gly Ile His
    50                  55

<210> SEQ ID NO 76
<211> LENGTH: 55
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
```

-continued

<223> OTHER INFORMATION: Staphylococcus hyicus mini-domain 3 from 12 mini-domain library

<400> SEQUENCE: 76

Asp Arg Val Lys His Leu Leu Ala Glu Tyr Asp Leu Leu Asp Leu Thr
1 5 10 15

Asn Ile Pro Lys Ser Thr Asn Pro Tyr Gln Thr Arg Val Lys Gly Leu
20 25 30

Asn Glu Lys Leu Ser Lys Asp Glu Leu Val Ile Ala Leu Leu His Ile
35 40 45

Ala Lys Arg Arg Gly Ile His
50 55

<210> SEQ ID NO 77
<211> LENGTH: 54
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 3 from 12 mini-domain library

<400> SEQUENCE: 77

Glu Arg Val Lys Ser Leu Leu Ser Glu Tyr Lys Ile Ile Ser Gly Leu
1 5 10 15

Ala Pro Thr Asn Asn Gln Pro Tyr Asn Ile Arg Val Lys Gly Leu Thr
20 25 30

Glu Gln Leu Thr Lys Asp Glu Leu Ala Val Ala Leu Leu His Ile Ala
35 40 45

Lys Arg Arg Gly Ile His
50

<210> SEQ ID NO 78
<211> LENGTH: 93
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 4 from 12 mini-domain library

<400> SEQUENCE: 78

Lys Ile Asp Val Ile Asp Ser Asn Asp Asp Val Gly Asn Glu Leu Ser
1 5 10 15

Thr Lys Glu Gln Leu Asn Lys Asn Ser Lys Leu Leu Lys Asp Lys Phe
20 25 30

Val Cys Gln Ile Gln Leu Glu Arg Met Asn Glu Gly Gln Val Arg Gly
35 40 45

Glu Lys Asn Arg Phe Lys Thr Ala Asp Ile Ile Lys Glu Ile Ile Gln
50 55 60

Leu Leu Asn Val Gln Lys Asn Phe His Gln Leu Asp Glu Asn Phe Ile
65 70 75 80

Asn Lys Tyr Ile Glu Leu Val Glu Met Arg Arg Glu Tyr
85 90

<210> SEQ ID NO 79
<211> LENGTH: 93
<212> TYPE: PRT

```
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 4 from 12
      mini-domain library

<400> SEQUENCE: 79

Asn Ile Asn Val Ser Ser Glu Asp Glu Asp Ala Ser Asn Glu Leu Ser
1               5                   10                  15

Thr Lys Glu Gln Ile Asn Arg Asn Asn Lys Leu Leu Lys Asp Lys Tyr
            20                  25                  30

Val Cys Glu Val Gln Leu Gln Arg Leu Lys Glu Gly Gln Ile Arg Gly
        35                  40                  45

Glu Lys Asn Arg Phe Lys Thr Thr Asp Ile Leu Lys Glu Ile Asp Gln
    50                  55                  60

Leu Leu Lys Val Gln Lys Asp Tyr His Asn Leu Asp Ile Asp Phe Ile
65                  70                  75                  80

Asn Gln Tyr Lys Glu Ile Val Glu Thr Arg Arg Glu Tyr
                85                  90

<210> SEQ ID NO 80
<211> LENGTH: 94
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 4 from 12
      mini-domain library

<400> SEQUENCE: 80

Asn Val Asn Val Met Met Asp Asp Asn Asp Ser Gly Asn Glu Leu Ser
1               5                   10                  15

Thr Lys Asp Gln Leu Lys Lys Asn Ala Lys Ala Leu Ser Asp Lys Tyr
            20                  25                  30

Val Cys Glu Leu Gln Leu Glu Arg Phe Glu Gln Asp Tyr Lys Val Arg
        35                  40                  45

Gly Glu Lys Asn Arg Phe Lys Thr Glu Asp Phe Val Arg Glu Ala Arg
    50                  55                  60

Lys Leu Leu Glu Thr Gln Ser Lys Phe Phe Glu Ile Asp Gln Thr Phe
65                  70                  75                  80

Ile Met Arg Tyr Ile Glu Leu Ile Glu Thr Arg Arg Glu Tyr
                85                  90

<210> SEQ ID NO 81
<211> LENGTH: 96
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 4 from 12
      mini-domain library

<400> SEQUENCE: 81

Asn Val Asp Val Ala Ala Asp Lys Glu Glu Thr Ala Ser Asp Ser Leu
1               5                   10                  15

Ser Thr Lys Asp Gln Ile Asn Lys Asn Ala Lys Phe Leu Glu Ser Arg
            20                  25                  30
```

Tyr Val Cys Glu Leu Gln Lys Glu Arg Leu Glu Asn Glu Gly His Val
            35                  40                  45

Arg Gly Val Glu Asn Arg Phe Leu Thr Lys Asp Ile Val Arg Glu Ala
        50                  55                  60

Lys Lys Ile Ile Asp Thr Gln Met Gln Tyr Tyr Pro Glu Ile Asp Glu
 65                  70                  75                  80

Thr Phe Lys Glu Lys Tyr Ile Ser Leu Val Glu Thr Arg Arg Glu Tyr
                85                  90                  95

<210> SEQ ID NO 82
<211> LENGTH: 114
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 5 from
      12 mini-domain library

<400> SEQUENCE: 82

Phe Glu Gly Pro Gly Lys Gly Ser Pro Tyr Gly Trp Glu Gly Asp Pro
1               5                   10                  15

Lys Ala Trp Tyr Glu Thr Leu Met Gly His Cys Thr Tyr Phe Pro Asp
            20                  25                  30

Glu Leu Arg Ser Val Lys Tyr Ala Tyr Ser Ala Asp Leu Phe Asn Ala
        35                  40                  45

Leu Asn Asp Leu Asn Asn Leu Val Ile Gln Arg Asp Gly Leu Ser Lys
 50                  55                  60

Leu Glu Tyr His Glu Lys Tyr His Ile Ile Glu Asn Val Phe Lys Gln
 65                  70                  75                  80

Lys Lys Lys Pro Thr Leu Lys Gln Ile Ala Asn Glu Ile Asn Val Asn
                85                  90                  95

Pro Glu Asp Ile Lys Gly Tyr Arg Ile Thr Lys Ser Gly Lys Pro Gln
            100                 105                 110

Phe Thr

<210> SEQ ID NO 83
<211> LENGTH: 114
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 5 from 12
      mini-domain library

<400> SEQUENCE: 83

Phe Glu Gly Pro Gly Gln Gly Ser Pro Phe Gly Trp Asn Gly Asp Leu
1               5                   10                  15

Lys Lys Trp Tyr Glu Met Leu Met Gly His Cys Thr Tyr Phe Pro Gln
            20                  25                  30

Glu Leu Arg Ser Val Lys Tyr Ala Tyr Ser Ala Asp Leu Phe Asn Ala
        35                  40                  45

Leu Asn Asp Leu Asn Asn Leu Ile Ile Gln Arg Asp Asn Ser Glu Lys
 50                  55                  60

Leu Glu Tyr His Glu Lys Tyr His Ile Ile Glu Asn Val Phe Lys Gln
 65                  70                  75                  80

Lys Lys Lys Pro Thr Leu Lys Gln Ile Ala Lys Glu Ile Gly Val Asn
                85                  90                  95

Pro Glu Asp Ile Lys Gly Tyr Arg Ile Thr Lys Ser Gly Thr Pro Gln
            100                 105                 110

Phe Thr

<210> SEQ ID NO 84
<211> LENGTH: 114
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 5 from 12
      mini-domain library

<400> SEQUENCE: 84

Phe Glu Gly Pro Gly Lys Gly Ser Pro Phe Gly Trp Glu Gly Asn Ile
1               5                   10                  15

Lys Lys Trp Phe Glu Gln Met Met Gly His Cys Thr Tyr Phe Pro Glu
                20                  25                  30

Glu Leu Arg Ser Val Lys Tyr Ser Tyr Ser Ala Glu Leu Phe Asn Ala
            35                  40                  45

Leu Asn Asp Leu Asn Asn Leu Val Ile Thr Arg Asp Glu Asp Ala Lys
50                  55                  60

Leu Asn Tyr Gly Glu Lys Phe Gln Ile Ile Glu Asn Val Phe Lys Gln
65                  70                  75                  80

Lys Lys Thr Pro Asn Leu Lys Gln Ile Ala Ile Glu Ile Gly Val His
                85                  90                  95

Glu Thr Glu Ile Lys Gly Tyr Arg Val Asn Lys Ser Gly Lys Pro Glu
            100                 105                 110

Phe Thr

<210> SEQ ID NO 85
<211> LENGTH: 114
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 5 from 12
      mini-domain library

<400> SEQUENCE: 85

Tyr Glu Gly Pro Gly Lys Gly Ser Pro Tyr Gly Trp Asp Ala Asp Val
1               5                   10                  15

Lys Lys Trp Tyr Gln Leu Met Met Gly His Cys Thr Tyr Phe Pro Val
                20                  25                  30

Glu Phe Arg Ser Val Lys Tyr Ala Tyr Thr Ala Asp Leu Tyr Asn Ala
            35                  40                  45

Leu Asn Asp Leu Asn Asn Leu Thr Ile Ala Arg Asp Asn Pro Lys
50                  55                  60

Leu Glu Tyr His Glu Lys Tyr His Ile Ile Glu Asn Val Phe Lys Gln
65                  70                  75                  80

Lys Arg Asn Pro Thr Leu Lys Gln Ile Ala Lys Glu Ile Gly Val Asn
                85                  90                  95

Asp Ile Asn Ile Ser Gly Tyr Arg Val Thr Lys Ser Gly Lys Pro Gln
            100                 105                 110

Phe Thr

<210> SEQ ID NO 86
<211> LENGTH: 128
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 6 from
      12 mini-domain library

<400> SEQUENCE: 86

Glu Phe Lys Leu Tyr His Asp Leu Lys Ser Val Leu Phe Asp Gln Ser
1               5                   10                  15

Ile Leu Glu Asn Glu Asp Val Leu Asp Gln Ile Ala Glu Ile Leu Thr
            20                  25                  30

Ile Tyr Gln Asp Lys Asp Ser Ile Lys Ser Lys Leu Thr Glu Leu Asp
        35                  40                  45

Ile Leu Leu Asn Glu Glu Asp Lys Glu Asn Ile Ala Gln Leu Thr Gly
    50                  55                  60

Tyr Thr Gly Thr His Arg Leu Ser Leu Lys Cys Ile Arg Leu Val Leu
65                  70                  75                  80

Glu Glu Gln Trp Tyr Ser Ser Arg Asn Gln Met Glu Ile Phe Thr His
                85                  90                  95

Leu Asn Ile Lys Pro Lys Lys Ile Asn Leu Thr Ala Ala Asn Lys Ile
            100                 105                 110

Pro Lys Ala Met Ile Asp Glu Phe Ile Leu Ser Pro Val Val Lys Arg
        115                 120                 125

<210> SEQ ID NO 87
<211> LENGTH: 128
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 6 from 12
      mini-domain library

<400> SEQUENCE: 87

Glu Phe Lys Leu Tyr His Asp Leu Lys Ser Ile Val Phe Asp Lys Ser
1               5                   10                  15

Ile Leu Glu Asn Glu Ala Ile Leu Asp Gln Ile Ala Glu Ile Leu Thr
            20                  25                  30

Ile Tyr Gln Asp Glu Gln Ser Ile Lys Glu Glu Leu Asn Lys Leu Pro
        35                  40                  45

Glu Ile Leu Asn Glu Gln Asp Lys Ala Glu Ile Ala Lys Leu Ile Gly
    50                  55                  60

Tyr Asn Gly Thr His Arg Leu Ser Leu Lys Cys Ile His Leu Ile Asn
65                  70                  75                  80

Glu Glu Leu Trp Gln Thr Ser Arg Asn Gln Met Glu Ile Phe Asn Tyr
                85                  90                  95

Leu Asn Ile Lys Pro Asn Lys Val Asp Leu Ser Glu Gln Asn Lys Ile
            100                 105                 110

Pro Lys Asp Met Val Asn Asp Phe Ile Leu Ser Pro Val Val Lys Arg
        115                 120                 125

<210> SEQ ID NO 88
<211> LENGTH: 128
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 6 from 12
      mini-domain library

<400> SEQUENCE: 88

Gln Phe Lys Leu Tyr His Asp Leu Lys Asn Ile Phe Lys Asp Pro Lys
1               5                   10                  15

Tyr Leu Asn Asp Ile Gln Leu Met Asp Asn Ile Ala Glu Ile Ile Thr
            20                  25                  30

Ile Tyr Gln Asp Ala Glu Ser Ile Ile Lys Glu Leu Asn Gln Leu Pro
        35                  40                  45

Glu Leu Leu Ser Glu Arg Glu Lys Glu Lys Ile Ser Ala Leu Ser Gly
    50                  55                  60

Tyr Ser Gly Thr His Arg Leu Ser Leu Lys Cys Ile Asn Leu Leu Leu
65                  70                  75                  80

Asp Asp Leu Trp Glu Ser Ser Leu Asn Gln Met Glu Leu Phe Thr Lys
                85                  90                  95

Leu Asn Leu Lys Pro Lys Lys Ile Asp Leu Ser Gln Gln His Lys Ile
            100                 105                 110

Pro Ser Lys Leu Val Asp Asp Phe Ile Leu Ser Pro Val Val Lys Arg
        115                 120                 125

<210> SEQ ID NO 89
<211> LENGTH: 128
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 6 from 12
mini-domain library

<400> SEQUENCE: 89

Ser Phe Lys Leu Phe His Asp Leu Lys Lys Val Val Lys Asp His Ala
1 5 10 15

Ile Leu Asp Asp Ile Asp Leu Leu Asn Gln Ile Ala Glu Ile Leu Thr
20 25 30

Ile Tyr Gln Asp Lys Asp Ser Ile Val Ala Glu Leu Gly Gln Leu Glu
35 40 45

Tyr Leu Met Ser Glu Ala Asp Lys Gln Ser Ile Ser Glu Leu Thr Gly
50 55 60

Tyr Thr Gly Thr His Ser Leu Ser Leu Lys Cys Met Asn Met Ile Ile
65 70 75 80

Asp Glu Leu Trp His Ser Ser Met Asn Gln Met Glu Val Phe Thr Tyr
85 90 95

Leu Asn Met Arg Pro Lys Lys Tyr Glu Leu Lys Gly Tyr Gln Arg Ile
100 105 110

Pro Thr Asp Met Ile Asp Asp Ala Ile Leu Ser Pro Val Val Lys Arg
115 120 125

<210> SEQ ID NO 90
<211> LENGTH: 86

```
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 7 from
      12 mini-domain library

<400> SEQUENCE: 90
```

Thr Phe Gly Gln Ala Ile Asn Leu Ile Asn Lys Ile Ile Glu Lys Tyr
1               5                   10                  15

Gly Val Pro Glu Asp Ile Ile Ile Glu Leu Ala Arg Glu Asn Asn Ser
            20                  25                  30

Lys Asp Lys Gln Lys Phe Ile Asn Glu Met Gln Lys Lys Asn Glu Asn
        35                  40                  45

Thr Arg Lys Arg Ile Asn Glu Ile Ile Gly Lys Tyr Gly Asn Gln Asn
    50                  55                  60

Ala Lys Arg Leu Val Glu Lys Ile Arg Leu His Asp Gln Gln Glu Gly
65                  70                  75                  80

Lys Cys Leu Tyr Ser Leu
                85

```
<210> SEQ ID NO 91
<211> LENGTH: 86
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 7 from 12
      mini-domain library

<400> SEQUENCE: 91
```

Thr Phe Ile Gln Ser Ile Asn Val Ile Asn Lys Val Ile Glu Lys Tyr
1               5                   10                  15

Gly Ile Pro Glu Asp Ile Ile Ile Glu Leu Ala Arg Glu Asn Asn Ser
            20                  25                  30

Asp Asp Arg Lys Lys Phe Ile Asn Asn Leu Gln Lys Lys Asn Glu Ala
        35                  40                  45

Thr Arg Lys Arg Ile Asn Glu Ile Ile Gly Gln Thr Gly Asn Gln Asn
    50                  55                  60

Ala Lys Arg Ile Val Glu Lys Ile Arg Leu His Asp Gln Gln Glu Gly
65                  70                  75                  80

Lys Cys Leu Tyr Ser Leu
                85

```
<210> SEQ ID NO 92
<211> LENGTH: 86
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 7 from 12
      mini-domain library

<400> SEQUENCE: 92
```

Ala Phe Ile Gln Ser Ile Gln Val Val Asn Ala Ile Ile Asp Lys Tyr
1               5                   10                  15

Gly Leu Pro Glu Asp Ile Ile Ile Glu Leu Ala Arg Glu Asn Asn Ser

```
                    20                  25                  30

Asp Asp Arg Arg Lys Phe Leu Asn Gln Leu Gln Lys Gln Asn Glu Glu
            35                  40                  45

Thr Arg Lys Gln Val Glu Lys Val Leu Arg Glu Tyr Gly Asn Asp Asn
        50                  55                  60

Ala Lys Arg Ile Val Gln Lys Ile Lys Leu His Asn Met Gln Glu Gly
65                  70                  75                  80

Lys Cys Leu Tyr Ser Leu
                85

<210> SEQ ID NO 93
<211> LENGTH: 86
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 7 from 12
      mini-domain library

<400> SEQUENCE: 93

Ser Phe Lys Gln Ala Ile Gly Val Val Asn Ala Ile Ile Lys Lys Tyr
1               5                   10                  15

Gly Leu Pro Lys Asp Ile Ile Ile Glu Leu Ala Arg Glu Ser Asn Ser
            20                  25                  30

Ala Glu Lys Ser Arg Tyr Leu Arg Ala Ile Gln Lys Lys Asn Glu Lys
        35                  40                  45

Thr Arg Glu Arg Ile Glu Ala Ile Ile Lys Glu Tyr Gly Asn Glu Asn
    50                  55                  60

Ala Lys Gly Leu Val Gln Lys Ile Lys Leu His Asp Ala Gln Glu Gly
65                  70                  75                  80

Lys Cys Leu Tyr Ser Leu
                85

<210> SEQ ID NO 94
<211> LENGTH: 92
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 8 from
      12 mini-domain library

<400> SEQUENCE: 94

Glu Ser Ile Pro Leu Glu Asp Leu Leu Asn Asn Pro Asn His Tyr Glu
1               5                   10                  15

Val Asp His Ile Ile Pro Arg Ser Val Ser Phe Asp Asn Ser Tyr His
            20                  25                  30

Asn Lys Val Leu Val Lys Gln Ser Glu Asn Ser Lys Lys Ser Asn Leu
        35                  40                  45

Thr Pro Tyr Gln Tyr Phe Asn Ser Gly Lys Ser Lys Leu Ser Tyr Asn
    50                  55                  60

Gln Phe Lys Gln His Ile Leu Asn Leu Ser Lys Ser Gln Asp Arg Ile
65                  70                  75                  80

Ser Lys Lys Lys Lys Glu Tyr Leu Leu Glu Glu Arg
                85                  90
```

```
<210> SEQ ID NO 95
<211> LENGTH: 92
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 8 from 12
      mini-domain library

<400> SEQUENCE: 95

Glu Ser Ile Ala Leu Met Asp Leu Leu Asn Asn Pro Gln Asn Tyr Glu
1               5                   10                  15

Val Asp His Ile Ile Pro Arg Ser Val Ala Phe Asp Asn Ser Ile His
            20                  25                  30

Asn Lys Val Leu Val Lys Gln Ile Glu Asn Ser Lys Lys Gly Asn Arg
        35                  40                  45

Thr Pro Tyr Gln Tyr Leu Asn Ser Ser Asp Ala Lys Leu Ser Tyr Asn
    50                  55                  60

Gln Phe Lys Gln His Ile Leu Asn Leu Ser Lys Ser Lys Asp Arg Ile
65                  70                  75                  80

Ser Lys Lys Lys Lys Asp Tyr Leu Leu Glu Glu Arg
                85                  90

<210> SEQ ID NO 96
<211> LENGTH: 92
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 8 from 12
      mini-domain library

<400> SEQUENCE: 96

Lys Asp Ile Pro Leu Glu Asp Leu Leu Arg Asn Pro His His Tyr Glu
1               5                   10                  15

Val Asp His Ile Ile Pro Arg Ser Val Ala Phe Asp Asn Ser Met His
            20                  25                  30

Asn Lys Val Leu Val Arg Ala Asp Glu Asn Ser Lys Lys Gly Asn Arg
        35                  40                  45

Thr Pro Tyr Gln Tyr Leu Asn Ser Ser Glu Ser Ser Leu Ser Tyr Asn
    50                  55                  60

Glu Phe Lys Gln His Ile Leu Asn Leu Ser Lys Thr Lys Asp Arg Ile
65                  70                  75                  80

Thr Lys Lys Lys Arg Glu Tyr Leu Leu Glu Glu Arg
                85                  90

<210> SEQ ID NO 97
<211> LENGTH: 92
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 8 from 12
      mini-domain library

<400> SEQUENCE: 97

Lys Asp Ile Pro Leu Glu Asp Leu Leu Arg Asn Pro Asn Asn Tyr Asp
1               5                   10                  15
```

Ile Asp His Ile Ile Pro Arg Ser Val Ser Phe Asp Ser Met His
            20                  25                  30

Asn Lys Val Leu Val Arg Arg Glu Gln Asn Ala Lys Lys Asn Asn Gln
        35                  40                  45

Thr Pro Tyr Gln Tyr Leu Thr Ser Gly Tyr Ala Asp Ile Lys Tyr Ser
    50                  55                  60

Val Phe Lys Gln His Val Leu Asn Leu Ala Glu Asn Lys Asp Arg Met
65                  70                  75                  80

Thr Lys Lys Lys Arg Glu Tyr Leu Leu Glu Glu Arg
                85                  90

<210> SEQ ID NO 98
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 9 from
      12 mini-domain library

<400> SEQUENCE: 98

Asp Ile Asn Lys Phe Glu Val Gln Lys Glu Phe Ile Asn Arg Asn Leu
1               5                   10                  15

Val Asp Thr Arg Tyr Ala Thr Arg Glu Leu Thr
            20                  25

<210> SEQ ID NO 99
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 9 from 12
      mini-domain library

<400> SEQUENCE: 99

Asp Ile Asn Lys Phe Glu Val Gln Lys Glu Phe Ile Asn Arg Asn Leu
1               5                   10                  15

Val Asp Thr Arg Tyr Ala Thr Arg Glu Leu Thr
            20                  25

<210> SEQ ID NO 100
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 9 from 12
      mini-domain library

<400> SEQUENCE: 100

Asp Ile Asn Lys Phe Asp Val Gln Lys Glu Phe Ile Asn Arg Asn Leu
1               5                   10                  15

Val Asp Thr Arg Tyr Ala Thr Arg Glu Leu Thr
            20                  25

<210> SEQ ID NO 101
<211> LENGTH: 27

```
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 9 from 12
      mini-domain library

<400> SEQUENCE: 101

Asn Ile Asn Lys Tyr Asp Val Gln Lys Glu Phe Ile Asn Arg Asn Leu
1               5                   10                  15

Val Asp Thr Arg Tyr Thr Thr Arg Glu Leu Thr
            20                  25

<210> SEQ ID NO 102
<211> LENGTH: 64
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 10 from
      12 mini-domain library

<400> SEQUENCE: 102

Asn Tyr Leu Lys Ala Tyr Phe Ser Ala Asn Asn Met Asn Val Lys Val
1               5                   10                  15

Lys Thr Ile Asn Gly Ser Phe Thr Asp Tyr Leu Arg Lys Val Trp Lys
            20                  25                  30

Phe Lys Lys Glu Arg Asn His Gly Tyr Lys His His Ala Glu Asp Ala
        35                  40                  45

Leu Ile Ile Ala Asn Ala Asp Phe Leu Phe Lys Glu Asn Lys Lys Leu
    50                  55                  60

<210> SEQ ID NO 103
<211> LENGTH: 64
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 10 from 12
      mini-domain library

<400> SEQUENCE: 103

Ser Tyr Leu Lys Ala Tyr Phe Ser Ala Asn Asn Met Asp Val Lys Val
1               5                   10                  15

Lys Thr Ile Asn Gly Ser Phe Thr Asn His Leu Arg Lys Val Trp Arg
            20                  25                  30

Phe Asp Lys Tyr Arg Asn His Gly Tyr Lys His His Ala Glu Asp Ala
        35                  40                  45

Leu Ile Ile Ala Asn Ala Asp Phe Leu Phe Lys Glu Asn Lys Lys Leu
    50                  55                  60

<210> SEQ ID NO 104
<211> LENGTH: 64
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 10 from 12
``` mini-domain library

<400> SEQUENCE: 104

Ser Leu Leu Lys Ala Tyr Phe Ser Ala Asn Asn Leu Asp Val Lys Val
1               5                   10                  15

Lys Thr Ile Asn Gly Ser Phe Thr Asn Tyr Leu Arg Lys Val Trp Lys
            20                  25                  30

Phe Asp Lys Asp Arg Asn Lys Gly Tyr Lys His His Ala Glu Asp Ala
        35                  40                  45

Leu Ile Ile Ala Asn Ala Asp Phe Leu Phe Lys His Asn Lys Lys Leu
    50                  55                  60

<210> SEQ ID NO 105
<211> LENGTH: 64
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 10 from 12
      mini-domain library

<400> SEQUENCE: 105

Thr Leu Leu Lys Thr Tyr Phe Thr Ile Asn Asn Leu Asp Val Lys Val
1               5                   10                  15

Lys Thr Ile Asn Gly Ser Phe Thr Asp Phe Leu Arg Lys Arg Trp Gly
            20                  25                  30

Phe Lys Lys Asn Arg Asp Glu Gly Tyr Lys His His Ala Glu Asp Ala
        35                  40                  45

Leu Ile Ile Ala Asn Ala Asp Tyr Leu Phe Lys Glu His Lys Leu Leu
    50                  55                  60

<210> SEQ ID NO 106
<211> LENGTH: 186
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 11 from
      12 mini-domain library

<400> SEQUENCE: 106

Lys Ala Val Asn Ser Val Leu Glu Lys Pro Glu Ile Glu Thr Lys Gln
1               5                   10                  15

Leu Asp Ile Gln Val Asp Ser Glu Asp Asn Tyr Ser Glu Met Phe Ile
            20                  25                  30

Ile Pro Lys Gln Val Gln Asp Ile Lys Asp Phe Arg Asn Phe Lys Tyr
        35                  40                  45

Ser His Arg Val Asp Lys Lys Pro Asn Arg Gln Leu Ile Asn Asp Thr
    50                  55                  60

Leu Tyr Ser Thr Arg Lys Lys Asp Asn Ser Thr Tyr Ile Val Gln Thr
65                  70                  75                  80

Ile Lys Asp Ile Tyr Ala Lys Asp Asn Thr Thr Leu Lys Lys Gln Phe
            85                  90                  95

Asp Lys Ser Pro Glu Lys Phe Leu Met Tyr Gln His Asp Pro Arg Thr
        100                 105                 110

Phe Glu Lys Leu Glu Val Ile Met Lys Gln Tyr Ala Asn Glu Lys Asn
            115                 120                 125

Pro Leu Ala Lys Tyr His Glu Glu Thr Gly Glu Tyr Leu Thr Lys Tyr
            130                 135                 140

Ser Lys Lys Asn Asn Gly Pro Ile Val Lys Ser Leu Lys Tyr Ile Gly
145                 150                 155                 160

Asn Lys Leu Gly Ser His Leu Asp Val Thr His Gln Phe Lys Ser Ser
                165                 170                 175

Thr Lys Lys Leu Val Lys Leu Ser Ile Lys
            180                 185

<210> SEQ ID NO 107
<211> LENGTH: 186
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 11 from 12
      mini-domain library

<400> SEQUENCE: 107

Gln Asn Thr Asn Lys Ile Leu Glu Lys Pro Thr Ile Glu Asn Asn Thr
1               5                   10                  15

Lys Lys Val Thr Val Glu Lys Glu Glu Asp Tyr Asn Asn Val Phe Glu
            20                  25                  30

Thr Pro Lys Leu Val Glu Asp Ile Lys Gln Tyr Arg Asp Tyr Lys Phe
            35                  40                  45

Ser His Arg Val Asp Lys Lys Pro Asn Arg Gln Leu Ile Asn Asp Thr
50                  55                  60

Leu Tyr Ser Thr Arg Met Lys Asp Glu His Asp Tyr Ile Val Gln Thr
65                  70                  75                  80

Ile Thr Asp Ile Tyr Gly Lys Asp Asn Thr Asn Leu Lys Lys Gln Phe
                85                  90                  95

Asn Lys Asn Pro Glu Lys Phe Leu Met Tyr Gln Asn Asp Pro Lys Thr
            100                 105                 110

Phe Glu Lys Leu Ser Ile Ile Met Lys Gln Tyr Ser Asp Glu Lys Asn
            115                 120                 125

Pro Leu Ala Lys Tyr Tyr Glu Glu Thr Gly Glu Tyr Leu Thr Lys Tyr
            130                 135                 140

Ser Lys Lys Asn Asn Gly Pro Ile Val Lys Lys Ile Lys Leu Leu Gly
145                 150                 155                 160

Asn Lys Val Gly Asn His Leu Asp Val Thr Asn Lys Tyr Glu Asn Ser
                165                 170                 175

Thr Lys Lys Leu Val Lys Leu Ser Ile Lys
            180                 185

<210> SEQ ID NO 108
<211> LENGTH: 184
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 11 from 12
      mini-domain library

<400> SEQUENCE: 108

Arg Asn Ile Asn Lys Val Leu Asp Ala Pro Ser Lys Glu Val Asp Lys
1               5                   10                  15

```
Lys Arg Val Thr Val Gln Ser Glu Asp Glu Tyr Asn Gln Ile Phe Glu
            20                  25                  30

Asp Thr Gln Lys Ala Gln Ala Ile Lys Lys Phe Glu Ile Arg Lys Phe
        35                  40                  45

Ser His Arg Val Asp Lys Lys Pro Asn Arg Gln Leu Ile Asn Asp Thr
    50                  55                  60

Leu Tyr Ser Thr Arg Asn Ile Asp Gly Ile Glu Tyr Val Val Glu Ser
65                  70                  75                  80

Ile Lys Asp Ile Tyr Ser Val Asn Asn Asp Lys Val Lys Thr Lys Phe
                85                  90                  95

Lys Lys Asp Pro His Arg Leu Leu Met Tyr Arg Asn Asp Pro Gln Thr
            100                 105                 110

Phe Glu Lys Phe Glu Lys Val Phe Lys Gln Tyr Glu Ser Glu Lys Asn
        115                 120                 125

Pro Phe Ala Lys Tyr Tyr Glu Glu Thr Gly Glu Lys Ile Arg Lys Phe
    130                 135                 140

Ser Lys Thr Gly Gln Gly Pro Tyr Ile Asn Lys Ile Lys Tyr Leu Arg
145                 150                 155                 160

Glu Arg Leu Gly Arg His Cys Asp Val Thr Asn Lys Tyr Ile Asn Ser
                165                 170                 175

Arg Asn Lys Ile Val Gln Leu Lys
            180

<210> SEQ ID NO 109
<211> LENGTH: 183
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 11 from 12
      mini-domain library

<400> SEQUENCE: 109

Lys Glu Ile Lys Asp Val Ser Asp Leu Ala Gly Asp Glu Arg Asn Ser
1               5                   10                  15

Asn Val Lys Asp Glu Asp Gln Tyr Glu Glu Val Phe Gly Gly Tyr Phe
            20                  25                  30

Lys Ile Glu Asp Ile Lys Lys Tyr Lys Ile Lys Lys Phe Ser His Arg
        35                  40                  45

Val Asp Lys Lys Pro Asn Arg Gln Leu Ile Asn Asp Thr Ile Tyr Ser
    50                  55                  60

Thr Arg Val Lys Asp Asp Lys Arg Tyr Leu Ile Asn Thr Leu Lys Asn
65                  70                  75                  80

Leu Tyr Asp Lys Ser Asn Gly Asp Leu Lys Glu Arg Met Gln Lys Asp
                85                  90                  95

Pro Glu Ser Leu Leu Met Tyr His His Asp Pro Gln Thr Phe Glu Lys
            100                 105                 110

Leu Lys Ile Val Met Ser Gln Tyr Glu Asn Glu Lys Asn Pro Leu Ala
        115                 120                 125

Lys Tyr Phe Glu Glu Thr Gly Gln Tyr Leu Thr Lys Tyr Ala Lys His
    130                 135                 140

Asp Asn Gly Pro Ala Ile His Lys Ile Lys Tyr Tyr Gly Asn Lys Leu
145                 150                 155                 160

Val Glu His Leu Asp Ile Thr Lys Asn Tyr His Asn Pro Gln Asn Lys
```

```
                        165                 170                 175
Val Val Gln Leu Ser Gln Lys
                180

<210> SEQ ID NO 110
<211> LENGTH: 145
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus lugdunensis mini-domain 12 from
      12 mini-domain library

<400> SEQUENCE: 110

Pro Tyr Arg Phe Asp Val Tyr Leu Thr Asp Lys Gly Tyr Lys Phe Ile
1               5                   10                  15

Thr Ile Ser Tyr Leu Asp Val Leu Lys Lys Asp Asn Tyr Tyr Tyr Ile
                20                  25                  30

Pro Glu Gln Lys Tyr Asp Lys Leu Lys Leu Gly Lys Ala Ile Asp Lys
            35                  40                  45

Asn Ala Lys Phe Ile Ala Ser Phe Tyr Lys Asn Asp Leu Ile Lys Leu
50                  55                  60

Asp Gly Glu Ile Tyr Lys Ile Ile Gly Val Asn Ser Asp Thr Arg Asn
65                  70                  75                  80

Met Ile Glu Leu Asp Leu Pro Asp Ile Arg Tyr Lys Glu Tyr Cys Glu
                85                  90                  95

Leu Asn Asn Ile Lys Gly Glu Pro Arg Ile Lys Lys Thr Ile Gly Lys
            100                 105                 110

Lys Val Asn Ser Ile Glu Lys Leu Thr Thr Asp Val Leu Gly Asn Val
        115                 120                 125

Phe Thr Asn Thr Gln Tyr Thr Lys Pro Gln Leu Leu Phe Lys Arg Gly
    130                 135                 140

Asn
145

<210> SEQ ID NO 111
<211> LENGTH: 145
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus pasteuri mini-domain 12 from 12
      mini-domain library

<400> SEQUENCE: 111

Asn Tyr Arg Phe Asp Val Tyr Leu Thr Glu Lys Gly Tyr Lys Phe Val
1               5                   10                  15

Thr Ile Ala Tyr Leu Asn Val Phe Lys Lys Asp Asn Tyr Tyr Tyr Ile
                20                  25                  30

Pro Lys Asp Lys Tyr Gln Glu Leu Lys Glu Lys Lys Ile Lys Asp
            35                  40                  45

Thr Asp Gln Phe Ile Ala Ser Phe Tyr Lys Asn Asp Leu Ile Lys Leu
50                  55                  60

Asn Gly Asp Leu Tyr Lys Ile Ile Gly Val Asn Ser Asp Asp Arg Asn
65                  70                  75                  80

Ile Ile Glu Leu Asp Tyr Tyr Asp Ile Lys Tyr Lys Asp Tyr Cys Glu
```

```
                    85                  90                  95

Ile Asn Asn Ile Lys Gly Glu Pro Arg Ile Lys Lys Thr Ile Gly Lys
                100                 105                 110

Lys Thr Glu Ser Ile Glu Lys Phe Thr Thr Asp Val Leu Gly Asn Leu
        115                 120                 125

Tyr Leu His Ser Thr Glu Lys Ala Pro Gln Leu Ile Phe Lys Arg Gly
    130                 135                 140

Leu
145

<210> SEQ ID NO 112
<211> LENGTH: 144
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus hyicus mini-domain 12 from 12
      mini-domain library

<400> SEQUENCE: 112

Ile Tyr Ser Tyr Arg Phe Asp Ile Tyr Gln Tyr Gly Asn Asn Tyr Lys
1               5                   10                  15

Met Ile Thr Ile Ser Tyr Ile Asp Leu Glu Gln Lys Ser Asn Tyr Tyr
            20                  25                  30

Tyr Ile Ser Arg Glu Lys Tyr Glu Gln Lys Lys Asp Lys Gln Ile
        35                  40                  45

Asp Asp Ser Tyr Lys Phe Ile Gly Ser Phe Tyr Lys Asn Asp Ile Ile
50                  55                  60

Asn Tyr Asn Gly Glu Met Tyr Arg Val Ile Gly Val Asn Asp Ser Glu
65                  70                  75                  80

Lys Asn Lys Ile Gln Leu Asp Met Ile Asp Ile Ser Ile Lys Asp Tyr
                85                  90                  95

Met Glu Leu Asn Asn Ile Lys Lys Thr Gly Val Ile Tyr Lys Thr Ile
                100                 105                 110

Gly Lys Ser Thr Thr His Ile Glu Lys Tyr Thr Thr Asp Ile Leu Gly
        115                 120                 125

Asn Leu Tyr Lys Ala Ala Pro Pro Lys Lys Pro Gln Leu Ile Phe Lys
    130                 135                 140

<210> SEQ ID NO 113
<211> LENGTH: 144
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Staphylococcus microti mini-domain 12 from 12
      mini-domain library

<400> SEQUENCE: 113

Ser Phe Arg Phe Asp Val Tyr Gln Thr Asp Lys Gly Tyr Lys Phe Ile
1               5                   10                  15

Ser Ile Ala Tyr Leu Thr Leu Lys Asn Glu Lys Asn Tyr Ala Ile
            20                  25                  30

Ser Gln Glu Lys Tyr Asp Gln Leu Lys Ser Glu Lys Lys Ile Ser Asn
        35                  40                  45

Asn Ala Val Phe Ile Gly Ser Phe Tyr Thr Ser Asp Ile Ile Glu Ile
```

```
            50                  55                  60
Asn Asn Glu Lys Phe Arg Val Ile Gly Val Asn Ser Asp Lys Asn Asn
 65                  70                  75                  80

Leu Ile Glu Val Asp Arg Ile Asp Ile Arg Gln Lys Glu Phe Ile Glu
                     85                  90                  95

Leu Glu Glu Glu Lys Lys Asn Asn Arg Ile Lys Val Thr Ile Gly Arg
                100                 105                 110

Lys Thr Thr Asn Ile Glu Lys Phe His Thr Asp Ile Leu Gly Asn Met
            115                 120                 125

Tyr Lys Ser Lys Arg Pro Lys Ala Pro Gln Leu Val Phe Lys Lys Gly
            130                 135                 140
```

<210> SEQ ID NO 114
<211> LENGTH: 104
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNAVEGFA

<400> SEQUENCE: 114
ggaccccctc cacccccgccu cguuuuagua cucuggaaac agaaucuacu gaaacaagac    60
aauaugucgu guuuauccca ucaauuuauu ggugggauuu uuuu    104

<210> SEQ ID NO 115
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: ATTO647N oligonucleotide with CGGGCGC-PAM

<400> SEQUENCE: 115
accccctcca ccccgcctcc gggcgcg    27

<210> SEQ ID NO 116
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Biotinylated oligonucleotide with CGGGCGC-PAM

<400> SEQUENCE: 116
gcgcgcgccc ggaggcgggg tggagggggt cgg    33

<210> SEQ ID NO 117
<211> LENGTH: 20
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: BFP targeting guide RNA

<400> SEQUENCE: 117
gggucagggu ggucacgagg    20

<210> SEQ ID NO 118
<211> LENGTH: 2188
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCas606

<400> SEQUENCE: 118

| | | | | | |
|---|---|---|---|---|---|
| ccactgtaga | agagcaaatg | ccacctgacg | tctaagaaat | tcgcgttaaa | ttttgttaa | 60 |
| atcagctcat | tttttaacca | ataggccgaa | atcggcaaaa | tcccttataa | atcaaaagaa | 120 |
| tagaccgaga | tagggttgag | tggccgctac | actagggcgc | gtctaatacg | actcactata | 180 |
| ggaccccctc | cacccgcct | cgttttagta | ctctggaaac | agaatctact | gaaacaagac | 240 |
| aatatgtcgt | gtttatccca | tcaatttatt | ggtgggattt | ttttctagca | taacccttg | 300 |
| gggcctctaa | acgggtcttg | aggggttttt | tgtcactgcc | cgctttccag | tcgggaaacc | 360 |
| tgtcgtgcca | gctgcattaa | tgaatcgttc | gtcagaactg | cttacgcggt | tgtcactcg | 420 |
| gtcgctacgc | tccgggcgtg | agactgcggc | gggcgctgcg | gacacataca | aagttaccca | 480 |
| cagattccgt | ggataagcag | gggactaaca | tgtgaggcaa | acagcaggg | ccgcgccggt | 540 |
| ggcgttttc | cataggctcc | gcccctcctgc | cagagttcac | ataaacagac | gcttttccgg | 600 |
| tgcatctgtg | ggagccgtga | ggctcaacca | tgaatctgac | agtacgggcg | aaacccgaca | 660 |
| ggacttaaag | atccccaccg | tttccggcgg | gtcgctccct | cttgcgctct | cctgttccga | 720 |
| ccctgccgtt | taccggatac | ctgttccgcc | tttctcccctt | acgggaagtg | tggcgctttc | 780 |
| tcatagctca | cacactggta | tctcggctcg | gtgtaggtcg | ttcgctccaa | gctgggctgt | 840 |
| aagcaagaac | tccccgttca | gcccgactgc | tgcgccttat | ccggtaactg | ttcacttgag | 900 |
| tccaaccccgg | aaaagcacgg | taaaacgcca | ctggcagcag | ccattggtaa | ctgggagttc | 960 |
| gcagaggatt | tgtttagcta | aacacgcggt | tgctcttgaa | gtgtgcgcca | aagtccggct | 1020 |
| acactggaag | gacagatttg | gttgctgtgc | tctgcgaaag | ccagttacca | cggttaagca | 1080 |
| gttccccaac | tgacttaacc | ttcgatcaaa | ccacctcccc | aggtggtttt | ttcgtttaca | 1140 |
| gggcaaaaga | ttacgcgcag | aaaaaaagga | tctcaagaag | atcctttgat | cttttctact | 1200 |
| gaaccgctca | atctaaagta | tatatgagta | aacttggtct | gacagttatt | agaaaaactc | 1260 |
| atcgagcatc | aaatgaaact | gcaattatt | catatcagga | ttatcaatac | catattttg | 1320 |
| aaaaagccgt | ttctgtaatg | aaggagaaaa | ctcaccgagg | cagttccata | ggatggcaag | 1380 |
| atcctggtat | cggtctgcga | ttccgactcg | tccaacatca | atacaaccta | ttaatttccc | 1440 |
| ctcgtcaaaa | ataaggttat | caagtgagaa | atcaccatga | gtgacgactg | aatccggtga | 1500 |
| gaatggcaaa | agtttatgca | tttctttcca | gacttgttca | acaggccagc | cattacgctc | 1560 |
| gtcatcaaaa | tcactcgcat | caaccaaacc | gttattcatt | cgtgattgcg | cctgagcgag | 1620 |
| acgaaatacg | cgatcgctgt | taaaaggaca | attacaaaca | ggaatcgaat | gcaaccggcg | 1680 |
| caggaacact | gccagcgcat | caacaatatt | ttcacctgaa | tcaggatatt | cttctaatac | 1740 |
| ctggaatgct | gtttttccgg | ggatcgcagt | ggtgagtaac | catgcatcat | caggagtacg | 1800 |
| gataaaatgc | ttgatggtcg | gaagaggcat | aaattccgtc | agccagttta | gtctgaccat | 1860 |
| ctcatctgta | acatcattgg | caacgctacc | tttgccatgt | ttcagaaaca | actctggcgc | 1920 |
| atcgggcttc | ccatacaatc | gatagattgt | cgcacctgat | tgcccgacat | tatcgcgagc | 1980 |

```
ccatttatac ccatataaat cagcatccat gttggaattt aatcgcggcc tagagcaaga    2040
cgtttcccgt tgaatatggc tcatactctt ccttttcaa tattattgaa gcatttatca     2100
gggttattgt ctcatgagcg gatacatatt tgaatgtatt tagaaaaata aacaaatagg    2160
ggttccgcgc acatttcccc gaaaagtg                                       2188

<210> SEQ ID NO 119
<211> LENGTH: 9489
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCas634

<400> SEQUENCE: 119
ccggtgatac cacgatacta tgactgagag tcaacgccat gagcggcctc atttcttatt      60
ctgagttaca acagtccgca ccgctgccgg tagctattga ctatccggct gcactagccc     120
tgcgtcagat ggctctgatc caaggcaaac tgccaaaata tctgctggca ccggaagtca     180
gcgccctgca ccattatgtt ccggatctgc atcgcaggat gctgctggct accctgtgga     240
acacctacat ctgtattaac gaagcgctgg cattgaccct gagtgatttt tctctggtgc     300
cgccctatcc ctttgtgcag cttgccacgc tcaaggggtt ttgaggtcca accgtacgaa     360
aacgtacggt aagaggaaaa ttatcgtctg aaaaatcgat tagtagacaa gaaagtccgt     420
taagtgccaa ttttcgatta aaaagacacc gttttgatgg cgttttccaa tgtacattat     480
gtttcgatat atcagacagt tacttcacta acgtacgttt tcgttctatt ggccttcaga     540
ccccatatcc ttaatgtcct ttatttgctg gggttatcag atccccccga cacgtttaat     600
taatgctttc tccgccggag atcgacgcac agcgttctgt gctctatgat gttatttctt     660
aataatcatc caggtattct ctttatcacc atacgtagtg cgagtgtcca ccttaacgca     720
gggctttccg tcacagcgcg atatgtcagc cagcggggct ttcttttgcc agaccgcttc     780
catcctctgc atttcagcaa tctggctata cccgtcattc ataaaccacg taatgccgt      840 cacgcaggaa gccaggacga agaatatcgt cagtacaaga taaatcgcgg atttccacgt     900
atagcgtgac atctcacgac gcatttcatg gatcatcgct ttcgccgtat cggcagcctg     960
attcagcgct tctgtcgccg gtttctgctg tgctaatccg gcttgtttca gttctttctc    1020
aacctgagtg agcgcggaac tcaccgattt cctgacggtg tcagtcatat taccggacgc    1080
gctgtccagc tcacgaatga ccctgctcag cgtttcactt tgctgctgta attgtgatga    1140
ggcggcctga aactgttctg tcagagaagt aacacgcttt tccagcgcct gatgatgccc    1200
gataagggcg gcaatttgtt taatttcgtc gctcatacaa aatcctgcct atcgtgagaa    1260
tgaccagcct ttatccggct tctgtcgtat ctgttcggcg agtcgctgtc gttctttctc    1320
ctgctgacgc tgttttccg ccagacgttc gcgctctctc tgccttccca tctcctgatg     1380
tatcccctgg aactccgcca tcgcatcgtt aacaagggac tgaagatcga tttcttcctg    1440
tatatccttc atggcatcac tgaccagtgc gttcagcttg tcaggctctt tttcaaaatc    1500
aaacgttctg ccggaatggg attcctgctc aggctctgac ttcagctcct gttttagcgt    1560
cagagtatcc ctctcgctga gggcttcccg taacgaggta gtcacgtcaa ttacgctgtc    1620
acgttcatca cgggactgct gcacctgcct ttcagcctcc ctgcgctcaa gaatggcctg    1680
tagctgctca gtatcgaatc gctgaacctg acccgcgccc agatgccgct caggctcacg    1740
```

```
gtcaatgccc tgcgccttca gggaacggga atcaacccgg tcagcgtgct gataccgttc    1800
aaggtgctta ttctggaggt cagcccagcg ttccctctgg gcaacaaggt attctttgcg    1860
ttcggtcggt gtttccccga aacgtgcctt ttttgcgcca ccgcgctccg gctctttggt    1920
gttagcccgt ttaaaatact gctcagggtc acggtgaata ccgtcattaa tgcgttcaga    1980
gaacatgata tgggcgtggg gctgctcgcc accggctatc gctgctttcg gattatggat    2040
agcgaactga taggcatggc ggtcgccaat ttcctgttgg acaaaatcgc ggacaagctc    2100
aagacgttgt tcgggtttta actcacgcgg caggcaatc tcgatttcac ggtaggtaca     2160
gccgttggca cgttcagacg tgtcagcggc tttccagaac tcggacggtt tatgcgctgc    2220
ccacgccggc atattgccgg actccttgtg ctcaaggtcg gagtcttttt cacgggcata    2280
ctttccctca cgcgcaatat aatcggcatg aggagaggca ctgccttttc cgccggtttt    2340
tacgctgaga tgataggatg ccatcgtgtt ttatcccgct gaaggcgcgc accgtttctg    2400
aacgaagtga agaaacgtct aagtgcgccc tgataaataa aagagttatc agggattgta    2460
gtgggatttg acctcctctg ccatcactga gcataatcat tccgttagca ttcaggaggt    2520
aaacagcatg aataaaagcg aaaaacagga acaatgggca gcagaaagag tgcagtatat    2580
tcgcggctta aagtcgccga atgagcaaca gaaacttatg ctgatactga cggataaagc    2640
agataaaaca gcacaggata tcaaaacgct gtccctgctg atgaaggctg aacaggcagc    2700
agagaaagcg caggaagcca gagcgaaagt catgaacctg atacaggcag aaaagcgagc    2760
cgaagccaga gccgcccgta aagcccgtga ccatgctctg taccagtctg ccggattgct    2820
tatcctggcg ggtctggttg acagtaagac gggtaagcct gttgatgata ccgctgcctt    2880
actgggtgca ttagccagtc tgaatgacct gtcacgggat aatccgaagt ggtcagactg    2940
gaaaatcaga gggcaggaac tgctgaacag caaaaagtca gatagcacca catagcagac    3000
ccgccataaa acgccctgag aagcccgtga cgggcttttc ttgtattatg ggtagtttcc    3060
ttgcatgaat ccataaaagg cgcctgtagt gccatttacc cccattcact gccagagccg    3120
tgagcgcagc gaactgaatg tcacgaaaaa gacagcgact caggtgcctg atggtcggag    3180
acaaaaggaa tattcagcga tttgcccgag cttgcgaggg tgctacttaa gcctttaggg    3240
ttttaaggtc tgttttgtag aggagcaaac agcgtttgcg acatcctttt gtaatactgc    3300
ggaactgact aaagtagtga gttatacaca gggctgggat ctattctttt tatctttttt    3360
tattctttct ttattctata aattataacc acttgaatat aaacaaaaaa aacacacaaa    3420
ggtctagcgg aatttacaga gggtctagca gaatttacaa gttttccagc aaaggtctag    3480
cagaatttac agatacccac aactcaaagg aaaaggacta gtaattatca ttgactagcc    3540
catctcaatt ggtatagtga ttaaaatcac ctagaccaat tgagatgtat gtctgaatta    3600
gttgttttca aagcaaatga actagcgatt agtcgctatg acttaacgga gcatgaaacc    3660
aagctaattt tatgctgtgt ggcactactc aaccccacga ttgaaaaccc tacaaggaaa    3720
gaacggacgg tatcgttcac ttataaccaa tacgctcaga tgatgaacat cagtagggaa    3780
aatgcttatg gtgtattagc taaagcaacc agagagctga tgacgagaac tgtggaaatc    3840
aggaatcctt tggttaaagg ctttgagatt ttccagtgga caaactatgc caagttctca    3900
agcgaaaaat tagaattagt ttttagtgaa gagatattgc cttatctttt ccagttaaaa    3960
aaattcataa aatataatct ggaacatgtt aagtctttg aaaacaaata ctctatgagg     4020
atttatgagt ggttattaaa agaactaaca caaagaaaa ctcacaaggc aaatatagag     4080
attagccttg atgaatttaa gttcatgtta atgcttgaaa ataactacca tgagtttaaa    4140
```

```
aggcttaacc aatgggtttt gaaaccaata agtaaagatt taaacactta cagcaatatg    4200
aaattggtgg ttgataagcg aggccgcccg actgatacgt tgattttcca agttgaacta    4260
gatagacaaa tggatctcgt aaccgaactt gagaacaacc agataaaaat gaatggtgac    4320
aaaataccaa caaccattac atcagattcc tacctacata acggactaag aaaaacacta    4380
cacgatgctt taactgcaaa aattcagctc accagttttg aggcaaaatt tttgagtgac    4440
atgcaaagta agtatgatct caatggttcg ttctcatggc tcacgcaaaa acaacgaacc    4500
acactagaga acatactggc taaatacgga aggatctgag gttcttatgg ctcttgtatc    4560
tatcagtgaa gcatcaagac taacaaacaa agtagaaca actgttcacc gttacatatc    4620
aaagggaaaa ctgtccatat gcacagatga aaacggtgta aaaagatag atacatcaga    4680 gcttttacga gttttggtg cattcaaagc tgttcaccat gaacagatcg acaatgtaac    4740
agatgaacag catgtaacac ctaatagaac aggtgaaacc agtaaaacaa agcaactaga    4800
acatgaaatt gaacacctga gacaacttgt tacagctcaa cagtcacaca tagacagcct    4860
gaaacaggcg atgctgctta tcgaatcaaa gctgccgaca acacgggagc cagtgacgcc    4920
tcccgtgggg aaaaaatcat ggcaattctg gaagaaatag cgctttcagc cggcaaaccg    4980
gctgaagccg gatctgcgat tctgataaca aactagcaac accagaacag cccgtttgcg    5040
ggcagcaaaa cccgtacttt tggacgttcc ggcggttttt tgtggcgagt ggtgttcggg    5100
cggtgcgcgc aagatccatt atgttaaacg ggcgagttta catctcaaaa ccgcccgctt    5160
aacaccatca gaaatcctca gcgcgatttt aagcaccaac ccccccccgt aacacccaaa    5220
tccatactga agtggctttt gttgaataaa tcgaactttt gctgagttga aggatcagat    5280
cacgcatcct cccgacaaca cagaccattc cgtggcaaag caaaagttca gaatcaccaa    5340
ctggtccacc tacaacaaag ctctcatcaa ccgtggctcc ctcactttct ggctggatga    5400
tgaggcgatt caggcctggt atgagtcggc aacaccttca tcacgaggaa ggccccagcg    5460
ctattctgat ctcgccatca ccaccgttct ggtgattaaa cgcgtattcc ggctgaccct    5520
gcgggctgcg cagggtttta ttgattccat ttttgccctg atgaacgttc cgttgcgctg    5580
cccggattac accagtgtca gtaagcgggc aaagtcggtt aatgtcagtt tcaaaacgtc    5640
cacccggggt gaaatcgcac acctggtgat tgattccacc gggctgaagg tctttggtga    5700
aggcgaatgg aaagtcagaa agcacggcaa agagcgccgt cgtatctggc gaaagttgca    5760
tcttgctgtt gacagcaaca cacatgaagt tgtctgtgca gacctgtcgc tgaataacgt    5820
cacggactca gaagccttcc cgggccttat ccggcagact cacagaaaaa tcagggcagc    5880
cgcggcagac ggggcttacg atacccggct ctgtcacgat gaactgcgcc gcaaaaaaat    5940
cagcgcgctt attcctcccc gaaaaggtgc gggttactgg cccggtgaat atgcagaccg    6000
taaccgtgca gtggctaatc agcgaatgac cgggagtaat gcgcggtgga aatggacaac    6060
agattacaac cgtcgctcga tagcggaaac ggcgatgtac cggtaaaac agctgttcgg    6120 gggttcactg acgctgcgtg actacgatgg tcaggttgcg gaggctatgg ccctggtacg    6180
agcgctgaac aaaatgacga aagcaggtat gcctgaaagc gtgcgtattg cctgaaaaca    6240
caacccgcta cggggggagac ttacccgaaa tctgatttat tcaacaaagc cgggtgtggt    6300
gaactacaaa gcagacccgt tgaggttatc agttcgatgc acaatcagca gcgcataaaa    6360
tatgcacaag aacaggagca cccttcgcat taagctgtgg tggtaacaag tagtgccggg    6420
ctaccatcag cgagcatgat gcgctcccac agcattcgcc ttggcagtat ggaagttcct    6480
```

```
cgctccagtt cgggccggta tccacctcga gctttctacg gggtctgacg ctcagtggaa    6540
cgaaaactca cgttaaggga ttttggtcat gagattatca aaaaggatct tcacctagat    6600
cctttctgac cgaataaata cctgtgacgg aagatcactt cgcagaataa ataaatcctg    6660
gtgtccctgt tgataccggg aagccctggg ccaacttttg cgaaaatga gacgttgatc     6720 ggcacgtaag aggttccaac tttcaccata atgaaataag atcactaccg ggcgtatttt    6780
ttgagttgtc gagattttca ggagctaagg aagctaaaat ggagaaaaaa atcactggat    6840
ataccaccgt tgatatatcc caatggcatc gtaaagaaca ttttgaggca tttcagtcag    6900
ttgctcaatg tacctataac cagaccgttc agctggatat tacggccttt ttaaagaccg    6960
taaagaaaaa taagcacaag ttttatccgg cctttattca cattcttgcc cgcctgatga    7020
atgctcatcc ggaattacgt atggcaatga aagacggtga gctggtgata tgggatagtg    7080
ttcacccttg ttacaccgtt ttccatgagc aaactgaaac gttttcatcg ctctggagtg    7140
aataccacga cgatttccgg cagtttctac acatatattc gcaagatgtg gcgtgttacg    7200
gtgaaaacct ggcctatttc cctaaagggt ttattgagaa tatgtttttc gtctcagcca    7260
atccctgggt gagtttcacc agttttgatt taaacgtggc caatatggac aacttcttcg    7320
cccccgtttt caccttgggc aaatattata cgcaaggcga caaggtgctg atgccgctgg    7380
cgattcaggt tcatcatgcc gtttgtgatg gcttccatgt cggcagaatg cttaatgaat    7440
tacaacagta ctgcgatgag tggcagggcg gggcgtaatt ttttttaaggc agttattggt    7500 gcccttaaac gcctggttgc tacgcctgaa taagtgataa taagcggatg aatggcagaa    7560
attcgaaagc aaattcgacc cggtcgtcgg ttcaggcag ggtcgttaaa tagccgctta    7620
tgtctattgc tggtttaccg gattattgac taccggaagc agtgtgaccg tgtgcttctc    7680
aaatgcctga ggcagttgtg ctcaggctct ccccgtggag gtaataattg acgatatgat    7740
cctttttttc tgatcaaaag tgctccatgg aattatgaca acttgacggc tacatcattc    7800
acttttcctt cacaaccggc acggaactcg ctcgggctgg ccccggtgca ttttttaaaat    7860 acccgcgaga aatagagttg atcgtcaaaa ccaacattgc gaccgacggt ggcgataggc    7920
atccgggtgg tgctcaaaag cagcttcgcc tggctgatac gttggtcctc gcgccagctt    7980
aagacgctaa tccctaactg ctggcggaaa agatgtgaca gacgcgacgg cgacaagcaa    8040
acatgctgtg cgacgctggc gatatcaaaa ttgctgtctg ccaggtgatc gctgatgtac    8100
tgacaagcct cgcgtacccg attatccatc ggtggatgga gcgactcgtt aatcgcttcc    8160
atgcgccgca gtaacaattg ctcaagcaga tttatcgcca gcagctccga atagcgccct    8220
tccccttgcc cggcgttaat gatttgccca aacaggtcgc tgaaatgcgg ctggtgcgct    8280
tcatccgggc gaaagaaccc cgtattggca aatattgacg gccagttaag ccattcatgc    8340
cagtaggcgc gcggacgaaa gtaaacccac tggtgatacc attgcgagc ctccggatga    8400 cgaccgtagt gatgaatctc tcctggcggg aacagcaaaa tatcacccgg tcggcaaaca    8460
aattctcgtc cctgattttt caccaccccc tgaccgcgaa tggtgagatt gagaatataa    8520
cctttcattc ccagcggtcg gtcgataaaa aaatcgagat aaccgttggc ctcaatcggc    8580
gttaaacccg ccaccagatg ggcattaaac gagtatcccg gcagcagggg atcatttgc     8640 gcttcagcca tactttttcat actcccgcca ttcagagaag aaaccaattg tccatattgc    8700
atcagacatt gccgtcactg cgtctttac tggctcttct cgctaaccaa accggaaacc    8760
ccgcttatta aaagcattct gtaacaaagc gggaccaaag cctgacaaa aacgcgtaac    8820 aaaagtgtct ataatcacgg cagaaaagtc cacattgatt atttgcacgg cgtcacactt    8880
```

```
tgctatgcca tagcattttt atccataaga ttagcggatc ctacctgacg cttttatcg      8940 caactctcta ctgtcgtgcg caacgcgtga catcgactag gaggcctttc tatgcagttc      9000
aaagtgtata cctataaacg cgaaagccgt tatcgtctgt tgttgatgt tcagagcgat       9060 attattgata caccgggtcg tcgtatggtt attccgctgg caagcgcacg tctgctgagc      9120
gataaagtta gccgtgaact gtatccggtt gttcatattg gtgatgaaag ctggcgtatg      9180
atgaccaccg atatggcaag cgttccggtt agcgttattg gtgaagaagt tgcagatctg      9240
agccatcgtg aaaacgatat caaaaatgcc atcaacctga tgttttgggg catcttatag      9300 gacccctcc accccgcctc gcgggcagtt tgcctggcgg cagtagcgcg gtggtcccac       9360
ctgaccccat gccgaactca gaagtgaaac gccgtagcgc cgatggtagt gtgggctctc      9420
cccatgcgag agtagggaac tgccaggcat caaataaaac gaaaggctca gtcgaaagac      9480
tgggcctta                                                              9489
```

<210> SEQ ID NO 120
<211> LENGTH: 6740
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCas81

<400> SEQUENCE: 120

```
ggtggaagcg gaggcagcgg gggatcaggc catcatcatc accatcatta atgaacgggt      60
cttgaggggt ttttggact tttgcgtatt gggcgctctt ccgcttcctc gctcactgac       120
tcgctgcgct cggtcgttcg gctgcggcga gcggtatcag ctcactcaaa ggcggtaata     180
cggttatcca cagaatcagg ggataacgca ggaaagaaca tgtgagcaaa aggccagcaa      240
aaggccagga accgtaaaaa ggccgcgttg ctggcgtttt tccataggct ccgcccccct     300
gacgagcatc acaaaaatcg acgctcaagt cagaggtggc gaaacccgac aggactataa      360
agataccagg cgtttccccc tggaagctcc ctcgtgcgct ctcctgttcc gaccctgccg      420
cttaccggat acctgtccgc ctttctccct tcgggaagcg tggcgctttc tcatagctca      480
cgctgtaggt atctcagttc ggtgtaggtc gttcgctcca agctgggctg tgtgcacgaa      540
ccccccgttc agcccgaccg ctgcgcctta tccggtaact atcgtcttga gtccaacccg      600
gtaagacacg acttatcgcc actggcagca gccactggta acaggattag cagagcgagg      660
tatgtaggcg gtgctacaga gttcttgaag tggtggccta actacggcta cactagaagg      720
acagtatttg gtatctgcgc tctgctgaag ccagttacct tcggaaaaag agttggtagc      780
tcttgatccg gcaaacaaac caccgctggt agcggtggtt tttttgtttg caagcagcag      840
attacgcgca gaaaaaaagg atctcaagaa gatcctttga tcttttctac ggggtctgac      900
gctcagtgga acgaaaactc acgttaaggg attttggtca tgagattatc aaaaaggatc      960
ttcacctaga tccttttaaa ttaaaaatga agttttaaat caatctaaag tatatatgag     1020
taaacttggt ctgacagtta ccaatgctta atcagtgagg cacctatctc agcgatctgt     1080
ctatttcgtt catccatagt tgcctgactc cccgtcgtgt agataactac gatacgggag     1140
ggcttaccat ctggccccag tgctgcaatg ataccgcgag atccacgctc accggctcca     1200
gatttatcag caataaacca gccagccgga agggccgagc gcagaagtgg tcctgcaact     1260
ttatccgcct ccatccagtc tattaattgt tgccgggaag ctagagtaag tagttcgcca     1320
```

-continued

```
gttaatagtt tgcgcaacgt tgttgccatt gctgcaggca tcgtggtgtc acgctcgtcg   1380
tttggtatgg cttcattcag ctccggttcc caacgatcaa ggcgagttac atgatccccc   1440
atgttgtgca aaaagcggt tagctccttc ggtcctccga tcgttgtcag aagtaagttg   1500
gccgcagtgt tatcactcat ggttatggca gcactgcata attctcttac tgtcatgcca   1560
tccgtaagat gcttttctgt gactggtgag tactcaacca agtcattctg agaatagtgt   1620
atgcggcgac cgagttgctc ttgcccggcg tcaatacggg ataataccgc gccacatagc   1680
agaactttaa aagtgctcat cattggaaaa cgttcttcgg ggcgaaaact ctcaaggatc   1740
ttaccgctgt tgagatccag ttcgatgtaa cccactcgtg cacccaactg atcttcagca   1800
tcttttactt tcaccagcgt ttctgggtga gcaaaaacag gaaggcaaaa tgccgcaaaa   1860
aagggaataa gggcgacacg gaaatgttga atactcatac tcttcctttt tcaatattat   1920
tgaagcattt atcagggtta ttgtctcatg agcggataca tatttgaatg tatttagaaa   1980
aataaacaaa taggggttcc gcgcacattt ccccgaaaag tgccactcct cttgctgtga   2040
ccgtctccgg gagctgcatg tgtcagaggt tttcaccgtc atcaccgaaa cgcgcgaggc   2100
agcagatcaa ttcgcgcgcg aaggcgaagc ggcatgcatt tacgttgaca ccatcgaatg   2160
gtgcaaaacc tttcgcggta tggcatgata gcgcccggaa gagagtcaat tcagggtggt   2220
gaatgtgaaa ccagtaacgt tatacgatgt cgcagagtat gccggtgtct cttatcagac   2280
cgtttcccgc gtggtgaacc aggccagcca cgtttctgcg aaaacgcggg aaaaagtgga   2340
agcggcgatg gcggagctga attacattcc caaccgcgtg gcacaacaac tggcgggcaa   2400
acagtcgttg ctgattggcg ttgccacctc cagtctggcc ctgcacgcgc cgtcgcaaat   2460
tgtcgcggcg attaaatctc gcgccgatca actgggtgcc agcgtggtgg tgtcgatggt   2520
agaacgaagc ggcgtcgaag cctgtaaagc ggcggtgcac aatcttctcg cgcaacgcgt   2580
cagtgggctg atcattaact atccgctgga tgaccaggat gccattgctg tggaagctgc   2640
ctgcactaat gttccggcgt tatttcttga tgtctctgac cagacaccca tcaacagtat   2700
tattttctcc catgaagatg gtacgcgact gggcgtggag catctggtcg cattgggtca   2760
ccagcaaatc gcgctgttag cgggcccatt aagttctgtc tcggcgcgtc tgcgtctggc   2820
tggctggcat aaatatctca ctcgcaatca aattcagccg atagcggaac gggaaggcga   2880
ctggagtgcc atgtccggtt ttcaacaaac catgcaaatg ctgaatgagg gcatcgttcc   2940
cactgcgatg ctggttgcca acgatcagat ggcgctgggc gcaatgcgcg ccattaccga   3000
gtccgggctg cgcgttggtg cggatatctc ggtagtggga tacgacgata ccgaagatag   3060
ctcatgttat atcccgccgt taaccaccat caaacaggat tttcgcctgc tggggcaaac   3120
cagcgtggac cgcttgctgc aactctctca gggccaggcg gtgaagggca atcagctgtt   3180
gcccgtctca ctggtgaaaa gaaaaaccac cctggcgccc aatacgcaaa ccgcctctcc   3240
ccgcgcgttg gccgattcat taatgcagct ggcacgacag gtttcccgac tggaaagcgg   3300
gcagtgagcg caatattctg aaatgagctg ttgacaatta atcatccggc tcgtataatg   3360
tgtggaattg tgagcggata caatttttca cacaggaaac agaattctag cattgtgagc   3420
ggataacaat tcccctctag aaataatttt gtttaacttt aagaaggaga taccatga   3480
aacgtccggc agcaaccaaa aaagcaggtc aggccaagaa aaaaaaggt ggtggttcag   3540
gtaaccagaa atttatcctg ggtctgggata ttggtattac cagcgttggt tatgccctga   3600
ttgattacga aaccaaaaac attattgatg ccggtgttcg tctgtttccg gaagcaaatg   3660
```

```
ttgaaaataa tgaaggtcgt cgtagcaaac gtggtagccg tcgtctgaaa cgtcgtcgta   3720
ttcatcgtct ggaacgtgtt aaaaaactgc tggaagatta aacctgctg gatcagagcc    3780
agattccgca gagcaccaat ccgtatgcaa ttcgtgttaa aggtctgagc gaagcactga   3840
gcaaagatga actggttatt gcactgctgc atattgcaaa acgccgtggc attcataaaa   3900
tcgatgtgat tgatagcaat gacgatgtgg gtaatgaact gagcaccaaa gaacagctga   3960
acaaaaatag caaactgctg aaagacaaat cgtgtgtca gattcagctg aacgtatga    4020
atgaaggcca ggttcgtggt gaaaagaatc gctttaaaac cgcagacatc atcaaagaaa   4080
ttatccagct gctgaacgtg cagaaaaact ccatcagct ggatgaaaac ttcatcaaca    4140
aatacatcga gctggttgaa atgcgtcgcg aatattttga aggtccgggt aaaggtagcc   4200
cgtatggttg ggaaggtgat ccgaaaagcat ggtatgaaac cctgatgggt cattgtacct  4260
attttccgga tgaactgcgt agcgttaaat atgcctatag cgcagacctg tttaatgcac   4320
tgaatgatct gaataacctg gtgattcagc gtgatggtct gagcaaactg gaatatcatg   4380
agaaatatca catcatcgaa aacgtgttca acagaagaa gaaaccgacc ctgaaacaaa    4440
tcgccaacga aattaatgtg aacccggaag atattaaagg ctaccgtatt accaaaagcg   4500
gtaaaccgca gttcaccgaa tttaaactgt atcacgatct gaaaagcgtg ctgtttgatc   4560
agagcattct ggaaaatgaa gatgtgctgg accagattgc agaaattctg accatttatc   4620
aggacaaaga cagcatcaaa agcaaactga ccgaactgga tattctgctg aatgaagaag   4680
ataaagagaa cattgcacag ctgaccggtt ataccggcac ccatcgtctg agcctgaaat   4740
gtattcgtct ggtactggaa gaacagtggt atagcagccg taatcagatg gaaatcttta   4800
cccatctgaa cattaaaccg aagaaaatca atctgaccgc agccaacaaa attccgaaag   4860
ccatgattga tgagtttatt ctgagtccgg ttgtgaaacg tacctttggt caggcaatta   4920
acctgatcaa caaaatcatt gaaaaatatg gcgtgcctga ggatatcatt attgaactgg   4980
cacgtgaaaa caacagcaaa gataaacaga aattcatcaa cgagatgcag aagaagaacg   5040
aaaatacccg caaacggatt aacgagatca ttggcaaata tggtaatcag aatgccaaac   5100
gcctggtgga aaaaattcgt ctgcatgatg aacaagaggg caaatgtctg tatagcctgg   5160
aaagcattcc tctggaagat ctgctgaaca atccgaatca ttatgaagtg gatcacatta   5220
ttccgcgtag cgtgagcttt gataattcct atcataataa agtgctggtg aaacagagcg   5280
aaaactccaa aaaatccaac ctgacaccgt atcagtattt caatagcggc aaatccaaac   5340
tgagctacaa ccagtttaaa cagcatattc tgaacctgag caaaagccag gatcgcatca   5400
gcaagaagaa gaaggagtac ctgctggaag aacgcgacat caacaaattt gaagtgcaga   5460
aagaatttat caaccgcaac ctggttgata cccgttatgc aacccgtgaa ctgaccaatt   5520
atctgaaagc atatttcagc gccaacaaca tgaacgtgaa agtgaaaacg attaacggca   5580
gctttaccga ttatctgcgt aaagtgtgga aattcaaaaa agaacgcaac cacggctata   5640
aacatcatgc cgaagatgcc ctgattattg caaatgcaga tttcctgttt aaagaaaaca   5700
aaaaactgaa agccgtcaac agcgtgctgg aaaaaccgga aattgagaca aaacagctgg   5760
acattccggt tgatagcgaa gataattaca gcgaaatgtt tatcatcccg aaacaggtgc   5820
aggatatcaa agattttcgc aacttcaaat atagccaccg cgttgacaaa aaacctaatc   5880
gtcagctgat taacgatacc ctgtatagca cccgcaaaaa agataacagc acctatattg   5940
tgcagaccat taaagacatc tacgccaaag ataataccac cctgaaaaaa cagttcgaca   6000
aaagcccaga aaaatttctg atgtatcagc atgatccgcg taccttcgaa aaactggaag   6060
```

```
ttattatgaa acagtatgcc aacgagaaaa atccgctggc caaatatcac gaagaaaccg    6120
gtgaatatct gaccaaatat tccaagaaga acaacggtcc gatcgttaaa tccctgaaat    6180
atatcggtaa taaactgggc agccatctgg atgttaccca tcagtttaaa agctccacaa    6240
agaagctggt taaactgtcc atcaaaccgt atcgctttga tgtgtatctg accgacaaag    6300
gctataaatt cattaccatc agctatctgg acgtgctgaa aaaagacaac tattattata    6360
tcccggaaca gaaatatgat aaactgaaac tgggtaaagc catcgataaa aacgccaaat    6420
ttatcgccag cttctacaaa aacgacctga ttaaactgga tggcgagatc tataaaatca    6480
tcggtgttaa tagcgacacc cgcaatatga ttgagctgga tctgccggat attcgctata    6540
aagaatattg cgaactgaac aacattaaag gcgaaccgcg tatcaaaaag accatcggca    6600
aaaaagtgaa tagcatcgag aaactgacca ccgatgttct gggtaatgtg tttaccaata    6660
cccagtatac caaacctcag ctgctgttca aacgcggtaa tggcggagga tctggcccc    6720 ctaagaaaaa gcggaaggtg                                                6740
```

<210> SEQ ID NO 121
<211> LENGTH: 6740
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCas888

<400> SEQUENCE: 121

```
tgccacctcc agtctggccc tgcacgcgcc gtcgcaaatt gtcgcggcga ttaaatctcg      60
cgccgatcaa ctgggtgcca gcgtggtggt gtcgatggta gaacgaagcg gcgtcgaagc     120
ctgtaaagcg gcggtgcaca atcttctcgc gcaacgcgtc agtgggctga tcattaacta    180
tccgctggat gaccaggatg ccattgctgt ggaagctgcc tgcactaatg ttccggcgtt    240
atttcttgat gtctctgacc agacacccat caacagtatt attttctccc atgaagatgg    300
tacgcgactg ggcgtggagc atctggtcgc attgggtcac cagcaaatcg cgctgttagc    360
gggcccatta agttctgtct cggcgcgtct gcgtctggct ggctggcata aatatctcac    420
tcgcaatcaa attcagccga tagcggaacg ggaaggcgac tggagtgcca tgtccggttt    480
tcaacaaacc atgcaaatgc tgaatgaggg catcgttccc actgcgatgc tggttgccaa    540
cgatcagatg cgctgggcg caatgcgcgc cattaccgag tccgggctgc gcgttggtgc    600
ggatatctcg gtagtgggat acgacgatac cgaagatagc tcatgttata tcccgccgtt    660
aaccaccatc aaacaggatt ttcgcctgct ggggcaaacc agcgtggacc gcttgctgca    720
actctctcag ggccaggcgg tgaagggcaa tcagctgttg cccgtctcac tggtgaaaag    780
aaaaaccacc ctggcgccca atacgcaaac cgcctctccc cgcgcgttgg ccgattcatt    840
aatgcagctg gcacgacagg tttcccgact ggaaagcggg cagtgagcgc aatattctga    900
aatgagctgt tgacaattaa tcatccggct cgtataatgt gtggaattgt gagcggataa    960
caattttcac acaggaaaca gaattctagc attgtgagcg ataacaatt cccctctaga   1020 aataattttg tttaacttta agaaggagat ataccatgaa acgtccggca gcaaccaaaa    1080
aagcaggtca ggccaagaaa aaaaaggtg gtggttcagg caacaactat attctgggtc    1140
tggatattgg tattaccagc gttggttatg gtattgttga tagcgatacc cgtgaaatta    1200
aagatgccgg tgttcgtctg tttccggaag caaatgttga taataatgaa ggtcgtcgta    1260
```

-continued

```
gcaaacgtgg tgcacgtcgt ctgaaacgtc gtcgtattca tcgtctggat cgtgttaaac    1320
atctgctggc agaatatgat ctgctggatc tgaccaatat tccgaaaagc accaatccgt    1380
atcagacccg tgttaaaggt ctgaatgaaa agctgagcaa agatgaactg gttattgcac    1440
tgctgcatat tgcaaaacgc cgtggcattc ataatgtgaa tgttatgatg gatgataacg    1500
atagcggtaa tgaactgagc accaaagatc agctgaagaa gaatgcaaaa gcactgagcg    1560
ataaatatgt ttgtgaactg cagctggaac gctttgagca ggattataaa gttcgtggtg    1620
aaaagaaccg cttcaaaacc gaagattttg ttcgtgaagc acgtaaactg ctggaaaccc    1680
agagcaaatt tttcgaaatt gatcagacgt tcatcatgcg ctatatcgaa ctgattgaaa    1740
cccgtcgcga atattttgaa ggtccgggta aaggtagccc gtttggttgg aaggtaata    1800
tcaagaaatg gtttgagcag atgatgggcc actgtaccta ttttccagaa gaactgcgta    1860
gcgtcaaata tagctattca gccgaactgt ttaacgccct gaatgatctg aataatctgg    1920
tgattacccg tgatgaagat gccaaactga attatggtga gaaattccag atcatcgaaa    1980
acgtgttcaa acagaagaaa acaccgaacc tgaaacaaat cgccattgaa attggtgtgc    2040
atgaaaccga aatcaaaggt tatcgtgtga acaaaagcgg caaaccggaa tttacccagt    2100
tcaaactgta tcacgatctg aagaacatct tcaaagaccc gaaatacctg aacgatatcc    2160
agctgatgga taacattgca gaaatcatca ccatttatca ggatgccgaa agcatcatca    2220
aagaactgaa tcagctgccg gaactgctga gcgaacgtga aaaggagaag atcagcgcac    2280
tgagcggtta tagcggcacc catcgtctga gcctgaaatg tattaatctg ctgctggatg    2340
atctgtggga aagcagcctg aatcagatgg aactgttcac aaaactgaat ctgaaaccga    2400
agaaaatcga tctgagccag cagcataaaa ttccgagcaa actggtggat gactttattc    2460
tgagtccggt tgttaaacgt gcatttattc agagtatcca ggtggtgaat gccatcattg    2520
ataaatacgg tctgccggaa gatatcatca ttgaactggc acgtgaaaac aatagtgatg    2580
atcgtcgcaa atttctgaac cagctgcaaa agcagaatga ggaaacccgt aaacaggttg    2640
aaaaggtgct gcgtgaatat ggcaatgata atgccaaacg tatcgtgcag aaaatcaaac    2700
tgcataatat gcaagagggg aaatgtctgt atagcctgaa agatattccg ctggaagatc    2760
tgctgcgtaa tccgcatcat tatgaagtgg atcatattat tccgcgtagc gtggcatttg    2820
ataatagcat gcataataaa gttctggtgc gtgccgatga gaatagcaag aaaggtaatc    2880
gtacccgta tcagtatctg aatagcagcg aaagcagtct gagctataac gaatttaaac    2940
agcatatcct gaacctgagc aaaaccaaag accgcatcac caagaagaag cgtgaatacc    3000
tgctggaaga acgcgacatc aacaaatttg atgtgcagaa agaattcatc aaccgcaatc    3060
tggttgatac acgttatgca acccgtgaac tgaccagcct gctgaaagca tatttcagcg    3120
caaataacct ggacgtgaaa gtgaaaacga ttaatggcag ctttaccaac tatctgcgta    3180
aagtgtggaa attcgataaa gatcgcaaca aaggctataa acatcatgca gaagatgccc    3240
tgattattgc caatgcagat tttctgttca acacaacaa gaaactgcgc aacattaaca    3300
aagtgctgga tgcaccgagc aaagaagttg ataagaaacg cgtgacagtt cagagcgaag    3360
atgaatataa ccagattttt gaggataccc agaaagccca ggcaatcaag aaattcgaaa    3420
tccgcaaatt tagccaccgc gtggacaaga accgaatcg tcagctgatt aatgataccc    3480
tgtatagcac ccgtaatatc gatggtattg aatatgtggt cgagagcatc aaagatatct    3540
atagcgtgaa caacgataaa gttaaaacca aattcaagaa agaccccgcac cgtctgctga    3600
```

```
tgtatcgtaa tgatccgcag acctttgaga aattcgagaa agtctttaaa cagtatgaga    3660
gcgagaagaa cccgttcgcc aaatattacg aagaaaccgg tgagaaaatt cgcaaattca    3720
gcaaaaccgg tcagggtccg tatatcaaca aaatcaaata tctgcgtgaa cgcctgggtc    3780
gtcattgtga tgttaccaac aaatatatca atagccgcaa caaaattgtg caactgtcca    3840
tcaaaccgta tcgctttgat gtgtatctga ccgacaaagg ctataaattc attaccatca    3900
gctatctgga cgtgctgaaa aaagacaact attattatat cccggaacag aaatatgata    3960
aactgaaact gggtaaagcc atcgataaaa acgccaaatt tatcgccagc ttctacaaaa    4020
acgacctgat taaactggat ggcgagatct ataaaatcat cggtgttaat agcgacaccc    4080
gcaatatgat tgagctggat ctgccggata ttcgctataa agaatattgc gaactgaaca    4140
acattaaagg cgaaccgcgt atcaaaaaga ccatcggcaa aaaagtgaat agcatcgaga    4200
aactgaccac cgatgttctg ggtaatgtgt ttaccaatac ccagtatacc aaacctcagc    4260
tgctgttcaa acgcggtaat ggcggaggat ctggcccccc taagaaaaag cggaaggtgg    4320
gtggaagcgg aggcagcggg ggatcaggcc atcatcatca ccatcattaa tgaacgggtc    4380
ttgaggggtt ttttggactt ttgcgtattg gcgctcttc cgcttcctcg ctcactgact    4440
cgctgcgctc ggtcgttcgg ctgcggcgag cggtatcagc tcactcaaag gcggtaatac    4500
ggttatccac agaatcaggg gataacgcag gaaagaacat gtgagcaaaa ggccagcaaa    4560
aggccaggaa ccgtaaaaag gccgcgttgc tggcgttttt ccataggctc cgcccccctg    4620
acgagcatca caaaaatcga cgctcaagtc agaggtggcg aaacccgaca ggactataaa    4680
gataccaggc gtttccccct ggaagctccc tcgtgcgctc tcctgttccg accctgccgc    4740
ttaccggata cctgtccgcc tttctccctt cgggaagcgt ggcgctttct catagctcac    4800
gctgtaggta tctcagttcg gtgtaggtcg ttcgctccaa gctgggctgt gtgcacgaac    4860
cccccgttca gcccgaccgc tgcgccttat ccggtaacta tcgtcttgag tccaacccgg    4920
taagacacga cttatcgcca ctggcagcag ccactggtaa caggattagc agagcgaggt    4980
atgtaggcgg tgctacagag ttcttgaagt ggtggcctaa ctacggctac actagaagga    5040
cagtatttgg tatctgcgct ctgctgaagc cagttacctt cggaaaaaga gttggtagct    5100
cttgatccgg caaacaaacc accgctggta gcggtggttt ttttgtttgc aagcagcaga    5160
ttacgcgcag aaaaaaagga tctcaagaag atcctttgat cttttctacg ggtctgacg    5220 ctcagtggaa cgaaaactca cgttaaggga ttttggtcat gagattatca aaaaggatct    5280
tcacctagat ccttttaaat taaaatgaa gttttaaatc aatctaaagt atatatgagt    5340
aaacttggtc tgacagttac caatgcttaa tcagtgaggc acctatctca gcgatctgtc    5400
tatttcgttc atccatagtt gcctgactcc ccgtcgtgta gataactacg atacgggagg    5460
gcttaccatc tggccccagt gctgcaatga taccgcgaga tccacgctca ccggctccag    5520
atttatcagc aataaaccag ccagccgaa gggccgagcg cagaagtggt cctgcaactt    5580
tatccgcctc catccagtct attaattgtt gccgggaagc tagagtaagt agttcgccag    5640
ttaatagttt gcgcaacgtt gttgccattg ctgcaggcat cgtggtgtca cgctcgtcgt    5700
ttggtatggc ttcattcagc tccggttccc aacgatcaag gcgagttaca tgatccccca    5760
tgttgtgcaa aaaagcggtt agctccttcg gtcctccgat cgttgtcaga agtaagttgg    5820
ccgcagtgtt atcactcatg gttatggcag cactgcataa ttctcttact gtcatgccat    5880
ccgtaagatg cttttctgtg actggtgagt actcaaccaa gtcattctga aatagtgta    5940 tgcggcgacc gagttgctct tgcccggcgt caatacggga taataccgcg ccacatagca    6000
```

| | | |
|---|---|---|
| gaactttaaa agtgctcatc attggaaaac gttcttcggg gcgaaaactc tcaaggatct | 6060 |
| taccgctgtt gagatccagt tcgatgtaac ccactcgtgc acccaactga tcttcagcat | 6120 |
| cttttacttt caccagcgtt tctgggtgag caaaaacagg aaggcaaaat gccgcaaaaa | 6180 |
| agggaataag ggcgacacgg aaatgttgaa tactcatact cttcctttt caatattatt | 6240 |
| gaagcattta tcagggttat tgtctcatga gcggatacat atttgaatgt atttagaaaa | 6300 |
| ataaacaaat aggggttccg cgcacatttc cccgaaaagt gccactcctc ttgctgtgac | 6360 |
| cgtctccggg agctgcatgt gtcagaggtt ttcaccgtca tcaccgaaac gcgcgaggca | 6420 |
| gcagatcaat tcgcgcgcga aggcgaagcg gcatgcattt acgttgacac catcgaatgg | 6480 |
| tgcaaaacct ttcgcggtat ggcatgatag cgcccggaag agagtcaatt cagggtggtg | 6540 |
| aatgtgaaac cagtaacgtt atacgatgtc gcagagtatg ccggtgtctc ttatcagacc | 6600 |
| gtttcccgcg tggtgaacca ggccagccac gtttctgcga aaacgcggga aaaagtggaa | 6660 |
| gcggcgatgg cggagctgaa ttacattccc aaccgcgtgg cacaacaact ggcgggcaaa | 6720 |
| cagtcgttgc tgattggcgt | 6740 |

<210> SEQ ID NO 122
<211> LENGTH: 1431
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCas889

<400> SEQUENCE: 122

| | | |
|---|---|---|
| cggaacggga aggcgactgg agtgccatgt ccggttttca acaaaccatg caaatgctga | 60 |
| atgagggcat cgttcccact gcgatgctgg ttgccaacga tcagatggcg ctgggcgcaa | 120 |
| tgcgcgccat taccgagtcc gggctgcgcg ttggtgcgga tatctcggta gtgggatacg | 180 |
| acgataccga agatagctca tgttatatcc cgccgttaac caccatcaaa caggattttc | 240 |
| gcctgctggg gcaaaccagc gtggaccgct tgctgcaact ctctcagggc caggcggtga | 300 |
| agggcaatca gctgttgccc gtctcactgg tgaaaagaaa aaccaccctg gcgcccaata | 360 |
| cgcaaaccgc ctctccccgc gcgttggccg attcattaat gcagctggca cgacaggttt | 420 |
| cccgactgga aagcgggcag tgagcgcaat attctgaaat gagctgttga caattaatca | 480 |
| tccggctcgt ataatgtgtg gaattgtgag cggataacaa ttttcacaca ggaaacagaa | 540 |
| ttctagcatt gtgagcggat aacaattccc ctctagaaat aattttgttt aactttaaga | 600 |
| aggagatata ccatgaaacg tccggcagca accaaaaaag caggtcaggc caagaaaaaa | 660 |
| aaaggtggtg gttcaggcaa caactatatt ctgggtctgg atattggtat taccagcgtt | 720 |
| ggttatggta ttgttgatag cgatacccgt gaaattaaag atgccggtgt tcgtctgttt | 780 |
| ccggaagcaa atgttgataa taatgaaggt cgtcgtagca acgtggtgc acgtcgtctg | 840 |
| aaacgtcgtc gtattcatcg tctggatcgt gttaaacatc tgctggcaga atatgatctg | 900 |
| ctggatctga ccaatattcc gaaaagcacc aatccgtatc agaccgtgt taaggtctg | 960 |
| aatgaaaagc tgagcaaaga tgaactggtt attgcactgc tgcatattgc aaaacgccgt | 1020 |
| ggcattcata tgtgaatgt tatgatggat gataacgata gcggtaatga actgagcacc | 1080 |
| aaagatcagc tgaagaagaa tgcaaaagca ctgagcgata aatatgtttg tgaactgcag | 1140 |
| ctggaacgct ttgagcagga ttataaagtt cgtggtgaaa agaaccgctt caaaaccgaa | 1200 |

```
gattttgttc gtgaagcacg taaactgctg gaaacccaga gcaaatttt cgaaattgat    1260 cagacgttca tcatgcgcta tatcgaactg attgaaaccc gtcgcgaata ttttgaaggt    1320
ccgggtaaag gtagcccgtt tggttgggaa ggtaatatca agaaatggtt tgagcagatg    1380
atgggccact gtacctattt tccagaagaa ctgcgtagcg tcaaatatag c             1431
```

<210> SEQ ID NO 123
<211> LENGTH: 156
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SluCas9 tracr RNA

<400> SEQUENCE: 123

```
cttgtactta tacctaaaat tacagaatct actgaaacaa gacaatatgt cgtgtttatc     60
ccatcaattt attggtggga ttttttatg tttttagcaa aaagtaatac catactttat    120 attttaaat tataataaag atataaataa aggtgg                              156
```

<210> SEQ ID NO 124
<211> LENGTH: 3315
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SluCas9 codon optimized DNA

<400> SEQUENCE: 124

```
atgaaacgtc cggcagcaac caaaaaagca ggtcaggcca agaaaaaaaa aggtggtggt     60
tcaggtaacc agaaatttat cctgggtctg gatattggta ttaccagcgt tggttatggc    120
ctgattgatt acgaaaccaa aaacattatt gatgccggtg ttcgtctgtt tccggaagca    180
aatgttgaaa ataatgaagg tcgtcgtagc aaacgtggta gccgtcgtct gaaacgtcgt    240
cgtattcatc gtctggaacg tgttaaaaaa ctgctggaag attataacct gctggatcag    300
agccagattc gcagagcac caatccgtat gcaattcgtg ttaaaggtct gagcgaagca    360
ctgagcaaag atgaactggt tattgcactg ctgcatattg caaaacgccg tggcattcat    420
aaaatcgatg tgattgatag caatgacgat gtgggtaatg aactgagcac caaagaacag    480
ctgaacaaaa atagcaaact gctgaaagac aaattcgtgt gtcagattca gctgaaacgt    540
atgaatgaag ccaggttcg tggtgaaaag aatcgcttta aaaccgcaga tcatcatcaa    600
gaaattatcc agctgctgaa cgtgcagaaa aacttccatc agctggatga aaacttcatc    660
aacaaataca tcgagctggt tgaaatgcgt cgcgaatatt ttgaaggtcc gggtaaaggt    720
agcccgtatg ttgggaagg tgatccgaaa gcatggtatg aaaccctgat gggtcattgt    780
acctattttc cggatgaact gcgtagcgtt aaatatgcct atagcgcaga cctgttttaat    840 gcactgaatg atctgaataa cctggtgatt cagcgtgatg gtctgagcaa actggaatat    900
catgagaaat atcacatcat cgaaaacgtg ttcaaacaga gaagaaacc gaccctgaaa    960 caaatcgcca acgaaattaa tgtgaaccg aagatatta aggctaccg tattaccaaa    1020 agcggtaaac cgcagttcac cgaatttaaa ctgtatcacg atctgaaaag cgtgctgttt    1080
gatcagagca ttctggaaaa tgaagatgtg ctggaccaga ttgcagaaat tctgaccatt    1140
```

```
tatcaggaca aagacagcat caaaagcaaa ctgaccgaac tggatattct gctgaatgaa    1200
gaagataaag agaacattgc acagctgacc ggttataccg gcacccatcg tctgagcctg    1260
aaatgtattc gtctggtact ggaagaacag tggtatagca gccgtaatca gatggaaatc    1320
tttacccatc tgaacattaa accgaagaaa atcaatctga ccgcagccaa caaaattccg    1380
aaagccatga ttgatgagtt tattctgagt ccggttgtga aacgtacctt tggtcaggca    1440
attaacctga tcaacaaaat cattgaaaaa tatggcgtgc tgaggatat cattattgaa     1500 ctggcacgtg aaaacaacag caaagataaa cagaaattca tcaacgagat gcagaagaag    1560
aacgaaaata cccgcaaacg gattaacgag atcattggca aatatggtaa tcagaatgcc    1620
aaacgcctgg tggaaaaaat tcgtctgcat gatgaacaag agggcaaatg tctgtatagc    1680
ctggaaagca ttcctctgga agatctgctg aacaatccga atcattatga agtggatcac    1740
attattccgc gtagcgtgag ctttgataat tcctatcata taaagtgct ggtgaaacag     1800 agcgaaaact ccaaaaaatc caacctgaca ccgtatcagt atttcaatag cggcaaatcc    1860
aaactgagct acaaccagtt taaacagcat attctgaacc tgagcaaaag ccaggatcgc    1920
atcagcaaga agaagaagga gtacctgctg aagaacgcg acatcaacaa atttgaagtg     1980
cagaaagaat ttatcaaccg caacctggtt gatacccgtt atgcaacccg tgaactgacc    2040
aattatctga agcatatttt cagcgccaac aacatgaacg tgaaagtgaa acgattaac     2100 ggcagcttta ccgattatct gcgtaaagtg tggaaattca aaaaagaacg caaccacggc    2160
tataaacatc atgccgaaga tgccctgatt attgcaaatg cagatttcct gtttaaagaa    2220
aacaaaaaac tgaaagccgt caacagcgtg ctggaaaaac cggaaattga cacaaaacag    2280
ctggacattc aggttgatag cgaagataat tacagcgaaa tgtttatcat cccgaaacag    2340
gtgcaggata tcaagatt tcgcaacttc aaatatagcc accgcgttga caaaaaacct    2400
aatcgtcagc tgattaacga taccctgtat agcacccgca aaaagataa cagcacctat     2460 attgtgcaga ccattaaaga catctacgcc aaagataata ccaccctgaa aaacagttc     2520 gacaaaagcc cagaaaaatt tctgatgtat cagcatgatc cgcgtacctt cgaaaaactg    2580
gaagttatta tgaaacagta tgccaacgag aaaaatccgc tggccaaata tcacgaagaa    2640
accggtgaat atctgaccaa atattccaag aagaacaacg gtccgatcgt taaatccctg    2700
aaatatatcg gtaataaact gggcagccat ctggatgtta cccatcagtt taaaagctcc    2760
acaaagaagc tggttaaact gtccatcaaa ccgtatcgct ttgatgtgta tctgaccgac    2820
aaaggctata aattcattac catcagctat ctggacgtgc tgaaaaaaga caactattat    2880
tatatcccgg aacagaaata tgataaactg aaactgggta aagccatcga taaaaacgcc    2940
aaatttatcg ccagcttcta caaaaacgac ctgattaaac tggatggcga gatctataaa    3000
atcatcggtg ttaatagcga cacccgcaat atgattgagc tggatctgcc ggatattcgc    3060
tataaagaat attgcgaact gaacaacatt aaaggcgaac gcgtatcaa aaagaccatc     3120 ggcaaaaaag tgaatagcat cgagaaactg accaccgatg ttctgggtaa tgtgtttacc    3180
aatacccagt ataccaaacc tcagctgctg ttcaaacgcg gtaatggcgg aggatctggc    3240 cccccctaaga aaaagcggaa ggtgggtgga agcggaggca gcggggatc aggccatcat     3300 catcaccatc attaa                                                    3315
```

<210> SEQ ID NO 125
<211> LENGTH: 1056
<212> TYPE: PRT
<213> ORGANISM: Artificial sequence

```
<220> FEATURE:
<223> OTHER INFORMATION: Synthetic polypeptide
<220> FEATURE:
<221> NAME/KEY: misc_feature
<223> OTHER INFORMATION: SluCas9  polypeptide

<400> SEQUENCE: 125
```

| | | | | | | | | | | | | | | | |
|---|---|---|---|---|---|---|---|---|---|---|---|---|---|---|---|
| Met | Asn | Gln | Lys | Phe | Ile | Leu | Gly | Leu | Asp | Ile | Gly | Ile | Thr | Ser | Val |
| 1 | | | | 5 | | | | | 10 | | | | | 15 | |
| Gly | Tyr | Gly | Leu | Ile | Asp | Tyr | Glu | Thr | Lys | Asn | Ile | Ile | Asp | Ala | Gly |
| | | | 20 | | | | | 25 | | | | | 30 | | |
| Val | Arg | Leu | Phe | Pro | Glu | Ala | Asn | Val | Glu | Asn | Asn | Glu | Gly | Arg | Arg |
| | | 35 | | | | | 40 | | | | | 45 | | | |
| Ser | Lys | Arg | Gly | Ser | Arg | Arg | Leu | Lys | Arg | Arg | Arg | Ile | His | Arg | Leu |
| | 50 | | | | | 55 | | | | | 60 | | | | |
| Glu | Arg | Val | Lys | Lys | Leu | Leu | Glu | Asp | Tyr | Asn | Leu | Leu | Asp | Gln | Ser |
| 65 | | | | | 70 | | | | | 75 | | | | | 80 |
| Gln | Ile | Pro | Gln | Ser | Thr | Asn | Pro | Tyr | Ala | Ile | Arg | Val | Lys | Gly | Leu |
| | | | | 85 | | | | | 90 | | | | | 95 | |
| Ser | Glu | Ala | Leu | Ser | Lys | Asp | Glu | Leu | Val | Ile | Ala | Leu | Leu | His | Ile |
| | | | 100 | | | | | 105 | | | | | 110 | | |
| Ala | Lys | Arg | Arg | Gly | Ile | His | Lys | Ile | Asp | Val | Ile | Asp | Ser | Asn | Asp |
| | | 115 | | | | | 120 | | | | | 125 | | | |
| Asp | Val | Gly | Asn | Glu | Leu | Ser | Thr | Lys | Glu | Gln | Leu | Asn | Lys | Asn | Ser |
| | 130 | | | | | 135 | | | | | 140 | | | | |
| Lys | Leu | Leu | Lys | Asp | Lys | Phe | Val | Cys | Gln | Ile | Gln | Leu | Glu | Arg | Met |
| 145 | | | | | 150 | | | | | 155 | | | | | 160 |
| Asn | Glu | Gly | Gln | Val | Arg | Gly | Glu | Lys | Asn | Arg | Phe | Lys | Thr | Ala | Asp |
| | | | | 165 | | | | | 170 | | | | | 175 | |
| Ile | Ile | Lys | Glu | Ile | Ile | Gln | Leu | Leu | Asn | Val | Gln | Lys | Asn | Phe | His |
| | | | 180 | | | | | 185 | | | | | 190 | | |
| Gln | Leu | Asp | Glu | Asn | Phe | Ile | Asn | Lys | Tyr | Ile | Glu | Leu | Val | Glu | Met |
| | | 195 | | | | | 200 | | | | | 205 | | | |
| Arg | Arg | Glu | Tyr | Phe | Glu | Gly | Pro | Gly | Lys | Gly | Ser | Pro | Tyr | Gly | Trp |
| 210 | | | | | 215 | | | | | 220 | | | | | |
| Glu | Gly | Asp | Pro | Lys | Ala | Trp | Tyr | Glu | Thr | Leu | Met | Gly | His | Cys | Thr |
| 225 | | | | | 230 | | | | | 235 | | | | | 240 |
| Tyr | Phe | Pro | Asp | Glu | Leu | Arg | Ser | Val | Lys | Tyr | Ala | Tyr | Ser | Ala | Asp |
| | | | | 245 | | | | | 250 | | | | | 255 | |
| Leu | Phe | Asn | Ala | Leu | Asn | Asp | Leu | Asn | Asn | Leu | Val | Ile | Gln | Arg | Asp |
| | | | 260 | | | | | 265 | | | | | 270 | | |
| Gly | Leu | Ser | Lys | Leu | Glu | Tyr | His | Glu | Lys | Tyr | His | Ile | Ile | Glu | Asn |
| | | 275 | | | | | 280 | | | | | 285 | | | |
| Val | Phe | Lys | Gln | Lys | Lys | Lys | Pro | Thr | Leu | Lys | Gln | Ile | Ala | Asn | Glu |
| | 290 | | | | | 295 | | | | | 300 | | | | |
| Ile | Asn | Val | Asn | Pro | Glu | Asp | Ile | Lys | Gly | Tyr | Arg | Ile | Thr | Lys | Ser |
| 305 | | | | | 310 | | | | | 315 | | | | | 320 |
| Gly | Lys | Pro | Gln | Phe | Thr | Glu | Phe | Lys | Leu | Tyr | His | Asp | Leu | Lys | Ser |
| | | | | 325 | | | | | 330 | | | | | 335 | |
| Val | Leu | Phe | Asp | Gln | Ser | Ile | Leu | Glu | Asn | Glu | Asp | Val | Leu | Asp | Gln |
| | | | 340 | | | | | 345 | | | | | 350 | | |
| Ile | Ala | Glu | Ile | Leu | Thr | Ile | Tyr | Gln | Asp | Lys | Asp | Ser | Ile | Lys | Ser |
| | | 355 | | | | | 360 | | | | | 365 | | | |
| Lys | Leu | Thr | Glu | Leu | Asp | Ile | Leu | Leu | Asn | Glu | Glu | Asp | Lys | Glu | Asn |
| 370 | | | | | 375 | | | | | 380 | | | | | |

-continued

```
Ile Ala Gln Leu Thr Gly Tyr Thr Gly Thr His Arg Leu Ser Leu Lys
385                 390                 395                 400

Cys Ile Arg Leu Val Leu Glu Glu Gln Trp Tyr Ser Ser Arg Asn Gln
                405                 410                 415

Met Glu Ile Phe Thr His Leu Asn Ile Lys Pro Lys Lys Ile Asn Leu
            420                 425                 430

Thr Ala Ala Asn Lys Ile Pro Lys Ala Met Ile Asp Glu Phe Ile Leu
        435                 440                 445

Ser Pro Val Val Lys Arg Thr Phe Gly Gln Ala Ile Asn Leu Ile Asn
    450                 455                 460

Lys Ile Ile Glu Lys Tyr Gly Val Pro Glu Asp Ile Ile Glu Leu
465                 470                 475                 480

Ala Arg Glu Asn Asn Ser Lys Asp Lys Gln Lys Phe Ile Asn Glu Met
                485                 490                 495

Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
        515                 520                 525

His Asp Glu Gln Glu Gly Lys Cys Leu Tyr Ser Leu Glu Ser Ile Pro
530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
                565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
        595                 600                 605

His Ile Leu Asn Leu Ser Lys Ser Gln Asp Arg Ile Ser Lys Lys Lys
    610                 615                 620

Lys Glu Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
        675                 680                 685

Val Trp Lys Phe Lys Lys Glu Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
        755                 760                 765

Phe Lys Tyr Ser His Arg Val Asp Lys Lys Pro Asn Arg Gln Leu Ile
    770                 775                 780

Asn Asp Thr Leu Tyr Ser Thr Arg Lys Lys Asp Asn Ser Thr Tyr Ile
785                 790                 795                 800
```

-continued

```
Val Gln Thr Ile Lys Asp Ile Tyr Ala Lys Asp Asn Thr Leu Lys
            805                 810                 815

Lys Gln Phe Asp Lys Ser Pro Glu Lys Phe Leu Met Tyr Gln His Asp
            820                 825                 830

Pro Arg Thr Phe Glu Lys Leu Glu Val Ile Met Lys Gln Tyr Ala Asn
            835                 840                 845

Glu Lys Asn Pro Leu Ala Lys Tyr His Glu Glu Thr Gly Glu Tyr Leu
            850                 855                 860

Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
                    885                 890                 895

Lys Ser Ser Thr Lys Lys Leu Val Lys Leu Ser Ile Lys Pro Tyr Arg
                    900                 905                 910

Phe Asp Val Tyr Leu Thr Asp Lys Gly Tyr Lys Phe Ile Thr Ile Ser
                    915                 920                 925

Tyr Leu Asp Val Leu Lys Lys Asp Asn Tyr Tyr Ile Pro Glu Gln
            930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                    965                 970                 975

Ile Tyr Lys Ile Ile Gly Val Asn Ser Asp Thr Arg Asn Met Ile Glu
                    980                 985                 990

Leu Asp Leu Pro Asp Ile Arg Tyr  Lys Glu Tyr Cys Glu  Leu Asn Asn
            995                 1000                1005

Ile Lys  Gly Glu Pro Arg Ile  Lys Lys Thr Ile Gly  Lys Lys Val
    1010                1015                1020

Asn Ser  Ile Glu Lys Leu Thr  Thr Asp Val Leu Gly  Asn Val Phe
    1025                1030                1035

Thr Asn  Thr Gln Tyr Thr Lys  Pro Gln Leu Leu Phe  Lys Arg Gly
    1040                1045                1050

Asn Gly  Gly
    1055
```

```
<210> SEQ ID NO 126
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Residues 47-57 of HIV-1 TAT

<400> SEQUENCE: 126

Tyr Gly Arg Lys Lys Arg Arg Gln Arg Arg Arg
1               5                   10

<210> SEQ ID NO 127
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Penetratin

<400> SEQUENCE: 127
```

```
Arg Gln Ile Lys Ile Trp Phe Gln Asn Arg Arg Met Lys Trp Lys Lys
1               5                   10                  15
```

<210> SEQ ID NO 128
<211> LENGTH: 150
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA-Ex6

<400> SEQUENCE: 128

```
ggugaacgug gaugaaguug guuuuaguac ucuggaaaca gaaucuacug aaacaagaca   60
auaugucgug uuuaucccau caauuuauug gugggauuuu uuucuagcau aacccuugg   120 ggccucuaaa cgggucuuga ggguuuuuu                                    150
```

<210> SEQ ID NO 129
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-1-A

<400> SEQUENCE: 129

```
ggtgaacgtg gatgaagttg tggggtac                                     28
```

<210> SEQ ID NO 130
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-1-B

<400> SEQUENCE: 130

```
gcggtacccc acaacttcat ccacgttcac cgg                               33
```

<210> SEQ ID NO 131
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-2-A

<400> SEQUENCE: 131

```
agtgaacgtg gatgaagttg tggggtac                                     28
```

<210> SEQ ID NO 132
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-2-B

<400> SEQUENCE: 132
gcggtacccc acaacttcat ccacgttcac tgg                               33

<210> SEQ ID NO 133
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-3-A

<400> SEQUENCE: 133
cgtgaacgtg gatgaagttg tggggtac                                    28

<210> SEQ ID NO 134
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-3-B

<400> SEQUENCE: 134
gcggtacccc acaacttcat ccacgttcac ggg                               33

<210> SEQ ID NO 135
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-4-A

<400> SEQUENCE: 135
tgtgaacgtg gatgaagttg tggggtac                                    28

<210> SEQ ID NO 136
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-4-B

<400> SEQUENCE: 136
gcggtacccc acaacttcat ccacgttcac agg                               33

<210> SEQ ID NO 137
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-5-A

<400> SEQUENCE: 137
gatgaacgtg gatgaagttg tggggtac                                    28

<210> SEQ ID NO 138
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-5-B

<400> SEQUENCE: 138
gcggtacccc acaacttcat ccacgttcat cgg                33

<210> SEQ ID NO 139
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-6-A

<400> SEQUENCE: 139
gctgaacgtg gatgaagttg tggggtac                28

<210> SEQ ID NO 140
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-6-B

<400> SEQUENCE: 140
gcggtacccc acaacttcat ccacgttcag cgg                33

<210> SEQ ID NO 141
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-7-A

<400> SEQUENCE: 141
gttgaacgtg gatgaagttg tggggtac                28

<210> SEQ ID NO 142
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-7-B

<400> SEQUENCE: 142
gcggtacccc acaacttcat ccacgttcaa cgg                33

<210> SEQ ID NO 143
<211> LENGTH: 28
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-8-A

<400> SEQUENCE: 143
ggagaacgtg gatgaagttg tggggtac                                          28

<210> SEQ ID NO 144
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-8-B

<400> SEQUENCE: 144
gcggtacccc acaacttcat ccacgttctc cgg                                    33

<210> SEQ ID NO 145
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-9-A

<400> SEQUENCE: 145
ggcgaacgtg gatgaagttg tggggtac                                          28

<210> SEQ ID NO 146
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-9-B

<400> SEQUENCE: 146
gcggtacccc acaacttcat ccacgttcgc cgg                                    33

<210> SEQ ID NO 147
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-10-A

<400> SEQUENCE: 147
ggggaacgtg gatgaagttg tggggtac                                          28

<210> SEQ ID NO 148
<211> LENGTH: 33
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: R01-10-B

<400> SEQUENCE: 148
gcggtacccc acaacttcat ccacgttccc cgg                              33

<210> SEQ ID NO 149
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-11-A

<400> SEQUENCE: 149
ggtaaacgtg gatgaagttg tggggtac                                    28

<210> SEQ ID NO 150
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-11-B

<400> SEQUENCE: 150
gcggtacccc acaacttcat ccacgtttac cgg                              33

<210> SEQ ID NO 151
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-12-A

<400> SEQUENCE: 151
ggtcaacgtg gatgaagttg tggggtac                                    28

<210> SEQ ID NO 152
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-12-B

<400> SEQUENCE: 152
gcggtacccc acaacttcat ccacgttgac cgg                              33

<210> SEQ ID NO 153
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-13-A

<400> SEQUENCE: 153
```

```
ggttaacgtg gatgaagttg tggggtac                                     28
```

<210> SEQ ID NO 154
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-13-B

<400> SEQUENCE: 154

```
gcggtacccc acaacttcat ccacgttaac cgg                                33
```

<210> SEQ ID NO 155
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-14-A

<400> SEQUENCE: 155

```
ggtgcacgtg gatgaagttg tggggtac                                     28
```

<210> SEQ ID NO 156
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-14-B

<400> SEQUENCE: 156

```
gcggtacccc acaacttcat ccacgtgcac cgg                                33
```

<210> SEQ ID NO 157
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-15-A

<400> SEQUENCE: 157

```
ggtgtacgtg gatgaagttg tggggtac                                     28
```

<210> SEQ ID NO 158
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-15-B

<400> SEQUENCE: 158

```
gcggtacccc acaacttcat ccacgtacac cgg                                33
```

```
<210> SEQ ID NO 159
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-16-A

<400> SEQUENCE: 159
ggtggacgtg gatgaagttg tggggtac                                          28

<210> SEQ ID NO 160
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-16-B

<400> SEQUENCE: 160
gcggtacccc acaacttcat ccacgtccac cgg                                    33

<210> SEQ ID NO 161
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-17-A

<400> SEQUENCE: 161
ggtgaccgtg gatgaagttg tggggtac                                          28

<210> SEQ ID NO 162
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-17-B

<400> SEQUENCE: 162
gcggtacccc acaacttcat ccacggtcac cgg                                    33

<210> SEQ ID NO 163
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-18-A

<400> SEQUENCE: 163
ggtgatcgtg gatgaagttg tggggtac                                          28

<210> SEQ ID NO 164
<211> LENGTH: 33
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<223> OTHER INFORMATION: R01-18-B

<400> SEQUENCE: 164
gcggtacccc acaacttcat ccacgatcac cgg                                    33

<210> SEQ ID NO 165
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-19-A

<400> SEQUENCE: 165
ggtgagcgtg gatgaagttg tggggtac                                          28

<210> SEQ ID NO 166
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-19-B

<400> SEQUENCE: 166
gcggtacccc acaacttcat ccacgctcac cgg                                    33

<210> SEQ ID NO 167
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-20-A

<400> SEQUENCE: 167
ggtgaaagtg gatgaagttg tggggtac                                          28

<210> SEQ ID NO 168
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-20-B

<400> SEQUENCE: 168
gcggtacccc acaacttcat ccactttcac cgg                                    33

<210> SEQ ID NO 169
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

```
<223> OTHER INFORMATION: R01-21-A

<400> SEQUENCE: 169
ggtgaatgtg gatgaagttg tggggtac                                    28

<210> SEQ ID NO 170
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-21-B

<400> SEQUENCE: 170
gcggtacccc acaacttcat ccacattcac cgg                              33

<210> SEQ ID NO 171
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-22-A

<400> SEQUENCE: 171
ggtgaaggtg gatgaagttg tggggtac                                    28

<210> SEQ ID NO 172
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-22-B

<400> SEQUENCE: 172
gcggtacccc acaacttcat ccaccttcac cgg                              33

<210> SEQ ID NO 173
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-23-A

<400> SEQUENCE: 173
ggtgaacatg gatgaagttg tggggtac                                    28

<210> SEQ ID NO 174
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-23-B

<400> SEQUENCE: 174
```

-continued gcggtacccc acaacttcat ccatgttcac cgg          33

<210> SEQ ID NO 175
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-24-A

<400> SEQUENCE: 175
ggtgaacctg gatgaagttg tggggtac          28

<210> SEQ ID NO 176
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-24-B

<400> SEQUENCE: 176
gcggtacccc acaacttcat ccaggttcac cgg          33

<210> SEQ ID NO 177
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-25-A

<400> SEQUENCE: 177
ggtgaacttg gatgaagttg tggggtac          28

<210> SEQ ID NO 178
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-25-B

<400> SEQUENCE: 178
gcggtacccc acaacttcat ccaagttcac cgg          33

<210> SEQ ID NO 179
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-26-A

<400> SEQUENCE: 179
ggtgaacgag gatgaagttg tggggtac          28

<210> SEQ ID NO 180

```
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-26-B

<400> SEQUENCE: 180
gcggtacccc acaacttcat cctcgttcac cgg                                   33

<210> SEQ ID NO 181
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-27-A

<400> SEQUENCE: 181
ggtgaacgcg gatgaagttg tggggtac                                         28

<210> SEQ ID NO 182
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-27-B

<400> SEQUENCE: 182
gcggtacccc acaacttcat ccgcgttcac cgg                                   33

<210> SEQ ID NO 183
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-28-A

<400> SEQUENCE: 183
ggtgaacggg gatgaagttg tggggtac                                         28

<210> SEQ ID NO 184
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-28-B

<400> SEQUENCE: 184
gcggtacccc acaacttcat ccccgttcac cgg                                   33

<210> SEQ ID NO 185
<211> LENGTH: 28
<212> TYPE: DNA
<213> ORGANISM: Artificial sequence
<220> FEATURE:
```

```
<223> OTHER INFORMATION: Synthetic polynucleotide
<220> FEATURE:
<221> NAME/KEY: misc_feature
<223> OTHER INFORMATION: R01-29-A

<400> SEQUENCE: 185
ggtgaacgta gatgaagttg tggggtac                                              28

<210> SEQ ID NO 186
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-29-B

<400> SEQUENCE: 186
gcggtacccc acaacttcat ctacgttcac cgg                                        33

<210> SEQ ID NO 187
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-30-A

<400> SEQUENCE: 187
ggtgaacgtc gatgaagttg tggggtac                                              28

<210> SEQ ID NO 188
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-30-B

<400> SEQUENCE: 188
gcggtacccc acaacttcat cgacgttcac cgg                                        33

<210> SEQ ID NO 189
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-31-A

<400> SEQUENCE: 189
ggtgaacgtt gatgaagttg tggggtac                                              28

<210> SEQ ID NO 190
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-31-B
```

```
<400> SEQUENCE: 190
gcggtacccc acaacttcat caacgttcac cgg                                33

<210> SEQ ID NO 191
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-32-A

<400> SEQUENCE: 191
ggtgaacgtg aatgaagttg tggggtac                                      28

<210> SEQ ID NO 192
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-32-B

<400> SEQUENCE: 192
gcggtacccc acaacttcat tcacgttcac cgg                                33

<210> SEQ ID NO 193
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-33-A

<400> SEQUENCE: 193
ggtgaacgtg catgaagttg tggggtac                                      28

<210> SEQ ID NO 194
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-33-B

<400> SEQUENCE: 194
gcggtacccc acaacttcat gcacgttcac cgg                                33

<210> SEQ ID NO 195
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-34-A

<400> SEQUENCE: 195
ggtgaacgtg tatgaagttg tggggtac                                      28
```

<210> SEQ ID NO 196
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-34-B

<400> SEQUENCE: 196
gcggtacccc acaacttcat acacgttcac cgg                                33

<210> SEQ ID NO 197
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-35-A

<400> SEQUENCE: 197
ggtgaacgtg gctgaagttg tggggtac                                      28

<210> SEQ ID NO 198
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-35-B

<400> SEQUENCE: 198
gcggtacccc acaacttcag ccacgttcac cgg                                33

<210> SEQ ID NO 199
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-36-A

<400> SEQUENCE: 199
ggtgaacgtg gttgaagttg tggggtac                                      28

<210> SEQ ID NO 200
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-36-B

<400> SEQUENCE: 200
gcggtacccc acaacttcaa ccacgttcac cgg                                33

<210> SEQ ID NO 201
<211> LENGTH: 28

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-37-A

<400> SEQUENCE: 201
ggtgaacgtg ggtgaagttg tggggtac                                        28

<210> SEQ ID NO 202
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-37-B

<400> SEQUENCE: 202
gcggtacccc acaacttcac ccacgttcac cgg                                  33

<210> SEQ ID NO 203
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-38-A

<400> SEQUENCE: 203
ggtgaacgtg gaagaagttg tggggtac                                        28

<210> SEQ ID NO 204
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-38-B

<400> SEQUENCE: 204
gcggtacccc acaacttctt ccacgttcac cgg                                  33

<210> SEQ ID NO 205
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-39-A

<400> SEQUENCE: 205
ggtgaacgtg gacgaagttg tggggtac                                        28

<210> SEQ ID NO 206
<211> LENGTH: 33
<212> TYPE: DNA
<213> ORGANISM: Artificial sequence
<220> FEATURE:
<223> OTHER INFORMATION: Synthetic polynucleotide
```

```
<220> FEATURE:
<221> NAME/KEY: misc_feature
<223> OTHER INFORMATION: R01-39-B

<400> SEQUENCE: 206
gcggtacccc acaacttcgt ccacgttcac cgg                              33

<210> SEQ ID NO 207
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-40-A

<400> SEQUENCE: 207
ggtgaacgtg gaggaagttg tggggtac                                    28

<210> SEQ ID NO 208
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-40-B

<400> SEQUENCE: 208
gcggtacccc acaacttcct ccacgttcac cgg                              33

<210> SEQ ID NO 209
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-41-A

<400> SEQUENCE: 209
ggtgaacgtg gataaagttg tggggtac                                    28

<210> SEQ ID NO 210
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-41-B

<400> SEQUENCE: 210
gcggtacccc acaactttat ccacgttcac cgg                              33

<210> SEQ ID NO 211
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-42-A
```

```
<400> SEQUENCE: 211
ggtgaacgtg gatcaagttg tggggtac                                              28

<210> SEQ ID NO 212
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-42-B

<400> SEQUENCE: 212
gcggtacccc acaacttgat ccacgttcac cgg                                        33

<210> SEQ ID NO 213
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-43-A

<400> SEQUENCE: 213
ggtgaacgtg gattaagttg tggggtac                                              28

<210> SEQ ID NO 214
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-43-B

<400> SEQUENCE: 214
gcggtacccc acaacttaat ccacgttcac cgg                                        33

<210> SEQ ID NO 215
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-44-A

<400> SEQUENCE: 215
ggtgaacgtg gatgcagttg tggggtac                                              28

<210> SEQ ID NO 216
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-44-B

<400> SEQUENCE: 216
gcggtacccc acaactgcat ccacgttcac cgg                                        33
```

<210> SEQ ID NO 217
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-45-A

<400> SEQUENCE: 217
ggtgaacgtg gatgtagttg tggggtac                                      28

<210> SEQ ID NO 218
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-45-B

<400> SEQUENCE: 218
gcggtacccc acaactacat ccacgttcac cgg                                33

<210> SEQ ID NO 219
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-46-A

<400> SEQUENCE: 219
ggtgaacgtg gatggagttg tggggtac                                      28

<210> SEQ ID NO 220
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-46-B

<400> SEQUENCE: 220
gcggtacccc acaactccat ccacgttcac cgg                                33

<210> SEQ ID NO 221
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-47-A

<400> SEQUENCE: 221
ggtgaacgtg gatgacgttg tggggtac                                      28

<210> SEQ ID NO 222
<211> LENGTH: 33
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-47-B

<400> SEQUENCE: 222
gcggtacccc acaacgtcat ccacgttcac cgg                                    33

<210> SEQ ID NO 223
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-48-A

<400> SEQUENCE: 223
ggtgaacgtg gatgatgttg tggggtac                                          28

<210> SEQ ID NO 224
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-48-B

<400> SEQUENCE: 224
gcggtacccc acaacatcat ccacgttcac cgg                                    33

<210> SEQ ID NO 225
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-49-A

<400> SEQUENCE: 225
ggtgaacgtg gatgaggttg tggggtac                                          28

<210> SEQ ID NO 226
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-49-B

<400> SEQUENCE: 226
gcggtacccc acaacctcat ccacgttcac cgg                                    33

<210> SEQ ID NO 227
<211> LENGTH: 27
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: R01-50-A

<400> SEQUENCE: 227
ggtgaacgtg gatgaaattg tggggta                                    27

<210> SEQ ID NO 228
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-50-B

<400> SEQUENCE: 228
gcggtacccc acaatttcat ccacgttcac cgg                             33

<210> SEQ ID NO 229
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-51-A

<400> SEQUENCE: 229
ggtgaacgtg gatgaacttg tggggtac                                   28

<210> SEQ ID NO 230
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-51-B

<400> SEQUENCE: 230
gcggtacccc acaagttcat ccacgttcac cgg                             33

<210> SEQ ID NO 231
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-52-A

<400> SEQUENCE: 231
ggtgaacgtg gatgaatttg tggggtac                                   28

<210> SEQ ID NO 232
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-52-B

<400> SEQUENCE: 232
```

```
gcggtacccc acaaattcat ccacgttcac cgg                                     33

<210> SEQ ID NO 233
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-53-A

<400> SEQUENCE: 233
ggtgaacgtg gatgaagatg tggggtac                                           28

<210> SEQ ID NO 234
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-53-B

<400> SEQUENCE: 234
gcggtacccc acatcttcat ccacgttcac cgg                                     33

<210> SEQ ID NO 235
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-54-A

<400> SEQUENCE: 235
ggtgaacgtg gatgaagctg tggggtac                                           28

<210> SEQ ID NO 236
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-54-B

<400> SEQUENCE: 236
gcggtacccc acagcttcat ccacgttcac cgg                                     33

<210> SEQ ID NO 237
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-55-A

<400> SEQUENCE: 237
ggtgaacgtg gatgaaggtg tggggtac                                           28
```

```
<210> SEQ ID NO 238
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-55-B

<400> SEQUENCE: 238
gcggtacccc acaccttcat ccacgttcac cgg                                     33

<210> SEQ ID NO 239
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-56-A

<400> SEQUENCE: 239
ggtgaacgtg gatgaagtag tggggtac                                           28

<210> SEQ ID NO 240
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-56-B

<400> SEQUENCE: 240
gcggtacccc actacttcat ccacgttcac cgg                                     33

<210> SEQ ID NO 241
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-57-A

<400> SEQUENCE: 241
ggtgaacgtg gatgaagtcg tggggtac                                           28

<210> SEQ ID NO 242
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-57-B

<400> SEQUENCE: 242
gcggtacccc acgacttcat ccacgttcac cgg                                     33

<210> SEQ ID NO 243
<211> LENGTH: 28
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<223> OTHER INFORMATION: R01-58-A

<400> SEQUENCE: 243
ggtgaacgtg gatgaagtgg tggggtac                                    28

<210> SEQ ID NO 244
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-58-B

<400> SEQUENCE: 244
gcggtacccc accacttcat ccacgttcac cgg                              33

<210> SEQ ID NO 245
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-59-A

<400> SEQUENCE: 245
ggtgaacgtg gatgaagtta tggggtac                                    28

<210> SEQ ID NO 246
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-59-B

<400> SEQUENCE: 246
gcggtacccc ataacttcat ccacgttcac cgg                              33

<210> SEQ ID NO 247
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-60-A

<400> SEQUENCE: 247
ggtgaacgtg gatgaagttc tggggtac                                    28

<210> SEQ ID NO 248
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

```
<223> OTHER INFORMATION: R01-60-B

<400> SEQUENCE: 248
gcggtacccc agaacttcat ccacgttcac cgg                                   33

<210> SEQ ID NO 249
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-61-A

<400> SEQUENCE: 249
ggtgaacgtg gatgaagttt tggggtac                                        28

<210> SEQ ID NO 250
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R01-61-B

<400> SEQUENCE: 250
gcggtacccc aaaacttcat ccacgttcac cgg                                   33

<210> SEQ ID NO 251
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 1 target sequence

<400> SEQUENCE: 251
ggagtccgag cagaagaaga a                                               21

<210> SEQ ID NO 252
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 2 target sequence

<400> SEQUENCE: 252
ggacatcgat gtcctcccca t                                               21

<210> SEQ ID NO 253
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 3 target sequence

<400> SEQUENCE: 253
```
ggtcacctcc aatgactagg g                                        21

<210> SEQ ID NO 254
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 4 target sequence

<400> SEQUENCE: 254
ggctccccat tggcctgctt cg                                       22

<210> SEQ ID NO 255
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 5 target sequence

<400> SEQUENCE: 255
ggtgcgccac cggttgatgt ga                                       22

<210> SEQ ID NO 256
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 6 target sequence

<400> SEQUENCE: 256
ggcgccaccg gttgatgtga t                                        21

<210> SEQ ID NO 257
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 7 target sequence

<400> SEQUENCE: 257
ggccgtttgt actttgtcct c                                        21

<210> SEQ ID NO 258
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 8 target sequence

<400> SEQUENCE: 258
ggcacagatg agaaactcag g                                        21

<210> SEQ ID NO 259

```
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 9 target sequence

<400> SEQUENCE: 259
ggattgggtg ttcagggcag ag                                          22

<210> SEQ ID NO 260
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 10 target sequence

<400> SEQUENCE: 260
ggtggcgaga ggggccgaga t                                           21

<210> SEQ ID NO 261
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 11 target sequence

<400> SEQUENCE: 261
ggggccgaga ttgggtgttc                                             20

<210> SEQ ID NO 262
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 12 target sequence

<400> SEQUENCE: 262
ggtgccatta gctaaatgca t                                           21

<210> SEQ ID NO 263
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 13 target sequence

<400> SEQUENCE: 263
ggtaccaccc acaggtgcca g                                           21

<210> SEQ ID NO 264
<211> LENGTH: 21
<212> TYPE: DNA
<213> ORGANISM: Artificial sequence
<220> FEATURE:
```

```
<223> OTHER INFORMATION: Synthetic polynucleotide
<220> FEATURE:
<221> NAME/KEY: misc_feature
<223> OTHER INFORMATION: sgRNA 14 target sequence

<400> SEQUENCE: 264
ggaaagcctc tgggccagga a                                              21

<210> SEQ ID NO 265
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 15 target sequence

<400> SEQUENCE: 265
ggacacccac ggagagcgct gt                                             22

<210> SEQ ID NO 266
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 16 target sequence

<400> SEQUENCE: 266
ggtccagttg gtgacaaata c                                              21

<210> SEQ ID NO 267
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 17 target sequence

<400> SEQUENCE: 267
ggttttaaca cttccctagc ca                                             22

<210> SEQ ID NO 268
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 18 target sequence

<400> SEQUENCE: 268
ggcttaatta gctcctttgg ct                                             22

<210> SEQ ID NO 269
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 19 target sequence
```

-continued

<400> SEQUENCE: 269
ggcttaatta gctcctttgg c                                              21

<210> SEQ ID NO 270
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 20 target sequence

<400> SEQUENCE: 270
ggtgcatatg atgatagtat ta                                             22

<210> SEQ ID NO 271
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 21 target sequence

<400> SEQUENCE: 271
ggaatgtatg ctggctttta ag                                             22

<210> SEQ ID NO 272
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 22 target sequence

<400> SEQUENCE: 272
ggaaatgtat gctggctttt aa                                             22

<210> SEQ ID NO 273
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 23 target sequence

<400> SEQUENCE: 273
ggaaaatgta tgctggcttt ta                                             22

<210> SEQ ID NO 274
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 24 target sequence

<400> SEQUENCE: 274
ggtaaaatgt atgctggctt tt                                             22

```
<210> SEQ ID NO 275
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 25 target sequence

<400> SEQUENCE: 275
ggcttaaaga tgatctctta cc                                                 22

<210> SEQ ID NO 276
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 26 target sequence

<400> SEQUENCE: 276
ggttaaagat gatctcttac ct                                                 22

<210> SEQ ID NO 277
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 27 target sequence

<400> SEQUENCE: 277
ggtaataaaa ttcaaacatc ct                                                 22

<210> SEQ ID NO 278
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 28 target sequence

<400> SEQUENCE: 278
ggtaaagcat agtgcaatgg at                                                 22

<210> SEQ ID NO 279
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 29 target sequence

<400> SEQUENCE: 279
ggttaaataa agcatagtgc aa                                                 22

<210> SEQ ID NO 280
<211> LENGTH: 22
```

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 30 target sequence

<400> SEQUENCE: 280
ggatttatga gatcaacagc ac                                              22

<210> SEQ ID NO 281
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 31 target sequence

<400> SEQUENCE: 281
ggcccatgct ctgaccgctc ga                                              22

<210> SEQ ID NO 282
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 32 target sequence

<400> SEQUENCE: 282
ggccatcgag cggtcagagc at                                              22

<210> SEQ ID NO 283
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 33 target sequence

<400> SEQUENCE: 283
gggcaaaagc tcatgtgata                                                 20

<210> SEQ ID NO 284
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 34 target sequence

<400> SEQUENCE: 284
ggactgaggc ttatgttcca tg                                              22

<210> SEQ ID NO 285
<211> LENGTH: 21
<212> TYPE: DNA
<213> ORGANISM: Artificial sequence
<220> FEATURE:
<223> OTHER INFORMATION: Synthetic polynucleotide
```

-continued

```
<220> FEATURE:
<221> NAME/KEY: misc_feature
<223> OTHER INFORMATION: sgRNA 35 target sequence

<400> SEQUENCE: 285
ggagagtgta caaactcaca a                                            21

<210> SEQ ID NO 286
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 36 target sequence

<400> SEQUENCE: 286
ggactagcat tataatgcac ca                                           22

<210> SEQ ID NO 287
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 37 target sequence

<400> SEQUENCE: 287
ggtcagaaga gattagttag ta                                           22

<210> SEQ ID NO 288
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 38 target sequence

<400> SEQUENCE: 288
ggtgagagtg ccatctcttc ct                                           22

<210> SEQ ID NO 289
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 39 target sequence

<400> SEQUENCE: 289
ggtggaccac atggctttgc tc                                           22

<210> SEQ ID NO 290
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 40 target sequence
```

```
<400> SEQUENCE: 290
ggtgagcaaa gccatgtggt cc                                      22

<210> SEQ ID NO 291
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 41 target sequence

<400> SEQUENCE: 291
ggattaatga catacgcatt t                                       21

<210> SEQ ID NO 292
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 42 target sequence

<400> SEQUENCE: 292
ggagattaat gacatacgca tt                                      22

<210> SEQ ID NO 293
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 43 target sequence

<400> SEQUENCE: 293
ggttcaatcc tcttgtcacc tg                                      22

<210> SEQ ID NO 294
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 44 target sequence

<400> SEQUENCE: 294
ggacatctct atgtcggcca c                                       21

<210> SEQ ID NO 295
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 45 target sequence

<400> SEQUENCE: 295
ggaaaaccta ccgcaagttg cc                                      22
```

```
<210> SEQ ID NO 296
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 46 target sequence

<400> SEQUENCE: 296
ggtggactac atagttgtgt ga                                              22

<210> SEQ ID NO 297
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 47 target sequence

<400> SEQUENCE: 297
ggctgccaga ctctctgaac cc                                              22

<210> SEQ ID NO 298
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 48 target sequence

<400> SEQUENCE: 298
ggatccctcg tataacaata                                                 20

<210> SEQ ID NO 299
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 49 target sequence

<400> SEQUENCE: 299
ggtatcgcat agtgcaaaga at                                              22

<210> SEQ ID NO 300
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 50 target sequence

<400> SEQUENCE: 300
ggctcggtcc tctcgtcacc tg                                              22

<210> SEQ ID NO 301
<211> LENGTH: 22
<212> TYPE: DNA
```

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 51 target sequence

<400> SEQUENCE: 301
ggacgctccc ggagagcgct gg                                              22

<210> SEQ ID NO 302
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 52 target sequence

<400> SEQUENCE: 302
ggccatggcg cggtcagagg gt                                              22

<210> SEQ ID NO 303
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 53 target sequence

<400> SEQUENCE: 303
ggctcggctc caatgacgag gg                                              22

<210> SEQ ID NO 304
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 54 target sequence

<400> SEQUENCE: 304
ggcacttcga tgacctcccc gt                                              22

<210> SEQ ID NO 305
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 55 target sequence

<400> SEQUENCE: 305
ggagtgggtg ttcaggaccg cg                                              22

<210> SEQ ID NO 306
<211> LENGTH: 22
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: sgRNA 56 target sequence

<400> SEQUENCE: 306
ggctgctacc cacaggtgca ag                                              22

<210> SEQ ID NO 307
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 57 target sequence

<400> SEQUENCE: 307
ggaagatgta tcctggaatt ta                                              22

<210> SEQ ID NO 308
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 58 target sequence

<400> SEQUENCE: 308
ggttttatca ctacccaaga ca                                              22

<210> SEQ ID NO 309
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 59 target sequence

<400> SEQUENCE: 309
ggcggccagg ctccctgaaa cc                                              22

<210> SEQ ID NO 310
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 60 target sequence

<400> SEQUENCE: 310
ggactggtat tataatacaa ca                                              22

<210> SEQ ID NO 311
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 61 target sequence

<400> SEQUENCE: 311
```
ggtgagagtg acatttcgta ct                                              22

<210> SEQ ID NO 312
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 62 target sequence

<400> SEQUENCE: 312
ggtgcgcccc cgggtgaggt gc                                              22

<210> SEQ ID NO 313
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 63 target sequence

<400> SEQUENCE: 313
ggcagtttga gcagaaaaag aa                                              22

<210> SEQ ID NO 314
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 64 target sequence

<400> SEQUENCE: 314
ggtctgtaga gataagtgag ta                                              22

<210> SEQ ID NO 315
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 65 target sequence

<400> SEQUENCE: 315
ggaagtgtgt acaaactcaa ga                                              22

<210> SEQ ID NO 316
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 66 target sequence

<400> SEQUENCE: 316
ggtatcatgg atgctgactt tt                                              22

```
<210> SEQ ID NO 317
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 67 target sequence

<400> SEQUENCE: 317
ggctttacta gcccctgtgg c                                              21

<210> SEQ ID NO 318
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 68 target sequence

<400> SEQUENCE: 318
ggcacggagg agaaaagcag g                                              21

<210> SEQ ID NO 319
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 69 target sequence

<400> SEQUENCE: 319
ggatttgtga gatctaaaga ac                                             22

<210> SEQ ID NO 320
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 70 target sequence

<400> SEQUENCE: 320
ggcgttgatg acattcgcat tt                                             22

<210> SEQ ID NO 321
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 71 target sequence

<400> SEQUENCE: 321
ggcttataga tcatctaata cc                                             22

<210> SEQ ID NO 322
<211> LENGTH: 22
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<223> OTHER INFORMATION: sgRNA 72 target sequence

<400> SEQUENCE: 322
ggtggcctcc atagttgggt gg                                              22

<210> SEQ ID NO 323
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 73 target sequence

<400> SEQUENCE: 323
ggtactagag ttcaaacata ct                                              22

<210> SEQ ID NO 324
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 74 target sequence

<400> SEQUENCE: 324
ggcccctgct ctgagcactc gg                                              22

<210> SEQ ID NO 325
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 75 target sequence

<400> SEQUENCE: 325
ggaggaccac atggcctgcc tc                                              22

<210> SEQ ID NO 326
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 76 target sequence

<400> SEQUENCE: 326
ggaacagctg ccgcaaattg cc                                              22

<210> SEQ ID NO 327
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

```
<223> OTHER INFORMATION: sgRNA 77 target sequence

<400> SEQUENCE: 327
ggctccgtat tggctggctt cg                                        22

<210> SEQ ID NO 328
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 78 target sequence

<400> SEQUENCE: 328
ggccagccga tgacaaatac                                           20

<210> SEQ ID NO 329
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 79 target sequence

<400> SEQUENCE: 329
ggacgtctct acgtcggcgg c                                         21

<210> SEQ ID NO 330
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 80 target sequence

<400> SEQUENCE: 330
ggccggcgcg aggggccgag ag                                        22

<210> SEQ ID NO 331
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 81 target sequence

<400> SEQUENCE: 331
ggactgtttg tacttttca tc                                         22

<210> SEQ ID NO 332
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 82 target sequence

<400> SEQUENCE: 332
```
ggtgcttatg atgatgacat ta                                                22

<210> SEQ ID NO 333
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 83 target sequence

<400> SEQUENCE: 333
ggccgcgtcc gattgatgtg at                                                22

<210> SEQ ID NO 334
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 84 target sequence

<400> SEQUENCE: 334
ggctttatga gcaccttagg ct                                                22

<210> SEQ ID NO 335
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 85 target sequence

<400> SEQUENCE: 335
ggatccctcc tatgaccatg                                                   20

<210> SEQ ID NO 336
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 86 target sequence

<400> SEQUENCE: 336
ggataaaggt gacctcttac gt                                                22

<210> SEQ ID NO 337
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 87 target sequence

<400> SEQUENCE: 337
ggactgtggc ttagggtcca gg                                                22

<210> SEQ ID NO 338

```
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 88 target sequence

<400> SEQUENCE: 338
ggtgaggaaa cccaggcggt cc                                                  22

<210> SEQ ID NO 339
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 89 target sequence

<400> SEQUENCE: 339
ggaaatgtat acaggcaatt aa                                                  22

<210> SEQ ID NO 340
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 90 target sequence

<400> SEQUENCE: 340
ggttgaatca agcatagtcc ga                                                  22

<210> SEQ ID NO 341
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 91 target sequence

<400> SEQUENCE: 341
gggctacggc tcatgagata                                                     20

<210> SEQ ID NO 342
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 92 target sequence

<400> SEQUENCE: 342
ggcgggccgc gattggcagt tc                                                  22

<210> SEQ ID NO 343
<211> LENGTH: 22
<212> TYPE: DNA
<213> ORGANISM: Artificial sequence
<220> FEATURE:
```

```
<223> OTHER INFORMATION: Synthetic polynucleotide
<220> FEATURE:
<221> NAME/KEY: misc_feature
<223> OTHER INFORMATION: sgRNA 93 target sequence

<400> SEQUENCE: 343
ggctgcgatt atctaaatcc at                                                  22

<210> SEQ ID NO 344
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 94 target sequence

<400> SEQUENCE: 344
ggagcttgat tacatacgca tg                                                  22

<210> SEQ ID NO 345
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 95 target sequence

<400> SEQUENCE: 345
ggaatgtttg ctggcctcta gg                                                  22

<210> SEQ ID NO 346
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA 96 target sequence

<400> SEQUENCE: 346
ggaaagcctc tgcgccgggg g                                                   21

<210> SEQ ID NO 347
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-1-A

<400> SEQUENCE: 347
cctgagtccg agcagaagaa gaatggggta c                                        31

<210> SEQ ID NO 348
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-1-B
```

<400> SEQUENCE: 348
gcggtacccc attcttcttc tgctcggact cagggg         36

<210> SEQ ID NO 349
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-2-A

<400> SEQUENCE: 349
ggtgacatcg atgtcctccc cattggggta c         31

<210> SEQ ID NO 350
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-2-B

<400> SEQUENCE: 350
gcggtacccc aatggggagg acatcgatgt caccgg         36

<210> SEQ ID NO 351
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-3-A

<400> SEQUENCE: 351
gatgtcacct ccaatgacta gggtggggta c         31

<210> SEQ ID NO 352
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-3-B

<400> SEQUENCE: 352
gcggtacccc accctagtca ttggaggtga catcgg         36

<210> SEQ ID NO 353
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-4-A

<400> SEQUENCE: 353
gtcctcccca ttggcctgct tcgtggggta c         31

<210> SEQ ID NO 354
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-4-B

<400> SEQUENCE: 354
gcggtacccc acgaagcagg ccaatgggga ggacgg                                36

<210> SEQ ID NO 355
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-5-A

<400> SEQUENCE: 355
caatgcgcca ccggttgatg tgatggggta c                                     31

<210> SEQ ID NO 356
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-5-B

<400> SEQUENCE: 356
gcggtacccc atcacatcaa ccggtggcgc attggg                                36

<210> SEQ ID NO 357
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-6-A

<400> SEQUENCE: 357
aatgcgccac cggttgatgt gattggggta c                                     31

<210> SEQ ID NO 358
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-6-B

<400> SEQUENCE: 358
gcggtacccc aatcacatca accggtggcg cattgg                                36

<210> SEQ ID NO 359
<211> LENGTH: 31

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-7-A

<400> SEQUENCE: 359
tctgccgttt gtactttgtc ctctggggta c                                    31

<210> SEQ ID NO 360
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-7-B

<400> SEQUENCE: 360
gcggtacccc agaggacaaa gtacaaacgg cagagg                               36

<210> SEQ ID NO 361
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-8-A

<400> SEQUENCE: 361
ggggcacaga tgagaaactc aggtggggta c                                    31

<210> SEQ ID NO 362
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-8-B

<400> SEQUENCE: 362
gcggtacccc acctgagttt ctcatctgtg ccccgg                               36

<210> SEQ ID NO 363
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-9-A

<400> SEQUENCE: 363
gagattgggt gttcagggca gagtggggta c                                    31

<210> SEQ ID NO 364
<211> LENGTH: 36
<212> TYPE: DNA
<213> ORGANISM: Artificial sequence
<220> FEATURE:
<223> OTHER INFORMATION: Synthetic polynucleotide
```

```
<220> FEATURE:
<221> NAME/KEY: misc_feature
<223> OTHER INFORMATION: Ext-A-P-9-B

<400> SEQUENCE: 364
gcggtacccc actctgccct gaacacccaa tctcgg                               36

<210> SEQ ID NO 365
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-10-A

<400> SEQUENCE: 365
agggtggcga gaggggccga gattggggta c                                    31

<210> SEQ ID NO 366
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-10-B

<400> SEQUENCE: 366
gcggtacccc aatctcggcc cctctcgcca ccctgg                               36

<210> SEQ ID NO 367
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-11-A

<400> SEQUENCE: 367
agaggggccg agattgggtg ttctggggta c                                    31

<210> SEQ ID NO 368
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-11-B

<400> SEQUENCE: 368
gcggtacccc agaacaccca atctcggccc ctctgg                               36

<210> SEQ ID NO 369
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-12-A
```

```
<400> SEQUENCE: 369
tgagtgccat tagctaaatg cattggggta c                              31

<210> SEQ ID NO 370
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-12-B

<400> SEQUENCE: 370
gcggtacccc aatgcattta gctaatggca ctcagg                         36

<210> SEQ ID NO 371
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-13-A

<400> SEQUENCE: 371
agggtaccac ccacaggtgc cagtggggta c                              31

<210> SEQ ID NO 372
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-13-B

<400> SEQUENCE: 372
gcggtacccc actggcacct gtgggtggta ccctgg                         36

<210> SEQ ID NO 373
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-14-A

<400> SEQUENCE: 373
tgggaaagcc tctgggccag gaatggggta c                              31

<210> SEQ ID NO 374
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-14-B

<400> SEQUENCE: 374
gcggtacccc attcctggcc cagaggcttt cccagg                         36
```

```
<210> SEQ ID NO 375
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-27-A

<400> SEQUENCE: 375
aggacaccca cggagagcgc tgttggggta c                                    31

<210> SEQ ID NO 376
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-27-B

<400> SEQUENCE: 376
gcggtacccc aacagcgctc tccgtgggtg tcctgg                               36

<210> SEQ ID NO 377
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-28-A

<400> SEQUENCE: 377
agggtccagt tggtgacaaa tactggggta c                                    31

<210> SEQ ID NO 378
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-28-B

<400> SEQUENCE: 378
gcggtacccc agtatttgtc accaactgga ccctgg                               36

<210> SEQ ID NO 379
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-29-A

<400> SEQUENCE: 379
aggttttaac acttccctag ccatggggta c                                    31

<210> SEQ ID NO 380
<211> LENGTH: 36
<212> TYPE: DNA
```

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-29-B

<400> SEQUENCE: 380
gcggtacccc atggctaggg aagtgttaaa acctgg                                36

<210> SEQ ID NO 381
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-30-A

<400> SEQUENCE: 381
aggcttaatt agctcctttg cttggggta c                                     31

<210> SEQ ID NO 382
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-30-B

<400> SEQUENCE: 382
gcggtacccc aagccaaagg agctaattaa gcctgg                               36

<210> SEQ ID NO 383
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-31-A

<400> SEQUENCE: 383
agggcttaat tagctccttt ggctggggta c                                    31

<210> SEQ ID NO 384
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-31-B

<400> SEQUENCE: 384
gcggtacccc agccaaagga gctaattaag ccctgg                               36

<210> SEQ ID NO 385
<211> LENGTH: 31
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: Ext-A-P-32-A

<400> SEQUENCE: 385
aggtgcatat gatgatagta ttatggggta c                                    31

<210> SEQ ID NO 386
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-32-B

<400> SEQUENCE: 386
gcggtacccc ataatactat catcatatgc acctgg                               36

<210> SEQ ID NO 387
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-33-A

<400> SEQUENCE: 387
aggaatgtat gctggctttt aagtggggta c                                    31

<210> SEQ ID NO 388
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-33-B

<400> SEQUENCE: 388
gcggtacccc acttaaaagc cagcatacat tcctgg                               36

<210> SEQ ID NO 389
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-34-A

<400> SEQUENCE: 389
aggaaatgta tgctggcttt taatggggta c                                    31

<210> SEQ ID NO 390
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-34-B

<400> SEQUENCE: 390
```

```
gcggtacccc attaaaagcc agcatacatt tcctgg                                  36

<210> SEQ ID NO 391
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-35-A

<400> SEQUENCE: 391
aggaaaatgt atgctggctt ttatggggta c                                       31

<210> SEQ ID NO 392
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-35-B

<400> SEQUENCE: 392
gcggtacccc ataaaagcca gcatacattt tcctgg                                  36

<210> SEQ ID NO 393
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-36-A

<400> SEQUENCE: 393
aggtaaaatg tatgctggct ttttggggta c                                       31

<210> SEQ ID NO 394
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-36-B

<400> SEQUENCE: 394
gcggtacccc aaaaagccag catacatttt acctgg                                  36

<210> SEQ ID NO 395
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-37-A

<400> SEQUENCE: 395
aggcttaaag atgatctctt acctggggta c                                       31
```

<210> SEQ ID NO 396
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-37-B

<400> SEQUENCE: 396
gcggtacccc aggtaagaga tcatctttaa gcctgg                                36

<210> SEQ ID NO 397
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-38-A

<400> SEQUENCE: 397
aggttaaaga tgatctctta ccttggggta c                                     31

<210> SEQ ID NO 398
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-38-B

<400> SEQUENCE: 398
gcggtacccc aaggtaagag atcatcttta acctgg                                36

<210> SEQ ID NO 399
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-39-A

<400> SEQUENCE: 399
aggtaataaa attcaaacat ccttggggta c                                     31

<210> SEQ ID NO 400
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-39-B

<400> SEQUENCE: 400
gcggtacccc aaggatgttt gaattttatt acctgg                                36

<210> SEQ ID NO 401
<211> LENGTH: 31
<212> TYPE: DNA
<213> ORGANISM: Artificial sequence

```
<220> FEATURE:
<223> OTHER INFORMATION: Synthetic polynucleotide
<220> FEATURE:
<221> NAME/KEY: misc_feature
<223> OTHER INFORMATION: Ext-A-P-40-A

<400> SEQUENCE: 401
aggtaaagca tagtgcaatg gattggggta c                              31

<210> SEQ ID NO 402
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-40-B

<400> SEQUENCE: 402
gcggtacccc aatccattgc actatgcttt acctgg                         36

<210> SEQ ID NO 403
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-41-A

<400> SEQUENCE: 403
aggttaaata aagcatagtg caatgggta c                               31

<210> SEQ ID NO 404
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-41-B

<400> SEQUENCE: 404
gcggtacccc attgcactat gctttattta acctgg                         36

<210> SEQ ID NO 405
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-42-A

<400> SEQUENCE: 405
aggatttatg agatcaacag cactggggta c                              31

<210> SEQ ID NO 406
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

<223> OTHER INFORMATION: Ext-A-P-42-B

<400> SEQUENCE: 406
gcggtacccc agtgctgttg atctcataaa tcctgg                    36

<210> SEQ ID NO 407
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-43-A

<400> SEQUENCE: 407
aggcccatgc tctgaccgct cgatggggta c                         31

<210> SEQ ID NO 408
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-43-B

<400> SEQUENCE: 408
gcggtacccc atcgagcggt cagagcatgg gcctgg                    36

<210> SEQ ID NO 409
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-44-A

<400> SEQUENCE: 409
aggccatcga gcggtcagag cattggggta c                         31

<210> SEQ ID NO 410
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-44-B

<400> SEQUENCE: 410
gcggtacccc aatgctctga ccgctcgatg gcctgg                    36

<210> SEQ ID NO 411
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-45-A

<400> SEQUENCE: 411 aggggggcaaa agctcatgtg atatggggta c                                    31

<210> SEQ ID NO 412
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-45-B

<400> SEQUENCE: 412
gcggtacccc atatcacatg agcttttgcc ccctgg                                36

<210> SEQ ID NO 413
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-46-A

<400> SEQUENCE: 413
aggactgagg cttatgttcc atgtggggta c                                     31

<210> SEQ ID NO 414
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-46-B

<400> SEQUENCE: 414
gcggtacccc acatggaaca taagcctcag tcctgg                                36

<210> SEQ ID NO 415
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-47-A

<400> SEQUENCE: 415
agggagagtg tacaaactca caatggggta c                                     31

<210> SEQ ID NO 416
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-47-B

<400> SEQUENCE: 416
gcggtacccc attgtgagtt tgtacactct ccctgg                                36

<210> SEQ ID NO 417

```
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-48-A

<400> SEQUENCE: 417
aggactagca ttataatgca ccatggggta c                              31

<210> SEQ ID NO 418
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-48-B

<400> SEQUENCE: 418
gcggtacccc atggtgcatt ataatgctag tcctgg                         36

<210> SEQ ID NO 419
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-49-A

<400> SEQUENCE: 419
aggtcagaag agattagtta gtatggggta c                              31

<210> SEQ ID NO 420
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-49-B

<400> SEQUENCE: 420
gcggtacccc atactaacta atctcttctg acctgg                         36

<210> SEQ ID NO 421
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-50-A

<400> SEQUENCE: 421
aggtgagagt gccatctctt ccttggggta c                              31

<210> SEQ ID NO 422
<211> LENGTH: 36
<212> TYPE: DNA
<213> ORGANISM: Artificial sequence
<220> FEATURE:
```

```
<223> OTHER INFORMATION: Synthetic polynucleotide
<220> FEATURE:
<221> NAME/KEY: misc_feature
<223> OTHER INFORMATION: Ext-A-P-50-B

<400> SEQUENCE: 422
gcggtacccc aaggaagaga tggcactctc acctgg                                   36

<210> SEQ ID NO 423
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-51-A

<400> SEQUENCE: 423
aggtggacca catggctttg ctctggggta c                                        31

<210> SEQ ID NO 424
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-51-B

<400> SEQUENCE: 424
gcggtacccc agagcaaagc catgtggtcc acctgg                                   36

<210> SEQ ID NO 425
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-52-A

<400> SEQUENCE: 425
aggtgagcaa agccatgtgg tcctggggta c                                        31

<210> SEQ ID NO 426
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-52-B

<400> SEQUENCE: 426
gcggtacccc aggaccacat ggctttgctc acctgg                                   36

<210> SEQ ID NO 427
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-53-A
```

<400> SEQUENCE: 427
agggattaat gacatacgca ttttggggta c                               31

<210> SEQ ID NO 428
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-53-B

<400> SEQUENCE: 428
gcggtacccc aaaatgcgta tgtcattaat ccctgg                          36

<210> SEQ ID NO 429
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-54-A

<400> SEQUENCE: 429
aggagattaa tgacatacgc atttggggta c                               31

<210> SEQ ID NO 430
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-54-B

<400> SEQUENCE: 430
gcggtacccc aaatgcgtat gtcattaatc tcctgg                          36

<210> SEQ ID NO 431
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-55-A

<400> SEQUENCE: 431
aggttcaatc ctcttgtcac ctgtggggta c                               31

<210> SEQ ID NO 432
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-55-B

<400> SEQUENCE: 432
gcggtacccc acaggtgaca agaggattga acctgg                          36

<210> SEQ ID NO 433
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-56-A

<400> SEQUENCE: 433
agggacatct ctatgtcggc cactggggta c                                    31

<210> SEQ ID NO 434
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-56-B

<400> SEQUENCE: 434
gcggtacccc agtggccgac atagagatgt ccctgg                               36

<210> SEQ ID NO 435
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-57-A

<400> SEQUENCE: 435
aggaaaacct accgcaagtt gcctggggta c                                    31

<210> SEQ ID NO 436
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-57-B

<400> SEQUENCE: 436
gcggtacccc aggcaacttg cggtaggttt tcctgg                               36

<210> SEQ ID NO 437
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-58-A

<400> SEQUENCE: 437
aggtggacta catagttgtg tgatggggta c                                    31

<210> SEQ ID NO 438
<211> LENGTH: 36

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-58-B

<400> SEQUENCE: 438
gcggtacccc atcacacaac tatgtagtcc acctgg                                  36

<210> SEQ ID NO 439
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-59-A

<400> SEQUENCE: 439
aggctgccag actctctgaa ccctggggta c                                       31

<210> SEQ ID NO 440
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-59-B

<400> SEQUENCE: 440
gcggtacccc agggttcaga gagtctggca gcctgg                                  36

<210> SEQ ID NO 441
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-60-A

<400> SEQUENCE: 441
aggggatccc tcgtataaca atatggggta c                                       31

<210> SEQ ID NO 442
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-60-B

<400> SEQUENCE: 442
gcggtacccc atattgttat acgagggatc ccctgg                                  36

<210> SEQ ID NO 443
<211> LENGTH: 31
<212> TYPE: DNA
<213> ORGANISM: Artificial sequence
<220> FEATURE:
<223> OTHER INFORMATION: Synthetic polynucleotide
```

```
<220> FEATURE:
<221> NAME/KEY: misc_feature
<223> OTHER INFORMATION: Ext-A-P-61-A

<400> SEQUENCE: 443
aggtatcgca tagtgcaaag aattggggta c                              31

<210> SEQ ID NO 444
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-61-B

<400> SEQUENCE: 444
gcggtacccc aattctttgc actatgcgat acctgg                         36

<210> SEQ ID NO 445
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-62-A

<400> SEQUENCE: 445
aggctcggtc ctctcgtcac ctgtggggta c                              31

<210> SEQ ID NO 446
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-62-B

<400> SEQUENCE: 446
gcggtacccc acaggtgacg agaggaccga gcctgg                         36

<210> SEQ ID NO 447
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-63-A

<400> SEQUENCE: 447
aggacgctcc cggagagcgc tggtggggta c                              31

<210> SEQ ID NO 448
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-63-B
```

<400> SEQUENCE: 448
gcggtacccc accagcgctc tccgggagcg tcctgg     36

<210> SEQ ID NO 449
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-64-A

<400> SEQUENCE: 449
aggccatggc gcggtcagag ggttggggta c     31

<210> SEQ ID NO 450
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-64-B

<400> SEQUENCE: 450
gcggtacccc aaccctctga ccgcgccatg gcctgg     36

<210> SEQ ID NO 451
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-65-A

<400> SEQUENCE: 451
aggctcggct ccaatgacga gggtggggta c     31

<210> SEQ ID NO 452
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-65-B

<400> SEQUENCE: 452
gcggtacccc accctcgtca ttggagccga gcctgg     36

<210> SEQ ID NO 453
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-66-A

<400> SEQUENCE: 453
aggcacttcg atgacctccc cgttggggta c     31

<210> SEQ ID NO 454
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-66-B

<400> SEQUENCE: 454
gcggtacccc aacggggagg tcatcgaagt gcctgg                                36

<210> SEQ ID NO 455
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-67-A

<400> SEQUENCE: 455
aggagtgggt gttcaggacc gcgtggggta c                                     31

<210> SEQ ID NO 456
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-67-B

<400> SEQUENCE: 456
gcggtacccc acgcggtcct gaacacccac tcctgg                                36

<210> SEQ ID NO 457
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-68-A

<400> SEQUENCE: 457
aggctgctac ccacaggtgc aagtggggta c                                     31

<210> SEQ ID NO 458
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-68-B

<400> SEQUENCE: 458
gcggtacccc acttgcacct gtgggtagca gcctgg                                36

<210> SEQ ID NO 459
<211> LENGTH: 31
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-69-A

<400> SEQUENCE: 459
aggaagatgt atcctggaat ttatggggta c                          31

<210> SEQ ID NO 460
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-69-B

<400> SEQUENCE: 460
gcggtacccc ataaattcca ggatacatct tcctgg                     36

<210> SEQ ID NO 461
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-70-A

<400> SEQUENCE: 461
aggttttatc actacccaag acatggggta c                          31

<210> SEQ ID NO 462
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-70-B

<400> SEQUENCE: 462
gcggtacccc atgtcttggg tagtgataaa acctgg                     36

<210> SEQ ID NO 463
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-71-A

<400> SEQUENCE: 463
aggcggccag gctccctgaa acctggggta c                          31

<210> SEQ ID NO 464
<211> LENGTH: 36
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: Ext-A-P-71-B

<400> SEQUENCE: 464
gcggtacccc aggtttcagg gagcctggcc gcctgg                              36

<210> SEQ ID NO 465
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-72-A

<400> SEQUENCE: 465
aggactggta ttataataca acatggggta c                                   31

<210> SEQ ID NO 466
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-72-B

<400> SEQUENCE: 466
gcggtacccc atgttgtatt ataataccag tcctgg                              36

<210> SEQ ID NO 467
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-73-A

<400> SEQUENCE: 467
aggtgagagt gacatttcgt acttggggta c                                   31

<210> SEQ ID NO 468
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-73-B

<400> SEQUENCE: 468
gcggtacccc aagtacgaaa tgtcactctc acctgg                              36

<210> SEQ ID NO 469
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-74-A

<400> SEQUENCE: 469
```

```
aggtgcgccc ccgggtgagg tgctggggta c                                   31

<210> SEQ ID NO 470
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-74-B

<400> SEQUENCE: 470
gcggtacccc agcacctcac ccggggggcgc acctgg                             36

<210> SEQ ID NO 471
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-75-A

<400> SEQUENCE: 471
aggcagtttg agcagaaaaa gaatggggta c                                   31

<210> SEQ ID NO 472
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-75-B

<400> SEQUENCE: 472
gcggtacccc attcttttttc tgctcaaact gcctgg                             36

<210> SEQ ID NO 473
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-76-A

<400> SEQUENCE: 473
aggtctgtag agataagtga gtatggggta c                                   31

<210> SEQ ID NO 474
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-76-B

<400> SEQUENCE: 474
gcggtacccc atactcactt atctctacag acctgg                              36
```

```
<210> SEQ ID NO 475
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-77-A

<400> SEQUENCE: 475
aggaagtgtg tacaaactca agatggggta c                                    31

<210> SEQ ID NO 476
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-77-B

<400> SEQUENCE: 476
gcggtacccc atcttgagtt tgtacacact tcctgg                               36

<210> SEQ ID NO 477
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-78-A

<400> SEQUENCE: 477
aggtatcatg gatgctgact ttttggggta c                                    31

<210> SEQ ID NO 478
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-78-B

<400> SEQUENCE: 478
gcggtacccc aaaaagtcag catccatgat acctgg                               36

<210> SEQ ID NO 479
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-79-A

<400> SEQUENCE: 479
agggctttac tagcccctgt ggctggggta c                                    31

<210> SEQ ID NO 480
<211> LENGTH: 36
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<223> OTHER INFORMATION: Ext-A-P-79-B

<400> SEQUENCE: 480
gcggtacccc agccacaggg gctagtaaag ccctgg                          36

<210> SEQ ID NO 481
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-80-A

<400> SEQUENCE: 481
agggcacgga ggagaaaagc aggtggggta c                              31

<210> SEQ ID NO 482
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-80-B

<400> SEQUENCE: 482
gcggtacccc acctgctttt ctcctccgtg ccctgg                         36

<210> SEQ ID NO 483
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-81-A

<400> SEQUENCE: 483
aggatttgtg agatctaaag aactggggta c                              31

<210> SEQ ID NO 484
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-81-B

<400> SEQUENCE: 484
gcggtacccc agttctttag atctcacaaa tcctgg                         36

<210> SEQ ID NO 485
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

<223> OTHER INFORMATION: Ext-A-P-82-A

<400> SEQUENCE: 485
aggcgttgat gacattcgca ttttggggta c                           31

<210> SEQ ID NO 486
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-82-B

<400> SEQUENCE: 486
gcggtacccc aaaatgcgaa tgtcatcaac gcctgg                      36

<210> SEQ ID NO 487
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-83-A

<400> SEQUENCE: 487
aggcttatag atcatctaat acctggggta c                           31

<210> SEQ ID NO 488
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-83-B

<400> SEQUENCE: 488
gcggtacccc aggtattaga tgatctataa gcctgg                      36

<210> SEQ ID NO 489
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-84-A

<400> SEQUENCE: 489
aggtggcctc catagttggg tggtggggta c                           31

<210> SEQ ID NO 490
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-84-B

<400> SEQUENCE: 490

```
gcggtacccc accacccaac tatggaggcc acctgg                                    36
```

<210> SEQ ID NO 491
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-85-A

<400> SEQUENCE: 491

```
aggtactaga gttcaaacat acttggggta c                                         31
```

<210> SEQ ID NO 492
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-85-B

<400> SEQUENCE: 492

```
gcggtacccc aagtatgttt gaactctagt acctgg                                    36
```

<210> SEQ ID NO 493
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-86-A

<400> SEQUENCE: 493

```
aggcccctgc tctgagcact cggtggggta c                                         31
```

<210> SEQ ID NO 494
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-86-B

<400> SEQUENCE: 494

```
gcggtacccc accgagtgct cagagcaggg gcctgg                                    36
```

<210> SEQ ID NO 495
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-87-A

<400> SEQUENCE: 495

```
aggaggacca catggcctgc ctctggggta c                                         31
```

<210> SEQ ID NO 496

-continued

```
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-87-B

<400> SEQUENCE: 496
gcggtacccc agaggcaggc catgtggtcc tcctgg                          36

<210> SEQ ID NO 497
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-88-A

<400> SEQUENCE: 497
aggaacagct gccgcaaatt gcctggggta c                              31

<210> SEQ ID NO 498
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-88-B

<400> SEQUENCE: 498
gcggtacccc aggcaatttg cggcagctgt tcctgg                          36

<210> SEQ ID NO 499
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-89-A

<400> SEQUENCE: 499
aggctccgta ttggctggct cgtggggta c                               31

<210> SEQ ID NO 500
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-89-B

<400> SEQUENCE: 500
gcggtacccc acgaagccag ccaatacgga gcctgg                          36

<210> SEQ ID NO 501
<211> LENGTH: 31
<212> TYPE: DNA
<213> ORGANISM: Artificial sequence
<220> FEATURE:
```

```
<223> OTHER INFORMATION: Synthetic polynucleotide
<220> FEATURE:
<221> NAME/KEY: misc_feature
<223> OTHER INFORMATION: Ext-A-P-90-A

<400> SEQUENCE: 501
aggggccagc cgatgacaaa tactggggta c                              31

<210> SEQ ID NO 502
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-90-B

<400> SEQUENCE: 502
gcggtacccc agtatttgtc atcggctggc ccctgg                         36

<210> SEQ ID NO 503
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-91-A

<400> SEQUENCE: 503
agggacgtct ctacgtcggc ggctggggta c                              31

<210> SEQ ID NO 504
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-91-B

<400> SEQUENCE: 504
gcggtacccc agccgccgac gtagagacgt ccctgg                         36

<210> SEQ ID NO 505
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-92-A

<400> SEQUENCE: 505
aggccggcgc gaggggccga gagtggggta c                              31

<210> SEQ ID NO 506
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-92-B
```

```
<400> SEQUENCE: 506
gcggtacccc actctcggcc cctcgcgccg gcctgg                                    36

<210> SEQ ID NO 507
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-93-A

<400> SEQUENCE: 507
aggactgttt gtacttttc atctggggta c                                          31

<210> SEQ ID NO 508
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-93-B

<400> SEQUENCE: 508
gcggtacccc agatgaaaaa gtacaaacag tcctgg                                    36

<210> SEQ ID NO 509
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-94-A

<400> SEQUENCE: 509
aggtgcttat gatgatgaca ttatggggta c                                         31

<210> SEQ ID NO 510
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-94-B

<400> SEQUENCE: 510
gcggtacccc ataatgtcat catcataagc acctgg                                    36

<210> SEQ ID NO 511
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-95-A

<400> SEQUENCE: 511
aggccgcgtc cgattgatgt gattggggta c                                         31
```

<210> SEQ ID NO 512
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-95-B

<400> SEQUENCE: 512
gcggtacccc aatcacatca atcggacgcg gcctgg                                    36

<210> SEQ ID NO 513
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-96-A

<400> SEQUENCE: 513
aggctttatg agcaccttag gcttggggta c                                         31

<210> SEQ ID NO 514
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-96-B

<400> SEQUENCE: 514
gcggtacccc aagcctaagg tgctcataaa gcctgg                                    36

<210> SEQ ID NO 515
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-97-A

<400> SEQUENCE: 515 agggatccc tcctatgacc atgtggggta c                                          31

<210> SEQ ID NO 516
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-97-B

<400> SEQUENCE: 516
gcggtacccc acatggtcat aggagggatc ccctgg                                    36

<210> SEQ ID NO 517
<211> LENGTH: 31

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-98-A

<400> SEQUENCE: 517
aggataaagg tgacctctta cgttggggta c                              31

<210> SEQ ID NO 518
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-98-B

<400> SEQUENCE: 518
gcggtacccc aacgtaagag gtcaccttta tcctgg                         36

<210> SEQ ID NO 519
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-99-A

<400> SEQUENCE: 519
aggactgtgg cttagggtcc aggtggggta c                              31

<210> SEQ ID NO 520
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-99-B

<400> SEQUENCE: 520
gcggtacccc acctggaccc taagccacag tcctgg                         36

<210> SEQ ID NO 521
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-100-A

<400> SEQUENCE: 521
aggtgaggaa acccaggcgg tcctggggta c                              31

<210> SEQ ID NO 522
<211> LENGTH: 36
<212> TYPE: DNA
<213> ORGANISM: Artificial sequence
<220> FEATURE:
<223> OTHER INFORMATION: Synthetic polynucleotide
```

```
<220> FEATURE:
<221> NAME/KEY: misc_feature
<223> OTHER INFORMATION: Ext-A-P-100-B

<400> SEQUENCE: 522
gcggtacccc aggaccgcct gggtttcctc acctgg                            36

<210> SEQ ID NO 523
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-101-A

<400> SEQUENCE: 523
aggaaatgta tacaggcaat taatggggta c                                 31

<210> SEQ ID NO 524
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-101-B

<400> SEQUENCE: 524
gcggtacccc attaattgcc tgtatacatt tcctgg                            36

<210> SEQ ID NO 525
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-102-A

<400> SEQUENCE: 525
aggttgaatc aagcatagtc cgatggggta c                                 31

<210> SEQ ID NO 526
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-102-B

<400> SEQUENCE: 526
gcggtacccc atcggactat gcttgattca acctgg                            36

<210> SEQ ID NO 527
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-103-A
```

<400> SEQUENCE: 527 aggggggctac ggctcatgag atatggggta c                              31

<210> SEQ ID NO 528
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-103-B

<400> SEQUENCE: 528
gcggtacccc atatctcatg agccgtagcc ccctgg                          36

<210> SEQ ID NO 529
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-104-A

<400> SEQUENCE: 529
aggcgggccg cgattggcag ttctggggta c                               31

<210> SEQ ID NO 530
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-104-B

<400> SEQUENCE: 530
gcggtacccc agaactgcca atcgcggccc gcctgg                          36

<210> SEQ ID NO 531
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-105-A

<400> SEQUENCE: 531
aggctgcgat tatctaaatc cattggggta c                               31

<210> SEQ ID NO 532
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-105-B

<400> SEQUENCE: 532
gcggtacccc aatggattta gataatcgca gcctgg                          36

<210> SEQ ID NO 533
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-106-A

<400> SEQUENCE: 533
aggagcttga ttacatacgc atgtggggta c                                      31

<210> SEQ ID NO 534
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-106-B

<400> SEQUENCE: 534
gcggtacccc acatgcgtat gtaatcaagc tcctgg                                 36

<210> SEQ ID NO 535
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-107-A

<400> SEQUENCE: 535
aggaatgttt gctggcctct aggtggggta c                                      31

<210> SEQ ID NO 536
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-107-B

<400> SEQUENCE: 536
gcggtacccc acctagaggc cagcaaacat tcctgg                                 36

<210> SEQ ID NO 537
<211> LENGTH: 31
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-108-A

<400> SEQUENCE: 537
agggaaagcc tctgcgccgg gggtggggta c                                      31

<210> SEQ ID NO 538
<211> LENGTH: 36
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Ext-A-P-108-B

<400> SEQUENCE: 538
gcggtacccc accccggcg cagaggcttt ccctgg                              36
```

RNA-PROGRAMMABLE ENDONUCLEASE SYSTEMS AND USES THEREOF

CROSS-REFERENCE TO RELATED APPLICATIONS

This application is a 35 U.S.C. § 371 national stage filing of International Application No. PCT/US2019/023044 filed on Mar. 19, 2019, which claims priority to European Patent Application No. 18162681.3, filed on Mar. 19, 2018, European Patent Application No. 18162683.9, filed on Mar. 19, 2018, European Patent Application No. 18172625.8, filed on May 16, 2018, European Patent Application No. 18174707.2, filed on May 29, 2018, European Patent Application No. 18181680.2, filed on Jul. 4, 2018, U.S. Patent Application No. 62/745,238, filed on Oct. 12, 2018, U.S. Patent Application No. 62/745,239, filed on Oct. 12, 2018, U.S. Patent Application No. 62/745,240, filed on Oct. 12, 2018, and U.S. Patent Application No. 62/745,246, filed on Oct. 12, 2018. The entire contents of these applications are incorporated herein by reference in their entirety.

INCORPORATION BY REFERENCE OF SEQUENCE LISTING

The instant application contains a Sequence Listing which has been submitted electronically in ASCII format via EFS-Web, and is hereby incorporated by reference in its entirety. Said ASCII copy, created on Sep. 18, 2020, is named CBTN_016US_Sequence_Listing.txt and is 467120 bytes in size.

FIELD

The present disclosure generally relates to the field of molecular biology, including compositions and methods relating to novel systems including RNA-programmable endonucleases, associated guide RNAs and/or target sequences, and methods for producing and using the same in various applications, including methods for modulating transcription, as well as methods for targeting, editing, and/or manipulating DNA in a cell.

BACKGROUND

Endonucleases such as Zinc-finger endonucleases (ZFNs), transcription-activator like effector nucleases (TALENs), and ribonucleases have been harnessed as site-specific nucleases for genome targeting, genome editing, gene silencing, transcription modulation, promoting recombination and other molecular biological techniques. Clustered Regularly Interspaced Short Palindromic Repeats (CRISPR)-CRISPR associated proteins (Cas) systems provide a source of novel nucleases and endonucleases, including CRISPR-Cas9.

CRISPR systems are prokaryotic systems that provides the prokaryote with resistance to foreign genetic elements such as phage. As demonstrated in *Streptococcus pyogenes*, Cas9 guided by the duplex formed between mature activating tracr RNA and targeting crRNA introduces site-specific double-stranded DNA (dsDNA) breaks in the invading cognate DNA. Cas9 is a multi-domain enzyme that uses an HNH nuclease domain to cleave the target strand (defined as complementary to the spacer sequence of crRNA) and a RuvC-like domain to cleave the non-target strand, enabling the conversion of the dsDNA cleaving Cas9 into a nickase by selective motif inactivation. DNA cleavage specificity is determined by two parameters: the variable, spacer-derived sequence of crRNA targeting the protospacer sequence (the sequence on the DNA target that is non-complementary to the spacer of crRNA) and a short sequence, the Protospacer Adjacent Motif (PAM), located immediately 3' (downstream) of the protospacer on the non-target DNA strand.

Editing genomes using the RNA-guided DNA targeting principle of CRISPR-Cas, as described in WO2013/176722, has been exploited widely over the past few years. Studies have demonstrated that RNA-guided Cas9 can be employed as a genome editing tool in human cells, mice, zebrafish, *drosophila*, worms, plants, yeast and bacteria, as well as various other species. The system is versatile, enabling multiplex genome engineering by programming Cas9 to edit several sites in a genome simultaneously by using multiple guide RNAs. The conversion of Cas9 into a nickase was shown to facilitate homology-directed repair in mammalian genomes with reduced mutagenic activity. In addition, the DNA-binding activity of a Cas9 catalytic inactive mutant has, for example, been exploited to engineer RNA-programmable transcriptional silencing and activating devices or epigenetic modifiers.

Despite the promise of CRISPR-Cas9 systems for gene editing, a number of problems are associated with the use of the system. For example, they have one or more of the following disadvantages:
a) Their size is too large to be carried inside the genome of established therapeutically-suitable viral transfection systems such as adeno-associated viruses (AAVs).
b) Their activity in heterologous environments is generally too low for use in these environments, for example, too low for efficient use in eukaryotic, and in particular in mammalian environments.
c) Their nuclease activity lacks fidelity, leading to unwanted off-target effects that would, for example, make them unsuitable for gene therapeutic uses or other applications requiring high precision.
d) They may trigger an immune response that can limit their use for in vivo applications in mammals
e) They require complex and/or long PAMs that restrict target selection for the DNA-targeting segments.
f) They exhibit poor expression from plasmid or viral vectors.

SUMMARY

This section provides a general summary of the disclosure, and is not comprehensive of its full scope or all of its features.

In some embodiments, provided herein are compositions and methods relating to novel RNA-programmable endonucleases, and systems for using such nucleases. The invention also relates to other components including guide RNAs and/or target sequences, and methods for producing and using the same in various applications. Examples of such applications include methods for modulating transcription, as well as methods for targeting, editing, and/or manipulating DNA using the novel nucleases and other components such as nucleic acids and/or polypeptides. Some embodiments of the disclosure also relate to recombinant cells and kits comprising one or more of the system elements disclosed herein.

In one aspect, provided herein is a synthetic RNA-guided nuclease (sRGN) polypeptide comprising, from N-terminus to C-terminus, 1) mini-domain 1 comprising the amino acid sequence of any one of SEQ ID NOs: 34-37 or a variant thereof having at least about 90% sequence identity to any one of SEQ ID NOs: 34-37, 2) mini-domain 2 comprising the amino acid sequence of any one of SEQ ID NOs: 38-41 or a variant thereof having at least about 90% sequence identity to any one of SEQ ID NOs: 38-41, 3) mini-domain 3 comprising the amino acid sequence of any one of SEQ ID NOs: 42-45 or a variant thereof having at least about 90% sequence identity to any one of SEQ ID NOs: 42-45, 4) mini-domain 4 comprising the amino acid sequence of any one of SEQ ID NOs: 46-49 or a variant thereof having at least about 90% sequence identity to any one of SEQ ID NOs: 46-49, 5) mini-domain 5 comprising the amino acid sequence of any one of SEQ ID NOs: 50-53 or a variant thereof having at least about 90% sequence identity to any one of SEQ ID NOs: 50-53, 6) mini-domain 6 comprising the amino acid sequence of any one of SEQ ID NOs: 54-57 or a variant thereof having at least about 90% sequence identity to any one of SEQ ID NOs: 54-57, 7) mini-domain 7 comprising the amino acid sequence of any one of SEQ ID NOs: 58-61 or a variant thereof having at least about 90% sequence identity to any one of SEQ ID NOs: 58-61, and 8) mini-domain 8 comprising the amino acid sequence of any one of SEQ ID NOs: 62-65 or a variant thereof having at least about 90% sequence identity to any one of SEQ ID NOs: 62-65, wherein at least 2 of the mini-domains are derived from different parental Cas9 endonucleases selected from the group consisting of *Staphylococcus lugdunensis* Cas9 (SEQ ID NO: 30), *Staphylococcus pasteuri* Cas9 (SEQ ID NO: 31), *Staphylococcus microti* Cas9 (SEQ ID NO: 33), and *Staphylococcus hyicus* Cas9 (SEQ ID NO: 32). In some embodiments, at least 3 of the mini-domains are derived from different parental Cas9 endonucleases selected from the group consisting of *Staphylococcus lugdunensis* Cas9 (SEQ ID NO: 30), *Staphylococcus pasteuri* Cas9 (SEQ ID NO: 31), *Staphylococcus microti* Cas9 (SEQ ID NO: 33), and *Staphylococcus hyicus* Cas9 (SEQ ID NO: 32). In some embodiments, mini-domain 8 comprises the amino acid sequence of SEQ ID NO: 62 or a variant thereof having at least about 90% sequence identity to SEQ ID NO: 62. In some embodiments, mini-domain 8 comprises the amino acid sequence of SEQ ID NO: 63 or a variant thereof having at least about 90% sequence identity to SEQ ID NO: 63. In some embodiments, mini-domain 1 comprises the amino acid sequence of SEQ ID NO: 34 or a variant thereof having at least about 90% sequence identity to SEQ ID NO: 34.

In another aspect, provided herein is an sRGN polypeptide comprising, from N-terminus to C-terminus, 1) mini-domain 1 comprising the amino acid sequence of any one of SEQ ID NOs: 66-69 or a variant thereof having at least about 90% sequence identity to any one of SEQ ID NOs: 66-69, 2) mini-domain 2 comprising the amino acid sequence of any one of SEQ ID NOs: 70-73 or a variant thereof having at least about 90% sequence identity to any one of SEQ ID NOs: 70-73, 3) mini-domain 3 comprising the amino acid sequence of any one of SEQ ID NOs: 74-77 or a variant thereof having at least about 90% sequence identity to any one of SEQ ID NOs: 74-77, 4) mini-domain 4 comprising the amino acid sequence of any one of SEQ ID NOs: 78-81 or a variant thereof having at least about 90% sequence identity to any one of SEQ ID NOs: 78-81, 5) mini-domain 5 comprising the amino acid sequence of any one of SEQ ID NOs: 82-85 or a variant thereof having at least about 90% sequence identity to any one of SEQ ID NOs: 82-85, 6) mini-domain 6 comprising the amino acid sequence of any one of SEQ ID NOs: 86-89 or a variant thereof having at least about 90% sequence identity to any one of SEQ ID NOs: 86-89, 7) mini-domain 7 comprising the amino acid sequence of any one of SEQ ID NOs: 90-93 or a variant thereof having at least about 90% sequence identity to any one of SEQ ID NOs: 90-93, 8) mini-domain 8 comprising the amino acid sequence of any one of SEQ ID NOs: 94-97 or a variant thereof having at least about 90% sequence identity to any one of SEQ ID NOs: 94-97, 9) mini-domain 9 comprising the amino acid sequence of any one of SEQ ID NOs: 98-101 or a variant thereof having at least about 90% sequence identity to any one of SEQ ID NOs: 98-101, 10) mini-domain 10 comprising the amino acid sequence of any one of SEQ ID NOs: 102-105 or a variant thereof having at least about 90% sequence identity to any one of SEQ ID NOs: 102-105, 11) mini-domain 11 comprising the amino acid sequence of any one of SEQ ID NOs: 106-109 or a variant thereof having at least about 90% sequence identity to any one of SEQ ID NOs: 106-109, and 12) mini-domain 12 comprising the amino acid sequence of any one of SEQ ID NOs: 110-113 or a variant thereof having at least about 90% sequence identity to any one of SEQ ID NOs: 110-113, wherein at least 2 of the mini-domains are derived from different parental Cas9 endonucleases selected from the group consisting of *Staphylococcus lugdunensis* Cas9 (SEQ ID NO: 30), *Staphylococcus pasteuri* Cas9 (SEQ ID NO: 31), *Staphylococcus microti* Cas9 (SEQ ID NO: 33), and *Staphylococcus hyicus* Cas9 (SEQ ID NO: 32). In some embodiments, at least 3 of the mini-domains are derived from different parental Cas9 endonucleases selected from the group consisting of *Staphylococcus lugdunensis* Cas9 (SEQ ID NO: 30), *Staphylococcus pasteuri* Cas9 (SEQ ID NO: 31), *Staphylococcus microti* Cas9 (SEQ ID NO: 33), and *Staphylococcus hyicus* Cas9 (SEQ ID NO: 32). In some embodiments, mini-domain 12 comprises the amino acid sequence of SEQ ID NO: 110 or a variant thereof having at least about 90% sequence identity to SEQ ID NO: 110. In some embodiments, mini-domain 12 comprises the amino acid sequence of SEQ ID NO: 111 or a variant thereof having at least about 90% sequence identity to SEQ ID NO: 111. In some embodiments, (i) mini-domain 1 comprises the amino acid sequence of SEQ ID NO: 66 or a variant thereof having at least about 90% sequence identity to SEQ ID NO: 66, and (ii) mini-domain 2 comprises the amino acid sequence of SEQ ID NO: 70 or a variant thereof having at least about 90% sequence identity to SEQ ID NO: 70.

In another aspect, provided herein is an sRGN polypeptide selected from the group consisting of: a) a Gib11 polypeptide comprising the amino acid sequence of SEQ ID NO: 1 or a variant thereof having at least about 90% sequence identity to SEQ ID NO: 1, b) a Gib11Spa-1 polypeptide comprising the amino acid sequence of SEQ ID NO: 2 or a variant thereof having at least about 90% sequence identity to SEQ ID NO: 2, c) a Gib11Spa-2 polypeptide comprising the amino acid sequence of SEQ ID NO: 3 or a variant thereof having at least about 90% sequence identity to SEQ ID NO: 3, d) a Gib11Spa-3 polypeptide comprising the amino acid sequence of SEQ ID NO: 4 or a variant thereof having at least about 90% sequence identity to SEQ ID NO: 4, e) a P2H12 polypeptide comprising the amino acid sequence of SEQ ID NO: 5 or a variant thereof having at least about 90% sequence identity to SEQ ID NO: 5, f) an E2 polypeptide comprising the amino acid sequence of SEQ ID NO: 6 or a variant thereof having at least about 90% sequence identity to SEQ ID NO: 6, g) an E2+K741D+L743K polypeptide comprising the amino acid sequence of SEQ ID NO: 7 or a variant thereof having at least about 90% sequence identity to SEQ ID NO: 7, h) an E2+S670T+N675D polypeptide comprising the amino acid sequence of SEQ ID NO: 8 or a variant thereof having at least about 90% sequence identity to SEQ ID NO:

8, i) an E2+K741N+L743N polypeptide comprising the amino acid sequence of SEQ ID NO: 9 or a variant thereof having at least about 90% sequence identity to SEQ ID NO: 9, j) an F8 polypeptide comprising the amino acid sequence of SEQ ID NO: 10 or a variant thereof having at least about 90% sequence identity to SEQ ID NO: 10; k) an F8+K737D+L739K polypeptide comprising the amino acid sequence of SEQ ID NO: 11 or a variant thereof having at least about 90% sequence identity to SEQ ID NO: 11; and l) an F8+K737N+L739N polypeptide comprising the amino acid sequence of SEQ ID NO: 12 or a variant thereof having at least about 90% sequence identity to SEQ ID NO: 12.

In some embodiments, the sRGN polypeptide is selected from the group consisting of: a) a Gib11 polypeptide comprising the amino acid sequence of SEQ ID NO: 1 or a variant thereof having at least about 90% sequence identity to SEQ ID NO: 1, b) a Gib11Spa-1 polypeptide comprising the amino acid sequence of SEQ ID NO: 2 or a variant thereof having at least about 90% sequence identity to SEQ ID NO: 2, and c) a Gib11Spa-3 polypeptide comprising the amino acid sequence of SEQ ID NO: 4 or a variant thereof having at least about 90% sequence identity to SEQ ID NO: 4. In some embodiments, the sRGN polypeptide is selected from the group consisting of: a) a Gib11 polypeptide comprising the amino acid sequence of SEQ ID NO: 1, b) a Gib11Spa-1 polypeptide comprising the amino acid sequence of SEQ ID NO: 2, and c) a Gib11Spa-3 polypeptide comprising the amino acid sequence of SEQ ID NO: 4.

In another aspect, provided herein is a nucleic acid encoding an sRGN polypeptide according to any of the embodiments described above. In some embodiments, the nucleic acid is codon-optimized for expression in a host cell. In some embodiments, the nucleic acid comprises the nucleotide sequence of any one of SEQ ID NOs: 13-29 or a variant thereof having at least about 90% sequence identity to any one of SEQ ID NOs: 13-29.

In another aspect, provided herein is a system comprising: (a) an sRGN polypeptide referenced above or a nucleic acid encoding the sRGN polypeptide; and (b) a guide RNA (gRNA) or nucleic acid encoding the gRNA, wherein the gRNA is capable of guiding the sRGN polypeptide or variant thereof to a target polynucleotide sequence. In some embodiments, the system further comprises a donor template comprising a heterologous polynucleotide sequence, wherein the heterologous polynucleotide sequence is capable of being inserted into the target polynucleotide sequence.

In some embodiments, according to any of the systems described above, the nucleic acid encoding the sRGN polypeptide is codon-optimized for expression in a host cell and/or the heterologous polynucleotide sequence is codon-optimized for expression in a host cell.

In some embodiments, according to any of the systems described above, the nucleic acid encoding the sRGN polypeptide is a deoxyribonucleic acid (DNA).

In some embodiments, according to any of the systems described above, the nucleic acid encoding the sRGN polypeptide is a ribonucleic acid (RNA). In some embodiments, the RNA encoding the sRGN polypeptide is an mRNA.

In some embodiments, according to any of the systems described above, the donor template is encoded in an Adeno Associated Virus (AAV) vector.

In some embodiments, according to any of the systems described above, the sRGN polypeptide or nucleic acid encoding the sRGN polypeptide is formulated in a liposome or lipid nanoparticle. In some embodiments, the liposome or lipid nanoparticle also comprises the gRNA or nucleic acid encoding the gRNA.

In some embodiments, according to any of the systems described above, the system comprises the sRGN polypeptide pre-complexed with the gRNA, forming a ribonucleoprotein (RNP) complex.

In another aspect, provided herein is a method of targeting, editing, modifying, or manipulating a target DNA at a target locus, the method comprising providing the following to the target DNA: (a) an sRGN polypeptide according to any of the embodiments described above or a nucleic acid encoding the sRGN polypeptide; and (b) a guide RNA (gRNA) or nucleic acid encoding the gRNA, wherein the gRNA is capable of guiding the sRGN polypeptide to the target locus. In some embodiments, the method further comprises providing to the target DNA a donor template comprising a heterologous polynucleotide sequence, wherein the heterologous polynucleotide sequence is capable of being inserted into the target locus.

In some embodiments, according to any of the methods described above, the nucleic acid encoding the sRGN polypeptide is codon-optimized for expression in a host cell and/or the heterologous polynucleotide sequence is codon-optimized for expression in a host cell.

In some embodiments, according to any of the methods described above, the nucleic acid encoding the sRGN polypeptide is a deoxyribonucleic acid (DNA).

In some embodiments, according to any of the methods described above, the nucleic acid encoding the sRGN polypeptide is a ribonucleic acid (RNA). In some embodiments, the RNA encoding the sRGN polypeptide is an mRNA.

In some embodiments, according to any of the methods described above, the donor template is encoded in an Adeno Associated Virus (AAV) vector.

In some embodiments, according to any of the methods described above, the sRGN polypeptide or nucleic acid encoding the sRGN polypeptide is formulated in a liposome or lipid nanoparticle. In some embodiments, the liposome or lipid nanoparticle also comprises the gRNA or nucleic acid encoding the gRNA. In some embodiments, the method comprises providing to the target DNA the sRGN polypeptide pre-complexed with the gRNA as an RNP complex.

In another aspect, provided herein is a modified cell comprising: (a) an sRGN polypeptide according to any of the embodiments described above or a nucleic acid encoding the sRGN polypeptide; and (b) a guide RNA (gRNA) or nucleic acid encoding the gRNA, wherein the gRNA is capable of guiding the sRGN polypeptide or variant thereof to a target polynucleotide sequence. In some embodiments, the modified cell further comprises a donor template comprising a heterologous polynucleotide sequence, wherein the heterologous polynucleotide sequence is capable of being inserted into the target polynucleotide sequence.

In another aspect, provided herein is a genetically modified cell in which the genome of the cell is edited by a method according to any of the embodiments described above.

In another aspect, provided herein is a kit comprising: (a) an sRGN polypeptide referenced above or a nucleic acid encoding the sRGN polypeptide; and (b) a guide RNA (gRNA) or nucleic acid encoding the gRNA, wherein the gRNA is capable of guiding the sRGN polypeptide or variant thereof to a target polynucleotide sequence. In some embodiments, the kit further comprises a donor template comprising a heterologous polynucleotide sequence, wherein the heterologous polynucleotide sequence is capable of being inserted into the target polynucleotide sequence.

DETAILED DESCRIPTION OF THE INVENTION

Figure 1:
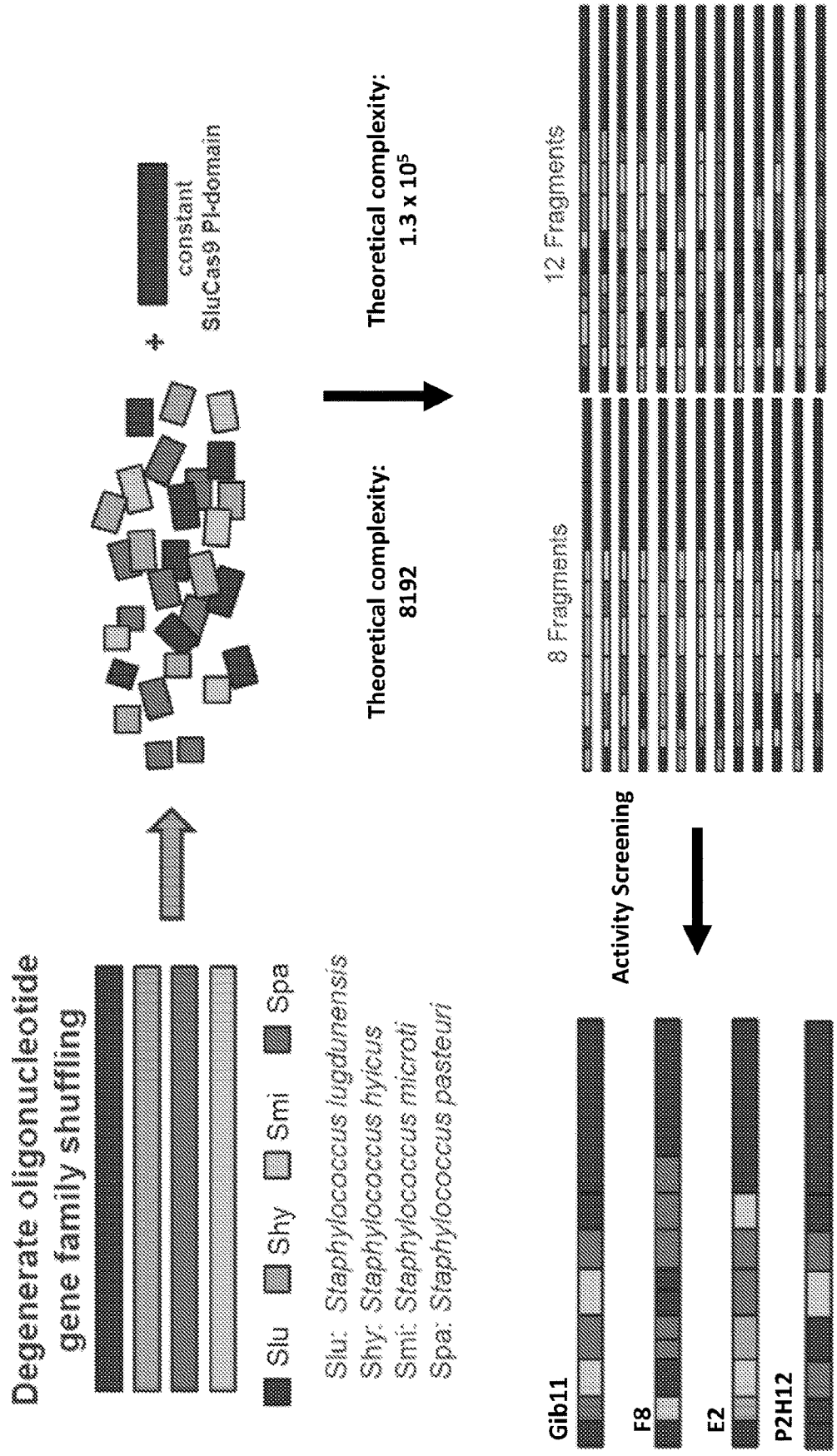
FIG. 1 shows a graphic representation of the gene family shuffling technique used to generate Gib11, P2H12, E2, and F8.

Most existing type II CRISPR Cas systems are based on the enzyme from *Streptococcus pyogenes*, which has the particular disadvantage of being too large for packaging into viral vectors as AAV (1638 amino acids). There is an alternative type II CRISPR Cas system based on the nuclease from *Staphylococcus aureus* (EP 2 898 075) which is significantly smaller in size. However, this nuclease requires a complex PAM which greatly restricts its use for gene editing applications. Furthermore, small nucleases can be more useful for gene editing methods, however, a limited number of such small nucleases have been identified and their optimal features for gene editing are, in at least most cases, not sufficiently defined for use in gene editing.

Provided herein are novel synthetic CRISPR-Cas polypeptides (also referred to herein as "sRGN polypeptides") derived from artificially defined mini-domains of CRISPR-Cas endonucleases of four different *Staphylococcus* species (*Staphylococcus lugdunensis, Staphylococcus pasteuri, Staphylococcus microti*, and *Staphylococcus hyicus*), and variants thereof having different and advantageous characteristics and functionalities. These sRGNs provides further opportunities for genome editing that previously did not exist. Cas nucleases can have differing activities depending on the system in which they are used. One feature of the present invention is providing additional engineered nucleases that increase the toolbox of nucleases available for gene editing and related methods.

In many cases, naturally occurring, known Cas nucleases target a longer PAM, such as NNAAAA, which may restrict the utility of those nucleases. The present invention provides synthetic nucleases (e.g., small nucleases) that are derived from naturally-occurring small nucleases, but can recognize an NNGG PAM.

The present invention further provides suitable PAM sequences and suitable guides, including single-guide-RNAs (sgRNAs), for use in prokaryotic, eukaryotic, and in vitro environments.

The sRGN polypeptides provided herein can exhibit advantageous characteristics over the already reported CRISPR-Cas endonucleases, such as, for example, a higher activity in prokaryotic, eukaryotic, and/or in vitro environments, and/or greater expression of the sRGN polypeptide from a nucleic acid in eukaryotic environments, such as, e.g., a human host cell. In some cases, an sRGN combines one or more of a small size, a high editing activity, and the requirement of only a short PAM sequence. A small size in reference to an RNA-guided nuclease means a nuclease that is no greater than about 1100 amino acids in length.

Also provided are systems for targeting, editing or manipulating DNA in a cell, comprising an sRGN polypeptide or nucleic acid encoding the sRGN polypeptide, and one or more guide RNAs (gRNAs), e.g., one or more single guide RNAs (sgRNAs), or nucleic acid encoding the one or more gRNAs.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Unless otherwise defined, all terms of art, notations and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

DEFINITIONS

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids/triple helices, or a polymer comprising purine and pyrimidine bases or other natural, chemically or biochemically modified, non-natural, or derivatized nucleotide bases.

"Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

"Genomic DNA" refers to the DNA of a genome of an organism including, but not limited to, the DNA of the genome of a bacterium, fungus, archea, protists, viral, plant or animal.

"Manipulating" DNA encompasses binding, nicking one strand, or cleaving (i.e., cutting) both strands of the DNA, or encompasses modifying or editing the DNA or a polypeptide associated with the DNA. Manipulating DNA can silence, activate, or modulate (either increase or decrease) the expression of an RNA or polypeptide encoded by the DNA, or prevent or enhance the binding of a polypeptide to DNA.

A "stem-loop structure" refers to a nucleic acid having a secondary structure that includes a region of nucleotides which are known or predicted to form a double-strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, i.e., not include any mismatches.

By "hybridizable" or "complementary" or "substantially complementary" it is meant that a nucleic acid (e.g., RNA) comprises a sequence of nucleotides that enables it to non-covalently bind, i.e., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary.

Hybridization and washing conditions are well known and exemplified in Sambrook, J. and Russell, W., Molecular Cloning: A Laboratory Manual, Third Edition, Cold Spring Harbor Laboratory Press, Cold Spring Harbor (2001); and Green, M. R., and Sambrook, J., Molecular cloning: A Laboratory Manual, Fourth Edition, Cold Spring Harbor Laboratory Press, Cold Spring Harbor (2012). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Generally, the length for a hybridizable nucleic acid is at least 10 nucleotides. Illustrative minimum lengths for a hybridizable nucleic acid are: at least 15 nucleotides; at least 20 nucleotides; at least 22 nucleotides; at least 25 nucleotides; and at least 30 nucleotides). Furthermore, the skilled artisan will recognize that the temperature and wash solution salt concentration maybe adjusted as necessary according to factors such as length of the region of complementation and the degree of complementation.

It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining non complementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol. 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math. 1981 (2) 482-489).

The terms "peptide", "polypeptide", and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g., with reference to an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Kd) of less than 10-6 M, less than 10-7 M, less than 10-8 M, less than 10-9 M, less than 10-10 M, less than 10-11 M, less than 10-12 M, less than 10-13 M, less than 10-14 M, or less than 10-15 M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein-binding protein). In the case of a protein domain-binding protein, it can bind to itself (to form homo-dimers, homo-trimers, etc.) and/or it can bind to one or more molecules of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee, ebi.Ac.Uk!Tools/msa/muscle, mafft.cbrc/alignment/software. See, e.g., Altschul et al. (1990), J. Mol. Biol. 215:403-10. Sequence alignments standard in the art are used according to the invention to determine amino acid residues in one sRGN variant that "correspond to" amino acid residues in another sRGN variant. The amino acid residues of sRGN variants that correspond to amino acid residues of other sRGN variants appear at the same position in alignments of the sequences.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g., tRNA, rRNA, or a guide RNA; also called "non-coding" RNA or "nRNA"). A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located at 3' of the coding sequence.

As used herein, a "promoter sequence" or "promoter" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAAT" boxes. Various promoters, including inducible promoters, may be used to drive the various vectors of the present invention. A promoter can be a constitutively active promoter (i.e., a promoter that is constitutively in an active "ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice). Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol Ill). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like. Examples of inducible promoters include, but are not limited to T7 RNA polymerase promoter, T3 RNA polymerase promoter, isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding an sRGN polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice). For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (e.g., EMBL HSENO2, X51956); an aromatic amino acid decarboxylase (AADC) promoter; a neurofilament promoter (e.g., GenBank HUMNFL, L04147); a synapsin promoter (e.g., GenBank HUMSYNIB, M55301); a thy-1 promoter (e.g., Chen et al. (1987) Cell 51:7-19; and Llewellyn, et al. (2010) Nat. Med. 16(10):1161-1166); a serotonin receptor promoter (e.g., GenBank S62283); a tyrosine hydroxylase promoter (TH) (e.g., Oh et al. (2009) Gene Ther. 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (e.g., Radovick et al. (1991) Proc. Natl. Acad. Sci. USA 88:3402-3406); an L7 promoter (e.g., Oberdick et al. (1990) Science 248:223-226); a DNMT promoter (e.g., Bartge et al. (1988) Proc. Natl. Acad. Sci. USA 85:3648-3652); an enkephalin promoter (e.g., Comb et al. (1988) EMBO J. 17:3793-3805); a myelin basic protein (MBP) promoter; a Ca2+-calmodulin-dependent protein kinase 11-alpha (CamKIM) promoter (e.g., Mayford et al. (1996) Proc. Natl. Acad. Sci. USA 93:13250; and Casanova et al. (2001) Genesis 31:37); a CMV enhancer/platelet-derived growth factor-p promoter (e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (e.g., Knight et al. (2003) Proc. Natl. Acad. Sci. USA 100:14725); a fatty acid translocase (FAT/CD36) promoter (e.g., Kuriki et al. (2002) Biol. Pharm. Bull. 25:1476; and Sato et al. (2002) J. Biol. Chem. 277:15703); a stearoyi-CoA desaturase-1 (SCD1) promoter (Tabor et al. (1999) J. Biol. Chem. 274:20603); a leptin promoter (e.g., Mason et al. (1998) Endocrinol. 139:1013; and Chen et al. (1999) Biochem. Biophys. Res. Comm. 262:187); an adiponectin promoter (e.g., Kita et al. (2005) Biochem. Biophys. Res. Comm. 331:484; and Chakrabarti (2010) Endocrinol. 151: 2408); an adipsin promoter (e.g., Platt et al. (1989) Proc. Natl. Acad. Sci. USA 86:7490); a resistin promoter (e.g., Seo et al. (2003) Molec. Endocrinol. 17:1522); and the like.

Cardiomyocyte-specific spatially restricted promoters include, but are not limited to control sequences derived from the following genes: myosin light chain-2, a-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22a promoter (e.g., Akyiirek et al. (2000) Mol. Med. 6:983; and U.S. Pat. No. 7,169,874); a smoothelin promoter (e.g., WO 2001/018048); an a-smooth muscle actin promoter; and the like. For example, a 0.4 kb region of the SM22a promoter, within which lie two CArG elements, has been shown to mediate vascular smooth muscle cell-specific expression (e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., sRGN polypeptide) and/or regulate translation of an encoded polypeptide.

The term "naturally-occurring" or "unmodified" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "chimeric" as used herein as applied to a nucleic acid or polypeptide refers to one entity that is composed of structures derived from different sources. For example, where "chimeric" is used in the context of a chimeric polypeptide (e.g., a chimeric sRGN polypeptide), the chimeric polypeptide includes amino acid sequences that are derived from different polypeptides, such as polypeptides that have a function other than a Cas nuclease, including, for example, polypeptides that have DNA-modifying activity, transcription factor activity, and/or DNA-associated polypeptide-modifying activity. A chimeric polypeptide may comprise either modified or naturally-occurring polypeptide sequences (e.g., a first amino acid sequence from a modified or unmodified sRGN protein; and a second amino acid sequence other than the sRGN protein). Similarly, "chimeric" in the context of a nucleic acid encoding a chimeric polypeptide includes nucleotide sequences derived from different coding regions (e.g., a first nucleotide sequence encoding a modified or unmodified sRGN protein; and a second nucleotide sequence encoding a polypeptide other than an sRGN protein).

The term "chimeric polypeptide" refers to a polypeptide which is not naturally occurring, e.g., is made by the artificial combination (i.e., "fusion") of two or more otherwise separated segments of amino sequence through human intervention. A polypeptide that comprises a chimeric amino acid sequence is a chimeric polypeptide. Some chimeric polypeptides can be referred to as "fusion variants."

"Heterologous," as used herein, means a nucleotide or peptide that is not found in the native nucleic acid or protein, respectively. For example, in a chimeric sRGN protein, the RNA-binding domain of a naturally-occurring bacterial sRGN polypeptide (or a variant thereof) may be fused to a heterologous polypeptide sequence (i.e., a polypeptide sequence from a protein other than sRGN or a polypeptide sequence from another organism). The heterologous polypeptide may exhibit an activity (e.g., enzymatic activity) that will also be exhibited by the chimeric sRGN protein (e.g., methyltransferase activity, acetyltransferase activity, kinase activity, ubiquitinating activity, etc.). A heterologous nucleic acid may be linked to a naturally-occurring nucleic acid (or a variant thereof) (e.g., by genetic engineering) to generate a chimeric nucleic acid encoding a chimeric polypeptide. As another example, in a fusion variant sRGN site-directed polypeptide, a variant sRGN site-directed polypeptide may be fused to a heterologous polypeptide (i.e., polypeptide other than sRGN), which exhibits an activity that will also be exhibited by the fusion variant sRGN site-directed polypeptide. A heterologous nucleic acid may be linked to a variant sRGN site-directed polypeptide (e.g., by genetic engineering) to generate a nucleic acid encoding a fusion variant sRGN site-directed polypeptide. "Heterologous," as used herein, additionally means a nucleotide or polypeptide in a cell that is not its native cell.

The term "cognate" refers to two biomolecules that normally interact or co-exist in nature.

"Recombinant," as used herein, means that a particular nucleic acid (DNA or RNA) or vector is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination can be accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nuclei acid segments of desired functions to generate a desired combination of functions. This artificial combination can be accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence. The term "non-naturally occurring" includes molecules that are markedly different from their naturally occurring counterparts, including chemically modified or mutated molecules.

A "vector" or "expression vector" is a replicon, such as plasmid, phage, virus, or cosmid, to which another DNA segment, i.e., an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression. The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The nucleic acid(s) may or may not be operably linked to a promoter sequence and may or may not be operably linked to DNA regulatory sequences.

A cell has been "genetically modified" or "transformed" or "transfected" by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell.

In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include but are not limited to, e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (e.g., Panyam et al., Adv Drug Deliv Rev. 2012 Sep. 13. pp: 50169-409X(12)00283-9. doi:10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a bacterial host cell is a genetically modified bacterial host cell by virtue of introduction into a suitable bacterial host cell of an exogenous nucleic acid (e.g., a plasmid or recombinant expression vector) and a eukaryotic host cell is a genetically modified eukaryotic host cell (e.g., a mammalian germ cell), by virtue of introduction into a suitable eukaryotic host cell of an exogenous nucleic acid.

A "target DNA" as used herein is a DNA polynucleotide that comprises a "target site" or "target sequence." The terms "target site," "target sequence," "target protospacer DNA," or "protospacer-like sequence" are used interchangeably herein to refer to a nucleic acid sequence present in a target DNA to which a DNA-targeting segment of a guide RNA will bind, provided sufficient conditions for binding exist. For example, the target site (or target sequence) 5'-GAG-CATATC-3' within a target DNA is targeted by (or is bound by, or hybridizes with, or is complementary to) the RNA sequence 5'-GAUAUGCUC-3'. Suitable DNA/RNA binding conditions include physiological conditions normally present in a cell. Other suitable DNA/RNA binding conditions (e.g., conditions in a cell-free system) are known in the art; e.g., Sambrook, supra. The strand of the target DNA that is complementary to and hybridizes with the guide RNA is referred to as the "complementary strand" and the strand of the target DNA that is complementary to the "complementary strand" (and is therefore not complementary to the guide RNA) is referred to as the "non-complementary strand" or "non-complementary strand." By "site-directed modifying polypeptide" or "RNA-binding site-directed polypeptide" or "RNA-binding site-directed modifying polypeptide" or "site-directed polypeptide" it is meant a polypeptide that binds RNA and is targeted to a specific DNA sequence. A site-directed modifying polypeptide as described herein is targeted to a specific DNA sequence by the RNA molecule to which it is bound. The RNA molecule comprises a sequence that binds, hybridizes to, or is complementary to a target sequence within the target DNA, thus targeting the bound polypeptide to a specific location within the target DNA (the target sequence). By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guide RNA and a site-directed modifying polypeptide is used for targeted double-stranded DNA cleavage.

"Nuclease" and "endonuclease" are used interchangeably herein to mean an enzyme which possesses endonucleolytic catalytic activity for polynucleotide cleavage.

By "cleavage domain" or "active domain" or "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

By "site-directed polypeptide" or "RNA-binding site-directed polypeptide" or "RNA-binding site-directed polypeptide" it is meant a polypeptide that binds RNA and is targeted to a specific DNA sequence. A site-directed polypeptide as described herein is targeted to a specific DNA sequence by the RNA molecule to which it is bound. The RNA molecule comprises a sequence that is complementary to a target sequence within the target DNA, thus targeting the bound polypeptide to a specific location within the target DNA (the target sequence).

The "guide sequence" or DNA-targeting segment (or "DNA-targeting sequence") comprises a nucleotide sequence that is complementary to a specific sequence within a target DNA (the complementary strand of the target DNA) designated the "protospacer-like" sequence herein. The protein-binding segment (or "protein-binding sequence") interacts with a site-directed modifying polypeptide. When the site-directed modifying polypeptide is an sRGN or sRGN related polypeptide (described in more detail below), site-specific cleavage of the target DNA occurs at locations determined by both (i) base-pairing complementarity between the guide RNA and the target DNA; and (ii) a short motif (referred to as the protospacer adjacent motif (PAM)) in the target DNA.

The protein-binding segment of a guide RNA comprises, in part, two complementary stretches of nucleotides that hybridize to one another to form a double-stranded RNA duplex (dsRNA duplex).

In some embodiments, a nucleic acid (e.g., a guide RNA, a nucleic acid comprising a nucleotide sequence encoding a guide RNA; a nucleic acid encoding a site-directed polypeptide; etc.) comprises a modification or sequence that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

In some embodiments, a guide RNA comprises an additional segment at either the 5' or 3' end that provides for any of the features described above. For example, a suitable third segment can comprise a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and protein complexes); a stability control sequence; a sequence that forms a dsRNA duplex (i.e., a hairpin)); a sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

A guide RNA and an sRGN polypeptide form a complex (i.e., bind via non-covalent interactions). The guide RNA provides target specificity to the complex by comprising a nucleotide sequence that is complementary to a sequence of a target DNA. The sRGN polypeptide of the complex provides the site-specific activity. In other words, the sRGN polypeptide is guided to a target DNA sequence (e.g., a target sequence in a chromosomal nucleic acid; a target sequence in an extrachromosomal nucleic acid, e.g., an episomal nucleic acid, a minicircle, etc.; a target sequence in a mitochondrial nucleic acid; a target sequence in a chloroplast nucleic acid; a target sequence in a plasmid; etc.) by virtue of its association with the protein-binding segment of the guide RNA. RNA aptamers are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the RNA molecule of which they are part. RNA aptamers usually comprise a sequence that folds into a particular structure (e.g., a hairpin), which specifically binds a particular drug (e.g., a small molecule). Binding of the drug causes a structural change in the folding of the RNA, which changes a feature of the nucleic acid of which the aptamer is a part. As non-limiting examples: (i) an activator-RNA with an aptamer may not be able to bind to the cognate targeter-RNA unless the aptamer is bound by the appropriate drug; (ii) a targeter-RNA with an aptamer may not be able to bind to the cognate activator-RNA unless the aptamer is bound by the appropriate drug; and (iii) a targeter-RNA and an activator-RNA, each comprising a different aptamer that binds a different drug, may not be able to bind to each other unless both drugs are present. As illustrated by these examples, a two-molecule guide RNA can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley lnterdiscip Rev RNA. 2012 May-June; 3(3):369-84; all of which are herein incorporated by reference in their entirety.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons. cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20).

Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, generally from the inner cell mass of the blastocyst. ESC lines are listed in the NIH Human Embryonic Stem Cell Registry, e.g., hESBGN-01, hES-BGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g., human, equine, bovine, porcine, canine, feline, rodent. e.g., mice, rats, hamster, primate, etc. (Thomson et al. (1998) Science 282:1145; Thomson et al. (1995) Proc. Natl. Acad. Sci. USA 92:7844; Thomson et al. (1996) Biol. Reprod. 55:254; Shamblott et al., Proc. Natl. Acad. Sci. USA 95:13726, 1998). In culture, ESCs generally grow as flat colonies with large nucleo-cytoplasmic ratios, defined borders and prominent nucleoli. In addition, ESCs express SSEA-3, SSEA-4, TRA-1-60, TRA-1-81, and alkaline phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920. By "embryonic germ stem cell" (EGSC) or "embryonic germ cell" or "EG cell" is meant a PSC that is derived from germ cells and/or germ cell progenitors, e.g., primordial germ cells, i.e., those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, Fox03, GDF3, Cyp26a1, TERT, and zfp42.

Examples of methods of generating and characterizing iPSCs may be found in, for example, US Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g., Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e., it is no longer undergoing divisions. This quiescent state may be temporary, i.e., reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

By "recombination" it is meant a process of exchange of genetic information between two polynucleotides. As used herein, "homology-directed repair (HDR)" refers to the specialized form DNA repair that takes place, for example, during repair of double-strand breaks in cells. This process requires nucleotide sequence homology, uses a "donor" molecule to template repair of a "target" molecule (i.e., the one that experienced the double-strand break), and leads to the transfer of genetic information from the donor to the target. Homology-directed repair may result in an alteration of the sequence of the target molecule (e.g., insertion, deletion, mutation), if the donor polynucleotide differs from the target molecule and part or all of the sequence of the donor polynucleotide is incorporated into the target DNA In some embodiments, the donor polynucleotide, a portion of the donor polynucleotide, a copy of the donor polynucleotide, or a portion of a copy of the donor polynucleotide integrates into the target DNA.

By "non-homologous end joining (NHEJ) it is meant the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

The terms "treatment", 'treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., Harboor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (1. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The phrase "consisting essentially of" is meant herein to exclude anything that is not the specified active component or components of a system, or that is not the specified active portion or portions of a molecule.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Synthetic RNA-Guided Nuclease (sRGN)

Synthetic RNA-guided nucleases (sRGNs) can be generated, for example, using homology-based gene family shuffling of artificially defined mini-domains of CRISPR-Cas9 endonucleases of different species, e.g., four different *Staphylococcus* species (*Staphylococcus lugdunensis, Staphylococcus pasteuri, Staphylococcus microti,* and *Staphylococcus hyicus*). One such gene family shuffling protocol is schematically depicted in FIG. 1. Briefly, the sequences of different Cas9 endonucleases are compared to identify regions with high homology to serve as anchor points, breaking each of the Cas9 endonucleases up into a plurality (such as 5, 6, 7, 8, 9, 10, 11, 12, 13, 14, 15, or more) corresponding mini-domains. Libraries of gene family shuffled sRGNs are prepared by randomly assigning each mini-domain to be derived from one of the original Cas9 endonucleases. In some instances, it may be desirable to keep the PAM-interacting (PI) domain fixed so that a single PAM sequence is recognized by each of the library constructs. For example, a library can be prepared by breaking each of the Cas9 endonucleases into 8 mini-domains, holding the C-terminal mini-domain fixed, resulting in a theoretical complexity of 8192. In another example, a library can be prepared by breaking each of the Cas9 endonucleases into 12 mini-domains, holding the C-terminal mini-domain fixed, resulting in a theoretical complexity of $1.3 \times 10^5$. The libraries can be screened using known assays for RNA-guided endonuclease activity, such as bacterial live/dead assays and reporter gene disruption assays, to identify sRGNs having high activity.

In one aspect, provided herein are candidate sRGNs designed according to a homology-based gene family shuffling protocol. The candidate sRGNs have not yet been shown to have any activity. Also provided are sRGNs that have been demonstrated to have at least one activity. In some embodiments, the at least one activity includes, for example, activity in a cleavage assay, such as a fluorescence polarization-based biochemical cleavage assay, a gene-editing assay such as a GFP-to-BFP conversion (Glaser et al., 2016, infra), a gene insertion assay, or assay of other suitable parameters. In some embodiments, on-target cutting is assayed, off-target cutting is assayed, and/or on-target editing (for example, correction of a mutation or insertion of a gene or portion of a gene) is assayed, which may be compared to off-target editing. In some cases, activity is compared to a reference or a control nuclease such as a wild type Cas9. Assays are described in the art and are available from commercial resources. A suitable assay may be carried out in an organism, for example, an animal having a deleterious mutation, and efficacy of an sRGN is assayed by improvement of one or more symptoms associated with the mutation in an animal to which an sRGN system was administered. In some embodiments, the at least one activity is greater than the corresponding activity in one or more of the parental Cas9 endonucleases from which the sRGN is derived. In some embodiments, the at least one activity is greater than the corresponding activity in another wild-type Cas9, such as SluCas9.

In some embodiments, provided herein is a candidate sRGN comprising 8 mini-domains, wherein the mini-domains, from N-terminus to C-terminus, are 1) mini-domain 1 comprising the amino acid sequence of any one of SEQ ID NOs: 34-37 or a variant thereof having at least about 90% (such as at least about any of 91%, 92%, 93%, 94%, 95%, 96%, 97%, 98%, 99%, or more) sequence identity to any one of SEQ ID NOs: 34-37, 2) mini-domain 2 comprising the amino acid sequence of any one of SEQ ID NOs: 38-41 or a variant thereof having at least about 90% (such as at least about any of 91%, 92%, 93%, 94%, 95%, 96%, 97%, 98%, 99%, or more) sequence identity to any one of SEQ ID NOs: 38-41, 3) mini-domain 3 comprising the amino acid sequence of any one of SEQ ID NOs: 42-45 or a variant thereof having at least about 90% (such as at least about any of 91%, 92%, 93%, 94%, 95%, 96%, 97%, 98%, 99%, or more) sequence identity to any one of SEQ ID NOs: 42-45, 4) mini-domain 4 comprising the amino acid sequence of any one of SEQ ID NOs: 46-49 or a variant thereof having at least about 90% (such as at least about any of 91%, 92%, 93%, 94%, 95%, 96%, 97%, 98%, 99%, or more) sequence identity to any one of SEQ ID NOs: 46-49, 5) mini-domain 5 comprising the amino acid sequence of any one of SEQ ID NOs: 50-53 or a variant thereof having at least about 90% (such as at least about any of 91%, 92%, 93%, 94%, 95%, 96%, 97%, 98%, 99%, or more) sequence identity to any one of SEQ ID NOs: 50-53, 6) mini-domain 6 comprising the amino acid sequence of any one of SEQ ID NOs: 54-57 or a variant thereof having at least about 90% (such as at least about any of 91%, 92%, 93%, 94%, 95%, 96%, 97%, 98%, 99%, or more) sequence identity to any one of SEQ ID NOs: 54-57, 7) mini-domain 7 comprising the amino acid sequence of any one of SEQ ID NOs: 58-61 or a variant thereof having at least about 90% (such as at least about any of 91%, 92%, 93%, 94%, 95%, 96%, 97%, 98%, 99%, or more) sequence identity to any one of SEQ ID NOs: 58-61, and 8) mini-domain 8 comprising the amino acid sequence of any one of SEQ ID NOs: 62-65 or a variant thereof having at least about 90% (such as at least about any of 91%, 92%, 93%, 94%, 95%, 96%, 97%, 98%, 99%, or more) sequence identity to any one of SEQ ID NOs: 62-65. In some embodiments, the candidate sRGN comprises mini-domains from *Staphylococcus lugdunensis, Staphylococcus pasteuri, Staphylococcus microti*, and *Staphylococcus hyicus* Cas9s. In some embodiments, the candidate sRGN comprises mini-domains from less than all 4 (such as 2 or 3) Cas9s of *Staphylococcus lugdunensis, Staphylococcus pasteuri, Staphylococcus microti*, and *Staphylococcus hyicus*. In some embodiments, mini-domain 8 comprises the amino acid sequence of SEQ ID NO: 62 or a variant thereof having at least about 90% (such as at least about any of 91%, 92%, 93%, 94%, 95%, 96%, 97%, 98%, 99%, or more) sequence identity to SEQ ID NO: 62. In some embodiments, mini-domain 8 comprises the amino acid sequence of SEQ ID NO: 63 or a variant thereof having at least about 90% (such as at least about any of 91%, 92%, 93%, 94%, 95%, 96%, 97%, 98%, 99%, or more) sequence identity to SEQ ID NO: 63. In some embodiments, mini-domain 1 comprises the amino acid sequence of SEQ ID NO: 34 or a variant thereof having at least about 90% (such as at least about any of 91%, 92%, 93%, 94%, 95%, 96%, 97%, 98%, 99%, or more) sequence identity to SEQ ID NO: 34.

In some embodiments, provided herein is a candidate sRGN comprising 12 mini-domains, wherein the mini-domains, from N-terminus to C-terminus, are 1) mini-domain 1 comprising the amino acid sequence of any one of SEQ ID NOs: 66-69 or a variant thereof having at least about 90% (such as at least about any of 91%, 92%, 93%, 94%, 95%, 96%, 97%, 98%, 99%, or more) sequence identity to any one of SEQ ID NOs: 66-69, 2) mini-domain 2 comprising the amino acid sequence of any one of SEQ ID NOs: 70-73 or a variant thereof having at least about 90% (such as at least about any of 91%, 92%, 93%, 94%, 95%, 96%, 97%, 98%, 99%, or more) sequence identity to any one of SEQ ID NOs: 70-73, 3) mini-domain 3 comprising the amino acid sequence of any one of SEQ ID NOs: 74-77 or a variant thereof having at least about 90% (such as at least about any of 91%, 92%, 93%, 94%, 95%, 96%, 97%, 98%, 99%, or more) sequence identity to any one of SEQ ID NOs: 74-77, 4) mini-domain 4 comprising the amino acid sequence of any one of SEQ ID NOs: 78-81 or a variant thereof having at least about 90% (such as at least about any of 91%, 92%, 93%, 94%, 95%, 96%, 97%, 98%, 99%, or more) sequence identity to any one of SEQ ID NOs: 78-81, 5) mini-domain 5 comprising the amino acid sequence of any one of SEQ ID NOs: 82-85 or a variant thereof having at least about 90% (such as at least about any of 91%, 92%, 93%, 94%, 95%, 96%, 97%, 98%, 99%, or more) sequence identity to any one of SEQ ID NOs: 82-85, 6) mini-domain 6 comprising the amino acid sequence of any one of SEQ ID NOs: 86-89 or a variant thereof having at least about 90% (such as at least about any of 91%, 92%, 93%, 94%, 95%, 96%, 97%, 98%, 99%, or more) sequence identity to any one of SEQ ID NOs: 86-89, 7) mini-domain 7 comprising the amino acid sequence of any one of SEQ ID NOs: 90-93 or a variant thereof having at least about 90% (such as at least about any of 91%, 92%, 93%, 94%, 95%, 96%, 97%, 98%, 99%, or more) sequence identity to any one of SEQ ID NOs: 90-93, 8) mini-domain 8 comprising the amino acid sequence of any one of SEQ ID NOs: 94-97 or a variant thereof having at least about 90% (such as at least about any of 91%, 92%, 93%, 94%, 95%, 96%, 97%, 98%, 99%, or more) sequence identity to any one of SEQ ID NOs: 94-97, 9) mini-domain 9 comprising the amino acid sequence of any one of SEQ ID NOs: 98-101 or a variant thereof having at least about 90% (such as at least about any of 91%, 92%, 93%, 94%, 95%, 96%, 97%, 98%, 99%, or more) sequence identity to any one of SEQ ID NOs: 98-101, 10) mini-domain 10 comprising the amino acid sequence of any one of SEQ ID NOs: 102-105 or a variant thereof having at least about 90% (such as at least about any of 91%, 92%, 93%, 94%, 95%, 96%, 97%, 98%, 99%, or more) sequence identity to any one of SEQ ID NOs: 102-105, 11) mini-domain 11 comprising the amino acid sequence of any one of SEQ ID NOs: 106-109 or a variant thereof having at least about 90% (such as at least about any of 91%, 92%, 93%, 94%, 95%, 96%, 97%, 98%, 99%, or more) sequence identity to any one of SEQ ID NOs: 106-109, and 12) mini-domain 12 comprising the amino acid sequence of any one of SEQ ID NOs: 110-113 or a variant thereof having at least about 90% (such as at least about any of 91%, 92%, 93%, 94%, 95%, 96%, 97%, 98%, 99%, or more) sequence identity to any one of SEQ ID NOs: 110-113. In some embodiments, the candidate sRGN comprises mini-domains from *Staphylococcus lugdunensis, Staphylococcus pasteuri, Staphylococcus microti*, and *Staphylococcus hyicus* Cas9s. In some embodiments, the candidate sRGN comprises mini-domains from less than all 4 (such as 2 or 3) Cas9s of *Staphylococcus lugdunensis, Staphylococcus pasteuri, Staphylococcus microti*, and *Staphylococcus hyicus*. In some embodiments, mini-domain 12 comprises the amino acid sequence of SEQ ID NO: 110 or a variant thereof having at least about 90% (such as at least about any of 91%, 92%, 93%, 94%, 95%, 96%, 97%, 98%, 99%, or more) sequence identity to SEQ ID NO: 110. In some embodiments, mini-domain 12 comprises the amino acid sequence of SEQ ID NO: 111 or a variant thereof having at least about 90% (such as at least about any of 91%, 92%, 93%, 94%, 95%, 96%, 97%, 98%, 99%, or more) sequence identity to SEQ ID NO: 111. In some embodiments, (i) mini-domain 1 comprises the amino acid sequence of SEQ ID NO: 66 or a variant thereof having at least about 90% (such as at least about any of 91%, 92%, 93%, 94%, 95%, 96%, 97%, 98%, 99%, or more) sequence identity to SEQ ID NO: 66 and (ii) mini-domain 2 comprises the amino acid sequence of SEQ ID NO: 70 or a variant thereof having at least about 90% (such as at least about any of 91%, 92%, 93%, 94%, 95%, 96%, 97%, 98%, 99%, or more) sequence identity to SEQ ID NO: 70.

The sRGN polypeptides Gib11 (SEQ ID NO: 1), P2H12 (SEQ ID NO: 5), E2 (SEQ ID NO: 6), and F8 (SEQ ID NO: 10) disclosed herein were identified using such a gene family shuffling protocol, and Gib11Spa variants (SEQ ID NOs: 2-4) were generated by replacing different C-terminal portions of Gib11 with the corresponding portions of *Staphylococcus pasteuri* Cas9.

The sRGN polypeptides disclosed herein are small compared to Cas9 from *Streptococcus pyogenes* (also referred to herein as "SpCas9" or "SpyCas9"), and interact with an NNGG PAM sequence.

In one aspect, provided herein is an sRGN polypeptide comprising the amino acid sequence of any one of SEQ ID NOs: 1-12 or a variant thereof having at least about 90% (such as at least about any of 91%, 92%, 93%, 94%, 95%, 96%, 97%, 98%, 99%, or more) sequence identity to any one of SEQ ID NOs: 1-12. In some embodiments, the sRGN polypeptide comprises the amino acid sequence of any one of SEQ ID NOs: 1-12.

In some embodiments, provided herein is an sRGN polypeptide comprising an amino acid sequence having at least about 90% (such as at least about any of 91%, 92%, 93%, 94%, 95%, 96%, 97%, 98%, 99%, or more) sequence identity to a subsequence of any one of SEQ ID NOs: 1-12, wherein the subsequence comprises one or more functional sRGN domains. In some embodiments, the sRGN polypeptide comprises (or consists of) a subsequence of any one of SEQ ID NOs: 1-12. In some embodiments, the one or more sRGN domains include a nuclease domain (e.g., an HNH or RuvC domain). In some embodiments, the one or more sRGN domains include an RNA-binding domain (e.g., a Rec I domain). In some embodiments, the one or more sRGN domains include a PAM-interacting domain.

In some embodiments, provided herein is a Gib11 variant including:
(I) variants of at least 90% (such as at least about any of 91%, 92%, 93%, 94%, 95%, 96%, 97%, 98%, 99%, or more) sequence identity to the amino acid sequence of SEQ ID NO: 1 over its entire length, or over the sequence from position 787 to position 1057 of SEQ ID NO: 1;
(II) variants according to (I) that further comprise components such as, e.g., nuclear localization signals, to obtain appropriate activity of a Gib11 CRISPR system not only in a cell-free reaction or in prokaryotic cells but also in eukaryotic cellular environments such as, for example, live organisms like plants or animals;
(III) codon-optimized variants of the corresponding polynucleotide sequences encoding Gib11 and the variants according to (I) and (II);
(IV) variants according to any of (I) to (III) that further comprise:
(a) one or more modification(s) or mutation(s) that result in an sRGN with a significantly reduced or non-detectable nuclease activity, for example, having an alanine, or any other exchange leading to a significantly reduced nuclease activity, in position 10 (e.g., D10A), position 562 (e.g., H562A), and/or position 585 (e.g., N585A) with respect to SEQ ID NO: 1; and
(b) a C- or N-terminally attached polypeptide with a nucleotide base editing activity or deaminase activity, such as via a linker peptide.

In some embodiments, provided herein is a P2H12 variant including:
(I) variants of at least 90% (such as at least about any of 91%, 92%, 93%, 94%, 95%, 96%, 97%, 98%, 99%, or more) sequence identity to the amino acid sequence of SEQ ID NO: 5 over its entire length, or over the sequence from position 784 to position 1055 of SEQ ID NO: 5;
(II) variants according to (I) that further comprise components such as, e.g., nuclear localization signals, to obtain appropriate activity of a P2H12 CRISPR system not only in a cell-free reaction or in prokaryotic cells but also in eukaryotic cellular environments such as, for example, live organisms like plants or animals;
(III) codon-optimized variants of the corresponding polynucleotide sequences encoding P2H12 and the variants according to (I) and (II);
(IV) variants according to any of (I) to (III) that further comprise:
(a) one or more modification(s) or mutation(s) that result in an sRGN with a significantly reduced or non-detectable nuclease activity, for example, having an alanine, or any other exchange leading to a significantly reduced nuclease activity, in position 10 (e.g., D10A), position 559 (e.g., H559A), and/or position 582 (e.g., N582A) with respect to SEQ ID NO: 5; and
(b) a C- or N-terminally attached polypeptide with a nucleotide base editing activity or deaminase activity, such as via a linker peptide.

In some embodiments, provided herein is an E2 variant including:
(I) variants of at least 90% (such as at least about any of 91%, 92%, 93%, 94%, 95%, 96%, 97%, 98%, 99%, or more) sequence identity to the amino acid sequence of SEQ ID NO: 6 over its entire length, or over the sequence from position 1 to position 789 of SEQ ID NO: 6;
(II) variants according to (I) that further comprise components such as, e.g., a nuclear localization signal, to obtain appropriate activity of a E2 CRISPR system not only in a cell-free reaction or in prokaryotic cells but also in eukaryotic cellular environments such as, for example, live organisms like plants or animals;
(III) codon-optimized variants of the corresponding polynucleotide sequences encoding E2 and the variants according to (I) and (II);
(IV) variants according to any of (I) to (III) that further comprise:
(a) one or more modification(s) or mutation(s) that result in an sRGN with a significantly reduced or non-detectable nuclease activity, for example, having an alanine, or any other exchange leading to a significantly reduced nuclease activity, in position 10 (e.g., D10A), position 562 (e.g., H562A), and/or position 585 (e.g., N585A) with respect to SEQ ID NO: 6; and
(b) a C- or N-terminally attached polypeptide with a nucleotide base editing activity or deaminase activity, such as via a linker peptide.

In some embodiments, provided herein is an F8 variant including:
(I) variants of at least 90% (such as at least about any of 91%, 92%, 93%, 94%, 95%, 96%, 97%, 98%, 99%, or more) sequence identity to the amino acid sequence of SEQ ID NO: 10 over its entire length, or over the sequence from position 1 to position 789 of SEQ ID NO: 10;
(II) variants according to (I) that further comprise components such as, e.g., nuclear localization signals, to obtain appropriate activity of a F8 CRISPR system not only in a cell-free reaction or in prokaryotic cells but also in eukaryotic cellular environments such as, for example, live organisms like plants or animals;
(III) codon-optimized variants of the corresponding polynucleotide sequences encoding F8 and the variants according to (I) and (II);
(IV) variants according to any of (I) to (III) that further comprise:
(a) one or more modification(s) or mutation(s) that result in an sRGN with a significantly reduced or non-detectable nuclease activity, for example, having an alanine, or any other exchange leading to a significantly reduced nuclease activity, in position 10 (e.g., D10A), position 562 (e.g., H562A), and/or position 585 (e.g., N585A) with respect to SEQ ID NO: 10; and
(b) a C- or N-terminally attached polypeptide with a nucleotide base editing activity or deaminase activity, such as via a linker peptide.

In some embodiments, provided herein is a Gib11Spa-1 variant including:
(I) variants of at least about 90% (such as at least about any of 91%, 92%, 93%, 94%, 95%, 96%, 97%, 98%, 99%, or more) sequence identity to the amino acid sequence of SEQ ID NO: 2;
(II) variants according to (I) that further comprise components such as, e.g., nuclear localization signals, to obtain appropriate activity of a Gib11Spa-1 CRISPR system not only in a cell-free reaction or in prokaryotic cells but also in eukaryotic cellular environments such as, for example, live organisms like plants or animals;
(III) codon-optimized variants of the corresponding polynucleotide sequences encoding Gib11Spa and the variants according to (I) and (II);
(IV) variants according to any of (I) to (III) that further comprise:
(a) one or more modification(s) or mutation(s) that result in an sRGN with a significantly reduced or non-detectable nuclease activity, for example, having an alanine, or any other exchange leading to a significantly reduced nuclease activity, in position 10 (e.g., D10A), position 562 (e.g., H562A), and/or position 585 (e.g., N585A) with respect to SEQ ID NO: 2; and
(b) a C- or N-terminally attached polypeptide with a nucleotide base editing activity or deaminase activity, such as via a linker peptide.

In some embodiments, provided herein is a Gib11Spa-2 variant including:
(I) variants of at least about 90% (such as at least about any of 91%, 92%, 93%, 94%, 95%, 96%, 97%, 98%, 99%, or more) sequence identity to the amino acid sequence of SEQ ID NO: 3;
(II) variants according to (I) that further comprise components such as, e.g., nuclear localization signals, to obtain appropriate activity of a Gib11Spa-2 CRISPR system not only in a cell-free reaction or in prokaryotic cells but also in eukaryotic cellular environments such as, for example, live organisms like plants or animals;
(III) codon-optimized variants of the corresponding polynucleotide sequences encoding Gib11Spa and the variants according to (I) and (II);
(IV) variants according to any of (I) to (III) that further comprise:
(a) one or more modification(s) or mutation(s) that result in an sRGN with a significantly reduced or non-detectable nuclease activity, for example, having an alanine, or any other exchange leading to a significantly reduced nuclease activity, in position 10 (e.g., D10A), position 562 (e.g., H562A), and/or position 585 (e.g., N585A) with respect to SEQ ID NO: 3; and
(b) a C- or N-terminally attached polypeptide with a nucleotide base editing activity or deaminase activity, such as via a linker peptide.

In some embodiments, provided herein is a Gib11Spa-3 variant including:
(I) variants of at least about 90% (such as at least about any of 91%, 92%, 93%, 94%, 95%, 96%, 97%, 98%, 99%, or more) sequence identity to the amino acid sequence of SEQ ID NO: 4;
(II) variants according to (I) that further comprise components such as, e.g., nuclear localization signals, to obtain appropriate activity of a Gib11Spa-3 CRISPR system not only in a cell-free reaction or in prokaryotic cells but also in eukaryotic cellular environments such as, for example, live organisms like plants or animals;
(III) codon-optimized variants of the corresponding polynucleotide sequences encoding Gib11Spa and the variants according to (I) and (II);
(IV) variants according to any of (I) to (III) that further comprise:
(a) one or more modification(s) or mutation(s) that result in an sRGN with a significantly reduced or non-detectable nuclease activity, for example, having an alanine, or any other exchange leading to a significantly reduced nuclease activity, in position 10 (e.g., D10A), position 562 (e.g., H562A), and/or position 585 (e.g., N585A) with respect to SEQ ID NO: 4; and
(b) a C- or N-terminally attached polypeptide with a nucleotide base editing activity or deaminase activity, such as via a linker peptide.

The term "significantly reduced" for example used in the context of an enzymatic activity means that such enzymatic activity is lower than about 10% of the activity of a reference protein (e.g., any one of SEQ ID NOs: 1-12), for example, lower than 5%, lower than 2%, lower than 1%, or lower than 0.1% of such reference enzymatic activity.

Suitable polypeptides under (IV) (b) and their attachment to the C-terminal domain of an sRGN under (I), (II), and (III) are described for example in WO2017/070632, Gaudelli et al., Nature 551(23 Nov. 2017), 464-471; Komor et al., Sci. Adv. 2017; 3eaao4774; Kim et al., Nature Biotechnol. 2017 April; 35(4) 371-376; Komor et al., Nature 533(7603); 420-424.

Instead of introducing double-strand breaks into the target DNA sequence, sRGN variants under (IV) could allow the conversion of any base pair into any possible other base pair. One non-limiting example is a deaminase activity that could act upon cytosine, guanine or adenine bases and their subsequent replication through the deaminated site and repair within the cell to yield guanine, thymine, and guanine, respectively.

If not otherwise specified, the term sRGN includes the sRGN polypeptide of any one of SEQ ID NOs: 1-12 as well as all of the variants thereof described herein, such as those specified under (I), (II), (III), and (IV).

In some embodiments, provided herein are mutants of E2 that with respect to SEQ ID NO: 6, comprise: a) an aspartate residue in position 741, and a lysine residue in position 743 (E2+K741D+L743K, SEQ ID NO: 7); or b) a threonine residue in position 670, and an aspartate residue in position 675 (E2+S670T+N675D, SEQ ID NO: 8); or c) an asparagine residue in position 741, and an asparagine residue in position 743 (E2+K741N+L743N, SEQ ID NO: 9); or d) any combination of the above (a) to (c).

In some embodiments, provided herein are mutants of E2 comprising i) at least about 90% (such as at least about any of 91%, 92%, 93%, 94%, 95%, 96%, 97%, 98%, 99%, or more) amino acid identity to the sequence according to SEQ ID NO: 6 over its entire length, or to the sequence from position 1 to position 789 of SEQ ID NO: 6; and ii) when aligned to a continuous stretch starting with 5 positions before a1 and ending 5 positions behind a1 of Table 1, exhibits the amino acid residue in position al as shown in Table 1; and iii) when aligned to a continuous stretch starting with 5 positions before a2 and ending 5 positions behind a2 of Table 1, exhibits the amino acid residue in position a2 as shown in Table 1; wherein aligned means the alignment of the stretch of 11 amino acid residues to the sequence according to SEQ ID NO: 6 using a standard local alignment tool or algorithm, including for example Protein BLAST (https://blast.ncbi.nlm.nih.gov, the National Center for Biotechnology [cited on May 17, 2018] Information; Altschul, S. F., Gish, W., Miller, W., Myers, E. W. & Lipman, D. J. (1990) "Basic local alignment search tool." J. Mol. Biol. 215:403-410) using standard parameters, and wherein at least 4 of the 5 preceding amino acids of a1 or a2 and 4 of the 5 amino acids behind a1 or a2 are identical.

TABLE 1

| Positions according to SEQ ID NO: 6 | Amino acid residue in position a1 | Amino acid residue in position a2 |
|---|---|---|
| a1 = 670, a2 = 675 | threonine | aspartate |
| a1 = 741, a2 = 743 | aspartate | lysine |
| a1 = 741, a2 = 743 | asparagine | asparagine |

If not otherwise specified, the term E2 comprises the E2 mutants, including E2+K741D+L743K; E2+S670T+N675D; and E2+K741N+L743N.

In some embodiments, provided herein are mutants of F8 that with respect to SEQ ID NO: 10 comprise a) an aspartate residue in position 737, and a lysine residue in position 739 (F8+K737D+L739K, SEQ ID NO: 11); or b) an asparagine residue in position 737, and an asparagine residue in position 739 (F8+K737N+L739N, SEQ ID NO: 12).

In some embodiments, provided herein are mutants of F8 comprising i) at least about 90% (such as at least about any of 91%, 92%, 93%, 94%, 95%, 96%, 97%, 98%, 99%, or more) amino acid identity to the sequence according to SEQ ID NO: 10 over its entire length, or to the sequence from position 1 to position 787 of SEQ ID NO: 10; and ii) when aligned to a continuous stretch starting with 5 positions before a1 and ending 5 positions behind a1 of Table 2 exhibits the amino acid residue in position al as shown in Table 2; and iii) when aligned to a continuous stretch starting with 5 positions before a2 and ending 5 positions behind a2 of Table 2 exhibits the amino acid residue in position a2 as shown in Table 2; wherein aligned means the alignment of the stretch of 11 amino acid residues to the sequence according to SEQ ID NO: 10 using a standard local alignment tool or algorithm, like for example Protein BLAST (blast.ncbi.nlm.nih.gov, the National Center for Biotechnology [cited on May 17, 2018] Information; Altschul, S. F., Gish, W., Miller, W., Myers, E. W. & Lipman, D. J. (1990) "Basic local alignment search tool." J. Mol. Biol. 215:403-410) using standard parameters, and wherein at least 4 of the 5 preceding amino acids of a1 or a2 and 4 of the 5 amino acids behind a1 or a2 are identical.

TABLE 2

| Positions according to SEQ ID NO: 10 | Amino acid residue in position a1 | Amino acid residue in position a2 |
|---|---|---|
| a1 = 737, a2 = 739 | aspartate | lysine |
| a1 = 737, a2 = 739 | asparagine | asparagine |

If not otherwise specified, the term F8 comprises the F8 mutants, including F8+K737D+L739K; and F8+K737N+L739N.

Additional sRGNs can be generated by identifying pairwise combinations of mini-domains in highly active sRGNs generated by gene family shuffling using a given library, and including at least one of these pairwise combination in a rationally designed sRGN, where the remaining sRGN mini-domains are selected from the library. The remaining mini-domains may be selected from those originating from the same parental Cas9s as the mini-domains in the pairwise combination. The rationally designed sRGN may further include one or more additional pairwise combinations of mini-domains in highly active sRGNs. For example, the rationally designed sRGN may comprise 2, 3, 4, 5, or more pairwise combinations of mini-domains present in highly active sRGNs.

Chimeric RNA-Guided Nuclease (cRGN)

Also provided herein are chimeric RNA-guided nucleases (cRGNs) comprising: A) an N-terminal part (cRGN-A), taken either from a type II CRISPR RNA-guided endonuclease Cas9 of a *Staphylococcus*, or a synthetic RNA-guided nuclease generated by DNA shuffling sequence of two or more *Staphylococcus* type II CRISPR RNA-guided endonuclease Cas proteins, such as any of the sRGNs described herein; and b) a C-terminal part (cRGN-B) taken from the type II CRISPR RNA-guided endonuclease Cas9 from *Staphylococcus pasteuri* (NCBI Refseq WP_023374365.1); wherein cRGN-B comprises i) the entire PI domain of the type II CRISPR RNA-guided endonuclease Cas9 from *Staphylococcus pasteuri* (NCBI Refseq WP_023374365.1), which is the sequence starting from amino acid position 905 and ending at amino acid position 1054 of the sequence according to NCBI Refseq WP_023374365.1; or ii) the entire PI domain of the type II CRISPR RNA-guided endonuclease Cas9 from *Staphylococcus pasteuri* (NCBI Refseq WP_023374365.1) and the entire WED domain, which is located from amino acid position 784 to amino acid position 904 of the sequence according to NCBI Refseq WP_023374365.1; cRGN-A comprises the first 700 amino acids of the respective type II CRISPR RNA-guided endonuclease Cas9 sequence, such as the first 739 amino acids, or the first 783 amino acids, with the exception of a sequence which is more than 99.9% identical, in some casesmore than 99.5% identical on amino acid level to the respective part of NCBI Refseq WP_023374365.1 from *Staphylococcus pasteuri*; and cRGN-A is attached to cRGN-B either directly or by a linker peptide sequence. In some embodiments, cRGN-A comprises more than the first 700 amino acids of the respective type II CRISPR RNA-guided endonuclease Cas9 sequence, such as the first 739 amino acids, or the first 783 amino acids.

Figure 6:
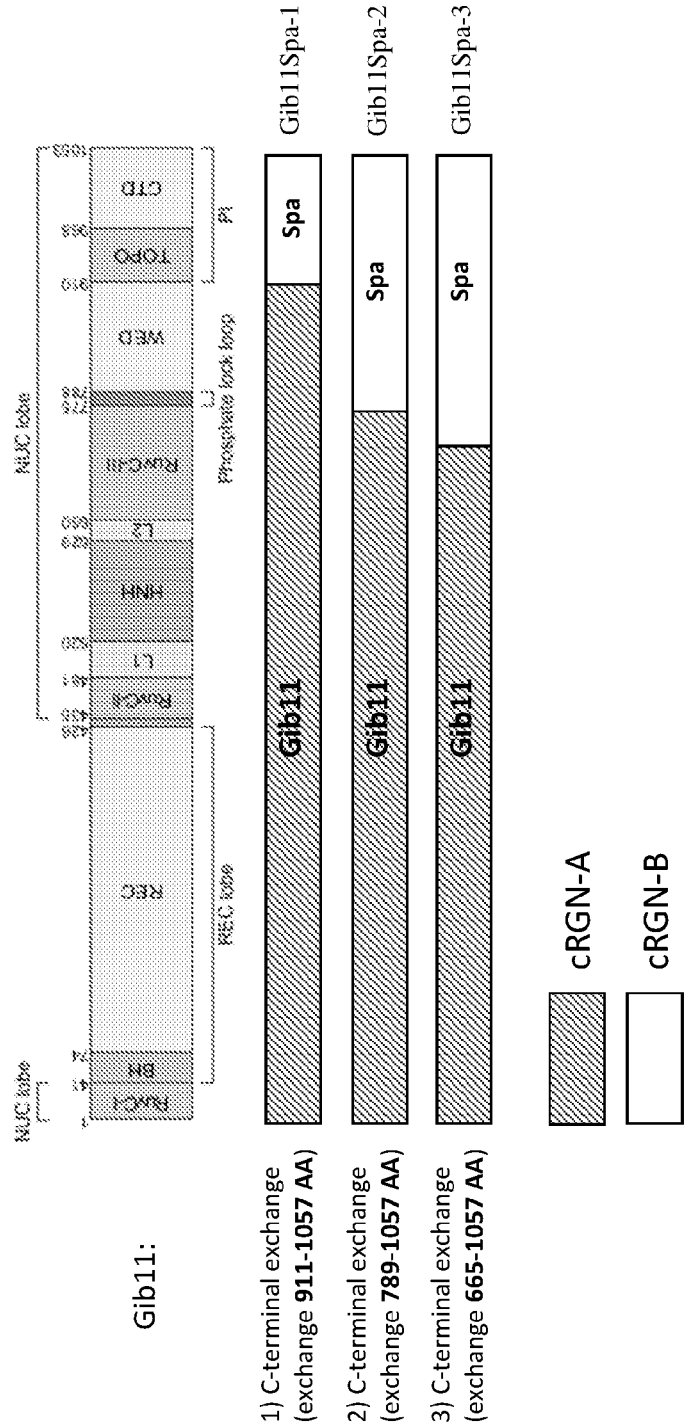
FIG. 6 shows the predicted domain structure of Gib11Spa-1, Gib11Spa-2, and Gib11Spa-3 based on the domain organization of the *Staphylococcus aureus* protein The bracket named PI denotes the PI domain of the underlying Gib11 sequence. The corresponding cRGN-A portion is shown as a hatched box (in this case for Gib11) and the cRGN-B *Staphylococcus pasteuri* portion is shown as a white box. Amino acid positions are in reference to the Gib11 protein (SEQ ID NO: 1).

The PI domain and WED domain for the type II CRISPR RNA-guided endonuclease Cas9 of *Staphylococcus aureus* are described in Nishimasu et al., Cell. 2015 Aug. 27;

162(5): 1113-1126. The potential localization of both domains is further shown in FIG. 6.

Any reference to the NCBI Refseq database within this patent application refers to the following citation: National Center for Biotechnology Information (NCBI) [Internet]. Bethesda (MD): National Library of Medicine (US), National Center for Biotechnology Information; [1988]-[cited 2018 May 11]. Available from: www.ncbi.nlm.nih.gov/protein. For example, for NCBI Refseq WP 048803085, this is www.ncbi.nlm.nih.gov/protein/WP_048803085.

Any reference to *Staphylococcus* alone means the genus *Staphylococcus*.

DNA shuffling in the context of this invention means the exchange of sequence fragments between different (e.g., from different *Staphylococcus* species) type II CRISPR Cas9 endonuclease DNA sequences to yield chimeric DNA sequences encoding synthetic proteins having an RNA-guided endonuclease activity, such as the activity of type II CRISPR Cas9 endonuclease. Such techniques are inter alia described in Joern J. M. (2003) DNA Shuffling. In: Arnold F. H., Georgiou G. (eds) Directed Evolution Library Creation. Methods in Molecular Biology™, vol 231. Humana Press, as well as in Gibbs et al., Gene. 2001 Jun. 13; 271(1):13-20.

In some embodiments, the type II CRISPR RNA-guided endonuclease Cas9 from *Staphylococcus* is identified by one of the following entries of the NCBI Refseq database:
WP_053019794, WP_071859985, WP_049437627, WP_081329738, WP_081330634, WP_088922804, WP_061854099, WP_096792116, WP_107588422, WP_107543406, WP_105966910, WP_083326931, WP_105977729, WP_107578657, WP_107533955, WP_107597066, WP_105980293, WP_105978400, WP_107539784, WP_083326835, WP_096754380, WP_107580550, WP_107530431, WP_107597643, WP_107596301, WP_082732265, WP_083310250, WP_082709447, WP_105994700, WP_107568091, WP_107544007, WP_103361957, WP_001573634, WP_107576310, WP_107571611, WP_107593728, WP_103167028, WP_107532850, WP_002460848, WP_107506206, WP_104681501, WP_107546539, WP_058710220, WP_075777761, WP_050331073, WP_050345681, WP_053017934, WP_049415449, WP_060829977, WP_070855141, WP_107641154, WP_107392933, WP_107389582, WP_107390356, WP_107378401, WP_107378676, WP_060552032, WP_107376447, WP_039643679, WP_101457364, WP_104039168, WP_104052030, WP_085237539, WP_103357343, WP_044361501, WP_107366415, WP_107393309, WP_107633689, WP_107397003, WP_107386954, WP_107371508, WP_107538271, WP_107642914, WP_107536061, WP_107605852, WP_107547877, WP_107634675, WP_107532082, WP_107604007, WP_103356745, WP_107642811, WP_103298901, WP_107611983, WP_107623815, WP_107522281, WP_107560076, WP_107368542, WP_081502240, WP_107604002, WP_107377516, WP_016424980, WP_009382362, WP_001573633, WP_016424981, WP_103298687, WP_103361956, WP_107637979, WP_107612621, WP_107642817, WP_103356723, WP_107593719, WP_070592992, WP_107536245, WP_103209613, WP_063284667, WP_101457463, WP_105503156, WP_096548249, WP_096536567, WP_014613259, WP_063278948, WP_096601671, WP_103863320, WP_096559644, WP_019167918, WP_086428210, WP_096665615, WP_105976295, WP_107576302, WP_105977863, WP_107544006, WP_107538330, WP_070848771, WP_096605716, WP_095105824, WP_105966809, WP_070469119, WP_096589032, WP_105996442, WP_107552556, WP_060803934, WP_107549437, WP_107579080, WP_107547813, WP_107591747, WP_105978348, WP_096598476, WP_107587102, WP_107533825, WP_107588308, WP_107567989, WP_096544347, WP_023015764, WP_103322053, WP_060803559, WP_048803085, WP_107530433, WP_107580731, WP_107368971, WP_107559912, WP_107371387, WP_107571609, WP_107559911, WP_107571610, WP_107530436, WP_107580472, WP_017000597, WP_023374365, WP_062197343, WP_035512507, WP_079708828, WP_101040307, WP_053216997, WP_106588293, WP_107585021, WP_082099322, WP_017185731, WP_101662761, WP_084780162, WP_016837331, WP_084781893, WP_106494556, WP_088825434, WP_088816271, WP_059140148, WP_007547525, WP_084347835, WP_070710475, WP_077907981, WP_035723552, WP_058095017, WP_006446566, WP_074693676, WP_050980543, WP_001271093, WP_001271092, WP_087971021, WP_061668060, WP_016119566, WP_016106885, WP_088031364, WP_088038716, WP_007476473, WP_003343632, WP_088049424, WP_003354196, WP_066148467, WP_082806588, WP_087094968, WP_048723014, WP_033844707, WP_055358891, WP_081209836, WP_033018780, WP_023633350, WP_046580811, WP_081157433, WP_087959824, WP_041267823, WP_018922791, WP_063577905, WP_066227285, WP_044736072, WP_033016936, WP_100664518, WP_064213580, WP_053532223, WP_042224718, WP_084138993, WP_010632729, WP_018130201, WP_088027793, WP_065212529, WP_048539452, WP_001105083, WP_001105082, WP_086397116, WP_086390158, WP_070006567, WP_003739838, WP_070034634, WP_075702521, WP_029090905, WP_038409211, WP_069125601, WP_046323366, WP_069887401, WP_069134523, WP_061665472, WP_070294293, WP_003749665, WP_070784981, WP_031669209, WP_106787163, WP_077287021, WP_085392451, WP_023548323, WP_061108493, WP_101152964, WP_101143843, WP_101143453, WP_101140817, WP_066465432, WP_033920898, WP_069001072, WP_085400884, WP_101057368, WP_088838826, WP_072240946, WP_033838504, WP_010991369, WP_072218760, WP_072238933, WP_070227966, WP_061663015, WP_003733029, WP_101142252, WP_070031693, WP_070785826, WP_003730785, WP_070274575, WP_003727705, WP_069890501, WP_070233243, WP_070039312, WP_031665337, WP_070222802, WP_070264592, WP_103682188, WP_070299153, WP_070307355, WP_061395959, WP_070764199, WP_061128889, WP_070283519, WP_069009724, WP_070228842, WP_014601172, WP_103757671, WP_070293394, WP_060587936, WP_070238603, WP_070215465, WP_003723650, WP_070214481, WP_058876445, WP_060567941, WP_029499861, WP_027129613, WP_003145379, WP_080151624, WP_021752441, WP_069132012, WP_084038511, WP_004632196, WP_066230975, WP_072520207, WP_082729137, WP_080149038, WP_072233091, WP_072240445, WP_072218465, WP_072239624, WP_080151670, WP_077914265, WP_080151712, WP_052025682, WP_077914264, WP_100353964, WP_046517046, WP_008341324, In some embodiments, a cRGN-A is from Gib11 (SEQ ID NO: 1). In some embodiments, the cRGN is Gib11Spa-1 (SEQ ID NO: 2), Gib11Spa-2 (SEQ ID NO: 3), or Gib11Spa-3 (SEQ ID NO: 4).

Other Small Cas Nucleases

In one aspect, provided herein is a Cas9 from *Staphylococcus pasteuri, Staphylococcus microti,* or *Staphylococcus hyicus*. In some embodiments, the Cas9 is from *Staphylococcus pasteuri*, and comprises the amino acid sequence of SEQ ID NO: 31 or a variant thereof having at least about 90% (such as at least about any of 91%, 92%, 93%, 94%, 95%, 96%, 97%, 98%, 99%, or more) sequence identity to SEQ ID NO: 31. *Staphylococcus pasteuri* Cas9, or "SpaCas9," recognizes the PAM sequence NNGG. In some embodiments, the Cas9 is from *Staphylococcus microti*, and comprises the amino acid sequence of SEQ ID NO: 33 or a variant thereof having at least about 90% (such as at least about any of 91%, 92%, 93%, 94%, 95%, 96%, 97%, 98%, 99%, or more) sequence identity to SEQ ID NO: 33. *Staphylococcus microti* Cas9, or "SmiCas9," recognizes the PAM sequence NNGG. In some embodiments, the Cas9 is from *Staphylococcus hyicus*, and comprises the amino acid sequence of SEQ ID NO: 32 or a variant thereof having at least about 90% (such as at least about any of 91%, 92%, 93%, 94%, 95%, 96%, 97%, 98%, 99%, or more) sequence identity to SEQ ID NO: 32. *Staphylococcus hyicus* Cas9, or "ShyCas9," recognizes the PAM sequence NNAAAA. In some cases, these small Cas9s can be used as an alternative to an sRGN in any of the systems, composition, and methods described herein.

CRISPR-Cas System Based on sRGN Polypeptides

In some embodiments, provided herein is a system comprising: (a) an sRGN polypeptide or variant thereof having at least about 90% (such as at least about any of 91%, 92%, 93%, 94%, 95%, 96%, 97%, 98%, 99%, or more) sequence identity to any one of SEQ ID NOs: 1-12, or a nucleic acid encoding the sRGN polypeptide or variant thereof; and (b) a guide RNA (gRNA) or nucleic acid encoding the gRNA, wherein the gRNA is capable of guiding the sRGN polypeptide or variant thereof to a target polynucleotide sequence. In some embodiments, the system comprises the sRGN polypeptide or variant thereof. In some embodiments, the sRGN polypeptide comprises (or consists of) the amino acid sequence of any one of SEQ ID NOs: 1-12. In some embodiments, the system comprises the nucleic acid encoding the sRGN. In some embodiments, the nucleic acid has at least about 90% (such as at least about any of 91%, 92%, 93%, 94%, 95%, 96%, 97%, 98%, 99%, or more) sequence identity to SEQ ID NO: 13-29. In some embodiments, the nucleic acid comprises (or consists of) the sequence of SEQ ID NO: 13-29. In some embodiments, the system comprises the gRNA. In some embodiments, the system comprises nucleic acid encoding the gRNA. In some embodiments, the gRNA is a single guide RNA (sgRNA). In some embodiments, the system further comprises one or more additional gRNAs or nucleic acid encoding the one or more additional gRNAs.

In some embodiments, according to any of the nucleic acids comprising a polynucleotide sequence encoding an sRGN polypeptide or variant thereof described herein, the polynucleotide sequence is operably linked to (i) a suitable promoter for the expression in a cellular or in vitro environment; and/or (ii) a suitable nuclear localization signal.

In some embodiments, according to any of the nucleic acids encoding a gRNA described herein, the nucleic acid comprises a polynucleotide sequence encoding the gRNA that is operably linked to (i) a suitable promoter for the expression in a cellular or in vitro environment; and/or (ii) a suitable nuclear localization signal.

In some embodiments, provided herein is a system comprising: (a) an sRGN polypeptide comprising the amino acid sequence of any one of SEQ ID NOs: 1-12 or a variant thereof having at least 90% sequence identity to any one of SEQ ID NOs: 1-12; and (b) a gRNA, wherein the gRNA is capable of guiding the sRGN polypeptide or variant thereof to a target polynucleotide sequence. In some embodiments, the gRNA is an sgRNA.

In some embodiments, provided herein is a system comprising: (a) an sRGN polypeptide comprising the amino acid sequence of any one of SEQ ID NOs: 1-12 or a variant thereof having at least 90% sequence identity to any one of SEQ ID NOs: 1-12; and (b) a nucleic acid encoding a gRNA, wherein the gRNA is capable of guiding the sRGN polypeptide or variant thereof to a target polynucleotide sequence. In some embodiments, the gRNA is an sgRNA.

In some embodiments, provided herein is a system comprising: (a) a nucleic acid encoding an sRGN polypeptide comprising the amino acid sequence of any one of SEQ ID NOs: 1-12 or a variant thereof having at least 90% sequence identity to any one of SEQ ID NOs: 1-12; and (b) a gRNA, wherein the gRNA is capable of guiding the sRGN polypeptide or variant thereof to a target polynucleotide sequence. In some embodiments, the nucleic acid comprises the polynucleotide sequence of any one of SEQ ID NOs: 13-29 or a variant thereof having at least 90% sequence identity to the polynucleotide sequence of any one of SEQ ID NOs: 13-29. In some embodiments, the gRNA is an sgRNA.

In some embodiments, provided herein is a system comprising: (a) a nucleic acid encoding an sRGN polypeptide comprising the amino acid sequence of any one of SEQ ID NOs: 1-12 or a variant thereof having at least 90% sequence identity to any one of SEQ ID NOs: 1-12; and (b) a nucleic acid encoding a gRNA, wherein the gRNA is capable of guiding the sRGN polypeptide or variant thereof to a target polynucleotide sequence. In some embodiments, the nucleic acid comprises the polynucleotide sequence of any one of SEQ ID NOs: 13-29 or a variant thereof having at least 90% sequence identity to the polynucleotide sequence of any one of SEQ ID NOs: 13-29. In some embodiments, the gRNA is an sgRNA. In some embodiments, the system comprises a nucleic acid comprising (i) the nucleic acid encoding an sRGN polypeptide or variant thereof; and (ii) a nucleic acid encoding the gRNA.

In some embodiments, according to any of the systems described herein, the system further comprises a donor template. In some embodiments, the donor template comprises a donor sequence for insertion into the target polynucleotide sequence. In some embodiments, the donor sequence is an exogenous sequence, such as a transgene for expression in a target. In some embodiments, the donor template comprises a donor sequence for modifying one or more bases in the target polynucleotide sequence. In some embodiments, the system further comprises one or more additional donor templates. In some embodiments, the donor template is physically linked to a gRNA in the system.

One embodiment according to the invention provides compositions comprising:

(a) an sRGN polypeptide or a nucleic acid encoding such sRGN;

(b) a single heterologous guide RNA (sgRNA) or a nucleic acid (e.g., DNA) that allows the generation of such sgRNA in situ (e.g., nucleic acid encoding the sgRNA), wherein the sgRNA comprises:
  i. a DNA-targeting segment comprised of RNA and capable of hybridizing to a target sequence in a polynucleotide locus,
  ii. a tracr mate sequence comprised of RNA, and
  iii. a tracr RNA sequence comprised of RNA,
    wherein the tracr mate sequence is capable of hybridizing to the tracr sequence, and wherein (i), (ii), and (iii) are arranged in a 5' to 3' orientation.

Within a sgRNA, a tracr mate sequence and a tracr sequence are generally connected by a suitable loop sequence and form a stem-loop structure.

Further, in some embodiments the nucleic acid encoding the sRGN polypeptide and/or the sgRNAs contains a suitable promoter for the expression in a cellular or in vitro environment and/or a suitable nuclear localization signal.

Another embodiment according to the invention provides methods of targeting, editing, modifying, or manipulating a target DNA at one or more locations in a cell or in vitro, comprising:
  (a) Introducing a heterologous sRGN polypeptide or a nucleic acid encoding the sRGN polypeptide into a cell or into an in vitro environment; and
  (b) Introducing a single heterologous guide RNA (sgRNA) or a nucleic acid (e.g., DNA) suitable for the generation of such sgRNA in situ (e.g., nucleic acid encoding the sgRNA), wherein the sgRNA comprises:
    i. a DNA-targeting segment comprised of RNA and capable of hybridizing to a target sequence in a polynucleotide locus,
    ii. a tracr mate sequence comprised of RNA, and
    iii. a tracr RNA sequence comprised of RNA,
  wherein the tracr mate sequence is capable of hybridizing to the tracr sequence, and wherein (i), (ii), and (iii) are arranged in a 5' to 3' orientation; and
  (c) creating one or more cuts, nicks or edits in the target DNA, wherein the sRGN polypeptide is directed to the target DNA by the gRNA in its processed or unprocessed form.

Another embodiment according to the invention is the use of a composition comprising:
  (a) an sRGN polypeptide or a nucleic acid encoding such sRGN;
  (b) a single heterologous guide RNA (sgRNA) or a nucleic acid (e.g., DNA) suitable for the generation of such sgRNA in situ (e.g., nucleic acid encoding the sgRNA), wherein the sgRNA comprises:
    i. a DNA-targeting segment comprised of RNA and capable of hybridizing to such target sequence in a polynucleotide locus,
    ii. a tracr mate sequence comprised of RNA, and
    iii. a tracr RNA sequence comprised of RNA,
  wherein the tracr mate sequence is capable of hybridizing to the tracr sequence, and wherein (i), (ii), and (iii) are arranged in a 5' to 3' orientation;
for targeting, editing, modifying, or manipulating a target DNA at one or more locations in a cell (e.g., in vitro or in vivo) or in a cell-free system.

Another embodiment according to the invention is a cell ex vivo or in vitro comprising:
  (a) a heterologous sRGN polypeptide or a nucleic acid encoding the same
  (b) a single heterologous guide RNA (sgRNA) or a nucleic acid (e.g., DNA) suitable for the generation of such sgRNA in situ (e.g., nucleic acid encoding the sgRNA), wherein the sgRNA comprises:
    i. a DNA-targeting segment comprised of RNA and capable of hybridizing to such target sequence in a polynucleotide locus,
    ii. a tracr mate sequence comprised of RNA, and
    iii. a tracr RNA sequence comprised of RNA,
  wherein the tracr mate sequence is capable of hybridizing to the tracr sequence, and wherein (i), (ii), and (iii) are arranged in a 5' to 3' orientation;
  or such a cell whose genome has been targeted, edited, modified, or manipulated using the above (a) and (b).

Additional embodiments according to the invention include kits comprising:
  (a) a nucleic acid encoding an sRGN polypeptide, wherein the nucleic acid is operably linked to a promoter or a ribosome binding site; and
  (b) a single heterologous guide RNA (sgRNA) or a nucleic acid (e.g., DNA) suitable for the generation of such sgRNA in situ (e.g., nucleic acid encoding the sgRNA), wherein the sgRNA comprises:
    i. a DNA-targeting segment comprised of RNA and capable of hybridizing to such target sequence in a polynucleotide locus,
    ii. a tracr mate sequence comprised of RNA, and
    iii. a tracr RNA sequence comprised of RNA,
  wherein the tracr mate sequence is capable of hybridizing to the tracr sequence, and wherein (i), (ii), and (iii) are arranged in a 5' to 3' orientation.

Or
  (a) an sRGN polypeptide; and
  (b) one or more single heterologous guide RNAs (sgRNAs), each of which comprise(s):
    iv. a DNA-targeting segment comprised of RNA and capable of hybridizing to such target sequence in a polynucleotide locus,
    v. a tracr mate sequence comprised of RNA, and
    vi. a tracr RNA sequence comprised of RNA,
  wherein the tracr mate sequence is capable of hybridizing to the tracr sequence, and wherein (iv), (v), and (vi) are arranged in a 5' to 3' orientation.

Yet another embodiment according to the invention comprises compositions and methods for targeting, editing, modifying, or manipulating one or more target DNA(s) at one or more locations in a cell (e.g., in vitro or in vivo) or in a cell-free system, comprising:
  (a) an sRGN polypeptide or nucleic acid encoding the sRGN polypeptide; and
  (b) a guide RNA (gRNA) or a nucleic acid (e.g., DNA) suitable for the generation of such gRNA in situ (e.g., nucleic acid encoding the gRNA), wherein the gRNA comprises:
    i. a DNA-targeting segment comprised of RNA and capable of hybridizing to such target sequence in a polynucleotide locus,
    ii. a tracr RNA sequence comprised of RNA;
  wherein (i) and (ii) are on a single RNA molecule and (iii) is on a separate RNA molecule.

Mutants

In some embodiments, the sRGN polypeptide is a mutant polypeptide with altered endoribonuclease activity or associated half-life of pre-crRNA, intermediate crRNA, or mature crRNA. In some embodiments, the sRGN polypeptide is a mutant polypeptide with altered or abrogated DNA endonuclease activity without substantially diminished or enhanced endoribonuclease activity or binding affinity to DNA. Such modification can allow for the sequence-specific DNA targeting of the sRGN polypeptide for the purpose of transcriptional modulation, activation, or repression; epigenetic modification or chromatin modification by methylation, demethylation, acetylation or deacetylation, or any other modifications of DNA binding and/or DNA-modifying proteins known in the art.

In some embodiments, the sRGN polypeptide is a mutant polypeptide with no DNA endonuclease activity.

In some embodiments, the cell is a bacterial cell, a fungal cell, an archaeal cell, a protist, a plant cell, or an animal cell.

In some embodiments, the sRGN polypeptide and the one or more guide RNAs (gRNAs), such as single heterologous guide RNA(s) (sgRNA(s)), are introduced into the cell by the same or different recombinant vectors encoding the polypeptide and the nucleic acid.

In some embodiments, the nucleic acid encoding the polypeptide, nucleic acid, or both the polypeptide and nucleic acid is modified.

In some embodiments, the method or system further comprises adding a donor DNA sequence, and wherein the target DNA sequence is edited by homology directed repair. In some embodiments, the polynucleotide donor template is physically linked to a crRNA or guide RNA In another aspect, provided herein is a method for modifying or editing double-stranded DNA or single stranded target DNA, without having activity against single stranded RNA (ssRNA), double-stranded RNA (dsRNA), or heteroduplexes of RNA and DNA.

Multiplexing

In another aspect, provided herein is a method for editing or modifying DNA at multiple locations in a cell consisting essentially of: i) introducing an sRGN polypeptide or a nucleic acid encoding an sRGN polypeptide into the cell; and ii) introducing a single heterologous nucleic acid comprising two or more pre-CRISPR RNAs (pre-crRNAs) either as RNA or encoded as DNA and under the control of one promoter into the cell, each pre-crRNA comprising a repeat-spacer array or repeat-spacer, wherein the spacer comprises a nucleic acid sequence that is complementary to a target sequence in the DNA and the repeat comprises a stem-loop structure, wherein the sRGN polypeptide cleaves the two or more pre-crRNAs upstream of the stem-loop structure to generate two or more intermediate crRNAs, wherein the two or more intermediate crRNAs are processed into two or more mature crRNAs, and wherein each two or more mature crRNAs guides the sRGN polypeptide to effect two or more double-strand breaks (DSBs) into the DNA. For example, one advantage of an sRGN polypeptide is that it is possible to introduce only one pre-crRNA which comprises several repeat-spacer units, which upon introduction, is processed by the sRGN polypeptide it into active repeat-spacer units targeting several different sequences on the DNA.

In some embodiments the pre-crRNA sequences in the single heterologous nucleic acid are joined together in specific locations, orientations, sequences or with specific chemical linkages to direct or differentially modulate the endonuclease activity of the sRGN polypeptide at each of the sites specified by the different crRNA sequences.

In another aspect, provided herein is an example of a general method for editing or modifying the structure or function of DNA at multiple locations in a cell consisting essentially of: i) introducing an RNA-guided endonuclease, such as sRGN, as a polypeptide or a nucleic acid encoding the RNA-guided endonuclease into the cell; and ii) introducing a single heterologous nucleic acid comprising or encoding two or more guide RNAs, either as RNA or encoded as DNA and under the control of one or more promoters, wherein the activity or function of the RNA-guided endonuclease is directed by the guide RNA sequences in the single heterologous nucleic acid.

Codon Optimized DNA Sequences for sRGN Polypeptides

In some embodiments of the method, the nucleic acid sequence encoding the sRGN polypeptide is a modified nucleic acid, for example, codon optimized. In some embodiments of the method, the single heterologous nucleic acid is a modified nucleic acid. In some embodiments of the method, the method further comprises introducing into the cell a polynucleotide donor template. In some embodiments, the polynucleotide donor template is physically linked to a crRNA or guide RNA. In some embodiments of the method, the DNA is repaired at DSBs by either homology directed repair, non-homologous end joining, or microhomology-mediated end joining.

In some embodiments of the method, the sRGN polypeptide is more readily complexed with a mature crRNA in the local milieu, and thus more readily available for directing DNA endonuclease activity as a consequence of the crRNA being processed by the same sRGN polypeptide from the pre-crRNA in the local milieu.

In some embodiments of the method, the sRGN polypeptide is used to cleave, isolate or purify one or more mature crRNA sequences from a modified pre-crRNA oligonucleotide sequence in which heterologous sequences are incorporated 5' or 3' to one or more crRNA sequences within RNA oligonucleotide or DNA expression construct. The heterologous sequences can be incorporated to modify the stability, half-life, expression level or timing, interaction with the sRGN polypeptide or target DNA sequence, or any other physical or biochemical characteristics known in the art.

In some embodiments of the method, the pre-crRNA sequence is modified to provide for differential regulation of two or more mature crRNA sequences within the pre-crRNA sequence, to differentially modify the stability, half-life, expression level or timing, interaction with the sRGN polypeptide or target DNA sequence, or any other physical or biochemical characteristics known in the art.

In some embodiments, the sRGN polypeptide (or nucleic acid encoded variants thereof) is modified to improve desired characteristics such as function, activity, kinetics, half-life or the like. One such non-limiting example of such a modification is to replace a 'cleavage domain' of the sRGN polypeptide with a homologous or heterologous cleavage domain from a different nuclease, such as the RuvC or HNH domain from the Type II CRISPR-associated nuclease Cas9.

In one aspect, provided herein is a method for targeting, editing or manipulating DNA in a cell comprising linking an intact or partially or fully deficient sRGN polypeptide or pre-crRNA or crRNA moiety, to a dimeric FOK1 nuclease to direct endonuclease cleavage, as directed to one or more specific DNA target sites by one or more crRNA molecules. In another embodiment, the FOK1 nuclease system is a nickase or temperature sensitive mutant or any other variant known in the art.

In some embodiments, the sRGN polypeptide linked with a dimeric FOK1 nuclease is introduced into the cell together with a single heterologous nucleic acid comprising two or more pre-CRISPR RNAs (pre-crRNAs) either as RNA or encoded as DNA and under the control of one promoter into the cell, each pre-crRNA comprising a repeat-spacer array, wherein the spacer comprises a nucleic acid sequence that is complementary to a target sequence in the DNA and the repeat comprises a stem-loop structure, wherein the sRGN polypeptide cleaves the two or more pre-crRNAs upstream of the stem-loop structure to generate two or more intermediate crRNAs.

In one aspect, provided herein is a method for targeting, editing or manipulating DNA in a cell comprising linking an intact or partially or fully deficient sRGN polypeptide or pre-crRNA, intermediate crRNA, mature crRNA moiety, or gRNA (collectively referred to as crRNA), to a donor single or double-strand DNA donor template to facilitate homologous recombination of exogenous DNA sequences, as directed to one or more specific DNA target sites by one or more guide RNA or crRNA molecules.

In yet another aspect, provided herein is a method for directing a DNA template, for homologous recombination or homology-directed repair, to the specific site of gene editing. In this regard, a single stranded or double-stranded DNA template is linked chemically or by other means known in the art to a crRNA or guide RNA. In some embodiments the DNA template remains linked to the crRNA or guide RNA; in yet other examples, the sRGN polypeptide cleaves the crRNA or guide RNA, liberating the DNA template to enable or facilitate homologous recombination.

In yet another aspect, provided herein is a method for targeting, editing or manipulating DNA in a cell comprising linking an intact or partially or fully deficient sRGN polypeptide or pre-crRNA or crRNA moiety, to a transcriptional activator or repressor, or epigenetic modifier such as a methylase, demethylase, acetylase, or deacetylase, or signaling or detection, all aspects of which have been previously described for Cas9 systems, as directed to one or more specific DNA target sites by one or more crRNA molecules.

In another aspect, provided herein is a composition comprising a polynucleotide donor template linked to a crRNA or a guide RNA. A method for targeting, editing or manipulating DNA in a cell comprising linking a pre-crRNA or crRNA or guide RNA to a donor single or double-strand polynucleotide donor template such that the donor template is cleaved from the pre-crRNA or crRNA or guide RNA by an sRGN polypeptide, thus facilitating homology directed repair by the donor template, as directed to one or more specific DNA target sites by one or more guide RNA or crRNA molecules.

An sRGN polypeptide can also be used to form a chimeric binding protein in which other domains and activities are introduced. By way of illustration, a FokI domain can be fused to an sRGN protein, which can contain a catalytically active endonuclease domain, or a FokI domain can be fused to an sRGN protein, which has been modified to render the sRGN polypeptide endonuclease domain inactive. Other domains that can be fused to make chimeric proteins with an sRGN polypeptide include transcriptional modulators, epigenetic modifiers, tags and other labels or imaging agents, histones, and/or other modalities known in the art that modulate or modify the structure or activity of gene sequences.

Nucleic Acid and/or Amino Acid Modifications

In some embodiments, polynucleotides introduced into cells comprise one or more modifications which can be used, for example, to enhance activity, stability or specificity, alter delivery, reduce innate immune responses in host cells, further reduce the protein size, or for other enhancements, as further described herein and known in the art.

In certain embodiments, modified polynucleotides are used in a CRISPR-Cas system based on an sRGN, in which case the guide RNAs and/or a DNA or an RNA encoding an sRGN polypeptide introduced into a cell can be modified, as described and illustrated below. Such modified polynucleotides can be used in the CRISPR-Cas system to edit any one or more genomic loci.

Components of CRISPR-Cas Systems

A. Guide RNAs/sgRNAs

In aspects of the invention the terms "chimeric RNA", "chimeric guide RNA", "guide RNA", "single guide RNA" and "synthetic guide RNA" are used interchangeably and refer to the polynucleotide sequence comprising the DNA-targeting segment, the tracr sequence and the tracr mate sequence. The term "guide sequence" or "DNA-targeting sequence" refers to the about 20 bp sequence within the guide RNA that specifies the target site and may be used interchangeably with the terms "guide" or "spacer'. The term "tracr mate sequence" may also be used interchangeably with the term "direct repeat(s)".

In some aspects, a single guide RNA (sgRNA) according to the invention comprises:
i. a DNA-targeting segment or DNA-targeting sequence comprised of RNA and capable of hybridizing to a target sequence in a polynucleotide locus,
ii. a tracr mate sequence comprised of RNA, and
iii. a tracr RNA sequence comprised of RNA,
wherein the tracr mate sequence is capable of hybridizing to the tracr sequence, and wherein (i), (ii), and (iii) are arranged in a 5' to 3' orientation. In some embodiments, components (i), (ii), and (iii) are on a single chimeric RNA.

Within a sgRNA, a tracr mate sequence and a tracr sequence can connected by a suitable loop sequence and form a stem-loop structure.

In general, a tracr mate sequence includes any sequence that has sufficient complementarity with a tracr sequence to promote one or more of: (1) excision of a DNA-targeting segment flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm and may further account for secondary structures, such as self-complementarity within either the tracr sequence or tracr mate sequence. In some embodiments, the degree of complementarity between the tracr sequence and tracr mate sequence along the 30 nucleotides length of the shorter of the two when optimally aligned is about or more than 25%, 30%, 40%, 50%, 60%, 70%, 80%, 90%, 95%, 97.5%, 99%, or higher. In some embodiments, the tracr sequence is about or more than 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins.

In some embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a DNA-targeting segment, a tracr mate sequence, and a tracr sequence are as follows (listed 5' to 3'), where "N" represents a base of a DNA-targeting segment, the first block of lower case letters represent the tracr mate sequence, and the second block of lower case letters represent the tracr sequence, and the final poly-T sequence represents the transcription terminator:

The DNA-targeting segment of a guide RNA comprises a nucleotide sequence that is complementary to a sequence in a target DNA. In other words, the DNA-targeting segment of a guide RNA interacts with a target DNA in a sequence-specific manner via hybridization (i.e., base pairing). As such, the nucleotide sequence of the DNA-targeting segment may vary and determines the location within the target DNA that the guide RNA and the target DNA will interact. The DNA-targeting segment of a guide RNA can be modified (e.g., by genetic engineering) to hybridize to any desired sequence within a target DNA.

The DNA-targeting segment can have a length of from 10 nucleotides to 30 nucleotides.

In some embodiments, the DNA-targeting segment has a length of from 13 nucleotides to 25 nucleotides.

In some embodiments, the DNA-targeting segment has a length of from 15 nucleotides to 23 nucleotides.

In some embodiments, the DNA-targeting segment has a length of from 18 nucleotides to 22 nucleotides, such as from 20 to 22 nucleotides.

The percent complementarity between the DNA-targeting sequence of the DNA-targeting segment and the target sequence of the target DNA can be at least 60% (e.g., at least 65%, at least 70%, at least 75%, at least 80%, at least 85%, at least 90%, at least 95%, at least 97%, at least 98%, at least 99%, or 100%) over the 20-22 nucleotides.

A protospacer sequence complementary to the target sequence in the target DNA can be adjacent to a suitable PAM sequence for an sRGN polypeptide at its 3' end, or such PAM sequence can be part of the 3' portion of the DNA-targeting segment.

Using the CRISPR-Cas system for purposes of non-limiting illustrations of such uses, modifications of guide RNAs can be used to enhance the formation or stability of the CRISPR-Cas genome editing complex comprising guide RNAs and a Cas endonuclease such as sRGN. Modifications of guide RNAs can also or alternatively be used to enhance the initiation, stability or kinetics of interactions between the genome editing complex with the target sequence in the genome, which can be used for example to enhance on-target activity. Modifications of guide RNAs can also or alternatively be used to enhance specificity, e.g., the relative rates of genome editing at the on-target site as compared to effects at other (off-target) sites.

Modifications can also or alternatively used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in embodiments in which a Cas endonuclease such as an sRGN polypeptide is introduced into the cell to be edited via an RNA that needs to be translated in order to generate the sRGN polypeptide, since increasing the half life of guide RNAs introduced at the same time as the RNA encoding the endonuclease can be used to increase the time that the guide RNAs and the encoded Cas endonuclease co-exist in the cell.

B. Protospacer-Adjacent Motif (PAM or PAM Sequence)

Suitable protospacer adjacent motif (PAM) sequences for an sRGN polypeptide include "ANGG" and "NNGG."

The site of cleavage generally occurs within one to three base pairs upstream of the PAM sequence, such as within either one or three base pairs upstream of the PAM sequence, within three base pairs of the PAM sequence, or within three base pairs upstream of the PAM sequence "NNGG". Other PAMs are known in the art and an sRGN can be engineered to target such PAMs.

C. Use in Eukaryotic Cells

In one embodiment according to the invention the sRGN system herein described can be used in eukaryotic cells, such as mammalian cells. In some embodiments, the cells are not human fetal cells or derived from human fetal cells. In some embodiments, the cells are not human embryonic cells or derived from human embryonic cells. In some embodiments, the compositions and methods disclosed herein do not involve the destruction of a human fetus or a human embryo. In some embodiments, the subject (or individual, whatever you're using in the spec) is not human fetus or embryo.

Other Features of the Invention

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease such as an sRGN polypeptide that are introduced into a cell, including, without limitation, modifications that enhance the stability of the RNA (such as by decreasing its degradation by RNases present in the cell), modifications that enhance translation of the resulting product (i.e., the endonuclease), and/or modifications that decrease the likelihood or degree to which the RNAs introduced into cells elicit innate immune responses. Combinations of modifications, such as the foregoing and others, can likewise be used. In the case of CRISPR-Cas, for example, one or more types of modifications can be made to guide RNAs (including those exemplified above), and/or one or more types of modifications can be made to RNAs encoding CAS endonuclease (including those exemplified above).

By way of illustration, guide RNAs used in the CRISPR-Cas system or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding an sRGN polypeptide, are more readily generated enzymatically. While fewer types of modifications are generally available for use in enzymatically produced RNAs, there are still modifications that can be used to, e.g., enhance stability, reduced the likelihood or degree of innate immune response, and/or enhance other attributes, as described further below and in the art; and new types of modifications are regularly being developed. By way of illustration of various types of modifications, especially those used frequently with smaller chemically synthesized RNAs, modifications can comprise one or more nucleotides modified at the 2' position of the sugar, in some embodiments a 2'-0-alkyl, 2'-0-alkyl-0-alkyl or 2'-fluoro-modified nucleotide. In some embodiments, RNA modifications include 2'-fluoro, 2'-amino and 2' 0-methyl modifications on the ribose of pyrimidines, basic residues or an inverted base at the 3' end of the RNA. Such modifications are routinely incorporated into oligonucleotides and these oligonucleotides have been shown to have a higher Tm (i.e., higher target binding affinity) than; 2'-deoxy oligonucleotides against a given target.

A number of nucleotide and nucleoside modifications have been shown to make the oligonucleotide into which they are incorporated more resistant to nuclease digestion than the native oligonucleotide; these modified oligonucleotides survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly CH$_2$—NH—O—CH$_2$, CH, —N(CH$_3$)—O—CH$_2$ (known as a methylene(methylimino) or MMI backbone), CH$_2$—O—N (CH$_3$)—CH$_2$, CH$_2$—N(CH$_3$)—N (CH$_3$)—CH$_2$ and O—N(CH$_3$)— CH$_2$—CH$_2$ backbones; amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243:209-214 (2002); Nasevicius et al., Nat. Genet., 26:216-220 (2000); Lacenra et al., Proc. Natl. Acad. Sci., 97: 9591-9596 (2000); and U.S. Pat. No. 5,034,506, issued Jul. 23, 1991. Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$, OCH$_3$O(CH$_2$)n CH$_3$, O(CH$_2$)n NH$_2$ or O(CH$_2$)$_n$ CH$_3$ where n is from 1 to 10; C$_1$ to C$_{10}$ lower alkyl, alkoxyalkoxy, substituted lower alkyl, alkaryl or aralkyl; Cl; Br; CN; CF3; OCF3; O-, S-, or N-alkyl; O-, S-, or N-alkenyl: SOCH$_3$; SO$_2$ CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some embodiments, a modification includes 2'-methoxyethoxy (2'-O—CH2CH2OCH3, also known as 2'-O-(2-methoxyethyl)) (Martin et al., Helv. Chim. Acta, 1995, 78, 486). Other modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group. In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262. Further teaching of PNA compounds can be found in Nielsen et al, Science, 254: 1497-1500 (1991).

Guide RNAs can also include, additionally or alternatively, nucleobase (alternately referred to as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and can be referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2.6-diaminopurine. Kornberg, A, DNA Replication, W. H. Freeman & Co., San Francisco, pp 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2 degrees C. (Sanghvi, Y. S., in Crooke, S. T. and Lebleu, B., eds., Antisense Research and Applications, CRC Press, Boca Raton, 1993, pp. 276-278) and are embodiments of base substitutions.

Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other a-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. l., ed. John Wiley & Sons, 1990, those disclosed by Englisch et al., Angewandte Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and —O-6 substituted purines, comprising 2-aminopropyladenine, 5-propynyluracil and 5-propynylcytosine. 5-methylcytosine substitutions have been shown to increase nucleic acid duplex stability by 0.6-1.2 oc (Sanghvi, Y. S., Crooke, S. T. and Lebleu, B., eds, 'Antisense Research and Applications', CRC Press, Boca Raton, 1993, pp. 276-278) and are embodiments of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,681,941; 5,750, 692; 5,763,588; 5,830,653; 6,005,096; and US Patent Application Publication 20030158403.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, the guide RNAs and/or mRNA (or DNA) encoding an endonuclease such as an sRGN polypeptide are chemically linked to one or more moieties or conjugates that enhance the activity, cellular distribution, or cellular uptake of the oligonucleotide. Such moieties comprise but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g., hexyi-S-tritylthiol [Manoharan et al, Ann. N. Y Acad. Sci., 660: 306-309 (1992) and Manoharan et al., Bioorg. Med. Chem. Let., 3. 2765-2770 (1993)); a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36:3651-3654 (1995) and Shea et al., Nucl. Acids Res., 18: 3777-3783 (1990)]; a polyamine or a polyethylene glycol chain [Mancharan et al., Nucfeosides & Nucleotides, 14: 969-973 (1995)]; adamantane acetic acid [Manoharan et at., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacal. Exp. Ther., 277: 923-937 (1996)]. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); e.g., Hu, et al., Protein Pept Lett. 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are generally produced by enzymatic synthesis can be modified by various means. Such modifications can include, for example, the introduction of certain nucleotide analogs, the incorporation of particular sequences or other moieties at the 5' or 3' ends of molecules, and other modifications. By way of illustration, the mRNA encoding an sRGN polypeptide is approximately 3 kb to 3.3 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that may occur following introduction of exogenous RNAs, particularly longer RNAs such as those encoding sRGN.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-methyl-CTP) or N6-methyl-ATP), or treatment with phosphatase to remove 5' terminal phosphates. These and other modifications are known in the art, and new modifications of RNAs are being developed.

Modified RNAs can be obtained, e.g., from a commercial supplier, including for example, Trilink Biotech, Axolabs, Bio-Synthesis Inc. Dharmacon and many others. As described by Trilink, for example, 5-methyl-CTP can be used to impart desirable characteristics such as increased nuclease stability, increased translation or reduced interaction of innate immune receptors with in vitro transcribed RNA. 5'-Methylcytidine-5'-triphosphate (5-methyl-CTP), N6-methyl-ATP, as well as Pseudo-UTP and 2-Thio-UTP, have also been shown to reduce innate immune stimulation in culture and in vivo while enhancing translation as illustrated in publications by Konmann et al. and Warren et al. referred to below.

It has been shown that chemically modified mRNA delivered in vivo can be used to achieve improved therapeutic effects; e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-methyl-A, 2-Thio-U and 5-methyl-C, it was found substituting just one quarter of the uridine and cytidine residues with 2-Thio-U and 5-methyl-C respectively, resulted in a significant decrease in toll-like receptor (TLR) mediated recognition of the mRNA in mice. By reducing the activation of the innate immune system, these modifications can therefore be used to effectively increase the stability and longevity of the mRNA in vivo; e.g., Konmann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs). and it was found that enzymatically synthesized RNA incorporating 5-methyl-CTP, Pseudo-UTP and an Anti Reverse Cap Analog (ARCA) could be used to effectively evade the cell's antiviral response; e.g., Warren et al., supra. Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates- and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9): 1130-46 (2011); Judge and Maclachlan, Hum Gene Ther 19(2):111-24 (2008); and references cited therein.

Modifications described in the art have been developed and applied to enhance RNA stability, reduce innate immune responses, and/or achieve other benefits that can be useful in connection with the introduction of polynucleotides into human cells as described herein; e.g. the reviews by Whitehead K A et al., Annual Review of Chemical and Biomolecular Engineering, 2:77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16:Unit 16.3 (2009); Behlke, Oligonucleotides 18(4):305-19 (2008): Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kale, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) has been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-methyl, 2'-fluoro, 2'-hydro has been reported to reduce TLR7/TLR8 interaction while generally preserving silencing activity; e.g., Judge et al., Mol. Ther. 13:494-505 (2006); and Cekaite et al., J Mol Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; e.g. Kariko, K. et al., Immunity 23:165-175 (2005).

As is also known in the art, and commercially available, a number of conjugates can be applied to polynucleotides such as RNAs for use herein that can enhance their delivery and/or uptake by cells, including for example, cholesterol, tocopherol and folic acid, lipids, peptides, polymers, linkers and aptamers; e.g., the review by Winkler, Ther Deliv. 4:791-809 (2013), and references cited therein.

Mimetics

A nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units, which gives PNA an amide containing backbone. The heterocyclic base moieties are bound directly or indirectly to aza nitrogen atoms of the amide portion of the backbone. Representative US patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are nonionic mimics of oligonucleotides, which are less likely to form undesired interactions with cellular proteins (Braasch, D. A., and Corey, D. R., Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (GeNA). The furanose ring normally present in a DNA/RNA molecule is replaced with a cydohexenyl ring. GeNA DMT protected phosphoramidite monomers have been prepared and used for oligomeric compound synthesis following classical phosphoramidite chemistry. Fully modified GeNA oligomeric compounds and oligonucleotides having specific positions modified with GeNA have been prepared and studied (see Wang et al., J. Am. Chem. Soc., 2000, 122, 8595-8602). In general the incorporation of GeNA monomers into a DNA chain increases its stability of a DNA/RNA hybrid. GeNA oligoadenylates formed complexes with RNA and DNA complements with similar stability to the native complexes. The study of incorporating GeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CHz-), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA ($T_m$=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A, 2000, 97, 5633-5638).

The synthesis and preparation of the LNA monomers adenine, cytosine, guanine, 5-methyl-cytosine. thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)nO)mCH_3$, $O(CHz)nOCH_3$, $O(CHz)nNH_2$, $O(CH_2)CH_3$, $O(CH_2)nONH_2$, and $O(CH_2)nON((CH_2)nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy 2'-O—CH2 CHzOCH3, also known as -2'-O-(2-methoxyethyl) or 2'-MOE) (Martin et al., Helv. Chim. Acta, 1995, 78, 486-

504) i.e., an alkoxyalkoxy group. A further suitable modification includes 2'-dimethylaminooxyethoxy, i.e., a O(CHz)zON(CH3)z group, also known as 2'-DMAOE, as described in examples hereinbelow, and 2'-dimethylaminoethoxyethoxy (also known in the art as 2'-O-dimethyl-aminoethoxy-ethyl or 2'-DMAEOE), i.e., 2'-O-CHz-O-CHz-N(CH3)z.

Other suitable sugar substituent groups include methoxy (—O—$CH_3$), aminopropoxy (—O—$CH_2CH_2CH_2NH_2$), allyl (—CHz-CH═CHz), —O-allyl (—O—$CH_z$—CH═$CH_z$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. l., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N—O and O-6 substituted purines, including 2-aminopropyladenine, 5-propynyluracil and 5-propynylcytosine. 5-methylcytosine substitutions have been shown to increase nucleic acid duplex stability by 0.6-1.2 oc. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

"Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., wobble base pairing and Hoogsteen base pairing).

It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santalucia, Nucl. Acids Research, 2005; 33 (19): 6258-6267.

Conjugates

Another possible modification of a nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyi-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654;

Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 36513654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacal. Exp. Ther., 1996, 277, 923-937).

A conjugate may include a "Protein Transduction Domain" or PTD (also known as a CPP-cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of an exogenous polypeptide (e.g., an sRGN polypeptide). In some embodiments, a PTD is covalently linked to the C-terminus or the N-terminus of an exogenous polypeptide (e.g., an sRGN polypeptide). In some embodiments, a PTD is covalently linked to a nucleic acid (e.g., a guide RNA, a nucleic acid encoding a guide RNA, a nucleic acid encoding an sRGN polypeptide, etc.). Exemplary PTDs include but are not limited to a minimal undecapeptide protein transduction domain (for example corresponding to residues 47-57 of HIV-1 TAT comprising the YGRKKRRQRRR (SEQ ID NO: 126) motif (for identifying but not for purposes of disclosure within this application); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); In some embodiments, the PTD is an activatable CPP (ACPP) (Aguilera et al. (2009) lntegr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane. In some embodiments the PTD is chemically modified in order to increase the bioavailability of the PTD. Exemplary modifications are disclosed in Expert Opin Drug Deliv. 2009 6(11):1195-205.

Nucleic Acids Encoding a Guide RNA and/or an sRGN Polypeptide

The present disclosure provides a nucleic acid comprising a nucleotide sequence encoding a guide RNA and/or an sRGN polypeptide. In some embodiments, a guide RNA-encoding nucleic acid is an expression vector, e.g., a recombinant expression vector.

In some embodiments, a method involves contacting a target DNA or introducing into a cell (or a population of cells) one or more nucleic acids comprising nucleotide sequences encoding a guide RNA and/or an sRGN polypeptide. In some embodiments a cell comprising a target DNA is in vitro. In some embodiments a cell comprising a target DNA is in vivo. Suitable nucleic acids comprising nucleotide sequences encoding a guide RNA and/or an sRGN polypeptide include expression vectors, where an expression vector comprising a nucleotide sequence encoding a guide RNA and/or an sRGN polypeptide is a "recombinant expression vector."

In some embodiments, the recombinant expression vector is a viral construct, e.g., a recombinant adeno-associated virus construct (e.g., U.S. Pat. No. 7,078,387), a recombinant adenoviral construct, a recombinant lentiviral construct, a recombinant retroviral construct, etc. [00248] Suitable expression vectors include, but are not limited to, viral vectors (e.g., viral vectors based on vaccinia virus; poliovirus; adenovirus (e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166:154-165; and Flotte et al., PNAS (1993) 90:10613-10617); SV40; herpes simplex virus; human immunodeficiency virus (e.g., Miyoshi et al., PNAS 94:10319 23, 1997; Takahashi et al., J Viral 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSGS (Stratagene), pSVK3, pBPV, pMSG, and pSVLSV40 (Phanmacia). However, any other vector may be used so long as it is compatible with the host cell. Depending on the host/vector system utilized, any of a number of suitable transcription and translation control elements, including constitutive and inducible promoters, transcription enhancer elements, transcription terminators, etc. may be used in the expression vector (e.g., Bitter et al. (1987) Methods in Enzymology, 153:516-544).

In some embodiments, a nucleotide sequence encoding a guide RNA and/or an sRGN polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a guide RNA and/or an sRGN polypeptide is operably linked to multiple control elements that allow expression of the nucleotide sequence encoding a guide RNA and/or an sRGN polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-1. Selection of the appropriate vector and promoter is within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to the sRGN polypeptide, thus resulting in a chimeric polypeptide.

In some embodiments, a nucleotide sequence encoding a guide RNA and/or an sRGN polypeptide is operably linked to an inducible promoter. In some embodiments, a nucleotide sequence encoding a guide RNA and/or an sRGN polypeptide is operably linked to a constitutive promoter.

Methods of introducing a nucleic acid into a host cell are known in the art, and such methods can be used to introduce a nucleic acid (e.g., an expression construct) into a cell. Suitable methods include, e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (e.g., Panyam et al., Adv Drug Deliv Rev. 2012 Sep. 13. pii:S0169-409X(12)00283-9.doi:10.1016/j.addr.2012.09.023), and the like.

Chimeric Polypeptides

The present disclosure provides a chimeric site-directed modifying polypeptide comprising a sequence derived from an sRGN polypeptide. A chimeric site-directed modifying polypeptide interacts with (e.g., binds to) a guide RNA (described above). The guide RNA guides the chimeric site-directed modifying polypeptide to a target sequence within target DNA (e.g., a chromosomal sequence or an extrachromosomal sequence, e.g., an episomal sequence, a minicircle sequence, a mitochondrial sequence, a chloroplast sequence, cell-free polynucleotide, etc.). A chimeric site-directed modifying polypeptide modifies target DNA (e.g., cleavage or methylation of target DNA) and/or a polypeptide associated with target DNA (e.g., methylation or acetylation of a histone tail). A chimeric site-directed modifying polypeptide is also referred to herein as a "chimeric site-directed polypeptide" or a "chimeric RNA binding site-directed modifying polypeptide."

A chimeric site-directed modifying polypeptide comprises two portions, an RNA-binding portion and an activity portion. A chimeric site-directed modifying polypeptide comprises amino acid sequences that are derived from at least two different polypeptides. A chimeric site-directed modifying polypeptide can comprise modified and/or naturally occurring polypeptide sequences (e.g., a first amino acid sequence from a modified or unmodified sRGN protein; and a second amino acid sequence other than the sRGN protein).

RNA-Binding Portion

In some embodiments, the RNA-binding portion of a chimeric site-directed modifying polypeptide comprises an amino acid sequence having at least 75%, at least 80%, at least 85%, at least 90%, at least 95%, at least 98%, at least 99%, or 100%, amino acid sequence identity to the RNA-binding portion of a polypeptide set forth in any one of SEQ ID NOs: 1-12.

Activity Portion

In addition to the RNA-binding portion, the chimeric site-directed modifying polypeptide comprises an "activity portion." In some embodiments, the activity portion of a chimeric site-directed modifying polypeptide comprises the activity portion of a site-directed modifying polypeptide (e.g., a Cas9 endonuclease or an sRGN). In other embodiments, the activity portion of a subject chimeric site-directed modifying polypeptide comprises a modified amino acid sequence (e.g., substitution, deletion, insertion) of a naturally-occurring activity portion of a site-directed modifying polypeptide. Naturally-occurring activity portions of interest are derived from site-directed modifying polypeptides known in the art. The activity portion of a chimeric site-directed modifying polypeptide is variable and may comprise any heterologous polypeptide sequence that may be useful in the methods disclosed herein. In some embodiments, the activity portion of a chimeric site-directed modifying polypeptide comprises a portion of an sRGN polypeptide that is at least 90% identical to the activity portion of any one of SEQ ID NOs: 1-12. In some embodiments, a chimeric site-directed modifying polypeptide comprises: (i) an RNA-binding portion that interacts with a guide RNA, wherein the guide RNA comprises a nucleotide sequence that is complementary to a sequence in a target DNA; (ii) an activity portion that exhibits site-directed enzymatic activity (e.g., activity for RNA cleavage), wherein the site of enzymatic activity is determined by the palindromic hairpin structures formed by the repeats of pre-crRNA and cleaves the pre-crRNA 4 nt upstream of the hairpins generating intermediate forms of crRNAs composed of repeat spacer (5'-3'); and (iii) an activity portion that exhibits site-directed enzymatic activity (e.g., activity for DNA cleavage), wherein the site of enzymatic activity is determined by the guide RNA.

Exemplary Chimeric Site-Directed Modifying Polypeptides

In some embodiments, the activity portion of the chimeric site-directed modifying polypeptide comprises a modified form of the sRGN protein, including modified forms of any of the sRGN orthologs. In some instances, the modified form of the sRGN protein comprises an amino acid change (e.g., deletion, insertion, or substitution) that reduces or increases the naturally occurring nuclease activity of the sRGN protein. For example, in some instances, the modified form of the sRGN protein has less than 50%, less than 40%, less than 30%, less than 20%, less than 10%, less than 5%, or less than 1% of the nuclease activity of the corresponding wild-type sRGN polypeptide. In some cases, the modified form of the sRGN polypeptide has no substantial nuclease activity. In other cases, it may have 50%, 2-fold, 4-fold or up to an over 10-fold more nuclease activity.

In some cases, the chimeric site-directed modifying polypeptide comprises an amino acid sequence having at least 75%, at least 80%, at least 85%, at least 90%, at least 95%, at least 99% or 100% amino acid sequence identity to any one of SEQ ID NOs: 1-12. In some embodiments, the activity portion of the site-directed modifying polypeptide comprises a heterologous polypeptide that has DNA-modifying activity and/or transcription factor activity and/or DNA-associated polypeptide-modifying activity. In some cases, a heterologous polypeptide replaces a portion of the sRGN polypeptide that provides nuclease activity. In other embodiments, a site-directed modifying polypeptide comprises both a portion of the sRGN polypeptide that normally provides nuclease activity (and that portion can be fully active or can instead be modified to have less than 100% of the corresponding wild-type activity) and a heterologous polypeptide. In other words, in some cases, a chimeric site-directed modifying polypeptide is a fusion polypeptide comprising both the portion of the sRGN polypeptide that normally provides nuclease activity and the heterologous polypeptide. In other cases, a chimeric site-directed modifying polypeptide is a fusion polypeptide comprising a modified variant of the activity portion of the sRGN polypeptide (e.g., amino acid change, deletion, insertion) and a heterologous polypeptide. In yet other cases, a chimeric site-directed modifying polypeptide is a fusion polypeptide comprising a heterologous polypeptide and the RNA-binding portion of a naturally occurring or a modified site-directed modifying polypeptide.

For example, in a chimeric sRGN protein, a naturally occurring (or modified, e.g., mutation, deletion, insertion) sRGN polypeptide may be fused to a heterologous polypeptide sequence (i.e., a polypeptide sequence from a protein other than sRGN or a polypeptide sequence from another organism). The heterologous polypeptide sequence may exhibit an activity (e.g., enzymatic activity) that will also be exhibited by the chimeric sRGN protein (e.g., methyltransferase activity, acetyltransferase activity, kinase activity, ubiquitinating activity, etc.). A heterologous nucleic acid sequence may be linked to another nucleic acid sequence (e.g., by genetic engineering) to generate a chimeric nucleotide sequence encoding a chimeric polypeptide. In some embodiments, a chimeric sRGN polypeptide is generated by fusing an sRGN polypeptide (e.g., wild type sRGN or an sRGN variant, e.g., an sRGN with reduced or inactivated nuclease activity) with a heterologous sequence that provides for subcellular localization (e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag for ease of tracking or purification (e.g., a fluorescent protein, e.g., green fluorescent protein (GFP), YFP, RFP, CFP, mCherry, tdTomato, and the like; a HIS tag, e.g., a 6×His tag; a hemagglutinin (HA) tag; a FLAG tag; a Myc tag; and the like). In some embodiments, the heterologous sequence can provide for increased or decreased stability. In some embodiments, the heterologous sequence can provide a binding domain (e.g., to provide the ability of a chimeric sRGN polypeptide to bind to another protein of interest, e.g., a DNA or histone modifying protein, a transcription factor or transcription repressor, a recruiting protein, etc.) or to a nucleotide of interest (e.g., an aptamer or target site of a nucleotide binding protein).

Nucleic Acid Encoding a Chimeric Site-Directed Modifying Polypeptide

The present disclosure provides a nucleic acid comprising a nucleotide sequence encoding a chimeric site-directed modifying polypeptide. In some embodiments, the nucleic acid comprising a nucleotide sequence encoding a chimeric site-directed modifying polypeptide is an expression vector, e.g., a recombinant expression vector.

In some embodiments, a method involves contacting a target DNA or introducing into a cell (or a population of cells) one or more nucleic acids comprising a chimeric site-directed modifying polypeptide. Suitable nucleic acids comprising nucleotide sequences encoding a chimeric site-directed modifying polypeptide include expression vectors, where an expression vector comprising a nucleotide sequence encoding a chimeric site-directed modifying polypeptide is a "recombinant expression vector."

In some embodiments, the recombinant expression vector is a viral construct, e.g., a recombinant adeno-associated virus construct (e.g., U.S. Pat. No. 7,078,387), a recombinant adenoviral construct, a recombinant lentiviral construct, etc. Suitable expression vectors include, but are not limited to, viral vectors (e.g., viral vectors based on vaccinia virus; poliovirus; adenovirus (e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769: WO 93/19191; WO 94/28938; WO 95/11984 and WO 95/00655); adeno-associated virus (e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166:154-165; and Flotte et al., PNAS (1993) 90:10613-10617); SV40; herpes simplex virus; human immunodeficiency virus (e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSGS (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, a nucleotide sequence encoding a chimeric site-directed modifying polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a chimeric site-directed modifying polypeptide is operably linked to multiple control elements that allow expression of the nucleotide sequence encoding a chimeric site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-1. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin (HA) tag, a fluorescent protein (e.g., a green fluorescent protein; a yellow fluorescent protein, etc.), etc.) that are fused to the chimeric site-directed modifying polypeptide.

In some embodiments, a nucleotide sequence encoding a chimeric site-directed modifying polypeptide is operably linked to an inducible promoter (e.g., heat shock promoter, Tetracycline-regulated promoter, Steroid-regulated promoter, Metal-regulated promoter, estrogen receptor-regulated promoter, etc.). In some embodiments, a nucleotide sequence encoding a chimeric site-directed modifying polypeptide is operably linked to a spatially restricted and/or temporally restricted promoter (e.g., a tissue specific promoter, a cell type specific promoter, etc.). In some embodiments, a nucleotide sequence encoding a chimeric site-directed modifying polypeptide is operably linked to a constitutive promoter.

Methods of introducing a nucleic acid into a host cell are known in the art, and any known method can be used to introduce a nucleic acid (e.g., an expression construct) into a stem cell or progenitor cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (e.g., Panyam et., al Adv Drug Deliv Rev. 2012 Sep. 13. pp: 50169-409X(12) 00283-9. doi: 10.1016/j.addr.2012.09.023), and the like.

Methods

The present disclosure provides methods for modifying a target DNA and/or a target DNA-associated polypeptide. Generally, a method involves contacting a target DNA with a complex (a "targeting complex"), which complex comprises a guide RNA and an sRGN polypeptide.

As discussed above, a gRNA or sgRNA and an sRGN polypeptide form a complex. The guide RNA provides target specificity to the complex by comprising a nucleotide sequence that is complementary to a sequence of a target DNA. The sRGN polypeptide of the complex provides the site-specific activity. In some embodiments, a complex modifies a target DNA, leading to, for example, DNA cleavage, DNA methylation, DNA damage, DNA repair, etc. In other embodiments, a complex modifies a target polypeptide associated with target DNA (e.g., a histone, a DNA-binding protein, etc.), leading to, for example, histone methylation, histone acetylation, histone ubiquitination, and the like. The target DNA may be, for example, naked (i.e., unbound by DNA associated proteins) DNA in vitro, chromosomal DNA in cells in vitro, chromosomal DNA in cells in vivo, etc.

sRGN proteins from various species may require different PAM sequences in the target DNA. Thus, for a particular sRGN protein of choice, the PAM sequence requirement may be different than the PAM sequence described above.

Exemplary methods are provided that take advantage of characteristics of sRGN orthologs include the following.

The nuclease activity cleaves target DNA to produce double-strand breaks. These breaks are then repaired by the cell in one of two ways: non-homologous end joining, and homology-directed repair. In non-homologous end joining (NHEJ), the double-strand breaks are repaired by direct ligation of the break ends to one another. In the process a few base pairs can be inserted or deleted at the cleavage site. In homology-directed repair, a donor polynucleotide with homology to the cleaved target DNA sequence is used as a template for repair of the cleaved target DNA sequence, resulting in the transfer of genetic information from the donor polynucleotide to the target DNA As such, new nucleic acid material may be inserted/copied into the site. In some cases, a target DNA is contacted with a donor polynucleotide. In some cases, a donor polynucleotide is introduced into a cell. The modifications of the target DNA due to NHEJ and/or homology-directed repair lead to, for example, gene correction, gene replacement, gene tagging, transgene insertion, nucleotide deletion, nucleotide insertion, gene disruption, gene mutation, sequence replacement, etc. Accordingly, cleavage of DNA by an sRGN polypeptide may be used to delete nucleic acid material from a target DNA sequence (e.g., to disrupt a gene that makes cells susceptible to infection (e.g., the CCR5 or CXCR4 gene, which makes T cells susceptible to HIV infection, to remove disease-causing trinucleotide repeat sequences in neurons, to create gene knockouts and mutations as disease models in research, etc.) by cleaving the target DNA sequence and allowing the cell to repair the sequence in the absence of an exogenously provided donor polynucleotide. Thus, the methods can be used to knock out a gene (resulting in complete lack of transcription or altered transcription) or to knock in genetic material into a locus of choice in the target DNA Alternatively, if a guide RNA and an sRGN polypeptide are co-administered to cells with a donor polynucleotide sequence that includes at least a segment with homology to the target DNA sequence, the subject methods may be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, a complex comprising a guide RNA and an sRGN polypeptide is useful in any in vitro or in vivo application in which it is desirable to modify DNA in a site-specific, i.e., "targeted", way, for example gene knockout, gene knock-in, gene editing, gene tagging, sequence replacement, etc., as used in, for example, gene therapy, e.g., to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In some embodiments, the sRGN polypeptide comprises a modified form of the sRGN protein. In some instances, the modified form of the sRGN protein comprises an amino acid change (e.g., deletion, insertion, or substitution) that reduces the naturally occurring nuclease activity of the sRGN protein. For example, in some instances, the modified form of the sRGN protein has less than 50%, less than 40%, less than 30%, less than 20%, less than 10%, less than 5%, or less than1 % of the nuclease activity of the corresponding wild-type sRGN polypeptide. In some cases, the modified form of the sRGN polypeptide has no substantial nuclease activity. When an sRGN polypeptide is a modified form of the sRGN protein that has no substantial nuclease activity, it can be referred to as "dsRGN."

In some embodiments, the sRGN polypeptide comprises a heterologous sequence (e.g., a fusion). In some embodiments, a heterologous sequence can provide for subcellular localization of the sRGN polypeptide (e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, a heterologous sequence can provide a tag for ease of tracking or purification (e.g., a fluorescent protein, e.g., green fluorescent protein (GFP), YFP, RFP, CFP, mCherry, tdTomato, and the like; a his tag, e.g., a 6×His tag;

a hemagglutinin (HA) tag; a FLAG tag; a Myc tag; and the like). In some embodiments, the heterologous sequence can provide for increased or decreased stability.

In certain embodiments, modified polynucleotides are used in a CRISPR-sRGN system described herein, in which the guide RNAs and/or a DNA or an RNA comprising a polynucleotide sequence encoding an sRGN polypeptide or variant thereof can be modified, as described and illustrated below. Such modified polynucleotides can be used in the CRISPR-sRGN system, for example, to edit any one or more genomic loci. In some embodiments, such modifications in the polynucleotides of the disclosure are achieved via codon-optimization, e.g., codon-optimization based on specific host cells in which the encoded polypeptide is to be expressed. It will be appreciated by the skilled artisan that any nucleotide sequence and/or recombinant nucleic acid of the present disclosure can be codon optimized for expression in any species of interest. Codon optimization is well known in the art and involves modification of a nucleotide sequence for codon usage bias using species specific codon usage tables. The codon usage tables are generated based on a sequence analysis of the most highly expressed genes for the species of interest. In a non-limiting example, when the nucleotide sequences are to be translated in a host cell, the codon usage tables are generated based on a sequence analysis of highly expressed nuclear genes for the species of interest. The modifications of the nucleotide sequences are determined by comparing the species specific codon usage table with the codons present in the native polynucleotide sequences. For example, if the intended target cell were a human cell, a human codon-optimized polynucleotide sequence encoding an sRGN (or an sRGN variant, e.g., enzymatically inactive variant) would be suitable. As another non-limiting example, if the intended host cell were a mouse cell, then a mouse codon-optimized polynucleotide sequence encoding an sRGN (or an sRGN variant, e.g., enzymatically inactive variant) would be suitable.

Strategies and methodologies for codon optimization are known in the art and have been described for various systems including, but not limited to yeast (Outchkourov et al., Protein Expr Purif, 24(1):18-24 (2002)) and *E. coli* (Feng et al., Biochemistry, 39(50):15399-15409 (2000)). In some embodiments, the codon optimization is performed by using GeneGPS® Expression Optimization Technology (ATUM) and using the manufacturer's recommended expression optimization algorithms. In some embodiments, the polynucleotides of the disclosure are codon-optimized for increased expression in a human cell. In some embodiments, the polynucleotides of the disclosure are codon-optimized for increased expression in an *E. coli* cell. In some embodiments, the polynucleotides of the disclosure are codon-optimized for increased expression in an insect cell. In some embodiments, the expression optimization algorithms used in a codon optimization procedure are defined to avoid putative poly-A signals (e.g., AATAAA and ATTAAA) as well as long (greater than 4) stretches of A's which can lead to polymerase slippage. Polyadenylation signals can also be chosen to optimize expression in the intended host. Polyadenylation signals can also be chosen to optimize expression in the intended host.

As is well understood in the art, codon optimization of a nucleotide sequence results in a nucleotide sequence having less than 100% identity (e.g., less than 70%, 71%. 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) to the native nucleotide sequence but which still encodes a polypeptide having the same function as that encoded by the original, native nucleotide sequence. Thus, in representative embodiments of the disclosure, the nucleotide sequence and/or recombinant nucleic acid of the disclosure can be codon optimized for expression in the particular species of interest.

In some embodiments, a codon-optimized polynucleotide sequence encoding an sRGN has at least 90%, 92%, 93%, 94%, 95%, 96%, 97%, 98%, 99%, 99.2%, 99.5%, 99.8%, 99.9%, or 100% sequence identity to any one of SEQ ID NOs: 15, 18, 20, 22, and 27. In some embodiments, the polynucleotides of the disclosure are codon-optimized for increased expression of the encoded sRGN polypeptide in a target cell. In some embodiments, the polynucleotides of the disclosure are codon-optimized for increased expression in a human cell. In some embodiments, the polynucleotides of the disclosure are codon-optimized for increased expression in an *E. coli* cell. In some embodiments, the polynucleotides of the disclosure are codon-optimized for increased expression in an insect cell.

In some embodiments, an sRGN polypeptide can be codon-optimized. This type of optimization is known in the art and entails the mutation of foreign-derived DNA to mimic the codon preferences of the intended host organism or cell while encoding the same protein. Thus, the codons are changed, but the encoded protein remains unchanged. For example, if the intended target cell were a human cell, a human codon-optimized sRGN (or variant, e.g., enzymatically inactive variant) would be suitable. Any suitable sRGN polypeptide (e.g., any sRGN such as the sequence set forth in any one of SEQ ID NOs: 1-12) can be codon optimized. As another non-limiting example, if the intended host cell were a mouse cell, than a mouse codon-optimized sRGN (or variant, e.g., enzymatically inactive variant) would be suitable.

In one aspect, provided herein is a nucleic acid comprising a codon-optimized polynucleotide sequence encoding an sRGN polypeptide (e.g., a polypeptide comprising the amino acid sequence of any one of SEQ ID NOs: 1-12) or a variant thereof having at least about 90% (such as at least about any of 91%, 92%, 93%, 94%, 95%, 96%, 97%, 98%, 99%, or more) sequence identity to any one of SEQ ID NOs: 1-12. Such a codon-optimized nucleic acid encoding an sRGN or a variant thereof is also referred to herein as a "codon-optimized sRGN polypeptide" or a "codon-optimized sRGN." In some embodiments, the codon-optimized sRGN encodes the sRGN polypeptide of any one of SEQ ID NOs: 1-12. In some embodiments, the codon-optimized sRGN is codon-optimized for expression in prokaryotic cells, such as bacterial cells. In some embodiments, the codon-optimized sRGN is codon-optimized for expression in eukaryotic cells, such as insect or mammalian cells. In some embodiments, the codon-optimized sRGN is codon-optimized for expression in human cells. In some embodiments, the codon optimization is performed according to GeneGPS® optimization (ATUM). In some embodiments, the codon optimization is performed according to a GeneOptimizer process (ThermoFisher Scientific). In some embodiments, the codon-optimized sRGN has at least about 90% (such as at least about any of 91%, 92%, 93%, 94%, 95%, 96%, 97%, 98%, 99%, or more) sequence identity to any one of SEQ ID NOs: 15, 18, 20, 22, and 27. In some embodiments, the codon-optimized sRGN comprises (or consists of) the sequence of any one of SEQ ID NOs: 15, 18, 20, 22, and 27.

In some embodiments, according to any of the nucleic acids described herein comprising a codon-optimized polynucleotide sequence encoding an sRGN polypeptide or a variant thereof, the nucleic acid further includes a nucleotide sequence encoding a gRNA. In some embodiments, the nucleic acid is an expression vector, e.g., a recombinant expression vector. In some embodiments, the nucleotide sequence encoding an sRGN polypeptide or a variant thereof comprises the codon-optimized polynucleotide sequence of any one of SEQ ID NOs: 15, 18, 20, 22, and 27 or a variant thereof having at least 90% sequence identity to the codon-optimized polynucleotide sequence of any one of SEQ ID NOs: 15, 18, 20, 22, and 27.

In some embodiments, provided herein is a nucleic acid comprising a polynucleotide sequence having at least 90%, 91%, 92%, 93%, 94%, 95%, 96%, 97%, 98%, or 99% sequence identity to any one of SEQ ID NOs: 15, 18, 20, 22, and 27, wherein the polynucleotide sequence encodes an sRGN polypeptide or variant thereof as described herein. In some embodiments, the polynucleotide sequence comprises (or consists of) the codon-optimized polynucleotide sequence of any one of SEQ ID NOs: 15, 18, 20, 22, and 27.

In some embodiments, provided herein is a nucleic acid comprising a polynucleotide sequence having at least 90%, 91%, 92%, 93%, 94%, 95%, 96%, 97%, 98% or 99% sequence identity to a subsequence of any one of SEQ ID NOs: 15, 18, 20, 22, and 27, wherein the polynucleotide sequence encodes one or more functional sRGN domains. In some embodiments, the polynucleotide sequence comprises (or consists of) a subsequence of any one of SEQ ID NOs: 15, 18, 20, 22, and 27. In some embodiments, the one or more sRGN domains include a nuclease domain (e.g., an HNH or RuvC domain). In some embodiments, the one or more sRGN domains include an RNA-binding domain (e.g., a Rec I domain). In some embodiments, the one or more sRGN domains include a PAM-interacting domain.

In some embodiments, according to any of the nucleic acids described herein comprising a codon-optimized polynucleotide sequence, the expression in a host cell of an sRGN polypeptide or variant thereof from the nucleic acid is increased as compared to the expression in the host cell of the sRGN polypeptide or variant thereof from a corresponding nucleic acid comprising a reference polynucleotide sequence from which the codon-optimized polynucleotide sequence is derived. In some embodiments, the codon-optimized polynucleotide sequence comprises the codon-optimized polynucleotide sequence of any one of SEQ ID NOs: 15, 18, 20, 22, and 27, or a variant thereof having at least 90% sequence identity to the codon-optimized polynucleotide sequence of any one of SEQ ID NOs: 15, 18, 20, 22, and 27. In some embodiments, the reference polynucleotide sequence comprises the sRGN-encoding polynucleotide sequence from any one of SEQ ID NOs: 13, 14, 16, 17, 19, 21, 23-26, 28, and 29, or a variant thereof having at least 90% sequence identity to the sRGN-encoding polynucleotide sequence from any one of SEQ ID NOs: 13, 14, 16, 17, 19, 21, 23-26, 28, and 29. In some embodiments, the expression of the sRGN polypeptide or variant thereof from the codon-optimized polynucleotide sequence in a host cell is increased by at least about 10% (such as by at least about any of 15%, 20%, 25%, 30%, 35%, 40%, 45%, 50%, 55%, 60%, 65%, 70%, 75%, 80%, 85%, 90%, 95%, 100%, or more) as compared to the expression in the host cell of the sRGN polypeptide or variant thereof from the reference polynucleotide sequence.

In some embodiments, a guide RNA and an sRGN polypeptide are used as an inducible system for shutting off gene expression in bacterial cells. In some cases, nucleic acids encoding an appropriate guide RNA and/or an appropriate sRGN polypeptide are incorporated into the chromosome of a target cell and are under control of an inducible promoter. When the guide RNA and/or the sRGN polypeptide are induced, the target DNA is cleaved (or otherwise modified) at the location of interest (e.g., a target gene on a separate plasmid), when both the guide RNA and the sRGN polypeptide are present and form a complex. As such, in some cases, bacterial expression strains are engineered to include nucleic acid sequences encoding an appropriate sRGN polypeptide in the bacterial genome and/or an appropriate guide RNA on a plasmid (e.g., under control of an inducible promoter), allowing experiments in which the expression of any targeted gene (expressed from a separate plasmid introduced into the strain) could be controlled by inducing expression of the guide RNA and the sRGN polypeptide. In some cases, the sRGN polypeptide has enzymatic activity that modifies target DNA in ways other than introducing double-strand breaks. Enzymatic activity of interest that may be used to modify target DNA (e.g., by fusing a heterologous polypeptide with enzymatic activity to an sRGN polypeptide, thereby generating a chimeric sRGN polypeptide) includes, but is not limited methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). Methylation and demethylation is recognized in the art as an important mode of epigenetic gene regulation while DNA damage and repair activity is essential for cell survival and for proper genome maintenance in response to environmental stresses. As such, the methods herein find use in the epigenetic modification of target DNA and may be employed to control epigenetic modification of target DNA at any location in a target DNA by genetically engineering the desired complementary nucleic acid sequence into the DNA-targeting segment of a guide RNA. The methods herein also find use in the intentional and controlled damage of DNA at any desired location within the target DNA. The methods herein also find use in the sequence-specific and controlled repair of DNA at any desired location within the target DNA. Methods to target DNA-modifying enzymatic activities to specific locations in target DNA find use in both research and clinical applications.

In some cases, the sRGN polypeptide has activity that modulates the transcription of target DNA (e.g., in the case of a chimeric sRGN polypeptide, etc.). In some cases, a chimeric sRGN polypeptides comprising a heterologous polypeptide that exhibits the ability to increase or decrease transcription (e.g., transcriptional activator or transcription repressor polypeptides) is used to increase or decrease the transcription of target DNA at a specific location in a target DNA, which is guided by the DNA-targeting segment of the guide RNA. Examples of source polypeptides for providing a chimeric sRGN polypeptide with transcription modulatory activity include, but are not limited to light-inducible transcription regulators, small molecule/drug-responsive transcription regulators, transcription factors, transcription repressors, etc. In some cases, the method is used to control the expression of a targeted coding-RNA (protein-encoding gene) and/or a targeted non-coding RNA (e.g., tRNA, rRNA, snoRNA, siRNA, miRNA, long ncRNA. etc.). In some cases, the sRGN polypeptide has enzymatic activity that modifies a polypeptide associated with DNA (e.g., histone). In some embodiments, the enzymatic activity is methyltransferase activity, demethylase activity, acetyltransferase activity, deacetylase activity, kinase activity, phosphatase activity, ubiquitin ligase activity (i.e., ubiquitination activity), deubiquitinating activity, adenylation activity, deadenylation activity, SUMOylating activity, deSUMOylating activity, ribosylation activity, deribosylation activity, myristoylation activity, demyristoylation activity glycosylation activity (e.g., from GlcNAc transferase) or deglycosylation activity. The enzymatic activities listed herein catalyze covalent modifications to proteins. Such modifications are known in the art to alter the stability or activity of the target protein (e.g., phosphorylation due to kinase activity can stimulate or silence protein activity depending on the target protein). Of particular interest as protein targets are histones. Histone proteins are known in the art to bind DNA and form complexes known as nucleosomes. Histones can be modified (e.g., by methylation, acetylation, ubiquitination, phosphorylation) to elicit structural changes in the surrounding DNA, thus controlling the accessibility of potentially large portions of DNA to interacting factors such as transcription factors, polymerases and the like. A single histone can be modified in many different ways and in many different combinations (e.g., trimethylation of lysine 27 of histone 3, H3K27, is associated with DNA regions of repressed transcription while trimethylation of lysine 4 of histone 3, H3K4, is associated with DNA regions of active transcription). Thus, a site-directed modifying polypeptide with histone-modifying activity finds use in the site specific control of DNA structure and can be used to alter the histone modification pattern in a selected region of target DNA. Such methods find use in both research and clinical applications.

In some embodiments, multiple guide RNAs are used simultaneously to simultaneously modify different locations on the same target DNA or on different target DNAs. In some embodiments, two or more guide RNAs target the same gene or transcript or locus. In some embodiments, two or more guide RNAs target different unrelated loci. In some embodiments, two or more guide RNAs target different, but related loci.

In some cases, the sRGN polypeptide is provided directly as a protein. As one non-limiting example, fungi (e.g., yeast) can be transformed with exogenous protein and/or nucleic acid using spheroplast transformation (see Kawai et al., Bioeng Bugs. 2010 November-December; 1(6):395-403: 'Transformation of *Saccharomyces cerevisiae* and other fungi: methods and possible underlying mechanism"; and Tanka et al., Nature. 2004 Mar. 18; 428(6980):323-8: "Conformational variations in an infectious protein determine prion strain differences"; both of which are herein incorporated by reference in their entirety). Thus, an sRGN polypeptide can be incorporated into a spheroplast (with or without nucleic acid encoding a guide RNA and with or without a donor polynucleotide) and the spheroplast can be used to introduce the content into a yeast cell. A sRGN polypeptide can be introduced into a cell (provided to the cell) by any convenient method; such methods are known to those of ordinary skill in the art. As another non-limiting example, an sRGN polypeptide can be injected directly into a cell (e.g., with or without nucleic acid encoding a guide RNA and with or without a donor polynucleotide), e.g., a cell of a zebrafish embryo, the pronucleus of a fertilized mouse oocyte, etc.

Target Cells of Interest

In some of the above applications, the methods may be employed to induce DNA cleavage, DNA modification, and/or transcriptional modulation in mitotic or post-mitotic cells in vivo and/or ex vivo and/or in vitro (e.g., to produce genetically modified cells that can be reintroduced into an individual). Because the guide RNA provide specificity by hybridizing to target DNA, a mitotic and/or post-mitotic cell of interest in the disclosed methods may include a cell from any organism (e.g., a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal, a cell from a rodent, a cell from a primate, a cell from a human, etc.).

Any type of cell may be of interest (e.g., a stem cell, e.g., an embryonic stem (ES) cell, an induced pluripotent stem (iPS) cell, a germ cell; a somatic cell, e.g., a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from an organism and allowed to grow in vitro for a limited number of passages, i.e., splittings, of the culture. For example, primary cultures are cultures that may have been passaged 0 times, 1 time, 2 times, 4 times, 5 times, 10 times, or 15 times, but not enough times go through the crisis stage. Generally, the primary cell lines of the present invention are maintained for fewer than 10 passages in vitro. Target cells are in many embodiments unicellular organisms, or are grown in culture.

If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g., normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

Nucleic Acids Encoding a Guide RNA and/or an sRGN Polypeptide

In some embodiments, a method involves contacting a target DNA or introducing into a cell (or a population of cells) one or more nucleic acids comprising nucleotide sequences encoding a guide RNA and/or an sRGN polypeptide and/or a donor polynucleotide. Suitable nucleic acids comprising nucleotide sequences encoding a guide RNA and/or an sRGN polypeptide include expression vectors, where an expression vector comprising a nucleotide sequence encoding a guide RNA and/or an sRGN polypeptide is a "recombinant expression vector."

In some embodiments, the recombinant expression vector is a viral construct, e.g., a recombinant adeno-associated virus construct (e.g., U.S. Pat. No. 7,078,387), a recombinant adenoviral construct, a recombinant lentiviral construct, etc.

Suitable expression vectors include, but are not limited to, viral vectors (e.g., viral vectors based on vaccinia virus; poliovirus; adenovirus (e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94112649, WO 93/03769; WO 93/19191; WO 94/28938; WO 95/11984 and WO 95/00655); adeno-associated virus (e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166:154-165; and Flotte et al., PNAS (1993) 90:10613-10617); SV40; herpes simplex virus; human immunodeficiency virus (e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

In some embodiments, a nucleotide sequence encoding a guide RNA and/or an sRGN polypeptide is operably linked to a control element, e.g., a transcriptional control element, such as a promoter. The transcriptional control element may be functional in either a eukaryotic cell, e.g., a mammalian cell, or a prokaryotic cell (e.g., bacterial or archaeal cell). In some embodiments, a nucleotide sequence encoding a guide RNA and/or an sRGN polypeptide is operably linked to multiple control elements that allow expression of the nucleotide sequence encoding a guide RNA and/or an sRGN polypeptide in both prokaryotic and eukaryotic cells.

Depending on the host/vector system utilized, any of a number of suitable transcription and translation control elements, including constitutive and inducible promoters, transcription enhancer elements, transcription terminators, etc. may be used in the expression vector (e.g., U6 promoter, H1 promoter, etc.; see above) (see e.g., Bitter et al. (1987) Methods in Enzymology, 153:516-544).

In some embodiments, a guide RNA and/or an sRGN polypeptide can be provided as RNA. In such cases, the guide RNA and/or the RNA encoding the sRGN polypeptide can be produced by direct chemical synthesis or may be transcribed in vitro from a DNA encoding the guide RNA. Methods of synthesizing RNA from a DNA template are well known in the art. In some cases, the guide RNA and/or the RNA encoding the sRGN polypeptide will be synthesized in vitro using an RNA polymerase enzyme (e.g., T7 polymerase, T3 polymerase, SP6 polymerase, etc.). Once synthesized, the RNA may directly contact a target DNA or may be introduced into a cell by any of the well-known techniques for introducing nucleic acids into cells (e.g., microinjection, electroporation, transfection, etc.).

Nucleotides encoding a guide RNA (introduced either as DNA or RNA) and/or an sRGN polypeptide (introduced as DNA or RNA) and/or a donor polynucleotide may be provided to the cells using well-developed transfection techniques; e.g., Angel and Yanik (2010) PLoS ONE 5(7): e 11756, and the commercially available TransMessenger® reagents from Qiagen, Stemfect™ RNA Transfection Kit from Stemgent, and TransiT®-mRNA Transfection Kit from Mims Bio. See also Beumer et al. (2008) Efficient gene targeting in Drosophila by direct embryo injection with zinc-finger nucleases. PNAS 105(50):19821-19826. Alternatively, nucleic acids encoding a guide RNA and/or an sRGN polypeptide and/or a chimeric sRGN polypeptide and/or a donor polynucleotide may be provided on DNA vectors. Many vectors, e.g., plasmids, cosmids, minicircles, phage, viruses, etc., useful for transferring nucleic acids into target cells are available. The vectors comprising the nucleic acid(s) may be maintained episomally, e.g., as plasmids, minicircle DNAs, viruses such cytomegalovirus, adenovirus, etc., or they may be integrated into the target cell genome, through homologous recombination or random integration, e.g., retrovirus-derived vectors such as MMLV, HIV-1, ALV, etc.

Vectors may be provided directly to the cells. In other words, the cells are contacted with vectors comprising the nucleic acid encoding guide RNA and/or an sRGN polypeptide and/or a chimeric sRGN polypeptide and/or a donor polynucleotide such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid encoding a guide RNA and/or an sRGN polypeptide and/or a chimeric sRGN polypeptide and/or a donor polynucleotide. Retroviruses, for example, lentiviruses, are particularly suitable to the method of the invention. Commonly used retroviral vectors are "defective", i.e., unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also be introduced by direct micro-injection (e.g., injection of RNA into a zebrafish embryo).

Vectors used for providing the nucleic acids encoding guide RNA and/or an sRGN polypeptide and/or a chimeric sRGN polypeptide and/or a donor polynucleotide to the cells will generally comprise suitable promoters for driving the expression, that is, transcriptional activation, of the nucleic acid of interest. In other words, the nucleic acid of interest will be operably linked to a promoter. This may include ubiquitously acting promoters, for example, the CMV-13-actin promoter, or inducible promoters, such as promoters that are active in particular cell populations or that respond to the presence of drugs such as tetracycline. By transcriptional activation, it is intended that transcription will be increased above basal levels in the target cell by at least 10 fold, by at least 100 fold, more usually by at least 1000 fold. In addition, vectors used for providing a guide RNA and/or an sRGN polypeptide and/or a chimeric sRGN polypeptide and/or a donor polynucleotide to the cells may include nucleic acid sequences that encode for selectable markers in the target cells, so as to identify cells that have taken up the guide RNA and/or an sRGN polypeptide and/or a chimeric sRGN polypeptide and/or a donor polynucleotide.

A guide RNA and/or an sRGN polypeptide and/or a chimeric sRGN polypeptide may instead be used to contact DNA or introduced into cells as RNA. Methods of introducing RNA into cells are known in the art and may include, for example, direct injection, transfection, or any other method used for the introduction of DNA.

A sRGN polypeptide may be provided to cells as a polypeptide. Such a polypeptide may optionally be fused to a polypeptide domain that increases solubility of the product. The domain may be linked to the polypeptide through a defined protease cleavage site, e.g., a TEV sequence, which is cleaved by TEV protease. The linker may also include one or more flexible sequences, e.g., from 1 to 10 glycine residues. In some embodiments, the cleavage of the fusion protein is performed in a buffer that maintains solubility of the product, e.g., in the presence of from 0.5 to 2 M urea, in the presence of polypeptides and/or polynucleotides that increase solubility, and the like. Domains of interest include endosomolytic domains, e.g., influenza HA domain; and other polypeptides that aid in production, e.g., IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the sRGN polypeptide may be fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 127) motif (for identifying but not for purposes of disclosure within this application) also disclosed in J. Biol. Chem., 271 (1996), pp. 18188-18193. As another example, the permeant peptide comprises the HIV-1 tat basic region amino acid sequence, which may include, for example, amino acids 49-57 of naturally occurring tat protein.

Other permeant domains include poly-arginine motifs, for example, the region of amino acids 34-56 of HIV-1 rev protein, nona-arginine, acta-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A. 2000 Nov. 21; 97(24):13003-8; published US Patent Application Publications Nos. 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation. In some embodiments the polypeptide permeant domain is chemically modified in order to increase the bioavailability of the PTD. Exemplary modifications are disclosed in Expert Opin Drug Deliv. 2009 November; 6(11):1195-205.

A sRGN polypeptide may be produced in vitro or by eukaryotic cells, by prokaryotic cells, or by in vitro transcription and translation (IVTT) and it may be further processed by unfolding, e.g., heat denaturation, OTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g., those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. Also embraced are sequences that have phosphorylated amino acid residues, e.g., phosphotyrosine, phosphoserine, or phosphothreonine.

Also included in the invention are guide RNAs and sRGN polypeptides that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable as a therapeutic agent. Analogs of such polypeptides include those containing residues other than naturally occurring L-amino acids, e.g., O-amino acids or non-naturally occurring synthetic amino acids. D-amino acids may be substituted for some or all of the amino acid residues. The sRGN polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

An sRGN polypeptide may also be isolated and purified in accordance with known methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, such as at least about 75% by weight or at least about 95% by weight, and for therapeutic purposes, at least 99.5% by weight, in relation to contaminants related to the method of preparation of the product and its purification. Usually, the percentages will be based upon total protein. To induce DNA cleavage and recombination, or any desired modification to a target DNA, or any desired modification to a polypeptide associated with target DNA, the guide RNA and/or the sRGN polypeptide and/or the donor polynucleotide, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the cells one or more times, e.g., one time, twice, three times, or more than three times, and the cells allowed to incubate with the agent(s) for some amount of time following each contacting event e.g., 16-24 hours, after which time the media is replaced with fresh media and the cells are cultured further. In cases in which two or more different targeting complexes are provided to the cell (e.g., two different guide RNAs that are complementary to different sequences within the same or different target DNA), the complexes may be provided simultaneously (e.g., as two polypeptides and/or nucleic acids), or delivered simultaneously. Alternatively, they may be provided consecutively, e.g., the targeting complex being provided first, followed by the second targeting complex, etc. or vice versa.

Generally, an effective amount of the guide RNA and/or sRGN polypeptide and/or donor polynucleotide is provided to the target DNA or cells to induce target modification. An effective amount of the guide RNA and/or sRGN polypeptide and/or donor polynucleotide is the amount to induce a 2-fold increase or more in the amount of target modification observed between two homologous sequences relative to a negative control, e.g., a cell contacted with an empty vector or irrelevant polypeptide. That is to say, an effective amount or dose of the guide RNA and/or sRGN polypeptide and/or donor polynucleotide will induce a 2-fold increase, a 3-fold increase, a 4-fold increase or more in the amount of target modification observed at a target DNA region, in some instances a 5-fold increase, a 6-fold increase or more, sometimes a 7-fold or 8-fold increase or more in the amount of recombination observed, e.g., an increase of 10-fold, 50-fold, or 100-fold or more, in some instances, an increase of 200-fold, 500-fold, 700-fold, or 1000-fold or more, e.g., a 5000-fold, or 10,000-fold increase in the amount of recombination observed. The amount of target modification may be measured by any convenient method. For example, a silent reporter construct comprising complementary sequence to the targeting segment (targeting sequence) of the guide RNA flanked by repeat sequences that, when recombined, will reconstitute a nucleic acid encoding an active reporter may be co-transfected into the cells, and the amount of reporter protein assessed after contact with the guide RNA and/or sRGN polypeptide and/or donor polynucleotide, e.g., 2 hours, 4 hours, 8 hours, 12 hours, 24 hours, 36 hours, 48 hours, 72 hours or more after contact with the guide RNA and/or sRGN polypeptide and/or donor polynucleotide. As another, more sensitivity assay, for example, the extent of recombination at a genomic DNA region of interest comprising target DNA sequences may be assessed by PCR or Southern hybridization of the region after contact with a guide RNA and/or sRGN polypeptide and/or donor polynucleotide, e.g., 2 hours, 4 hours, 8 hours, 12 hours, 24 hours, 36 hours, 48 hours, 72 hours or more after contact with the guide RNA and/or sRGN polypeptide and/or donor polynucleotide.

Contacting the cells with a guide RNA and/or sRGN polypeptide and/or donor polynucleotide may occur in any culture media and under any culture conditions that promote the survival of the cells. For example, cells may be suspended in any appropriate nutrient medium that is convenient, such as Iscove's modified DMEM or RPMI1640, supplemented with fetal calf serum or heat inactivated goat serum (about 5-10%), L-glutamine, a thiol, particularly 2-mercaptoethanol, and antibiotics, e.g., penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are generally permissive of nonhomologous end joining and homology-directed repair. In applications in which it is desirable to insert a polynucleotide sequence into a target DNA sequence, a polynucleotide comprising a donor sequence to be inserted is also provided to the cell. By a "donor sequence" or "donor polynucleotide" it is meant a nucleic acid sequence to be inserted at the cleavage site induced by an sRGN polypeptide. The donor polynucleotide will contain sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g., 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is generally not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide. The donor sequence may comprise certain sequence differences as compared to the genomic sequence, e.g., restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and 0-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked (i.e., unmodified) nucleic acid, as nucleic acid complexed with an agent such as a liposome or poloxamer, or can be delivered by viruses (e.g., adenovirus, AAV), as described above for nucleic acids encoding a guide RNA and/or sRGN polypeptide and/or donor polynucleotide.

Following the methods described above, a DNA region of interest may be cleaved and modified, i.e., "genetically modified", ex vivo. In some embodiments, as when a selectable marker has been inserted into the DNA region of interest, the population of cells may be enriched for those comprising the genetic modification by separating the genetically modified cells from the remaining population. Prior to enriching, the "genetically modified" cells may make up only about 1% or more (e.g., 2% or more, 3% or more, 4% or more, 5% or more, 6% or more, 7% or more, 8% or more, 9% or more, 10% or more, 15% or more, or 20% or more) of the cellular population. Separation of "genetically modified" cells may be achieved by any convenient separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g., magnetic separation, affinity chromatography, "panning" with an affinity reagent attached to a solid matrix, or other convenient technique. Techniques providing accurate separation include fluorescence activated cell sorters, which can have varying degrees of sophistication. Such as multiple color channels, low angle and obtuse light scattering detecting channels, impedance channels, etc. The cells may be selected against dead cells by employing dyes associated with dead cells (e.g., propidium iodide). Any technique may be employed which is not unduly detrimental to the viability of the genetically modified cells. Cell compositions that are highly enriched for cells comprising modified DNA are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

Genetically modified cells produced by the methods described herein may be used immediately. Alternatively, the cells may be frozen at liquid nitrogen temperatures and stored for long periods of time, being thawed and capable of being reused. In such cases, the cells will usually be frozen in 10% dimethylsulfoxide (DMSO), 50% serum, 40% buffered medium, or some other such solution as is commonly used in the art to preserve cells at such freezing temperatures, and thawed in a manner as commonly known in the art for thawing frozen cultured cells.

The genetically modified cells may be cultured in vitro using methods known in the art. The cells may be expanded in culture, i.e., grown under conditions that promote their proliferation. Culture medium may be liquid or semi-solid, e.g., containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g., penicillin and streptomycin. The culture may contain growth factors to which the respective cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Cells that have been genetically modified in this way may be transplanted to a subject for purposes such as gene therapy, e.g., to treat a disease or as an antiviral, antipathogenic, or anticancer therapeutic, for the production of genetically modified organisms in agriculture, or for biological research. In some cases, cells for use in humans are cultured in a Xeno-free medium. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g., mouse, rat, guinea pig, hamster, lagomorph (e.g., rabbit), etc.) may be used for experimental investigations.

Cells may be provided to the subject alone or with a suitable substrate or matrix, e.g., to support their growth and/or organization in the tissue to which they are being transplanted. Usually, at least $1 \times 10^3$ cells will be administered, for example $5 \times 10^3$ cells, $1 \times 10^4$ cells, $5 \times 10^4$ cells, $1 \times 10^5$ cells, $1 \times 10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g., through an Ommaya reservoir, e.g., for intrathecal delivery (e.g., U.S. Pat. Nos. 5,222,982 and 5,385,582, incorporated herein by reference); by bolus injection, e.g., by a syringe, e.g., into a joint; by continuous infusion, e.g., by cannulation, e.g., with convection (e.g., US Application No. 20070254842, incorporated herein by reference); or by implanting a device upon which the cells have been reversibly affixed (e.g., US Application Nos. 20080081064 and 20090196903, incorporated herein by reference). Cells may also be introduced into an embryo (e.g., a blastocyst) for the purpose of generating a transgenic animal (e.g., a transgenic mouse).

Delivery of sRGN Systems

Guide RNA polynucleotides (RNA or DNA) and/or sRGN polypeptides (RNA or DNA) can be delivered by viral or non-viral delivery vehicles known in the art.

Polynucleotides may be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

A recombinant adeno-associated virus (AAV) vector may be used for delivery. Techniques to produce rAAV particles, in which an AAV genome to be packaged that includes the polynucleotide to be delivered, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692.

TABLE 3

| AAV Serotype | Genbank Accession No. |
|---|---|
| AAV-1 | NC_002077.1 |
| AAV-2 | NC_001401.2 |
| AAV-3 | NC_001729.1 |
| AAV-38 | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | 00813647.1 |
| AAV-13 | EU285562.1 |

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Micro Biol. and Immunol., 158:97-129). Various approaches are described in Ratschin et al., Mol. Cell. Bio. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types transduced by the indicated AAV serotypes among others.

TABLE 4

| Tissue/Cell Type | Serotype |
|---|---|
| Liver | AAV8, AAV9 |
| Skeletal muscle | AAV1, AAV7, AAV6, AAV8, AAV9 |
| Central nervous system | AAV5, AAV1, AAV4 |
| RPE | AAV5, AAV4 |
| Photoreceptor cells | AAV5 |
| Lung | AAV9 |
| Heart | AAV8 |
| Pancreas | AAV8 |
| Kidney | AAV2 |

The number of administrations of treatment to a subject may vary. Introducing the genetically modified cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

In other aspects of the disclosure, the guide RNA and/or sRGN polypeptide and/or donor polynucleotide are employed to modify cellular DNA in vivo, for example for purposes such as gene therapy, e.g., to treat a disease or as an antiviral, antipathogenic, or anticancer therapeutic, for the production of genetically modified organisms in agriculture, or for biological research. In these in vivo embodiments, a guide RNA and/or sRGN polypeptide and/or donor polynucleotide are administered directly to the individual. A guide RNA and/or sRGN polypeptide and/or donor polynucleotide may be administered by any of a number of methods known in the art for the administration of peptides, small molecules, and nucleic acids to a subject. A guide RNA and/or sRGN polypeptide and/or donor polynucleotide can be incorporated into a variety of formulations. More particularly, a guide RNA and/or sRGN polypeptide and/or donor polynucleotide of the present invention can be formulated into pharmaceutical compositions by combination with appropriate pharmaceutically acceptable carriers or diluents. In some cases, the guide RNA and sRGN are formulated for ex vivo delivery.

Pharmaceutical preparations are compositions that include one or more a guide RNA and/or sRGN polypeptide and/or donor polynucleotide present in a pharmaceutically acceptable vehicle. "Pharmaceutically acceptable vehicles" may be vehicles approved by a regulatory agency of the Federal or a state government or listed in the US Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g., liposomes, e.g., liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semisolid, liquid or gaseous forms, such as tablets, capsules, powders, granules, ointments, solutions, suppositories, injections, inhalants, gels, microspheres, and aerosols. As such, administration of a guide RNA and/or sRGN polypeptide and/or donor polynucleotide can be achieved in various ways, including oral, buccal, rectal, parenteral, intraperitoneal, intradermal, transdermal, intra-tracheal, intraocular, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the BBB entails disruption of the BBB, either by osmotic means such as mannitol or leukotrienes, or biochemically by the use of vasoactive substances such as bradykinin. The potential for using BBB opening to target specific agents to brain tumors is also an option. A BBB-disrupting agent can be co-administered with the therapeutic compositions of the invention when the compositions are administered by intravascular injection. Other strategies for delivery through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such asp-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g., through an Ommaya reservoir (see e.g., U.S. Pat. Nos. 5,222,982 and 5,385,582, incorporated herein by reference); by bolus injection, e.g., by a syringe, e.g., intravitreally or intracranially; by continuous infusion, e.g., by cannulation, e.g., with convection (see e.g., US Application No. 20070254842, incorporated here by reference); or by implanting a device upon which the agent has been reversibly affixed (see e.g., US Application Nos. 20080081064 and 20090196903, incorporated herein by reference).

Generally, an effective amount of a guide RNA and/or sRGN polypeptide and/or donor polynucleotide are provided. As discussed above with regard to ex vivo methods, an effective amount or effective dose of a guide RNA and/or sRGN polypeptide and/or donor polynucleotide in vivo is the amount to induce a 2 fold increase or more in the amount of recombination observed between two homologous sequences relative to a negative control, e.g., a cell contacted with an empty vector or irrelevant polypeptide. The amount of recombination may be measured by any convenient method, e.g., as described above and known in the art. The calculation of the effective amount or effective dose of a guide RNA and/or sRGN polypeptide and/or donor polynucleotide to be administered is within the skill of one of ordinary skill in the art, and will be routine to those persons skilled in the art. The final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For example, an intravenously administered dose may have a greater amount of therapeutic agent than an intrathecally-administered dose, given the greater body of fluid into which the therapeutic composition is being administered. Similarly, compositions, which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, a guide RNA and/or sRGN polypeptide and/or donor polynucleotide may be obtained from a suitable commercial source. As a general proposition, the total pharmaceutically effective amount of a guide RNA and/or sRGN polypeptide and/or donor polynucleotide administered parenterally per dose will be in a range that can be measured by a dose response curve.

Therapies based on a guide RNA and/or sRGN polypeptide and/or donor polynucleotides, i.e., preparations of a guide RNA and/or sRGN polypeptide and/or donor polynucleotide to be used for therapeutic administration, must be sterile. Sterility is readily accomplished by filtration through sterile filtration membranes (e.g., 0.2 1-1 m membranes). Therapeutic compositions generally are placed into a container having a sterile access port, for example, an intravenous solution bag or vial having a stopper pierceable by a hypodermic injection needle. The therapies based on a guide RNA and/or sRGN polypeptide and/or donor polynucleotide may be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration are known in the art, for example, Remington's Pharmaceutical Sciences, Mace Publishing Company, Philadelphia, Pa., 21st ed. (2006). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices may be preferred.

The data obtained from cell culture and/or animal studies can be used in formulating a range of dosages for humans. The dosage of the active ingredient generally lies within a range of circulating concentrations that include the ED50 with low toxicity. The dosage can vary within this range depending upon the dosage form employed and the route of administration utilized. The components used to formulate the pharmaceutical compositions are in some embodiments of high purity and substantially free of potentially harmful contaminants (e.g., at least National Food (NF) grade, generally at least analytical grade, including at least pharmaceutical grade). Moreover, compositions intended for in vivo use are usually sterile. To the extent that a given compound must be synthesized prior to use, the resulting product is generally substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions that are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Genetically Modified Host Cells

The present disclosure provides genetically modified host cells, including isolated genetically modified host cells, where a genetically modified host cell comprises (has been genetically modified with:

1) an exogenous guide RNA; 2) an exogenous nucleic acid comprising a nucleotide sequence encoding a guide RNA; 3) an exogenous sRGN polypeptide (e.g., a naturally occurring sRGN; a modified, i.e., mutated or variant, sRGN; a chimeric sRGN; etc.); 4) an exogenous nucleic acid comprising a nucleotide sequence encoding an sRGN polypeptide; or 5) any combination of the above. A genetically modified cell is generated by genetically modifying a host cell with, for example: 1) an exogenous guide RNA; 2) an exogenous nucleic acid comprising a nucleotide sequence encoding a guide RNA; 3) an exogenous sRGN polypeptide; 4) an exogenous nucleic acid comprising a nucleotide sequence encoding an sRGN polypeptide; or 5) any combination of the above).

All cells suitable to be a target cell are also suitable to be a genetically modified host cell. For example, a genetically modified host cells of interest can be a cell from any organism (e.g., a bacterial cell, an archaeal cell, a cell of a single-cell eukaryotic organism, a plant cell, an algal cell, e.g., *Botryococcus braunii, Chlamydomonas reinhardtii, Nannochloropsis* gaditana, *Chlorella pyrenoidosa, Sargassum patens C. Agardh*, and the like, a fungal cell (e.g., a yeast cell), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent. a rat, a mouse, a non-human primate, a human, etc.), etc.

In some embodiments, a genetically modified host cell has been genetically modified with an exogenous nucleic acid comprising a nucleotide sequence encoding an sRGN polypeptide (e.g., a naturally occurring sRGN; a modified, i.e., mutated or variant, sRGN; a chimeric sRGN; etc.). The DNA of a genetically modified host cell can be targeted for modification by introducing into the cell a guide RNA (or a DNA encoding a guide RNA, which determines the genomic location/sequence to be modified) and optionally a donor nucleic acid. In some embodiments, the nucleotide sequence encoding an sRGN polypeptide is operably linked to an inducible promoter (e.g., heat shock promoter, Tetracycline-regulated promoter, Steroid-regulated promoter, Metal-regulated promoter, estrogen receptor-regulated promoter, etc.). In some embodiments, the nucleotide sequence encoding an sRGN polypeptide is operably linked to a spatially restricted and/or temporally restricted promoter (e.g., a tissue specific promoter, a cell type specific promoter, a cell cycle specific promoter). In some embodiments, the nucleotide sequence encoding an sRGN polypeptide is operably linked to a constitutive promoter.

In some embodiments, a genetically modified host cell is in vitro. In some embodiments, a genetically modified host cell is in vivo. In some embodiments, a genetically modified host cell is a prokaryotic cell or is derived from a prokaryotic cell. In some embodiments, a genetically modified host cell is a bacterial cell or is derived from a bacterial cell. In some embodiments, a genetically modified host cell is an archaeal cell or is derived from an archaeal cell. In some embodiments, a genetically modified host cell is a eukaryotic cell or is derived from a eukaryotic cell. In some embodiments, a genetically modified host cell is a plant cell or is derived from a plant cell. In some embodiments, a genetically modified host cell is an animal cell or is derived from an animal cell. In some embodiments, a genetically modified host cell is an invertebrate cell or is derived from an invertebrate cell. In some embodiments, a genetically modified host cell is a vertebrate cell or is derived from a vertebrate cell. In some embodiments, a genetically modified host cell is a mammalian cell or is derived from a mammalian cell. In some embodiments, a genetically modified host cell is a rodent cell or is derived from a rodent cell. In some embodiments, a genetically modified host cell is a human cell or is derived from a human cell.

The present disclosure further provides progeny of a genetically modified cell, where the progeny can comprise the same exogenous nucleic acid or polypeptide as the genetically modified cell from which it was derived. The present disclosure further provides a composition comprising a genetically modified host cell.

Genetically Modified Stem Cells and Genetically Modified Progenitor Cells

In some embodiments, a genetically modified host cell is a genetically modified stem cell or progenitor cell. Suitable host cells include, e.g., stem cells (adult stem cells, embryonic stem cells, iPS cells, etc.) and progenitor cells (e.g., cardiac progenitor cells, neural progenitor cells, etc.). Suitable host cells include mammalian stem cells and progenitor cells, including, e.g., rodent stem cells, rodent progenitor cells, human stem cells, human progenitor cells, etc. Suitable host cells include in vitro host cells, e.g., isolated host cells.

In some embodiments, a genetically modified host cell comprises an exogenous guide RNA nucleic acid. In some embodiments, a genetically modified host cell comprises an exogenous nucleic acid comprising a nucleotide sequence encoding a guide RNA. In some embodiments, a genetically modified host cell comprises an exogenous sRGN polypeptide (e.g., a naturally occurring sRGN; a modified, i.e., mutated or variant, sRGN; a chimeric sRGN; etc.). In some embodiments, a genetically modified host cell comprises an exogenous nucleic acid comprising a nucleotide sequence encoding an sRGN polypeptide. In some embodiments, a genetically modified host cell comprises exogenous nucleic acid comprising a nucleotide sequence encoding 1) a guide RNA and 2) an sRGN polypeptide.

In some cases, the sRGN polypeptide comprises an amino acid sequence having at least 75%, at least 80%, at least 85%, at least 90%, at least 95%, at least 99%, or 100% amino acid sequence identity to any of the sequences in SEQ ID NO: 1-12, or an active portion thereof which is at least 100, 150, 200, 300, 350, 400, or 500 amino acids long. In some embodiments, the active portion comprises an RNase domain. In other embodiments, the active portion comprises a DNase domain.

Compositions

The present disclosure provides a composition comprising a guide RNA and/or a site-directed modifying polypeptide. In some cases, the sRGN polypeptide is a chimeric polypeptide. A composition is useful for carrying out a method of the present disclosure, e.g., a method for site-specific modification of a target DNA; a method for site-specific modification of a polypeptide associated with a target DNA; etc.

Compositions Comprising a Guide RNA

The present disclosure provides a composition comprising a guide RNA. The composition can comprise, in addition to the guide RNA, one or more of: a salt, e.g. NaCl, MgCl, KCl, MgS04, etc.; a buffering agent, e.g. a Tris buffer, N-(2-hydroxyethyl)piperazine-N'-(2-ethanesulfonic acid) (HEPES), 2-(N-morpholino)ethanesulfonic acid (MES), MES sodium salt, 3-(N-morpholino)propanesulfonic acid (MOPS), N-tris[hydroxymethyl]methyl-3-aminopropanesulfonic acid (TAPS), etc.; a solubilizing agent; a detergent, e.g. a non-ionic detergent such as Tween®20, etc.; a nuclease inhibitor; and the like. For example, in some cases, a composition comprises a guide RNA and a buffer for stabilizing nucleic acids.

In some embodiments, a guide RNA present in a composition is pure, e.g., at least 75%, at least 80%, at least 85%, at least 90%, at least 95%, at least 98%, at least 99%, or more than 99% pure, where "% purity" means that guide RNA is the recited percent free from other macromolecules, or contaminants that may be present during the production of the guide RNA.

Compositions Comprising a Chimeric Polypeptide

The present disclosure provides a composition of a chimeric polypeptide. The composition can comprise, in addition to the guide RNA, one or more of: a salt, e.g., NaCl, MgCl, KCl, MgS04, etc.; a buffering agent, e.g., a Tris buffer, HEPES, MES, MES sodium salt, MOPS, TAPS, etc.; a solubilizing agent; a detergent, e.g., a non-ionic detergent such as Tween®20, etc.; a protease inhibitor; a reducing agent (e.g., dithiothreitol); and the like.

In some embodiments, a chimeric polypeptide present in a composition is pure, e.g., at least 75%, at least 80%, at least 85%, at least 90%, at least 95%, at least 98%, at least 99%, or more than 99% pure, where "% purity" means that the site-directed modifying polypeptide is the recited percent free from other proteins, other macromolecules, or contaminants that may be present during the production of the chimeric polypeptide.

Compositions Comprising a Guide RNA and an sRGN Polypeptide

The present disclosure provides a composition comprising: (i) a guide RNA or a DNA nucleic acid encoding the same; and ii) an sRGN polypeptide, or a nucleic acid encoding the same. In some cases, the sRGN polypeptide is a chimeric sRGN polypeptide. In other cases, the sRGN polypeptide is a naturally occurring sRGN polypeptide. In some instances, the sRGN polypeptide exhibits enzymatic activity that modifies a target DNA. In other cases, the sRGN polypeptide exhibits enzymatic activity that modifies a polypeptide that is associated with a target DNA. In still other cases, the sRGN polypeptide modulates transcription of the target DNA.

The present disclosure provides a composition comprising: (i) a guide RNA, as described above, or a DNA nucleic acid encoding the same, the guide RNA comprising: (a) a first segment comprising a nucleotide sequence that is complementary to a sequence in a target DNA; and (b) a second segment that interacts with an sRGN polypeptide; and (ii) the sRGN polypeptide, or a nucleic acid encoding the same, the sRGN polypeptide comprising: (a) an RNA-binding portion that interacts with the guide RNA; and (b) an activity portion that exhibits site-directed enzymatic activity, wherein the site of enzymatic activity is determined by the guide RNA.

In some instances, a composition comprises: (i) a guide RNA, the guide RNA comprising: (a) a first segment comprising a nucleotide sequence that is complementary to a sequence in a target DNA; and (b) a second segment that interacts with an sRGN polypeptide; and (ii) the sRGN polypeptide, the sRGN polypeptide comprising: (a) an RNA-binding portion that interacts with the guide RNA; and (b) an activity portion that exhibits site-directed enzymatic activity, wherein the site of enzymatic activity is determined by the guide RNA.

In other embodiments, a composition comprises: (i) a nucleic acid encoding a guide RNA, the guide RNA comprising: (a) a first segment comprising a nucleotide sequence that is complementary to a sequence in a target DNA; and (b) a second segment that interacts with a site-directed modifying polypeptide; and (ii) a nucleic acid encoding the sRGN polypeptide, the sRGN polypeptide comprising: (a) an RNA-binding portion that interacts with the guide RNA; and (b) an activity portion that exhibits site-directed enzymatic activity, wherein the site of enzymatic activity is determined by the guide RNA.

The present disclosure provides a composition comprising: (i) a guide RNA, or a DNA nucleic acid encoding the same, the guide RNA comprising: (a) a first segment comprising a nucleotide sequence that is complementary to a sequence in a target DNA; and (b) a second segment that interacts with an sRGN polypeptide; and (ii) the sRGN polypeptide, or a nucleic acid encoding the same, the sRGN polypeptide comprising: (a) an RNA-binding portion that interacts with the guide RNA; and (b) an activity portion that modulates transcription within the target DNA, wherein the site of modulated transcription within the target DNA is determined by the guide RNA.

For example, in some cases, a composition comprises: (i) a guide RNA the guide RNA comprising: (a) a first segment comprising a nucleotide sequence that is complementary to a sequence in a target DNA; and (b) a second segment that interacts with an sRGN polypeptide; and (ii) the sRGN polypeptide, the sRGN polypeptide comprising: (a) an RNA-binding portion that interacts with the guide RNA; and (b) an activity portion that modulates transcription within the target DNA, wherein the site of modulated transcription within the target DNA is determined by the guide RNA.

As another example, in some cases, a composition comprises: (i) a DNA nucleic acid encoding a guide RNA, the guide RNA comprising: (a) a first segment comprising a nucleotide sequence that is complementary to a sequence in a target DNA; and (b) a second segment that interacts with an sRGN polypeptide; and (ii) a nucleic acid encoding the site-directed modifying polypeptide, the sRGN polypeptide comprising: (a) an RNA-binding portion that interacts with the guide RNA; and (b) an activity portion that modulates transcription within the target DNA, wherein the site of modulated transcription within the target DNA is determined by the guide RNA. A composition can comprise, in addition to i) a guide RNA, or a DNA nucleic acid encoding the same; and ii) an sRGN polypeptide, or a nucleic acid encoding the same, one or more of: a salt, e.g. NaCl, MgCl, KCl, MgSO4, etc.; a buffering agent, e.g. a Tris buffer, HEPES, MES, MES sodium salt, MOPS, TAPS, etc.; a solubilizing agent a detergent, e.g. a non-ionic detergent such as Tween-20, etc.; a protease inhibitor; a reducing agent (e.g. dithiothreitol); and the like.

In some cases, the components of the composition are individually pure, e.g., each of the components is at least 75%, at least 80%, at least 90%, at least 95%, at least 98%, at least 99%, or at least 99%, pure. In some cases, the individual components of a composition are pure before being added to the composition.

For example, in some embodiments, an sRGN polypeptide present in a composition is pure, e.g., at least 75%, at least 80%, at least 85%, at least 90%, at least 95%, at least 98%, at least 99%, or more than 99% pure, where "% purity" means that the sRGN polypeptide is the recited percent free from other proteins (e.g., proteins other than the sRGN polypeptide), other macromolecules, or contaminants that may be present during the production of the sRGN polypeptide.

Kits

The present disclosure provides kits for carrying out a method. A kit can include one or more of: an sRGN polypeptide; a nucleic acid comprising a nucleotide encoding a site-directed modifying polypeptide; a guide RNA; a nucleic acid comprising a nucleotide sequence encoding a guide RNA. A kit may comprise a complex that comprises two or more of: an sRGN polypeptide; a nucleic acid comprising a nucleotide encoding an sRGN polypeptide; a guide RNA; a nucleic acid comprising a nucleotide sequence encoding a guide RNA. In some embodiments, a kit comprises an sRGN polypeptide, or a nucleic acid encoding the same. In some embodiments, the sRGN polypeptide comprises: (a) an RNA-binding portion that interacts with the guide RNA; and (b) an activity portion that modulates transcription within the target DNA, wherein the guide RNA determines the site of modulated transcription within the target DNA. In some cases, the activity portion of the sRGN polypeptide exhibits reduced or inactivated nuclease activity. In some cases, the sRGN polypeptide is a chimeric sRGN polypeptide.

In some embodiments, a kit comprises: an sRGN polypeptide, or a nucleic acid encoding the same, and a reagent for reconstituting and/or diluting the sRGN polypeptide. In other embodiments, a kit comprises a nucleic acid (e.g., DNA, RNA) comprising a nucleotide encoding an sRGN polypeptide. In some embodiments, a kit comprises: a nucleic acid (e.g., DNA, RNA) comprising a nucleotide encoding an sRGN polypeptide; and a reagent for reconstituting and/or diluting the sRGN polypeptide.

A kit comprising an sRGN polypeptide, or a nucleic acid encoding the same, can further include one or more additional reagents, where such additional reagents can be selected from: a buffer for introducing the sRGN polypeptide into a cell; a wash buffer; a control reagent; a control expression vector or RNA polynucleotide; a reagent for in vitro production of the sRGN polypeptide from DNA, and the like. In some cases, the site-directed modifying polypeptide included in a kit is a chimeric sRGN polypeptide, as described above.

In some embodiments, a kit comprises a guide RNA, or a DNA nucleic acid encoding the same, the guide RNA comprising: (a) a first segment comprising a nucleotide sequence that is complementary to a sequence in a target DNA; and (b) a second segment that interacts with a site-directed modifying polypeptide. In some embodiments, a kit comprises: (i) a guide RNA, or a DNA nucleic acid encoding the same, the guide RNA comprising: (a) a first segment comprising a nucleotide sequence that is complementary to a sequence in a target DNA; and (b) a second segment that interacts with an sRGN polypeptide; and (ii) an sRGN polypeptide, or a nucleic acid encoding the same, the sRGN polypeptide comprising: (a) an RNA-binding portion that interacts with the guide RNA; and (b) an activity portion that exhibits site-directed enzymatic activity, wherein the site of enzymatic activity is determined by the guide RNA. In some embodiments, the activity portion of the sRGN polypeptide does not exhibit enzymatic activity (comprises an inactivated nuclease, e.g., via mutation). In some cases, the kit comprises a guide RNA and an sRGN polypeptide. In other cases, the kit comprises: (i) a nucleic acid comprising a nucleotide sequence encoding a guide RNA; and (ii) a nucleic acid comprising a nucleotide sequence encoding sRGN polypeptide. As another example, a kit can include: (i) a guide RNA, or a DNA nucleic acid encoding the same, comprising:

(a) a first segment comprising a nucleotide sequence that is complementary to a sequence in a target DNA; and (b) a second segment that interacts with an sRGN polypeptide; and (ii) the sRGN polypeptide, or a nucleic acid encoding the same, comprising: (a) an RNA-binding portion that interacts with the guide RNA; and (b) an activity portion that modulates transcription within the target DNA, wherein the site of modulated transcription within the target DNA is determined by the guide RNA In some cases, the kit comprises: (i) a guide RNA; and an sRGN polypeptide. In other cases, the kit comprises: (i) a nucleic acid comprising a nucleotide sequence encoding a guide RNA; and (ii) a nucleic acid comprising a nucleotide sequence encoding sRGN polypeptide. The present disclosure provides a kit comprising: (1) a recombinant expression vector comprising (i) a nucleotide sequence encoding a guide RNA, wherein the guide RNA comprises: (a) a first segment comprising a nucleotide sequence that is complementary to a sequence in a target DNA; and (b) a second segment that interacts with an sRGN polypeptide; and (ii) a nucleotide sequence encoding the sRGN polypeptide, wherein the sRGN polypeptide comprises: (a) an RNA-binding portion that interacts with the guide RNA; and (b) an activity portion that exhibits site-directed enzymatic activity, wherein the site of enzymatic activity is determined by the guide RNA; and (2) a reagent for reconstitution and/or dilution of the expression vector.

The present disclosure provides a kit comprising: (1) a recombinant expression vector comprising: (i) a nucleotide sequence encoding a guide RNA, wherein the guide RNA comprises: (a) a first segment comprising a nucleotide sequence that is complementary to a sequence in a target DNA; and (b) a second segment that interacts with an sRGN polypeptide; and (ii) a nucleotide sequence encoding the sRGN polypeptide, wherein the sRGN polypeptide comprises: (a) an RNA-binding portion that interacts with the guide RNA; and (b) an activity portion that modulates transcription within the target DNA, wherein the site of modulated transcription within the target DNA is determined by the guide RNA; and (2) a reagent for reconstitution and/or dilution of the recombinant expression vector.

The present disclosure provides a kit comprising: (1) a recombinant expression vector comprising a nucleic acid comprising a nucleotide sequence that encodes a DNA targeting RNA comprising: (i) a first segment comprising a nucleotide sequence that is complementary to a sequence in a target DNA; and (ii) a second segment that interacts with an sRGN polypeptide; and (2) a reagent for reconstitution and/or dilution of the recombinant expression vector. In some embodiments of this kit, the kit comprises: a recombinant expression vector comprising a nucleotide sequence that encodes an sRGN polypeptide, wherein the sRGN polypeptide comprises: (a) an RNA-binding portion that interacts with the guide RNA; and (b) an activity portion that exhibits site-directed enzymatic activity, wherein the site of enzymatic activity is determined by the guide RNA. In other embodiments of this kit, the kit comprises: a recombinant expression vector comprising a nucleotide sequence that encodes an sRGN polypeptide, wherein the sRGN polypeptide comprises: (a) an RNA-binding portion that interacts with the guide RNA; and (b) an activity portion that modulates transcription within the target DNA, wherein the site of modulated transcription within the target DNA is determined by the guide RNA.

In some embodiments of any of the above kits, the kit comprises a single-molecule guide RNA. In some embodiments of any of the above kits, the kit comprises two or more single-molecule guide RNAs. In some embodiments of any of the above kits, a guide RNA (e.g., including two or more guide RNAs) can be provided as an array (e.g., an array of RNA molecules, an array of DNA molecules encoding the guide RNA(s), etc.). Such kits can be useful, for example, for use in conjunction with the above described genetically modified host cells that comprise an sRGN polypeptide. In some embodiments of any of the above kits, the kit further comprises a donor polynucleotide to effect the desired genetic modification. Components of a kit can be in separate containers; or can be combined in a single container.

In some cases, a kit further comprises one or more variant sRGN site-directed polypeptides that exhibit reduced endodeoxyribonuclease activity relative to wild-type sRGN.

In some cases, a kit further comprises one or more nucleic acids comprising a nucleotide sequence encoding a variant sRGN site-directed polypeptide that exhibits reduced endodeoxyribonuclease activity relative to wild-type sRGN.

Any of the above-described kits can further include one or more additional reagents, where such additional reagents can be selected from: a dilution buffer; a reconstitution solution; a wash buffer; a control reagent; a control expression vector or RNA polynucleotide; a reagent for in vitro production of the sRGN polypeptide from DNA, and the like.

In addition to above-mentioned components, a kit can further include instructions for using the components of the kit to practice the methods. The instructions for practicing the methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, flash drive, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Non-Human Genetically Modified Organisms

In some embodiments, a genetically modified host cell has been genetically modified with an exogenous nucleic acid comprising a nucleotide sequence encoding an sRGN polypeptide (e.g., a naturally occurring sRGN; a modified, i.e., mutated or variant, sRGN; a chimeric sRGN; etc.). If such a cell is a eukaryotic single-cell organism, then the modified cell can be considered a genetically modified organism. In some embodiments, the non-human genetically modified organism is an sRGN transgenic multicellular organism.

In some embodiments, a genetically modified non-human host cell (e.g., a cell that has been genetically modified with an exogenous nucleic acid comprising a nucleotide sequence encoding a site-directed modifying polypeptide, e.g., a naturally occurring sRGN; a modified, i.e., mutated or variant, sRGN; a chimeric sRGN; etc.) can generate a genetically modified nonhuman organism (e.g., a mouse, a fish, a frog, a fly, a worm, etc.). For example, if the genetically modified host cell is a pluripotent stem cell (i.e., PSC) or a germ cell (e.g., sperm, oocyte, etc.), an entire genetically modified organism can be derived from the genetically modified host cell. In some embodiments, the genetically modified host cell is a pluripotent stem cell (e.g., ESC, iPSC, pluripotent plant stem cell, etc.) or a germ cell (e.g., sperm cell, oocyte, etc.), either in vivo or in vitro that can give rise to a genetically modified organism. In some embodiments the genetically modified host cell is a vertebrate PSC (e.g., ESC, iPSC, etc.) and is used to generate a genetically modified organism (e.g., by injecting a PSC into a blastocyst to produce a chimeric/mosaic animal, which could then be mated to generate non-chimeric/non-mosaic genetically modified organisms; grafting in the case of plants; etc.). Any convenient method/protocol for producing a genetically modified organism, including the methods described herein, is suitable for producing a genetically modified host cell comprising an exogenous nucleic acid comprising a nucleotide sequence encoding an sRGN polypeptide (e.g., a naturally occurring sRGN; a modified, i.e., mutated or variant, sRGN; a chimeric sRGN; etc.). Methods of producing genetically modified organisms are known in the art. For example, see Cho et al., Curr Protoc Cell Biol. 2009 March; Chapter 19:Unit 19.11: Generation of transgenic mice; Gama et al., Brain Struct Funct. 2010 March; 214(2-3):91-109. Epub 2009 Nov. 25: Animal transgenesis: an overview; Husaini et al., GM Crops. 2011 June-December; 2(3):150-62. Epub 2011 Jun. 1: Approaches for gene targeting and targeted gene expression in plants.

In some embodiments, a genetically modified organism comprises a target cell for methods of the invention, and thus can be considered a source for target cells. For example, if a genetically modified cell comprising an exogenous nucleic acid comprising a nucleotide sequence encoding a site-directed modifying polypeptide (e.g., a naturally occurring sRGN; a modified, i.e., mutated or variant, sRGN; a chimeric sRGN; etc.) is used to generate a genetically modified organism, then the cells of the genetically modified organism comprise the exogenous nucleic acid comprising a nucleotide sequence encoding an sRGN polypeptide (e.g., a naturally occurring sRGN; a modified, i.e., mutated or variant, sRGN; a chimeric sRGN; etc.). In some such embodiments, the DNA of a cell or cells of the genetically modified organism can be targeted for modification by introducing into the cell or cells a guide RNA (or a DNA encoding a guide RNA) and optionally a donor nucleic acid. For example, the introduction of a guide RNA (or a DNA encoding a guide RNA) into a subset of cells (e.g., brain cells, intestinal cells, kidney cells, lung cells, blood cells, etc.) of the genetically modified organism can target the DNA of such cells for modification, the genomic location of which will depend on the DNA-targeting sequence of the introduced guide RNA.

In some embodiments, a genetically modified organism is a source of target cells for methods of the invention. For example, a genetically modified organism comprising cells that are genetically modified with an exogenous nucleic acid comprising a nucleotide sequence encoding an sRGN polypeptide (e.g., a naturally occurring sRGN; a modified, i.e., mutated or variant, sRGN; a chimeric sRGN; etc.) can provide a source of genetically modified cells, for example PSCs (e.g., ESCs, iPSCs, sperm, oocytes, etc.), neurons, progenitor cells, cardiomyocytes, etc.

In some embodiments, a genetically modified cell is a PSC comprising an exogenous nucleic acid comprising a nucleotide sequence encoding an sRGN polypeptide (e.g., a naturally occurring sRGN; a modified, i.e., mutated or variant, sRGN; a chimeric sRGN; etc.). As such, the PSC can be a target cell such that the DNA of the PSC can be targeted for modification by introducing into the PSC a guide RNA (or a DNA encoding a guide RNA) and optionally a donor nucleic acid, and the genomic location of the modification will depend on the DNA-targeting sequence of the introduced guide RNA. Thus, in some embodiments, the methods described herein can be used to modify the DNA (e.g., delete and/or replace any desired genomic location) of PSCs derived from a genetically modified organism. Such modified PSCs can then be used to generate organisms having both (i) an exogenous nucleic acid comprising a nucleotide sequence encoding an sRGN polypeptide (e.g., a naturally occurring sRGN; a modified, i.e., mutated or variant, sRGN; a chimeric sRGN; etc.) and (ii) a DNA modification that was introduced into the PSC.

An exogenous nucleic acid comprising a nucleotide sequence encoding an sRGN polypeptide (e.g., a naturally occurring sRGN; a modified, i.e., mutated or variant, sRGN; a chimeric sRGN; etc.) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

A genetically modified organism (e.g., an organism whose cells comprise a nucleotide sequence encoding an sRGN polypeptide, e.g., a naturally occurring sRGN; a modified, i.e., mutated or variant, sRGN; a chimeric sRGN; etc.) can be any organism including for example, a plant; algae; an invertebrate (e.g., a cnidarian, an echinoderm, a worm, a fly, etc.); a vertebrate (e.g., a fish (e.g., zebrafish, puffer fish, goldfish, etc.), an amphibian (e.g., salamander, frog, etc.), a reptile, a bird, a mammal, etc.); an ungulate (e.g., a goat, a pig, a sheep, a cow, etc.); a rodent (e.g., a mouse, a rat, a hamster, a guinea pig); a lagomorph (e.g., a rabbit); etc.

In some cases, the sRGN polypeptide comprises an amino acid sequence having at least 75%, at least 80%, at least 85%, at least 90%, at least 95%, at least 99%, or 100% amino acid sequence identity to SEQ ID NO: 1-12.

Transgenic Non-Human Animals

As described above, in some embodiments, a nucleic acid (e.g., a nucleotide sequence encoding an sRGN polypeptide, e.g., a naturally occurring sRGN; a modified, i.e., mutated or variant, sRGN; a chimeric sRGN; etc.) or a recombinant expression vector is used as a transgene to generate a transgenic animal that produces an sRGN polypeptide. Thus, the present disclosure further provides a transgenic non-human animal, which animal comprises a transgene comprising a nucleic acid comprising a nucleotide sequence encoding a site-directed modifying polypeptide, e.g., a naturally occurring sRGN; a modified, i.e., mutated or variant, sRGN; a chimeric sRGN; etc., as described above. In some embodiments, the genome of the transgenic non-human animal comprises a nucleotide sequence encoding an sRGN polypeptide. In some embodiments, the transgenic non-human animal is homozygous for the genetic modification. In some embodiments, the transgenic non-human animal is heterozygous for the genetic modification. In some embodiments, the transgenic non-human animal is a vertebrate, for example, a fish (e.g., zebrafish, goldfish, puffer fish, cave fish, etc.), an amphibian (frog, salamander, etc.), a bird (e.g., chicken, turkey, etc.), a reptile (e.g., snake, lizard, etc.), a mammal (e.g., an ungulate, e.g., a pig, a cow, a goat, a sheep, etc.; a lagomorph (e.g., a rabbit); a rodent (e.g., a rat, a mouse); a nonhuman primate; etc.), etc.

An exogenous nucleic acid comprising a nucleotide sequence encoding an sRGN polypeptide (e.g., a naturally occurring sRGN; a modified, i.e., mutated or variant, sRGN; a chimeric sRGN; etc.) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some embodiments, a nucleic acid (e.g., a nucleotide sequence encoding an sRGN polypeptide, e.g., a naturally occurring sRGN; a modified, i.e., mutated or variant, sRGN; a chimeric sRGN; etc.) or a recombinant expression vector is used as a transgene to generate a transgenic plant that produces an sRGN polypeptide. Thus, the present disclosure further provides a transgenic plant, which plant comprises a transgene comprising a nucleic acid comprising a nucleotide sequence encoding sRGN polypeptide, e.g., a naturally occurring sRGN; a modified, i.e., mutated or variant, sRGN; a chimeric sRGN; etc., as described above. In some embodiments, the genome of the transgenic plant comprises a nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double-stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e., in vitro, ex vivo, or in vivo). Transformation methods based upon the soil bacterium Agrobacterium tumefaciens are particularly useful for introducing an exogenous nucleic acid molecule into a vascular plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid may be introduced into a plant in a manner such that the nucleic acid is able to enter a plant cell(s), e.g., via an in vivo or ex vivo protocol. By "in vivo," it is meant in the nucleic acid is administered to a living body of a plant e.g., infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of Agrobacterium tumefaciens, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for Agrobacterium-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Daniell et al. Nat. Biotechnol 16:345-348, 1998; Staub et al. Nat. Biotechnol 18: 333-338, 2000; O'Neill et al. Plant J. 3:729-738, 1993; Knoblauch et al. Nat. Biotechnol 17: 906-909; U.S. Pat. Nos. 5,451,513, 5,545,817, 5,545,818, and 5,576,198; in Inti. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double-stranded DNA vector may be used as a transformation vector, especially when the method of introduction does not utilize *Agrobacterium*.

Plants, which can be genetically modified, include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

Also provided by the disclosure are transformed plant cells, tissues, plants and products that contain the transformed plant cells. A feature of the transformed cells, and tissues and products that include the same is the presence of a nucleic acid integrated into the genome, and production by plant cells of an sRGN polypeptide, e.g., a naturally occurring sRGN; a modified, i.e., mutated or variant, sRGN; a chimeric sRGN; etc. Recombinant plant cells of the present invention are useful as populations of recombinant cells, or as a tissue, seed, whole plant, stem, fruit, leaf, root, flower, stem, tuber, grain, animal feed, a field of plants, and the like.

A nucleic acid comprising a nucleotide sequence encoding an sRGN polypeptide (e.g., a naturally occurring sRGN; a modified, i.e., mutated or variant, sRGN; a chimeric sRGN; etc.) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

The present disclosure provides methods of modulating transcription of a target nucleic acid in a host cell. The methods generally involve contacting the target nucleic acid with an enzymatically inactive sRGN polypeptide and a guide RNA. The methods are useful in a variety of applications, which are also provided.

A transcriptional modulation method of the present disclosure overcomes some of the drawbacks of methods involving RNAi. A transcriptional modulation method of the present disclosure finds use in a wide variety of applications, including research applications, drug discovery (e.g., high throughput screening), target validation, industrial applications (e.g., crop engineering; microbial engineering, etc.), diagnostic applications, therapeutic applications, and imaging techniques.

Methods of Modulating Transcription

The present disclosure provides a method of selectively modulating transcription of a target DNA in a host cell. The method generally involves: a) introducing into the host cell: i) a guide RNA, or a nucleic acid comprising a nucleotide sequence encoding the guide RNA; and ii) a variant sRGN site-directed polypeptide ("variant sRGN polypeptide"), or a nucleic acid comprising a nucleotide sequence encoding the variant sRGN polypeptide, where the variant sRGN polypeptide exhibits reduced endodeoxyribonuclease activity.

The guide RNA (also referred to herein as "guide RNA"; or "gRNA") comprises: i) a first segment comprising a nucleotide sequence that is complementary to a target sequence in a target DNA; ii) a second segment that interacts with an sRGN polypeptide; and iii) a transcriptional terminator. The first segment, comprising a nucleotide sequence that is complementary to a target sequence in a target DNA, is referred to herein as a "targeting segment". The second segment, which interacts with an sRGN polypeptide, is also referred to herein as a "protein-binding sequence" or "dsRGN-binding hairpin," or "dsRGN handle." By "segment" it is meant a segment/section/region of a molecule, e.g., a contiguous stretch of nucleotides in an RNA. The definition of "segment," unless otherwise specifically defined in a particular context, is not limited to a specific nuber of total base pairs, and may include regions of RNA molecules that are of any total length and may or may not include regions with complementarity to other molecules. The variant sRGN site-directed polypeptide comprises: i) an RNA-binding portion that interacts with the guide RNA; and an activity portion that exhibits reduced endodeoxyribonuclease activity.

The guide RNA and the variant sRGN polypeptide form a complex in the host cell; the complex selectively modulates transcription of a target DNA in the host cell.

In some cases, a transcription modulation method of the present disclosure provides for selective modulation (e.g., reduction or increase) of a target nucleic acid in a host cell. For example, "selective" reduction of transcription of a target nucleic acid reduces transcription of the target nucleic acid by at least 10%, at least 20%, at least 30%, at least 40%, at least 50%, at least 60%, at least 70%, at least 80%, at least 90%, or greater than 90%, compared to the level of transcription of the target nucleic acid in the absence of a guide RNA/variant sRGN polypeptide complex. Selective reduction of transcription of a target nucleic acid reduces transcription of the target nucleic acid, but does not substantially reduce transcription of a non-target nucleic acid, e.g., transcription of a non-target nucleic acid is reduced, if at all, by less than 10% compared to the level of transcription of the non-target nucleic acid in the absence of the guide RNA/variant sRGN polypeptide complex.

Increased Transcription

"Selective" increased transcription of a target DNA can increase transcription of the target DNA by at least 1.1 fold (e.g., at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20-fold) compared to the level of transcription of the target DNA in the absence of a guide RNA/variant sRGN polypeptide complex. Selective increase of transcription of a target DNA increases transcription of the target DNA, but does not substantially increase transcription of a non-target DNA, e.g., transcription of a non-target DNA is increased, if at all, by less than about 5-fold (e.g., less than about 4-fold, less than about 3-fold, less than about 2-fold, less than about 1.8-fold, less than about 1.6-fold, less than about 1.4-fold, less than about 1.2-fold, or less than about 1.1-fold) compared to the level of transcription of the non-targeted DNA in the absence of the guide RNA/variant sRGN polypeptide complex.

As a non-limiting example, increased transcription can be achieved by fusing dsRGN to a heterologous sequence. Suitable fusion partners include, but are not limited to, a polypeptide that provides an activity that indirectly increases transcription by acting directly on the target DNA or on a polypeptide (e.g., a histone or other DNA-binding protein) associated with the target DNA. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, crotonylation, decrotonylation, propionylation, depropionylation, myristoylation activity, or demyristoylation activity.

Additional suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.).

A non-limiting example of a method using a dsRGN fusion protein to increase transcription in a prokaryote includes a modification of the bacterial one-hybrid (B1H) or two-hybrid (B2H) system. In the B1H system, a DNA binding domain (BD) is fused to a bacterial transcription activation domain (AD, e.g., the alpha subunit of the *Escherichia coli* RNA polymerase (RNAPa)). Thus, a dsRGN can be fused to a heterologous sequence comprising an AD. When the dsRGN fusion protein arrives at the upstream region of a promoter (targeted there by the guide RNA) the AD (e.g., RNAPa) of the dsRGN fusion protein recruits the RNAP holoenzyme, leading to transcription activation. In the B2H system, the BD is not directly fused to the AD; instead, their interaction is mediated by a protein-protein interaction (e.g., GAL11P-GAL4 interaction). To modify such a system for use in the methods, dsRGN can be fused to a first protein sequence that provides for protein-protein interaction (e.g., the yeast GAL11P and/or GAL4 protein) and RNAa can be fused to a second protein sequence that completes the protein-protein interaction (e.g., GAL4 if GAL11Pis fused to dsRGN, GAL11P if GAL4 is fused to dsRGN, etc.). The binding affinity between GAL11P and GAL4 increases the efficiency of binding and transcription firing rate.

A non-limiting example of a method using a dsRGN fusion protein to increase transcription in eukaryotes includes fusion of dsRGN to an activation domain (AD) (e.g., GAL4, herpesvirus activation protein VP16 or VP64, human nuclear factor NF-KB p65 subunit, etc.). To render the system inducible, expression of the dsRGN fusion protein can be controlled by an inducible promoter (e.g., Tet-ON, Tet-OFF, etc.). The guide RNA can be design to target known transcription response elements (e.g., promoters, enhancers, etc.), known upstream activating sequences (UAS), sequences of unknown or known function that are suspected of being able to control expression of the target DNA, etc.

Additional Fusion Partners

Non-limiting examples of fusion partners to accomplish increased or decreased transcription include, but are not limited to, transcription activator and transcription repressor domains (e.g., the Kruppel associated box (KRAB or SKD); the Mad mSIN3 interaction domain (SID); the ERF repressor domain (ERD), etc.). In some such cases, the dsRGN fusion protein is targeted by the guide RNA to a specific location (i.e., sequence) in the target DNA and exerts locus-specific regulation such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones). In some embodiments, the heterologous sequence can be fused to the C-terminus of the dsRGN polypeptide. In some embodiments, the heterologous sequence can be fused to the N-terminus of the dsRGN polypeptide. In some embodiments, the heterologous sequence can be fused to an internal portion (i.e., a portion other than the N- or C-terminus) of the dsRGN polypeptide. The biological effects of a method using a dsRGN fusion protein can be detected by any convenient method (e.g., gene expression assays; chromatin-based assays, e.g., Chromatin ImmunoPrecipitation (ChIP), Chromatin in vivo Assay (CiA), etc.).

In some cases, a method involves use of two or more different guide RNAs. For example, two different guide RNAs can be used in a single host cell, where the two different guide RNAs target two different target sequences in the same target nucleic acid. Thus, for example, a transcriptional modulation method can further comprise introducing into the host cell a second guide RNA, or a nucleic acid comprising a nucleotide sequence encoding the second guide RNA, where the second guide RNA comprises: i) a first segment comprising a nucleotide sequence that is complementary to a second target sequence in the target DNA; ii) a second segment that interacts with the site-directed polypeptide; and iii) a transcriptional terminator. In some cases, use of two different guide RNAs targeting two different targeting sequences in the same target nucleic acid provides for increased modulation (e.g., reduction or increase) in transcription of the target nucleic acid.

As another example, two different guide RNAs can be used in a single host cell, where the two different guide RNAs target two different target nucleic acids. Thus, for example, a transcriptional modulation method can further comprise introducing into the host cell a second guide RNA, or a nucleic acid comprising a nucleotide sequence encoding the second guide RNA, where the second guide RNA comprises: i) a first segment comprising a nucleotide sequence that is complementary to a target sequence in at least a second target DNA; ii) a second segment that interacts with the site-directed polypeptide; and iii) a transcriptional terminator.

In some embodiments, a nucleic acid (e.g., a guide RNA, e.g., a single-molecule guide RNA; a donor polynucleotide; a nucleic acid encoding an sRGN polypeptide; etc.) comprises a modification or sequence that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m 7G)); a 3' polyadenylated tail (i.e., a 3' poly(A) tail); a riboswitch sequence or an aptamer sequence (e.g., to allow for regulated stability and/or regulated accessibility by proteins and/or protein complexes); a terminator sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); a modification of RNA that alters the structure of such RNA, consequently the sRGN ribonucleoprotein; and combinations thereof.

DNA-Targeting Segment

The DNA-targeting segment (or "DNA-targeting sequence") of a guide RNA comprises a nucleotide sequence that is complementary to a specific sequence within a target DNA (the complementary strand of the target DNA).

In other words, the DNA-targeting segment of a guide RNA interacts with a target DNA in a sequence-specific manner via hybridization (i.e., base pairing). As such, the nucleotide sequence of the DNA-targeting segment may vary and determines the location within the target DNA that the guide RNA and the target DNA will interact. The DNA-targeting segment of a guide RNA can be modified (e.g., by genetic engineering) to hybridize to any desired sequence within a target DNA Stability Control Sequence (e.g., Transcriptional Terminator Segment)

A stability control sequence influences the stability of an RNA (e.g., a guide RNA). One example of a suitable stability control sequence is a transcriptional terminator segment (i.e., a transcription termination sequence). A transcriptional terminator segment of a guide RNA can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Nucleotide sequences that can be included in a stability control sequence (e.g., transcriptional termination segment, or in any segment of the guide RNA to provide for increased stability) include, for example, a Rho-independent trp termination site.

Additional Sequences

In some embodiments, a guide RNA comprises at least one additional segment at either the 5' or 3' end. For example, a suitable additional segment can comprise a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and protein complexes); a sequence that forms a dsRNA duplex (i.e., a hairpin)); a sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like) a modification or sequence that provides for increased, decreased, and/or controllable stability; and combinations thereof.

Multiple Simultaneous Guide RNAs

In some embodiments, multiple guide RNAs are used simultaneously in the same cell to simultaneously modulate transcription at different locations on the same target DNA or on different target DNAs. In some embodiments, two or more guide RNAs target the same gene or transcript or locus. In some embodiments, two or more guide RNAs target different unrelated loci. In some embodiments, two or more guide RNAs target different, but related loci.

Because the guide RNAs are small and robust they can be simultaneously present on the same expression vector and can even be under the same transcriptional control if so desired. In some embodiments, two or more (e.g., 3 or more, 4 or more, 5 or more, 10 or more, 15 or more, 20 or more, 25 or more, 30 or more, 35 or more, 40 or more, 45 or more, or 50 or more) guide RNAs are simultaneously expressed in a target cell (from the same or different vectors/from the same or different promoters). In some cases, multiple guide RNAs can be encoded in an array mimicking naturally occurring CRISPR arrays of targeter RNAs. The targeting segments are encoded as approximately 30 nucleotide long sequences (can be about 16 to about 100 nt) and are separated by CRISPR repeat sequences. The array may be introduced into a cell by DNAs encoding the RNAs or as RNAs.

To express multiple guide RNAs, an artificial RNA processing system mediated by the Csy4 endoribonuclease can be used. For example, multiple guide RNAs can be concatenated into a tandem array on a precursor transcript (e.g., expressed from a U6 promoter), and separated by Csy4-specific RNA sequence. Co-expressed Csy4 protein cleaves the precursor transcript into multiple guide RNAs. Advantages for using an RNA processing system include: first, there is no need to use multiple promoters; second, since all guide RNAs are processed from a precursor transcript, their concentrations are normalized for similar dsRGN-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9%) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

Variant sRGN Site-Directed Polypeptide

As noted above, a guide RNA and a variant sRGN site-directed polypeptide form a complex. The guide RNA provides target specificity to the complex by comprising a nucleotide sequence that is complementary to a sequence of a target DNA. The variant sRGN site-directed polypeptide has reduced endodeoxyribonuclease activity. For example, a variant sRGN site-directed polypeptide suitable for use in a transcription modulation method of the present disclosure exhibits less than about 20%, less than about 15%, less than about 10%, less than about 5%, less than about 1%, or less than about 0.1%, of the endodeoxyribonuclease activity of a reference sRGN polypeptide, e.g., a reference sRGN polypeptide comprising an amino acid sequence set forth in any one of SEQ ID NOs: 1-12. In some embodiments, the variant sRGN site-directed polypeptide has substantially no detectable endodeoxyribonuclease activity (dsRGN). In some embodiments when a variant sRGN site-directed polypeptide has reduced catalytic activity, the polypeptide can still bind to target DNA in a site-specific manner (because it is still guided to a target DNA sequence by a guide RNA) as long as it retains the ability to interact with the guide RNA. In some cases, a suitable variant sRGN site-directed polypeptide comprises an amino acid sequence having at least 75%, at least 80%, at least 85%, at least 90%, at least 95%, at least 99%, or greater amino acid sequence identity to any one of SEQ ID NOs: 1-12.

In some cases, the variant sRGN site-directed polypeptide is a nickase that can cleave the complementary strand of the target DNA but has reduced ability to cleave the non-complementary strand of the target DNA In some cases, the variant sRGN site-directed polypeptide in a nickase that can cleave the non-complementary strand of the target DNA but has reduced ability to cleave the complementary strand of the target DNA.

In some cases, the variant sRGN site-directed polypeptide has a reduced ability to cleave both the complementary and the non-complementary strands of the target DNA. For example, alanine substitutions are contemplated.

In some cases, the variant sRGN site-directed polypeptide is a fusion polypeptide (a "variant sRGN fusion polypeptide"), i.e., a fusion polypeptide comprising: i) a variant sRGN site-directed polypeptide; and ii) a covalently linked heterologous polypeptide (also referred to as a "fusion partner").

The heterologous polypeptide may exhibit an activity (e.g., enzymatic activity) that will also be exhibited by the variant sRGN fusion polypeptide (e.g., methyltransferase activity, acetyltransferase activity, kinase activity, ubiquitinating activity, etc.). A heterologous nucleic acid sequence may be linked to another nucleic acid sequence (e.g., by genetic engineering) to generate a chimeric nucleotide sequence encoding a chimeric polypeptide. In some embodiments, a variant sRGN fusion polypeptide is generated by fusing a variant sRGN polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target DNA (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a chimeric dsRGN polypeptide to bind to another protein of interest, e.g., a DNA or histone modifying protein, a transcription factor or transcription repressor, a recruiting protein, etc.).

Suitable fusion partners that provide for increased or decreased stability include, but are not limited to degron sequences. Degrons are understood by one of ordinary skill in the art to be amino acid sequences that control the stability of the protein of which they are part. For example, the stability of a protein comprising a degron sequence is controlled at least in part by the degron sequence. In some cases, a suitable degron is constitutive such that the degron exerts its influence on protein stability independent of experimental control (i.e., the degron is not drug inducible, temperature inducible, etc.) In some cases, the degron provides the variant sRGN polypeptide with controllable stability such that the variant sRGN polypeptide can be turned "on" (i.e., stable) or "off" (i.e., unstable, degraded) depending on the desired conditions. For example, if the degron is a temperature sensitive degron, the variant sRGN polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11:Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1): Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well characterized and tested in both cells and animals. Thus, fusing sRGN to a degron sequence produces a "tunable" and "inducible" sRGN polypeptide. Any of the fusion partners described herein can be used in any desirable combination. As one non-limiting example to illustrate this point, an sRGN fusion protein can comprise a YFP sequence for detection, a degron sequence for stability, and transcription activator sequence to increase transcription of the target DNA Furthermore, the number of fusion partners that can be used in an sRGN fusion protein is unlimited. In some cases, an sRGN fusion protein comprises one or more (e.g., two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, crotonylation activity, decrotonylation activity, propionylation activity, depropionylationa activity, myristoylation activity, or demyristoylation activity, any of which can be directed at modifying the DNA directly (e.g., methylation of DNA) or at modifying a DNA-associated polypeptide (e.g., a histone or DNA binding protein). Further suitable fusion partners include, but are not limited to boundary elements (e.g., CTCF), proteins and fragments thereof that provide periphery recruitment (e.g., LaminA, Lamin B, etc.), and protein docking elements (e.g., FKBP/FRB, Pil 1/Aby 1, etc.).

In some embodiments, an sRGN polypeptide can be codon-optimized. This type of optimization is known in the art and entails the mutation of foreign-derived DNA to mimic the codon preferences of the intended host organism or cell while encoding the same protein. Thus, the codons are changed, but the encoded protein remains unchanged. For example, if the intended target cell were a human cell, a human codon-optimized dsRGN (or dsRGN variant) would be a suitable site-directed modifying polypeptide. As another non-limiting example, if the intended host cell were a mouse cell, than a mouse codon-optimized sRGN (or variant, e.g., enzymatically inactive variant) would be a suitable sRGN site-directed polypeptide. While codon optimization is not required, it is acceptable and may be preferable in certain cases.

Polyadenylation signals can also be chosen to optimize expression in the intended host.

Host Cells

A method of the present disclosure to modulate transcription may be employed to induce transcriptional modulation in mitotic or post-mitotic cells in vivo and/or ex vivo and/or in vitro. Because the guide RNA provides specificity by hybridizing to target DNA, a mitotic and/or post-mitotic cell can be any of a variety of host cell, where suitable host cells include, but are not limited to, a bacterial cell; an archaeal cell; a single-celled eukaryotic organism; a plant cell; an algal cell, e.g., *Botryococcus braunii, Chlamydomonas reinhardtii, Nannochloropsis gaditana, Chlorella pyrenoidosa, Sargassum patens (C. Agardh)*, and the like; a fungal cell; an animal cell; a cell from an invertebrate animal (e.g., an insect, a cnidarian, an echinoderm, a nematode, etc.); a eukaryotic parasite (e.g., a malarial parasite, e.g., *Plasmodium fakiparum*; a helminth; etc.); a cell from a vertebrate animal (e.g., fish, amphibian, reptile, bird, mammal); a mammalian cell, e.g., a rodent cell, a human cell, a non-human primate cell, etc. Suitable host cells include naturally occurring cells; genetically modified cells (e.g., cells genetically modified in a laboratory, e.g., by the "hand of man"); and cells manipulated in vitro in any way. In some cases, a host cell is isolated.

Any type of cell may be of interest (e.g., a stem cell, e.g., an embryonic stem (ES) cell, an induced pluripotent stem (iPS) cell, a germ cell; a somatic cell, e.g., a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e., splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. Target cells are in many embodiments unicellular organisms, or are grown in culture.

If the cells are primary cells, such cells may be harvested from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g., normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% dimethyl sulfoxide (DMSO), 50% serum, 40% buffered medium, or some other such solution as is commonly used in the art to preserve cells at such freezing temperatures, and thawed in a manner as commonly known in the art for thawing frozen cultured cells.

Introducing Nucleic Acid into a Host Cell

A guide RNA, or a nucleic acid comprising a nucleotide sequence encoding same, can be introduced into a host cell by any of a variety of well-known methods. Similarly, where a method involves introducing into a host cell a nucleic acid comprising a nucleotide sequence encoding a variant sRGN site-directed polypeptide, such a nucleic acid can be introduced into a host cell by any of a variety of well-known methods.

Methods of introducing a nucleic acid into a host cell are known in the art, and any known method can be used to introduce a nucleic acid (e.g., an expression construct) into a stem cell or progenitor cell. Suitable methods include, e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (e.g., Panyam et., al Adv Drug Deliv Rev. 2012 Sep. 13. pii: 50169-409X(12) 00283-9. doi: 10.1016/j.addr.2012.09.023), and the like, including but not limiting to exosome delivery.

Nucleic Acids

The present disclosure provides an isolated nucleic acid comprising a nucleotide sequence encoding a guide RNA. In some cases, a nucleic acid also comprises a nucleotide sequence encoding a variant sRGN site-directed polypeptide.

In some embodiments, a method involves introducing into a host cell (or a population of host cells) one or more nucleic acids comprising nucleotide sequences encoding a guide RNA and/or a variant sRGN site-directed polypeptide. In some embodiments a cell comprising a target DNA is in vitro. In some embodiments a cell comprising a target DNA is in vivo. Suitable nucleic acids comprising nucleotide sequences encoding a guide RNA and/or a variant sRGN site-directed polypeptide include expression vectors, where an expression vector comprising a nucleotide sequence encoding a guide Expression Vectors In some embodiments, the recombinant expression vector is a viral construct, e.g., a recombinant adeno-associated virus construct (e.g., U.S. Pat. No. 7,078,387), a recombinant adenoviral construct, a recombinant lentiviral construct, a recombinant retroviral construct, etc. Suitable expression vectors include, but are not limited to, viral vectors (e.g., viral vectors based on vaccinia virus; poliovirus; adenovirus (e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:10881097, 1999; WO 94/12649, WO 93/03769; WO 93/19191; WO 94/28938; WO 95/11984 and WO 95/00655); adeno-associated virus (e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683-690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166:154-165; and Flotte et al., PNAS (1993) 90:10613-10617); SV40; herpes simplex virus; human immunodeficiency virus (e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, a nucleotide sequence encoding a guide RNA and/or a variant sRGN site-directed polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a guide RNA and/or a variant sRGN site-directed polypeptide is operably linked to multiple control elements that allow expression of the nucleotide sequence encoding a guide RNA and/or a variant sRGN site-directed polypeptide in both prokaryotic and eukaryotic cells.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, polII, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter (e.g., Tet-ON, Tet-OFF, etc.), steroid-regulated promoter, metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a variant sRGN site-directed polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (e.g., EMBL HSENO2, X51956); an aromatic amino acid decarboxylase (AADC) promoter; a neurofilament promoter (e.g., GenBank HUMNFL, L04147); a synapsin promoter (e.g., GenBank HUMSYNIB, M55301); a thy-1 promoter (e.g., Chen et al. (1987) Ce/151:7-19; and Llewellyn, et al. (2010) Nat. Med. 16(10):1161-1166); a serotonin receptor promoter (e.g., GenBank S62283); a tyrosine hydroxylase promoter (TH) (e.g., Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (e.g., Radovick et al. (1991) Proc. Natl. Acad. Sci. USA 88:3402-3406); an L7 promoter (e.g., Oberdick et al. (1990) Science 248:223-226); a DNMT promoter (e.g., Bartge et al. (1988) Proc. Natl. Acad. Sci. USA 85:3648-3652); an enkephalin promoter (e.g., Comb et al. (1988) EMBO J. 17:3793-3805); a myelin basic protein (MBP) promoter; a Ca2+-calmodulin-dependent protein kinase 11-alpha (CamKIIa) promoter (e.g., Mayford et al. (1996) Proc. Natl. Acad. Sci. USA 93:13250; and Casanova et al. (2001) Genesis 31:37); a CMV enhancer/platelet-derived growth factor-0 promoter (e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (e.g., Tozzo et al. (1997) Endocrinol. 138:1604; Ross et al. (1990) Proc. Natl Acad. Sci. USA 87:9590; and Pavjani et al. (2005) Nat. Med. 11:797); a glucose transporter-4 (GLUT4) promoter (e.g., Knight et al. (2003) Proc. Natl. Acad. Sci. USA 100:14725); a fatty acid translocase (FAT/CD36) promoter (e.g., Kuriki et al. (2002) Biol. Pharm. Bull. 25:1476; and Sato et al. (2002) J. Biol. Chem. 277:15703); a stearoyi-CoA desaturase-1 (SCD1) promoter (Tabor et al. (1999) J. Biol. Chem. 274:20603); a leptin promoter (e.g., Mason et al. (1998) Endocrinol. 139:1013; and Chen et al. (1999) Biochem. Biophys. Res. Comm. 262:187); an adiponectin promoter (e.g., Kita et al. (2005) Biochem. Biophys. Res. Comm. 331:484; and Chakrabarti (2010) Endocrinol. 151: 2408); an adipsin promoter (e.g., Platt et al. (1989) Proc. Natl. Acad. Sci. USA 86:7490); a resistin promoter (e.g., Seo et al. (2003) Malec. Endocrinol. 17:1522); and the like.

Cardiomyocyte-specific spatially restricted promoters include, but are not limited to control sequences derived from the following genes: myosin light chain-2, a-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22a promoter (e.g., Akyilrek et al. (2000) Mol. Med. 6:983; and U.S. Pat. No. 7,169,874); a smoothelin promoter (e.g., WO 2001/018048); an a-smooth muscle actin promoter; and the like. For example, a 0.4 kb region of the SM22a promoter, within which lie two CArG elements, has been shown to mediate vascular smooth muscle cell-specific expression (e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

Uses

A method for modulating transcription according to the present disclosure finds use in a variety of applications, which are also provided. Applications include research applications; diagnostic applications; industrial applications; and therapeutic applications.

Research applications include, e.g., determining the effect of reducing or increasing transcription of a target nucleic acid on, e.g., development, metabolism, expression of a downstream gene, and the like. High through-put genomic analysis can be carried out using a transcription modulation method, in which only the DNA-targeting segment of the guide RNA needs to be varied, while the protein-binding segment and the transcription termination segment can (in some cases) be held constant. A library (e.g., a library) comprising a plurality of nucleic acids used in the genomic analysis would include: a promoter operably linked to a guide RNA-encoding nucleotide sequence, where each nucleic acid would include a common protein-binding segment, a different DNA-targeting segment, and a common transcription termination segment. A chip could contain over $5 \times 10^4$ unique guide RNAs. Applications would include large-scale phenotyping, gene-to-function mapping, and meta-genomic analysis.

The methods disclosed herein find use in the field of metabolic engineering. Because transcription levels can be efficiently and predictably controlled by designing an appropriate guide RNA, as disclosed herein, the activity of metabolic pathways (e.g., biosynthetic pathways) can be precisely controlled and tuned by controlling the level of specific enzymes (e.g., via increased or decreased transcription) within a metabolic pathway of interest. Metabolic pathways of interest include those used for chemical (fine chemicals, fuel, antibiotics, toxins, agonists, antagonists, etc.) and/or drug production.

Biosynthetic pathways of interest include but are not limited to (1) the mevalonate pathway (e.g., HMG-CoA reductase pathway) (converts acetyl-GoA to dimethylallyl pyrophosphate (DMAPP) and isopentenyl pyrophosphate (IPP), which are used for the biosynthesis of a wide variety of biomolecules including terpenoids/isoprenoids), (2) the non-mevalonate pathway (i.e., the "2-C-methyl-D-erythritol 4-phosphate/1-deoxy-D-xylulose 5-phosphate pathway" or "MEP/DOXP pathway" or "DXP pathway")(also produces DMAPP and IPP, instead by converting pyruvate and glyceraldehyde 3-phosphate into DMAPP and IPP via an alternative pathway to the mevalonate pathway), (3) the polyketide synthesis pathway (produces a variety of polyketides via a variety of polyketide synthase enzymes. Polyketides include naturally occurring small molecules used for chemotherapy (e. g., tetracyclin, and macrolides) and industrially important polyketides include rapamycin (immunosuppressant), erythromycin (antibiotic), lovastatin (anticholesterol drug), and epothilone B (anticancer drug)), (4) fatty acid synthesis pathways, (5) the DAHP (3-deoxy-D-arabino-heptulosonate 7-phosphate) synthesis pathway, (6) pathways that produce potential biofuels (such as short-chain alcohols and alkane, fatty acid methyl esters and fatty alcohols, isoprenoids, etc.), etc.

Networks and Cascades

The methods disclosed herein can be used to design integrated networks (i.e., a cascade or cascades) of control. For example, a guide RNA I variant sRGN site-directed polypeptide may be used to control (i.e., modulate, e.g., increase, decrease) the expression of another DNA-targeting RNA or another variant sRGN site-directed polypeptide. For example, a first guide RNA may be designed to target the modulation of transcription of a second chimeric dsRGN polypeptide with a function that is different than the first variant sRGN site-directed polypeptide (e.g., methyltransferase activity, demethylase activity, acetyltansferase activity, deacetylase activity, etc.). In addition, because different dsRGN proteins (e.g., derived from different species) may require a different sRGN handle (i.e., protein binding segment), the second chimeric dsRGN polypeptide can be derived from a different species than the first dsRGN polypeptide above. Thus, in some cases, the second chimeric dsRGN polypeptide can be selected such that it may not interact with the first guide RNA. In other cases, the second chimeric dsRGN polypeptide can be selected such that it does interact with the first guide RNA. In some such cases, the activities of the two (or more) dsRGN proteins may compete (e.g., if the polypeptides have opposing activities) or may synergize (e.g., if the polypeptides have similar or synergistic activities). Likewise, as noted above, any of the complexes (i.e., guide RNA I dsRGN polypeptide) in the network can be designed to control other guide RNAs or dsRGN polypeptides. Because a guide RNA and variant sRGN site-directed polypeptide can be targeted to any desired DNA sequence, the methods described herein can be used to control and regulate the expression of any desired target. The integrated networks (i.e., cascades of interactions) that can be designed range from very simple to very complex, and are without limit.

In a network where two or more components (e.g. guide RNAs or dsRGN polypeptides) are each under regulatory control of another guide RNA/dsRGN polypeptide complex, the level of expression of one component of the network may affect the level of expression (e.g. may increase or decrease the expression) of another component of the network. Through this mechanism, the expression of one component may affect the expression of a different component in the same network, and the network may include a mix of components that increase the expression of other components. as well as components that decrease the expression of other components. As would be understood by one of skill in the art, the above examples whereby the level of expression of one component may affect the level of expression of one or more different component(s) are for illustrative purposes, and are not limiting. Optionally an additional layer of complexity may be introduced into a network when one or more components are modified (as described above) to be manipulable (i.e., under experimental control, e.g. temperature control; drug control, i.e., drug inducible control; light control; etc.).

As one non-limiting example, a first guide RNA can bind to the promoter of a second guide RNA, which controls the expression of a target therapeutic/metabolic gene. In such a case, conditional expression of the first guide RNA indirectly activates the therapeutic/metabolic gene. RNA cascades of this type are useful, for example, for converting a repressor into an activator, and can be used to control the logics or dynamics of expression of a target gene.

A transcription modulation method can also be used for drug discovery and target validation.

Various aspects of the invention make use of the following materials and methods and are illustrated by the following non-limiting examples.

Genome Editing

Genome editing generally refers to the process of modifying the nucleotide sequence of a genome, such as in a precise or predetermined manner. Examples of methods of genome editing described herein include methods of using site-directed nucleases to cut DNA at precise target locations in the genome, thereby creating double-strand or single-strand DNA breaks at particular locations within the genome. Such breaks can be and regularly are repaired by natural, endogenous cellular processes such as homology-directed repair (HDR) and non-homologous end-joining (NHEJ), as recently reviewed in Cox et al., Nature Medicine 21(2), 121-31 (2015). NHEJ directly joins the DNA ends resulting from a double-strand break sometimes with the loss or addition of nucleotide sequence which may disrupt or enhance gene expression. HDR utilizes a homologous sequence, or donor sequence, as a template for inserting a defined DNA sequence at the break point. The homologous sequence may be in the endogenous genome, such as a sister chromatid. Alternatively, the donor may be an exogenous nucleic acid such as a plasmid, a single-strand oligonucleotide, a duplex oligonucleotide or a virus, that has regions of high homology with the nuclease-cleaved locus, but which may also contain additional sequence or sequence changes including deletions that can be incorporated into the cleaved target locus. A third repair mechanism is microhomology-mediated end joining (MMEJ), also referred to as "Alternative NHEJ," in which the genetic outcome is similar to NHEJ in that small deletions and insertions can occur at the cleavage site. MMEJ makes use of homologous sequences of a few base pairs flanking the DNA break site to drive a more favored DNA end joining repair outcome, and recent reports have further elucidated the molecular mechanism of this process; see, e.g. Cho and Greenberg, Nature 518, 174-76 (2015); Kent et al., Nature Structural and Molecular Biology, Adv. Online doi:10.1038/nsmb.2961(2015); Mateos-Gomez et al., Nature 518, 254-57 (2015); Ceccaldi et al., Nature 528, 258-62 (2015). In some instances likely repair outcomes can be predicted based on analysis of potential microhomologies at the site of the DNA break.

Each of these genome editing mechanisms can be used to create desired genomic alterations. The genome editing process creates generally one or two DNA breaks in the target locus as close as possible to the site of intended mutation. This can achieved via the use of site-directed polypeptides, as described and illustrated herein.

Site-directed polypeptides can introduce double-strand breaks or single-strand breaks in nucleic acid, (e.g., genomic DNA). The double-strand break can stimulate a cell's endogenous DNA-repair pathways (e.g., homology-dependent repair (HDR) and non-homologous end joining (NHEJ) or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage and can lead to disruption or alteration of gene expression. HDR can occur when a homologous repair template, or donor, is available. The homologous donor template comprises sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide or viral nucleic acid. With exogenous donor templates it is common to introduce additional nucleic acid sequence (such as a transgene) or modification (such as a single base change or a deletion) between the flanking regions of homology so additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few basepairs flanking the cleavage site to drive a favored end-joining DNA repair outcome. In some instances it may be possible to predict likely repair outcomes based on analysis of potential microhomologies in the nuclease target regions. Thus, in some cases, homologous recombination is used to insert an exogenous polynucleotide sequence into the target nucleic acid cleavage site. An exogenous polynucleotide sequence is termed a donor polynucleotide herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

EXAMPLES

Example 1A: Confirmation of the Activity of sRGN Polypeptide Gib11

Gib11 and SluCas9 were tested in a fluorescence polarization-based biochemical cleavage assay.
Protocol Fluorescence Polarization Assay:
Oligonucleotide duplexes were prepared in 10 mM Tris (pH=7.8) 50 mM NaCl as 10 µM solutions (from 100 µM stocks) and annealed at 95° C. for 5 minutes and then slowly cooled down in thermo cycler (6° C. per minute). The stocks were subsequently diluted in 10 mM Tris (pH=7.8) 50 mM NaCl+0.05% pluronic. 20 nM oligo (20 µL) were immobilized on streptavidin coated plate, washed twice after 5 minutes and then incubated with a 20 µL sample for a kinetics of 60 minutes (excitation wavelength: 635 nm; emission wavelength: 670 nm). Prior to the cleavage, the reaction RNP was formed. Nuclease and sgRNAvEGFA (SEQ ID NO: 114), transcribed from pCas606 (SEQ ID NO: 118), were added to 817.6 µl 1×PBS MgCl$_2$, and incubated at 37° C. for 10 minutes. 20 µl RNP was added to each well and the polarization was measured for 60 minutes at 37° C. See, for example, Methods Enzymol. 2014; 546:1-20.

Figure 2A:
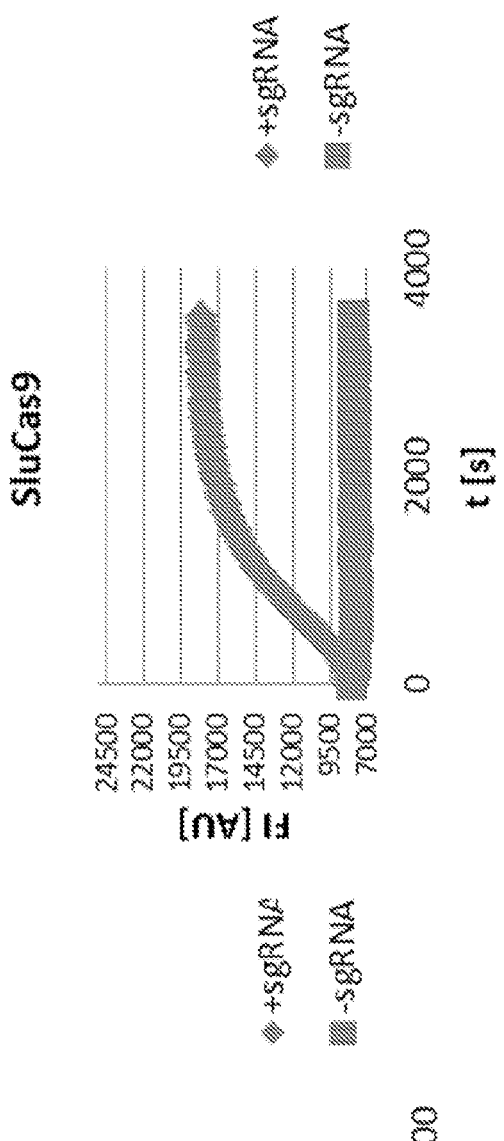
FIG. 2A shows the results of a fluorescence polarization-based biochemical activity in the disruption assay (in some cases, activity exceeding that of a wild type Cas9 such as a SluCas9), Fluorescence polarization assay for Gib11. Diamonds depict the condition with sgRNA and boxes depict the control condition without sgRNA.
Figure 2B:
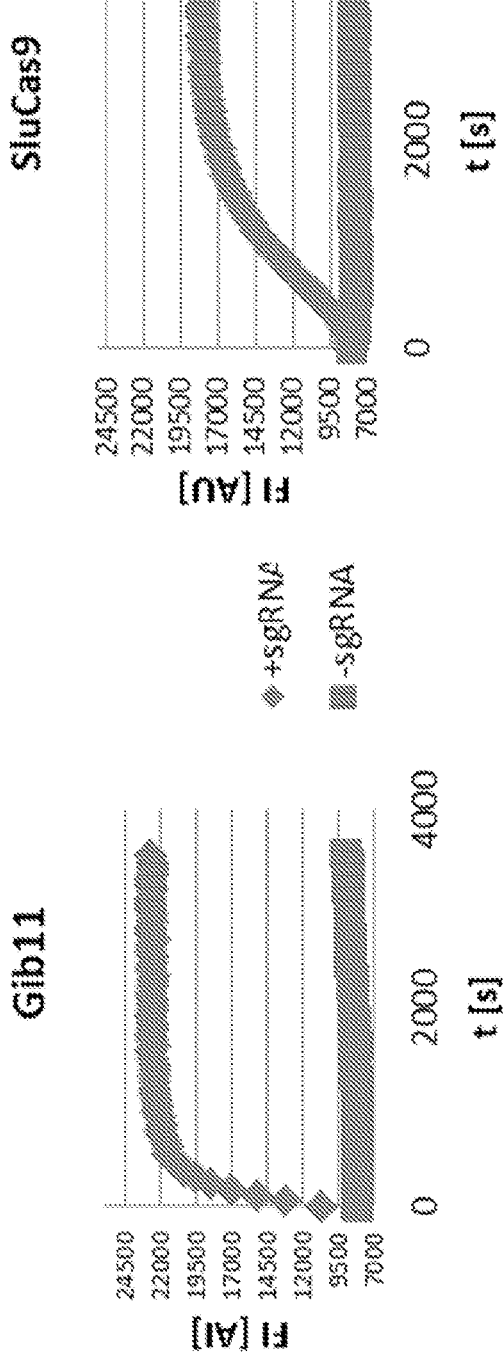
FIG. 2B shows the results of a fluorescence polarization-based biochemical cleavage assay for SluCas9. Diamonds depict the condition with sgRNA and boxes depict the control condition without sgRNA.
Figure 2C:
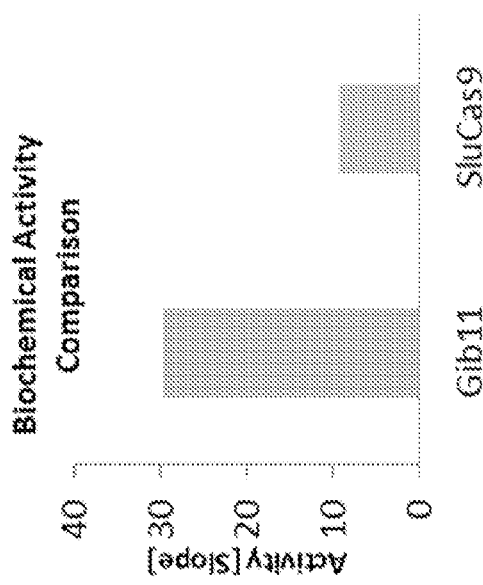
FIG. 2C shows the relative activity of Gib11 and SluCas9 in the cleavage assay, as determined by the initial slope of the curves for the conditions with sgRNA shown in FIGS. 2A and 2B, respectively.

The amount of protein was titrated against a constant level of sgRNA. Upon incubation of the Gib11- or SluCas9-RNP complex targeting the VEGFA oligonucleotide sequence, cleavage can be observed by changes in the fluorescence polarization and fluorescence intensity signal (decrease of polarization values and increase in fluorescence intensity over time upon successful cleavage). As a quantitative estimate of the cleavage reaction, the initial slope of the graph was analyzed. The results (represented in FIGS. 2A and 2B) show that Gib11 and SluCas9 successfully cleave an oligonucleotide substrate. The cleavage kinetics are shown in FIG. 2C.

Example 1B: Confirmation of the Gib11 "NNGG" PAM Motif

The activity of Gib11 was confirmed in liquid cultures and on agar plates.
In Liquid Culture:
BL21DE3 origami cells harboring a toxic reporter plasmid (pCas634, SEQ ID NO: 119, encoding an arabinose-inducible ccdB toxic gene with a VEGFA target site and a "NNGG" PAM) and a plasmid encoding an sgRNA targeting VEGFA (pCas606, SEQ ID NO: 118) were transformed with a plasmid encoding chimeric construct 1 (PI/WEDGE domain exchanged, pCas889 according to SEQ ID NO: 122) or a chimeric construct 2 (PI domain exchanged, pCas888 according to SEQ ID NO: 121) under an IPTG-inducible Trc promotor. After transformation, the cell suspension was rescued with 1 ml SOC and incubated at 37° C. with 1000 rpm shaking (Eppendorf Thermomix). 200 µl were used to inoculate LB medium (supplemented with kanamycin, chloramphenicol and ampicillin) and the liquid culture was incubated overnight at 37° C. with 190 rpm shaking. 200 µl of this overnight culture were used to inoculate 5 ml LB medium supplemented with kanamycin and ampicillin and with/without 0.5% L-arabinose, with/without 0.05 mM IPTG. After incubation at 37° C. overnight (18 h) with 190 rpm shaking, $OD_{600}$ was determined.

Figure 3:
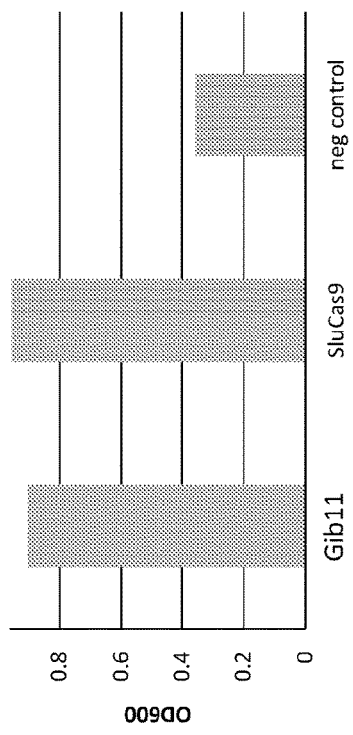
FIG. 3 shows results for recognition of the "NNGG" PAM motif by Gib11, as determined by a "live-dead" assay in liquid culture.

The $OD_{600}$ measurement is visualized in the bar chart in FIG. 3 with $OD_{600}$ values obtained for Gib11, SluCas9, and the negative control.
On Plates:
BL21DE3 origami cells harboring a toxic reporter plasmid (pCas634, SEQ ID NO: 119, encoding an arabinose-inducible ccdB toxic gene with a VEGFA target site and an "NNGG" PAM) and a plasmid encoding an sgRNA targeting VEGFA (pCas606, SEQ ID NO: 118) were transformed with a plasmid encoding chimeric construct 1 (PI/WEDGE domain exchanged, pCas889, according to SEQ ID NO: 122) or chimeric construct 2 (PI domain exchanged, pCas888, according to SEQ ID NO: 121) under an IPTG-inducible Trc promotor (pCas81, SEQ ID NO: 120). After transformation, the cell suspension was rescued with 1 ml SOC medium and incubated at 37° C. with 1000 rpm shaking (Eppendorf Thermomix). 200 µl were plated in LB-Agar plates supplemented with kanamycin, ampicillin, 0.05 mM IPTG and 0.5% L-arabinose. After incubation at 37° C. for 18 h, colonies were counted.

BL21DE3 origami cells harboring a plasmid encoding Gib11 successfully cleaved a toxic reporter plasmid and survived the incubation after induction of the toxic reporter protein ccdB. The survival is measured by increased $OD_{600}$ values in liquid culture and by colony formation on agar plates.

TABLE 5

| Colony formation on agar plates | Gib11 | SluCas9 WT | negative control |
|---|---|---|---|
| normalized Growth to SluCas9 wild-type [%] | 94 | 100 | 37 |

Example 1C: Confirmation of Gib11-Mediated Genome Editing in Mammalian Cells Activity of Gib11 in mammalian cells was demonstrated in the following assays: BFP Disruption assay using guide targeting BFP gene:

HEK293T cells harboring a gene encoding blue fluorescent protein (BFP) in the AAVS1 locus were transfected with plasmid expressing Gib11 and an sgRNA (BFP targeting guide RNA [SEQ ID NO: 117] and SluCas9 tracr RNA [SEQ ID NO: 123]) targeting the reverse strand of BFP genomic sequence as described. Transfection of plasmids was performed using Lipofectamine 3000 (Thermo Fischer Scientific, Cat no. L3000015) as described by the supplier. Flow cytometric analyses of BFP signal disruption was carried out 7 days post-transfection. Cells were prepared by washing with 1×PBS, trypsinization, and resuspension in 200 μl FACS buffer (1×PBS supplemented with 2% FCS). BFP signal from 10,000 cells was assayed using the V450 filter set in the BD FACS Canto® II (Glaser et al., 2016).

HEK293T cells were transfected with a plasmid encoding Gib11 and a sgRNA targeting the BFP gene. A significant decrease in blue fluorescence was observed (quantified as % BFP disruption). In line with the function of Cas9 proteins, the likely reason for this is a Gib11-assisted DNA cleavage followed by insertions/deletions at the BFP open-reading-frame (ORF) resulting in disruption of the BFP ORF. Gib11 lead to 34.35%±7.15% BFP disruption.

TABLE 6

| Samples | % BFP Disruption | Std Dev |
|---|---|---|
| Neg control | 4.1 | 0 |
| SluCas9 | 6.35 | 0.65 |
| Gib11 | 34.35 | 7.15 |

Example 2A: Confirmation of the Activity of sRGN Polypeptide P2H12

Protocol Fluorescence Polarization Assay:

Oligonucleotide duplexes were prepared in 10 mM Tris (pH=7.8) 50 mM NaCl as 10 μM solutions (from 100 μM stocks) and annealed at 95° C. for 5 minutes and then slowly cooled down in thermo cycler (6° C. per minute). The stocks were subsequently diluted in 10 mM Tris (pH=7.8) 50 mM NaCl+0.05% pluronic. 20 nM oligo (20 μL) were immobilized on streptavidin coated plate, washed twice after 5 minutes and then incubated with a 20 μL sample for a kinetics of 60 minutes (excitation wavelength: 635 nm; emission wavelength: 670 nm). Prior to the cleavage the reaction RNP was formed. Nuclease and sgRNAvEGFA (SEQ ID NO: 114), transcribed from pCas606 (SEQ ID NO: 118), were added to 817.6 μl 1×PBS MgCl₂, and incubated at 37° C. for 10 minutes. 20 μl RNP was added to each well and the polarization was measured for 60 minutes at 37° C. See, for example, Methods Enzymol. 2014; 546:1-20.

Figure 4:
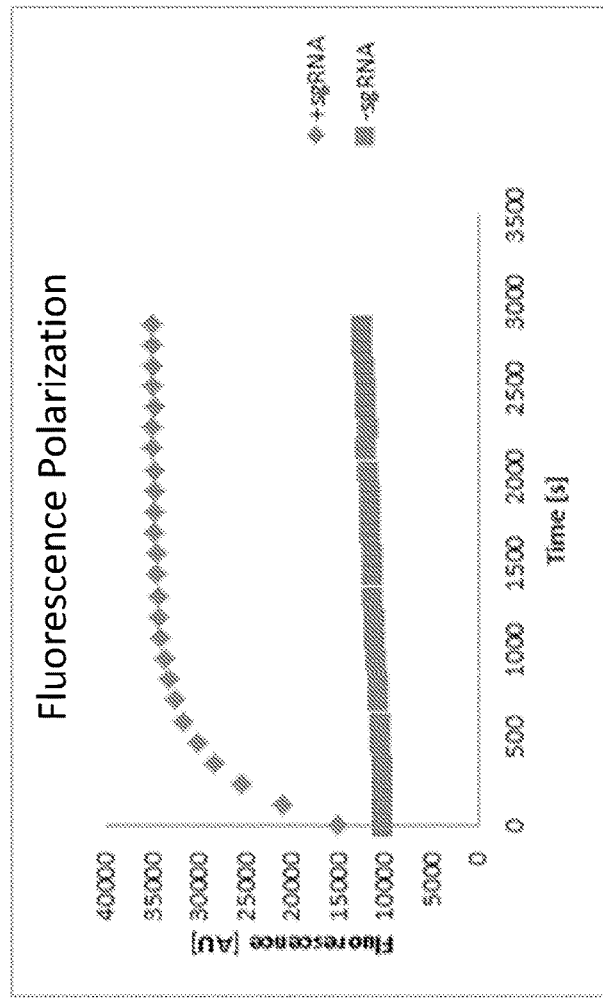
FIG. 4 shows the results of a fluorescence polarization-based biochemical cleavage assay for P2H12. Diamonds depict the condition with sgRNA and boxes depict the control condition without sgRNA.

Upon incubation of the P2H12-RNP complex targeting the VEGFA oligonucleotide sequence, cleavage was observed by marked changes in the fluorescence polarization and fluorescence intensity signal (decrease of polarization values and increase in fluorescence intensity over time upon successful cleavage) as represented in FIG. 4.

Example 2B: Confirmation of P2H12-Mediated Genome Editing in Mammalian Cells The activity of P2H12 in mammalian cells was demonstrated in the following assays: BFP Disruption assay using guide targeting BFP gene:

HEK293T cells harboring a gene encoding BFP in the AAVS1 locus were transfected with plasmid expressing P2H12 and a sgRNA (BFP targeting guide RNA [SEQ ID NO: 117] and SluCas9 tracr RNA [SEQ ID NO: 123]) targeting the reverse strand of BFP genomic sequence as described. Transfection of plasmids was performed using Lipofectamine 3000 (Thermo Fischer Scientific, Cat no. L3000015) as described by the supplier. Flow cytometric analyses of BFP signal disruption was carried out 7 days post-transfection. Cells were prepared by washing with 1×PBS, trypsinization, and resuspension in 200 μl FACS buffer (1×PBS supplemented with 2% FCS). BFP signal from 10,000 cells was assayed using the V450 filter set in the BD FACS Canto II (Glaser et al., 2016).

HEK293T cells were transfected with a plasmid encoding P2H12 and an sgRNA targeting the BFP gene. A significant decrease in blue fluorescence was observed (quantified as % BFP disruption). In line with the function of Cas9 proteins, the likely reason for this is a P2H12-assisted DNA cleavage followed by insertions/deletions at the BFP open-reading-frame (ORF) resulting in disruption of the BFP ORF. P2H12 lead to 22.9%±4.4% BFP disruption.

TABLE 7

| Samples | % BFP Disruption |
|---|---|
| Neg Control | 4.1 |
| SluCas9 | 6.35 ± 0.65 |
| P2H12 | 22.9 ± 4.4 |

Example 3: Confirmation of E2-Mediated Genome Editing in Mammalian Cells

The activity of E2 in mammalian cells was demonstrated in the following assays:

BFP Disruption Assay Using Guide Targeting BFP Gene:

HEK293T cells harboring a gene encoding BFP in the AAVS1 locus were transfected with plasmid expressing E2 and a sgRNA (BFP targeting guide RNA [SEQ ID NO: 117] and SluCas9 tracr RNA [SEQ ID NO: 123]) targeting the reverse strand of BFP genomic sequence as described. Transfection of plasmids was performed using Lipofectamine 3000 (Thermo Fischer Scientific, Cat no. L3000015) as described by the supplier. Flow cytometric analyses of BFP signal disruption was carried out 7 days post-transfection. Cells were prepared by washing with 1×PBS, trypsinization, and resuspension in 200 μl FACS buffer (1×PBS supplemented with 2% FCS). BFP signal from 10,000 cells was assayed using the V450 filter set in the BD FACS Canto II (Glaser et al., 2016).

Figure 5:
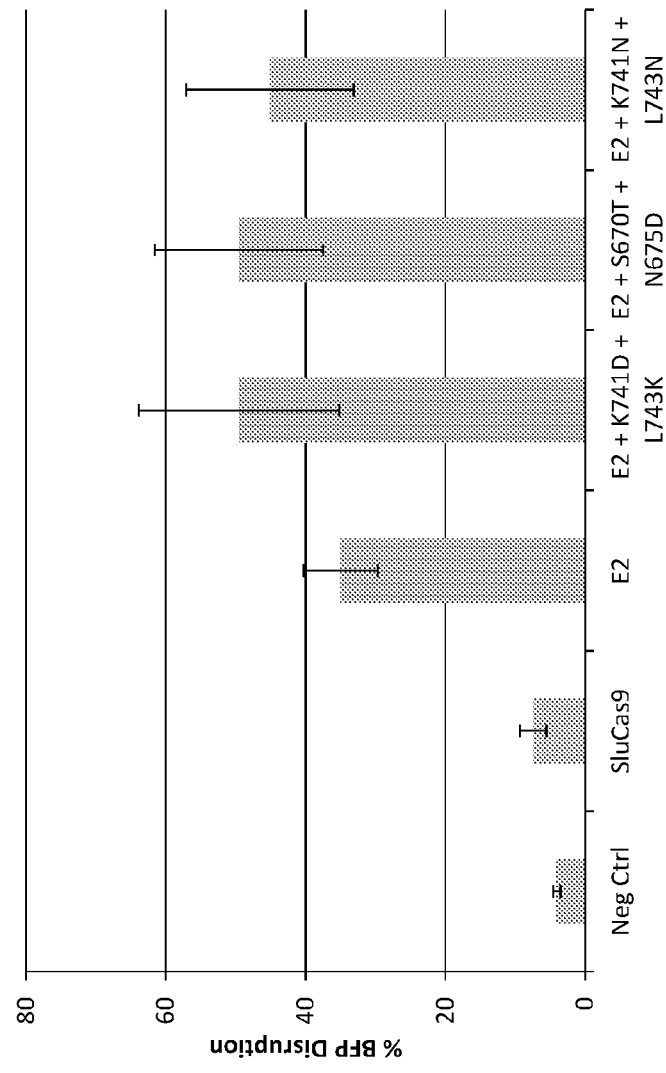
FIG. 5 shows the results of a BFP disruption-based cleavage assay for E2.

The results of three replicates of this experiment with E2, three E2 mutants, a negative control, and for reference SluCas9 (SEQ ID NO: 125) are shown in Table 8, and depicted in FIG. 5. These results show that E2 and the three mutants are able to mediate targeted DNA cleavage.

TABLE 8

| Cas9 Protein | % BFP Disruption | Std Dev |
|---|---|---|
| Neg Ctrl | 4.05 | 0.55 |
| SluCas9 | 7.4 | 1.9 |
| E2 | 35.0 | 5.3 |
| E2 + K741D + L743K | 49.5 | 14 |
| E2 + S670T + N675D | 49.5 | 12 |
| E2 + K741N + L743N | 45.1 | 12 |

Example 4: Confirmation of Gib11Spa-Mediated Genome Editing in Mammalian Cells The activity of Gib11Spa-1, Gib11Spa-2, and Gib11Spa-3 in mammalian cells was demonstrated in the following assay:
BFP Disruption Assay Using Guide Targeting BFP Gene:

HEK293T cells harboring a gene encoding BFP in the AAVS1 locus were transfected with plasmid expressing Gib11Spa-1, Gib11Spa-2, or Gib11Spa-3 and a sgRNA (BFP targeting guide RNA (SEQ ID NO: 117) and SluCas9 tracr RNA (SEQ ID NO: 123)) targeting the reverse strand of BFP genomic sequence as described. Transfection of plasmids was performed using Lipofectamine 3000 (Thermo Fischer Scientific, Cat no. L3000015) as described by the supplier. Flow cytometric analyses of BFP signal disruption was carried out 7 days post-transfection. Cells were prepared by washing with 1×PBS, trypsinization, and resuspension in 200 µl FACS buffer (1×PBS supplemented with 2% FCS). BFP signal from 10,000 cells was assayed using the V450 filter set in the BD FACS Canto II (Glaser et al., 2016, Molecular Therapy Nucleic Acids 5, e334).
Editing in Mammalian Cells Using Gib11Spa-1, Gib11Spa-2, and Gib11Spa-3

Figure 7:
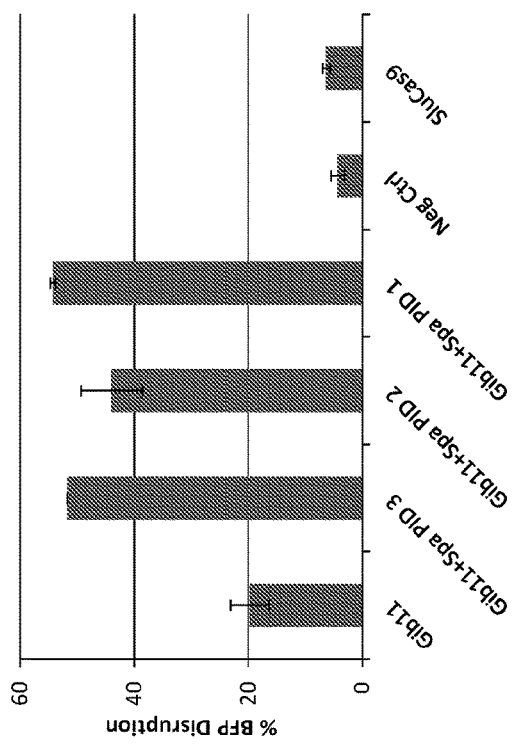
FIG. 7 shows the results of a BFP disruption-based cleavage assay for Gib11Spa-1, Gib11Spa-2, and Gib11Spa-3.

Upon transfecting HEK293T cells with a plasmid encoding Gib11Spa-1, Gib11Spa-2, or Gib11Spa-3 and a sgRNA targeting the BFP gene, a significant decrease in blue fluorescence was observed (quantified as % BFP disruption). In line with the function of Cas9 proteins, the likely reason for this is Gib11Spa-assisted DNA cleavage followed by insertions/deletions at the BFP open-reading-frame (ORF) and resulting disruption of the BFP ORF. Results are shown in Table 9 and in the bar graph in FIG. 7.

TABLE 9

| Cas9 | % BFP Disruption | Std Dev |
|---|---|---|
| Gib11 | 19.7 | 3.4 |
| Gib11 + Spa PID 3 | 51.7 | — |
| Gib11 + Spa PID 2 | 44.0 | 5.4 |
| Gib11 + Spa PID 1 | 54.2 | 0.5 |
| Neg Ctrl | 4.4 | 1.1 |
| SluCas9 | 6.3 | 0.7 |

Example 5: Confirmation of F8-Mediated Genome Editing in Mammalian Cells

The activity of F8 in mammalian cells was demonstrated in the following assay:
BFP Disruption Assay Using Guide Targeting BFP Gene:

HEK293T cells harboring a gene encoding BFP in the AAVS1 locus were transfected with plasmid expressing F8 and a sgRNA (BFP targeting guide RNA [SEQ ID NO: 117] and SluCas9 tracr RNA [SEQ ID NO: 123]) targeting the reverse strand of BFP genomic sequence as described. Transfection of plasmids was performed using Lipofectamine 3000 (Thermo Fischer Scientific, Cat no. L3000015) as described by the supplier. Flow cytometric analyses of BFP signal disruption was carried out 7 days post-transfection. Cells were prepared by washing with 1×PBS, trypsinization, and resuspension in 200 µl FACS buffer (1×PBS supplemented with 2% FCS). BFP signal from 10,000 cells was assayed using the V450 filter set in the BD FACS Canto II (Glaser et al., 2016).

Figure 8:
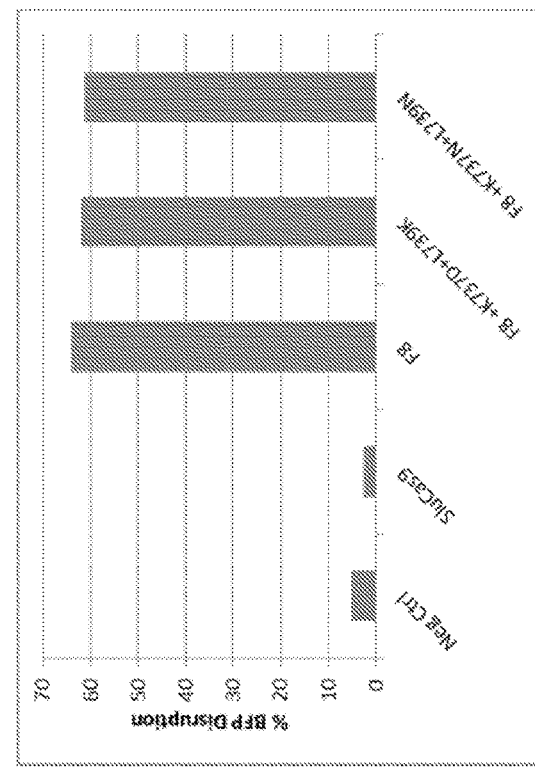
FIG. 8 shows the results of a BFP disruption-based cleavage assay for F8.

The results of three replicates of this experiment with F8, two F8 mutants, a negative control, and for reference SluCas9 (SEQ ID NO: 125) are shown in Table 10 and depicted in FIG. 8. These results show that F8 and the two mutants are able to mediate targeted DNA cleavage.

TABLE 10

| Cas9 | % BFP Disruption |
|---|---|
| Neg Ctrl | 5.2 |
| SluCas9 | 2.6 |
| F8 | 64 |
| F8 + K737D + L739K | 61.9 |
| F8 + K737N + L739N | 61.3 |

Example 6: Determination of Biochemical Specificity Profile for sRGNs

To assess the specificity profile of Gib11, Gib11Spa-1, Gib11Spa-3, E2, and F8, biochemical cleavage of an on-target sequence and all 60-derived single nucleotide mismatched dsDNA substrates (according to SEQ ID NOs: 129-250 used as pairs, e.g., R01-1-A and R01-1-B with SEQ ID NOs: 129 and 130, respectively, represent one duplex pair) were determined. Oligonucleotide duplexes were prepared in 10 mM Tris (pH 7.8) 50 mM NaCl as 10 µM solutions (from 100 µM stocks) and annealed at 95° C. for 5 minutes then slowly cooled down in thermo cycler (6° C. per minute). The stocks were subsequently diluted in 10 mM Tris (pH 7.8), 50 mM NaCl, and 0.05% Pluronic. 20 µl of each oligonucleotide (20 nM) was immobilized on streptavidin coated plates, washed twice after 10 minutes and then incubated with a 20 µL sample for a kinetics of 60 minutes (excitation wavelength: 635 nm; emission wavelength: 670 nm). Prior to the cleavage the reaction RNP was formed. RNP was assembled by mixing 12.03 µl of the respective sRGN protein (1.21 µg/µl) in 3200 µl 1×PBS+5 mM MgCl$_2$ with and without sgRNA (SEQ ID NO: 128; 60 nM final concentration), RNPs were incubated 5 min at 37° C. prior to the reaction. 20 µl RNP was added to each well and the polarization was measured for 60 minutes at 37° C.

The cleavage kinetics were analyzed by calculating the initial slope of the oligonucleotide cleavage reaction. The slopes were calculated for each of the 61 substrates and normalized to the value of the on-target substrate (defined as 1). The normalized cleavage values for all 60 off-target substrates where then grouped according to their position. For each of the 20 nucleotide positions in the target sequence, the normalized cleavage value of the three single nucleotide mismatches was blotted to illustrate the position-specific nucleotide tolerance of the tested nuclease.

Figure 9:
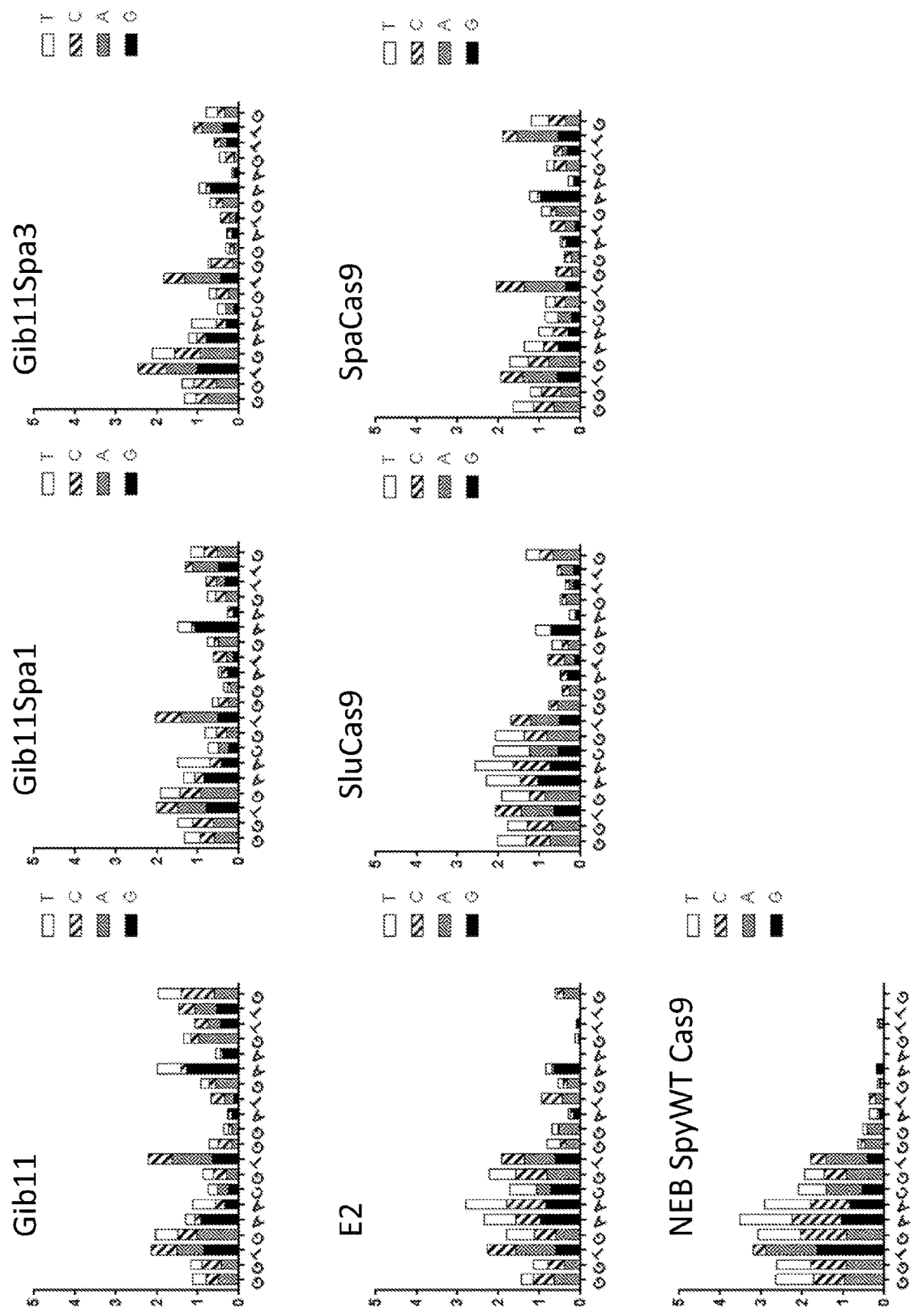
FIG. 9 shows specificity profiles of Gib11, Gib11Spa-1, Gib11Spa-3, E2, and F8, as assessed using a biochemical cleavage assay.
Figure 10:
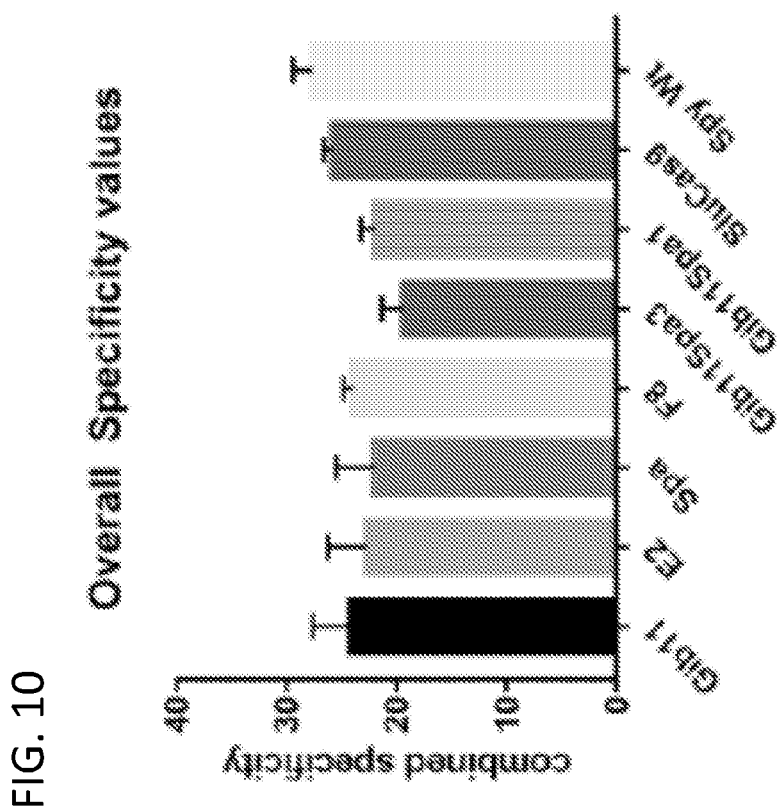
FIG. 10 shows the overall specificity of Gib11, Gib11Spa-1, Gib11Spa-3, E2, and F8 based on their specificity profiles.

The results are shown in FIG. 9. The specificity profile of E2 was comparable to that of SluCas9 using this guide/target combination. Gib11, Gib11Spa-1, and Gib11Spa-3 had specificity profiles comparable to SpaCas9.
Overall Specificity of sRGNs:

The cleavage kinetics for a) Gib11; b) Gib11Spa-1; c) Gib11Spa-2, d) E2, e) F8, f) SluCas9, g) *Staphylococcus pyogenes* wild type (New England Biolabs), and h) *Staphylococcus aureus* were analyzed by calculating the initial slope of the oligonucleotide cleavage reaction. The slopes were calculated for each of the 61 substrates and were normalized to the value of the on-target substrate (defined as 1). All normalized values across the entire panel of 60 off-target substrates were summed to yield an overall specificity value (as depicted in the bar graph in FIG. 10). The sRGNs were more specific than SpyCas9 using this guide/target combination.

Example 7: Determination of Activity Profile for sRGNs

To assess the activity profile of Gib11, Gib11Spa-1, Gib11Spa-3, E2, and F8, biochemical cleavage of 96 on-target DNA substrates (according to SEQ ID NOs: 347-538 used as pairs, e.g., Ext-A-P-1-A and Ext-A-P-1-B with SEQ ID NOs: 347 and 348, respectively, represent one duplex pair) with varying GC-content was determined.

Protocol Fluorescence Polarization Assay:

Oligonucleotide duplexes were prepared in 10 mM Tris (pH=7.8) 50 mM NaCl as 10 µM solutions (from 100 µM stocks) and annealed at 95° C. for 5 minutes and then slowly cooled down in thermo cycler (6° C. per minute). The stocks were subsequently diluted in 10 mM Tris (pH=7.8) 50 mM NaCl+0.05% pluronic. 20 nM oligo (20 µL) were immobilized on streptavidin coated plate, washed twice after 5 minutes and then incubated with a 20 µL sample for a kinetics of 60 minutes (excitation wavelength: 635 nm; emission wavelength: 670 nm). Prior to the cleavage the reaction RNP was formed. For each guide sequence of SEQ ID NOs: 251-346, nuclease and an sgRNA containing the guide sequence were added to 817.6 µl 1×PBS MgCl$_2$, and incubated at 37° C. for 10 minutes. 20 µl RNP was added to wells containing the respective DNA substrate for the sgRNA in the RNP, and the polarization was measured for 60 minutes at 37° C. See, for example, Methods Enzymol. 2014; 546:1-20.

Figure 11:
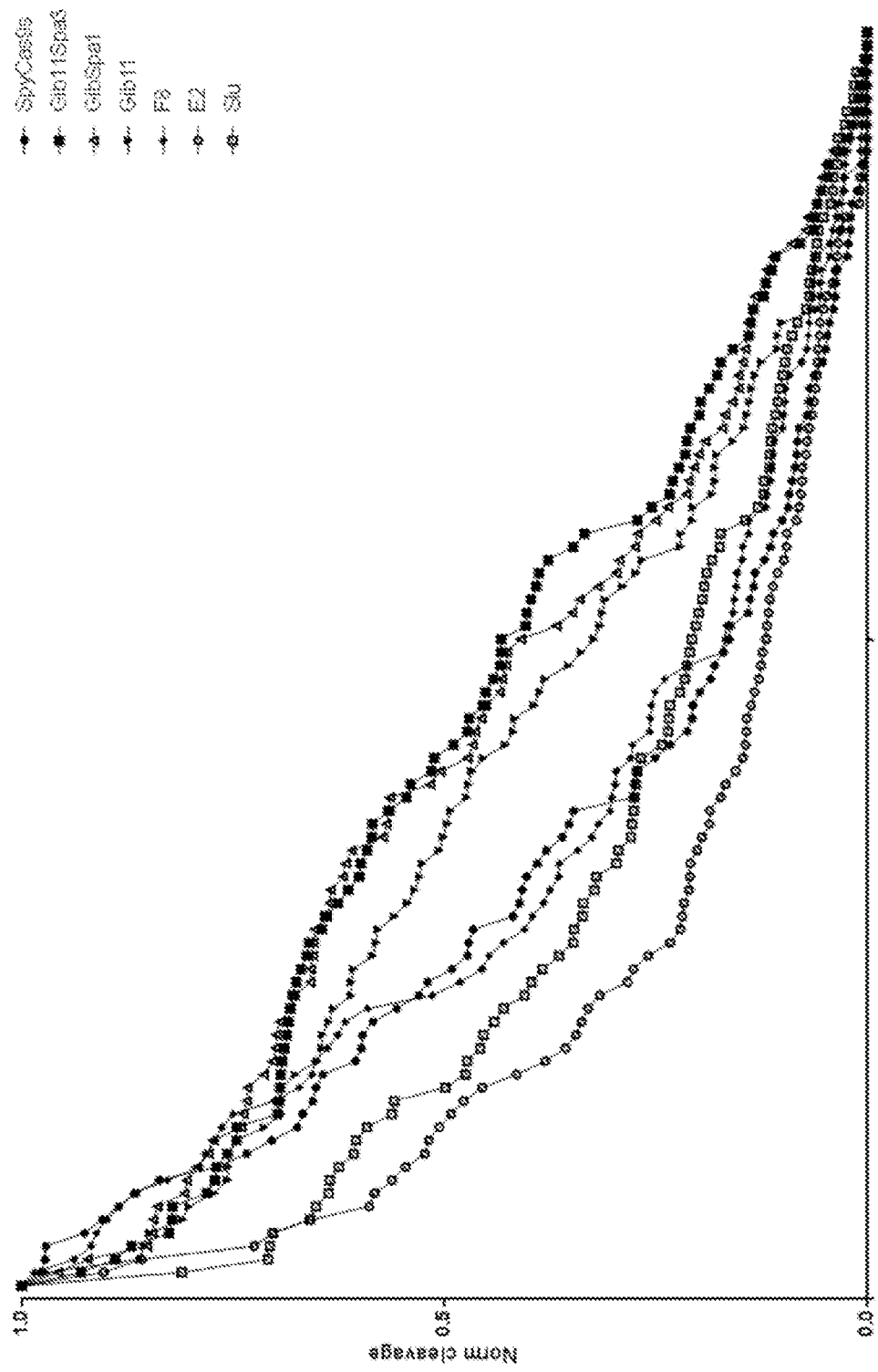
FIG. 11 shows the distribution of activity profiles for Gib11, Gib11Spa-1, Gib11Spa-3, E2, and F8, as assessed using a biochemical cleavage assay. On the x-axis, going from left to right, are the target DNA substrates sorted by highest to lowest activity for each indicated nuclease.

Indicated variants were tested in a fluorescence polarization-based biochemical cleavage assay. The amount of protein was titrated against a constant level of sgRNA. Upon incubation of the variant-RNP complex targeting the VEGFA oligonucleotide sequence, cleavage can be observed by changes in the fluorescence polarization and fluorescence intensity signal (decrease of polarization values and increase in fluorescence intensity over time upon successful cleavage). As a quantitative estimate of the cleavage reaction, the initial slope of the graph was analyzed. The data was normalized to the substrate with the highest activity for one RNA-guided nuclease, and results are shown in FIG. 11. Gib11Spa1/3 and Gib11 displayed a higher activity across a broader range of targets as compared to the other sRGNs and SpyCas9.

SEQUENCE LISTING

| SEQ ID NO | Sequence | Description |
|---|---|---|
| 1 | MNQKFILGLDIGITSVGYGLIDYETKNIIDAGVRLFPEANVENNEGRRSKRGS RRLKRRRIHRLERVKLLLTEYDLINKEQIPTSNNPYQIRVKGLSEILSKDELAIA LLHLAKRRGIHNVDVAADKEETASDSLSTKDQINKNAKFLESRYVCELQKER LENEGHVRGVENRFLTKDIVREAKKIIDTQMQYYPEIDETFKEKYISLVETRR EYFEGPGQGSPFGWNGDLKKWYEMLMGHCTYFPQELRSVKYAYSADLFNA LNDLNNLIIQRDNSEKLEYHEKYHIIENVFKQKKKPTLKQIAKEIGVNPEDIKG YRITKSGTPEFTSFKLFHDLKKVVKDHAILDDIDLLNQIAEILTIYQDKDSIVAE LGQLEYLMSEADKQSISELTGYTGTHSLSLKCMNMIIDELWHSSMNQMEVFT YLNMRPKKYELKGYQRIPTDMIDDAILSPVVKRTFIQSINVINKVIEKYGIPEDI IIELARENNSDDRKKFINNLQKKNEATRKRINEIIGQTGNQNAKRIVEKIRLHD QQEGKCLYSLESIPLEDLLNNPNHYEVDHIIPRSVSFDNSYHNKVLVKQSENS KKSNLTPYQYFNSGKSKLSYNQFKQHILNLSKSQDRISKKKKEYLLEERDINK FEVQKEFINRNLVDTRYATRELTNYLKAYFSANNMNVKVKTINGSFTDYLR KVWKFKKERNHGYKHHAEDALIIANADFLFKENKKLKAVNSVLEKPEIETK QLDIQVDSEDNYSEMFIIPKQVQDIKDFRNFKYSHRVDKKPNRQLINDTLYST RKKDNSTYIVQTIKDIYAKDNTTLKKQFDKSPEKFLMYQHDPRTFEKLEVIM KQYANEKNPLAKYHEETGEYLTKYSKKNNGPIVKSLKYIGNKLGSHLDVTH QFKSSTKKLVKLSIKPYRFDVYLTDKGYKFITISYLDVLKKDNYYYIPEQKYD KLKLGKAIDKNAKFIASFYKNDLIKLDGEIYKIIGVNSDTRNMIELDLPDIRYK EYCELNNIKGEPRIKKTIGKKVNSIEKLTTDVLGNVFTNTQYTKPQLLFKRGN | Polypeptide sequence of Gib11 |
| 2 | MNQKFILGLDIGITSVGYGLIDYETKNIIDAGVRLFPEANVENNEGRRSKRGS RRLKRRRIHRLERVKLLLTEYDLINKEQIPTSNNPYQIRVKGLSEILSKDELAIA LLHLAKRRGIHNVDVAADKEETASDSLSTKDQINKNAKFLESRYVCELQKER LENEGHVRGVENRFLTKDIVREAKKIIDTQMQYYPEIDETFKEKYISLVETRR EYFEGPGQGSPFGWNGDLKKWYEMLMGHCTYFPQELRSVKYAYSADLFNA LNDLNNLIIQRDNSEKLEYHEKYHIIENVFKQKKKPTLKQIAKEIGVNPEDIKG YRITKSGTPEFTSFKLFHDLKKVVKDHAILDDIDLLNQIAEILTIYQDKDSIVAE LGQLEYLMSEADKQSISELTGYTGTHSLSLKCMNMIIDELWHSSMNQMEVFT YLNMRPKKYELKGYQRIPTDMIDDAILSPVVKRTFIQSINVINKVIEKYGIPEDI IIELARENNSDDRKKFINNLQKKNEATRKRINEIIGQTGNQNAKRIVEKIRLHD QQEGKCLYSLESIPLEDLLNNPNHYEVDHIIPRSVSFDNSYHNKVLVKQSENS KKSNLTPYQYFNSGKSKLSYNQFKQHILNLSKSQDRISKKKKEYLLEERDINK FEVQKEFINRNLVDTRYATRELTNYLKAYFSANNMNVKVKTINGSFTDYLR KVWKFKKERNHGYKHHAEDALIIANADFLFKENKKLKAVNSVLEKPEIETK QLDIQVDSEDNYSEMFIIPKQVQDIKDFRNFKYSHRVDKKPNRQLINDTLYST RKKDNSTYIVQTIKDIYAKDNTTLKKQFDKSPEKFLMYQHDPRTFEKLEVIM KQYANEKNPLAKYHEETGEYLTKYSKKNNGPIVKSLKYIGNKLGSHLDVTH QFKSSTKKLVKLSIKNYRFDVYLTEKGYKFVTIAYLNVFKKDNYYYIPKDKY QELKEKKKIKDTDQFIASFYKNDLIKLNGDLYKIIGVNSDDRNIIELDYYDIKY KDYCEINNIKGEPRIKKTIGKKTESIEKFTTDVLGNLYLHSTEKAPQLIFKRGL | Polypeptide sequence of Gib11Spa-1 |

SEQUENCE LISTING

| SEQ ID NO | Sequence | Description |
|---|---|---|
| 3 | MNQKFILGLDIGITSVGYGLIDYETKNIIDAGVRLFPEANVENNEGRRSKRGS<br>RRLKRRRIHRLERVKLLLTEYDLINKEQIPTSNNPYQIRVKGLSEILSKDELAIA<br>LLHLAKRRGIHNVDVAADKEETASDSLSTKDQINKNAKFLESRYVCELQKER<br>LENEGHVRGVENRFLTKDIVREAKKIIDTQMQYYPEIDETFKEKYISLVETRR<br>EYFEGPGQGSPFGWNGDLKKWYEMLGHCTYFPQELRSVKYAYSADLFNA<br>LNDLNNLIIQRDNSEKLEYHEKYHIIENVFKQKKKPTLKQIAKEIGVNPEDIKG<br>YRITKSGTPEFTSFKLFHDLKKVVKDHAILDDIDLLNQIAEILTIYQDKDSIVAE<br>LGQLEYLMSEADKQSISELTGYTGTHSLSLKCMNMIIDELWHSSMNQMEVFT<br>YLNMRPKKYELKGYQRIPTDMIDDAILSPVVKRTFIQSINVINKVIEKYGIPEDI<br>IIELARENNSDDRKKFINNLQKKNEATRKRINEIIGQTGNQNAKRIVEKIRLHD<br>QQEGKCLYSLESIPLEDLLNNPNHYEVDHIIPRSVSFDNSYHNKVLVKQSENS<br>KKSNLTPYQYFNSGKSKLSYNQFKQHILNLSKSQDRISKKKKEYLLEERDINK<br>FEVQKEFINRNLVDTRYATRELTNYLKAYFSANNMNVKVKTINGSFTDYLR<br>KVWKFKKERNHGYKHHAEDALIIANADFLFKENKKLKAVNSVLEKPEIETK<br>QLDIQVDSEDNYSEMFIIPKQVQDIKDFRNFKFSHRVDKKPNRQLINDTLYST<br>RMKDEHDYIVQTITDIYGKDNTNLKKQFNKNPEKFLMYQNDPKTFEKLSII<br>KQYSDEKNPLAKYYEETGEYLTKYSKKNNGPIVKKIKLLGNKVGNHLDVTN<br>KYENSTKKLVKLSIKNYRFDVYLTEKGYKFVTIAYLNVFKKDNYYYIPKDKY<br>QELKEKKKIKDTDQFIASFYKNDLIKLNGDLYKIIGVNSDDRNIIELDYYDIKY<br>KDYCEINNIKGEPRIKKTIGKKTESIEKFTTDVLGNLYLHSTEKAPQLIFKRGL | Polypeptide sequence of Gib11Spa-2 |
| 4 | MNQKFILGLDIGITSVGYGLIDYETKNIIDAGVRLFPEANVENNEGRRSKRGS<br>RRLKRRRIHRLERVKLLLTEYDLINKEQIPTSNNPYQIRVKGLSEILSKDELAIA<br>LLHLAKRRGIHNVDVAADKEETASDSLSTKDQINKNAKFLESRYVCELQKER<br>LENEGHVRGVENRFLTKDIVREAKKIIDTQMQYYPEIDETFKEKYISLVETRR<br>EYFEGPGQGSPFGWNGDLKKWYEMLGHCTYFPQELRSVKYAYSADLFNA<br>LNDLNNLIIQRDNSEKLEYHEKYHIIENVFKQKKKPTLKQIAKEIGVNPEDIKG<br>YRITKSGTPEFTSFKLFHDLKKVVKDHAILDDIDLLNQIAEILTIYQDKDSIVAE<br>LGQLEYLMSEADKQSISELTGYTGTHSLSLKCMNMIIDELWHSSMNQMEVFT<br>YLNMRPKKYELKGYQRIPTDMIDDAILSPVVKRTFIQSINVINKVIEKYGIPEDI<br>IIELARENNSDDRKKFINNLQKKNEATRKRINEIIGQTGNQNAKRIVEKIRLHD<br>QQEGKCLYSLESIPLEDLLNNPNHYEVDHIIPRSVSFDNSYHNKVLVKQSENS<br>KKSNLTPYQYFNSGKSKLSYNQFKQHILNLSKSQDRISKKKKEYLLEERDINK<br>FEVQKEFINRNLVDTRYATRELTSYLKAYFSANNMDVKVKTINGSFTNHLRK<br>VWRFDKYRNHGYKHHAEDALIIANADFLFKENKKLQNTNKILEKPTIENNTK<br>KVTVEKEEDYNNVFETPKLVEDIKQYRDYKFSHRVDKKPNRQLINDTLYSTR<br>MKDEHDYIVQTITDIYGKDNTNLKKQFNKNPEKFLMYQNDPKTFEKLSIIMK<br>QYSDEKNPLAKYYEETGEYLTKYSKKNNGPIVKKIKLLGNKVGNHLDVTNK<br>YENSTKKLVKLSIKNYRFDVYLTEKGYKFVTIAYLNVFKKDNYYYIPKDKYQ<br>ELKEKKKIKDTDQFIASFYKNDLIKLNGDLYKIIGVNSDDRNIIELDYYDIKYK<br>DYCEINNIKGEPRIKKTIGKKTESIEKFTTDVLGNLYLHSTEKAPQLIFKRGL | Polypeptide sequence of Gib11Spa-3 |
| 5 | MNQKFILGLDIGITSVGYGLIDYETKNIIDAGVRLFPEANVENNEGRRSKRGS<br>RRLKRRRIHRLERVKKLLEDYNLLDQSQIPQSTNPYAIRVKGLSEALSKDELV<br>IALLHIAKRRGIHNINVSSEDEDASNELSTKEQINRNNKLLKDKYVCEVQLQR<br>LKEGQIRGEKNRFKTTDILKEIDQLLKVQKDYHNLDIDFINQYKEIVETRREY<br>FEGPGKGSPYGWEGDKAWYETLMGHCTYFPDELRSVKYAYSADLFNALN<br>DLNNLVIQRDGLSKLEYHEKYHIIENVFKQKKKPTLKQIANEINVNPEDIKGY<br>RITKSGKPEFTSFKLFHDLKKVVKDHAILDDIDLLNQIAEILTIYQDKDSIVAEL<br>GQLEYLMSEADKQSISELTGYTGTHSLSLKCMNMIIDELWHSSMNQMEVFT<br>YLNMRPKKYELKGYQRIPTDMIDDAILSPVVKRTFIQSINVINKVIEKYGIPEDI<br>IIELARENNSDDRKKFINNLQKKNEATRKRINEIIGQTGNQNAKRIVEKIRLHD<br>QQEGKCLYSLESIPLEDLLNNPNHYEVDHIIPRSVSFDNSYHNKVLVKQSENS<br>KKSNLTPYQYFNSGKSKLSYNQFKQHILNLSKSQDRISKKKKEYLLEERDINK<br>FEVQKEFINRNLVDTRYATRELTNYLKAYFSANNMNVKVKTINGSFTDYLR<br>KVWKFKKERNHGYKHHAEDALIIANADFLFKENKKLKAVNSVLEKPEIETK<br>QLDIQVDSEDNYSEMFIIPKQVQDIKDFRNFKFSHRVDKKPNRQLINDTLYST<br>RKKDNSTYIVQTIKDIYAKDNTTLKKQFDKSPEKFLMYQHDPRTFEKLEVIM<br>KQYANEKNPLAKYHEETGEYLTKYSKKNNGPIVKSLKYIGNKLGSHLDVTH<br>QFKSSTKKLVKLSIKPYRFDVYLTDKGYKFITISYLDVLKKDNYYYIPEQKYD<br>KLKLGKAIDKNAKFIASFYKNDLIKLDGEIYKIIGVNSDTRNMIELDLPDIRYK<br>EYCELNNIKGEPRIKKTIGKKVNSIEKLTTDVLGNVFTNTQYTKPQLLFKRGN | Polypeptide sequence of P2H12 |
| 6 | MNQKFILGLDIGITSVGYGLIDYETKNIIDAGVRLFPEANVENNEGRRSKRGS<br>RRLKRRRIHRLDRVKHLLAEYDLLDLTNIPKSTNPYQTRVKGLNEKLSKDEL<br>VIALLHIAKRRGIHNVDVAADKEETASDSLSTKDQINKNAKFLESRYVCELQ<br>KERLENEGHVRGVENRFLTKDIVREAKKIIDTQMQYYPEIDETFKEKYISLVE<br>TRREYFEGPGKGSPFGWEGNIKKWFEQMMGHCTYFPEELRSVKYSYSAELF<br>NALNDLNNLVITRDEDAKLNYGEKFQIIENVFKQKKTPNLKQIAIEIGVHETEI<br>KGYRVNKSGTPEFTEFKLYHDLKSIVFDKSILENEAILDQIAEILTIYQDEQSIK<br>EELNKLPEILNEQDKAEIAKLIGYNGTHRLSLKCIHLINEELWQTSRNQMEIFN<br>YLNIKPNKVDLSEQNKIPKDMVNDFILSPVVKRTFIQSINVINKVIEKYGIPEDI<br>IIELARENNSDDRKKFINNLQKKNEATRKRINEIIGQTGNQNAKRIVEKIRLHD | Polypeptide sequence of E2 |

SEQUENCE LISTING

| SEQ ID NO | Sequence | Description |
|---|---|---|
| | QQEGKCLYSLKDIPLEDLLRNPNNYDIDHIIPRSVSFDDSMHNKVLVRREQNA<br>KKNNQTPYQYLTSGYADIKYSVFKQHVLNLAENKDRMTKKKREYLLEERDI<br>NKFEVQKEFINRNLVDTRYATRELTNYLKAYFSANNMNVKVKTINGSFTDY<br>LRKVWKFKKERNHGYKHHAEDALIIANADFLFKENKKLKAVNSVLEKPEIET<br>KQLDIQVDSEDNYSEMFIIPKQVQDIKDFRNFKYSHRVDKKPNRQLINDTLYS<br>TRKKDNSTYIVQTIKDIYAKDNTTLKKQFDKSPEKFLMYQHDPRTFEKLEVI<br>MKQYANEKNPLAKYHEETGEYLTKYSKKNNGPIVKSLKYIGNKLGSHLDVT<br>HQFKSSTKKLVKLSIKPYRFDVYLTDKGYKFITISYLDVLKKDNYYYIPEQKY<br>DKLKLGKAIDKNAKFIASFYKNDLIKLDGEIYKIIGVNSDTRNMIELDLPDIRY<br>KEYCELNNIKGEPRIKKTIGKKVNSIEKLTTDVLGNVFTNTQYTKPQLLFKRG<br>N | |
| 7 | MNQKFILGLDIGITSVGYGLIDYETKNIIDAGVRLFPEANVENNEGRRSKRGS<br>RRLKRRRIHRLDRVKHLLAEYDLLDLTNIPKSTNPYQTRVKGLNEKLSKDEL<br>VIALLHIAKRRGIHNVDVAADKEETASDSLSTKDQINKNAKFLESRYVCELQ<br>KERLENEGHVRGVENRFLTKDIVREAKKIIDTQMQYYPEIDETFKEKYISLVE<br>TRREYFEGPGKGSPFGWEGNIKKWFEQMMGHCTYFPEELRSVKYSYSAELF<br>NALNDLNNLVITRDEDAKLNYGEKFQIIENVFKQKKTPNLKQIAIEIGVHETEI<br>KGYRVNKSGTPEFTEFKLYHDLKSIVFDKSILENEAILDQIAEILTIYQDEQSIK<br>EELNKLPEILNEQDKAEIAKLIGYNGTHRLSLKCIHLINEEELWQTSRNQMEIFN<br>YLNIKPNKVDLSEQNKIPKDMVNDFILSPVVKRTFIQSINVINKVIEKYGIPEDI<br>IIELARENNSDDRKKFINNLQKKNEATRKRINEIIGQTGNQNAKRIVEKIRLHD<br>QQEGKCLYSLKDIPLEDLLRNPNNYDIDHIIPRSVSFDDSMHNKVLVRREQNA<br>KKNNQTPYQYLTSGYADIKYSVFKQHVLNLAENKDRMTKKKREYLLEERDI<br>NKFEVQKEFINRNLVDTRYATRELTNYLKAYFSANNMNVKVKTINGSFTDY<br>LRKVWKFKKERNHGYKHHAEDALIIANADFLFKENKKLKAVNSVLEKPEIET<br>DQKDIQVDSEDNYSEMFIIPKQVQDIKDFRNFKYSHRVDKKPNRQLINDTLYS<br>TRKKDNSTYIVQTIKDIYAKDNTTLKKQFDKSPEKFLMYQHDPRTFEKLEVI<br>MKQYANEKNPLAKYHEETGEYLTKYSKKNNGPIVKSLKYIGNKLGSHLDVT<br>HQFKSSTKKLVKLSIKPYRFDVYLTDKGYKFITISYLDVLKKDNYYYIPEQKY<br>DKLKLGKAIDKNAKFIASFYKNDLIKLDGEIYKIIGVNSDTRNMIELDLPDIRY<br>KEYCELNNIKGEPRIKKTIGKKVNSIEKLTTDVLGNVFTNTQYTKPQLLFKRG<br>N | Polypeptide sequence of E2 + K741D + L743K |
| 8 | MNQKFILGLDIGITSVGYGLIDYETKNIIDAGVRLFPEANVENNEGRRSKRGS<br>RRLKRRRIHRLDRVKHLLAEYDLLDLTNIPKSTNPYQTRVKGLNEKLSKDEL<br>VIALLHIAKRRGIHNVDVAADKEETASDSLSTKDQINKNAKFLESRYVCELQ<br>KERLENEGHVRGVENRFLTKDIVREAKKIIDTQMQYYPEIDETFKEKYISLVE<br>TRREYFEGPGKGSPFGWEGNIKKWFEQMMGHCTYFPEELRSVKYSYSAELF<br>NALNDLNNLVITRDEDAKLNYGEKFQIIENVFKQKKTPNLKQIAIEIGVHETEI<br>KGYRVNKSGTPEFTEFKLYHDLKSIVFDKSILENEAILDQIAEILTIYQDEQSIK<br>EELNKLPEILNEQDKAEIAKLIGYNGTHRLSLKCIHLINEEELWQTSRNQMEIFN<br>YLNIKPNKVDLSEQNKIPKDMVNDFILSPVVKRTFIQSINVINKVIEKYGIPEDI<br>IIELARENNSDDRKKFINNLQKKNEATRKRINEIIGQTGNQNAKRIVEKIRLHD<br>QQEGKCLYSLKDIPLEDLLRNPNNYDIDHIIPRSVSFDDSMHNKVLVRREQNA<br>KKNNQTPYQYLTSGYADIKYSVFKQHVLNLAENKDRMTKKKREYLLEERDI<br>NKFEVQKEFINRNLVDTRYATRELTNYLKAYFTANNMDVKVKTINGSFTDY<br>LRKVWKFKKERNHGYKHHAEDALIIANADFLFKENKKLKAVNSVLEKPEIET<br>KQLDIQVDSEDNYSEMFIIPKQVQDIKDFRNFKYSHRVDKKPNRQLINDTLYS<br>TRKKDNSTYIVQTIKDIYAKDNTTLKKQFDKSPEKFLMYQHDPRTFEKLEVI<br>MKQYANEKNPLAKYHEETGEYLTKYSKKNNGPIVKSLKYIGNKLGSHLDVT<br>HQFKSSTKKLVKLSIKPYRFDVYLTDKGYKFITISYLDVLKKDNYYYIPEQKY<br>DKLKLGKAIDKNAKFIASFYKNDLIKLDGEIYKIIGVNSDTRNMIELDLPDIRY<br>KEYCELNNIKGEPRIKKTIGKKVNSIEKLTTDVLGNVFTNTQYTKPQLLFKRG<br>N | Polypeptide sequence of E2 + S670T + N675D |
| 9 | MNQKFILGLDIGITSVGYGLIDYETKNIIDAGVRLFPEANVENNEGRRSKRGS<br>RRLKRRRIHRLDRVKHLLAEYDLLDLTNIPKSTNPYQTRVKGLNEKLSKDEL<br>VIALLHIAKRRGIHNVDVAADKEETASDSLSTKDQINKNAKFLESRYVCELQ<br>KERLENEGHVRGVENRFLTKDIVREAKKIIDTQMQYYPEIDETFKEKYISLVE<br>TRREYFEGPGKGSPFGWEGNIKKWFEQMMGHCTYFPEELRSVKYSYSAELF<br>NALNDLNNLVITRDEDAKLNYGEKFQIIENVFKQKKTPNLKQIAIEIGVHETEI<br>KGYRVNKSGTPEFTEFKLYHDLKSIVFDKSILENEAILDQIAEILTIYQDEQSIK<br>EELNKLPEILNEQDKAEIAKLIGYNGTHRLSLKCIHLINEEELWQTSRNQMEIFN<br>YLNIKPNKVDLSEQNKIPKDMVNDFILSPVVKRTFIQSINVINKVIEKYGIPEDI<br>IIELARENNSDDRKKFINNLQKKNEATRKRINEIIGQTGNQNAKRIVEKIRLHD<br>QQEGKCLYSLKDIPLEDLLRNPNNYDIDHIIPRSVSFDDSMHNKVLVRREQNA<br>KKNNQTPYQYLTSGYADIKYSVFKQHVLNLAENKDRMTKKKREYLLEERDI<br>NKFEVQKEFINRNLVDTRYATRELTNYLKAYFSANNMNVKVKTINGSFTDY<br>LRKVWKFKKERNHGYKHHAEDALIIANADFLFKENKKLKAVNSVLEKPEIET<br>NQNDIQVDSEDNYSEMFIIPKQVQDIKDFRNFKYSHRVDKKPNRQLINDTLYS<br>TRKKDNSTYIVQTIKDIYAKDNTTLKKQFDKSPEKFLMYQHDPRTFEKLEVI<br>MKQYANEKNPLAKYHEETGEYLTKYSKKNNGPIVKSLKYIGNKLGSHLDVT | Polypeptide sequence of E2 + K741N + L743N |

| SEQ ID NO | Sequence | Description |
|---|---|---|
| | HQFKSSTKKLVKLSIKPYRFDVYLTDKGYKFITISYLDVLKKDNYYYIPEQKY DKLKLGKAIDKNAKFIASFYKNDLIKLDGEIYKIIGVNSDTRNMIELDLPDIRY KEYCELNNIKGEPRIKKTIGKKVNSIEKLTTDVLGNVFTNTQYTKPQLLFKRG N | |
| 10 | MNQKFILGLDIGITSVGYGLIDYETKNIIDAGVRLFPEANVENNEGRRSKRGS RRLKRRRIHRLERVKSLLSEYKIISGLAPTNNQPYNIRVKGLTEQLTKDELAV ALLHIAKRRGIHKIDVIDSNDDVGNELSTKEQLNKNSKLLKDKFVCQIQLER MNEGQVRGEKNRFKTADIIKEIIQLLNVQKNFHQLDENFINKYIELVEMRREY FEGPGQGSPFGWNGDLKKWYEMLMGHCTYFPQELRSVKYAYSADLNALN DLNNLIIQRDNSEKLEYHEKYHIIENVFKQKKKPTLKQIAKEIGVNPEDIKGYR ITKSGTPEFTEFKLYHDLKSVLFDQSILENEDVLDQIAEILTIYQDKDSIKSKLT ELDILLNEEDKENIAQLTGYNGTHRLSLKCIRLVLEEQWYSSRNQMEIFTHLN IKPKKINLTAANKIPKAMIDEFILSPVVKRTFIQSINVINKVIEKYGIPEDIIIELA RENNSDDRKKFINNLQKKNEATRKRINEIIGQTGNQNAKRIVEKIRLHDQQEG KCLYSLESIALMDLLNNPQNYEVDHIIPRSVAFDNSIHNKVLVKQIENSKKGN RTPYQYLNSSDAKLSYNQFKQHILNLSKSKDRISKKKKDYLLEERDINKFEVQ KEFINRNLVDTRYATRELTSYLKAYFSANNMDVKVKTINGSFTNHLRKVWR FDKYRNHGYKHHAEDALIIANADFLFKENKKLKAVNSVLEKPEIETKQLDIQ VDSEDNYSEMFIIPKQVQDIKDFRNFKYSHRVDKKPNRQLINDTLYSTRKKD NSTYIVQTIKDIYAKDNTTLKKQFDKSPEKFLMYQHDPRTFEKLEVIMKQYA NEKNPLAKYHEETGEYLTKYSKKNNGPIVKSLKYIGNKLGSHLDVTHQFKSS TKKLVKLSIKPYRFDVYLTDKGYKFITISYLDVLKKDNYYYIPEQKYDKLKL GKAIDKNAKFIASFYKNDLIKLDGEIYKIIGVNSDTRNMIELDLPDIRYKEYCE LNNIKGEPRIKKTIGKKVNSIEKLTTDVLGNVFTNTQYTKPQLLFKRGN | Polypeptide sequence of F8 |
| 11 | MNQKFILGLDIGITSVGYGLIDYETKNIIDAGVRLFPEANVENNEGRRSKRGS RRLKRRRIHRLERVKSLLSEYKIISGLAPTNNQPYNIRVKGLTEQLTKDELAV ALLHIAKRRGIHKIDVIDSNDDVGNELSTKEQLNKNSKLLKDKFVCQIQLER MNEGQVRGEKNRFKTADIIKEIIQLLNVQKNFHQLDENFINKYIELVEMRREY FEGPGQGSPFGWNGDLKKWYEMLMGHCTYFPQELRSVKYAYSADLNALN DLNNLIIQRDNSEKLEYHEKYHIIENVFKQKKKPTLKQIAKEIGVNPEDIKGYR ITKSGTPEFTEFKLYHDLKSVLFDQSILENEDVLDQIAEILTIYQDKDSIKSKLT ELDILLNEEDKENIAQLTGYNGTHRLSLKCIRLVLEEQWYSSRNQMEIFTHLN IKPKKINLTAANKIPKAMIDEFILSPVVKRTFIQSINVINKVIEKYGIPEDIIIELA RENNSDDRKKFINNLQKKNEATRKRINEIIGQTGNQNAKRIVEKIRLHDQQEG KCLYSLESIALMDLLNNPQNYEVDHIIPRSVAFDNSIHNKVLVKQIENSKKGN RTPYQYLNSSDAKLSYNQFKQHILNLSKSKDRISKKKKDYLLEERDINKFEVQ KEFINRNLVDTRYATRELTSYLKAYFSANNMDVKVKTINGSFTNHLRKVWR FDKYRNHGYKHHAEDALIIANADFLFKENKKLKAVNSVLEKPEIETDQKDIQ VDSEDNYSEMFIIPKQVQDIKDFRNFKYSHRVDKKPNRQLINDTLYSTRKKD NSTYIVQTIKDIYAKDNTTLKKQFDKSPEKFLMYQHDPRTFEKLEVIMKQYA NEKNPLAKYHEETGEYLTKYSKKNNGPIVKSLKYIGNKLGSHLDVTHQFKSS TKKLVKLSIKPYRFDVYLTDKGYKFITISYLDVLKKDNYYYIPEQKYDKLKL GKAIDKNAKFIASFYKNDLIKLDGEIYKIIGVNSDTRNMIELDLPDIRYKEYCE LNNIKGEPRIKKTIGKKVNSIEKLTTDVLGNVFTNTQYTKPQLLFKRGN | Polypeptide sequence of F8 + K737D + L739K |
| 12 | MNQKFILGLDIGITSVGYGLIDYETKNIIDAGVRLFPEANVENNEGRRSKRGS RRLKRRRIHRLERVKSLLSEYKIISGLAPTNNQPYNIRVKGLTEQLTKDELAV ALLHIAKRRGIHKIDVIDSNDDVGNELSTKEQLNKNSKLLKDKFVCQIQLER MNEGQVRGEKNRFKTADIIKEIIQLLNVQKNFHQLDENFINKYIELVEMRREY FEGPGQGSPFGWNGDLKKWYEMLMGHCTYFPQELRSVKYAYSADLNALN DLNNLIIQRDNSEKLEYHEKYHIIENVFKQKKKPTLKQIAKEIGVNPEDIKGYR ITKSGTPEFTEFKLYHDLKSVLFDQSILENEDVLDQIAEILTIYQDKDSIKSKLT ELDILLNEEDKENIAQLTGYNGTHRLSLKCIRLVLEEQWYSSRNQMEIFTHLN IKPKKINLTAANKIPKAMIDEFILSPVVKRTFIQSINVINKVIEKYGIPEDIIIELA RENNSDDRKKFINNLQKKNEATRKRINEIIGQTGNQNAKRIVEKIRLHDQQEG KCLYSLESIALMDLLNNPQNYEVDHIIPRSVAFDNSIHNKVLVKQIENSKKGN RTPYQYLNSSDAKLSYNQFKQHILNLSKSKDRISKKKKDYLLEERDINKFEVQ KEFINRNLVDTRYATRELTSYLKAYFSANNMDVKVKTINGSFTNHLRKVWR FDKYRNHGYKHHAEDALIIANADFLFKENKKLKAVNSVLEKPEIETNQNDIQ VDSEDNYSEMFIIPKQVQDIKDFRNFKYSHRVDKKPNRQLINDTLYSTRKKD NSTYIVQTIKDIYAKDNTTLKKQFDKSPEKFLMYQHDPRTFEKLEVIMKQYA NEKNPLAKYHEETGEYLTKYSKKNNGPIVKSLKYIGNKLGSHLDVTHQFKSS TKKLVKLSIKPYRFDVYLTDKGYKFITISYLDVLKKDNYYYIPEQKYDKLKL GKAIDKNAKFIASFYKNDLIKLDGEIYKIIGVNSDTRNMIELDLPDIRYKEYCE LNNIKGEPRIKKTIGKKVNSIEKLTTDVLGNVFTNTQYTKPQLLFKRGN | Polypeptide sequence of F8 + K737N + L739N |
| 13 | ATGAACCAGAAATTTATCCTGGGTCTGGATATTGGTATTACCAGCGTTGG TTATGGCCTGATTGATTACGAAACCAAAAACATTATTGATGCCGGTGTTC GTCTGTTTCCGGAAGCAAATGTTGAAAATAATGAAGGTCGTCGTAGCAAA CGTGGTAGCCGTCGTCTGAAACGTCGTATTCATCGTCTGGAACGTGT TAAACTGCTGCTGACCGAATATGATCTGATTAACAAAGAGCAGATTCCGA | DNA sequence encoding Gib11 |

SEQUENCE LISTING

| SEQ ID NO | Sequence | Description |
|---|---|---|
| | CCAGCAATAACCCGTATCAGATTCGTGTTAAAGGTCTGAGCGAAATCCTG<br>AGCAAAGATGAACTGGCAATTGCACTGCTGCATCTGGCAAAACGCCGTG<br>GCATTCATAATGTTGATGTTGCAGCAGATAAAGAAGAAACCGCAAGCGA<br>TAGCCTGAGCACCAAAGATCAGATTAACAAAAACGCCAAATTTCTGGAA<br>AGCCGCTATGTTTGTGAACTGCAGAAAGAACGTCTGGAAAATGAAGGTC<br>ATGTTCGTGGTGTTGAAAATCGCTTTCTGACGAAAGATATTGTGCGTGAG<br>GCCAAAAAAATCATCGATACCCAGATGCAGTATTACCCGGAAATTGATG<br>AAACCTTCAAAGAGAAATATATCAGCCTGGTTGAAACCCGTCGCGAATAT<br>TTTGAAGGTCCTGGTCAGGGTAGCCCGTTTGGTTGGAATGGTGATCTGAA<br>AAAATGGTACGAAATGCTGATGGGTCACTGTACCTATTTTCCGCAAGAAC<br>TGCGTAGCGTTAAATATGCCTATAGCGCAGACCTGTTTAATGCACTGAAT<br>GATCTGAACAACCTGATTATTCAGCGCGATAATAGCGAGAAACTGGAAT<br>ACCATGAGAAGTATCACATCATCGAGAACGTGTTCAAGCAGAAAAAAAA<br>GCCGACGCTGAAACAAATCGCAAAGAGATTGGCGTTAACCCGGAAGAT<br>ATTAAAGGTTATCGTATTACCAAAAGCGGCACACCGGAGTTTACATCCTT<br>TAAACTGTTCCACGATCTGAAAAAAGTGGTGAAAGATCATGCCATCCTGG<br>ATGATATTGATCTGCTGAATCAGATTGCAGAAATCCTGACCATCTATCAG<br>GATAAAGATAGCATTGTTGCAGAACTGGGTCAGCTGGAATATCTGATGAG<br>CGAAGCCGATAAACAGAGCATTAGCGAACTGACCGGTTATACCGGTACA<br>CATAGCCTGTCACTGAAATGCATGAACATGATTATCGATGAACTGTGGCA<br>TAGCAGCATGAACCAGATGGAAGTTTTTACCTATCTGAATATGCGTCCGA<br>AAAAGTATGAGCTGAAAGGTTATCAGCGTATTCCGACCGATATGATTGAT<br>GATGCAATTCTGAGTCCGGTTGTGAAACGCACCTTTATTCAGAGCATCAA<br>CGTGATCAACAAAGTGATCGAGAAATATGGCATCCCCGAAGATATCATTA<br>TCGAACTGGCACGTGAAAATAACTCCGATGATCGCAAAAAGTTCATCAAC<br>AACCTGCAGAAAAAGAATGAAGCAACCCGCAAACGCATTAACGAAATTA<br>TTGGTCAGACCGGTAATCAGAATGCCAAACGTATTGTGGAAAAAATCCGT<br>CTGCATGATCAGCAAGAGGGCAAATGTCTGTATAGCCTGGAAAGCATTCC<br>TCTGGAAGATCTGCTGAACAATCCGAATCATTATGAAGTGGATCACATTA<br>TTCCGCGTAGCGTGAGCTTTGATAATTCCTATCATAATAAAGTGCTGGTG<br>AAACAGAGCGAAAACTCCAAAAAATCCAACCTGACACCGTATCAGTATT<br>TCAATAGCGGCAAATCCAAACTGAGCTACAACCAGTTTAAACAGCATATT<br>CTGAACCTGAGCAAAAGCCAGGATCGCATCAGCAAGAAGAAGAAGGAGT<br>ACCTGCTGGAAGAACGCGACATCAACAAATTTGAAGTGCAGAAAGAATT<br>TATCAACCGCAACCTGGTTGATACCCGTTATGCAACCCGTGAACTGACCA<br>ATTATCTGAAAGCATATTTCAGCGCCAACAACATGAACGTGAAAGTGAA<br>AACGATTAACGGCAGCTTTACCGATTATCTGCGTAAAGTGTGGAAATTCA<br>AAAAAGAACGCAACCACGGCTATAAACATCATGCCGAAGATGCCCTGAT<br>TATTGCAAATGCAGATTTCCTGTTTAAAGAAAACAAAAAACTGAAAGCCG<br>TCAACAGCGTGCTGGAAAAACCGGAAATTGAGACAAAACAGCTGGACAT<br>TCAGGTTGATAGCGAAGATAATTACAGCGAAATGTTTATCATCCCGAAAC<br>AGGTGCAGGATATCAAAGATTTTCGCAACTTCAAATATAGCCACCGCGTT<br>GACAAAAAACCTAATCGTCAGCTGATTAACGATACCCTGTATAGCACCCG<br>CAAAAAAGATAACAGCACCTATATTGTGCAGACCATTAAAGACATCTAC<br>GCCAAAGATAATACCACCCTGAAAAAACAGTTCGACAAAAGCCCAGAAA<br>AATTTCTGATGTATCAGCATGATCCGCGTACCTTCGAAAAACTGGAAGTT<br>ATTATGAAACAGTATGCCAACGAGAAAAATCCGCTGGCCAAATATCACG<br>AAGAAACCGGTGAATATCTGACCAAATATTCCAAGAAGAACAACGGTCC<br>GATCGTTAAATCCCTGAAATATATCGGTAATAAACTGGGCAGCCATCTGG<br>ATGTTACCCATCAGTTTAAAAGCTCCACAAAGAAGCTGGTTAAACTGTCC<br>ATCAAACCGTATCGCTTTGATGTGTATCTGACCGACAAAGGCTATAAATT<br>CATTACCATCAGCTATCTGGACGTGCTGAAAAAAGACAACTATTATTATA<br>TCCCGGAACAGAAATATGATAAACTGAACTGGGTAAAGCCATCGATAA<br>AAACGCCAAATTTATCGCCAGCTTCTACAAAAACGACCTGATTAAACTGG<br>ATGGCGAGATCTATAAAATCATCGGTGTTAATAGCGACACCCGCAATATG<br>ATTGAGCTGGATCTGCCGGATATTCGCTATAAAGAATATTGCGAACTGAA<br>CAACATTAAAGGCGAACCGCGTATCAAAAAGACCATCGGCAAAAAAGTG<br>AATAGCATCGAGAAACTGACCACCGATGTTCTGGGGTAATGTGTTTACCAA<br>TACCCAGTATACCAAACCTCAGCTGCTGTTCAAACGCGGTAAT | |
| 14 | ATGAACCAGAAATTTATCCTGGGTCTGGATATTGGTATTACCAGCGTTGG<br>TTATGGCCTGATTGATTACGAAACCAAAAACATTATTGATGCCGGTGTTC<br>GTCTGTTTCCGGAAGCAAATGTTGAAAATAATGAAGGTCGTCGTAGCAAA<br>CGTGGGTAGCCGTCGTCTGAAACGTCGTCGTATTCATCGTCTGGAACGTGT<br>TAAACTGCTGCTGACCGAATATGATCTGATTAACAAAGAGCAGATTCCGA<br>CCAGCAATAACCCGTATCAGATTCGTGTTAAAGGTCTGAGCGAAATCCTG<br>AGCAAAGATGAACTGGCAATTGCACTGCTGCATCTGGCAAAACGCCGTG<br>GCATTCATAATGTTGATGTTGCAGCAGATAAAGAAGAAACCGCAAGCGA<br>TAGCCTGAGCACCAAAGATCAGATTAACAAAAACGCCAAATTTCTGGAA<br>AGCCGCTATGTTTGTGAACTGCAGAAAGAACGTCTGGAAAATGAAGGTC<br>ATGTTCGTGGTGTTGAAAATCGCTTTCTGACGAAAGATATTGTGCGTGAG<br>GCCAAAAAAATCATCGATACCCAGATGCAGTATTACCCGGAAATTGATG<br>AAACCTTCAAAGAGAAATATATCAGCCTGGTTGAAACCCGTCGCGAATAT | DNA sequence encoding Gib11Spa-1 |

| SEQ ID NO | Sequence | Description |
|---|---|---|
| | TTTGAAGGTCCTGGTCAGGGTAGCCCGTTTGGTTGGAATGGTGATCTGAA<br>AAAATGGTACGAAATGCTGATGGGTCACTGTACCTATTTTCCGCAAGAAC<br>TGCGTAGCGTTAAATATGCCTATAGCGCAGACCTGTTTAATGCACTGAAT<br>GATCTGAACAACCTGATTATTCAGCGCGATAATAGCGAGAAACTGGAAT<br>ACCATGAGAAGTATCACATCATCGAGAACGTGTTCAAGCAGAAAAAAAA<br>GCCGACGCTGAAACAAATCGCAAAAGAGATTGGCGTTAACCCGGAAGAT<br>ATTAAAGGTTATCGTATTACCAAAAGCGGCACACCGGAGTTTACATCCTT<br>TAAACTGTTCCACGATCTGAAAAAAGTGGTGAAAGATCATGCCATCCTGG<br>ATGATATTGATCTGCTGAATCAGATTGCAGAAATCCTGACCATCTATCAG<br>GATAAAGATAGCATTGTTGCAGAACTGGGTCAGCTGGAATATCTGATGAG<br>CGAAGCCGATAAACAGAGCATTAGCGAACTGACCGGTTATACCGGTACA<br>CATAGCCTGTCACTGAAATGCATGAACATGATTATCGATGAACTGTGGCA<br>TAGCAGCATGAACCAGATGGAAGTTTTTACCTATCTGAATATGCGTCCGA<br>AAAAGTATGAGCTGAAAGGTTATCAGCGTATTCCGACCGATATGATTGAT<br>GATGCAATTCTGAGTCCGGTTGTGAAACGCACCTTTATTCAGAGCATCAA<br>CGTGATCAACAAAGTGATCGAGAAATATGGCATCCCCGAAGATATCATTA<br>TCGAACTGGCACGTGAAATAACTCCGATGATCGCAAAAAGTTCATCAAC<br>AACCTGCAGAAAAAGAATGAAGCAACCCGCAAACGCATTAACGAAATTA<br>TTGGTCAGACCGGTAATCAGAATGCCAAACGTATTGTGGAAAAAATCCGT<br>CTGCATGATCAGCAAGAGGGCAAATGTCTGTATAGCCTGGAAAGCATTCC<br>TCTGGAAGATCTGCTGAACAATCCGAATCATTATGAAGTGGATCACATTA<br>TTCCGCGTAGCGTGAGCTTTGATAATTCCTATCATAATAAAGTGCTGGTG<br>AAACAGAGCGAAAACTCCAAAAAATCCAACCTGACACCGTATCAGTATT<br>TCAATAGCGGCAAATCCAAACTGAGCTACAACCAGTTTAAACAGCATATT<br>CTGAACCTGAGCAAAAGCCAGGATCGCATCAGCAAGAAGAAGAAGGAGT<br>ACCTGCTGGAAGAACGCGATATTAACAAATTTGAAGTGCAGAAAGAATT<br>TATCAACCGCAACCTGGTTGATACCCGTTATGCAACCCGTGAACTGACCA<br>ATTATCTGAAAGCATATTTCAGCGCCAACAACATGAACGTGAAAGTGAA<br>AACGATTAACGGCAGCTTTACCGATTATCTGCGTAAAGTGTGGAAATTCA<br>AAAAAGAACGCAACCACGGCTATAAACATCATGCCGAAGATGCCCTGAT<br>TATTGCAAATGCAGATTTCCTGTTTAAAGAAAACAAAAAACTGAAAGCCG<br>TCAACAGCGTGCTGGAAAAACCGGAAATTGAGACAAAACAGCTGGACAT<br>TCAGGTTGATAGCGAAGATAATTACAGCGAAATGTTTATCATCCCGAAAC<br>AGGTGCAGGATATCAAAGATTTTCGCAACTTCAAATATAGCCACCGCGTT<br>GACAAAAAACCTAATCGTCAGCTGATTAACGATACCCTGTATAGCACCCG<br>CAAAAAGATAACAGCACCTATATTGTGCAGACCATTAAAGACATCTAC<br>GCCAAAGATAATACCACCCTGAAAAAACAGTTCGACAAAAGCCCAGAAA<br>AATTTCTGATGTATCAGCATGATCCGCGTACCTTCGAAAAACTGGAAGTT<br>ATTATGAAACAGTATGCCAACGAGAAAAATCCGCTGGCCAAATATCACG<br>AAGAAACCGGTGAATATCTGACCAAATATTCCAAGAAGAACAACGGTCC<br>GATCGTTAAATCCCTGAAATATATCGGTAATAAACTGGGCAGCCATCTGG<br>ATGTTACCCATCAGTTTAAAAGCTCCACAAAGAAGCTGGTTAAGCTGTCC<br>ATTAAAACTATCGCTTCGATGTGTATCTGACCGAGAAAGGTTATAAGTT<br>TGTGACCATTGCCTACCTGAATGTGTTCAAAAAAGACAACTATTACTATA<br>TTCCGAAAGACAAATACCAAGAACTTAAAGAGAAGAAGAAAATCAAGGA<br>CACCGATCAGTTTATCGCCAGCTTCTATAAAAACGATCTGATCAAGCTGA<br>ACGGCGACCTGTATAAAATCATTGGTGTGAATAGTGATGACCGAACATC<br>ATTGAGCTGGATTATTACGACATCAAATACAAGGATTACTGCGAGATCAA<br>CAACATTAAAGGTGAACCGCGTATCAAAAAGACCATTGGCAAAAAAACG<br>GAAAGCATCGAAAAGTTTACCACCGATGTTCTGGGTAATCTGTATCTGCA<br>TAGTACCGAAAAAGCACCGCAGCTGATTTTCAAACGCGGTCTG | |
| 15 | ATGAACCAGAAGTTCATTCTCGGTCTGGACATTGGCATTACTAGCGTGGG<br>ATACGGCTTGATTGACTACGAGACTAAGAACATCATCGATGCCGGCGTCC<br>GCCTGTTCCCGGAAGCCAACGTGGAGAACAATGAGGGCCGGAGGTCGAA<br>GAGAGGCTCCCGCCGCCTGAAGCGGCGGCGAATCCACCGGCTGGAGAGA<br>GTGAAGCTGCTGCTCACCGAATACGACCTGATCAACAAAGAACAGATCC<br>CGACCTCCAACAACCCGTACCAGATCAGAGTGAAGGGTCTGTCAGAAAT<br>CCTGTCCAAGGACGAACTGGCAATCGCCCTGCTGCACCTGGCCAAGCGGC<br>GCGGAATCCACAACGTGGATGTGGCTGCCGACAAGGAAGAAACCGCTTC<br>CGACTCCCTGAGCACTAAGGACCAGATCAACAAGAACGCCAAGTTCTTG<br>GAGTCCCGCTACGTGTGCGAGCTGCAGAAGGAACGGCTGGAAAACGAAG<br>GTCACGTGCGCGGAGTGGAAAACCGGTTCCTGACAAAGGACATTGTGCG<br>CGAAGCGAAGAAGATCATTGATACCCAAATGCAGTACTACCCTGAAATC<br>GACGAGACTTTCAAGGAAAAGTACATTTCCTGGTGGAAACCCGGCGGG<br>AATACTTCGAAGGCCCCGGACAGGGATCGCCGTTCGGATGGAACGGGGA<br>CCTCAAGAAGTGGTACGAGATGCTGATGGGCACTGTACCTACTTTCCGC<br>AAGAACTGCGCTCCGTGAAGTACGCGTACTCCGCGGATCTCTTCAACGCG<br>TTGAATGACCTGAACAACCTGATCATTCAGAGAGACAATTCCGAAAAGCT<br>CGAGTACCACGAGAAGTATCACATCATCGAGAATGTGTTCAAGCAGAAG<br>AAGAAACCGACCCTCAAGCAAATCGCCAAGGAGATTGGCGTCAACCCAG<br>AGGACATCAAGGGATATCGGATTACCAAGAGCGGCACTCCCGAGTTTAC<br>CTCTTTCAAGCTGTTTCATGATCTGAAGAAAGTCGTGAAGGACCATGCCA | Codon-optimized Gib11Spa-1 polynucleotide |

SEQUENCE LISTING

| SEQ ID NO | Sequence | Description |
|---|---|---|
| | TTCTCGACGACATTGATCTCCTGAATCAGATCGCAGAGATCCTGACTATC<br>TACCAAGACAAGGACTCGATTGTGGCAGAGCTGGGTCAGCTCGAATACCT<br>GATGTCCGAGGCCGACAAGCAGTCCATCTCCGAACTGACAGGGTACACG<br>GGGACTCATAGCCTGTCGCTGAAGTGCATGAACATGATCATTGATGAACT<br>GTGGCACAGCTCCATGAACCAAATGGAAGTGTTTACCTACCTCAACATGC<br>GCCCTAAGAAGTACGAACTGAAAGGCTACCAGCGCATCCCCACCGACAT<br>GATCGACGACGCGATCTTGTCCCCTGTGGTCAAGAGGACCTTCATTCAAT<br>CCATCAACGTGATCAACAAGGTCATCGAAAAGTACGGAATACCAGAAGA<br>TATCATCATTGAGCTCGCTCGGGAGAACAACTCGGATGACCGGAAGAAG<br>TTCATCAACAATCTTCAGAAGAAGAACGAAGCGACTCGGAAACGGATCA<br>ACGAGATCATCGGACAGACCGGAAACCAGAACGCCAAACGGATTGTCGA<br>AAAGATTAGACTGCACGACCAGCAGGAAGGGAAGTGCCTGTACTCACTC<br>GAGTCAATACCGCTCGAGGACCTGTTGAACAACCCTAACCACTATGAAGT<br>GGACCACATCATCCCTCGGTCCGTGAGCTTCGACAACTCGTACCACAACA<br>AAGTGCTCGTGAAGCAGTCCGAAAACTCCAAGAAATCCAACCTGACCCC<br>GTACCAATACTTCAATTCGGGAAAGTCGAAGCTGTCGTACAACCAGTTCA<br>AACAACACATACTCAACCTTAGCAAAAGCCAGGATCGCATTTCCAAGAA<br>GAAGAAGGAATACCTCCTCGAGGAAAGGGACATCAACAAGTTCGAAGTG<br>CAGAAAGAGTTCATCAATCGCAACTTGGTGGATACCAGATATGCCACCCG<br>GGAACTCACCAACTATCTCAAGGCCTACTTTTCCGCCAACAACATGAACG<br>TGAAGGTCAAGACCATCAACGGGTCCTTCACTGACTACCTGAGAAAGGTC<br>TGGAAGTTCAAGAAGGAACGCAACCACGGATACAAGCACCACGCTGAGG<br>ACGCTCTGATCATCGCCAATGCCGACTTCCTGTTCAAGGAAAACAAGAAG<br>CTGAAAGCTGTCAACTCAGTGCTGGAAAAGCCTGAAATCGAGACTAAGC<br>AGCTGGATATCCAAGTGGACTCTGAGGACAACTACAGCGAGATGTTCATC<br>ATCCCTAAACAAGTGCAGGATATCAAGGACTTTCGCAACTTCAAGTACTC<br>ACACCGGGTGGACAAGAAACCGAATAGACAGCTGATCAACGACACGTTG<br>TATTCCACCCGGAAGAAGGATAACTCAACCTACATTGTGCAGACTATCAA<br>GGATATCTACGCCAAAGATAACACTACTCTGAAGAAACAATTCGACAAG<br>TCCCCAGAGAAGTTCCTGATGTACCAGCACGACCCCCGAACCTTTGAGAA<br>GCTTGAAGTGATCATGAAGCAGTACGCCAACGAGAAGAACCCGCTGGCC<br>AAGTACCATGAAGAAACCGGAGAATACCTGACCAAGTACAGCAAGAAGA<br>ACAACGGTCCCATTGTCAAGAGCCTGAAGTACATCGGCAACAAGCTGGG<br>ATCCCACCTCGACGTGACACATCAGTTCAAGTCGTCGACTAAGAAGCTTG<br>TGAAGCTGTCAATCAAGAACTATAGATTCGACGTGTACTTGACCGAAAAG<br>GGATACAAGTTCGTGACCATAGCCTATCTGAACGTGTTCAAGAAAGATAA<br>CTACTACTACATCCCCAAGGACAAGTACCAGGAGCTCAAAGAAAAGAAG<br>AAGATCAAAGACACCGACCAGTTCATTGCCTCCTTCTACAAGAACGACCT<br>GATCAAACTGAACGGCGACCTCTACAAGATCATTGGAGTGAACAGCGAT<br>GACAGGAACATCATTGAGCTGGACTACTACGACATCAAGTACAAGGACT<br>ACTGCGAGATCAACAACATCAAGGGCGAACCCCGGATCAAGAAAACTAT<br>TGGAAAGAAAACCGAGTCCATTGAGAAGTTCACCACTGACGTGCTGGGA<br>AACCTTTACCTCCACTCCACCGAGAAGGCACCACAACTGATCTTCAAGCG<br>CGGCCTG | |
| 16 | ATGAACCAGAAATTTATCCTGGGTCTGGATATTGGTATTACCAGCGTTGG<br>TTATGGCCTGATTGATTACGAAACCAAAAACATTATTGATGCCGGTGTTC<br>GTCTGTTTCCGGAAGCAAATGTTGAAAATAATGAAGGTCGTCGTAGCAAA<br>CGTGGTAGCCGTCGTCTGAAACGTCGTCGTATTCATCGTCTGGAACGTGT<br>TAAACTGCTGCTGACCGAATATGATCTGATTAACAAAGAGCAGATTCCGA<br>CCAGCAATAACCCGTATCAGATTCGTGTTAAAGGTCTGAGCGAAATCCTG<br>AGCAAAGATGAACTGGCAATTGCACTGCTGCATCTGGCAAAACGCCGTG<br>GCATTCATAATGTTGATGTTGCAGCAGATAAAGAAGAAACCGCAAGCGA<br>TAGCCTGAGCACCAAAGATCAGATTAACAAAAACGCCAAATTTCTGGAA<br>AGCCGCTATGTTTGTGAACTGCAGAAAGAACGTCTGGAAAATGAAGGTC<br>ATGTTCGTGGTGTTGAAAATCGCTTTCTGACGAAAGATATTGTGCGTGAG<br>GCCAAAAAATCATCGATACCCAGATGCAGTATTACCCGGAAATTGATG<br>AAACCTTCAAAGAGAAATATATCAGCCTGGTTGAAACCCGTCGCAATAT<br>TTTGAAGGTCCTGGTCAGGGTAGCCCGTTTGGTTGGAATGGTGATCTGAA<br>AAAATGGTACGAAATGCTGATGGGTCACTGTACCTATTTTCCGAAGAAC<br>TGCGTAGCGTTAAATATGCCTATAGCGCAGACCTGTTTAATGCACTGAAT<br>GATCTGAACAACCTGATTATTCAGCGCGATAATAGCGAGAAACTGGAAT<br>ACCATGAGAAGTATCACATCATCGAGAACGTGTTCAAGCAGAAAAAAAA<br>GCCGACGCTGAAACAAATCGCAAAAGAGATTGGCGTTAACCCGGAAGAT<br>ATTAAAGGTTATCGTATTACCAAAAGCGGCACACCGGAGTTTACATCCTT<br>TAAACTGTTCCACGATCTGAAAAAGTGGTGAAAGATCATGCCATCCTGG<br>ATGATATTGATCTGCTGAATCAGATTGCAGAAATCCTGACCATCTATCAG<br>GATAAAGATAGCATTGTTGCAGAACTGGGTCAGCTGGAATATCTGATGAG<br>CGAAGCCGATAAACAGAGCATTAGCGAACTGACCGGTTATACCGGTACA<br>CATAGCCTGTCACTGAAATGCATGAACATGATTATCGATGAACTGTGGCA<br>TAGCAGCATGAACCAGATGGAAGTTTTTACCTATCTGAATATGCGTCCGA<br>AAAAGTATGAGCTGAAAGGTTATCAGCGTATTCCGACCGATATGATTGAT<br>GATGCAATTCTGAGTCCGGTTGTGAAACGCACCTTTATTCAGAGCATCAA | DNA sequence encoding Gib11Spa-2 |

| SEQ ID NO | Sequence | Description |
|---|---|---|
| | CGTGATCAACAAAGTGATCGAGAAATATGGCATCCCCGAAGATATCATTA<br>TCGAACTGGCACGTGAAAATAACTCCGATGATCGCAAAAAGTTCATCAAC<br>AACCTGCAGAAAAAGAATGAAGCAACCCGCAAACGCATTAACGAATTA<br>TTGGTCAGACCGGTAATCAGAATGCCAAACGTATTGTGGAAAAAATCCGT<br>CTGCATGATCAGCAAGAGGGCAAATGTCTGTATAGCCTGGAAAGCATTCC<br>TCTGGAAGATCTGCTGAACAATCCGAATCATTATGAAGTGGATCACATTA<br>TTCCGCGTAGCGTGAGCTTTGATAATTCCTATCATAATAAAGTGCTGGTG<br>AAACAGAGCGAAAACTCCAAAAAATCCAACCTGACACCGTATCAGTATT<br>TCAATAGCGGCAAATCCAAACTGAGCTACAACCAGTTTAAACAGCATATT<br>CTGAACCTGAGCAAAAGCCAGGATCGCATCAGCAAGAAGAAGAAGGAGT<br>ACCTGCTGGAAGAACGCGATATTAACAAATTTGAAGTGCAGAAAGAATT<br>TATCAACCGCAACCTGGTTGATACCCGTTATGCAACCCGTGAACTGACCA<br>ATTATCTGAAAGCATATTTCAGCGCCAACAACATGAACGTGAAAGTGAA<br>AACGATTAACGGCAGCTTTACCGATTATCTGCGTAAAGTGTGGAAATTCA<br>AAAAAGAACGCAACCACGGCTATAAACATCATGCCGAAGATGCCCTGAT<br>TATTGCAAATGCAGATTTCCTGTTTAAAGAAAACAAAAAACTGAAAGCCG<br>TCAACAGCGTGCTGGAAAAACCGGAAATTGAGACAAAACAGCTGGACAT<br>TCAGGTTGATAGCGAAGATAATTACAGCGAAATGTTTATCATCCCGAAAC<br>AGGTGCAGGATATCAAAGATTTTCGCAACTTCAAATTCAGCCACCGCGTT<br>GATAAAAAACCGAATCGTCAGCTGATTAACGATACCCTGTATAGCACCCG<br>TATGAAAGATGAGCATGATTATATTGTGCAGACCATCACGGATATCTATG<br>GCAAAGATAATACCAACCTGAAAAAACAGTTCAACAAAAACCCGGAAAA<br>ATTTCTGATGTATCAGAACGATCCGAAAACCTTTGAGAAACTGAGCATCA<br>TCATGAAACAGTACAGCGACGAAAAAAACCCGCTGGCCAAATATTACGA<br>AGAAACCGGTGAATATCTGACCAAATATAGCAAGAAAAACAACGGTCCG<br>ATCGTGAAAAAGATCAAACTGCTGGGTAATAAAGTGGGCAATCATCTGG<br>ATGTGACCAACAAATATGAAAACTCCACGAAGAAGCTGGTTAAGCTGTC<br>CATTAAAAACTATCGCTTCGATGTGTATCTGACCGAGAAAGGTTATAAGT<br>TTGTGACCATTGCCTACCTGAATGTGTTCAAAAAAGACAACTATTACTAT<br>ATTCCGAAAGACAAATACCAAGAACTTAAAGAGAAGAAGAAATCAAGG<br>ACACCGATCAGTTTATCGCCAGCTTCTATAAAAACGATCTGATCAAGCTG<br>AACGGCGACCTGTATAAAATCATTGGTGTGAATAGTGATGACCGCAACAT<br>CATTGAGCTGGATTATTACGACATCAAATACAAGGATTACTGCGAGATCA<br>ACAACATTAAAGGTGAACCGCGTATCAAAAAGACCATTGGCAAAAAAAC<br>GGAAAGCATCGAAAAGTTTACCACCGATGTTCTGGGTAATCTGTATCTGC<br>ATAGTACCGAAAAAGCACCGCAGCTGATTTTCAAACGCGGTCTG | |
| 17 | ATGAACCAGAAATTTATCCTGGGTCTGGATATTGGTATTACCAGCGTTGG<br>TTATGGCCTGATTGATTACGAAACCAAAAACATTATTGATGCCGGTGTTC<br>GTCTGTTTCCGGAAGCAAATGTTGAAAATAATGAAGGTCGTCGTAGCAAA<br>CGTGGTAGCCGTCGTCTGAAACGTCGTCGTATTCATCGTCTGGAACGTGT<br>TAAACTGCTGCTGACCGAATATGATCTGATTAACAAAGAGCAGATTCCGA<br>CCAGCAATAACCCGTATCAGATTCGTGTTAAAGGTCTGAGCGAAATCCTG<br>AGCAAAGATGAACTGGCAATTGCACTGCTGCATCTGGCAAAACGCCGTG<br>GCATTCATAATGTTGATGTTGCAGCAGATAAAGAAGAAACCGCAAGCGA<br>TAGCCTGAGCACCAAAGATCAGATTAACAAAAACGCCAAATTTCTGGAA<br>AGCCGCTATGTTTGTGAACTGCAGAAAGAACGTCTGGAAAATGAAGGTC<br>ATGTTCGTGGTGTTGAAAATCGCTTTCTGACGAAAGATATTGTGCGTGAG<br>GCCAAAAAAATCATCGATACCCAGATGCAGTATTACCCGGAAATTGATG<br>AAACCTTCAAAGAGAAATATATCAGCCTGGTTGAAACCCGTCGCGAATAT<br>TTTGAAGGTCCTGGTCAGGGTAGCCCGTTTGGTTGGAATGGTGATCTGAA<br>AAAATGGTACGAAATGCTGATGGGTCACTGTACCTATTTTCCGCAAGAAC<br>TGCGTAGCGTTAAATATGCCTATAGCGCAGACCTGTTTAATGCACTGAAT<br>GATCTGAACAACCTGATTATTCAGCGCGATAATAGCGAGAAACTGGAAT<br>ACCATGAGAAGTATCACATCATCGAGAACGTGTTCAAGCAGAAAAAAAA<br>GCCGACGCTGAAACAAATCGCAAAAGAGATTGGCGTTAACCCGGAAGAT<br>ATTAAAGGTTATCGTATTACCAAAAGCGGCACACCGGAGTTTACATCCTT<br>TAAACTGTTCCACGATCTGAAAAAAGTGGTGAAAGATCATGCCATCCTGG<br>ATGATATTGATCTGCTGAATCAGATTGCAGAAATCCTGACCATCTATCAG<br>GATAAAGATAGCATTGTTGCAGAACTGGGTCAGCTGGAATATCTGATGAG<br>CGAAGCCGATAAACAGAGCATTAGCGAACTGACCGGTTATACCGGTACA<br>CATAGCCTGTCACTGAAATGCATGAACATGATTATCGATGAACTGTGGCA<br>TAGCAGCATGAACCAGATGGAAGTTTTTACCTATCTGAATATGCGTCCGA<br>AAAAGTATGAGCTGAAAGGTTATCAGCGTATTCCGACCGATATGATTGAT<br>GATGCAATTCTGAGTCCGGTTGTGAAACGCACCTTTATTCAGAGCATCAA<br>CGTGATCAACAAAGTGATCGAGAAATATGGCATCCCCGAAGATATCATTA<br>TCGAACTGGCACGTGAAAATAACTCCGATGATCGCAAAAAGTTCATCAAC<br>AACCTGCAGAAAAAGAATGAAGCAACCCGCAAACGCATTAACGAATTA<br>TTGGTCAGACCGGTAATCAGAATGCCAAACGTATTGTGGAAAAAATCCGT<br>CTGCATGATCAGCAAGAGGGCAAATGTCTGTATAGCCTGGAAAGCATTCC<br>TCTGGAAGATCTGCTGAACAATCCGAATCATTATGAAGTGGATCACATTA<br>TTCCGCGTAGCGTGAGCTTTGATAATTCCTATCATAATAAAGTGCTGGTG<br>AAACAGAGCGAAAACTCCAAAAAATCCAACCTGACACCGTATCAGTATT | DNA sequence encoding Gib11Spa-3 |

| SEQ ID NO | Sequence | Description |
|---|---|---|
|  | TCAATAGCGGCAAATCCAAACTGAGCTACAACCAGTTTAAACAGCATATT<br>CTGAACCTGAGCAAAAGCCAGGATCGCATCAGCAAGAAGAAGAAGGAGT<br>ACCTGCTGGAAGAACGCGATATCAACAAATTTGAAGTCCAGAAAGAGTT<br>TATCAACCGCAATCTGGTTGATACCCGTTATGCAACCCGTGAACTGACCA<br>GCTATCTGAAAGCATATTTCAGCGCCAATAACATGGACGTGAAAGTGAA<br>AACAATTAACGGCAGCTTTACCAACCATCTGCGTAAAGTTTGGCGCTTTG<br>ATAAATATCGCAACCACGGCTATAAACATCATGCCGAAGATGCACTGATT<br>ATTGCCAATGCAGATTTCCTGTTCAAAGAAAACAAAAAACTGCAGAACA<br>CCAACAAGATCCTGGAAAAACCGACCATTGAAAACAACACCAAAAAAGT<br>GACCGTCGAGAAGAAGAGGATTACAACAACGTTTTTGAAACCCCGAAA<br>CTGGTCGAGGATATTAAACAGTATCGCGACTATAAATTCAGCCACCGCGT<br>TGATAAAAAACCGAATCGTCAGCTGATTAACGATACCCTGTATAGCACCC<br>GTATGAAAGATGAGCATGATTATATTGTGCAGACCATCACGGATATCTAT<br>GGCAAAGATAATACCAACCTGAAAAACAGTTCAACAAAAACCCGGAAA<br>AATTTCTGATGTATCAGAACGATCCGAAAACCTTTGAGAAACTGAGCATC<br>ATCATGAAACAGTACAGCGACGAAAAAAACCCGCTGGCCAAATATTACG<br>AAGAAACCGGTGAATATCTGACCAAATATAGCAAGAAAAACAACGGTCC<br>GATCGTGAAAAGATCAAACTGCTGGGTAATAAAGTGGGCAATCATCTG<br>GATGTGACCAACAAATATGAAAACTCCACGAAGAAGCTGGTTAAGCTGT<br>CCATTAAAAACTATCGCTTCGATGTGTATCTGACCGAGAAAGGTTATAAG<br>TTTGTGACCATTGCCTACCTGAATGTGTTCAAAAAAGACAACTATTACTA<br>TATTCCGAAAGACAAATACCAAGAACTTAAAGAAGAAGAAAATCAAG<br>GACACCGATCAGTTTATCGCCAGCTTCTATAAAAACGATCTGATCAAGCT<br>GAACGGCGACCTGTATAAAATCATTGGTGTGAATAGTGATGACCGCAAC<br>ATCATTGAGCTGGATTATTACGACATCAAATACAAGGATTACTGCGAGAT<br>CAACAACATTAAAGGTGAACCGCGTATCAAAAGACCATTGGCAAAAAA<br>ACGGAAAGCATCGAAAAGTTTACCACCGATGTTCTGGGTAATCTGTATCT<br>GCATAGTACCGAAAAAGCACCGCAGCTGATTTTCAAACGCGGTCTG |  |
| 18 | ATGAACCAGAAGTTCATTCTCGGTCTGGACATTGGCATTACTAGCGTGGG<br>ATACGGCTTGATTGACTACGAGACTAAGAACATCATCGATGCCGGCGTCC<br>GCCTGTTCCCGGAAGCCAACGTGGAGAACAATGAGGGCCGGAGGTCGAA<br>GAGAGGCTCCCGCCGCCTGAAGCGGCGGCGAATCCACCGGCTGGAGAGA<br>GTGAAGCTGCTGCTCACCGAATACGACCTGATCAACAAAGAACAGATCC<br>CGACCTCCAACAACCCGTACCAGATCAGAGTGAAGGGTCTGTCAGAAAT<br>CCTGTCCAAGGACGAACTGGCAATCGCCCTGCTGCACCTGGCCAAGCGGC<br>GCGGAATCCACAACGTGGATGTGGCTGCCGACAAGGAAGAAACCGCTTC<br>CGACTCCCTGAGCACTAAGGACCAGATCAACAAGAACGCCAAGTTCTTG<br>GAGTCCCGCTACGTGTGCGAGCTGCAGAAGGAACGGCTGGAAAACGAAG<br>GTCACGTGCGCGGAGTGGAAAACCGGTTCCTGACAAAGGACATTGTGCG<br>CGAAGCGAAGAAGATCATTGATACCCAAATGCAGTACTACCCTGAAATC<br>GACGAGACTTTCAAGGAAAAGTACATTTCCCTGGTGGAAACCCGGCGGG<br>AATACTTCGAAGGCCCCGGACAGGGATCGCCGTTCGGATGGAACGGGGA<br>CCTCAAGAAGTGGTACGAGATGCTGATGGGGCACTGTACCTACTTTCCGC<br>AAGAACTGCGCTCCGTGAAGTACGCGTACTCCGCGGATCTCTTCAACGCG<br>TTGAATGACCTGAACAACCTGATCATTCAGAGAGACAATTCCGAAAAGCT<br>CGAGTACCACGAGAAGTATCACATCATCGAGAATGTGTTCAAGCAGAAG<br>AAGAAACCGACCCTCAAGCAAATCGCCAAGGAGATTGGCGTCAACCCAG<br>AGGACATCAAGGGATATCGGATTACCAAGAGCGGCACTCCCGAGTTTAC<br>CTCTTTCAAGCTGTTTCATGATCTGAAGAAAGTCGTGAAGGACCATGCCA<br>TTCTCGACGACATTGATCTCCTGAATCAGATCGCAGAGATCCTGACTATC<br>TACCAAGACAAGGACTCGATTGTGGCAGAGCTGGGTCAGCTCGAATACCT<br>GATGTCCGAGGCCGACAAGCAGTCCATCTCCGAACTGACAGGGTACACG<br>GGGACTCATAGCCTGTCGCTGAAGTGCATGAACATGATCATTGATGAACT<br>GTGGCACAGCTCCATGAACCAAATGGAAGTGTTTACCTACCTCAACATGC<br>GCCCTAAGAAGTACGAACTGAAAGGCTACCAGCGCATCCCCACCGACAT<br>GATCGACGACGCGATCTTGTCCCCTGTGGTCAAGAGGACCTTCATTCAAT<br>CCATCAACGTGATCAACAAGGTCATCGAAAAGTACGGTATTCCAGAAGA<br>TATCATCATTGAGCTCGCTCGGGAGAACAACTCGGATGACCGGAAGAAG<br>TTCATCAACAATCTTCAGAAGAAGAACGAAGCGACTCGGAAACGGATCA<br>ACGAGATCATCGGACAGACCGGAAACCAGAACGCCAAACGGATTGTCGA<br>AAAGATTAGACTGCACGACCAGCAGGAAGGGAAGTGCCTGTACTCACTC<br>GAGTCAATACCGCTCGAGGACCTGTTGAACAACCCTAACCACTATGAAGT<br>GGACCACATCATCCCTCGGTCCGTGAGCTTCGACAACTCGTACCACAACA<br>AAGTGCTCGTGAAGCAGTCCGAAAACTCCAAGAAATCCAACCTGACCCC<br>GTACCAATACTTCAATTCGGGAAAGTCGAAGCTGTCGTACAACCAGTTCA<br>AACAACACATACTCAACCTTAGCAAAAGCCAGGATCGCATTTCCAAGAA<br>GAAGAAGGAATACCTCCTCGAGGAAAGGGACATCAACAAGTTCGAAGTG<br>CAGAAAGAGTTCATCAATCGCAACTTGGTGGATACCAGATATGCCACCCG<br>GGAACTCACCAGCTATCTCAAGGCCTACTTTTCCGCCAACAACATGGACG<br>TGAAGGTCAAGACCATCAACGGGTCCTTCACTAACCATCTGAGAAAGGTC<br>TGGCGGTTTGACAAGTACCGCAACCACGGATACAAGCACCACGCTGAAG<br>ACGCTCTGATCATCGCCAATGCCGACTTCCTGTTCAAGGAAAACAAGAAG | Codon-optimized Gib11Spa-3 polynucleotide |

SEQUENCE LISTING

| SEQ ID NO | Sequence | Description |
|---|---|---|
| | CTGCAGAACACGAACAAGATTCTGGAAAAGCCTACCATTGAGAACAACA<br>CTAAGAAGGTCACCGTGGAGAAGGAAGAGGACTACAACAACGTGTTCGA<br>AACTCCTAAACTGGTGGAGGATATCAAGCAATACCGCGACTACAAGTTCT<br>CACACCGGGTGGACAAGAAACCGAATAGACAGCTGATCAACGACACGTT<br>GTATTCCACCCGGATGAAGGATGAGCATGACTACATTGTGCAGACTATCA<br>CCGATATCTACGGAAAAGATAACACTAACCTGAAGAAACAATTCAACAA<br>GAACCCAGAGAAGTTCCTGATGTACCAGAACGACCCCAAGACCTTTGAG<br>AAGCTTTCCATCATCATGAAGCAGTACTCCGACGAGAAGAACCCGCTGGC<br>CAAGTACTACGAAGAAACCGGAGAATACCTGACCAAGTACAGCAAGAAG<br>AACAACGGTCCCATTGTCAAGAAGATCAAGCTGCTCGGCAACAAGGTCG<br>GAAACCACCTCGACGTGACAAACAAGTACGAGAACTCGACTAAGAAGCT<br>TGTGAAGCTGTCAATCAAGAACTATAGATTCGACGTGTACTTGACCGAAA<br>AGGGATACAAGTTCGTGACCATAGCCTATCTGAACGTGTTCAAGAAAGAT<br>AACTACTACTACATCCCCAAGGACAAGTACCAGGAGCTCAAAGAAAGA<br>AGAAGATCAAAGACACCGACCAGTTCATTGCCTCCTTCTACAAGAACGAC<br>CTGATCAAACTGAACGGCGACCTCTACAAGATCATTGGAGTGAACAGCG<br>ATGACAGGAACATCATTGAGCTGGACTACTACGACATCAAGTACAAGGA<br>CTACTGCGAGATCAACAACATCAAGGGCGAACCCCGGATCAAGAAAACT<br>ATTGGAAAGAAAACCGAGTCCATTGAGAAGTTCACCACTGACGTGCTGG<br>GAAACCTTTACCTCCACTCCACCGAGAAGGCACCACAACTGATCTTCAAG<br>CGCGGCCTG | |
| 19 | ATGAACCAGAAATTTATCCTGGGTCTGGATATTGGTATTACCAGCGTTGG<br>TTATGGCCTGATTGATTACGAAACCAAAAACATTATTGATGCCGGTGTTC<br>GTCTGTTTCCGGAAGCAAATGTTGAAATAATGAAGGTCGTCGTAGCAAA<br>CGTGGTAGCCGTCGTCTGAAACGTCGTCGTATTCATCGTCTGGAACGTGT<br>TAAAAAACTGCTGGAAGATTATAACCTGCTGGATCAGAGCCAGATTCCGC<br>AGAGCACCAATCCGTATGCAATTCGTGTTAAAGGTCTGAGCGAAGCACTG<br>AGCAAAGATGAACTGGTTATTGCACTGCTGCATATTGCAAAACGCCGTGG<br>CATTCATAATATCAATGTTAGCAGCGAAGATGAGGATGCAAGCAATGAA<br>CTGAGCACCAAAGAACAAATTAACCGCAATAATAAGCTGCTGAAGGACA<br>AATATGTTGCGAAGTTCAGCTGCAGCGTCTGAAAGAAGGTCAGATTCGC<br>GGAGAAAAAAATCGCTTTAAAACCACCGATATCCTGAAAGAAATTGATC<br>AGCTGCTTAAAGTGCAGAAGGATTATCATAACCTGGACATCGATTTCATC<br>AACCAGTACAAAGAAATCGTTGAAACCCGTCGCGAATATTTTGAAGGTCC<br>GGGTAAAGGTAGCCCGTATGGTTGGGAAGGTGATCCGAAAGCATGGTAT<br>GAAACCCTGATGGGTCATTGTACCTATTTTCCGGATGAACTGCGTAGCGT<br>TAAATATGCCTATAGCGCAGACCTGTTTAATGCACTGAATGATCTGAATA<br>ACCTGGTGATTCAGCGTGATGGTCTGAGCAAACTGGAATATCATGAGAAA<br>TATCACATCATCGAAAACGTGTTCAAACAGAAGAAGAAACCGACCCTGA<br>AACAAATCGCCAACGAAATTAATGTGAACCCGGAAGATATTAAAGGCTA<br>CCGTATTACCAAAAGCGGCAAACCGGAATTTACATCCTTTAAACTGTTCC<br>ACGATCTGAAAAAAGTGGTGAAAGATCATGCCATCCTGGATGATATTGAT<br>CTGCTGAATCAGATTGCAGAAATCCTGACCATCTATCAGGATAAAGATAG<br>CATTGTTGCAGAACTGGGTCAGCTGGAATATCTGATGAGCGAAGCCGATA<br>AACAGAGCATTAGCGAACTGACCGGTTATACCGGTACACATAGCCTGTCA<br>CTGAAATGCATGAACATGATTATCGATGAACTGTGGCATAGCAGCATGAA<br>CCAGATGGAAGTTTTTACCTATCTGAATATGCGTCCGAAAAAGTATGAGC<br>TGAAAAGGTTATCAGCGTATTCCGACCGATATGATTGATGATGCAATTCTG<br>AGTCCGGTTGTGAAACGCACCTTTATTCAGAGCATCAACGTGATCAACAA<br>AGTGATCGAGAAATATGGCATCCCCGAAGATATCATTATCGAACTGGCAC<br>GTGAAAATAACTCCGATGATCGCAAAAAGTTCATCAACAACCTGCAGAA<br>AAAGAATGAAGCAACCCGCAAACGCATTAACGAAATTATTGGTCAGACC<br>GGTAATCAGAATGCCAAACGTATTGTGGAAAAAAATCCGTCTGCATGATCA<br>GCAAGAGGGTAAATGTCTGTATAGCCTGGAAAGCATTCCTCTGGAAGATC<br>TGCTGAACAATCCGAATCATTATGAAGTGGATCACATTATTCCGCGTAGC<br>GTGAGCTTTGATAATTCCTATCATAATAAAGTGCTGGTGAAACAGAGCGA<br>AAACTCCAAAAAATCCAACCTGACACCGTATCAGTATTTCAATAGCGGCA<br>AATCCAAACTGAGCTACAACCAGTTTAAACAGCATATTCTGAACCTGAGC<br>AAAAAGCCAGGATCGCATCAGCAAGAAGAAGAAGGAGTACCTGCTGGAAG<br>AACGCGATATTAACAAATTTGAAGTCAGAAAGAATTTATCAACCGCAA<br>CCTGGTTGATACCCGTTATGCAACCCGTGAACTGACCAATTATTGAAAG<br>CATATTTCAGCGCCAACAACATGAACGTGAAAGTGAAAACGATTAACGG<br>CAGCTTTACCGATTATCTGCGTAAAGTGTGGAAATTCAAAAAAGAACGCA<br>ACCACGGCTATAAACATCATGCCGAAGATGCCCTGATTATTGCAAATGCA<br>GATTTCCTGTTTAAAGAAAACAAAAAACTGAAAGCCGTCAACAGCGTGCT<br>GGAAAAACCGGAAATTGAGACAAAACAGCTGGACATTCAGGTTGATAGC<br>GAAGATAATTACAGCGAAATGTTTATCATCCCGAAACAGGTGCAGGATAT<br>CAAAGATTTTCGCAACTTCAAATATAGCCACCGCGTTGACAAAAAACCTA<br>ATCGTCAGCTGATTAACGATACCCTGTATAGCACCCGCAAAAAGATAAC<br>AGCACCTATATTGTGCAGACCATTAAAGACATCTACGCCAAAGATAATAC<br>CACCCTGAAAAACAGTTCGACAAAAGCCCAGAAAAATTTCTGATGTATC<br>AGCATGATCCGCGTACCTTCGAAAAACTGGAAGTTATTATGAAACAGTAT | DNA sequence encoding P2H12 |

| SEQ ID NO | Sequence | Description |
|---|---|---|
| | GCCAACGAGAAAAATCCGCTGGCCAAATATCACGAAGAAACCGGTGAAT<br>ATCTGACCAAATATTCCAAGAAGAACAACGGTCCGATCGTTAAATCCCTG<br>AAATATATCGGTAATAAACTGGGCAGCCATCTGGATGTTACCCATCAGTT<br>TAAAAGCTCCACAAAGAAGCTGGTTAAACTGTCCATCAAACCGTATCGCT<br>TTGATGTGTATCTGACCGACAAAGGCTATAAATTCATTACCATCAGCTAT<br>CTGGACGTGCTGAAAAAAGACAACTATTATTATATCCCGGAACAGAAAT<br>ATGATAAACTGAAACTGGGTAAAGCCATCGATAAAAACGCCAAATTTAT<br>CGCCAGCTTCTACAAAAACGACCTGATTAAACTGGATGGCGAGATCTATA<br>AAATCATCGGTGTTAATAGCGACACCCGCAATATGATTGAGCTGGATCTG<br>CCGGATATTCGCTATAAAGAATATTGCGAACTGAACAACATTAAAGGCG<br>AACCGCGTATCAAAAAGACCATCGGCAAAAAGTGAATAGCATCGAGAA<br>ACTGACCACCGATGTTCTGGGTAATGTGTTTACCAATACCCAGTATACCA<br>AACCTCAGCTGCTGTTCAAACGCGGTAATGGTG | |
| 20 | ATGAACCAAAAGTTCATTCTGGGGCTCGATATCGGCATCACCTCCGTGGG<br>ATATGGTCTGATCGACTACGAGACTAAGAACATCATCGACGCTGGAGTGC<br>GACTGTTCCCGGAAGCGAACGTGGAGAACAACGAAGGCCGCAGATCCAA<br>GCGCGGGTCCAGAAGGCTCAAGAGGCGGAGGATCCATAGACTCGAGAGA<br>GTGAAGAAGCTCCTTGAAGATTACAATCTGTTGGACCAGTCACAGATTCC<br>CCAAAGCACCAACCCGTACGCATCAGAGTGAAGGGCCTGTCAGAAGCA<br>CTGTCGAAAGATGAACTGGTCATTGCCCTGCTGCATATTGCCAAACGGCG<br>CGGAATCCATAACATCAACGTGTCGAGCGAAGATGAGGACGCGTCCAAC<br>GAACTGTCAACCAAGGAACAGATCAACCGGAACAACAAACTGCTGAAGG<br>ACAAATACGTCTGCGAGGTGCAGCTTCAACGGCTGAAAGAGGGACAGAT<br>CAGGGGAGAGAAAACCGGTTCAAGACCACCGACATCCTTAAGGAGATC<br>GACCAACTCCTGAAAGTGCAGAAGGACTATCACAACCTCGACATTGATTT<br>TATCAACCAGTACAAGGAGATTGTGGAAACTCGGAGGGAGTACTTCGAG<br>GGACCTGGAAAGGGATCCCCTTATGGCTGGGAAGGGGACCCCAAGGCTT<br>GGTACGAAACCCTGATGGGCCATTGCACTTACTTTCCGGATGAACTCCGG<br>TCCGTGAAGTACGCTTACTCTGCCGACCTGTTCAATGCACTCAACGACCTT<br>AACAACTTGGTGATCCAACGCGATGGTCTTTCCAAGTTGGAGTACCACGA<br>AAAGTACCACATCATCGAGACGTGTTCAAGCAGAAAAAGAAGCCAACT<br>CTGAAGCAGATTGCCAACGAAATTAACGTGAACCCCGAGGATATCAAGG<br>GATACCGGATTACCAAGTCCGGCAAACCAGAGTTCACCTCATTCAAGCTG<br>TTTCACGATCTGAAGAAGGTCGTGAAGGACCACGCCATCCTGGATGACAT<br>TGATCTTCTGAACCAGATTGCTGAGATCCTGACCATCTACCAGGACAAGG<br>ACTCGATTGTGGCCGAACTGGGACAGCTCGAGTACCTGATGTCCGAAGCC<br>GATAAGCAGTCCATCAGCGAACTCACCGGTTACACCGGTACCCACTCCTT<br>GTCCCTTAAGTGCATGAACATGATCATTGACGAACTGTGGCACTCCAGCA<br>TGAACCAGATGGAGGTGTTCACCTACTTGAACATGCGCCCGAAGAAGTAC<br>GAGCTGAAGGGCTACCAGCGCATACCCACGGACATGATCGACGACGCCA<br>TCCTCTCACCGGTGGTCAAGCGCACCTTCATTCAATCTATCAACGTGATCA<br>ACAAGGTCATCGAGAAGTACGGCATTCCTGAGGATATCATCATCGAGCTG<br>GCTCGGGAGAACAACTCAGACGATAGGAAGAAGTTCATTAACAACCTCC<br>AGAAAAAGAACGAGGCCACTCGCAAGCGGATTAATGAGATCATCGGTCA<br>GACCGGGAACCAGAACGCCAAGCGGATCGTGGAAAAGATTCGGCTCCAC<br>GACCAACAGGAGGGAAAGTGTCTGTACTCGCTGGAGTCCATTCCCCTGGA<br>GGACCTCCTGAACAACCCAAACCACTACGAGGTCGATCACATAATCCCCC<br>GCAGCGTGTCATTCGACAACTCCTACCATAACAAGGTCCTCGTGAAGCAG<br>TCGGAGAATAGCAAGAAGTCGAACCTGACTCCGTACCAGTACTTCAACTC<br>CGGCAAATCCAAGCTGTCCTACAATCAGTTCAAACAGCACATTCTCAACC<br>TGTCCAAGAGCCAGGACAGGATTTCGAAGAAGAAGAAGGAATACCTTCT<br>CGAGGAACGGGATATCAATAAGTTCGAGGTGCAGAAGGAGTTTATCAAT<br>AGAAACCTGGTGGACACTCGCTATGCCACCCGCGAACTGACCAACTACCT<br>GAAGGCGTACTTCTCCGCCAACAACATGAACGTGAAGGTCAAAACTATTA<br>ACGGCAGCTTCACCGACTATCTGCGCAAGGTCTGGAAGTTCAAGAAGGA<br>ACGCAACCACGGTTACAAGCACCACGCGGAAGATGCGCTGATTATCGCC<br>AACGCTGACTTCCTGTTCAAGGAAAACAAGAAGCTCAAGGCCGTGAACT<br>CAGTGCTCGAGAAGCCTGAAATCGAGACTAAGCAGCTGGACATCCAGGT<br>CGATTCGGAAGATAACTACTCCGAAATGTTCATCATCCCTAAGCAAGTGC<br>AGGACATCAAGGACTTCAGGAATTTCAAGTACAGCCATCGCGTGGACAA<br>GAAGCCAAACAGACAGCTGATCAACGATACACTGTATTCCACCCGGAAG<br>AAGGACAACTCCACCTACATCGTCCAAACCATTAAGGACATCTACGCAAA<br>GGACAACACCACGCTTAAGAAGCAGTTCGACAAGAGCCCCGAAAAGTTC<br>CTCATGTACCAGCACGACCCCAGAACCTTCGAGAAGCTTGAAGTGATCAT<br>GAAGCAGTACGCCAACGAAAAGAACCCACTGGCTAAGTACCACGAGGAA<br>ACCGGCGAATACCTGACCAAGTACTCCAAAAAGAACAACGGACCGATCG<br>TCAAGTCCCTGAAGTACATTGGGAACAAGCTCGGCTCGCACCTCGATGTG<br>ACCCACCAGTTCAAGTCCTCGACCAAAAAGCTCGTGAAGCTGTCCATCAA<br>GCCGTACCGGTTCGACGTGTACCTGACTGACAAGGGATATAAGTTCATCA<br>CCATTTCCTACCTCGACGTGTTGAAGAAGGATAACTACTACTACATTCCG<br>GAACAGAAGTACGACAAGCTCAAGCTCGGAAAGGCCATCGACAAAAATG<br>CGAAGTTCATCGCGAGCTTCTACAAGAATGACTTGATCAAGCTGGATGGC | Codon-optimized P2H12 polynucleotide |

| SEQ ID NO | Sequence | Description |
|---|---|---|
| | GAAATCTACAAGATCATCGGGGTCAACTCCGATACCCGCAACATGATTGA<br>GCTGGATCTGCCCGACATTCGGTACAAGGAATACTGCGAGCTGAACAAC<br>ATCAAGGGAGAACCGCGGATCAAGAAAACCATCGGAAAGAAAGTGAAC<br>AGCATCGAGAAACTGACTACTGACGTCCTGGGAAACGTGTTCACCAACAC<br>ACAATACACCAAACCCCAGCTGCTGTTTAAGCGCGGGAAC | |
| 21 | ATGAACCAGAAATTTATCCTGGGTCTGGATATTGGTATTACCAGCGTTGG<br>TTATGGCCTGATTGATTACGAAACCAAAACCATTATTGATGCCGGTGTTC<br>GTCTGTTTCCGGAAGCAAATGTTGAAATAATGAAGGTCGTCGTAGCAAA<br>CGTGGTAGCCGTCGTCTGAAACGTCGTCGTATTCATCGTCTGGATCGTGTT<br>AAACATCTGCTGGCAGAATATGATCTGCTGGATCTGACCAATATTCCGAA<br>AAGCCACCAATCCGTATCAGACCCGTGTTAAAGGTCTGAATGAAAAGCTG<br>AGCAAAGATGAACTGGTTATTGCACTGCTGCATATTGCAAAACGCCGTGG<br>CATTCATAACGTTGATGTTGCAGCAGATAAAGAAGAAACCGCAAGCGAT<br>AGCCCTGAGCACCAAAGATCAGATTAACAAAAACGCCAAATTTCTGGAAA<br>GCCGCTATGTTTGTGAACTGCAGAAAGAACGTCTGGAAAATGAAGGTCAT<br>GTTCGTGGTGTTGAAAATCGCTTTCTGACGAAAGATATTGTGCGTGAGGC<br>CAAAAAAATCATCGATACCCAGATGCAGTATTACCCGGAAATTGATGAA<br>ACCTTCAAAGAGAAATATATCAGCCTGGTTGAAACCCGTCGCGAATATTT<br>TGAAGGTCCGGGTAAAGGTAGCCCGTTTGGTTGGGAAGGTAATATCAAG<br>AAATGGTTTGAGCAGATGATGGGCCACTGTACCTATTTTCCAGAAGAACT<br>GCGTAGCGTCAAATATAGCTATTCAGCCGAACTGTTTAACGCCCTGAATG<br>ATCTGAATAATCTGGTGATTACCCGTGATGAAGATGCCAAACTGAATTAT<br>GGTGAGAAATTCCAGATCATCGAAAACGTGTTCAAACAGAAGAAAACAC<br>CGAACCTGAAACAAATCGCCATTGAAATTGGTGTGCATGAAACCGAAAT<br>CAAAGGTTATCGTGTGAACAAAAGCGGTACACCGGAATTTACCGAATTTA<br>AACTGTATCATGACCTGAAAAGCATCGTGTTCGATAAAAGCATTCTGGAA<br>AATGAAGCCATCCTGGATCAGATTGCAGAAATTCTGACCATCTATCAGGA<br>TGAGCAGAGCATTAAAGAGGAACTGAATAAACTGCCGGAAATACTGAAC<br>GAACAGGATAAAGCAGAAATCGCCAAACTGATTGGTTATAATGGCACCC<br>ATCGTCTGAGCCTGAAATGTATTCACCTGATTAATGAAGAACTGTGGCAG<br>ACCAGCCGTAATCAGATGGAAATTTTCAACTACCTGAACATCAAACCGAA<br>CAAAGTGGATCTGAGTGAGCAGAACAAAATCCCGAAAGATATGGTGAAC<br>GACTTTATTCTGAGTCCGGTTGTGAAACGCACCTTTATTCAGAGCATCAA<br>CGTGATCAACAAAGTGATCGAGAAATATGGCATCCCCGAAGATATCATTA<br>TCGAACTGGCACGTGAAAATAACTCCGATGATCGCAAAAAGTTCATCAAC<br>AACCTGCAGAAAAAGAATGAAGCAACCCGCAAACGCATTAACGAAATTA<br>TTGGTCAGACCGGTAATCAGAATGCCAAACGTATTGTGGAAAAAATCCGT<br>CTGCATGATCAGCAAGAGGGTAAATGTCTGTATAGCCTGAAAGATATCCC<br>GCTGGAAGATCTGCTGCGCAATCCGAACAATTATGATATCGACCATATTA<br>TTCCGCGAAGCGTGAGCTTTGATGATAGCATGCATAACAAAGTTCTGGTT<br>CGTCGCGAACAGAATGCCAAAAGAATAATCAGACCCCGTATCAGTATC<br>TGACCAGTGGTTATGCAGATATCAAATACAGCGTGTTTAAGCAGCATGTT<br>CTGAATCTGGCCGAAAATAAAGATCGCATGACCAAAAAAAAGCGCGAGT<br>ATCTGCTGGAAGAACGCGACATTAACAAATTTGAAGTGCAGAAAGAATT<br>TATCAACCGCAACCTGGTTGATACCCGTTATGCAACCCGTGAACTGACCA<br>ATTATCTGAAAGCATATTTCAGCGCCAACAACATGAACGTGAAAGTGAA<br>AACGATTAACGGCAGCTTTACCGATTATCTGCGTAAAGTGTGGAAATTCA<br>AAAAAGAACGCAACCACGGCTATAAACATCATGCCGAAGATGCCCTGAT<br>TATTGCAAATGCAGATTTCCTGTTTAAAGAAAACAAAAACTGAAAGCCG<br>TCAACAGCGTGCTGGAAAACCGGAAATTGAGACAAAACAGCTGGACAT<br>TCAGGTTGATAGCGAAGATAATTACAGCGAAATGTTTATCATCCCGAAAC<br>AGGTGCAGGATATCAAAGATTTTCGCAACTTCAAATATAGCCACCGCGTT<br>GACAAAAAACCTAATCGTCAGCTGATTAACGATACCCTGTATAGCACCCG<br>CAAAAAAGATAACAGCACCTATATTGTGCAGACCATTAAAGACATCTAC<br>GCCAAAGATAATACCACCCTGAAAAACAGTTCGACAAAAGCCCAGAAA<br>AATTTCTGATGTATCAGCATGATCCGCGTACCTTCGAAAAACTGGAAGTT<br>ATTATGAAACAGTATGCCAACGAGAAAAATCCGCTGGCCAAATATCACG<br>AAGAAACCGGTGAATATCTGACCAAATATTCCAAGAAGAACAACGGTCC<br>GATCGTTAAATCCCTGAAATATATCGGTAATAAACTGGGCAGCATCTGG<br>ATGTTACCCATCAGTTTAAAAGCTCCACAAAGAAGCTGGTTAAACTGTCC<br>ATCAAACCGTATCGCTTTGATGTGTATCTGACCGACAAAGGCTATAAATT<br>CATTACCATCAGCTATCTGGACGTGCTGAAAAAAGACAACTATTATTATA<br>TCCCGGAACAGAAATATGATAAACTGAAACTGGGTAAAGCCATCGATAA<br>AAACGCCAAATTTATCGCCAGCTTCTACAAAAACGACCTGATTAAACTGG<br>ATGGCGAGATCTATAAAATCATCGGTGTTAATAGCGACACCCGCAATATG<br>ATTGAGCTGGATCTGCCGGATATTCGCTATAAAGAATATTGCGAACTGAA<br>CAACATTAAAGGCGAACCGCGTATCAAAAAGACCATCGGCAAAAAGTG<br>AATAGCATCGAGAAACTGACCACCGATGTTCTGGGTAATGTGTTTACCAA<br>TACCCAGTATACCAAACCTCAGCTGCTGTTCAAACGCGGTAAT | DNA sequence encoding E2 |

-continued

SEQUENCE LISTING

| SEQ ID NO | Sequence | Description |
|---|---|---|
| 22 | ATGAACCAAAAGTTCATTCTGGGGCTCGATATCGGCATCACCTCCGTGGG<br>ATATGGTCTGATCGACTACGAGACTAAGAACATCATCGACGCTGGAGTGC<br>GACTGTTCCCGGAAGCGAACGTGGAGAACAACGAAGGCCGCAGATCCAA<br>GCGCGGGTCCAGAAGGCTCAAGAGGCGGAGGATCCATAGACTCGACAGA<br>GTGAAGCACCTCCTTGCCGAATACGATCTGTTGGACCTTACCAACATTCC<br>CAAGAGCACCAACCCGTACCAAACCAGAGTGAAGGGCCTGAACGAAAAG<br>CTGTCGAAAGATGAACTGGTCATTGCCCTGCTGCATATTGCCAAACGGCG<br>CGGAATCCATAACGTGGACGTGGCCGCTGACAAGGAAGAGACTGCGTCC<br>GACTCGCTGTCAACCAAGGACCAGATCAACAAGAACGCCAAATTCCTGG<br>AAAGCCGCTACGTCTGCGAGCTTCAAAAAGAACGGCTGGAGAACGAGGG<br>ACACGTCAGGGGAGTGGAGAACCGGTTCCTGACCAAGGACATCGTGCGG<br>GAAGCCAAGAAGATCATCGACACCCAAATGCAGTATTATCCGGAAATTG<br>ATGAAACTTTTAAGGAGAAGTACATTTCCCTGGTGGAAACTCGGAGGGA<br>GTACTTCGAGGGACCTGGAAAGGGATCCCCTTTCGGCTGGGAAGGGAAC<br>ATTAAGAAGTGGTTTGAACAGATGATGGGCCATTGCACTTACTTTCCGGA<br>AGAACTCCGGTCCGTGAAGTACTCATACTCTGCCGAGCTGTTCAATGCAC<br>TCAACGACCTTAACAACTTGGTGATCACCCGCGATGAAGATGCCAAGTTG<br>AACTACGGAGAAAAGTTCCAGATCATCGAGAACGTGTTCAAGCAGAAAA<br>AGACCCCAAATCTGAAGCAGATTGCCATCGAAATTGGCGTGCACGAGAC<br>TGAGATCAAGGGATACCGGGTCAACAAGTCCGGCACGCCAGAGTTCACC<br>GAGTTCAAGCTGTACCACGATCTGAAGTCGATCGTGTTTGACAAGTCCAT<br>CCTGGAAAACGAAGCCATTCTGGACCAGATTGCTGAGATCCTGACCATCT<br>ACCAGGACGAGCAATCGATTAAGGAAGAACTGAACAAGCTCCCCGAGAT<br>TCTGAACGAACAGGATAAGGCCGAGATCGCGAAGCTCATTGGTTACAAT<br>GGTACCCACCGCTTGTCCCTTAAGTGCATCCATCTGATCAATGAGGAACT<br>GTGGCAGACCAGCCGGAACCAGATGGAGATCTTCAATTACTTGAACATCA<br>AGCCGAACAAGGTGGACCTGTCCGAACAGAACAAGATACCCAAGGACAT<br>GGTCAACGACTTTATCCTCTCACCGGTGGTCAAGCGCACCTTCATTCAATC<br>TATCAACGTGATCAACAAGGTCATCGAGAAGTACGGCATTCCTGAGGATA<br>TCATCATCGAGCTGGCTCGGGAGAACAACTCAGACGATAGGAAGAAGTT<br>CATTAACAACCTCCAGAAAAAGAACGAGGCCACTCGCAAGCGGATTAAT<br>GAGATCATCGGTCAGACCGGGAACCAGAACGCCAAGCGGATCGTGGAAA<br>AGATTCGGCTCCACGACCAACAGGAGGGAAAGTGTCTGTACTCGCTGAA<br>GGACATTCCCCTGGAGGACCTCCTGAGGAACCCAAACAACTACGACATC<br>GATCACATAATCCCCCGCAGCGTGTCATTCGACGATTCCATGCATAACAA<br>GGTCCTCGTGCGGAGAGAGCAGAATGCCAAGAAGAACAACCAGACTCCG<br>TACCAGTACCTGACGTCCGGCTACGCAGACATCAAGTACTCAGTGTTCAA<br>ACAGCACGTGCTCAACCTGGCCGAGAACAAGGACAGGATGACCAAGAAG<br>AAGCGCGAATACCTTCTCGAGGAACGGGATATCAATAAGTTCGAGGTGC<br>AGAAGGAGTTTATCAATAGAAACCTGGTGGACACTCGCTATGCCACCCGC<br>GAACTGACCAACTACCTGAAGGCGTACTTCTCCGCCAACAACATGAACGT<br>GAAGGTCAAAACTATTAACGGCAGCTTCACCGACTATCTGCGCAAGGTCT<br>GGAAGTTCAAGAAGGAACGCAACCACGGTTACAAGCACCACGCGGAAGA<br>TGCGCTGATTATCGCCAACGCTGACTTCCTGTTCAAGGAAAACAAGAAGC<br>TCAAGGCCGTGAACTCAGTGCTCGAGAAGCCTGAAATCGAGACTAAGCA<br>GCTGGACATCCAGGTCGATTCGGAAGATAACTACTCCGAAATGTTCATCA<br>TCCCTAAGCAAGTGCAGGACATCAAGGACTTCAGGAATTTCAAGTACAGC<br>CATCGCGTGGACAAGAAGCCAAACAGACAGCTGATCAACGATACACTGT<br>ATTCCACCCGGAAGAAGGACAACTCCACCTACATCGTCCAAACCATTAAG<br>GACATCTACGCAAAGGACAACACCACGCTTAAGAAGCAGTTCGACAAGA<br>GCCCCGAAAAGTTCCTCATGTACCAGCACGACCCCAGAACCTTCGAGAAG<br>CTTGAAGTGATCATGAAGCAGTACGCCAACGAAAAGAACCCACTGGCTA<br>AGTACCACGAGGAAACCGGCGAATACCTGACCAAGTACTCCAAAAAGAA<br>CAACGGACCGATCGTCAAGTCCCTGAAGTACATTGGGAACAAGCTCGGCT<br>CGCACCTCGATGTGACCCACCAGTTCAAGTCCTCGACCAAAAAGCTCGTG<br>AAGCTGTCCATCAAGCCGTACCGGTTCGACGTGTACCTGACTGACAAGGG<br>ATATAAGTTCATCACCATTTCCTACCTCGACGTGTTGAAGAAGGATAACT<br>ACTACTACATTCCGGAACAGAAGTACGACAAGCTCAAGCTCGGAAAGGC<br>CATCGACAAAAATGCGAAGTTCATCGCGAGCTTCTACAAGAATGACTTGA<br>TCAAGCTGGATGGCGAAATCTACAAGATCATCGGGGTCAACTCCGATACC<br>CGCAACATGATTGAGCTGGATCTGCCCGACATTCGGTACAAGGAATACTG<br>CGAGCTGAACAACATCAAGGGAGAACCGCGGATCAAGAAAACCATCGGA<br>AAGAAAGTGAACAGCATCGAGAAACTGACTACTGACGTCCTGGGAAACG<br>TGTTCACCAACACACAATACACCAAACCCCAGCTGCTGTTTAAGCGCGGG<br>AAC | Codon-optimized E2 polynucleotide |
| 23 | ATGAACCAGAAATTTATCCTGGGTCTGGATATTGGTATTACCAGCGTTGG<br>TTATGGCCTGATTGATTACGAAACCAAAAACATTATTGATGCCGGTGTTC<br>GTCTGTTTCCGGAAGCAAATGTTGAAAATAATGAAGGTCGTCGTAGCAAA<br>CGTGGTAGCCGTCGTCTGAAACGTCGTCGTATTCATCGTCTGGATCGTGTT<br>AAACATCTGCTGGCAGAATATGATCTGCTGGATCTGACCAATATTCCGAA<br>AAGCACCAATCCGTATCAGACCCGTGTTAAAGGTCTGAATGAAAAGCTG<br>AGCAAAGATGAACTGGTTATTGCACTGCTGCATATTGCAAAACGCCGTGG | DNA sequence encoding for E2 + K741D + L743K |

| SEQ ID NO | Sequence | Description |
|---|---|---|
| | CATTCATAACGTTGATGTTGCAGCAGATAAAGAAGAAACCGCAAGCGAT<br>AGCCTGAGCACCAAAGATCAGATTAACAAAAACGCCAAATTTCTGGAAA<br>GCCGCTATGTTTGTGAACTGCAGAAAGAACGTCTGGAAAATGAAGGTCAT<br>GTTCGTGGTGTTGAAAATCGCTTTCTGACGAAAGATATTGTGCGTGAGGC<br>CAAAAAAATCATCGATACCCAGATGCAGTATTACCCGGAAATTGATGAA<br>ACCTTCAAAGAGAAATATATCAGCCTGGTTGAAACCCGTCGCGAATATTT<br>TGAAGGTCCGGGTAAAGGTAGCCCGTTTGGTTGGGAAGGTAATATCAAG<br>AAATGGTTTGAGCAGATGATGGGCCACTGTACCTATTTTCCAGAAGAACT<br>GCGTAGCGTCAAATATAGCTATTCAGCCGAACTGTTTAACGCCCTGAATG<br>ATCTGAATAATCTGGTGATTACCCGTGATGAAGATGCCAAACTGAATTAT<br>GGTGAGAAATTCCAGATCATCGAAAACGTGTTCAAACAGAAGAAAACAC<br>CGAACCTGAAACAAATCGCCATTGAAATTGGTGTGCATGAAACCGAAAT<br>CAAAGGTTATCGTGTGAACAAAAGCGGTACACCGGAATTTACCGAATTTA<br>AACTGTATCATGACCTGAAAAGCATCGTGTTCGATAAAAGCATTCTGGAA<br>AATGAAGCCATCCTGGATCAGATTGCAGAAATTCTGACCATCTATCAGGA<br>TGAGCAGAGCATTAAAGAGGAACTGAATAAACTGCCGGAAATACTGAAC<br>GAACAGGATAAAGCAGAAATCGCCAAACTGATTGGTTATAATGGCACCC<br>ATCGTCTGAGCCTGAATGTATTCACCTGATTAATGAAGAACTGTGGCAG<br>ACCAGCCGTAATCAGATGGAAATTTTCAACTACCTGAACATCAAACCGAA<br>CAAAGTGGATCTGAGTGAGCAGAACAAAATCCCGAAAGATATGGTGAAC<br>GACTTTATTCTGAGTCCGGTTGTGAAACGCACCTTTATTCAGAGCATCAA<br>CGTGATCAACAAAGTGATCGAGAAATATGGCATCCCCGAAGATATCATTA<br>TCGAACTGGCACGTGAAAATAACTCCGATGATCGCAAAAAGTTCATCAAC<br>AACCTGCAGAAAAAGAATGAAGCAACCCGCAAACGCATTAACGAAATTA<br>TTGGTCAGACCGGTAATCAGAATGCCAAACGTATTGTGGAAAAAATCCGT<br>CTGCATGATCAGCAAGAGGGTAAATGTCTGTATAGCCTGAAAGATATCCC<br>GCTGGAAGATCTGCTGCGCAATCCGAACAATTATGATATCGACCATATTA<br>TTCCGCGAAGCGTGAGCTTTGATGATAGCATGCATAACAAAGTTCTGGTT<br>CGTCGCGAACAGAATGCCAAAAAGAATAATCAGACCCCGTATCAGTATC<br>TGACCAGTGGTTATGCAGATATCAAATACAGCGTGTTTAAGCAGCATGTT<br>CTGAATCTGGCCGAAAATAAAGATCGCATGACCAAAAAAAAGCGCGAGT<br>ATCTGCTGGAAGAACGCGACATTAACAAATTTGAAGTGCAGAAAGAATT<br>TATCAACCGCAACCTGGTTGATACCCGTTATGCAACCCGTGAACTGACCA<br>ATTATCTGAAAGCATATTTCAGCGCCAACAACATGAACGTGAAAGTGAA<br>AACGATTAACGGCAGCTTTACCGATTATCTGCGTAAAGTGTGGAAATTCA<br>AAAAAGAACGCAACCACGGCTATAAACATCATGCCGAAGATGCCCTGAT<br>TATTGCAAATGCAGATTTCCTGTTTAAAGAAAACAAAAAACTGAAAGCCG<br>TCAACAGCGTGCTGGAAAAACCGGAAATTGAGACAGATCAGAAAGACAT<br>TCAGGTTGATAGCGAAGATAATTACAGCGAAATGTTTATCATCCCGAAAC<br>AGGTGCAGGATATCAAAGATTTTCGCAACTTCAAATATAGCCACCGCGTT<br>GACAAAAAACCTAATCGTCAGCTGATTAACGATACCCTGTATAGCACCCG<br>CAAAAAAGATAACAGCACCTATATTGTGCAGACCATTAAAGACATCTAC<br>GCCAAAGATAATACCACCCTGAAAAAACAGTTCGACAAAAGCCCAGAAA<br>AATTTCTGATGTATCAGCATGATCCGCGTACCTTCGAAAAACTGGAAGTT<br>ATTATGAAACAGTATGCCAACGAGAAAAATCCGCTGGCCAAATATCACG<br>AAGAAACCGGTGAATATCTGACCAAATATTCCAAGAAGAACAACGGTCC<br>GATCGTTAAATCCCTGAAATATATCGGTAATAAACTGGGCAGCCATCTGG<br>ATGTTACCCATCAGTTTAAAAGCTCCACAAAGAAGCTGGTTAAACTGTCC<br>ATCAAACCGTATCGCTTTGATGTGTATCTGACCGACAAAGGCTATAAATT<br>CATTACCATCAGCTATCTGGACGTGCTGAAAAAAGACAACTATTATTATA<br>TCCCGGAACAGAAATATGATAAACTGAAACTGGGTAAAGCCATCGATAA<br>AAACGCCAAATTTATCGCCAGCTTCTACAAAAACGACCTGATTAAACTGG<br>ATGGCGAGATCTATAAAAATCATCGGTGTTAATAGCGACACCCGCAATATG<br>ATTGAGCTGGATCTGCCGGATATTCGCTATAAAGAATATTGCGAACTGAA<br>CAACATTAAAGGCGAACCGCGTATCAAAAAGACCATCGGCAAAAAGTG<br>AATAGCATCGAGAAACTGACCACCGATGTTCTGGGTAATGTGTTTACCAA<br>TACCCAGTATACCAAACCTCAGCTGCTGTTCAAACGCGGTAAT | |
| 24 | ATGAACCAGAAATTTATCCTGGGTCTGGATATTGGTATTACCAGCGTTGG<br>TTATGGCCTGATTGATTACGAAACCAAAAACATTATTGATGCCGGTGTTC<br>GTCTGTTTCCGGAAGCAAATGTTGAAAATAATGAAGGTCGTCGTAGCAAA<br>CGTGGTAGCCGTCGTCTGAAACGTCGTCGTATTCATCGTCTGGATCGTGTT<br>AAACATCTGCTGGCAGAATATGATCTGCTGGATCTGACCAATATTCCGAA<br>AAGCACCAATCCGTATCAGACCCGTGTTAAAGGTCTGAATGAAAAGCTG<br>AGCAAAGATGAACTGGTTATTGCACTGCTGCATATTGCAAAACGCCGTGG<br>CATTCATAACGTTGATGTTGCAGCAGATAAAGAAGAAACCGCAAGCGAT<br>AGCCTGAGCACCAAAGATCAGATTAACAAAAACGCCAAATTTCTGGAAA<br>GCCGCTATGTTTGTGAACTGCAGAAAGAACGTCTGGAAAATGAAGGTCAT<br>GTTCGTGGTGTTGAAAATCGCTTTCTGACGAAAGATATTGTGCGTGAGGC<br>CAAAAAAATCATCGATACCCAGATGCAGTATTACCCGGAAATTGATGAA<br>ACCTTCAAAGAGAAATATATCAGCCTGGTTGAAACCCGTCGCGAATATTT<br>TGAAGGTCCGGGTAAAGGTAGCCCGTTTGGTTGGGAAGGTAATATCAAG<br>AAATGGTTTGAGCAGATGATGGGCCACTGTACCTATTTTCCAGAAGAACT | DNA sequence encoding for E2 + S670T + N

| SEQ ID NO | Sequence | Description |
|---|---|---|
| | GCGTAGCGTCAAATATAGCTATTCAGCCGAACTGTTTAACGCCCTGAATG<br>ATCTGAATAATCTGGTGATTACCCGTGATGAAGATGCCAAACTGAATTAT<br>GGTGAGAAATTCCAGATCATCGAAAACGTGTTCAAACAGAAGAAAACAC<br>CGAACCTGAAACAAATCGCCATTGAAATTGGTGTGCATGAAACCGAAAT<br>CAAAGGTTATCGTGTGAACAAAGCGGTACACCGGAATTTACCGAATTTA<br>AACTGTATCATGACCTGAAAAGCATCGTGTTCGATAAAAGCATTCTGGAA<br>AATGAAGCCATCCTGGATCAGATTGCAGAAATTCTGACCATCTATCAGGA<br>TGAGCAGAGCATTAAAGAGGAACTGAATAAACTGCCGGAAATACTGAAC<br>GAACAGGATAAAGCAGAAATCGCCAAACTGATTGGTTATAATGGCACCC<br>ATCGTCTGAGCCTGAAATGTATTCACCTGATTAATGAAGAACTGTGGCAG<br>ACCAGCCGTAATCAGATGGAAATTTTCAACTACCTGAACATCAAACCGAA<br>CAAAGTGGATCTGAGTGAGCAGAACAAAATCCCGAAAGATATGGTGAAC<br>GACTTTATTCTGAGTCCGGTTGTGAAACGCACCTTTATTCAGAGCATCAA<br>CGTGATCAACAAAGTGATCGAGAAATATGGCATCCCCGAAGATATCATTA<br>TCGAACTGGCACGTGAAAATAACTCCGATGATCGCAAAAAGTTCATCAAC<br>AACCTGCAGAAAAAGAATGAAGCAACCCGCAAACGCATTAACGAATTA<br>TTGGTCAGACCGGTAATCAGAATGCCAAACGTATTGTGGAAAAAATCCGT<br>CTGCATGATCAGCAAGAGGGTAAATGTCTGTATAGCCTGAAAGATATCCC<br>GCTGGAAGATCTGCTGCGCAATCCGAACAATTATGATATCGACCATATTA<br>TTCCGCGAAGCGTGAGCTTTGATGATAGCATGCATAACAAAGTTCTGGTT<br>CGTCGCGAACAGAATGCCAAAAAGAATAATCAGACCCCGTATCAGTATC<br>TGACCAGTGGTTATGCAGATATCAAATACAGCGTGTTTAAGCAGCATGTT<br>CTGAATCTGGCCGAAAATAAAGATCGCATGACCAAAAAAAAGCGCGAGT<br>ATCTGCTGGAAGAACGCGACATTAACAAATTTGAAGTGCAGAAAGAATT<br>TATCAACCGCAACCTGGTTGATACCCGTTATGCAACCCGTGAACTGACCA<br>ATTATCTGAAAGCATATTTCACCGCCAACAACATGGATGTGAAAGTGAAA<br>ACGATTAACGGCAGCTTTACCGATTATCTGCGTAAAGTGTGGAAATTCAA<br>AAAAGAACGCAACCACGGCTATAAACATCATGCCGAAGATGCCCTGATT<br>ATTGCAAATGCAGATTTCCTGTTTAAAGAAAACAAAAAACTGAAAGCCGT<br>CAACAGCGTGCTGGAAAAACCGGAAATTGAGACAAAACAGCTGGACATT<br>CAGGTTGATAGCGAAGATAATTACAGCGAAATGTTTATCATCCCGAAACA<br>GGTGCAGGATATCAAAGATTTTCGCAACTTCAAATATAGCCACCGCGTTG<br>ACAAAAAACCTAATCGTCAGCTGATTAACGATACCCTGTATAGCACCCGC<br>AAAAAAGATAACAGCACCTATATTGTGCAGACCATTAAAGACATCTACG<br>CCAAAGATAATACCACCCTGAAAAAACAGTTCGACAAAAGCCCAGAAAA<br>ATTTCTGATGTATCAGCATGATCGCGTACCTTCGAAAAACTGGAAGTTA<br>TTATGAAACAGTATGCCAACGAGAAAAATCCGCTGGCCAAATATCACGA<br>AGAAACCGGTGAATATCTGACCAAATATTCCAAGAAGAACAACGGTCCG<br>ATCGTTAAATCCCTGAAATATATCGGTAATAAACTGGGCAGCCATCTGGA<br>TGTTACCCATCAGTTTAAAAGCTCCACAAAGAAGCTGGTTAAACTGTCCA<br>TCAAACCGTATCGCTTTGATGTGTATCTGACCGACAAAGGCTATAAATTC<br>ATTACCATCAGCTATCTGGACGTGCTGAAAAAAGACAACTATTATTATAT<br>CCCGGAACAGAAATATGATAAACTGAAACTGGGTAAAGCCATCGATAAA<br>AACGCCAAATTTATCGCCAGCTTCTACAAAAACGACCTGATTAAACTGGA<br>TGGCGAGATCTATAAAATCATCGGTGTTAATAGCGACACCCGCAATATGA<br>TTGAGCTGGATCTGCCGGATATTCGCTATAAAGAATATTGCGAACTGAAC<br>AACATTAAAGGCGAACCGCGTATCAAAAAGACCATCGGCAAAAAGTGA<br>ATAGCATCGAGAAACTGACCACCGATGTTCTGGGTAATGTGTTTACCAAT<br>ACCCAGTATACCAAACCTCAGCTGCTGTTCAAACGCGGTAAT | |
| 25 | ATGAACCAGAAATTTATCCTGGGTCTGGATATTGGTATTACCAGCGTTGG<br>TTATGGCCTGATTGATTACGAAACCAAAACATTATTGATGCCGGTGTTC<br>GTCTGTTTCCGGAAGCAAATGTTGAAAATAATGAAGGTCGTCGTAGCAAA<br>CGTGGTAGCCGTCGTCTGAAACGTCGTCGTATTCATCGTCTGGATCGTGTT<br>AAACATCTGCTGGCAGAATATGATCTGCTGGATCTGACCAATATTCCGAA<br>AAGCACCAATCCGTATCAGACCCGTGTTAAAGGTCTGAATGAAAAGCTG<br>AGCAAAGATGAACTGGTTATTGCACTGCTGCATATTGCAAAACGCCGTGG<br>CATTCATAACGTTGATGTTGCAGCAGATAAAGAAGAAACCGCAAGCGAT<br>AGCCTGAGCACCAAAGATCAGATTAACAAAAACGCCAAATTTCTGGAAA<br>GCCGCTATGTTTGTGAACTGCAGAAAGAACGTCTGGAAAATGAAGGTCAT<br>GTTCGTGGTGTTGAAAATCGCTTTCTGACGAAAGATATTGTGCGTGAGGC<br>CAAAAAAATCATCGATACCCAGATGCAGTATTACCCGGAAATTGATGAA<br>ACCTTCAAAGAGAAATATATCAGCCTGGTTGAAACCCGTCGCGAATATTT<br>TGAAGGTCCGGGTAAAGGTAGCCCGTTTGGTTGGGAAGGTAATATCAAG<br>AAATGGTTTGAGCAGATGATGGGCCACTGTACCTATTTTCCAGAAGAACT<br>GCGTAGCGTCAAATATAGCTATTCAGCCGAACTGTTTAACGCCCTGAATG<br>ATCTGAATAATCTGGTGATTACCCGTGATGAAGATGCCAAACTGAATTAT<br>GGTGAGAAATTCCAGATCATCGAAAACGTGTTCAAACAGAAGAAAACAC<br>CGAACCTGAAACAAATCGCCATTGAAATTGGTGTGCATGAAACCGAAAT<br>CAAAGGTTATCGTGTGAACAAAGCGGTACACCGGAATTTACCGAATTTA<br>AACTGTATCATGACCTGAAAAGCATCGTGTTCGATAAAAGCATTCTGGAA<br>AATGAAGCCATCCTGGATCAGATTGCAGAAATTCTGACCATCTATCAGGA<br>TGAGCAGAGCATTAAAGAGGAACTGAATAAACTGCCGGAAATACTGAAC | DNA sequence encoding for E2 + K741N + L743N |

SEQUENCE LISTING

| SEQ ID NO | Sequence | Description |
|---|---|---|
| | GAACAGGATAAAGCAGAAATCGCCAAACTGATTGGTTATAATGGCACCC<br>ATCGTCTGAGCCTGAAATGTATTCACCTGATTAATGAAGAACTGTGGCAG<br>ACCAGCCGTAATCAGATGGAAATTTTCAACTACCTGAACATCAAACCGAA<br>CAAAGTGGATCTGAGTGAGCAGAACAAAATCCCGAAAGATATGGTGAAC<br>GACTTTATTCTGAGTCCGGTTGTGAAACGCACCTTTATTCAGAGCATCAA<br>CGTGATCAACAAAGTGATCGAGAAATATGGCATCCCCGAAGATATCATTA<br>TCGAACTGGCACGTGAAAATAACTCCGATGATCGCAAAAAGTTCATCAAC<br>AACCTGCAGAAAAAGAATGAAGCAACCCGCAAACGCATTAACGAAATTA<br>TTGGTCAGACCGGTAATCAGAATGCCAAACGTATTGTGGAAAAAATCCGT<br>CTGCATGATCAGCAAGAGGGTAAATGTCTGTATAGCCTGAAAGATATCCC<br>GCTGGAAGATCTGCTGCGCAATCCGAACAATTATGATATCGACCATATTA<br>TTCCGCGAAGCGTGAGCTTTGATGATAGCATGCATAACAAAGTTCTGGTT<br>CGTCGCGAACAGAATGCCAAAAAGAATAATCAGACCCCGTATCAGTATC<br>TGACCAGTGGTTATGCAGATATCAAATACAGCGTGTTTAAGCAGCATGTT<br>CTGAATCTGGCCGAAAATAAAGATCGCATGACCAAAAAAAGCGCGAGT<br>ATCTGCTGGAAGAACGCGACATTAACAAATTTGAAGTGCAGAAAGAATT<br>TATCAACCGCAACCTGGTTGATACCCGTTATGCAACCCGTGAACTGACCA<br>ATTATCTGAAAGCATATTTCAGCGCCAACAACATGAACGTGAAAGTGAA<br>AACGATTAACGGCAGCTTTACCGATTATCTGCGTAAAGTGTGGAAATTCA<br>AAAAGAACGCAACCACGGCTATAAACATCATGCCGAAGATGCCCTGAT<br>TATTGCAAATGCAGATTTCCTGTTTAAAGAAAACAAAAAACTGAAAGCCG<br>TCAACAGCGTGCTGGAAAAACCGGAAATTGAGACAAATCAGAATGACAT<br>TCAGGTTGATAGCGAAGATAATTACAGCGAAATGTTTATCATCCCGAAAC<br>AGGTGCAGGATATCAAAGATTTTCGCAACTTCAAATATAGCCACCGCGTT<br>GACAAAAAACCTAATCGTCAGCTGATTAACGATACCCTGTATAGCACCCG<br>CAAAAAGATAACAGCACCTATATTGTGCAGACCATTAAAGACATCTAC<br>GCCAAAGATAATACCACCCTGAAAAAACAGTTCGACAAAAGCCCAGAAA<br>AATTTCTGATGTATCAGCATGATCCGCGTACCTTCGAAAAACTGGAAGTT<br>ATTATGAAACAGTATGCCAACGAGAAAAATCCGCTGGCCAAATATCACG<br>AAGAAACCGGTGAATATCTGACCAAATATTCCAAGAAGAACAACGGTCC<br>GATCGTTAAATCCCTGAAATATATCGGTAATAAACTGGGCAGCCATCTGG<br>ATGTTACCCATCAGTTTAAAAGCTCCACAAAGAAGCTGGTTAAACTGTCC<br>ATCAAACCGTATCGCTTTGATGTGTATCTGACCGACAAAGGCTATAAATT<br>CATTACCATCAGCTATCTGGACGTGCTGAAAAAAGACAACTATTATTATA<br>TCCCGGAACAGAAATATGATAAACTGAAACTGGGTAAAGCCATCGATAA<br>AAACGCCAAATTTATCGCCAGCTTCTACAAAAACGACCTGATTAAACTGG<br>ATGGCGAGATCTATAAAATCATCGGTGTTAATAGCGACACCCGCAATATG<br>ATTGAGCTGGATCTGCCGGATATTCGCTATAAAGAATATTGCGAACTGAA<br>CAACATTAAAGGCGAACCGCGTATCAAAAAGACCATCGGCAAAAAGTG<br>AATAGCATCGAGAAACTGACCACCGATGTTCTGGGTAATGTGTTTACCAA<br>TACCCAGTATACCAAACCTCAGCTGCTGTTCAAACGCGGTAAT | |
| 26 | ATGAACCAGAAATTTATCCTGGGTCTGGATATTGGTATTACCAGCGTTGG<br>TTATGGCCTGATTGATTACGAAACCAAAACATTATTGATGCCGGTGTTC<br>GTCTGTTTCCGGAAGCAAATGTTGAAAATAATGAAGGTCGTCGTAGCCAA<br>CGTGGTAGCCGTCGTCTGAAACGTCGTCGTATTCATCGTCTGGAACGTGT<br>TAAAAGCCTGCTGAGCGAATATAAGATTATTAGCGGTCTGGCACCGACCA<br>ATAATCAGCCGTATAACATTCGTGTTAAAGGTCTGACCGAACAGCTGACC<br>AAAGATGAACTGGCAGTTGCACTGCTGCATATTCCAAACGCCGTGGCAT<br>TCATAAAATCGATGTGATTGATAGCAATGACGATGTGGGTAATGAACTGA<br>GCACCAAAGAACAGCTGAACAAAAATAGCAAACTGCTGAAAGACAAATT<br>CGTGTGTCAGATTCAGCTGGAACGTATGAATGAAGGCCAGGTTCGTGGTG<br>AAAAGAATCGCTTTAAAACCGCAGACATCATCAAAGAAATTATCCAGCT<br>GCTGAACGTGCAGAAAAACTTCCATCAGCTGGATGAAAACTTCATCAACA<br>AATACATCGAGCTGGTTGAAATGCGTCGCGAATATTTTGAAGGTCCTGGT<br>CAGGGTAGCCCGTTTGGTTGGAATGGTGATCTGAAAAAATGGTACGAAAT<br>GCTGATGGGTCACTGTACCTATTTTCCGCAAGAACTGCGTAGCGTTAAAT<br>ATGCCTATAGCGCAGACCTGTTTAATGCACTGAATGATCTGAACAACCTG<br>ATTATTCAGCGCGATAATAGCGAGAAACTGGAATACCATGAGAAGTATC<br>ACATCATCGAGAACGTGTTCAAGCAGAAAAAAAGCCGACGCTGAAACA<br>AATCGCAAAAGAGATTGGCGTTAACCCGGAAGATATTAAGGTTATCGT<br>ATTACCAAAAGCGGTACACCGGAATTCACCGAATTTAAACTGTATCACGA<br>TCTGAAAAGCGTGCTGTTTGATCAGAGCATTCTGGAAAATGAAGATGTGC<br>TGGACCAGATTGCAGAAATTCTGACCATTTATCAGGACAAAGACAGCATC<br>AAAAGCAAACTGACCGAACTGGATATTCTGCTGAATGAAGAAGATAAAG<br>AGAACATTGCACAGCTGACCGGTTATAACGGCACACATCGCCTGAGCCTG<br>AAATGTATTCGTCTGGTACTGGAAGAACAGTGGTATAGCAGCCGTAATCA<br>GATGGAAATCTTTACCCATCTGAACATTAAACCGAAGAAAATCAATCTGA<br>CCGCAGCCAACAAAATTCCGAAAGCCATGATTGATGAGTTTATTCTGAGT<br>CCGGTTGTGAAACGCACCTTTATTCAGAGCATCAACGTGATCAACAAAGT<br>GATCGAGAAATATGGCATCCCCGAAGATATCATTATCGAACTGGCACGTG<br>AAAATAACTCCGATGATCGCAAAAAGTTCATCAACAACCTGCAGAAAAA<br>GAATGAAGCAACCCGCAAACGCATTAACGAAATTATTGGTCAGACCGGT | DNA sequence encoding F8 |

| SEQ ID NO | Sequence | Description |
|---|---|---|
| | AATCAGAATGCCAAACGTATTGTGGAAAAAATCCGTCTGCATGATCAGCA<br>AGAGGGGAAATGTCTGTATAGCCTGGAAAGCATTGCCCTGATGGATCTGC<br>TGAATAACCCGCAGAATTATGAAGTGGATCATATTATTCCGCGTAGCGTG<br>GCATTTGATAATTCCATTCATAACAAAGTGCTGGTGAAGCAGATCGAGAA<br>TAGCAAAAAAGGTAATCGTACGCCGTATCAGTATCTGAATAGCAGTGATG<br>CAAAACTGAGCTACAACCAGTTTAAACAGCATATTCTGAATCTGAGCAAA<br>AGCAAAGATCGCATCAGCAAAAAAAAGAAGGACTACCTGCTGGAAGAAC<br>GCGATATCAACAAATTTGAAGTCCAGAAAGAGTTTATCAACCGCAATCTG<br>GTTGATACCCGTTATGCAACCCGTGAACTGACCAGCTATCTGAAAGCATA<br>TTTCAGCGCCAATAACATGGACGTGAAAGTGAAAACAATTAACGGCAGC<br>TTTACCAACCATCTGCGTAAAGTTTGGCGCTTTGATAAATATCGCAACCA<br>CGGCTATAAACATCATGCAGAAGATGCCCTGATTATTGCAAATGCAGATT<br>TCCTGTTTAAAGAAAACAAAAAACTGAAAGCCGTCAACAGCGTGCTGGA<br>AAAACCGGAAATTGAGACAAAACAGCTGGACATTCAGGTTGATAGCGAA<br>GATAATTACAGCGAAATGTTTATCATCCCGAAACAGGTGCAGGATATCAA<br>AGATTTTCGCAACTTCAAATATAGCCACCGCGTTGACAAAAAACCTAATC<br>GTCAGCTGATTAACGATACCCTGTATAGCACCCGCAAAAAGATAACAG<br>CACCTATATTGTGCAGACCATTAAAGACATCTACGCCAAGATAATACCA<br>CCCTGAAAAAACAGTTCGACAAAAGCCCAGAAAAATTTCTGATGTATCA<br>GCATGATCCGCGTACCTTCGAAAAACTGGAAGTTATTATGAAACAGTATG<br>CCAACGAGAAAAATCCGCTGGCCAAATATCACGAAGAAACCGGTGAATA<br>TCTGACCAATATTCCAAGAAGAACAACGGTCCGATCGTTAAATCCCTGA<br>ATATATCGGTAATAAACTGGGCAGCCATCTGGATGTTACCCATCAGTTT<br>AAAAGCTCCACAAAGAAGCTGGTTAAACTGTCCATCAAACCGTATCGCTT<br>TGATGTGTATCTGACCGACAAAGGCTATAAATTCATTACCATCAGCTATC<br>TGGACGTGCTGAAAAAGACAACTATTATTATATCCCGGAACAGAAATAT<br>GATAAACTGAAACTGGGTAAAGCCATCGATAAAAACGCCAAATTTATCG<br>CCAGCTTCTACAAAAACGACCTGATTAAACTGGATGGCGAGATCTATAAA<br>ATCATCGGTGTTAATAGCGACACCCGCAATATGATTGAGCTGGATCTGCC<br>GGATATTCGCTATAAGAATATTGCGAACTGAACAACATTAAAGGCGAA<br>CCGCGTATCAAAAAGACCATCGGCAAAAAGTGAATAGCATCGAGAAAC<br>TGACCACCGATGTTCTGGGTAATGTGTTTACCAATACCCAGTATACCAAA<br>CCTCAGCTGCTGTTCAAACGCGGTAAT | |
| 27 | ATGAACCAAAGTTCATTCTGGGGCTCGATATCGGCATCACCTCCGTGGG<br>ATATGGTCTGATCGACTACGAGACTAAGAACATCATCGACGCTGGAGTGC<br>GACTGTTCCCGGAAGCGAACGTGGAGAACAACGAAGGCCGCAGATCCAA<br>GCGCGGGTCCAGAAGGCTCAAGAGGCGGAGGATCCATAGACTCAGAGA<br>GTGAAGTCGCTCCTTTCGGAATACAAGATTATCAGCGGTCTTGCCCCCAC<br>CAACAACCAACCGTACAACATCAGAGTGAAGGGCCTGACCGAACAGCTG<br>ACCAAAGATGAACTGGCCGTCGCCCTGCTGCATATTGCCAAACGGCGCGG<br>AATCCATAAGATCGACGTGATTGACAGCAACGATGACGTGGGAAACGAG<br>CTGTCAACCAAGGAACAGCTTAACAAGAACAGCAAATTGCTGAAGGACA<br>AGTTTGTCTGCCAAATTCAACTGGAACGGATGAACGAGGGACAAGTCAG<br>GGGAGAGAAAAACCGGTTCAAGACCGCCGACATCATCAAGGAGATCATC<br>CAACTGCTGAACGTGCAGAAGAACTTCCACCAACTGGATGAAAACTTCAT<br>TAACAAGTACATTGAACTGGTGGAAATGCGGAGGGAGTACTTCGAGGGA<br>CCTGGACAGGGATCCCCTTTCGGCTGGAATGGGGACCTTAAGAAGTGGTA<br>CGAAATGTTGATGGGCCATTGCACTTACTTTCCGCAAGAACTCCGGTCCG<br>TGAAGTACGCATACTCTGCCGACCTGTTCAATGCACTCAACGACCTTAAC<br>AACTTGATCATCCAGCGCGATAACTCGGAAAAGTTGGAATACCACGAAA<br>AGTATCACATCATCGAGAACGTGTTCAAGCAGAAAAAGAAGCCAACTCT<br>GAAGCAGATTGCCAAGGAAATTGGCGTGAATCCGGAGGATATCAAGGGA<br>TACCGGATCACTAAGTCCGGCACGCCAGAGTTCACCGAGTTCAAGCTGTA<br>CCACGATCTGAAGTCGGTGCTCTTTGACCAGTCCATCCTGGAAAACGAAG<br>ATGTGCTGGACCAGATTGCTGAGATCCTGACCATCTACCAGGACAAGGAC<br>TCGATTAAGTCCAAGCTCACCGAGCTGGACATTCTGCTGAACGAAGAAGA<br>TAAGGAGAACATCGCGCAGCTCACCGGTTACAATGGTACCCACCGCTTGT<br>CCCTTAAGTGCATCCGCCTGGTGCTGGAGGAACAGTGGTACTCGAGCCGG<br>AACCAGATGGAGATCTTCACTCACTTGAACATCAAGCCGAAAAAGATTA<br>ACCTGACTGCCGCCAACAAGATACCCAAGGCCATGATCGACGAGTTTATC<br>CTCTCACCGGTGGTCAAGCGCACCTTCATTCAATCTATCAACGTGATCAA<br>CAAGGTCATCGAGAAGTACGGCATTCCTGAGGATATCATCATCGAGCTGG<br>CTCGGGAGAACAACTCAGACGATAGGAAGAAGTTCATTAACAACCTCCA<br>GAAAAGAACGAGGCCACTCGCAAGCGGATTAATGAGATCATCGGTCAG<br>ACCGGGAACCAGAACGCCAAGCGGATCGTGGAAAAGATTCGGCTCCACG<br>ACCAACAGGAGGGAAAGTGTCTGTACTCGCTGGAGTCGATTGCACTGATG<br>GACCTCCTGAACAACCCACAGAACTACGAAGTCGATCACATAATCCCCCG<br>CAGCGTGGCATTCGACAACTCCATCCATAACAAGGTCCTCGTGAAGCAGA<br>TCGAGAATAGCAAGAAGGGGAACCGGACTCCGTACCAGTACCTGAACTC<br>CTCCGACGCCAAGCTGTCATACAATCAGTTCAAACAGCACATTCTCAACC<br>TGTCCAAGTCAAAGGACAGGATCTCCAAGAAGAAGAAGGACTACCTTCT<br>CGAGGAACGGGATATCAATAAGGTTCGAGGTGCAGAAGGAGTTTATCAAT | Codon-optimized F8 polynucleotide |

SEQUENCE LISTING

| SEQ ID NO | Sequence | Description |
|---|---|---|
| | AGAAACCTGGTGGACACTCGCTATGCCACCCGCGAACTGACCAGCTACCT GAAGGCGTACTTCTCCGCAACAACATGGACGTGAAGGTCAAAACTATTA ACGGCAGCTTCACCAACCATCTGCGCAAGGTCTGGAGGTTCGACAAGTAC CGCAACCACGGTTACAAGCACCACGCGGAAGATGCGCTGATTATCGCCA ACGCTGACTTCCTGTTCAAGGAAAACAAGAAGCTCAAGGCCGTGAACTC AGTGCTCGAGAAGCCTGAAATCGAGACTAAGCAGCTGGACATCCAGGTC GATTCGGAAGATAACTACTCCGAAATGTTCATCATCCCTAAGCAAGTGCA GGACATCAAGGACTTCAGGAATTTCAAGTACAGCCATCGCGTGGACAAG AAGCCAAACAGACAGCTGATCAACGATACACTGTATTCCACCCGGAAGA AGGACAACTCCACCTACATCGTCCAAACCATTAAGGACATCTACGCAAAG GACAACACCACGCTTAAGAAGCAGTTCGACAAGAGCCCCGAAAAGTTCC TCATGTACCAGCACGACCCCAGAACCTTCGAGAAGCTTGAAGTGATCATG AAGCAGTACGCCAACGAAAAGAACCCACTGGCTAAGTACCACGAGGAAA CCGGCGAATACCTGACCAAGTACTCCAAAAAGAACAACGGACCGATCGT CAAGTCCCTGAAGTACATTGGGAACAAGCTCGGCTCGCACCTCGATGTGA CCCACCAGTTCAAGTCCTCGACCAAAAAGCTCGTGAAGCTGTCCATCAAG CCGTACCGGTTCGACGTGTACCTGACTGACAAGGGATATAAGTTCATCAC CATTTCCTACCTCGACGTGTTGAAGAAGGATAACTACTACTACATTCCGG AACAGAAGTACGACAAGCTCAAGCTCGGAAAGGCCATCGACAAAAATGC GAAGTTCATCGCGAGCTTCTACAAGAATGACTTGATCAAGCTGGATGGCG AAATCTACAAGATCATCGGGGTCAACTCCGATACCCGCAACATGATTGAG CTGGATCTGCCCGACATTCGGTACAAGGAATACTGCGAGCTGAACAACAT CAAGGGAGAACCGCGGATCAAGAAAACCATCGGAAAGAAAGTGAACAG CATCGAGAAACTGACTACTGACGTCCTGGGAAACGTGTTCACCAACACAC AATACACCAAACCCCAGCTGCTGTTTAAGCGCGGGAAC | |
| 28 | ATGAACCAGAAATTTATCCTGGGTCTGGATATTGGTATTACCAGCGTTGG TTATGGCCTGATTGATTACGAAACCAAAAACATTATTGATGCCGGTGTTC GTCTGTTTCCGGAAGCAAATGTTGAAATAATGAAGGTCGTCGTAGCAAA CGTGGTAGCCGTCGTCTGAAACGTCGTCGTATTCATCGTCTGGAACGTGT TAAAAGCCTGCTGAGCGAATATAAGATTATTAGCGGTCTGGACACCGACA ATAATCAGCCGTATAACATTCGTGTTAAAGGTCTGACCGAACAGCTGACC AAAGATGAACTGGCAGTTGCACTGCTGCATATTGCCAAACGCCGTGGCAT TCATAAAATCGATGTGATTGATAGCAATGACGATGTGGGTAATGAACTGA GCACCAAAGAACAGCTGAACAAAAATAGCAAACTGCTGAAAGACAAATT CGTGTGTCAGATTCAGCTGGAACGTATGAATGAAGGCCAGGTTCGTGGTG AAAAGAATCGCTTTAAAACCGCAGACATCATCAAAGAAATTATCCAGCT GCTGAACGTGCAGAAAAACTTCCATCAGCTGGATGAAAACTTCATCAACA AATACATCGAGCTGGTTGAAATGCGTCGCGAATATTTTGAAGGTCCTGGT CAGGGTAGCCCGTTTGGTTGGAATGGTGATCTGAAAAAATGGTACGAAAT GCTGATGGGTCACTGTACCTATTTTCCGAAGAACTGCGTAGCGTTAAAT ATGCCTATAGCGCAGACCTGTTTAATGCACTGAATGATCTGAACAACCTG ATTATTCAGCGCGATAATAGCGAGAAACTGGAATACCATGAGAAGTATC ACATCATCGAGAACGTGTTCAAGCAGAAAAAAAGCCGACGCTGAAACA AATCGCAAAAGAGATTGGCGTTAACCCGGAAGATATTAAAGGTTATCGT ATTACCAAAAGCGGTACACCGGAATTCACCGAATTTAAACTGTATCACGA TCTGAAAAGCGTGCTGTTTGATCAGAGCATTCTGGAAAATGAAGATGTGC TGGACCAGATTGCAGAAATTCTGACCATTTATCAGGACAAAGACAGCATC AAAAGCAAACTGACCGAACTGGATATTCTGCTGAATGAAGAAGATAAAG AGAACATTGCACAGCTGACCGGTTATAACGGCACACATCGCCTGAGCCTG AAATGTATTCGTCTGGTACTGGAAGAACAGTGGTATAGCAGCCGTAATCA GATGGAAATCTTTACCCATCTGAACATTAAACCGAAGAAAATCAATCTGA CCGCAGCCAACAAAATTCCGAAAGCCATGATTGATGAGTTTATTCTGAGT CCGGTTGTGAAACGCACCTTTATTCAGAGCATCAACGTGATCAACAAAGT GATCGAGAAATATGGCATCCCCGAAGATATCATTATCGAACTGGCACGTG AAAATAACTCCGATGATCGCAAAAAGTTCATCAACAACCTGCAGAAAAA GAATGAAGCAACCCGCAAACGCATTAACGAAATTATTGGTCAGACCGGT AATCAGAATGCCAAACGTATTGTGGAAAAAATCCGTCTGCATGATCAGCA AGAGGGGAAATGTCTGTATAGCCTGGAAAGCATTGCCCTGATGGATCTGC TGAATAACCCGCAGAATTATGAAGTGGATCATATTATTCCGCGTAGCGTG GCATTTGATAATTCCATTCATAACAAAGTGCTGGTGAAGCAGATCGAGAA TAGCAAAAAAGGTAATCGTACGCCGTATCAGTATCTGAATAGCAGTGATG CAAAACTGAGCTACAACCAGTTTAAACAGCATATTCTGAATCTGAGCAAA AGCAAAGATCGCATCAGCAAAAAAAAGAAGGACTACCTGCTGGAAGAAC GCGATATCAACAAATTTGAAGTCCAGAAAGAGTTTATCAACCGCAATCTG GTTGATACCCGTTATGCAACCCGTGAACTGACCAGCTATCTGAAAGCATA TTTCAGCGCCAATAACATGGACGTGAAAGTGAAAACAATTAACGGCAGC TTTACCAACCATCTGCGTAAAGTTTGGCGCTTTGATAAATATCGCAACCA CGGCTATAAACATCATGCAGAAGATGCCCTGATTATTGCAAATGCAGATT TCCTGTTTAAGAAAACAAAAACTGAAAGCCGTCAACAGCGTGCTGGA AAAACCGGAAATTGAGACAGATCAGAAGACATTCAGGTTGATAGCGAA GATAATTACAGCGAAATGTTTATCATCCCGAAACAGGTGCAGGATATCAA AGATTTTCGCAACTTCAAATATAGCCACCGCGTTGACAAAAAACCTAATC | DNA sequence encoding F8 + K737D + L739K |

| SEQ ID NO | Sequence | Description |
|---|---|---|
| | GTCAGCTGATTAACGATACCCTGTATAGCACCCGCAAAAAGATAACAG<br>CACCTATATTGTGCAGACCATTAAAGACATCTACGCCAAAGATAATACCA<br>CCCTGAAAAAACAGTTCGACAAAAGCCCAGAAAATTTCTGATGTATCA<br>GCATGATCCGCGTACCTTCGAAAAACTGGAAGTTATTATGAAACAGTATG<br>CCAACGAGAAAAATCCGCTGGCCAAATATCACGAAGAAACCGGTGAATA<br>TCTGACCAAATATTCCAAGAAGAACAACGGTCCGATCGTTAAATCCCTGA<br>AATATATCGGTAATAAACTGGGCAGCCATCTGGATGTTACCCATCAGTTT<br>AAAAGCTCCACAAAGAAGCTGGTTAAACTGTCCATCAAACCGTATCGCTT<br>TGATGTGTATCTGACCGACAAAGGCTATAAATTCATTACCATCAGCTATC<br>TGGACGTGCTGAAAAAAGACAACTATTATTATATCCCGGAACAGAAATAT<br>GATAAACTGAAACTGGGTAAAGCCATCGATAAAAACGCCAAATTTATCG<br>CCAGCTTCTACAAAAACGACCTGATTAAACTGGATGGCGAGATCTATAAA<br>ATCATCGGTGTTAATAGCGACACCCGCAATATGATTGAGCTGGATCTGCC<br>GGATATTCGCTATAAGAATATTGCGAACTGAACAACATTAAAGGCGAA<br>CCGCGTATCAAAAAGACCATCGGCAAAAAAGTGAATAGCATCGAGAAAC<br>TGACCACCGATGTTCTGGGTAATGTGTTTACCAATACCCAGTATACCAAA<br>CCTCAGCTGCTGTTCAAACGCGGTAAT | |
| 29 | ATGAACCAGAAATTTATCCTGGGTCTGGATATTGGTATTACCAGCGTTGG<br>TTATGGCCTGATTGATTACGAAACCAAAAACATTATTGATGCCGGTGTTC<br>GTCTGTTTCCGGAAGCAAATGTTGAAAATAATGAAGGTCGTCGTAGCAAA<br>CGTGGTAGCCGTCGTCTGAAACGTCGTCGTATTCATCGTCTGGAACGTGT<br>TAAAAGCCTGCTGAGCGAATATAAGATTATTAGCGGTCTGGCACCGACCA<br>ATAATCAGCCGTATAACATTCGTGTTAAAGGTCTGACCGAACAGCTGACC<br>AAAGATGAACTGGCAGTTGCACTGCTGCATATTGCCAAACGCCGTGGCAT<br>TCATAAAATCGATGTGATTGATAGCAATGACGATGTGGGTAATGAACTGA<br>GCACCAAAGAACAGCTGAACAAAAATAGCAAACTGCTGAAAGACAAATT<br>CGTGTGTGTCAGATTCAGCTGGAACGTATGAATGAAGGCCAGGTTCGTGGTG<br>AAAAGAATCGCTTTAAAACCGCAGACATCATCAAAGAAATTATCCAGCT<br>GCTGAACGTGCAGAAAAACTTCCATCAGCTGGATGAAAACTTCATCAACA<br>AATACATCGAGCTGGTTGAAATGCGTCGCGAATATTTTGAAGGTCCTGGT<br>CAGGGTAGCCCGTTTGGTTGGAATGGTGATCTGAAAAAATGGTACGAAAT<br>GCTGATGGGTCACTGTACCTATTTTCCGCAAGAACTGCGTAGCGTTAAAT<br>ATGCCTATAGCGCAGACCTGTTTAATGCACTGATGATCTGAACAACCTG<br>ATTATTCAGCGCGATAATAGCGAGAAACTGGAATACCATGAGAAGTATC<br>ACATCATCGAGAACGTGTTCAAGCAGAAAAAAAAGCCGACGCTGAAACA<br>AATCGCAAAAGAGATTGGCGTTAACCCGGAAGATATTAAAGGTTATCGT<br>ATTACCAAAAGCGGTACACCGGAATTCACCGAATTTAAACTGTATCACGA<br>TCTGAAAAGCGTGCTGTTTGATCAGAGCATTCTGGAAAATGAAGATGTGC<br>TGGACCAGATTGCAGAAATTCTGACCATTTATCAGGACAAAGACAGCATC<br>AAAAGCAAACTGACCGAACTGGATATTCTGCTGAATGAAGAAGATAAAG<br>AGAACATTGCACAGCTGACCGGTTATAACGGCACACATCGCCTGAGCCTG<br>AAATGTATTCGTCTGGTACTGGAAGAACAGTGGTATAGCAGCCGTAATCA<br>GATGGAAATCTTTACCCATCTGAACATTAAACCGAAGAAAATCAATCTGA<br>CCGCAGCCAACAAAATTCCGAAAGCCATGATTGATGAGTTTATTCTGAGT<br>CCGGTTGTGAAACGCACCTTTATTCAGAGCATCAACGTGATCAACAAAGT<br>GATCGAGAAATATGGCATCCCCGAAGATATCATTATCGAACTGGCACGTG<br>AAAATAACTCCGATGATCGCAAAAAGTTCATCAACAACCTGCAGAAAAA<br>GAATGAAGCAACCCGCAAACGCATTAACGAAATTATTGGTCAGACCGGT<br>AATCAGAATGCCAAACGTATTGTGGAAAAAATCCGTCTGCATGATCAGCA<br>AGAGGGGAAATGTCTGTATAGCCTGGAAAGCATTGCCCTGATGGATCTGC<br>TGAATAACCCGCAGAATTATGAAGTGGATCATATTATTCCGCGTAGCGTG<br>GCATTTGATAATTCCATTCATAACAAAGTGCTGGTGAAGCAGATCGAGAA<br>TAGCAAAAAAGGTAATCGTACGCCGTATCAGTATCTGAATAGCAGTGATG<br>CAAAACTGAGCTACAACCAGTTTAAACAGCATATTCTGAATCTGAGCAAA<br>AGCAAAGATCGCATCAGCAAAAAAAGAAGGACTACCTGCTGGAAGAAC<br>GCGATATCAACAAATTTGAAGTCCAGAAAGAGTTTATCAACCGCAATCTG<br>GTTGATACCCGTTATGCAACCCGTGAACTGACCAGCTATCTGAAAGCATA<br>TTTCAGCGCCAATAACATGGACGTGAAAGTGAAAACAATTAACGGCAGC<br>TTTACCAACCATCTGCGTAAAGTTTGGCGCTTTGATAAATATCGCAACCA<br>CGGCTATAAACATCATGCAGAAGATGCCCTGATTATTGCAAATGCAGATT<br>TCCTGTTTAAAGAAAACAAAAAACTGAAAGCCGTCAACAGCGTGCTGGA<br>AAAACCGGAAATTGAGACAAATCAGAATGACATTCAGGTTGATAGCGAA<br>GATAATTACAGCGAAATGTTTATCATCCCGAAACAGGTGCAGGATATCAA<br>AGATTTTCGCAACTTCAAATATAGCCACCGCGTTGACAAAAAACCTAATC<br>GTCAGCTGATTAACGATACCCTGTATAGCACCCGCAAAAAGATAACAG<br>CACCTATATTGTGCAGACCATTAAAGACATCTACGCCAAAGATAATACCA<br>CCCTGAAAAAACAGTTCGACAAAAGCCCAGAAAATTTCTGATGTATCA<br>GCATGATCCGCGTACCTTCGAAAAACTGGAAGTTATTATGAAACAGTATG<br>CCAACGAGAAAAATCCGCTGGCCAAATATCACGAAGAAACCGGTGAATA<br>TCTGACCAAATATTCCAAGAAGAACAACGGTCCGATCGTTAAATCCCTGA<br>AATATATCGGTAATAAACTGGGCAGCCATCTGGATGTTACCCATCAGTTT<br>AAAAGCTCCACAAAGAAGCTGGTTAAACTGTCCATCAAACCGTATCGCTT | DNA sequence encoding F8 + K737N + L739N |

SEQUENCE LISTING

| SEQ ID NO | Sequence | Description |
|---|---|---|
| | TGATGTGTATCTGACCGACAAAGGCTATAAATTCATTACCATCAGCTATC<br>TGGACGTGCTGAAAAAAGACAACTATTATTATATCCCGGAACAGAAATAT<br>GATAAACTGAAACTGGGTAAAGCCATCGATAAAAACGCCAAATTTATCG<br>CCAGCTTCTACAAAAACGACCTGATTAAACTGGATGGCGAGATCTATAAA<br>ATCATCGGTGTTAATAGCGACACCCGCAATATGATTGAGCTGGATCTGCC<br>GGATATTCGCTATAAAGAATATTGCGAACTGAACAACATTAAAGGCGAA<br>CCGCGTATCAAAAAGACCATCGGCAAAAAAGTGAATAGCATCGAGAAAC<br>TGACCACCGATGTTCTGGGTAATGTGTTTACCAATACCCAGTATACCAAA<br>CCTCAGCTGCTGTTCAAACGCGGTAAT | |
| 30 | MNQKFILGLDIGITSVGYGLIDYETKNIIDAGVRLFPEANVENNEGRRSKRGS<br>RRLKRRRIHRLERVKKLLEDYNLLDQSQIPQSTNPYAIRVKGLSEALSKDELV<br>IALLHIAKRRGIHKIDVIDSNDDVGNELSTKEQLNKNSKLLKDKFVCQIQLER<br>MNEGQVRGEKNRFKTADIIKEIIQLLNVQKNFHQLDENFINKYIELVEMRREY<br>FEGPGKGSPYGWEGDPKAWYETLMGHCTYFPDELRSVKYAYSADLFNALN<br>DLNNLVIQRDGLSKLEYHEKYHIIENVFKQKKKPTLKQIANEINVNPEDIKGY<br>RITKSGKPQFTEFKLYHDLKSVLFDQSILENEDVLDQIAEILTIYQDKDSIKSKL<br>TELDILLNEEDKENIAQLTGYTGTHRLSLKCIRLVLEEQWYSSRNQMEIFTHL<br>NIKPKKINLTAANKIPKAMIDEFILSPVVKRTFGQAINLINKIIEKYGVPEDIIIEL<br>ARENNSKDKQKFINEMQKKNENTRKRINEIIGKYGNQNAKRLVEKIRLHDEQ<br>EGKCLYSLESIPLEDLLNNPNHYEVDHIIPRSVSFDNSYHNKVLVKQSENSKK<br>SNLTPYQYFNSGKSKLSYNQFKQHILNLSKSQDRISKKKKEYLLEERDINKFE<br>VQKEFINRNLVDTRYATRELTNYLKAYFSANNMNVKVKTINGSFTDYLRKV<br>WKFKKERNHGYKHHAEDALIIANADPFLFKENKKLKAVNSVLEKPEIETKQL<br>DIQVDSEDNYSEMFIIPKQVQDIKDFRNFKYSHRVDKKPNRQLINDTLYSTRK<br>KDNSTYIVQTIKDIYAKDNTTLKKQFDKSPEKFLMYQHDPRTFEKLEVIMKQ<br>YANEKNPLAKYHEETGEYLTKYSKKNNGPIVKSLKYIGNKLGSHLDVTHQF<br>KSSTKKLVKLSIKPYRFDVYLTDKGYKFITISYLDVLKKDNYYYIPEQKYDKL<br>KLGKAIDKNAKFIASFYKNDLIKLDGEIYKIIGVNSDTRNMIELDLPDIRYKEY<br>CELNNIKGEPRIKKTIGKKVNSIEKLTTDVLGNVFTNTQYTKPQLLFKRGN | *Staphylococcus lugdunensis* Cas9 |
| 31 | MKEKYILGLDLGITSVGYGIINFETKKIIDAGVRLFPEANVDNNEGRRSKRGS<br>RRLKRRRIHRLERVKLLLTEYDLINKEQIPTSNNPYQIRVKGLSEILSKDELAIA<br>LLHLAKRRGIHNINVSSEDEDASNELSTKEQINRNNKLLKDKYVCEVQLQRL<br>KEGQIRGEKNRFKTTDILKEIDQLLKVQKDYHNLDIDFINQYKEIVETRREYF<br>EGPGQGSPFGWNGDLKKWYEMLMGHCTYFPQELRSVKYAYSADLFNALND<br>LNNLIIQRDNSEKLEYHEKYHIIENVFKQKKKPTLKQIAKEIGVNPEDIKGYRI<br>TKSGTPQFTEFKLYHDLKSIVFDKSILENEAILDQIAEILTIYQDEQSIKEELNK<br>LPEILNEQDKAEIAKLIGYNGTHRLSLKCIHLINEELWQTSRNQMEIFNYLNIK<br>PNKVDLSEQNKIPKDMVNDFILSPVVKRTFIQSINVINKVIEKYGIPEDIIIELAR<br>ENNSDDRKKFINNLQKKNEATRKRINEIIGQTGNQNAKRIVEKIRLHDQQEGK<br>CLYSLESIALMDLLNNPQNYEVDHIIPRSVAFDNSIHNKVLVKQIENSKKGNR<br>TPYQYLNSSDAKLSYNQFKQHILNLSKSKDRISKKKKDYLLEERDINKFEVQ<br>KEFINRNLVDTRYATRELTSYLKAYFSANNMDVKVKTINGSFTNHLRKVWR<br>FDKYRNHGYKHHAEDALIIANADPFLFKENKKLQNTNKILEKPTIENNTKKVT<br>VEKEEDYNNVFETPKLVEDIKQYRDYKFSHRVDKKPNRQLINDTLYSTRMK<br>DEHDYIVQTITDIYGKDNTNLKKQFNKNPEKFLMYQNDPKTFEKLSIIMKQY<br>SDEKNPLAKYYEETGEYLTKYSKKNNGPIVKKIKLLGNKVGNHLDVTNKYE<br>NSTKKLVKLSIKNYRFDVYLTEKGYKFVTIAYLNVFKKDNYYYIPKDKYQEL<br>KEKKKIKDTQFIASFYKNDLIKLNGDLYKIIGVNSDDRNIIELDYYDIKYKD<br>YCEINNIKGEPRIKKTIGKKTESIEKFTTDVLGNLYLHSTEKAPQLIFKRGL | *Staphylococcus pasteuri* Cas9 |
| 32 | MNNYILGLDIGITSVGYGIVDSDTREIKDAGVRLFPEANVDNNEGRRSKRGA<br>RRLKRRRIHRLDRVKHLLAEYDLLDLTNIPKSTNPYQTRVKGLNEKLSKDEL<br>VIALLHIAKRRGIHNVNVMMDDNDSGNELSTKDQLKKNAKALSDKYVCELQ<br>LERFEQDYKVRGEKNRFKTEDFVREARKLLETQSKFFEIDQTFIMRYIELIETR<br>REYFEGPGKGSPFGWEGNIKKWFEQMMGHCTYFPEELRSVKYSYSAELFNA<br>LNDLNNLVITRDEDAKLNYGEKFQIIENVFKQKKTPNLKQIAIEIGVHETEIKG<br>YRVNKSGKPEFTQFKLYHDLKNIFKDPKYLNDIQLMDNIAEIITIYQDAESIIK<br>ELNQLPELLSEREKEKISALSGYSGTHRLSLKCINLLLDDLWESSLNQMELFT<br>KLNLKPKKIDLSQQHKIPSKLVDDFILSPVVKRAFIQSIQVVNAIIDKYGLPEDI<br>IIELARENNSDDRRKFLNQLQKQNEETRKQVEKVLREYGNDNAKRIVQKIKL<br>HNMQEGKCLYSLKDIPLEDLLRNPHHYEVDHIIPRSVAFDNSMHNKVLVRAD<br>ENSKKGNRTPYQYLNSSESSLSYNEFKQHILNLSKTKDRITKKKREYLLEERD<br>INKFDVQKEFINRNLVDTRYATRELTSLLKAYFSANNLDVKVKTINGSFTNYL<br>RKVWKFDKDRNKGYKHHAEDALIIANADPFLFKHNKKLRNINKVLDAPSKEV<br>DKKRVTVQSEDEYNQIFEDTQKAQAIKKFEIRKFSHRVDKKPNRQLINDTLYS<br>TRNIDGIEYVVESIKDIYSVNNDKVKTKFKKDPHRLLMYRNDPQTFEKFEKV<br>FKQYESEKNPFAKYYEETGEKIRKFSKTGQGPYINKIKYLRERLGRHCDVTN<br>KYINSRNKIVQLKIYSYRFDIYQYGNNYKMITISYIDLEQKSNYYYISREKYEQ<br>KKKDKQIDDSYKFIGSFYKNDIINYNGEMYRVIGVNDSEKNKIQLDMIDISIK<br>DYMELNNIKKTGVIYKTIGKSTTHIEKYTTDILGNLYKAAPPKKPQLIFK | *Staphylococcus hyicus* Cas9 |

SEQUENCE LISTING

| SEQ ID NO | Sequence | Description |
|---|---|---|
| 33 | MEKDYILGLDIGIGSVGYGLIDYDTKSIIDAGVRLFPEANADNNLGRRAKRGA RRLKRRRIHRLERVKSLLSEYKIISGLAPTNNQPYNIRVKGLTEQLTKDELAV ALLHIAKRRGIHNVDVAADKEETASDSLSTKDQINKNAKFLESRYVCELQKE RLENEGHVRGVENRFLTKDIVREAKKIIDTQMQYYPEIDETFKEKYISLVETR REYYEGPGKGSPYGWDADVKKWYQLMMGHCTYFPVEFRSVKYAYTADLY NALNDLNNLTIARDDNPKLEYHEKYHIIENVFKQKRNPTLKQIAKEIGVNDIN ISGYRVTKSGKPQFTSFKLFHDLKKVVKDHAILDDIDLLNQIAEILTIYQDKDS IVAELGQLEYLMSEADKQSISELTGYTGTHSLSLKCMNMIIDELWHSSMNQM EVFTYLNMRPKKYELKGYQRIPTDMIDDAILSPVVKRSFKQAIGVVNAIIKKY GLPKDIIIELARESNSAEKSRYLRAIQKKNEKTRERIEAIIKEYGNENAKGLVQ KIKLHDAQEGKCLYSLKDIPLEDLLRNPNNYDIDHIIPRSVSFDDSMHNKVLV RREQNAKKNNQTPYQYLTSGYADIKYSVFKQHVLNLAENKDRMTKKKREY LLEERNINKYDVQKEFINRNLVDTRYTTRELTTLLKTYFTINNLDVKVKTING SFTDFLRKRWGFKKNRDEGYKHHAEDALIIANADYLFKEHKLLKEIKDVSDL AGDERNSNVKDEDQYEEVFGGYFKIEDIKKYKIKKFSHRVDKKPNRQLINDT IYSTRVKDDKRYLINTLKNLYDKSNGDLKERMQKDPESLLMYHHDPQTFEK LKIVMSQYENEKNPLAKYFEETGQYLTKYAKHDNGPAIHKIKYYGNKLVEH LDITKNYHNPQNKVVQLSQKSFRFDVYQTDKGYKFISIAYLTLKNEKNYYAI SQEKYDQLKSEKKISNNAVFIGSFYTSDIIEINNEKFRVIGVNSDKNNLIEVDRI DIRQKEFIELEEEKKNNRIKVTIGRKTTNIEKFHTDILGNMYKSKRPKAPQLVF KKG | *Staphylococcus microti* Cas9 |
| 34 | MNQKFILGLDIGITSVGYGLIDYETKNIIDAGVRLFPEANVENNEGRRSKRGS RRLKRRRIHRLERV | *Staphylococcus lugdunensis* mini-domain 1 from 8 mini-domain library |
| 35 | MKEKYILGLDLGITSVGYGIINFETKKIIDAGVRLFPEANVDNNEGRRSKRGS RRLKRRRIHRLERV | *Staphylococcus pasteuri* mini-domain 1 from 8 mini-domain library |
| 36 | MNNYILGLDIGITSVGYGIVDSDTREIKDAGVRLFPEANVDNNEGRRSKRGA RRLKRRRIHRLDRV | *Staphylococcus hyicus* mini-domain 1 from 8 mini-domain library |
| 37 | MEKDYILGLDIGIGSVGYGLIDYDTKSIIDAGVRLFPEANADNNLGRRAKRGA RRLKRRRIHRLERV | *Staphylococcus microti* mini-domain 1 from 8 mini-domain library |
| 38 | KKLLEDYNLLDQSQIPQSTNPYAIRVKGLSEALSKDELVIALLHIAKRRGIH | *Staphylococcus lugdunensis* mini-domain 2 from 8 mini-domain library |
| 39 | KLLLTEYDLINKEQIPTSNNPYQIRVKGLSEILSKDELAIALLHLAKRRGIH | *Staphylococcus pasteuri* mini-domain 2 from 8 mini-domain library |
| 40 | KHLLAEYDLLDLTNIPKSTNPYQTRVKGLNEKLSKDELVIALLHIAKRRGIH | *Staphylococcus hyicus* mini-domain 2 from 8 mini-domain library |
| 41 | KSLLSEYKIISGLAPTNNQPYNIRVKGLTEQLTKDELAVALLHIAKRRGIH | *Staphylococcus microti* mini-domain 2 from 8 mini-domain library |

SEQUENCE LISTING

| SEQ ID NO | Sequence | Description |
|---|---|---|
| 42 | KIDVIDSNDDVGNELSTKEQLNKNSKLLKDKFVCQIQLERMNEGQVRGEKN RFKTADIIKEIIQLLNVQKNFHQLDENFINKYIELVEMRRE | *Staphylococcus lugdunensis* mini-domain 3 from 8 mini-domain library |
| 43 | NINVSSEDEDASNELSTKEQINRNNKLLKDKYVCEVQLQRLKEGQIRGEKNR FKTTDILKEIDQLLKVQKDYHNLDIDFINQYKEIVETRRE | *Staphylococcus pasteuri* mini-domain 3 from 8 mini-domain library |
| 44 | NVNVMMDDNDSGNELSTKDQLKKNAKALSDKYVCELQLERFEQDYKVRG EKNRFKTEDFVREARKLLETQSKFFEIDQTFIMRYIELIETRRE | *Staphylococcus hyicus* mini-domain 3 from 8 mini-domain library |
| 45 | NVDVAADKEETASDSLSTKDQINKNAKFLESRYVCELQKERLENEGHVRGV ENRFLTKDIVREAKKIIDTQMQYYPEIDETFKEKYISLVETRRE | *Staphylococcus microti* mini-domain 3 from 8 mini-domain library |
| 46 | YFEGPGKGSPYGWEGDPKAWYETLMGHCTYFPDELRSVKYAYSADLFNAL NDLNNLVIQRDGLSKLEYHEKYHIIENVFKQKKKPTLKQIANEINVNPEDIKG YRITKSGK | *Staphylococcus lugdunensis* mini-domain 4 from 8 mini-domain library |
| 47 | YFEGPGQGSPFGWNGDLKKWYEMLMGHCTYFPQELRSVKYAYSADLFNAL NDLNNLIIQRDNSEKLEYHEKYHIIENVFKQKKKPTLKQIAKEIGVNPEDIKGY RITKSGT | *Staphylococcus pasteuri* mini-domain 4 from 8 mini-domain library |
| 48 | YFEGPGKGSPFGWEGNIKKWFEQMMGHCTYFPEELRSVKYSYSAELFNALN DLNNLVITRDEDAKLNYGEKFQIIENVFKQKKTPNLKQIAIEIGVHETEIKGYR VNKSGK | *Staphylococcus hyicus* mini-domain 4 from 8 mini-domain library |
| 49 | YYEGPGKGSPYGWDADVKKWYQLMMGHCTYFPVEFRSVKYAYTADLYNA LNDLNNLTIARDDNPKLEYHEKYHIIENVFKQKRNPTLKQIAKEIGVNDINISG YRVTKSGK | *Staphylococcus microti* mini-domain 4 from 8 mini-domain library |
| 50 | PQFTEFKLYHDLKSVLFDQSILENEDVLDQIAEILTIYQDKDSIKSKLTELDILL NEEDKENIAQLTGYTGTHRLSLKCIRLVLEEQWYSSRNQMEIFTHLNIKPKKI NLTAANKIPKAMIDEFILSPVVK | *Staphylococcus lugdunensis* mini-domain 5 from 8 mini-domain library |
| 51 | PQFTEFKLYHDLKSIVFDKSILENEAILDQIAEILTIYQDEQSIKEELNKLPEILN EQDKAEIAKLIGYNGTHRLSLKCIHLINEELWQTSRNQMEIFNYLNIKPNKVD LSEQNKIPKDMVNDFILSPVVK | *Staphylococcus pasteuri* mini-domain 5 from 8 mini-domain library |
| 52 | PEFTQFKLYHDLKNIFKDPKYLNDIQLMDNIAEIITIYQDAESIIKELNQLPELL SEREKEKISALSGYSGTHRLSLKCINLLLDDLWESSLNQMELFTKLNLKPKKI DLSQQHKIPSKLVDDFILSPVVK | *Staphylococcus hyicus* mini-domain 5 from 8 mini-domain library |
| 53 | PQFTSFKLFHDLKKVVKDHAILDDIDLLNQIAEILTIYQDKDSIVAELGQLEYL MSEADKQSISELTGYTGTHSLSLKCMNMIIDELWHSSMNQMEVFTYLNMRP KKYELKGYQRIPTDMIDDAILSPVVK | *Staphylococcus microti* mini-domain 5 from 8 mini-domain library |

SEQUENCE LISTING

| SEQ ID NO | Sequence | Description |
|---|---|---|
| 54 | RTFGQAINLINKIIEKYGVPEDIIIELARENNSKDKQKFINEMQKKNENTRKRI NEIIGKYGNQNAKRLVEKIRLHDEQEGKCLYSLES | *Staphylococcus lugdunensis* mini-domain 6 from 8 mini-domain library |
| 55 | RTFIQSINVINKVIEKYGIPEDIIIELARENNSDDRKKFINNLQKKNEATRKRINE IIGQTGNQNAKRIVEKIRLHDQQEGKCLYSLES | *Staphylococcus pasteuri* mini-domain 6 from 8 mini-domain library |
| 56 | RAFIQSIQVVNAIIDKYGLPEDIIIELARENNSDDRRKFLNQLQKQNEETRKQV EKVLREYGNDNAKRIVQKIKLHNMQEGKCLYSLKD | *Staphylococcus hyicus* mini-domain 6 from 8 mini-domain library |
| 57 | RSFKQAIGVVNAIIKKYGLPKDIIIELARESNSAEKSRYLRAIQKKNEKTRERIE AIIKEYGNENAKGLVQKIKLHDAQEGKCLYSLKD | *Staphylococcus microti* mini-domain 6 from 8 mini-domain library |
| 58 | IPLEDLLNNPNHYEVDHIIPRSVSFDNSYHNKVLVKQSENSKKSNLTPYQYFN SGKSKLSYNQFKQHILNLSKSQDRISKKKKEYLLEERDINKFEVQKEFINRNL VDTRYATREL | *Staphylococcus lugdunensis* mini-domain 7 from 8 mini-domain library |
| 59 | IALMDLLNNPQNYEVDHIIPRSVAFDNSIHNKVLVKQIENSKKGNRTPYQYLN SSDAKLSYNQFKQHILNLSKSKDRISKKKKDYLLEERDINKFEVQKEFINRNL VDTRYATREL | *Staphylococcus pasteuri* mini-domain 7 from 8 mini-domain library |
| 60 | IPLEDLLRNPHHYEVDHIIPRSVAFDNSMHNKVLVRADENSKKGNRTPYQYL NSSESSLSYNEFKQHILNLSKTKDRITKKKREYLLEERDINKFDVQKEFINRNL VDTRYATREL | *Staphylococcus hyicus* mini-domain 7 from 8 mini-domain library |
| 61 | IPLEDLLRNPNNYDIDHIIPRSVSFDDSMHNKVLVRREQNAKKNNQTPYQYLT SGYADIKYSVFKQHVLNLAENKDRMTKKKREYLLEERNINKYDVQKEFINR NLVDTRYTTREL | *Staphylococcus microti* mini-domain 7 from 8 mini-domain library |
| 62 | TNYLKAYFSANNMNVKVKTINGSFTDYLRKVWKFKKERNHGYKHHAEDAL IIANADFLFKENKKLKAVNSVLEKPEIETKQLDIQVDSEDNYSEMFIIPKQVQD IKDFRNFKYSHRVDKKPNRQLINDTLYSTRKKDNSTYIVQTIKDIYAKDNTTL KKQFDKSPEKFLMYQHDPRTFEKLEVIMKQYANEKNPLAKYHEETGEYLTK YSKKNNGPIVKSLKYIGNKLGSHLDVTHQFKSSTKKLVKLSIKPYRFDVYLT DKGYKFITISYLDVLKKDNYYYIPEQKYDKLKLGKAIDKNAKFIASFYKNDLI KLDGEIYKIIGVNSDTRNMIELDLPDIRYKEYCELNNIKGEPRIKKTIGKKVNSI EKLTTDVLGNVFTNTQYTKPQLLFKRGN | *Staphylococcus lugdunensis* mini-domain 8 from 8 mini-domain library |
| 63 | TSYLKAYFSANNMDVKVKTINGSFTNHLRKVWRFDKYRNHGYKHHAEDAL IIANADFLFKENKKLQNTNKILEKPTIENNTKKVTVEKEEDYNNVFETPKLVE DIKQYRDYKFSHRVDKKPNRQLINDTLYSTRMKDEHDYIVQTITDIYGKDNT NLKKQFNKNPEKFLMYQNDPKTFEKLSIIMKQYSDEKNPLAKYYEETGEYLT KYSKKNNGPIVKKIKLLGNKVGNHLDVTNKYENSTKKLVKLSIKNYRFDVY LTEKGYKFVTIAYLNVFKKDNYYYIPKDKYQELKEKKKIKDTDQFIASFYKN DLIKLNGDLYKIIGVNSDDRNIIELDYYDIKYKDYCEINNIKGEPRIKKTIGKKT ESIEKFTTDVLGNLYLHSTEKAPQLIFKRGL | *Staphylococcus pasteuri* mini-domain 8 from 8 mini-domain library |

SEQUENCE LISTING

| SEQ ID NO | Sequence | Description |
|---|---|---|
| 64 | TSLLKAYFSANNLDVKVKTINGSFTNYLRKVWKFDKDRNKGYKHHAEDALI IANADFLFKHNKKLRNINKVLDAPSKEVDKKRVTVQSEDEYNQIFEDTQKAQ AIKKFEIRKFSHRVDKKPNRQLINDTLYSTRNIDGIEYVVESIKDIYSVNNDKV KTKFKKDPHRLLMYRNDPQTFEKFEKVFKQYESEKNPFAKYYEETGEKIRKF SKTGQGPYINKIKYLRERLGRHCDVTNKYINSRNKIVQLKIYSYRFDIYQYGN NYKMITISYIDLEQKSNYYYISREKYEQKKKDKQIDDSYKFIGSFYKNDIINYN GEMYRVIGVNDSEKNKIQLDMIDISIKDYMELNNIKKTGVIYKTIGKSTTHIEK YTTDILGNLYKAAPPKKPQLIFK | *Staphylococcus hyicus* mini-domain 8 from 8 mini-domain library |
| 65 | TTLLKTYFTINNLDVKVKTINGSFTDFLRKRWGFKKNRDEGYKHHAEDALII ANADYLFKEHKLLKEIKDVSDLAGDERNSNVKDEDQYEEVFGGYFKIEDIKK YKIKKFSHRVDKKPNRQLINDTIYSTRVKDDKRYLINTLKNLYDKSNGDLKE RMQKDPESLLMYHHDPQTFEKLKIVMSQYENEKNPLAKYFEETGQYLTKYA KHDNGPAIHKIKYYGNKLVEHLDITKNYHNPQNKVVQLSQKSFRFDVYQTD KGYKFISIAYLTLKNEKNYYAISQEKYDQLKSEKKISNNAVFIGSFYTSDIIEIN NEKFRVIGVNSDKNNLIEVDRIDIRQKEFIELEEEKKNNRIKVTIGRKTTNIEKF HTDILGNMYKSKRPKAPQLVFKKG | *Staphylococcus microti* mini-domain 8 from 8 mini-domain library |
| 66 | MNQKFILGLDIGITSVGYGLIDYETKNIIDAGVRLFPEANV | *Staphylococcus lugdunensis* mini-domain 1 from 12 mini-domain library |
| 67 | MKEKYILGLDLGITSVGYGIINFETKKIIDAGVRLFPEANV | *Staphylococcus pasteuri* mini-domain 1 from 12 mini-domain library |
| 68 | MNNYILGLDIGITSVGYGIVDSDTREIKDAGVRLFPEANV | *Staphylococcus hyicus* mini-domain 1 from 12 mini-domain library |
| 69 | MEKDYILGLDIGIGSVGYGLIDYDTKSIIDAGVRLFPEANA | *Staphylococcus microti* mini-domain 1 from 12 mini-domain library |
| 70 | ENNEGRRSKRGSRRLKRRRIHRL | *Staphylococcus lugdunensis* mini-domain 2 from 12 mini-domain library |
| 71 | DNNEGRRSKRGSRRLKRRRIHRL | *Staphylococcus pasteuri* mini-domain 2 from 12 mini-domain library |
| 72 | DNNEGRRSKRGARRLKRRRIHRL | *Staphylococcus hyicus* mini-domain 2 from 12 mini-domain library |
| 73 | DNNLGRRAKRGARRLKRRRIHRL | *Staphylococcus microti* mini-domain 2 from 12 mini-domain library |
| 74 | ERVKKLLEDYNLLDQSQIPQSTNPYAIRVKGLSEALSKDELVIALLHIAKRRGIH | *Staphylococcus lugdunensis* mini-domain 3 from 12 mini-domain library |

SEQUENCE LISTING

| SEQ ID NO | Sequence | Description |
|---|---|---|
| 75 | ERVKLLLTEYDLINKEQIPTSNNPYQIRVKGLSEILSKDELAIALLHLAKRRGIH | *Staphylococcus pasteuri* mini-domain 3 from 12 mini-domain library |
| 76 | DRVKHLLAEYDLLDLTNIPKSTNPYQTRVKGLNEKLSKDELVIALLHIAKRRGIH | *Staphylococcus hyicus* mini-domain 3 from 12 mini-domain library |
| 77 | ERVKSLLSEYKIISGLAPTNNQPYNIRVKGLTEQLTKDELAVALLHIAKRRGIH | *Staphylococcus microti* mini-domain 3 from 12 mini-domain library |
| 78 | KIDVIDSNDDVGNELSTKEQLNKNSKLLKDKFVCQIQLERMNEGQVRGEKNRFKTADIIKEIIQLLNVQKNFHQLDENFINKYIELVEMRREY | *Staphylococcus lugdunensis* mini-domain 4 from 12 mini-domain library |
| 79 | NINVSSEDEDASNELSTKEQINRNNKLLKDKYVCEVQLQRLKEGQIRGEKNRFKTTDILKEIDQLLKVQKDYHNLDIDFINQYKEIVETRREY | *Staphylococcus pasteuri* mini-domain 4 from 12 mini-domain library |
| 80 | NVNVMMDDNDSGNELSTKDQLKKNAKALSDKYVCELQLERFEQDYKVRGEKNRFKTEDFVREARKLLETQSKFFEIDQTFIMRYIELIETRREY | *Staphylococcus hyicus* mini-domain 4 from 12 mini-domain library |
| 81 | NVDVAADKEETASDSLSTKDQINKNAKFLESRYVCELQKERLENEGHVRGVENRFLTKDIVREAKKIIDTQMQYYPEIDETFKEKYISLVETRREY | *Staphylococcus microti* mini-domain 4 from 12 mini-domain library |
| 82 | FEGPGKGSPYGWEGDPKAWYETLMGHCTYFPDELRSVKYAYSADLFNALNDLNNLVIQRDGLSKLEYHEKYHIIENVFKQKKKPTLKQIANEINVNPEDIKGYRITKSGKPQFT | *Staphylococcus lugdunensis* mini-domain 5 from 12 mini-domain library |
| 83 | FEGPGQGSPFGWNGDLKKWYEMLMGHCTYFPQELRSVKYAYSADLFNALNDLNNLIIQRDNSEKLEYHEKYHIIENVFKQKKKPTLKQIAKEIGVNPEDIKGYRITKSGTPQFT | *Staphylococcus pasteuri* mini-domain 5 from 12 mini-domain library |
| 84 | FEGPGKGSPFGWEGNIKKWFEQMMGHCTYFPEELRSVKYSYSAELFNALNDLNNLVITRDEDAKLNYGEKFQIIENVFKQKKTPNLKQIAIEIGVHETEIKGYRVNKSGKPEFT | *Staphylococcus hyicus* mini-domain 5 from 12 mini-domain library |
| 85 | YEGPGKGSPYGWDADVKKWYQLMMGHCTYFPVEFRSVKYAYTADLYNALNDLNNLTIARDDNPKLEYHEKYHIIENVFKQKRNPTLKQIAKEIGVNDINISGYRVTKSGKPQFT | *Staphylococcus microti* mini-domain 5 from 12 mini-domain library |
| 86 | EFKLYHDLKSVLFDQSILENEDVLDQIAEILTIYQDKDSIKSKLTELDILLNEEDKENIAQLTGYTGTHRLSLKCIRLVLEEQWYSSRNQMEIFTHLNIKPKKINLTAANKIPKAMIDEFILSPVVKR | *Staphylococcus lugdunensis* mini-domain 6 from 12 mini-domain library |

SEQUENCE LISTING

| SEQ ID NO | Sequence | Description |
|---|---|---|
| 87 | EFKLYHDLKSIVFDKSILENEAILDQIAEILTIYQDEQSIKEELNKLPEILNEQDK AEIAKLIGYNGTHRLSLKCIHLINEELWQTSRNQMEIFNYLNIKPNKVDLSEQ NKIPKDMVNDFILSPVVKR | Staphylococcus pasteuri mini-domain 6 from 12 mini-domain library |
| 88 | QFKLYHDLKNIFKDPKYLNDIQLMDNIAEIITIYQDAESIIKELNQLPELLSERE KEKISALSGYSGTHRLSLKCINLLLDDLWESSLNQMELFTKLNLKPKKIDLSQ QHKIPSKLVDDFILSPVVKR | Staphylococcus hyicus mini-domain 6 from 12 mini-domain library |
| 89 | SFKLFHDLKKVVKDHAILDDIDLLNQIAEILTIYQDKDSIVAELGQLEYLMSE ADKQSISELTGYTGTHSLSLKCMNMIIDELWHSSMNQMEVFTYLNMRPKKY ELKGYQRIPTDMIDDAILSPVVKR | Staphylococcus microti mini-domain 6 from 12 mini-domain library |
| 90 | TFGQAINLINKIIEKYGVPEDIIIELARENNSKDKQKFINEMQKKNENTRKRINE IIGKYGNQNAKRLVEKIRLHDEQEGKCLYSL | Staphylococcus lugdunensis mini-domain 7 from 12 mini-domain library |
| 91 | TFIQSINVINKVIEKYGIPEDIIIELARENNSDDRKKFINNLQKKNEATRKRINEII GQTGNQNAKRIVEKIRLHDQQEGKCLYSL | Staphylococcus pasteuri mini-domain 7 from 12 mini-domain library |
| 92 | AFIQSIQVVNAIIDKYGLPEDIIIELARENNSDDRRKFLNQLQKQNEETRKQVE KVLREYGNDNAKRIVQKIKLHNMQEGKCLYSL | Staphylococcus hyicus mini-domain 7 from 12 mini-domain library |
| 93 | SFKQAIGVVNAIIKKYGLPKDIIIELARESNSAEKSRYLRAIQKKNEKTRERIEA IIKEYGNENAKGLVQKIKLHDAQEGKCLYSL | Staphylococcus microti mini-domain 7 from 12 mini-domain library |
| 94 | ESIPLEDLLNNPNHYEVDHIIPRSVSFDNSYHNKVLVKQSENSKKSNLTPYQY FNSGKSKLSYNQFKQHILNLSKSQDRISKKKKEYLLEER | Staphylococcus lugdunensis mini-domain 8 from 12 mini-domain library |
| 95 | ESIALMDLLNNPQNYEVDHIIPRSVAFDNSIHNKVLVKQIENSKKGNRTPYQY LNSSDAKLSYNQFKQHILNLSKSKDRISKKKKDYLLEER | Staphylococcus pasteuri mini-domain 8 from 12 mini-domain library |
| 96 | KDIPLEDLLRNPHHYEVDHIIPRSVAFDNSMHNKVLVRADENSKKGNRTPYQ YLNSSESSLSYNEFKQHILNLSKTKDRITKKKREYLLEER | Staphylococcus hyicus mini-domain 8 from 12 mini-domain library |
| 97 | KDIPLEDLLRNPNNYDIDHIIPRSVSFDDSMHNKVLVRREQNAKKNNQTPYQ YLTSGYADIKYSVFKQHVLNLAENKDRMTKKKREYLLEER | Staphylococcus microti mini-domain 8 from 12 mini-domain library |
| 98 | DINKFEVQKEFINRNLVDTRYATRELT | Staphylococcus lugdunensis mini-domain 9 from 12 mini-domain library |

SEQUENCE LISTING

| SEQ ID NO | Sequence | Description |
|---|---|---|
| 99 | DINKFEVQKEFINRNLVDTRYATRELT | *Staphylococcus pasteuri* mini-domain 9 from 12 mini-domain library |
| 100 | DINKFDVQKEFINRNLVDTRYATRELT | *Staphylococcus hyicus* mini-domain 9 from 12 mini-domain library |
| 101 | NINKYDVQKEFINRNLVDTRYTTRELT | *Staphylococcus microti* mini-domain 9 from 12 mini-domain library |
| 102 | NYLKAYFSANNMNVKVKTINGSFTDYLRKVWKFKKERNHGYKHHAEDALIIANADFLFKENKKL | *Staphylococcus lugdunensis* mini-domain 10 from 12 mini-domain library |
| 103 | SYLKAYFSANNMDVKVKTINGSFTNHLRKVWRFDKYRNHGYKHHAEDALIIANADFLFKENKKL | *Staphylococcus pasteuri* mini-domain 10 from 12 mini-domain library |
| 104 | SLLKAYFSANNLDVKVKTINGSFTNYLRKVWKFDKDRNKGYKHHAEDALIIANADFLFKHNKKL | *Staphylococcus hyicus* mini-domain 10 from 12 mini-domain library |
| 105 | TLLKTYFTINNLDVKVKTINGSFTDFLRKRWGFKKNRDEGYKHHAEDALIIANADYLFKEHKLL | *Staphylococcus microti* mini-domain 10 from 12 mini-domain library |
| 106 | KAVNSVLEKPEIETKQLDIQVDSEDNYSEMFIIPKQVQDIKDFRNFKYSHRVDKKPNRQLINDTLYSTRKKDNSTYIVQTIKDIYAKDNTTLKKQFDKSPEKFLMYQHDPRTFEKLEVIMKQYANEKNPLAKYHEETGEYLTKYSKKNNGPIVKSLKYIGNKLGSHLDVTHQFKSSTKKLVKLSIK | *Staphylococcus lugdunensis* mini-domain 11 from 12 mini-domain library |
| 107 | QNTNKILEKPTIENNTKKVTVEKEEDYNNVFETPKLVEDIKQYRDYKFSHRVDKKPNRQLINDTLYSTRMKDEHDYIVQTITDIYGKDNTNLKKQFNKNPEKFLMYQNDPKTFEKLSIIMKQYSDEKNPLAKYYEETGEYLTKYSKKNNGPIVKKIKLLGNKVGNHLDVTNKYENSTKKLVKLSIK | *Staphylococcus pasteuri* mini-domain 11 from 12 mini-domain library |
| 108 | RNINKVLDAPSKEVDKKRVTVQSEDEYNQIFEDTQKAQAIKKFEIRKFSHRVDKKPNRQLINDTLYSTRNIDGIEYVVESIKDIYSVNNDKVKTKFKKDPHRLLMYRNDPQTFEKFEKVFKQYESEKNPFAKYYEETGEKIRKFSKTGQGPYINKIKYLRERLGRHCDVTNKYINSRNKIVQLK | *Staphylococcus hyicus* mini-domain 11 from 12 mini-domain library |
| 109 | KEIKDVSDLAGDERNSNVKDEDQYEEVFGGYFKIEDIKKYKIKKFSHRVDKKPNRQLINDTIYSTRVKDDKRYLINTLKNLYDKSNGDLKERMQKDPESLLMYHHDPQTFEKLKIVMSQYENEKNPLAKYFEETGQYLTKYAKHDNGPAIHKIKYYGNKLVEHLDITKNYHNPQNKVVQLSQK | *Staphylococcus microti* mini-domain 11 from 12 mini-domain library |
| 110 | PYRFDVYLTDKGYKFITISYLDVLKKDNYYYIPEQKYDKLKLGKAIDKNAKFIASFYKNDLIKLDGEIYKIIGVNSDTRNMIELDLPDIRYKEYCELNNIKGEPRIKKTIGKKVNSIEKLTTDVLGNVFTNTQYTKPQLLFKRGN | *Staphylococcus lugdunensis* mini-domain 12 from 12 mini-domain library |

SEQUENCE LISTING

| SEQ ID NO | Sequence | Description |
|---|---|---|
| 111 | NYRFDVYLTEKGYKFVTIAYLNVPKKDNYYYIPKDKYQELKEKKKIKDTDQ FIASFYKNDLIKLNGDLYKIIGVNSDDRNIIELDYYDIKYKDYCEINNIKGEPRI KKTIGKKTESIEKFTTDVLGNLYLHSTEKAPQLIFKRGL | *Staphylococcus pasteuri* mini-domain 12 from 12 mini-domain library |
| 112 | IYSYRFDIYQYGNNYKMITISYIDLEQKSNYYYISREKYEQKKKDKQIDDSYK FIGSFYKNDIINYNGEMYRVIGVNDSEKNKIQLDMIDISIKDYMELNNIKKTG VIYKTIGKSTTHIEKYTTDILGNLYKAAPPKKPQLIFK | *Staphylococcus hyicus* mini-domain 12 from 12 mini-domain library |
| 113 | SFRFDVYQTDKGYKFPISIAYLTLKNEKNYYAISQEKYDQLKSEKKISNNAVFI GSFYTSDIIEINNEKFRVIGVNSDKNNLIEVDRIDIRQKEFIELEEEKNNRIKV TIGRKTTNIEKFHTDILGNMYKSKRPKAPQLVFKKG | *Staphylococcus microti* mini-domain 12 from 12 mini-domain library |
| 114 | GGACCCCCUCCACCCCGCCUCGUUUUAGUACUCUGGAAACAGAAUCUAC UGAAACAAGACAAUAUGUCGUGUUUAUCCCAUCAAUUUAUUGGUGGGA UUUUUUU | sgRNAVEGFA |
| 115 | ACCCCCTCCACCCCGCCTCCGGGCGCG | ATTO647N oligonucleotide with "CGGGCGC"-PAM |
| 116 | GCGCGCGCCCGGAGGCGGGGTGGAGGGGGTCGG | Biotinylated oligonucleotide with "CGGGCGC"-PAM |
| 117 | GGGUCAGGGUGGUCACGAGG | BFP targeting guide RNA |
| 118 | CCACTGTAGAAGAGCAAATGCCACCTGACGTCTAAGAAATTCGCGTTAAA TTTTTGTTAAATCAGCTCATTTTTTAACCAATAGGCCGAAATCGGCAAAAT CCCTTATAAATCAAAAGAATAGACCGAGATAGGGTTGAGTGGCCGCTAC ACTAGGGCGCGTCTAATACGACTCACTATAGGACCCCCTCCACCCCGCCT CGTTTTAGTACTCTGGAAACAGAATCTACTGAAACAAGACAATATGTCGT GTTTATCCCATCAATTTATTGGTGGGATTTTTTTCTAGCATAACCCCTTGG GGCCTCTAAACGGGTCTTGAGGGGTTTTTTGTCACTGCCCGCTTTCCAGTC GGGAAACCTGTCGTGCCAGCTGCATTAATGAATCGTTCGTCAGAACTGCT TACGCGGTTTGTCACTCGGTCGCTACGCTCCGGGCGTGAGACTGCGGCGG GCGCTGCGGACACATACAAAGTTACCCACAGATTCCGTGGATAAGCAGG GGACTAACATGTGAGGCAAAACAGCAGGGCCGCGCCGGTGGCGTTTTTC CATAGGCTCCGCCCTCCTGCCAGAGTTCACATAAACAGACGCTTTTCCGG TGCATCTGTGGGAGCCGTGAGGCTCAACCATGAATCTGACAGTACGGGCG AAACCCGACAGGACTTAAAGATCCCCACCGTTTCCGGCGGGTCGCTCCCT CTTGCGCTCTCCTGTTCCGACCCTGCCGTTTACCGGATACCTGTTCCGCCT TTCTCCCTTACGGGAAGTGTGGCGCTTTCTCATAGCTCACACACTGGTATC TCGGCTCGGTGTAGGTCGTTCGCTCCAAGCTGGGCTGTAAGCAAGAACTC CCCGTTCAGCCCGACTGCTGCGCCTTATCCGGTAACTGTTCACTTGAGTCC AACCCGGAAAAGCACGGTAAAACGCCACTGGCAGCAGCCATTGGTAACT GGGAGTTCGCAGAGGATTGTTTAGCTAAACACGCGGTTGCTCTTGAAGT GTGCGCCAAAGTCCGGCTACACTGGAAGGACAGATTTGGTTGCTGTGCTC TGCGAAAGCCAGTTACCACGGTTAAGCAGTTCCCCAACTGACTTAACCTT CGATCAAACCACCTCCCCAGGTGGTTTTTTCGTTTACAGGGCAAAGATT ACGCGCAGAAAAAAGGATCTCAAGAAGATCCTTTGATCTTTTCTACTGA ACCGCTCAATCTAAAGTATATATGAGTAAACTTGGTCTGACAGTTATTAG AAAAACTCATCGAGCATCAAATGAAACTGCAATTTATTCATATCAGGATT ATCAATACCATATTTTTGAAAAAGCCGTTTCTGTAATGAAGGAGAAAACT CACCGAGGCAGTTCCATAGGATGGCAAGATCCTGGTATCGGTCTGCGATT CCGACTCGTCCAACATCAATACAACCTATTAATTTCCCCTCGTCAAAAAT AAGGTTATCAAGTGAGAAATCACCATGAGTGACGACTGAATCCGGTGAG AATGGCAAAGTTTATGCATTTCTTTCCAGACTTGTTCAACAGGCCAGCC ATTACGCTCGTCATCAAAATCACTCGCATCAACCAAACCGTTATTCATTC GTGATTGCGCCTGAGCGAGACGAAATACGCGATCGCTGTTAAAGGACA ATTACAAACAGGAATCGAATGCAACCGGCGCAGGAACACTGCCAGCGCA TCAACAATATTTTCACCTGAATCAGGATATTCTTCTAATACCTGGAATGCT GTTTTCCCGGGGATCGCAGTGGTGAGTAACCATGCATCATCAGGAGTACG | pCas606 |

SEQUENCE LISTING

| SEQ ID NO | Sequence | Description |
|---|---|---|
| | GATAAAATGCTTGATGGTCGGAAGAGGCATAAATTCCGTCAGCCAGTTTA<br>GTCTGACCATCTCATCTGTAACATCATTGGCAACGCTACCTTTGCCATGTT<br>TCAGAAACAACTCTGGCGCATCGGGCTTCCCATACAATCGATAGATTGTC<br>GCACCTGATTGCCCGACATTATCGCGAGCCCATTTATACCCATATAAATC<br>AGCATCCATGTTGGAATTTAATCGCGGCCTAGAGCAAGACGTTTCCCGTT<br>GAATATGGCTCATACTCTTCCTTTTTCAATATTATTGAAGCATTTATCAGG<br>GTTATTGTCTCATGAGCGGATACATATTTGAATGTATTTAGAAAAATAAA<br>CAAATAGGGGTTCCGCGCACATTTCCCCGAAAAGTG | |
| 119 | CCGGTGATACCACGATACTATGACTGAGAGTCAACGCCATGAGCGGCCTC<br>ATTTCTTATTCTGAGTTACAACAGTCCGCACCGCTGCCGGTAGCTATTGAC<br>TATCCGGCTGCACTAGCCCTGCGTCAGATGGCTCTGATCCAAGGCAAACT<br>GCCAAAATATCTGCTGGCACCGGAAGTCAGCGCCCTGCACCATTATGTTC<br>CGGATCTGCATCGCAGGATGCTGCTGGCTACCCTGTGGAACACCTACATC<br>TGTATTAACGAAGCGCTGGCATTGACCCTGAGTGATTTTTCTCTGGTGCCG<br>CCCTATCCCTTTGTGCAGCTTGCCACGCTCAAAGGGGTTTGAGGTCCAAC<br>CGTACGAAAACGTACGGTAAGAGGAAAATTATCGTCTGAAAAATCGATT<br>AGTAGACAAGAAAGTCCGTTAAGTGCCAATTTTCGATTAAAAAGACACC<br>GTTTTGATGGCGTTTTCCAATGTACATTATGTTTCGATATATCAGACAGTT<br>ACTTCACTAACGTACGTTTTCGTTCTATTGGCCTTCAGACCCCATATCCTT<br>AATGTCCTTTATTTGCTGGGGTTATCAGATCCCCCCGACACGTTTAATTAA<br>TGCTTTCTCCGCCGGAGATCGACGCACAGCGTTCTGTGCTCTATGATGTTA<br>TTTCTTAATAATCATCCAGGTATTCTCTTTATCACCATACGTAGTGCGAGT<br>GTCCACCTTAACGCAGGGCTTTCCGTCACAGCGCGATATGTCAGCCAGCG<br>GGGCTTTCTTTTGCCAGACCGCTTCCATCCTCTGCATTTCAGCAATCTGGC<br>TATACCCGTCATTCATAAACCACGTAAATGCCGTCACGCAGGAAGCCAGG<br>ACGAAGAATATCGTCAGTACAAGATAAATCGCGGATTTCCACGTATAGCG<br>TGACATCTCACGACGCATTTCATGGATCATCGCTTTCGCCGTATCGGCAG<br>CCTGATTCAGCGCTTCTGTCGCCGGTTTCTGCTGTGCTAATCCGGCTTGTT<br>TCAGTTCTTTCTCAACCTGAGTGAGCGCGGAACTCACCGATTTCCTGACG<br>GTGTCAGTCATATTACCGGACGCGCTGTCCAGCTCACGAATGACCCTGCT<br>CAGCGTTTCACTTTGCTGCTGTAATTGTGATGAGGCGGCCTGAAACTGTTC<br>TGTCAGAGAAGTAACACGCTTTTCCAGCGCCTGATGATGCCCGATAAGGG<br>CGGCAATTTGTTTAATTTCGTCGCTCATACAAAATCCTGCCTATCGTGAGA<br>ATGACCAGCCTTTATCCGGCTTCTGTCGTATCTGTTCGGCGAGTCGCTGTC<br>GTTCTTTCTCCTGCTGACGCTGTTTTTCCGCCAGACGTTCGCGCTCTCTCTG<br>CCTTTCCATCTCCTGATGTATCCCCTGGAACTCCGCCATCGCATCGTTAAC<br>AAGGGACTGAAGATCGATTTCTTCCTGTATATCCTTCATGGCATCACTGA<br>CCAGTGCGTTCAGCTTGTCAGGCTCTTTTTCAAAATCAAACGTTCTGCCGG<br>AATGGGATTCCTGCTCAGGCTCTGACTTCAGCTCCTGTTTTAGCGTCAGAG<br>TATCCCTCTCGCTGAGGGCTTCCCGTAACGAGGTAGTCACGTCAATTACG<br>CTGTCACGTTCATCACGGGACTGCTGCACCTGCCTTTCAGCCTCCCTGCGC<br>TCAAGAATGGCCTGTAGCTGCTCAGTATCGAATCGCTGAACCTGACCCGC<br>GCCCAGATGCCGCTCAGGCTCACGGTCAATGCCCTGCGCCTTCAGGGAAC<br>GGGAATCAACCCGGTCAGCGTGCTGATACCGTTCAAGGTGCTTATTCTGG<br>AGGTCAGCCCAGCGTTCCCTCTGGGCAACAAGGTATTCTTTGCGTTCGGT<br>CGGTGTTTCCCCGAAACGTGCCTTTTTTGCGCCACCGCGCTCCGGCTCTTT<br>GGTGTTAGCCCGTTTAAAATACTGCTCAGGGTCACGGTGAATACCGTCAT<br>TAATGCGTTCAGAGAACATGATATGGGCGTGGGGCTGCTCGCCACCGGCT<br>ATCGCTGCTTTCGGATTATGGATAGCGAACTGATAGGCATGGCGGTCGCC<br>AATTTCCTGTTGGACAAAATCGCGGACAAGCTCAAGACGTTGTTCGGGTT<br>TTAACTCACGCGGCAGGGCAATCTCGATTTCACGGTAGGTACAGCCGTTG<br>GCACGTTCAGACGTGTCAGCGGCTTTCCAGAACTCGGACGGTTTATGCGC<br>TGCCCACGCCGGCATATTGCCGGACTCCTTGTGCTCAAGGTCGGAGTCTT<br>TTTCACGGGCATACTTTCCCTCACGCGCAATATAATCGGCATGAGGAGAG<br>GCACTGCCTTTTCCGCCGGTTTTTACGCTGAGATGATAGGATGCCATCGTG<br>TTTTATCCCGCTGAAGGCGCGCACCGTTTCTGAACGAAGTGAAGAAACGT<br>CTAAGTGCGCCCTGATAAATAAAAGAGTTATCAGGGATTGTAGTGGGATT<br>TGACCTCCTCTGCCATCACTGAGCATAATCATTCCGTTAGCATTCAGGAG<br>GTAAACAGCATGAATAAAAGCGAAAAACAGGAACAATGGGCAGCAGAA<br>AGAGTGCAGTATATTCGCGGCTTAAAGTCGCCGAATGAGCAACAGAAAC<br>TTATGCTGATACTGACGGATAAAGCAGATAAAACAGCACAGATATCAA<br>AACGCTGTCCCTGCTGATGAAGGCTGAACAGGCAGCAGAGAAAGCGCAG<br>GAAGCCAGAGCGAAAGTCATGAACCTGATACAGGCAGAAAAGCGAGCCG<br>AAGCCAGAGCCGCCCGTAAAGCCCGTGACCATGCTCTGTACCAGTCTGCC<br>GGATTGCTTATCCTGGCGGGTCTGGTTGACAGTAAGACGGGTAAGCCTGT<br>TGATGATACCGCTGCCTTACTGGGTGCATTAGCCAGTCTGAATGACCTGT<br>CACGGGATAATCCGAAGTGGTCAGACTGGAAAATCAGAGGGCAGGAACT<br>GCTGAACAGCAAAAGTCAGATAGCACCACATAGCAGACCCGCCATAAA<br>ACGCCCTGAGAAGCCCGTGACGGGCTTTTCTTGTATTATGGGTAGTTTCCT<br>TGCATGAATCCATAAAAGGCGCCTGTAGTGCCATTTACCCCCATTCACTG<br>CCAGAGCCGTGAGCGCAGCGAACTGAATGTCACGAAAAAGACAGCGACT<br>CAGGTGCCTGATGGTCGGAGACAAAAGGAATATTCAGCGATTTGCCCGA | pCas634 |

SEQUENCE LISTING

| SEQ ID NO | Sequence | Description |
|---|---|---|
| | GCTTGCGAGGGTGCTACTTAAGCCTTTAGGGTTTTAAGGTCTGTTTTGTAG | |
| | AGGAGCAAACAGCGTTTGCGACATCCTTTTGTAATACTGCGGAACTGACT | |
| | AAAGTAGTGAGTTATACACAGGGCTGGGATCTATTCTTTTTATCTTTTTT | |
| | ATTCTTTCTTTATTCTATAAATTATAACCACTTGAATATAAACAAAAAAA | |
| | CACACAAAGGTCTAGCGGAATTTACAGAGGGTCTAGCAGAATTTACAAG | |
| | TTTTCCAGCAAAGGTCTAGCAGAATTTACAGATACCCACAACTCAAAGGA | |
| | AAAGGACTAGTAATTATCATTGACTAGCCCATCTCAATTGGTATAGTGAT | |
| | TAAAATCACCTAGACCAATTGAGATGTATGTCTGAATTAGTTGTTTTCAA | |
| | AGCAAATGAACTAGCGATTAGTCGCTATGACTTAACGGAGCATGAAACC | |
| | AAGCTAATTTTATGCTGTGTGGCACTACTCAACCCCACGATTGAAAACCC | |
| | TACAAGGAAAGAACGGACGGTATCGTTCACTTATAACCAATACGCTCAG | |
| | ATGATGAACATCAGTAGGGAAAATGCTTATGGTGTATTAGCTAAAGCAAC | |
| | CAGAGAGCTGATGACGAGAACTGTGGAAATCAGGAATCCTTTGGTTAAA | |
| | GGCTTTGAGATTTTCCAGTGGACAAACTATGCCAAGTTCTCAAGCGAAAA | |
| | ATTAGAATTAGTTTTTAGTGAAGAGATATTGCCTTATCTTTTCCAGTTAAA | |
| | AAAATTCATAAAATATAATCTGGAACATGTTAAGTCTTTTGAAAACAAAT | |
| | ACTCTATGAGGATTTATGAGTGGTTATTAAAAGAACTAACACAAAAGAA | |
| | AACTCACAAGGCAATATAGAGATTAGCCTTGATGAATTTAAGTTCATGT | |
| | TAATGCTTGAAAATAACTACCATGAGTTTAAAAGGCTTAACCAATGGGTT | |
| | TTGAAACCAATAAGTAAAGATTTAAACACTTACAGCAATATGAAATTGGT | |
| | GGTTGATAAGCGAGGCCGCCCGACTGATACGTTGATTTTCCAAGTTGAAC | |
| | TAGATAGACAAATGGATCTCGTAACCGAACTTGAGAACAACCAGATAAA | |
| | AATGAATGGTGACAAAATACCAACAACCATTACATCAGATTCCTACCTAC | |
| | ATAACGGACTAAGAAAAACACTACACGATGCTTTAACTGCAAAAATTCA | |
| | GCTCACCAGTTTTGAGGCAAAATTTTTGAGTGACATGCAAAGTAAGTATG | |
| | ATCTCAATGGTTCGTTCTCATGGCTCACGCAAAAACAACGAACCACACTA | |
| | GAGAACATACTGGCTAAATACGGAAGGATCTGAGGTTCTTATGGCTCTTG | |
| | TATCTATCAGTGAAGCATCAAGACTAACAAACAAAAGTAGAACAACTGT | |
| | TCACCGTTACATATCAAAGGGAAAACTGTCCATATGCACAGATGAAAAC | |
| | GGTGTAAAAAGATAGATACATCAGAGCTTTTACGAGTTTTTGGTGCATT | |
| | CAAAGCTGTTCACCATGAACAGATCGACAATGTAACAGATGAACAGCAT | |
| | GTAACACCTAATAGAACAGGTGAAACCAGTAAAACAAAGCAACTAGAAC | |
| | ATGAAATTGAACACCTGAGACAACTTGTTACAGCTCAACAGTCACACATA | |
| | GACAGCCTGAAACAGGCGATGCTGCTTATCGAATCAAAGCTGCCGACAA | |
| | CACGGGAGCCAGTGACGCCTCCCGTGGGGAAAAAATCATGGCAATTCTG | |
| | GAAGAAATAGCGCTTTCAGCCGGCAAACCGGCTGAAGCCGGATCTGCGA | |
| | TTCTGATAACAAACTAGCAACACCAGAACAGCCCGTTTGCGGGCAGCAA | |
| | AACCCGTACTTTTGGACGTTCCGGCGGTTTTTTGTGGCGAGTGGTGTTCGG | |
| | GCGGTGCGCGCAAGATCCATTATGTTAAACGGGCGAGTTTACATCTCAAA | |
| | ACCGCCCGCTTAACACCATCAGAAATCCTCAGCGCGATTTTAAGCACCAA | |
| | CCCCCCCCCGTAACACCCAAATCCATACTGAAAGTGGCTTTGTTGAATAA | |
| | ATCGAACTTTTGCTGAGTTGAAGGATCAGATCACGCATCCTCCCGACAAC | |
| | ACAGACCATTCCGTGGCAAAGCAAAAGTTCAGAATCACCAACTGGTCCA | |
| | CCTACAACAAAGCTCTCATCAACCGTGGCTCCCTCACTTTCTGGCTGGAT | |
| | GATGAGGCGATTCAGGCCTGGTATGAGTCGGCAACACCTTCATCACGAGG | |
| | AAGGCCCCAGCGCTATTCTGATCTCGCCATCACCACCGTTCTGGTGATTA | |
| | AACGCGTATTCCGGCTGACCCTGCGGGCTGCGCAGGGTTTTATTGATTCC | |
| | ATTTTTGCCCTGATGAACGTTCCGTTGCGCTGCCCGGATTACACCAGTGTC | |
| | AGTAAGCGGGCAAAGTCGGTTAATGTCAGTTTCAAAACGTCCACCCGGG | |
| | GTGAAATCGCACACCTGGTGATTGATTCCACCGGGCTGAAGGTCTTTGGT | |
| | GAAGGCGAATGGAAAGTCAGAAAGCACGGCAAAGAGCGCCGTCGTATCT | |
| | GGCGAAAGTTGCATCTTGCTGTTGACAGCAACACACATGAAGTTGTCTGT | |
| | GCAGACCTGTCGCTGAATAACGTCACGGACTCAGAAGCCTTCCCGGGCCT | |
| | TATCCGGCAGACTCACAGAAAAATCAGGGCAGCCGCGGCAGACGGGGCT | |
| | TACGATACCCGGCTCTGTCACGATGAACTGCGCCGCAAAAAAATCAGCGC | |
| | GCTTATTCCTCCCCGAAAAGGTGCGGGTTACTGGCCCGGTGAATATGCAG | |
| | ACCGTAACCGTGCAGTGGCTAATCAGCGAATGACCGGGAGTAATGCGCG | |
| | GTGGAAATGGACAACAGATTACAACCGTCGCTCGATAGCGGAAACGGCG | |
| | ATGTACCGGGTAAAACAGCTGTTCGGGGGTTCACTGACGCTGCGTGACTA | |
| | CGATGGTCAGGTTGCGGAGGCTATGGCCCTGGTACGAGCGCTGAACAAA | |
| | ATGACGAAAGCAGGTATGCCTGAAAGCGTGCGTATTGCCTGAAAACACA | |
| | ACCCGCTACGGGGGAGACTTACCCGAAATCTGATTTATTCAACAAAGCCG | |
| | GGTGTGGTGAACTACAAAGCAGACCCGTTGAGGTTATCAGTTCGATGCAC | |
| | AATCAGCAGCGCATAAAATATGCACAAGAACAGGAGCACCCTTCGCATT | |
| | AAGCTGTGGTGGTAACAAGTAGTGCCGGGCTACCATCAGCGAGCATGAT | |
| | GCGCTCCCACAGCATTCGCCTTGGCAGTATGGAAGTTCCTCGCTCCAGTT | |
| | CGGGCCGGTATCCACCTCGAGCTTTCTACGGGGTCTGACGCTCAGTGGAA | |
| | CGAAAACTCACGTTAAGGGATTTTGGTCATGAGATTATCAAAAAGGATCT | |
| | TCACCTAGATCCTTTTCGACCGAATAAATACCTGTGACGGAAGATCACTT | |
| | CGCAGAATAAATAAATCCTGGTGTCCCTGTTGATACCGGGAAGCCCTGGG | |
| | CCAACTTTTGGCGAAAATGAGACGTTGATCGGCACGTAAGAGGTTCCAAC | |
| | TTTCACCATAATGAAATAAGATCACTACCGGGCGTATTTTTGAGTTGTCG | |
| | AGATTTTCAGGAGCTAAGGAAGCTAAAATGGAGAAAAAAATCACTGGAT | |

| SEQ ID NO | Sequence | Description |
|---|---|---|
| | ATACCACCGTTGATATATCCCAATGGCATCGTAAAGAACATTTTGAGGCA<br>TTTCAGTCAGTTGCTCAATGTACCTATAACCAGACCGTTCAGCTGGATATT<br>ACGGCCTTTTTAAAGACCGTAAAGAAAAATAAGCACAAGTTTTATCCGGC<br>CTTTATTCACATTCTTGCCCGCCTGATGAATGCTCATCCGGAATTACGTAT<br>GGCAATGAAAGACGGTGAGCTGGTGATATGGGATAGTGTTCACCCTTGTT<br>ACACCGTTTTCCATGAGCAAACTGAAACGTTTTCATCGCTCTGGAGTGAA<br>TACCACGACGATTTCCGGCAGTTTCTACACATATATTCGCAAGATGTGGC<br>GTGTTACGGTGAAAACCTGGCCTATTTCCCTAAAGGGTTTATTGAGAATA<br>TGTTTTTCGTCTCAGCCAATCCCTGGGTGAGTTTCACCAGTTTTGATTTAA<br>ACGTGGCCAATATGGACAACTTCTTCGCCCCCGTTTTCACCTTGGGCAAA<br>TATTATACGCAAGGCGACAAGGTGCTGATGCCGCTGGCGATTCAGGTTCA<br>TCATGCCGTTTGTGATGGCTTCCATGTCGGCAGAATGCTTAATGAATTAC<br>AACAGTACTGCGATGAGTGGCAGGGCGGGGCGTAATTTTTTTAAGGCAGT<br>TATTGGTGCCCTTAAACGCCTGGTTGCTACGCCTGAATAAGTGATAATAA<br>GCGGATGAATGGCAGAAATTCGAAAGCAAATTCGACCCGGTCGTCGGTT<br>CAGGGCAGGGTCGTTAAATAGCCGCTTATGTCTATTGCTGGTTTACCGGA<br>TTATTGACTACCGGAAGCAGTGTGACCGTGTGCTTCTCAAATGCCTGAGG<br>CCAGTTTGCTCAGGCTCTCCCGTGGAGGTAATAATTGACGATATGATCC<br>TTTTTTTCTGATCAAAGTGCTCCATGGAATTATGACAACTTGACGGCTAC<br>ATCATTCACTTTTTCTTCACAACCGGCACGGAACTCGCTCGGGCTGGCCC<br>GGTGCATTTTTTAAATACCCGCGAGAAATAGAGTTGATCGTCAAAACCAA<br>CATTGCGACCGACGGTGGCGATAGGCATCCGGGTGGTGCTCAAAAGCAG<br>CTTCGCCTGGCTGATACGTTGGTCCTCGCGCCAGCTTAAGACGCTAATCC<br>CTAACTGCTGGCGGAAAAGATGTGACAGACGCGACGGCGACAAGCAAAC<br>ATGCTGTGCGACGCTGGCGATATCAAAATTGCTGTCTGCCAGGTGATCGC<br>TGATGTACTGACAAGCCTCGCGTACCCGATTATCCATCGGTGGATGGAGC<br>GACTCGTTAATCGCTTCCATGCGCCGCAGTAACAATTGCTCAAGCAGATT<br>TATCGCCAGCAGCTCCGAATAGCGCCCTTCCCCTTGCCCGGCGTTAATGA<br>TTTGCCCAAACAGGTCGCTGAAATGCGGCTGGTGCGCTTCATCCGGGCGA<br>AAGAACCCCGTATTGGCAAATATTGACGGCCAGTTAAGCCATTCATGCCA<br>GTAGGCGCGCGGACGAAAGTAAACCCACTGGTGATACCATTCGCGAGCC<br>TCCGGATGACGACCGTAGTGATGAATCTCTCCTGGCGGGAACAGCAAAT<br>ATCACCCGGTCGGCAAACAAATTCTCGTCCCTGATTTTTCACCACCCCTG<br>ACCGCGAATGGTGAGATTGAGAATATAACCTTTCATTCCCAGCGGTCGGT<br>CGATAAAAAAATCGAGATAACCGTTGGCCTCAATCGGCGTTAAACCCGCC<br>ACCAGATGGGCATTAAACGAGTATCCCGGCAGCAGGGGATCATTTTGCGC<br>TTCAGCCATACTTTTCATACTCCCGCCATTCAGAGAAGAAACCAATTGTC<br>CATATTGCATCAGACATTGCCGTCACTGCGTCTTTTACTGGCTCTTCTCGC<br>TAACCAAACCGGAAACCCCGCTTATTAAAAGCATTCTGTAACAAAGCGG<br>GACCAAAGCCATGACAAAAACGCGTAACAAAAGTGTCTATAATCACGGC<br>AGAAAAGTCCACATTGATTATTTGCACGGCGTCACACTTTGCTATGCCAT<br>AGCATTTTATCCATAAGATTAGCGGATCCTACCTGACGCTTTTTATCGCA<br>ACTCTCTACTGTCGTGCGCAACGCGTGACATCGACTAGGAGGCCTTTCTA<br>TGCAGTTCAAAGTGTATACCTATAAACGCGAAAGCCGTTATCGTCTGTTT<br>GTTGATGTTCAGAGCGATATTATTGATACACCGGGTCGTCGTATGGTTATT<br>CCGCTGGCAAGCGCACGTCTGCTGAGCGATAAAGTTAGCCGTGAACTGTA<br>TCCGGTTGTTCATATTGGTGATGAAAGCTGGCGTATGATGACCACCGATA<br>TGGCAAGCGTTCCGGTTAGCGTTATTGGTGAAGAAGTTGCAGATCTGAGC<br>CATCGTGAAAACGATATCAAAAATGCCATCAACCTGATGTTTTGGGGCAT<br>CTTATAGGACCCCCTCCACCCCGCCTCGCGGGCAGTTTGCCTGGCGGCAG<br>TAGCGCGGTGGTCCCACCTGACCCCATGCCGAACTCAGAAGTGAAACGCC<br>GTAGCGCCGATGGTAGTGTGGGCTCTCCCCATGCGAGAGTAGGGAACTGC<br>CAGGCATCAAATAAAACGAAAGGCTCAGTCGAAAGACTGGGCCTTA | |
| 120 | GGTGGAAGCGGAGGCAGCGGGGGATCAGGCCATCATCATCACCATCATT<br>AATGAACGGGTCTTGAGGGGTTTTTTGGACTTTTGCGTATTGGGCGCTCTT<br>CCGCTTCCTCGCTCACTGACTCGCTGCGCTCGGTCGTTCGGCTGCGGCGA<br>GCGGTATCAGCTCACTCAAAGGCGGTAATACGGTTATCCACAGAATCAGG<br>GGATAACGCAGGAAAGAACATGTGAGCAAAAGGCCAGCAAAAGGCCAG<br>GAACCGTAAAAAGGCCGCGTTGCTGGCGTTTTTCCATAGGCTCCGCCCCC<br>CTGACGAGCATCACAAAAATCGACGCTCAAGTCAGAGGTGGCGAAACCC<br>GACAGGACTATAAAGATACCAGGCGTTTCCCCCTGGAAGCTCCCTCGTGC<br>GCTCTCCTGTTCCGACCCTGCCGCTTACCGGATACCTGTCCGCCTTTCTCC<br>CTTCGGGAAGCGTGGCGCTTTCTCATAGCTCACGCTGTAGGTATCTCAGTT<br>CGGTGTAGGTCGTTCGCTCCAAGCTGGGCTGTGTGCACGAACCCCCCGTT<br>CAGCCCGACCGCTGCGCCTTATCCGGTAACTATCGTCTTGAGTCCAACCC<br>GGTAAGACACGACTTATCGCCACTGGCAGCAGCCACTGGTAACAGGATT<br>AGCAGAGCGAGGTATGTAGGCGGTGCTACAGAGTTCTTGAAGTGGTGGC<br>CTAACTACGGCTACACTAGAAGGACAGTATTTGGTATCTGCGCTCTGCTG<br>AAGCCAGTTACCTTCGGAAAAAGAGTTGGTAGCTCTTGATCCGGCAAACA<br>AACCACCGCTGGTAGCGGTGGTTTTTTTGTTTGCAAGCAGCAGATTACGC<br>GCAGAAAAAAAGGATCTCAAGAAGATCCTTTGATCTTTTCTACGGGGTCT<br>GACGCTCAGTGGAACGAAAACTCACGTTAAGGGATTTTGGTCATGAGATT | pCas81 |

SEQUENCE LISTING

| SEQ ID NO | Sequence | Description |
|---|---|---|
| | ATCAAAAAGGATCTTCACCTAGATCCTTTTAAATTAAAAATGAAGTTTTA | |
| | AATCAATCTAAAGTATATATGAGTAAACTTGGTCTGACAGTTACCAATGC | |
| | TTAATCAGTGAGGCACCTATCTCAGCGATCTGTCTATTTCGTTCATCCATA | |
| | GTTGCCTGACTCCCCGTCGTGTAGATAACTACGATACGGGAGGGCTTACC | |
| | ATCTGGCCCCAGTGCTGCAATGATACCGCGAGATCCACGCTCACCGGCTC | |
| | CAGATTTATCAGCAATAAACCAGCCAGCCGGAAGGGCCGAGCGCAGAAG | |
| | TGGTCCTGCAACTTTATCCGCCTCCATCCAGTCTATTAATTGTTGCCGGGA | |
| | AGCTAGAGTAAGTAGTTCGCCAGTTAATAGTTTGCGCAACGTTGTTGCCA | |
| | TTGCTGCAGGCATCGTGGTGTCACGCTCGTCGTTTGGTATGGCTTCATTCA | |
| | GCTCCGGTTCCCAACGATCAAGGCGAGTTACATGATCCCCATGTTGTGC | |
| | AAAAAAGCGGTTAGCTCCTTCGGTCCTCCGATCGTTGTCAGAAGTAAGTT | |
| | GGCCGCAGTGTTATCACTCATGGTTATGGCAGCACTGCATAATTCTCTTAC | |
| | TGTCATGCCATCCGTAAGATGCTTTTCTGTGACTGGTGAGTACTCAACCA | |
| | AGTCATTCTGAGAATAGTGTATGCGGCGACCGAGTTGCTCTTGCCCGGCG | |
| | TCAATACGGGATAATACCGCGCCACATAGCAGAACTTTAAAAGTGCTCAT | |
| | CATTGGAAAACGTTCTTCGGGGCGAAAACTCTCAAGGATCTTACCGCTGT | |
| | TGAGATCCAGTTCGATGTAACCCACTCGTGCACCCAACTGATCTTCAGCA | |
| | TCTTTTACTTTCACCAGCGTTTCTGGGTGAGCAAAAACAGGAAGGCAAAA | |
| | TGCCGCAAAAAAGGGAATAAGGGCGACACGGAAATGTTGAATACTCATA | |
| | CTCTTCCTTTTTCAATATTATTGAAGCATTTATCAGGGTTATTGTCTCATG | |
| | AGCGGATACATATTTGAATGTATTTAGAAAAATAAACAAATAGGGGTTCC | |
| | GCGCACATTTCCCCGAAAAGTGCCACCTCCTCTTGCTGTGACCGTCTCCGG | |
| | GAGCTGCATGTGTCAGAGGTTTTCACCGTCATCACCGAAACGCGCGAGGC | |
| | AGCAGATCAATTCGCGCGCGAAGGCGAAGCGGCATGCATTTACGTTGAC | |
| | ACCATCGAATGGTGCAAAACCTTTCGCGGTATGGCATGATAGCGCCCGGA | |
| | AGAGAGTCAATTCAGGGTGGTGAATGTGAAACCAGTAACGTTATACGAT | |
| | GTCGCAGAGTATGCCGGTGTCTCTTATCAGACCGTTTCCCGCGTGGTGAA | |
| | CCAGGCCAGCCACGTTTCTGCGAAAACGCGGGAAAAAGTGGAAGCGGCG | |
| | ATGGCGGAGCTGAATTACATTCCCAACCGCGTGGCACAACAACTGGCGG | |
| | GCAAACAGTCGTTGCTGATTGGCGTTGCCACCTCCAGTCTGGCCCTGCAC | |
| | GCGCCGTCGCAAATTGTCGCGGCGATTAAATCTCGCGCCGATCAACTGGG | |
| | TGCCAGCGTGGTGGTGTCGATGGTAGAACGAAGCGGCGTCGAAGCCTGT | |
| | AAAGCGGCGGTGCACAATCTTCTCGCGCAACGCGTCAGTGGGCTGATCAT | |
| | TAACTATCCGCTGGATGACCAGGATGCCATTGCTGTGGAAGCTGCCTGCA | |
| | CTAATGTTCCGGCGTTATTTCTTGATGTCTCTGACCAGACACCCATCAACA | |
| | GTATTATTTTCTCCCATGAAGATGGTACGCGACTGGGCGTGGAGCATCTG | |
| | GTCGCATTGGGTCACCAGCAAATCGCGCTGTTAGCGGGCCCATTAAGTTC | |
| | TGTCTCGGCGCGTCTGCGTCTGGCTGGCTGGCATAAATATCTCACTCGCA | |
| | ATCAAATTCAGCCGATAGCGGAACGGGAAGGCGACTGGAGTGCCATGTC | |
| | CGGTTTTCAACAAACCATGCAAATGCTGAATGAGGGCATCGTTCCCACTG | |
| | CGATGCTGGTTGCCAACGATCAGATGGCGCTGGGCGCAATGCGCGCCATT | |
| | ACCGAGTCCGGGCTGCGCGTTGGTGCGGATATCTCGGTAGTGGGATACGA | |
| | CGATACCGAAGATAGCTCATGTTATATCCCGCCGTTAACCACCATCAAAC | |
| | AGGATTTTCGCCTGCTGGGGCAAACCAGCGTGGACCGCTTGCTGCAACTC | |
| | TCTCAGGGCCAGGCGGTGAAGGGCAATCAGCTGTTGCCCGTCTCACTGGT | |
| | GAAAAGAAAAACCACCCTGGCGCCCAATACGCAAACCGCCTCTCCCCGC | |
| | GCGTTGGCCGATTCATTAATGCAGCTGGCACGACAGGTTTCCCGACTGGA | |
| | AAGCGGGCAGTGAGCGCAATATTCTGAAATGAGCTGTTGACAATTAATCA | |
| | TCCGGCTCGTATAATGTGTGGAATTGTGAGCGGATAACAATTTTCACACA | |
| | GGAAACAGAATTCTAGCATTGTGAGCGGATAACAATTCCCCTCTAGAAAT | |
| | AATTTTGTTTAACTTTAAGAAGGAGATATACCATGAAACGTCCGCAGCA | |
| | ACCAAAAAAGCAGGTCAGGCCAAGAAAAAAAAGGTGGTGGTTCAGGTA | |
| | ACCAGAAATTTATCCTGGGTCTGGATATTGGTATTACCAGCGTTGGTTAT | |
| | GGCCTGATTGATTACGAAACCAAAAACATTATTGATGCCGGTGTTCGTCT | |
| | GTTTCCGGAAGCAAATGTTGAAAATAATGAAGGTCGTCGTAGCAAACGT | |
| | GGTAGCCGTCGTCTGAAACGTCGTCGTATTCATCGTCTGGAACGTGTTAA | |
| | AAAACTGCTGGAAGATTATAACCTGCTGGATCAGAGCCAGATTCCGCAG | |
| | AGCACCAATCCGTATGCAATTCGTGTTAAAGGTCTGAGCGAAGCACTGAG | |
| | CAAAGATGAACTGGTTATTGCACTGCTGCATATTGCAAAACGCCGTGGCA | |
| | TTCATAAAATCGATGTGATTGATAGCAATGACGATGTGGGTAATGAACTG | |
| | AGCACCAAAGAACAGCTGAACAAAAATAGCAAACTGCTGAAAGACAAAT | |
| | TCGTGTGTCAGATTCAGCTGGAACGTATGAATGAAGGCCAGGTTCGTGGT | |
| | GAAAAGAATCGCTTTAAAACCGCAGACATCATCAAAGAAATTATCCAGC | |
| | TGCTGAACGTGCAGAAAAACTTCCATCAGCTGGATGAAAACTTCATCAAC | |
| | AAATACATCGAGCTGGTTGAAATGCGTCGCGAATATTTTGAAGGTCCGGG | |
| | TAAAGGTAGCCCGTATGGTTGGGAAGGTGATCCGAAAGCATGGTATGAA | |
| | ACCCTGATGGGTCATTGTACCTATTTTCGGATGAACTGCGTAGCGTTAA | |
| | ATATGCCTATAGCGCAGACCTGTTTAATGCACTGAATGATCTGAATAACC | |
| | TGGTGATTCAGCGTGATGGTCTGAGCAAACTGGAATATCATGAGAAATAT | |
| | CACATCATCGAAACGTGTTCAAACAGAAGAAGAAACCGACCCTGAAAC | |
| | AAATCGCCAACGAAATTAATGTGAACCCGGAAGATATTAAAGGCTACCG | |
| | TATTACCAAAAGCGGTAAACCGCAGTTCACCGAATTTAAACTGTATCACG | |
| | ATCTGAAAAGCGTGCTGTTTGATCAGAGCATTCTGGAAAATGAAGATGTG | |

| SEQ ID NO | Sequence | Description |
|---|---|---|
| | CTGGACCAGATTGCAGAAATTCTGACCATTTATCAGGACAAAGACAGCAT<br>CAAAAGCAAACTGACCGAACTGGATATTCTGCTGAATGAAGAAGATAAA<br>GAGAACATTGCACAGCTGACCGGTTATACCGGCACCCATCGTCTGAGCCT<br>GAAATGTATTCGTCTGGTACTGGAAGAACAGTGGTATAGCAGCCGTAATC<br>AGATGGAAATCTTTACCCATCTGAACATTAAACCGAAGAAAATCAATCTG<br>ACCGCAGCCAACAAAATTCCGAAAGCCATGATTGATGAGTTTATTCTGAG<br>TCCGGTTGTGAAACGTACCTTTGGTCAGGCAATTAACCTGATCAACAAAA<br>TCATTGAAAAATATGGCGTGCCTGAGGATATCATTATTGAACTGGCACGT<br>GAAAACAACAGCAAAGATAAACAGAAATTCATCAACGAGATGCAGAAG<br>AAGAACGAAAATACCCGCAAACGGATTAACGAGATCATTGGCAAATATG<br>GTAATCAGAATGCCAAACGCCTGGTGGAAAAAATTCGTCTGCATGATGA<br>ACAAGAGGGCAAATGTCTGTATAGCCTGGAAAGCATTCCTCTGGAAGATC<br>TGCTGAACAATCCGAATCATTATGAAGTGGATCACATTATTCCGCGTAGC<br>GTGAGCTTTGATAATTCCTATCATAATAAAGTGCTGGTGAAACAGAGCGA<br>AAACTCCAAAAAATCCAACCTGACACCGTATCAGTATTTCAATAGCGGCA<br>AATCCAAACTGAGCTACAACCAGTTTAAACAGCATATTCTGAACCTGAGC<br>AAAAGCCAGGATCGCATCAGCAAGAAGAAGAAGGAGTACCTGCTGGAAG<br>AACGCGACATCAACAAATTTGAAGTGCAGAAAGAATTTATCAACCGCAA<br>CCTGGTTGATACCCGTTATGCAACCCGTGAACTGACCAATTATCTGAAAG<br>CATATTTCAGCGCCAACAACATGAACGTGAAAGTGAAAACGATTAACGG<br>CAGCTTTACCGATTATCTGCGTAAAGTGTGGAAATTCAAAAAAGAACGCA<br>ACCACGGCTATAAACATCATGCCGAAGATGCCCTGATTATTGCAAATGCA<br>GATTTCCTGTTTAAAGAAAACAAAAAACTGAAAGCCGTCAACAGCGTGCT<br>GGAAAAAACCGGAAATTGAGACAAAACAGCTGGACATTCAGGTTGATAGC<br>GAAGATAATTACAGCGAAATGTTTATCATCCCGAAACAGGTGCAGGATAT<br>CAAAGATTTTCGCAACTTCAAATATAGCCACCGCGTTGACAAAAAACCTA<br>ATCGTCAGCTGATTAACGATACCCTGTATAGCACCCGCAAAAAGATAAC<br>AGCACCTATATTGTGCAGACCATTAAAGACATCTACGCCAAAGATAACA<br>CACCCTGAAAAACAGTTCGACAAAAGCCCAGAAAAATTTCTGATGTATC<br>AGCATGATCCGCGTACCTTCGAAAAACTGGAAGTTATTATGAAACAGTAT<br>GCCAACGAGAAAAATCCGCTGGCCAAATATCACGAAGAAACCGGTGAAT<br>ATCTGACCAAATATTCCAAGAAGAACAACGGTCCGATCGTTAAATCCCTG<br>AAATATATCGGTAATAAACTGGGCAGCCATCTGGATGTTACCCATCAGTT<br>TAAAAGCTCCACAAAGAAGCTGGTTAAACTGTCCATCAAACCGTATCGCT<br>TTGATGTGTATCTGACCGACAAAGGCTATAAATTCATTACCATCAGCTAT<br>CTGGACGTGCTGAAAAAAGACAACTATTATTATATCCCGGAACAGAAAT<br>ATGATAAACTGAAACTGGGGTAAAGCCATCGATAAAAACGCCAAATTTAT<br>CGCCAGCTTCTACAAAAACGACCTGATTAAACTGGATGGCGAGATCTATA<br>AAATCATCGGTGTTAATAGCGACACCCGCAATATGATTGAGCTGGATCTG<br>CCGGATATTCGCTATAAAGAATATTGCGAACTGAACAACATTAAAGGCG<br>AACCGCGTATCAAAAAGACCATCGGCAAAAAGTGAATAGCATCGAGAA<br>ACTGACCACCGATGTTCTGGGTAATGTGTTTACCAATACCCAGTATACCA<br>AACCTCAGCTGCTGTTCAAACGCGGTAATGGCGGAGGATCTGGCCCCCCT<br>AAGAAAAAGCGGAAGGTG | |
| 121 | TGCCACCTCCAGTCTGGCCCTGCACGCGCCGTCGCAAATTGTCGCGGCGA<br>TTAAATCTCGCGCCGATCAACTGGGTGCCAGCGTGGTGGTGTCGATGGTA<br>GAACGAAGCGGCGTCGAAGCCTGTAAAGCGGCGGTGCACAATCTTCTCG<br>CGCAACGCGTCAGTGGGCTGATCATTAACTATCCGCTGGATGACCAGGAT<br>GCCATTGCTGTGGAAGCTGCCTGCACTAATGTTCCGGCGTTATTTCTTGAT<br>GTCTCTGACCAGACACCCATCAACAGTATTATTTTCTCCCATGAAGATGG<br>TACGCGACTGGGCGTGGAGCATCTGGTCGCATTGGGTCACCAGCAAATCG<br>CGCTGTTAGCGGGCCCATTAAGTTCTGTCTCGGCGCGTCTGCGTCTGGCTG<br>GCTGGCATAAATATCTCACTCGCAATCAAATTCAGCCGATAGCGGAACGG<br>GAAGGCGACTGGAGTGCCATGTCCGGTTTTCAACAAACCATGCAAATGCT<br>GAATGAGGGCATCGTTCCCACTGCGATGCTGGTTGCCAACGATCAGATGG<br>CGCTGGGCGCAATGCGCGCCATTACCGAGTCCGGGCTGCGCGTTGGTGCG<br>GATATCTCGGTAGTGGGATACGACGATACCGAAGATAGCTCATGTTATAT<br>CCCGCCGTTAACCACCATCAAACAGGATTTTCGCCTGCTGGGGCAAACCA<br>GCGTGGACCGCTTGCTGCAACTCTCTCAGGGCCAGGCGGTGAAGGGCAAT<br>CAGCTGTTGCCCGTCTCACTGGTGAAAAGAAAAACCACCCTGGCGCCCAA<br>TACGGCAAACCGCCTCTCCCCGCGCGTTGGCCGATTCATTAATGCAGCTGG<br>CACGACAGGTTTCCCGACTGGAAAGCGGGCAGTGAGCGCAATATTCTGA<br>AATGAGCTGTTGACAATTAATCATCCGGCTCGTATAATGTGTGGAATTGT<br>GAGCGGATAACAATTTTCACACAGGAAACAGAATTCTAGCATTGTGAGC<br>GGATAACAATTCCCCTCTAGAAATAATTTTGTTTAACTTTAAGAAGGAGA<br>TATACCATGAAACGTCCGGCAGCAACCAAAAAAGCAGGTCAGGCCAAGA<br>AAAAAAAGGTGGTGGTTCAGGCAACAACTATATTCTGGGTCTGGATATT<br>GGTATTACCAGCGTTGGTTATGGTATTGTTGATAGCGATACCCGTGAAAT<br>TAAAGATGCCGGTGTTCGTCGTTTCCGGAAGCAAATGTTGATAATAATG<br>AAGGTCGTCGTAGCAAACGTGGTGCACGTCGTCTGAAACGTCGTCGTATT<br>CATCGTCTGGATCGTGTTAAACATCTGCTGGCAGAATATGATCTGCTGGA<br>TCTGACCAATATTCCGAAAAGCACCAATCCGTATCAGACCCGTGTTAAAG | pCas888 |

SEQUENCE LISTING

| SEQ ID NO | Sequence | Description |
|---|---|---|
| | GTCTGAATGAAAAGCTGAGCAAAGATGAACTGGTTATTGCACTGCTGCAT | |
| | ATTGCAAAACGCCGTGGCATTCATAATGTGAATGTTATGATGGATGATAA | |
| | CGATAGCGGTAATGAACTGAGCACCAAAGATCAGCTGAAGAAGAATGCA | |
| | AAAGCACTGAGCGATAAATATGTTTGTGAACTGCAGCTGGAACGCTTTGA | |
| | GCAGGATTATAAAGTTCGTGGTGAAAAGAACCGCTTCAAAACCGAAGAT | |
| | TTTGTTCGTGAAGCACGTAAACTGCTGGAAACCCAGAGCAAATTTTTCGA | |
| | AATTGATCAGACGTTCATCATGCGCTATATCGAACTGATTGAAACCCGTC | |
| | GCGAATATTTTGAAGGTCCGGGTAAAGGTAGCCCGTTTGGTTGGGAAGGT | |
| | AATATCAAGAATGGTTTGAGCAGATGATGGGCCACTGTACCTATTTTCC | |
| | AGAAGAACTGCGTAGCGTCAAATATAGCTATTCAGCCGAACTGTTTAACG | |
| | CCCTGAATGATCTGAATAATCTGGTGATTACCCGTGATGAAGATGCCAAA | |
| | CTGAATTATGGTGAGAAATTCCAGATCATCGAAAACGTGTTCAAACAGAA | |
| | GAAAACACCGAACCTGAAACAAATCGCCATTGAAATTGGTGTGCATGAA | |
| | ACCGAAATCAAAGGTTATCGTGTGAACAAAAGCGGCAAACCGGAATTTA | |
| | CCCAGTTCAAACTGTATCACGATCTGAAGAACATCTTCAAAGACCCGAAA | |
| | TACCTGAACGATATCCAGCTGATGGATAACATTGCAGAAATCATCACCAT | |
| | TTATCAGGATGCCGAAAGCATCATCAAAGAACTGAATCAGCTGCCGGAA | |
| | CTGCTGAGCGAACGTGAAAAGGAGAAGATCAGCGCACTGAGCGGTTATA | |
| | GCGGCACCCATCGTCTGAGCCTGAAATGTATTAATCTGCTGCTGGATGAT | |
| | CTGTGGGAAAGCAGCCTGAATCAGATGGAACTGTTCACAAAACTGAATCT | |
| | GAAACCGAAGAAAATCGATCTGAGCCAGCAGCATAAAATTCCGAGCAAA | |
| | CTGGTGGATGACTTTATTCTGAGTCCGGTTGTTAAACGTGCATTTATTCAG | |
| | AGTATCCAGGTGGTGAATGCCATCATTGATAAATACGGTCTGCCGGAAGA | |
| | TATCATCATTGAACTGGCACGTGAAAACAATAGTGATGATCGTCGCAAAT | |
| | TTCTGAACCAGCTGCAAAAGCAGAATGAGGAAACCCGTAAACAGGTTGA | |
| | AAAGGTGCTGCGTGAATATGGCAATGATAATGCCAAACGTATCGTGCAG | |
| | AAAATCAAACTGCATAATATGCAAGAGGGGAAATGTCTGTATAGCCTGA | |
| | AAGATATTCCGCTGGAAGATCTGCTGCGTAATCCGCATCATTATGAAGTG | |
| | GATCATATTATTCCGCGTAGCGTGGCATTTGATAATAGCATGCATAATAA | |
| | AGTTCTGGTGCGTGCCGATGAGAATAGCAAGAAAGGTAATCGTACCCCGT | |
| | ATCAGTATCTGAATAGCAGCGAAAGCAGTCTGAGCTATAACGAATTTAAA | |
| | CAGCATATCCTGAACCTGAGCAAAACCAAAGACCGCATCACCAAGAAGA | |
| | AGCGTGAATACCTGCTGGAAGAACGCGACATCAACAAATTTGATGTGCA | |
| | GAAAGAATTCATCAACCGCAATCTGGTTGATACACGTTATGCAACCCGTG | |
| | AACTGACCAGCCTGCTGAAAGCATATTTCAGCGCAAATAACCTGGACGTG | |
| | AAAGTGAAAACGATTAATGGCAGCTTTACCAACTATCTGCGTAAAGTGTG | |
| | GAAATTCGATAAAGATCGCAACAAAGGCTATAAACATCATGCAGAAGAT | |
| | GCCCTGATTATTGCCAATGCAGATTTTCTGTTCAAACACAACAAGAAACT | |
| | GCGCAACATTAACAAAGTGCTGGATGCACCGAGCAAAGAAGTTGATAAG | |
| | AAACGCGTGACAGTTCAGAGCGAAGATGAATATAACCAGATTTTTGAGG | |
| | ATACCCAGAAAGCCCAGGCAATCAAGAAATTCGAAATCCGCAAATTTAG | |
| | CCACCGCGTGGACAAGAAACCGAATCGTCAGCTGATTAATGATACCCTGT | |
| | ATAGCACCCGTAATATCGATGGTATTGAATATGTGGTCGAGAGCATCAAA | |
| | GATATCTATAGCGTGAACAACGATAAAGTTAAAACCAAATTCAAGAAAG | |
| | ACCCGCACCGTCTGCTGATGTATCGTAATGATCCGCAGACCTTTGAGAAA | |
| | TTCGAGAAAGTCTTTAAACAGTATGAGAGCGAGAAGAACCCGTTCGCCA | |
| | AATATTACGAAGAAACCGGTGAGAAAATTCGCAAATTCAGCAAAACCGG | |
| | TCAGGGTCCGTATATCAACAAAATCAAATATCTGCGTGAACGCCTGGGTC | |
| | GTCATTGTGATGTTACCAACAAATATATCAATAGCCGCAACAAATTTGTG | |
| | CAACTGTCCATCAAACCGTATCGCTTTGATGTGTATCTGACCGACAAAGG | |
| | CTATAAATTCATTACCATCAGCTATCTGGACGTGCTGAAAAAAGACAACT | |
| | ATTATTATATCCCGGAACAGAAATATGATAAACTGAAACTGGGTAAAGCC | |
| | ATCGATAAAAACGCCAAATTTATCGCCAGCTTCTACAAAAAACGACCTGAT | |
| | TAAACTGGATGGCGAGATCTATAAAATCATCGGTGTTAATAGCGACACCC | |
| | GCAATATGATTGAGCTGGATCTGCCGGATATTCGCTATAAAGAATATTGC | |
| | GAACTGAACAACATTAAAGGCGAACCGCGTATCAAAAAGACCATCGGCA | |
| | AAAAAGTGAATAGCATCGAGAAACTGACCACCGATGTTCTGGGGTAATGT | |
| | GTTTACCAATACCCAGTATACCAAACCTCAGCTGCTGTTCAAACGCGGTA | |
| | ATGGCGGAGGATCTGGCCCCCCTAAGAAAAAGCGGAAGGTGGGTGGAAG | |
| | CGGAGGCAGCGGGGGATCAGGCCATCATCATCACCATCATTAATGAACG | |
| | GGTCTTGAGGGGTTTTTTGGACTTTTGCGTATTGGGCGCTCTTCCGCTTCC | |
| | TCGCTCACTGACTCGCTGCGCTCGGTCGTTCGGCTGCGGCGAGCGGTATC | |
| | AGCTCACTCAAAGGCGGTAATACGGTTATCCACAGAATCAGGGGATAAC | |
| | GCAGGAAAGAACATGTGAGCAAAAGGCCAGCAAAAGGCCAGGAACCGT | |
| | AAAAAGGCCGCGTTGCTGGCGTTTTTCCATAGGCTCCGCCCCCCTGACGA | |
| | GCATCACAAAAATCGACGCTCAAGTCAGAGGTGGCGAAACCCGACAGGA | |
| | CTATAAAGATACCAGGCGTTTCCCCCTGGAAGCTCCCTCGTGCGCTCTCCT | |
| | GTTCCGACCCTGCCGCTTACCGGATACCTGTCCGCCTTTCTCCCTTCGGGA | |
| | AGCGTGGCGCTTTCTCATAGCTCACGCTGTAGGTATCTCAGTTCGGTGTA | |
| | GGTCGTTCGCTCCAAGCTGGGCTGTGTGCACGAACCCCCCGTTCAGCCCG | |
| | ACCGCTGCGCCTTATCCGGTAACTATCGTCTTGAGTCCAACCCGGTAAGA | |
| | CACGACTTATCGCCACTGGCAGCAGCCACTGGTAACAGGATTAGCAGAG | |
| | CGAGGTATGTAGGCGGTGCTACAGAGTTCTTGAAGTGGTGGCCTAACTAC |

| SEQ ID NO | Sequence | Description |
|---|---|---|
| | GGCTACACTAGAAGGACAGTATTTGGTATCTGCGCTCTGCTGAAGCCAGT<br>TACCTTCGGAAAAAGAGTTGGTAGCTCTTGATCCGGCAAACAAACCACCG<br>CTGGTAGCGGTGGTTTTTTTGTTTGCAAGCAGCAGATTACGCGCAGAAAA<br>AAAGGATCTCAAGAAGATCCTTTGATCTTTTCTACGGGGTCTGACGCTCA<br>GTGGAACGAAAACTCACGTTAAGGGATTTTGGTCATGAGATTATCAAAAA<br>GGATCTTCACCTAGATCCTTTTAAATTAAAAATGAAGTTTTAAATCAATCT<br>AAAGTATATATGAGTAAACTTGGTCTGACAGTTACCAATGCTTAATCAGT<br>GAGGCACCTATCTCAGCGATCTGTCTATTTCGTTCATCCATAGTTGCCTGA<br>CTCCCCGTCGTGTAGATAACTACGATACGGGAGGGCTTACCATCTGGCCC<br>CAGTGCTGCAATGATACCGCGAGATCCACGCTCACCGGCTCCAGATTTAT<br>CAGCAATAAACCAGCCAGCCGGAAGGGCCGAGCGCAGAAGTGGTCCTGC<br>AACTTTATCCGCCTCCATCCAGTCTATTAATTGTTGCCGGGAAGCTAGAGT<br>AAGTAGTTCGCCAGTTAATAGTTTGCGCAACGTTGTTGCCATTGCTGCAG<br>GCATCGTGGTGTCACGCTCGTCGTTTGGTATGGCTTCATTCAGCTCCGGTT<br>CCCAACGATCAAGGCGAGTTACATGATCCCCCATGTTGTGCAAAAAAGCG<br>GTTAGCTCCTTCGGTCCTCCGATCGTTGTCAGAAGTAAGTTGGCCGCAGT<br>GTTATCACTCATGGTTATGGCAGCACTGCATAATTCTCTTACTGTCATGCC<br>ATCCGTAAGATGCTTTTCTGTGACTGGTGAGTACTCAACCAAGTCATTCTG<br>AGAATAGTGTATGCGGCGACCGAGTTGCTCTTGCCCGGCGTCAATACGGG<br>ATAATACCGCGCCACATAGCAGAACTTTAAAAGTGCTCATCATTGGAAAA<br>CGTTCTTCGGGGCGAAAACTCTCAAGGATCTTACCGCTGTTGAGATCCAG<br>TTCGATGTAACCCACTCGTGCACCCAACTGATCTTCAGCATCTTTTACTTT<br>CACCAGCGTTTCTGGGTGAGCAAAAACAGGAAGGCAAAATGCCGCAAAA<br>AAGGGAATAAGGGCGACACGGAAATGTTGAATACTCATACTCTTCCTTTT<br>TCAATATTATTGAAGCATTTATCAGGGTTATTGTCTCATGAGCGGATACAT<br>ATTTGAATGTATTTAGAAAAATAAACAAATAGGGGTTCCGCGCACATTTC<br>CCCGAAAAGTGCCACTCCTCTTGCTGTGACCGTCTCCGGGAGCTGCATGT<br>GTCAGAGGTTTTCACCGTCATCACCGAAACGCGCGAGGCAGCAGATCAAT<br>TCGCGCGCGAAGGCGAAGCGGCATGCATTTACGTTGACACCATCGAATG<br>GTGCAAAACCTTTCGCGGTATGGCATGATAGCGCCCGGAAGAGAGTCAA<br>TTCAGGGTGGTGAATGTGAAACCAGTAACGTTATACGATGTCGCAGAGTA<br>TGCCGGTGTCTCTTATCAGACCGTTTCCCGCGTGGTGAACCAGGCCAGCC<br>ACGTTTCTGCGAAAACGCGGGAAAAAGTGGAAGCGGCGATGCGGAGCT<br>GAATTACATTCCCAACCGCGTGGCACAACAACTGGCGGGCAAACAGTCG<br>TTGCTGATTGGCGT | |
| 122 | CGGAACGGGAAGGCGACTGGAGTGCCATGTCCGGTTTTCAACAAACCAT<br>GCAAATGCTGAATGAGGGCATCGTTCCCACTGCGATGCTGGTTGCCAACG<br>ATCAGATGGCGCTGGGCGCAATGCGCGCCATTACCGAGTCCGGCTGCGC<br>GTTGGTGCGGATATCTCGGTAGTGGGATACGACGATACCGAAGATAGCTC<br>ATGTTATATCCCGCCGTTAACCACCATCAAACAGGATTTTCGCCTGCTGG<br>GGCAAACCAGCGTGGACCGCTTGCTGCAACTCTCTCAGGGCCAGGCGGTG<br>AAGGGCAATCAGCTGTTGCCCGTCTCACTGGTGAAAAGAAAAACCACCCT<br>GGCGCCCAATACGCAAACCGCCTCTCCCCGCGCGTTGGCCGATTCATTAA<br>TGCAGCTGGCACGACAGGTTTCCCGACTGGAAAGCGGGCAGTGAGCGCA<br>ATATTCTGAAATGAGCTGTTGACAATTAATCATCCGGCTCGTATAATGTG<br>TGGAATTGTGAGCGGATAACAATTTTCACACAGGAAACAGAATTCTAGCA<br>TTGTGAGCGGATAACAATTCCCCTCTAGAAATAATTTTGTTTAACTTTAAG<br>AAGGAGATATACCATGAAACGTCCGGCAGCAACCAAAAAAGCAGGTCAG<br>GCCAAGAAAAAAAAGGTGGTGGTTCAGGCAACAACTATATTCTGGGTC<br>TGGATATTGGTATTACCAGCGTTGGTTATGGTATTGTTGATAGCGATACCC<br>GTGAAATTAAAGATGCCGGTGTTCGTCTGTTTCCGGAAGCAAATGTTGAT<br>AATAATGAAGGTCGTCGTAGCAAACGTGGTGCACGTCGTCTGAAACGTCG<br>TCGTATTCATCGTCTGGATCGTGTTAAACATCTGCTGGCAGAATATGATCT<br>GCTGGATCTGACCAATATTCCGAAAAGCACCAATCCGTATCAGACCCGTG<br>TTAAAGGTCTGAATGAAAAGCTGAGCAAAGATGAACTGGTTATTGCACTG<br>CTGCATATTCAAAACGCCGTGGCATTCATAATGTGAATGTTATGATGGA<br>TGATAACGATAGCGGTAATGAACTGAGCACCAAAGATCAGCTGAAGAAG<br>AATGCAAAAGCACTGAGCGATAAATATGTTTGTGAACTGCAGCTGGAAC<br>GCTTTGAGCAGGATTATAAAGTTCGTGGTGAAAAGAACCGCTTCAAAACC<br>GAAGATTTTGTTCGTGAAGCACGTAAACTGCTGGAAACCCAGAGCAAATT<br>TTTTCGAAATTGATCAGACGTTCATCATGCGCTATATCGAACTGATTGAAA<br>CCCGTCGCGAATATTTTGAAGGTCCGGGTAAAGGTAGCCCGTTTGGTTGG<br>GAAGGTAATATCAAGAAATGGTTTGAGCAGATGATGGGCCACTGTACCT<br>ATTTTCCAGAAGAACTGCGTAGCGTCAAATATAGC | pCas889 |
| 123 | CTTGTACTTATACCTAAAATTACAGAATCTACTGAAACAAGACAATATGT<br>CGTGTTTATCCCATCAATTTATTGGTGGGATTTTTTTATGTTTTTAGCAAA<br>AAGTAATACCATACTTTATATTTTAAATTATAATAAAGATATAAATAAA<br>GGTGG | SluCas9 tracr RNA |
| 124 | ATGAAACGTCCGGCAGCAACCAAAAAAGCAGGTCAGGCCAAGAAAAAA<br>AAAGGTGGTGGTTCAGGTAACCAGAAATTTATCCTGGGTCTGGATATTGG | SluCas9 codon optimized DNA |

SEQUENCE LISTING

| SEQ ID NO | Sequence | Description |
|---|---|---|
| | TATTACCAGCGTTGGTTATGGCCTGATTGATTACGAAACCAAAACATTA<br>TTGATGCCGGTGTTCGTCTGTTTCCGGAAGCAAATGTTGAAAATAATGAA<br>GGTCGTCGTAGCAAACGTGGTAGCCGTCGTCTGAAACGTCGTCGTATTCA<br>TCGTCTGGAACGTGTTAAAAAACTGCTGGAAGATTATAACCTGCTGGATC<br>AGAGCCAGATTCCGCAGAGCACCAATCCGTATGCAATTCGTGTTAAAGGT<br>CTGAGCGAAGCACTGAGCAAAGATGAACTGGTTATTGCACTGCTGCATAT<br>TGCAAAACGCCGTGGCATTCATAAAATCGATGTGATTGATAGCAATGACG<br>ATGTGGGTAATGAACTGAGCACCAAAGAACAGCTGAACAAAAATAGCAA<br>ACTGCTGAAAGACAAATTCGTGTGTCAGATTCAGCTGGAACGTATGAATG<br>AAGGCCAGGTTCGTGGTGAAAAGAATCGCTTTAAAACCGCAGACATCAT<br>CAAAGAAATTATCCAGCTGCTGAACGTGCAGAAAAACTTCCATCAGCTGG<br>ATGAAAACTTCATCAACAAATACATCGAGCTGGTTGAAATGCGTCGCGAA<br>TATTTTGAAGGTCCGGGTAAAGGTAGCCCGTATGGTTGGGAAGGTGATCC<br>GAAAGCATGGTATGAAACCCTGATGGGTCATTGTACCTATTTTCCGGATG<br>AACTGCGTAGCGTTAAATATGCCTATAGCGCAGACCTGTTTAATGCACTG<br>AATGATCTGAATAACCTGGTGATTCAGCGTGATGGTCTGAGCAAACTGGA<br>ATATCATGAGAAATATCACATCATCGAAAACGTGTTCAAACAGAAGAAG<br>AAACCGACCCTGAAACAAATCGCCAACGAATTAATGTGAACCCGGAAG<br>ATATTAAAGGCTACCGTATTACCAAAAGCGGTAAACCGCAGTTCACCGAA<br>TTTAAACTGTATCACGATCTGAAAAGCGTGCTGTTTGATCAGAGCATTCT<br>GGAAAATGAAGATGTGCTGGACCAGATTGCAGAAATTCTGACCATTTATC<br>AGGACAAAGACAGCATCAAAAGCAAACTGACCGAACTGGATATTCTGCT<br>GAATGAAGAAGATAAAGAGAACATTGCACAGCTGACCGGTTATACCGGC<br>ACCCATCGTCTGAGCCTGAAATGTATTCGTCTGGTACTGGAAGAACAGTG<br>GTATAGCAGCCGTAATCAGATGGAAATCTTTACCCATCTGAACATTAAAC<br>CGAAGAAAATCAATCTGACCGCAGCCAACAAATTCCGAAAGCATGAT<br>TGATGAGTTTATTCTGAGTCCGGTTGTGAAACGTACCTTTGGTCAGGCAA<br>TTAACCTGATCAACAAAATCATTGAAAAATATGGCGTGCCTGAGGATATC<br>ATTATTGAACTGGCACGTGAAAACAACAGCAAAGATAAACAGAAATTCA<br>TCAACGAGATGCAGAAGAAGAACGAAATACCCGCAAACGGATTAACGA<br>GATCATTGGCAAATATGGTAATCAGAATGCCAAACGCCTGGTGGAAAAA<br>ATTCGTCTGCATGATGAACAAGAGGGCAAATGTCTGTATAGCCTGGAAAG<br>CATTCCTCTGGAAGATCTGCTGAACAATCCGAATCATTATGAAGTGGATC<br>ACATTATTCCGCGTAGCGTGAGCTTTGATAATTCCTATCATAATAAAGTG<br>CTGGTGAAACAGAGCGAAAACTCCAAAAAATCCAACCTGACACCGTATC<br>AGTATTTCAATAGCGGCAAATCCAAACTGAGCTACAACCAGTTTAAACAG<br>CATATTCTGAACCTGAGCAAAAGCCAGGATCGCATCAGCAAGAAGAAGA<br>AGGAGTACCTGCTGGAAGAACGCGACATCAACAAATTTGAAGTGCAGAA<br>AGAATTTATCAACCGCAACCTGGTTGATACCCGTTATGCAACCCGTGAAC<br>TGACCAATTATCTGAAAGCATATTTCAGCGCCAACAACATGAACGTGAAA<br>GTGAAAACGATTAACGGCAGCTTTACCGATTATCTGCGTAAAGTGTGGAA<br>ATTCAAAAAAGAACGCAACCACGGCTATAAACATCATGCCGAAGATGCC<br>CTGATTATTGCAAATGCAGATTTCCTGTTTAAAGAAAACAAAAACTGAA<br>AGCCGTCAACAGCGTGCTGGAAAAACCGGAAATTGAGACAAAACAGCTG<br>GACATTCAGGTTGATAGCGAAGATAATTACAGCGAAATGTTTATCATCCC<br>GAAACAGGTGCAGGATATCAAAGATTTTCGCAACTTCAAATATAGCCACC<br>GCGTTGACAAAAAACCTAATCGTCAGCTGATTAACGATACCCTGTATAGC<br>ACCCGCAAAAAGATAACAGCACCTATATTGTGCAGACCATTAAAGACA<br>TCTACGCCAAAGATAATACCACCCTGAAAAAACAGTTCGACAAAAGCCC<br>AGAAAATTTCTGATGTATCAGCATGATCCGCGTACCTTCGAAAAACTGG<br>AAGTTATTATGAAACAGTATGCCAACGAGAAAAATCCGCTGGCCAAATA<br>TCACGAAGAAACCGGTGAATATCTGACCAAATATTCCAAGAAGAACAAC<br>GGTCCGATCGTTAAATCCCTGAAATATATCGGTAATAAACTGGGCAGCCA<br>TCTGGATGTTACCCATCAGTTTAAAAGCTCCACAAAGAAGCTGGTTAAAC<br>TGTCCATCAAACCGTATCGCTTTGATGTGTATCTGACCGACAAAGGCTAT<br>AAATTCATTACCATCAGCTATCTGGACGTGCTGAAAAAAGACAACTATTA<br>TTATATCCCGGAACAGAAATATGATAAACTGAACTGGGTAAAGCCATC<br>GATAAAAACGCCAAATTTATCGCCAGCTTCTACAAAAACGACCTGATTAA<br>ACTGGATGGCGAGATCTATAAAATCATCGGTGTTAATAGCGACACCCGCA<br>ATATGATTGAGCTGGATCTGCCGGATATTCGCTATAAAGAATATTGCGAA<br>CTGAACAACATTAAAGGCGAACCGCGTATCAAAAAGACCATCGGCAAAA<br>AAGTGAATAGCATCGAGAAACTGACCACCGATGTTCTGGGTAATGTGTTT<br>ACCAATACCCAGTATACCAAACCTCAGCTGCTGTTCAAACGCGGTAATGG<br>CGGAGGATCTGGCCCCCCTAAGAAAAAGCGGAAGGTGGGTGGAAGCGGA<br>GGCAGCGGGGGATCAGGCCATCATCATCACCATCATTAA | |
| 125 | MNQKFILGLDIGITSVGYGLIDYETKNIIDAGVRLFPEANVENNEGRRSKRGS<br>RRLKRRRIHRLERVKKLLEDYNLLDQSQIPQSTNPYAIRVKGLSEALSKDELV<br>IALLHIAKRRGIHKIDVIDSNDDVGNELSTKEQLNKNSKLLKDKFVCQIQLER<br>MNEGQVRGEKNRFKTADIIKEIIQLLNVQKNFHQLDENFINKYIELVEMRREY<br>FEGPGKGSPYGWEGDPKAWYETLMGHCTYFPDELRSVKYAYSADLFNALN<br>DLNNLVIQRDGLSKLEYHEKYHIIENVFKQKKKPTLKQIANEINVNPEDIKGY<br>RITKSGKPQFTEFKLYHDLKSVLFDQSILENEDVLDQIAEILTIYQDKDSIKSKL | SluCas9 polypeptide |

SEQUENCE LISTING

| SEQ ID NO | Sequence | Description |
|---|---|---|
| | TELDILLNEEDKENIAQLTGYTGTHRLSLKCIRLVLEEQWYSSRNQMEIFTHL<br>NIKPKKINLTAANKIPKAMIDEFILSPVVKRTFGQAINLINKIIEKYGVPEDIII<br>ELARENNSKDKQKFINEMQKKNENTRKRINEIIGKYGNQNAKRLVEKIRLHDEQ<br>EGKCLYSLESIPLEDLLNNPNHYEVDHIIPRSVSFDNSYHNKVLVKQSENSKK<br>SNLTPYQYFNSGKSKLSYNQFKQHILNLSKSQDRISKKKKEYLLEERDINKFE<br>VQKEFINRNLVDTRYATRELTNYLKAYFSANNMNVKVKTINGSFTDYLRKV<br>WKFKKERNHGYKHHAEDALIIANADFLFKENKKLKAVNSVLEKPEIETKQL<br>DIQVDSEDNYSEMFIIPKQVQDIKDFRNFKYSHRVDKKPNRQLINDTLYSTRK<br>KDNSTYIVQTIKDIYAKDNTTLKKQFDKSPEKFLMYQHDPRTFEKLEVIMKQ<br>YANEKNPLAKYHEETGEYLTKYSKKNNGPIVKSLKYIGNKLGSHLDVTHQF<br>KSSTKKLVKLSIKPYRFDVYLTDKGYKFITISYLDVLKKDNYYYIPEQKYDKL<br>KLGKAIDKNAKFIASFYKNDLIKLDGEIYKIIGVNSDTRNMIELDLPDIRYKEY<br>CELNNIKGEPRIKKTIGKKVNSIEKLTTDVLGNVFTNTQYTKPQLLFKRGNGG | |
| 126 | YGRKKRRQRRR | Residues 47-57 of HIV-1 TAT |
| 127 | RQIKIWFQNRRMKWKK | Penetratin |
| 128 | ggugaacguggaugaaguugguuuuaguacucuggaaacagaaucuacugaaaca<br>agacaauaugucguguuuauccaucaauuuauuggugggauuuuuuucuagcau<br>aaccccuuggggccucuaaacgggucuugaggggguuuuuu | sgRNA_Ex6 |
| 129 | ggtgaacgtggatgaagttgtggggtac | R01-1-A |
| 130 | gcggtaccccacaacttcatccacgttcaccgg | R01-1-B |
| 131 | agtgaacgtggatgaagttgtggggtac | R01-2-A |
| 132 | gcggtaccccacaacttcatccacgttcactgg | R01-2-B |
| 133 | cgtgaacgtggatgaagttgtggggtac | R01-3-A |
| 134 | gcggtaccccacaacttcatccacgttcacggg | R01-3-B |
| 135 | tgtgaacgtggatgaagttgtggggtac | R01-4-A |
| 136 | gcggtaccccacaacttcatccacgttcacagg | R01-4-B |
| 137 | gatgaacgtggatgaagttgtggggtac | R01-5-A |
| 138 | gcggtaccccacaacttcatccacgttcatcgg | R01-5-B |
| 139 | gctgaacgtggatgaagttgtggggtac | R01-6-A |
| 140 | gcggtaccccacaacttcatccacgttcagcgg | R01-6-B |
| 141 | gttgaacgtggatgaagttgtggggtac | R01-7-A |
| 142 | gcggtaccccacaacttcatccacgttcaacgg | R01-7-B |
| 143 | ggagaacgtggatgaagttgtggggtac | R01-8-A |
| 144 | gcggtaccccacaacttcatccacgttctccgg | R01-8-B |
| 145 | ggcgaacgtggatgaagttgtggggtac | R01-9-A |
| 146 | gcggtaccccacaacttcatccacgttcgccgg | R01-9-B |
| 147 | gggggaacgtggatgaagttgtggggtac | R01-10-A |
| 148 | gcggtaccccacaacttcatccacgttccccgg | R01-10-B |
| 149 | ggtaaacgtggatgaagttgtggggtac | R01-11-A |
| 150 | gcggtaccccacaacttcatccacgttttaccgg | R01-11-B |
| 151 | ggtcaacgtggatgaagttgtggggtac | R01-12-A |
| 152 | gcggtaccccacaacttcatccacgttgaccgg | R01-12-B |
| 153 | ggttaacgtggatgaagttgtggggtac | R01-13-A |

SEQUENCE LISTING

| SEQ ID NO | Sequence | Description |
|---|---|---|
| 154 | gcggtaccccacaacttcatccacgttaaccgg | R01-13-B |
| 155 | ggtgcacgtggatgaagttgtggggtac | R01-14-A |
| 156 | gcggtaccccacaacttcatccacgtgcaccgg | R01-14-B |
| 157 | ggtgtacgtggatgaagttgtggggtac | R01-15-A |
| 158 | gcggtaccccacaacttcatccacgtacaccgg | R01-15-B |
| 159 | ggtggacgtggatgaagttgtggggtac | R01-16-A |
| 160 | gcggtaccccacaacttcatccacgtccaccgg | R01-16-B |
| 161 | ggtgaccgtggatgaagttgtggggtac | R01-17-A |
| 162 | gcggtaccccacaacttcatccacggtcaccgg | R01-17-B |
| 163 | ggtgatcgtggatgaagttgtggggtac | R01-18-A |
| 164 | gcggtaccccacaacttcatccacgatcaccgg | R01-18-B |
| 165 | ggtgagcgtggatgaagttgtggggtac | R01-19-A |
| 166 | gcggtaccccacaacttcatccacgctcaccgg | R01-19-B |
| 167 | ggtgaaagtggatgaagttgtggggtac | R01-20-A |
| 168 | gcggtaccccacaacttcatccactttcaccgg | R01-20-B |
| 169 | ggtgaatgtggatgaagttgtggggtac | R01-21-A |
| 170 | gcggtaccccacaacttcatccacattcaccgg | R01-21-B |
| 171 | ggtgaaggtggatgaagttgtggggtac | R01-22-A |
| 172 | gcggtaccccacaacttcatccaccttcaccgg | R01-22-B |
| 173 | ggtgaacatggatgaagttgtggggtac | R01-23-A |
| 174 | gcggtaccccacaacttcatccatgttcaccgg | R01-23-B |
| 175 | ggtgaacctggatgaagttgtggggtac | R01-24-A |
| 176 | gcggtaccccacaacttcatccaggttcaccgg | R01-24-B |
| 177 | ggtgaacttggatgaagttgtggggtac | R01-25-A |
| 178 | gcggtaccccacaacttcatccaagttcaccgg | R01-25-B |
| 179 | ggtgaacgaggatgaagttgtggggtac | R01-26-A |
| 180 | gcggtaccccacaacttcatcctcgttcaccgg | R01-26-B |
| 181 | ggtgaacgcggatgaagttgtggggtac | R01-27-A |
| 182 | gcggtaccccacaacttcatccgcgttcaccgg | R01-27-B |
| 183 | ggtgaacggggatgaagttgtggggtac | R01-28-A |
| 184 | gcggtaccccacaacttcatccccgttcaccgg | R01-28-B |
| 185 | ggtgaacgtagatgaagttgtggggtac | R01-29-A |
| 186 | gcggtaccccacaacttcatctacgttcaccgg | R01-29-B |
| 187 | ggtgaacgtcgatgaagttgtggggtac | R01-30-A |
| 188 | gcggtaccccacaacttcatcgacgttcaccgg | R01-30-B |
| 189 | ggtgaacgttgatgaagttgtggggtac | R01-31-A |
| 190 | gcggtaccccacaacttcatcaacgttcaccgg | R01-31-B |

-continued

SEQUENCE LISTING

| SEQ ID NO | Sequence | Description |
|---|---|---|
| 191 | ggtgaacgtgaatgaagttgtggggtac | R01-32-A |
| 192 | gcggtaccccacaacttcattcacgttcaccgg | R01-32-B |
| 193 | ggtgaacgtgcatgaagttgtggggtac | R01-33-A |
| 194 | gcggtaccccacaacttcatgcacgttcaccgg | R01-33-B |
| 195 | ggtgaacgtgtatgaagttgtggggtac | R01-34-A |
| 196 | gcggtaccccacaacttcatacacgttcaccgg | R01-34-B |
| 197 | ggtgaacgtggctgaagttgtggggtac | R01-35-A |
| 198 | gcggtaccccacaacttcagccacgttcaccgg | R01-35-B |
| 199 | ggtgaacgtggttgaagttgtggggtac | R01-36-A |
| 200 | gcggtaccccacaacttcaaccacgttcaccgg | R01-36-B |
| 201 | ggtgaacgtgggtgaagttgtggggtac | R01-37-A |
| 202 | gcggtaccccacaacttcacccacgttcaccgg | R01-37-B |
| 203 | ggtgaacgtggaagaagttgtggggtac | R01-38-A |
| 204 | gcggtaccccacaacttcttccacgttcaccgg | R01-38-B |
| 205 | ggtgaacgtggacgaagttgtggggtac | R01-39-A |
| 206 | gcggtaccccacaacttcgtccacgttcaccgg | R01-39-B |
| 207 | ggtgaacgtggaggaagttgtggggtac | R01-40-A |
| 208 | gcggtaccccacaacttcctccacgttcaccgg | R01-40-B |
| 209 | ggtgaacgtggataaagttgtggggtac | R01-41-A |
| 210 | gcggtaccccacaactttatccacgttcaccgg | R01-41-B |
| 211 | ggtgaacgtggatcaagttgtggggtac | R01-42-A |
| 212 | gcggtaccccacaacttgatccacgttcaccgg | R01-42-B |
| 213 | ggtgaacgtggattaagttgtggggtac | R01-43-A |
| 214 | gcggtaccccacaacttaatccacgttcaccgg | R01-43-B |
| 215 | ggtgaacgtggatgcagttgtggggtac | R01-44-A |
| 216 | gcggtaccccacaactgcatccacgttcaccgg | R01-44-B |
| 217 | ggtgaacgtggatgtagttgtggggtac | R01-45-A |
| 218 | gcggtaccccacaactacatccacgttcaccgg | R01-45-B |
| 219 | ggtgaacgtggatggagttgtggggtac | R01-46-A |
| 220 | gcggtaccccacaactccatccacgttcaccgg | R01-46-B |
| 221 | ggtgaacgtggatgacgttgtggggtac | R01-47-A |
| 222 | gcggtaccccacaacgtcatccacgttcaccgg | R01-47-B |
| 223 | ggtgaacgtggatgatgttgtggggtac | R01-48-A |
| 224 | gcggtaccccacaacatcatccacgttcaccgg | R01-48-B |
| 225 | ggtgaacgtggatgaggttgtggggtac | R01-49-A |
| 226 | gcggtaccccacaacctcatccacgttcaccgg | R01-49-B |

SEQUENCE LISTING

| SEQ ID NO | Sequence | Description |
|---|---|---|
| 227 | ggtgaacgtggatgaaattgtggggta | R01-50-A |
| 228 | gcggtaccccacaatttcatccacgttcaccgg | R01-50-B |
| 229 | ggtgaacgtggatgaacttgtggggtac | R01-51-A |
| 230 | gcggtaccccacaagttcatccacgttcaccgg | R01-51-B |
| 231 | ggtgaacgtggatgaatttgtggggtac | R01-52-A |
| 232 | gcggtaccccacaaattcatccacgttcaccgg | R01-52-B |
| 233 | ggtgaacgtggatgaagatgtggggtac | R01-53-A |
| 234 | gcggtaccccacatcttcatccacgttcaccgg | R01-53-B |
| 235 | ggtgaacgtggatgaagctgtggggtac | R01-54-A |
| 236 | gcggtaccccacagcttcatccacgttcaccgg | R01-54-B |
| 237 | ggtgaacgtggatgaaggtgtggggtac | R01-55-A |
| 238 | gcggtaccccacaccttcatccacgttcaccgg | R01-55-B |
| 239 | ggtgaacgtggatgaagtagtggggtac | R01-56-A |
| 240 | gcggtaccccactacttcatccacgttcaccgg | R01-56-B |
| 241 | ggtgaacgtggatgaagtcgtggggtac | R01-57-A |
| 242 | gcggtaccccacgacttcatccacgttcaccgg | R01-57-B |
| 243 | ggtgaacgtggatgaagtggtggggtac | R01-58-A |
| 244 | gcggtaccccaccacttcatccacgttcaccgg | R01-58-B |
| 245 | ggtgaacgtggatgaagttatggggtac | R01-59-A |
| 246 | gcggtaccccataacttcatccacgttcaccgg | R01-59-B |
| 247 | ggtgaacgtggatgaagttctggggtac | R01-60-A |
| 248 | gcggtaccccagaacttcatccacgttcaccgg | R01-60-B |
| 249 | ggtgaacgtggatgaagttttggggtac | R01-61-A |
| 250 | gcggtaccccaaaacttcatccacgttcaccgg | R01-61-B |
| 251 | GGAGTCCGAGCAGAAGAAGAA | sgRNA 1 target sequence |
| 252 | GGACATCGATGTCCTCCCCAT | sgRNA 2 target sequence |
| 253 | GGTCACCTCCAATGACTAGGG | sgRNA 3 target sequence |
| 254 | GGCTCCCCATTGGCCTGCTTCG | sgRNA 4 target sequence |
| 255 | GGTGCGCCACCGGTTGATGTGA | sgRNA 5 target sequence |
| 256 | GGCGCCACCGGTTGATGTGAT | sgRNA 6 target sequence |
| 257 | GGCCGTTTGTACTTTGTCCTC | sgRNA 7 target sequence |
| 258 | GGCACAGATGAGAAACTCAGG | sgRNA 8 target sequence |

SEQUENCE LISTING

| SEQ ID NO | Sequence | Description |
|---|---|---|
| 259 | GGATTGGGTGTTCAGGGCAGAG | sgRNA 9 target sequence |
| 260 | GGTGGCGAGAGGGGCCGAGAT | sgRNA 10 target sequence |
| 261 | GGGGCCGAGATTGGGTGTTC | sgRNA 11 target sequence |
| 262 | GGTGCCATTAGCTAAATGCAT | sgRNA 12 target sequence |
| 263 | GGTACCACCCACAGGTGCCAG | sgRNA 13 target sequence |
| 264 | GGAAAGCCTCTGGGCCAGGAA | sgRNA 14 target sequence |
| 265 | GGACACCCACGGAGAGCGCTGT | sgRNA 15 target sequence |
| 266 | GGTCCAGTTGGTGACAAATAC | sgRNA 16 target sequence |
| 267 | GGTTTTAACACTTCCCTAGCCA | sgRNA 17 target sequence |
| 268 | GGCTTAATTAGCTCCTTTGGCT | sgRNA 18 target sequence |
| 269 | GGCTTAATTAGCTCCTTTGGC | sgRNA 19 target sequence |
| 270 | GGTGCATATGATGATAGTATTA | sgRNA 20 target sequence |
| 271 | GGAATGTATGCTGGCTTTTAAG | sgRNA 21 target sequence |
| 272 | GGAAATGTATGCTGGCTTTTAA | sgRNA 22 target sequence |
| 273 | GGAAAATGTATGCTGGCTTTTA | sgRNA 23 target sequence |
| 274 | GGTAAAATGTATGCTGGCTTTT | sgRNA 24 target sequence |
| 275 | GGCTTAAAGATGATCTCTTACC | sgRNA 25 target sequence |
| 276 | GGTTAAAGATGATCTCTTACCT | sgRNA 26 target sequence |
| 277 | GGTAATAAAATTCAAACATCCT | sgRNA 27 target sequence |
| 278 | GGTAAAGCATAGTGCAATGGAT | sgRNA 28 target sequence |
| 279 | GGTTAAATAAAGCATAGTGCAA | sgRNA 29 target sequence |
| 280 | GGATTTATGAGATCAACAGCAC | sgRNA 30 target sequence |
| 281 | GGCCCATGCTCTGACCGCTCGA | sgRNA 31 target sequence |
| 282 | GGCCATCGAGCGGTCAGAGCAT | sgRNA 32 target sequence |

SEQUENCE LISTING

| SEQ ID NO | Sequence | Description |
|---|---|---|
| 283 | GGGCAAAAGCTCATGTGATA | sgRNA 33 target sequence |
| 284 | GGACTGAGGCTTATGTTCCATG | sgRNA 34 target sequence |
| 285 | GGAGAGTGTACAAACTCACAA | sgRNA 35 target sequence |
| 286 | GGACTAGCATTATAATGCACCA | sgRNA 36 target sequence |
| 287 | GGTCAGAAGAGATTAGTTAGTA | sgRNA 37 target sequence |
| 288 | GGTGAGAGTGCCATCTCTTCCT | sgRNA 38 target sequence |
| 289 | GGTGGACCACATGGCTTTGCTC | sgRNA 39 target sequence |
| 290 | GGTGAGCAAAGCCATGTGGTCC | sgRNA 40 target sequence |
| 291 | GGATTAATGACATACGCATTT | sgRNA 41 target sequence |
| 292 | GGAGATTAATGACATACGCATT | sgRNA 42 target sequence |
| 293 | GGTTCAATCCTCTTGTCACCTG | sgRNA 43 target sequence |
| 294 | GGACATCTCTATGTCGGCCAC | sgRNA 44 target sequence |
| 295 | GGAAAACCTACCGCAAGTTGCC | sgRNA 45 target sequence |
| 296 | GGTGGACTACATAGTTGTGTGA | sgRNA 46 target sequence |
| 297 | GGCTGCCAGACTCTCTGAACCC | sgRNA 47 target sequence |
| 298 | GGATCCCTCGTATAACAATA | sgRNA 48 target sequence |
| 299 | GGTATCGCATAGTGCAAAGAAT | sgRNA 49 target sequence |
| 300 | GGCTCGGTCCTCTCGTCACCTG | sgRNA 50 target sequence |
| 301 | GGACGCTCCCGGAGAGCGCTGG | sgRNA 51 target sequence |
| 302 | GGCCATGGCGCGGTCAGAGGGT | sgRNA 52 target sequence |
| 303 | GGCTCGGCTCCAATGACGAGGG | sgRNA 53 target sequence |
| 304 | GGCACTTCGATGACCTCCCCGT | sgRNA 54 target sequence |
| 305 | GGAGTGGGTGTTCAGGACCGCG | sgRNA 55 target sequence |
| 306 | GGCTGCTACCCACAGGTGCAAG | sgRNA 56 target sequence |

SEQUENCE LISTING

| SEQ ID NO | Sequence | Description |
|---|---|---|
| 307 | GGAAGATGTATCCTGGAATTTA | sgRNA 57 target sequence |
| 308 | GGTTTTATCACTACCCAAGACA | sgRNA 58 target sequence |
| 309 | GGCGGCCAGGCTCCCTGAAACC | sgRNA 59 target sequence |
| 310 | GGACTGGTATTATAATACAACA | sgRNA 60 target sequence |
| 311 | GGTGAGAGTGACATTTCGTACT | sgRNA 61 target sequence |
| 312 | GGTGCGCCCCCGGGTGAGGTGC | sgRNA 62 target sequence |
| 313 | GGCAGTTTGAGCAGAAAAAGAA | sgRNA 63 target sequence |
| 314 | GGTCTGTAGAGATAAGTGAGTA | sgRNA 64 target sequence |
| 315 | GGAAGTGTGTACAAACTCAAGA | sgRNA 65 target sequence |
| 316 | GGTATCATGGATGCTGACTTTT | sgRNA 66 target sequence |
| 317 | GGCTTTACTAGCCCCTGTGGC | sgRNA 67 target sequence |
| 318 | GGCACGGAGGAGAAAAGCAGG | sgRNA 68 target sequence |
| 319 | GGATTTGTGAGATCTAAAGAAC | sgRNA 69 target sequence |
| 320 | GGCGTTGATGACATTCGCATTT | sgRNA 70 target sequence |
| 321 | GGCTTATAGATCATCTAATACC | sgRNA 71 target sequence |
| 322 | GGTGGCCTCCATAGTTGGGTGG | sgRNA 72 target sequence |
| 323 | GGTACTAGAGTTCAAACATACT | sgRNA 73 target sequence |
| 324 | GGCCCCTGCTCTGAGCACTCGG | sgRNA 74 target sequence |
| 325 | GGAGGACCACATGGCCTGCCTC | sgRNA 75 target sequence |
| 326 | GGAACAGCTGCCGCAAATTGCC | sgRNA 76 target sequence |
| 327 | GGCTCCGTATTGGCTGGCTTCG | sgRNA 77 target sequence |
| 328 | GGCCAGCCGATGACAAATAC | sgRNA 78 target sequence |
| 329 | GGACGTCTCTACGTCGGCGGC | sgRNA 79 target sequence |
| 330 | GGCCGGCGCGAGGGGCCGAGAG | sgRNA 80 target sequence |

-continued

SEQUENCE LISTING

| SEQ ID NO | Sequence | Description |
|---|---|---|
| 331 | GGACTGTTTGTACTTTTTCATC | sgRNA 81 target sequence |
| 332 | GGTGCTTATGATGATGACATTA | sgRNA 82 target sequence |
| 333 | GGCCGCGTCCGATTGATGTGAT | sgRNA 83 target sequence |
| 334 | GGCTTTATGAGCACCTTAGGCT | sgRNA 84 target sequence |
| 335 | GGATCCCTCCTATGACCATG | sgRNA 85 target sequence |
| 336 | GGATAAAGGTGACCTCTTACGT | sgRNA 86 target sequence |
| 337 | GGACTGTGGCTTAGGGTCCAGG | sgRNA 87 target sequence |
| 338 | GGTGAGGAAACCCAGGCGGTCC | sgRNA 88 target sequence |
| 339 | GGAAATGTATACAGGCAATTAA | sgRNA 89 target sequence |
| 340 | GGTTGAATCAAGCATAGTCCGA | sgRNA 90 target sequence |
| 341 | GGGCTACGGCTCATGAGATA | sgRNA 91 target sequence |
| 342 | GGCGGGCCGCGATTGGCAGTTC | sgRNA 92 target sequence |
| 343 | GGCTGCGATTATCTAAATCCAT | sgRNA 93 target sequence |
| 344 | GGAGCTTGATTACATACGCATG | sgRNA 94 target sequence |
| 345 | GGAATGTTTGCTGGCCTCTAGG | sgRNA 95 target sequence |
| 346 | GGAAAGCCTCTGCGCCGGGGG | sgRNA 96 target sequence |
| 347 | CCTGAGTCCGAGCAGAAGAAGAATGGGGTAC | Ext-A-P-1-A |
| 348 | GCGGTACCCCATTCTTCTTCTGCTCGGACTCAGGGG | Ext-A-P-1-B |
| 349 | GGTGACATCGATGTCCTCCCCATTGGGGTAC | Ext-A-P-2-A |
| 350 | GCGGTACCCCAATGGGGAGGACATCGATGTCACCGG | Ext-A-P-2-B |
| 351 | GATGTCACCTCCAATGACTAGGGTGGGGTAC | Ext-A-P-3-A |
| 352 | GCGGTACCCCACCCTAGTCATTGGAGGTGACATCGG | Ext-A-P-3-B |
| 353 | GTCCTCCCCATTGGCCTGCTTCGTGGGGTAC | Ext-A-P-4-A |
| 354 | GCGGTACCCCACGAAGCAGGCCAATGGGGAGGACGG | Ext-A-P-4-B |
| 355 | CAATGCGCCACCGGTTGATGTGATGGGGTAC | Ext-A-P-5-A |
| 356 | GCGGTACCCCATCACATCAACCGGTGGCGCATTGGG | Ext-A-P-5-B |
| 357 | AATGCGCCACCGGTTGATGTGATTGGGGTAC | Ext-A-P-6-A |
| 358 | GCGGTACCCCAATCACATCAACCGGTGGCGCATTGG | Ext-A-P-6-B |
| 359 | TCTGCCGTTTGTACTTTGTCCTCTGGGGTAC | Ext-A-P-7-A |

-continued

SEQUENCE LISTING

| SEQ ID NO | Sequence | Description |
|---|---|---|
| 360 | GCGGTACCCCAGAGGACAAAGTACAAACGGCAGAGG | Ext-A-P-7-B |
| 361 | GGGGCACAGATGAGAAACTCAGGTGGGGTAC | Ext-A-P-8-A |
| 362 | GCGGTACCCCACCTGAGTTTCTCATCTGTGCCCCGG | Ext-A-P-8-B |
| 363 | GAGATTGGGTGTTCAGGGCAGAGTGGGGTAC | Ext-A-P-9-A |
| 364 | GCGGTACCCCACTCTGCCCTGAACACCCAATCTCGG | Ext-A-P-9-B |
| 365 | AGGGTGGCGAGAGGGGCCGAGATTGGGGTAC | Ext-A-P-10-A |
| 366 | GCGGTACCCCAATCTCGGCCCCTCTCGCCACCCTGG | Ext-A-P-10-B |
| 367 | AGAGGGGCCGAGATTGGGTGTTCTGGGGTAC | Ext-A-P-11-A |
| 368 | GCGGTACCCCAGAACACCCAATCTCGGCCCCTCTGG | Ext-A-P-11-B |
| 369 | TGAGTGCCATTAGCTAAATGCATTGGGGTAC | Ext-A-P-12-A |
| 370 | GCGGTACCCCAATGCATTTAGCTAATGGCACTCAGG | Ext-A-P-12-B |
| 371 | AGGGTACCACCCACAGGTGCCAGTGGGGTAC | Ext-A-P-13-A |
| 372 | GCGGTACCCCACTGGCACCTGTGGGTGGTACCCTGG | Ext-A-P-13-B |
| 373 | TGGGAAAGCCTCTGGGCCAGGAATGGGGTAC | Ext-A-P-14-A |
| 374 | GCGGTACCCCATTCCTGGCCCAGAGGCTTTCCCAGG | Ext-A-P-14-B |
| 375 | AGGACACCCACGGAGAGCGCTGTTGGGGTAC | Ext-A-P-27-A |
| 376 | GCGGTACCCCAACAGCGCTCTCCGTGGGTGTCCTGG | Ext-A-P-27-B |
| 377 | AGGGTCCAGTTGGTGACAAATACTGGGGTAC | Ext-A-P-28-A |
| 378 | GCGGTACCCCAGTATTTGTCACCAACTGGACCCTGG | Ext-A-P-28-B |
| 379 | AGGTTTTAACACTTCCCTAGCCATGGGGTAC | Ext-A-P-29-A |
| 380 | GCGGTACCCCATGGCTAGGGAAGTGTTAAAACCTGG | Ext-A-P-29-B |
| 381 | AGGCTTAATTAGCTCCTTTGGCTTGGGGTAC | Ext-A-P-30-A |
| 382 | GCGGTACCCCAAGCCAAAGGAGCTAATTAAGCCTGG | Ext-A-P-30-B |
| 383 | AGGGCTTAATTAGCTCCTTTGGCTGGGGTAC | Ext-A-P-31-A |
| 384 | GCGGTACCCCAGCCAAAGGAGCTAATTAAGCCCTGG | Ext-A-P-31-B |
| 385 | AGGTGCATATGATGATAGTATTATGGGGTAC | Ext-A-P-32-A |
| 386 | GCGGTACCCCATAATACTATCATCATATGCACCTGG | Ext-A-P-32-B |
| 387 | AGGAATGTATGCTGGCTTTTAAGTGGGGTAC | Ext-A-P-33-A |
| 388 | GCGGTACCCCACTTAAAAGCCAGCATACATTCCTGG | Ext-A-P-33-B |
| 389 | AGGAAATGTATGCTGGCTTTTAATGGGGTAC | Ext-A-P-34-A |
| 390 | GCGGTACCCCATTAAAAGCCAGCATACATTTCCTGG | Ext-A-P-34-B |
| 391 | AGGAAAATGTATGCTGGCTTTTATGGGGTAC | Ext-A-P-35-A |
| 392 | GCGGTACCCCATAAAAGCCAGCATACATTTTCCTGG | Ext-A-P-35-B |
| 393 | AGGTAAAATGTATGCTGGCTTTTTGGGGTAC | Ext-A-P-36-A |
| 394 | GCGGTACCCCAAAAAGCCAGCATACATTTTACCTGG | Ext-A-P-36-B |
| 395 | AGGCTTAAAGATGATCTCTTACCTGGGGTAC | Ext-A-P-37-A |

SEQUENCE LISTING

| SEQ ID NO | Sequence | Description |
|---|---|---|
| 396 | GCGGTACCCCAGGTAAGAGATCATCTTTAAGCCTGG | Ext-A-P-37-B |
| 397 | AGGTTAAAGATGATCTCTTACCTTGGGGTAC | Ext-A-P-38-A |
| 398 | GCGGTACCCCAAGGTAAGAGATCATCTTTAACCTGG | Ext-A-P-38-B |
| 399 | AGGTAATAAAATTCAAACATCCTTGGGGTAC | Ext-A-P-39-A |
| 400 | GCGGTACCCCAAGGATGTTTGAATTTTATTACCTGG | Ext-A-P-39-B |
| 401 | AGGTAAAGCATAGTGCAATGGATTGGGGTAC | Ext-A-P-40-A |
| 402 | GCGGTACCCCAATCCATTGCACTATGCTTTACCTGG | Ext-A-P-40-B |
| 403 | AGGTTAAATAAAGCATAGTGCAATGGGGTAC | Ext-A-P-41-A |
| 404 | GCGGTACCCCATTGCACTATGCTTTATTTAACCTGG | Ext-A-P-41-B |
| 405 | AGGATTTATGAGATCAACAGCACTGGGGTAC | Ext-A-P-42-A |
| 406 | GCGGTACCCCAGTGCTGTTGATCTCATAAATCCTGG | Ext-A-P-42-B |
| 407 | AGGCCCATGCTCTGACCGCTCGATGGGGTAC | Ext-A-P-43-A |
| 408 | GCGGTACCCCATCGAGCGGTCAGAGCATGGGCCTGG | Ext-A-P-43-B |
| 409 | AGGCCATCGAGCGGTCAGAGCATTGGGGTAC | Ext-A-P-44-A |
| 410 | GCGGTACCCCAATGCTCTGACCGCTCGATGGCCTGG | Ext-A-P-44-B |
| 411 | AGGGGGCAAAAGCTCATGTGATATGGGGTAC | Ext-A-P-45-A |
| 412 | GCGGTACCCCATATCACATGAGCTTTTGCCCCCTGG | Ext-A-P-45-B |
| 413 | AGGACTGAGGCTTATGTTCCATGTGGGGTAC | Ext-A-P-46-A |
| 414 | GCGGTACCCCACATGGAACATAAGCCTCAGTCCTGG | Ext-A-P-46-B |
| 415 | AGGGAGAGTGTACAAACTCACAATGGGGTAC | Ext-A-P-47-A |
| 416 | GCGGTACCCCATTGTGAGTTTGTACACTCTCCCTGG | Ext-A-P-47-B |
| 417 | AGGACTAGCATTATAATGCACCATGGGGTAC | Ext-A-P-48-A |
| 418 | GCGGTACCCCATGGTGCATTATAATGCTAGTCCTGG | Ext-A-P-48-B |
| 419 | AGGTCAGAAGAGATTAGTTAGTATGGGGTAC | Ext-A-P-49-A |
| 420 | GCGGTACCCCATACTAACTAATCTCTTCTGACCTGG | Ext-A-P-49-B |
| 421 | AGGTGAGAGTGCCATCTCTTCCTTGGGGTAC | Ext-A-P-50-A |
| 422 | GCGGTACCCCAAGGAAGAGATGGCACTCTCACCTGG | Ext-A-P-50-B |
| 423 | AGGTGGACCACATGGCTTTGCTCTGGGGTAC | Ext-A-P-51-A |
| 424 | GCGGTACCCCAGAGCAAAGCCATGTGGTCCACCTGG | Ext-A-P-51-B |
| 425 | AGGTGAGCAAAGCCATGTGGTCCTGGGGTAC | Ext-A-P-52-A |
| 426 | GCGGTACCCCAGGACCACATGGCTTTGCTCACCTGG | Ext-A-P-52-B |
| 427 | AGGGATTAATGACATACGCATTTTGGGGTAC | Ext-A-P-53-A |
| 428 | GCGGTACCCCAAAATGCGTATGTCATTAATCCCTGG | Ext-A-P-53-B |
| 429 | AGGAGATTAATGACATACGCATTTGGGGTAC | Ext-A-P-54-A |
| 430 | GCGGTACCCCAAATGCGTATGTCATTAATCTCCTGG | Ext-A-P-54-B |
| 431 | AGGTTCAATCCTCTTGTCACCTGTGGGGTAC | Ext-A-P-55-A |
| 432 | GCGGTACCCCACAGGTGACAAGAGGATTGAACCTGG | Ext-A-P-55-B |

-continued

SEQUENCE LISTING

| SEQ ID NO | Sequence | Description |
|---|---|---|
| 433 | AGGGACATCTCTATGTCGGCCACTGGGGTAC | Ext-A-P-56-A |
| 434 | GCGGTACCCCAGTGGCCGACATAGAGATGTCCCTGG | Ext-A-P-56-B |
| 435 | AGGAAAACCTACCGCAAGTTGCCTGGGGTAC | Ext-A-P-57-A |
| 436 | GCGGTACCCCAGGCAACTTGCGGTAGGTTTTCCTGG | Ext-A-P-57-B |
| 437 | AGGTGGACTACATAGTTGTGTGATGGGGTAC | Ext-A-P-58-A |
| 438 | GCGGTACCCCATCACACAACTATGTAGTCCACCTGG | Ext-A-P-58-B |
| 439 | AGGCTGCCAGACTCTCTGAACCCTGGGGTAC | Ext-A-P-59-A |
| 440 | GCGGTACCCCAGGGTTCAGAGAGTCTGGCAGCCTGG | Ext-A-P-59-B |
| 441 | AGGGGATCCCTCGTATAACAATATGGGGTAC | Ext-A-P-60-A |
| 442 | GCGGTACCCCATATTGTTATACGAGGGATCCCCTGG | Ext-A-P-60-B |
| 443 | AGGTATCGCATAGTGCAAAGAATTGGGGTAC | Ext-A-P-61-A |
| 444 | GCGGTACCCCAATTCTTTGCACTATGCGATACCTGG | Ext-A-P-61-B |
| 445 | AGGCTCGGTCCTCTCGTCACCTGTGGGGTAC | Ext-A-P-62-A |
| 446 | GCGGTACCCCACAGGTGACGAGAGGACCGAGCCTGG | Ext-A-P-62-B |
| 447 | AGGACGCTCCCGGAGAGCGCTGGTGGGGTAC | Ext-A-P-63-A |
| 448 | GCGGTACCCCACCAGCGCTCTCCGGGAGCGTCCTGG | Ext-A-P-63-B |
| 449 | AGGCCATGGCGCGGTCAGAGGGTTGGGGTAC | Ext-A-P-64-A |
| 450 | GCGGTACCCCAACCCTCTGACCGCGCCATGGCCTGG | Ext-A-P-64-B |
| 451 | AGGCTCGGCTCCAATGACGAGGGTGGGGTAC | Ext-A-P-65-A |
| 452 | GCGGTACCCCACCCTCGTCATTGGAGCCGAGCCTGG | Ext-A-P-65-B |
| 453 | AGGCACTTCGATGACCTCCCCGTTGGGGTAC | Ext-A-P-66-A |
| 454 | GCGGTACCCCAACGGGGAGGTCATCGAAGTGCCTGG | Ext-A-P-66-B |
| 455 | AGGAGTGGGTGTTCAGGACCGCGTGGGGTAC | Ext-A-P-67-A |
| 456 | GCGGTACCCCACGCGGTCCTGAACACCCACTCCTGG | Ext-A-P-67-B |
| 457 | AGGCTGCTACCCACAGGTGCAAGTGGGGTAC | Ext-A-P-68-A |
| 458 | GCGGTACCCCACTTGCACCTGTGGGTAGCAGCCTGG | Ext-A-P-68-B |
| 459 | AGGAAGATGTATCCTGGAATTTATGGGGTAC | Ext-A-P-69-A |
| 460 | GCGGTACCCCATAAATTCCAGGATACATCTTCCTGG | Ext-A-P-69-B |
| 461 | AGGTTTTATCACTACCCAAGACATGGGGTAC | Ext-A-P-70-A |
| 462 | GCGGTACCCCATGTCTTGGGTAGTGATAAAACCTGG | Ext-A-P-70-B |
| 463 | AGGCGGCCAGGCTCCCTGAAACCTGGGGTAC | Ext-A-P-71-A |
| 464 | GCGGTACCCCAGGTTTCAGGGAGCCTGGCCGCCTGG | Ext-A-P-71-B |
| 465 | AGGACTGGTATTATAATACAACATGGGGTAC | Ext-A-P-72-A |
| 466 | GCGGTACCCCATGTTGTATTATAATACCAGTCCTGG | Ext-A-P-72-B |
| 467 | AGGTGAGAGTGACATTTCGTACTTGGGGTAC | Ext-A-P-73-A |
| 468 | GCGGTACCCCAAGTACGAAATGTCACTCTCACCTGG | Ext-A-P-73-B |

SEQUENCE LISTING

| SEQ ID NO | Sequence | Description |
|---|---|---|
| 469 | AGGTGCGCCCCCGGGTGAGGTGCTGGGGTAC | Ext-A-P-74-A |
| 470 | GCGGTACCCCAGCACCTCACCCGGGGGCGCACCTGG | Ext-A-P-74-B |
| 471 | AGGCAGTTTGAGCAGAAAAAGAATGGGGTAC | Ext-A-P-75-A |
| 472 | GCGGTACCCCATTCTTTTTCTGCTCAAACTGCCTGG | Ext-A-P-75-B |
| 473 | AGGTCTGTAGAGATAAGTGAGTATGGGGTAC | Ext-A-P-76-A |
| 474 | GCGGTACCCCATACTCACTTATCTCTACAGACCTGG | Ext-A-P-76-B |
| 475 | AGGAAGTGTGTACAAACTCAAGATGGGGTAC | Ext-A-P-77-A |
| 476 | GCGGTACCCCATCTTGAGTTTGTACACACTTCCTGG | Ext-A-P-77-B |
| 477 | AGGTATCATGGATGCTGACTTTTTGGGGTAC | Ext-A-P-78-A |
| 478 | GCGGTACCCCAAAAAGTCAGCATCCATGATACCTGG | Ext-A-P-78-B |
| 479 | AGGGCTTTACTAGCCCCTGTGGCTGGGGTAC | Ext-A-P-79-A |
| 480 | GCGGTACCCCAGCCACAGGGGCTAGTAAAGCCCTGG | Ext-A-P-79-B |
| 481 | AGGGCACGGAGGAGAAAAGCAGGTGGGGTAC | Ext-A-P-80-A |
| 482 | GCGGTACCCCACCTGCTTTTCTCCTCCGTGCCCTGG | Ext-A-P-80-B |
| 483 | AGGATTTGTGAGATCTAAAGAACTGGGGTAC | Ext-A-P-81-A |
| 484 | GCGGTACCCCAGTTCTTTAGATCTCACAAATCCTGG | Ext-A-P-81-B |
| 485 | AGGCGTTGATGACATTCGCATTTTGGGGTAC | Ext-A-P-82-A |
| 486 | GCGGTACCCCAAAATGCGAATGTCATCAACGCCTGG | Ext-A-P-82-B |
| 487 | AGGCTTATAGATCATCTAATACCTGGGGTAC | Ext-A-P-83-A |
| 488 | GCGGTACCCCAGGTATTAGATGATCTATAAGCCTGG | Ext-A-P-83-B |
| 489 | AGGTGGCCTCCATAGTTGGGTGGTGGGGTAC | Ext-A-P-84-A |
| 490 | GCGGTACCCCACCACCCAACTATGGAGGCCACCTGG | Ext-A-P-84-B |
| 491 | AGGTACTAGAGTTCAAACATACTTGGGGTAC | Ext-A-P-85-A |
| 492 | GCGGTACCCCAAGTATGTTTGAACTCTAGTACCTGG | Ext-A-P-85-B |
| 493 | AGGCCCCTGCTCTGAGCACTCGGTGGGGTAC | Ext-A-P-86-A |
| 494 | GCGGTACCCCACCGAGTGCTCAGAGCAGGGGCCTGG | Ext-A-P-86-B |
| 495 | AGGAGGACCACATGGCCTGCCTCTGGGGTAC | Ext-A-P-87-A |
| 496 | GCGGTACCCCAGAGGCAGGCCATGTGGTCCTCCTGG | Ext-A-P-87-B |
| 497 | AGGAACAGCTGCCGCAAATTGCCTGGGGTAC | Ext-A-P-88-A |
| 498 | GCGGTACCCCAGGCAATTTGCGGCAGCTGTTCCTGG | Ext-A-P-88-B |
| 499 | AGGCTCCGTATTGGCTGGCTTCGTGGGGTAC | Ext-A-P-89-A |
| 500 | GCGGTACCCCACGAAGCCAGCCAATACGGAGCCTGG | Ext-A-P-89-B |
| 501 | AGGGGCCAGCCGATGACAAATACTGGGGTAC | Ext-A-P-90-A |
| 502 | GCGGTACCCCAGTATTTGTCATCGGCTGGCCCCTGG | Ext-A-P-90-B |
| 503 | AGGGACGTCTCTACGTCGGCGGCTGGGGTAC | Ext-A-P-91-A |
| 504 | GCGGTACCCCAGCCGCCGACGTAGAGACGTCCCTGG | Ext-A-P-91-B |
| 505 | AGGCCGGCGCGAGGGGCCGAGAGTGGGGTAC | Ext-A-P-92-A |

-continued

SEQUENCE LISTING

| SEQ ID NO | Sequence | Description |
|---|---|---|
| 506 | GCGGTACCCCACTCTCGGCCCCTCGCGCCGGCCTGG | Ext-A-P-92-B |
| 507 | AGGACTGTTTGTACTTTTTCATCTGGGGTAC | Ext-A-P-93-A |
| 508 | GCGGTACCCCAGATGAAAAAGTACAAACAGTCCTGG | Ext-A-P-93-B |
| 509 | AGGTGCTTATGATGATGACATTATGGGGTAC | Ext-A-P-94-A |
| 510 | GCGGTACCCCATAATGTCATCATCATAAGCACCTGG | Ext-A-P-94-B |
| 511 | AGGCCGCGTCCGATTGATGTGATTGGGGTAC | Ext-A-P-95-A |
| 512 | GCGGTACCCCAATCACATCAATCGGACGCGGCCTGG | Ext-A-P-95-B |
| 513 | AGGCTTTATGAGCACCTTAGGCTTGGGGTAC | Ext-A-P-96-A |
| 514 | GCGGTACCCCAAGCCTAAGGTGCTCATAAAGCCTGG | Ext-A-P-96-B |
| 515 | AGGGGATCCCTCCTATGACCATGTGGGGTAC | Ext-A-P-97-A |
| 516 | GCGGTACCCCACATGGTCATAGGAGGGATCCCCTGG | Ext-A-P-97-B |
| 517 | AGGATAAAGGTGACCTCTTACGTTGGGGTAC | Ext-A-P-98-A |
| 518 | GCGGTACCCCAACGTAAGAGGTCACCTTTATCCTGG | Ext-A-P-98-B |
| 519 | AGGACTGTGGCTTAGGGTCCAGGTGGGGTAC | Ext-A-P-99-A |
| 520 | GCGGTACCCCACCTGGACCCTAAGCCACAGTCCTGG | Ext-A-P-99-B |
| 521 | AGGTGAGGAAACCCAGGCGGTCCTGGGGTAC | Ext-A-P-100-A |
| 522 | GCGGTACCCCAGGACCGCCTGGGTTTCCTCACCTGG | Ext-A-P-100-B |
| 523 | AGGAAATGTATACAGGCAATTAATGGGGTAC | Ext-A-P-101-A |
| 524 | GCGGTACCCCATTAATTGCCTGTATACATTTCCTGG | Ext-A-P-101-B |
| 525 | AGGTTGAATCAAGCATAGTCCGATGGGGTAC | Ext-A-P-102-A |
| 526 | GCGGTACCCCATCGGACTATGCTTGATTCAACCTGG | Ext-A-P-102-B |
| 527 | AGGGGGCTACGGCTCATGAGATATGGGGTAC | Ext-A-P-103-A |
| 528 | GCGGTACCCCATATCTCATGAGCCGTAGCCCCCTGG | Ext-A-P-103-B |
| 529 | AGGCGGGCCGCGATTGGCAGTTCTGGGGTAC | Ext-A-P-104-A |
| 530 | GCGGTACCCCAGAACTGCCAATCGCGGCCCGCCTGG | Ext-A-P-104-B |
| 531 | AGGCTGCGATTATCTAAATCCATTGGGGTAC | Ext-A-P-105-A |
| 532 | GCGGTACCCCAATGGATTTAGATAATCGCAGCCTGG | Ext-A-P-105-B |
| 533 | AGGAGCTTGATTACATACGCATGTGGGGTAC | Ext-A-P-106-A |
| 534 | GCGGTACCCCACATGCGTATGTAATCAAGCTCCTGG | Ext-A-P-106-B |
| 535 | AGGAATGTTTGCTGGCCTCTAGGTGGGGTAC | Ext-A-P-107-A |
| 536 | GCGGTACCCCACCTAGAGGCCAGCAAACATTCCTGG | Ext-A-P-107-B |
| 537 | AGGGAAAGCCTCTGCGCCGGGGGTGGGGTAC | Ext-A-P-108-A |
| 538 | GCGGTACCCCACCCCCGGCGCAGAGGCTTTCCCTGG | Ext-A-P-108-B |

The invention claimed is:

1. A synthetic RNA-guided nuclease (sRGN) polypeptide comprising an amino acid sequence having at least 95% identity to the amino acid sequence of SEQ ID NO: 2.

2. The sRGN of claim 1, wherein the amino acid sequence comprises a PAM-interacting domain that recognizes the PAM sequence NNGG.

3. The sRGN polypeptide of SEQ ID NO: 2, wherein the amino acid sequence has at least 96%, 97%, 98%, or 99% identity to the amino acid sequence of SEQ ID NO: 2, or wherein the amino acid sequence is SEQ ID NO: 2.

4. The sRGN of claim 3, wherein the sRGN polypeptide further comprises:
   (i) one or more nuclear localization signals (NLSs);
   (ii) one or more mutations that result in reduced nuclease activity as compared to the polypeptide of SEQ ID NO: 2, wherein the one or more mutations are selected from an amino acid substitution at a position corresponding to position 10 of the polypeptide of SEQ ID NO: 2, at a position corresponding to position 562 of the polypeptide of SEQ ID NO: 2, and at a position corresponding to position 585 of the polypeptide of SEQ ID NO: 2; and/or
   (iii) a C- or N-terminally attached polypeptide with a nucleobase editing activity or deaminase activity, optionally attached via a linker peptide sequence.

5. A pharmaceutical composition comprising the sRGN polypeptide of claim 1, and a pharmaceutically acceptable carrier.

6. A kit comprising:
   (a) the sRGN polypeptide according to claim 1;
   (b) a guide RNA (gRNA), wherein the gRNA is capable of guiding the sRGN polypeptide to a target polynucleotide, and
   (c) instructions for targeting, editing, modifying, or manipulating a target DNA at a target locus.

7. A system for introducing a single-stranded or a double-stranded break in a target polynucleotide, the system comprising:
   (a) a sRGN polypeptide comprising an amino acid sequence having at least 95% identity to the amino acid sequence of SEQ ID NO: 2; and
   (b) a single guide RNA (sgRNA) comprising a DNA targeting segment capable of hybridizing to a target polynucleotide,
      wherein the sgRNA combines with the sRGN polypeptide to induce a single-stranded or double-stranded break in the target polynucleotide.

8. The system of claim 7, further comprising a donor template comprising a heterologous polynucleotide, wherein the heterologous polynucleotide is capable of being inserted into the target polynucleotide.

9. The system of claim 7, wherein the sRGN polypeptide is pre-complexed with the sgRNA to form a ribonucleoprotein (RNP) complex.

10. The system of claim 7, wherein the sRGN polypeptide is formulated in a liposome or lipid nanoparticle, optionally wherein the liposome or lipid nanoparticle further comprises the sgRNA.

* * * * *